(12) United States Patent
Timmer et al.

(10) Patent No.: US 7,112,587 B2
(45) Date of Patent: Sep. 26, 2006

(54) METHODS AND COMPOSITIONS OF NOVEL TRIAZINE COMPOUNDS

(75) Inventors: Richard T. Timmer, Decatur, GA (US); Christopher W. Alexander, Norcross, GA (US); Sivaram Pillarisetti, Norcross, GA (US); Uday Saxena, Atlanta, GA (US); Koteswar Rao Yeleswarapu, Hyderabad (IN); Manojit Pal, Hyderabad (IN); Jangalgar Tirupathy Reddy, Hyderabad (IN); Velagala Venkata Rama Murali Krishna Reddy, Hyderabad (IN); Bhatlapenumarthy Sesha Sridevi, Gandhinagar (IN); Potlapally Rajendar Kumar, Hyderabad (IN); Gaddam Om Reddy, Hyderabad (IN)

(73) Assignee: Reddy US Therapeutics, Inc., Norcross, GA (US)

( * ) Notice: Subject to any disclaimer, the term of this patent is extended or adjusted under 35 U.S.C. 154(b) by 0 days.

(21) Appl. No.: 10/400,134

(22) Filed: Mar. 26, 2003

(65) Prior Publication Data

US 2004/0209881 A1 Oct. 21, 2004

Related U.S. Application Data

(63) Continuation-in-part of application No. 10/390,485, filed on Mar. 17, 2003, which is a continuation of application No. 10/253,388, filed on Sep. 23, 2002, now abandoned.

(60) Provisional application No. 60/324,147, filed on Sep. 21, 2001.

(51) Int. Cl.
*C07D 251/30* (2006.01)
*C07D 251/46* (2006.01)
*C07D 251/48* (2006.01)
*A61K 31/53* (2006.01)
*A61P 35/00* (2006.01)

(52) U.S. Cl. .............. 514/241; 544/197; 544/198; 544/206; 544/209; 544/219; 540/480; 540/598; 514/183; 514/212.08

(58) Field of Classification Search ........... 544/197, 544/198, 207, 208, 209, 219, 206; 514/241, 514/183, 212.08; 540/480, 598; 541/241
See application file for complete search history.

(56) References Cited

U.S. PATENT DOCUMENTS

| 3,758,471 | A | 9/1973 | Irikura et al. |
|---|---|---|---|
| 5,470,921 | A | 11/1995 | Kaul et al. |
| 6,117,996 | A | 9/2000 | Lowe et al. |
| 6,123,763 | A | 9/2000 | Kamikubo et al. |
| 6,150,360 | A | 11/2000 | Daeyaert et al. |
| 6,284,710 | B1 | 9/2001 | Riebel et al. |
| 6,645,964 | B1 | 11/2003 | Mailliet et al. |
| 2002/0065270 | A1 | 5/2002 | Moriarty et al. |

FOREIGN PATENT DOCUMENTS

| WO | WO 97/08156 A1 | 3/1997 |
|---|---|---|
| WO | WO 99/31088 A1 | 6/1999 |
| WO | WO 99/36410 A1 | 7/1999 |
| WO | WO 01/47897 A1 | 7/2001 |
| WO | WO 01/47921 A | 7/2001 |
| WO | WO 03/024926 A2 | 3/2003 |

*Primary Examiner*—Venkataraman Balasubramanian
(74) *Attorney, Agent, or Firm*—Womble Carlyle Sandridge & Rice, PLLC

(57) ABSTRACT

The present invention relates to methods and compositions comprising compounds that treat pathophysiological conditions arising from inflammatory responses. In particular, the present invention is directed to compounds that inhibit or block glycated protein produced induction of the signaling-associated inflammatory response in endothelial cells. The present invention relates to compounds that inhibit smooth muscle proliferation. In particular, the present invention is directed to compounds that inhibit smooth muscle cell proliferation by modulating HSPGs such as Perlecan. The present invention further relates to the use of compounds to treat vascular occlusive conditions characterized by smooth muscle proliferation such as restenosis and atherosclerosis.

6 Claims, 86 Drawing Sheets

600 MHz, DMSO-d$_6$, TMS, 55 C

600 MHz, CDCl₃, TMS, 55 C

600 MHz, CDCl₃, TMS, 55 C

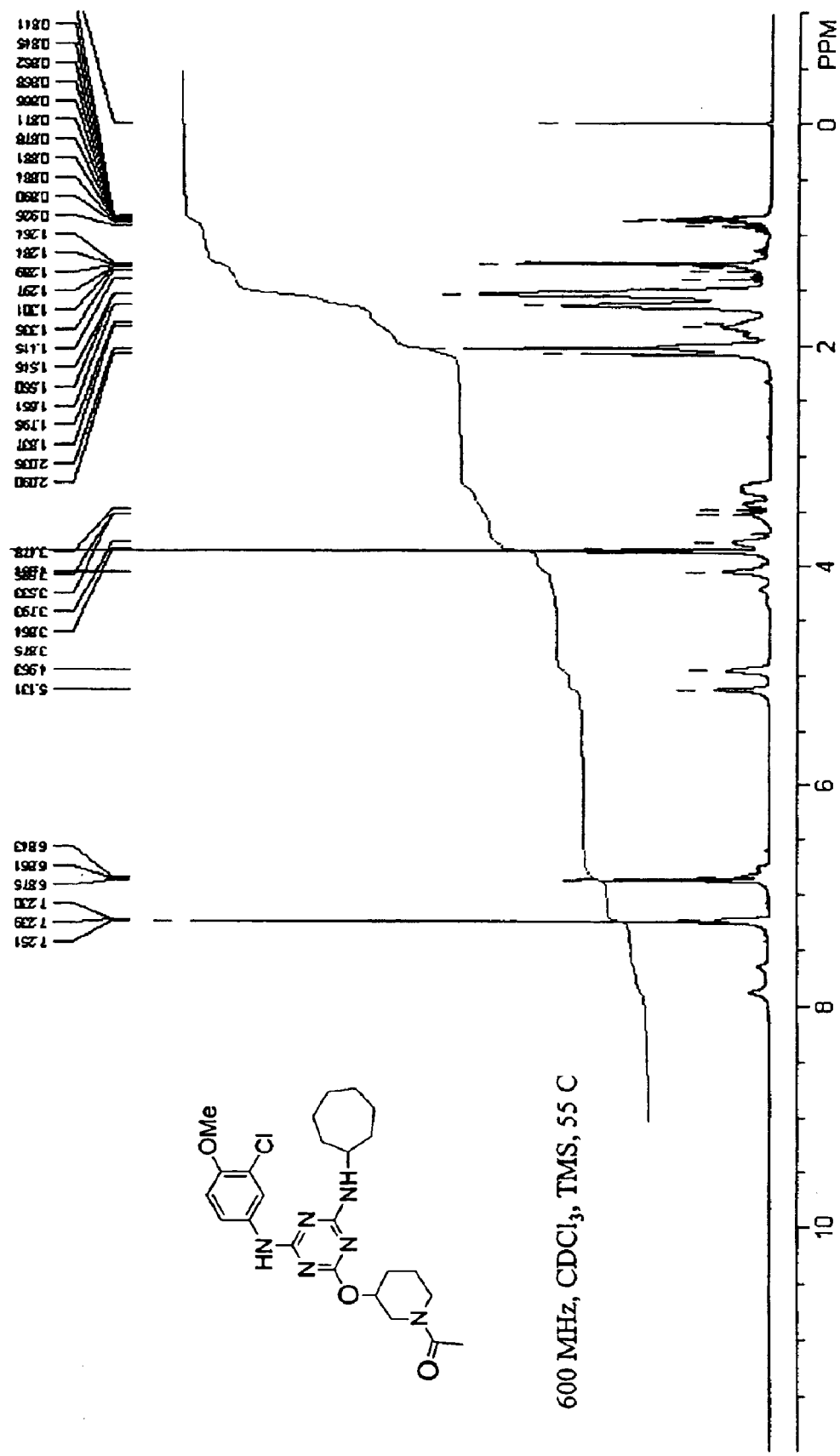
Fig. 73
600 MHz, CDCl₃, TMS, 55 C
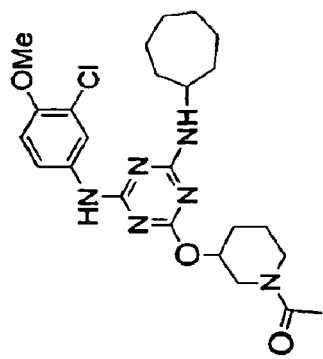

METHODS AND COMPOSITIONS OF NOVEL TRIAZINE COMPOUNDS

PRIOR RELATED U.S. APPLICATION DATA

This application is a continuation-in-part of U.S. patent application Ser. No. 10/390,485 filed Mar. 17, 2003, which is a continuation of U.S. patent application Ser. No. 10/253,388 filed Sep. 23, 2002, now abandoned, which claims priority to U.S. Provisional Application Ser. No. 60/324,147 filed Sep. 21, 2001, which is incorporated herein by reference.

FIELD OF THE INVENTION

The present invention relates to triazine compounds. More particularly, the invention relates to methods and compositions for making and using triazine compounds.

BACKGROUND OF THE INVENTION

Synthesis of novel compounds leads to new possibilities for discovery of novel therapeutic interventions. By using structure and activity relationship investigations, compounds can be tailored so that the compounds have at least one activity that can be predicted from its structure. Using high-throughput assays allows for the rapid determination of the activity of the newly synthesized compounds.

Novel compounds for new therapeutic interventions are needed for many areas of medicine and disease treatment. For example, chronic and acute inflammatory conditions form the basis for diseases affecting all organ systems including, but not limited to, asthma, acute inflammatory diseases, vascular inflammatory disease, chronic inflammation, atherosclerosis, angiopathy, myocarditis, nephritis, Crohn's disease, arthritis, type I and II diabetes and associated vascular pathologies. The incidence of these inflammatory conditions is on the rise in the population as a whole, with diabetes alone affecting 16 million people.

While inflammation in and of itself is a normal immune response, chronic inflammation leads to complications and ongoing system damage due to the interactions of unknown cellular factors. In particular, chronic inflammation can cause endothelial damage resulting in vascular complications. Coronary artery, cerbrovascular and peripheral vascular disease resulting from atherosclerotic and thromboembolic macroangiopathy are the primary causes of mortality in chronic inflammatory diseases.

Many humans and animals have limited lifespans and lifestyles because of conditions relating to lifestyle choices, such as diet and exercise, or because of genetic predispositions to develop a disease. For example, vascular smooth muscle cell proliferation is a common consequence of endothelial injury and is believed to be an early pathogenetic event in the formation of atherosclerotic plaques or complications related to vascular injury or as a result surgical interventions. Abnormal vascular smooth muscle cell (SMC) proliferation is thought to contribute to the pathogenesis of vascular occlusive lesions, including arteriosclerosis, atherosclerosis, restenosis, and graft atherosclerosis after organ transplantation.

Percutaneous coronary artery intervention (PTCA) procedures are the most common in-patient hospital procedure in the United States. According to the American Heart Association, about one-third of the patients that undergo balloon angioplasty have restenosis of the widened segment of the vessel within approximately 6 months. It may be necessary to perform another angioplasty or coronary artery bypass surgery on restenosed arteries. A key feature of restenosis is an injury response that results in activation of an inflammatory cascade and remodeling of the cells both inside and outside the carotid artery wall. This includes excessive growth of connective tissue and smooth muscle into the lumen of the artery known as neointimal hyperplasia. Currently there are no effective pharmacological treatments available that control the pathogenesis of vascular occlusive lesions, such as, but not limited to, arteriosclerosis, atherosclerosis, restenosis, and graft atherosclerosis after organ transplantation. Identification of effective therapeutics with minimal side effects will restore quality of life without requiring additional surgical procedures such as coronary artery bypass surgery.

Control or modulation of factors produced by the body in response to injury, surgery, metabolic factors or loss of control of in feedback mechanisms, leading to too much or too little of a factor has long been the goal of administering pharmacological agents. One disease that rapidly growing in the industrialized countries is the occurrence of diabetes and all of its attendant sequellae. One of the factors important in the damage associated with diabetes is the presence of glycated proteins.

Glycated proteins and advanced glycation end products (AGE) contribute to cellular damage, particularly, diabetic tissue injury, by at least by two major mechanisms; modulation of cellular functions through interactions with specific cell surface receptors, and alteration of the extracellular matrix leading to the formation of protein cross-links. Studies suggest that glycated protein and AGE interactions with cells may promote inflammatory processes and oxidative cellular injury. AGE increases lipoprotein oxidisability and atherogenicity. Its binding to matrix proteins induces synthesis of cytokines and activates cellular messangers. Diseases where glycated protein and AGE accumulation is a suspected etiological factor include vascular complications of diabetes, microangiopathies, renal insufficiency and Alzheimer's disease.

The exact mechanisms by which high plasma glucose, as seen in diabetes, causes microvascular damage are not completely understood. One potential mechanism by which hyperglycemia can be linked to microangiopathies is through the process of non-enzymatic glycation of critical proteins. Non-enzymatic glycation, i.e. the linking of proteins with glucose, leads to the formation of glycated proteins. The first step in this glycation pathway involves the non-enzymatic condensation of glucose with free amino groups in the protein, primarily the epsilon-amino groups of lysine residues, forming the Amadori adducts. These early glycation products can undergo further reactions such as rearrangements, dehydration and condensations to form irreversible advanced glycation end products (AGE). These are a highly reactive group of molecules whose interaction with specific receptors on the cell-surface which are thought to lead to pathogenic outcomes.

Other major area of disease of where treatments are needed and for which adequate and effective therapies do not exist are cellular proliferative disorders, or disorders caused by unwanted or unintended cellular growth. As mentioned, smooth muscle cell (SMC) hyperplasia is a major event in the development of atherosclerosis and is also responsible for the significant number of failure rates following vascular procedures such as angioplasty, stent implantation and coronary artery bypass surgery. In the normal vessel, SMC are quiescent, but they proliferate when damage to the endothelium occurs. Naturally occurring growth modulators, many of which are derived from the endothelium, tightly control SMC proliferation in vivo. When the control becomes unregulated, a pathological state is induced in the subject.

Another major area of unwanted cellular growth, that is unchecked by the body's regulatory systems, is cancer or oncological conditions. Many therapies have been used and are being used in an effort to restore health or at least stop the unwanted cell growth. Many times, therapeutic agents can have an effect individually, but often, therapeutic regimes require combinations of different pharmacological agents with treatments such as surgery or radiation.

There is a present need for treatments of chronic or acute diseases, such as atherosclerosis, unwanted cellular growth or cellular proliferation, diabetes, inflammatory conditions and vascular occlusive pathologic conditions, because occurrence is frequent, the currently available treatments are costly and the conditions are refractory to many pharmacological therapies. The mechanisms involved in the control or prevention of such diseases are not clear and there exists a need for preventive and therapeutic treatments of these and other diseases Thus, what is presently needed are novel compounds that find utility in methods and compositions for treatment and prevention of chronic and acute diseases.

SUMMARY OF THE INVENTION

The present invention is directed to methods and compositions comprising novel compounds, primarily based on a substituted triazine core. Disclosed herein are methods for making novel compounds, the compounds, compositions comprising the compounds, and methods and compositions for using the compounds. The compounds and compositions comprising the compounds have utility in treatment of a variety of diseases.

Compositions in accordance with the present invention comprise triazine compounds, analogs, derivatives, and mixtures thereof. Such triazine compounds comprise the following structure, where $N^A$, $N^B$ and $N^C$ are typically used to represent pendant substituted amino groups attached to 1,3,5-triazine at the 2,4 and 6 positions:

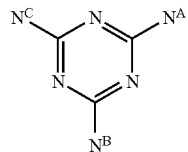

An example of such triazine compounds includes compounds having the following structure.

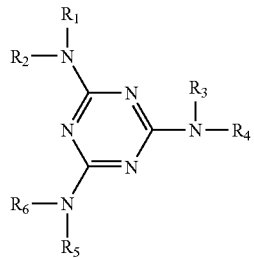

In this example, each pendent amino (NRR') group can represent simply an $NH_2$ group or a secondary or tertiary amino group, including a cyclic secondary amide, and a range of other substituents as described herein. Compositions in accordance with the present invention also comprise analogs of the tris(amino) compounds, that include intermediate compounds in the synthesis of the tris(amino) triazine compounds indicated above, for example diamino chlorotriazine compounds, or amino diclorotriazine compounds shown below, where $N^A$ and $N^B$ are pendant substituted amino groups as described above.

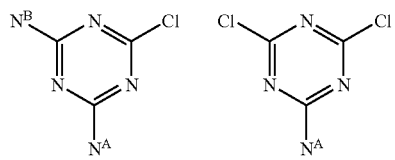

Compositions in accordance with the present invention also comprise analogs of the tris(amino) triazine compounds indicated above, including compounds that are isolated as byproducts in the synthesis of the tris(amino) triazine compounds, such as bis(amino)alkoxy triazine compounds as shown below, where E=O or S and the like.

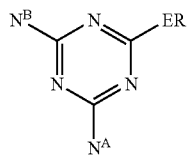

The present invention also comprises compositions used in making the novel compounds and methods of making the novel compounds disclosed herein.

The present invention is directed to methods and compositions comprising compounds that have utility in treatment of pathological conditions. One aspect of the present invention comprises compounds and compositions comprising such compounds in methods for treating diseases related to unwanted cellular proliferation. Many vascular diseases, such as cardiovascular diseases, organ transplant sequellae, vascular occlusive conditions including, but not limited to, neointimal hyperplasia, restenosis, transplant vasculopathy, cardiac allograft vasculopathy, atherosclerosis, and arteriosclerosis. are caused by or have collateral damage due to unwanted cellular proliferation, such as smooth muscle cell (SMC) hyperplasia. At least one activity of one or more of these compounds is that the compound has the activity of effecting the synthesis of proteoglycans including induction and synthesis of proteoglycans and active fragments of proteoglycans. Methods comprise administration of compositions comprising compounds that have at least the activity of effecting cellular proliferation and effecting proteoglycan synthesis and activity.

The present invention also comprises methods and compositions comprising compounds described herein that have an activity associated with modulation of glycosidase enzymes and thus, effecting the substrates for such enzymes. Glycosidase enzymes and their activity with their substrates, such as proteoglycans or glycated proteins, are aspects of a variety of diseases such as vascular conditions, proteoglycan-associated diseases, kidney disease, autoimmune disease and inflammatory diseases. Compounds described herein that have an activity that effects the concentrations of substrates of glycosidase enzymes are used in methods of treatment of such vascular, inflammatory, metastatic and systemic diseases.

An embodiment of the present invention comprises methods and compositions comprising compounds of the present invention for the treatment and prevention of conditions or diseases that have as an aspect of the disease or condition, inflammation. An aspect of the present invention is directed to methods and compositions comprising compounds that are effective in inhibiting inflammation, particularly inflammation associated with the accumulation or presence of glycated proteins or AGE. Methods of treatment comprise administration of compositions comprising having compounds having at least the activity of modulating inflammatory reactions that are components of biological conditions including, but not limited to, vascular complications of type I and type II diabetic-induced vasculopathies, other vasculopathies, microangiopathies, renal insufficiency, Alzheimer's syndrome, and inflammation-induced diseases such as atherosclerosis. An aspect of the present invention comprises methods and compositions for the treatment of diseases, preconditions or pathologies associated with inflammatory cytokines and other inflammation related molecules.

Another embodiment of the present invention comprises methods and compositions comprising compounds that have at least the activity of causing cellular death or a cessation of cellular activity, referred to herein as cytotoxic activity. This activity can be used in methods for in vitro or in vivo cytotoxicity. For example, compounds having this activity can be selectively delivered to an area within a living organism to selectively kill cells in that area. Such methods are using in treating hyperproliferative cells, such as cancers, or other unwanted cellular growth or cellular activities. One aspect of the invention provides compositions comprising compounds that nonselectively kill cells. Another aspect of the invention provides compounds that selectively kill cells, for example, cells that have a particular cellular marker or other identifying characteristic such as metabolic rate or uptake of a particular compound.

The present invention also comprises pharmaceutical compositions comprising the compounds disclosed herein. Routes of administration and dosages of effective amounts of the compounds and pharmaceutical compositions are also disclosed. For example, the compounds of the present invention can be administered in combination with other pharmaceutical agents in a variety of protocols for effective treatment of disease.

In another aspect, the present invention relates to drug delivering or eluting medical devices that contain or are coated with at least one compound disclosed herein. The medical device suitable for use with the compounds of the present invention include, but are not limited to, stents and other medical devices that can provide a substrate for delivery of at least one compound.

Other aspects of the present invention comprise compositions and methods for microarray devices. Such microarray devices and methods comprise a variety of microarrays that may be used, for example, to study and monitor gene expression in response to treatment with the compounds of the present invention. The microarrays may comprise nucleic acid sequences, carbohydrates or proteins that are determinative for specific cells, tissues, species, disease states, prognoses, disease progression, or any other combination of molecules that can be used to determine an effect of one or more of the compounds of the present invention. Other embodiments of the present invention comprise methods using databases and computer applications.

BRIEF DESCRIPTION OF THE FIGURES

FIG. 73. ¹H NMR of 1-[3-{4-(3-chloro-4-methoxyanilino)-6-cycloheptylamino-1,3,5-triazine-2-yloxy}piperidino]-1-ethanone.

DETAILED DESCRIPTION OF THE INVENTION

Figure 1:
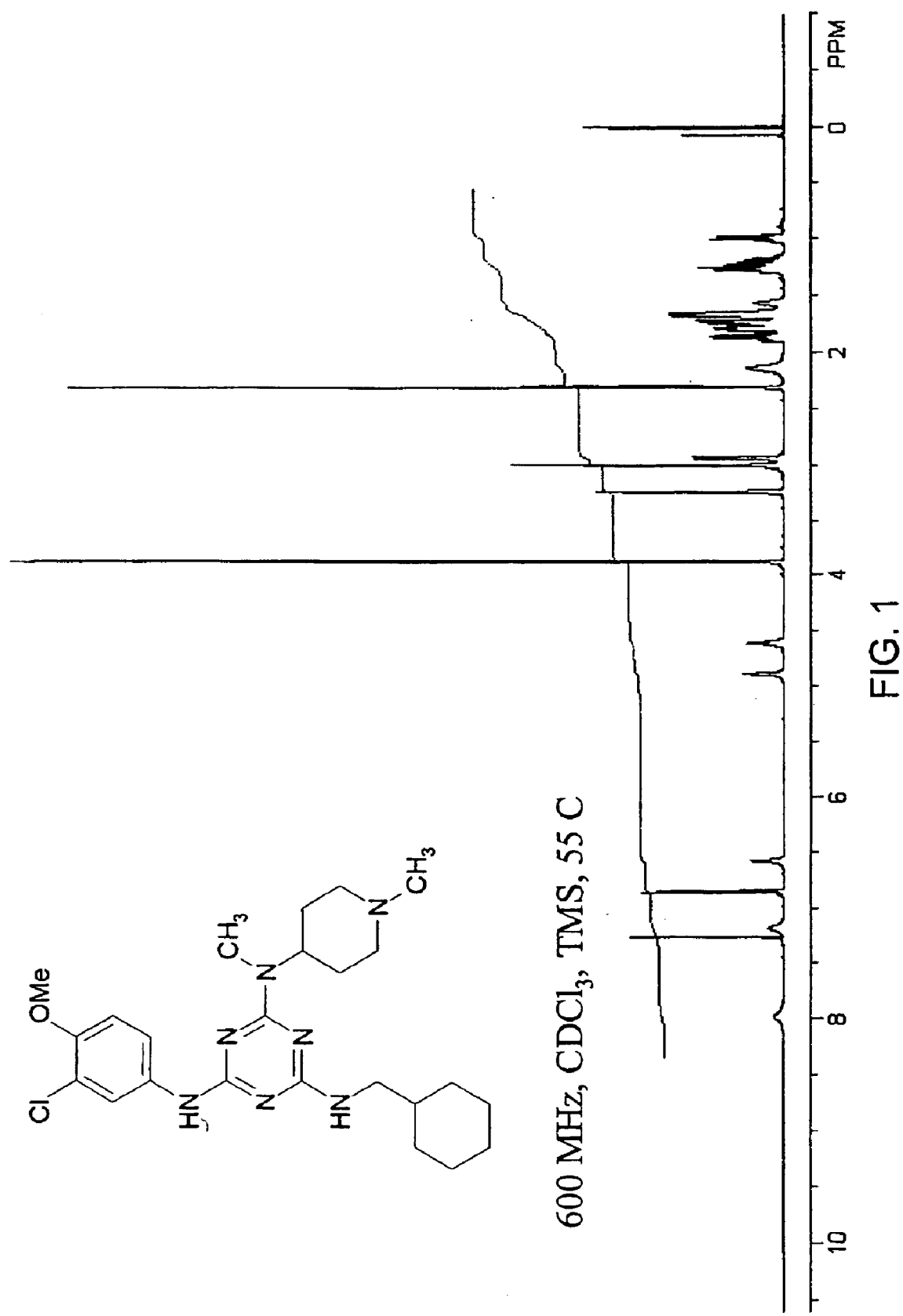
FIG. 1. $^1$H NMR of N-(3-Chloro-4-methoxy-phenyl)-N'-cyclohexylmethyl-N'''-methyl-N''-(1-methyl-piperidin-4-yl)-[1,3,5]triazine-2,4,6-triamine.
Figure 2:
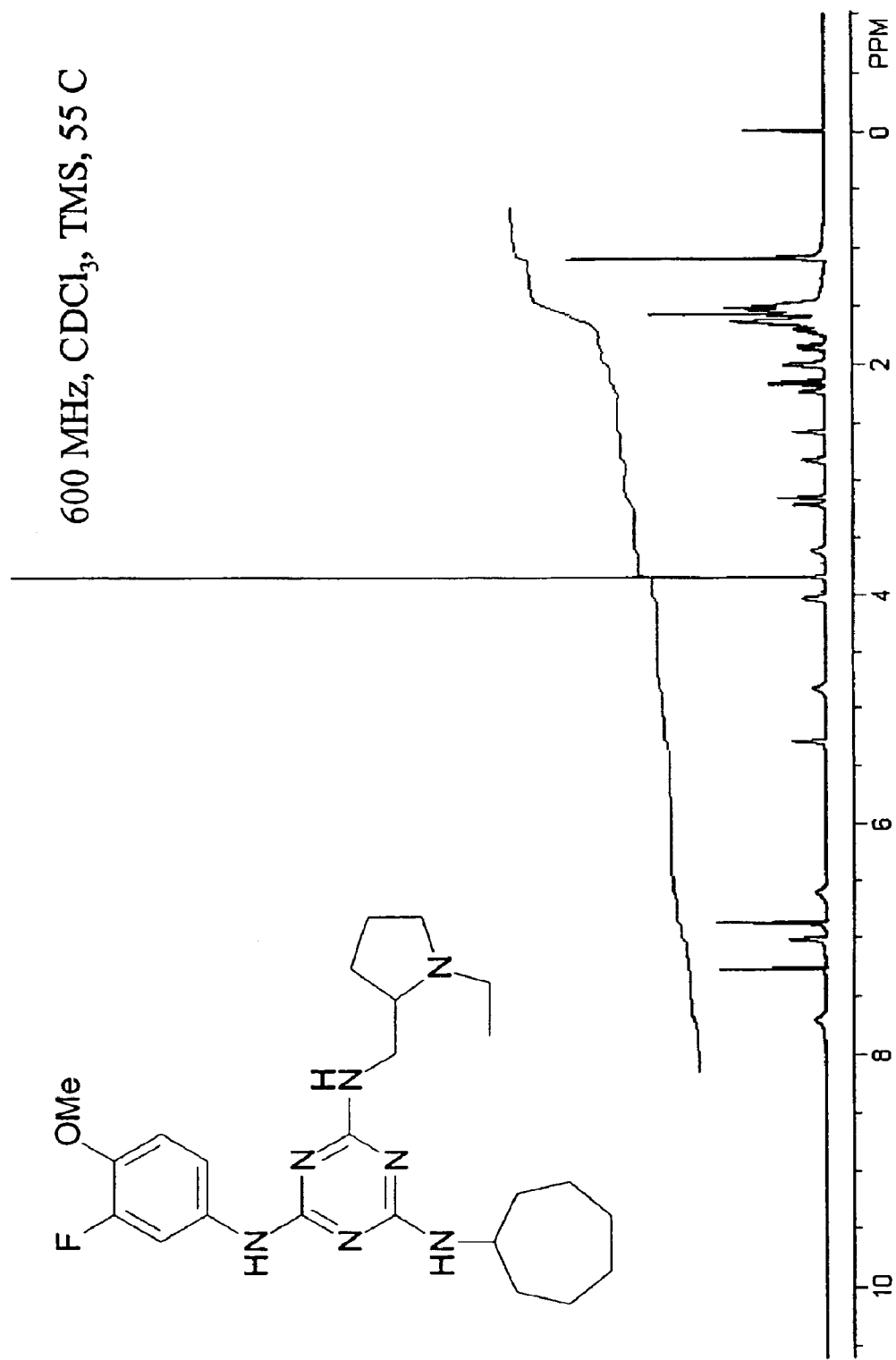
FIG. 2. $^1$H NMR of N-Cycloheptyl-N'-(1-ethyl-pyrrolidin-2-ylmethyl)-N''-(3-fluoro-4-methoxy-phenyl)-[1,3,5]triazine-2,4,6-triamine.
Figure 3:
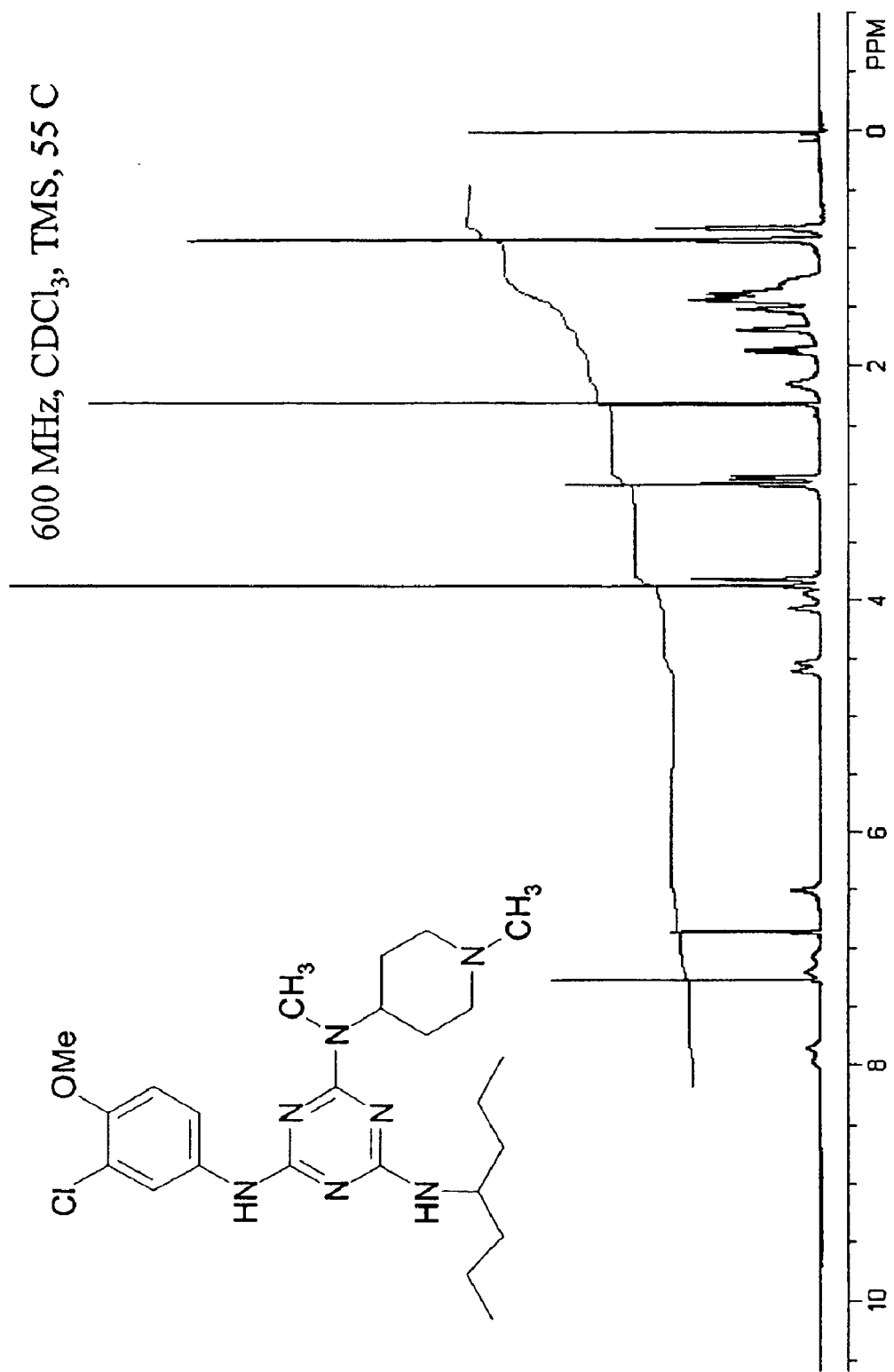
FIG. 3. $^1$H NMR of N-(3-Chloro-4-methoxy-phenyl)-N'-methyl-N'-(1-methyl-piperidin-4-yl)-N''-(1-propyl-butyl)-[1,3,5]triazine-2,4,6-triamine.
Figure 4:
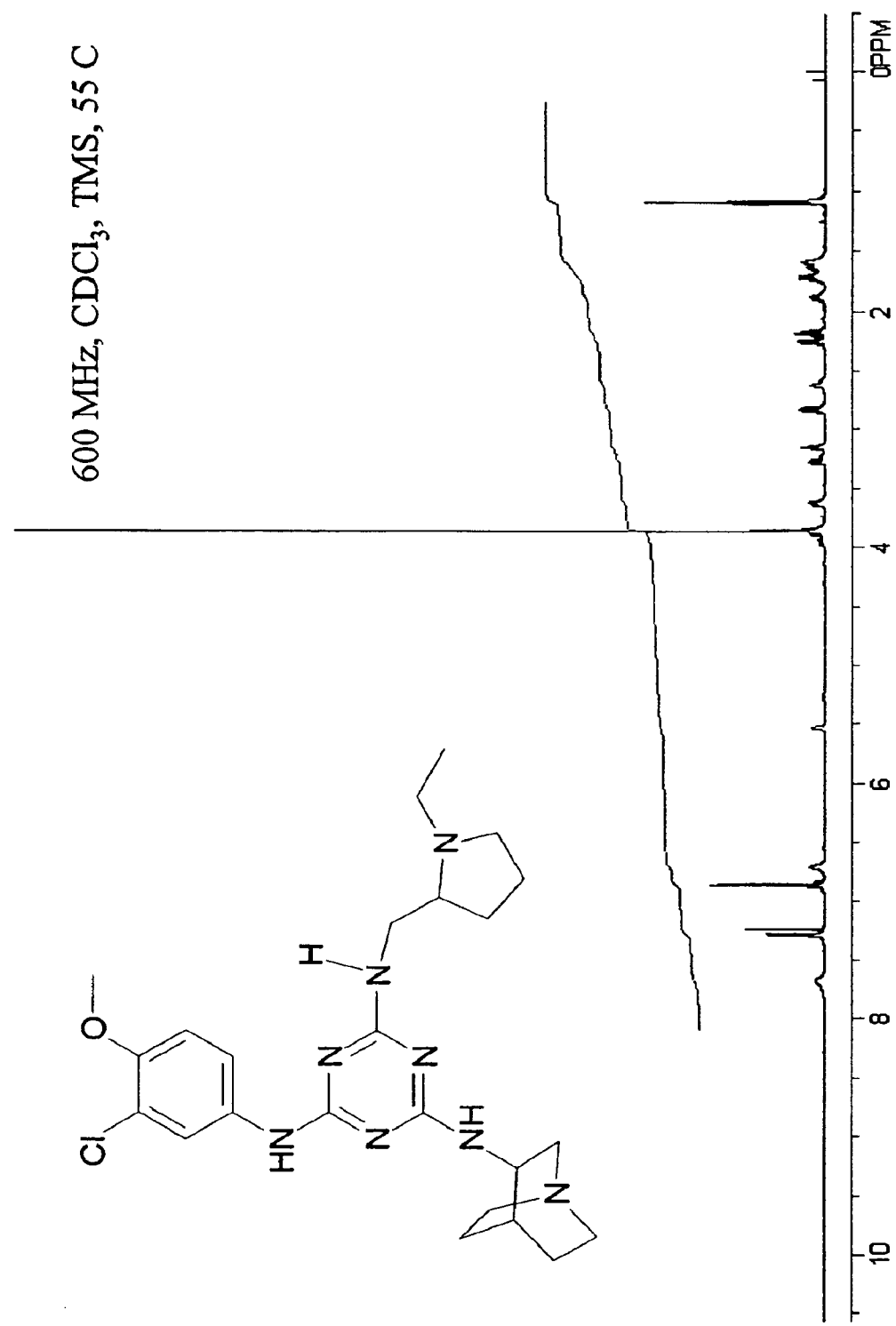
FIG. 4. $^1$H NMR of N-(1-Aza-bicyclo[2.2.2]oct-3-yl)-N'-(3-chloro-4-methoxy-phenyl)-N''-)1-ethyl-pyrrolidin-2-ylmethyl)-[1,3,5]triazine-2,4,6-triamine.
Figure 5:
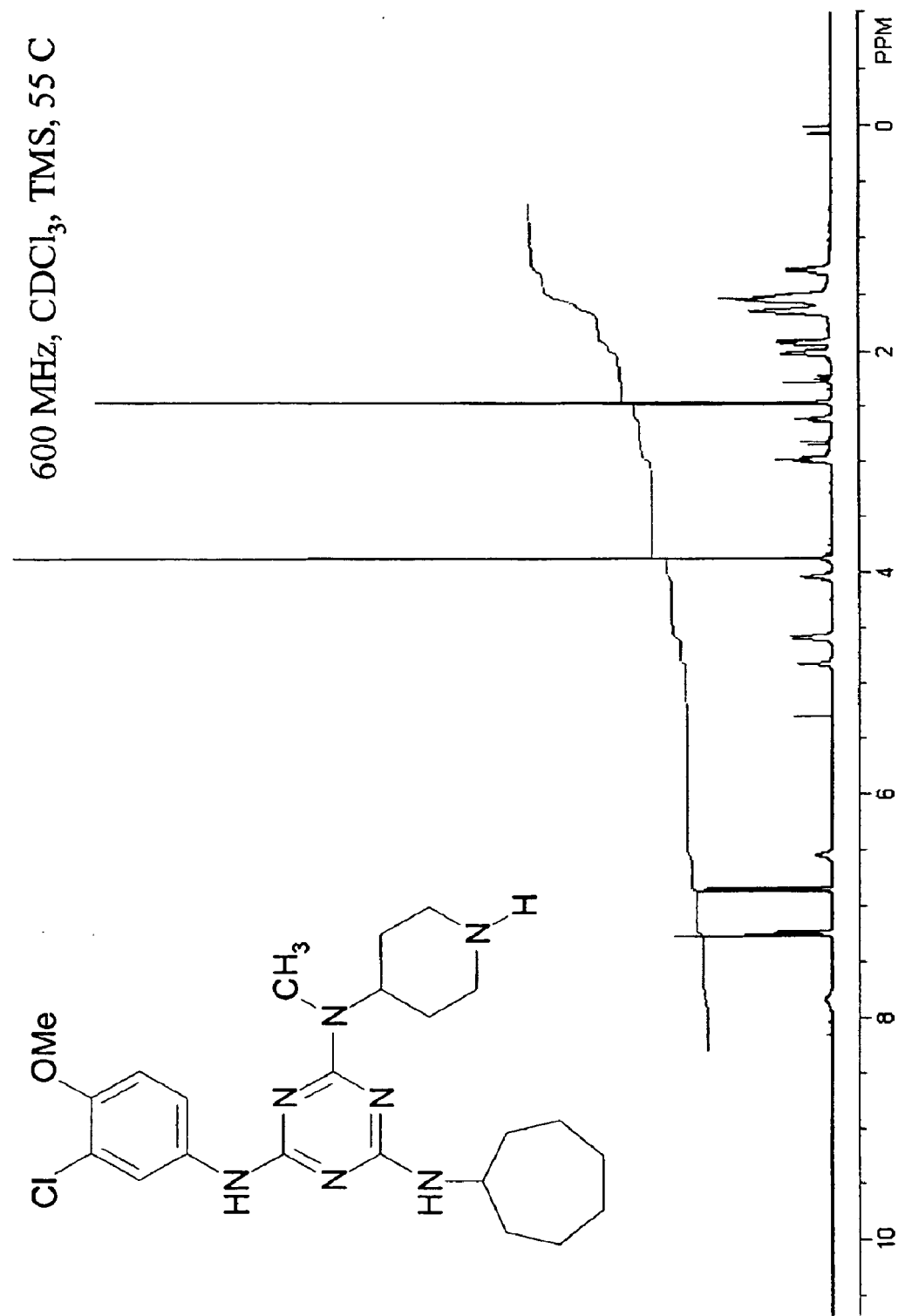
FIG. 5. $^1$H NMR of N2-(3-chloro-4-methoxy-phenyl)-N4-cycloheptyl-N6-methyl-N6-piperidin-4-yl-1,3,5-triazine-2,4,6-triamine.
Figure 6:
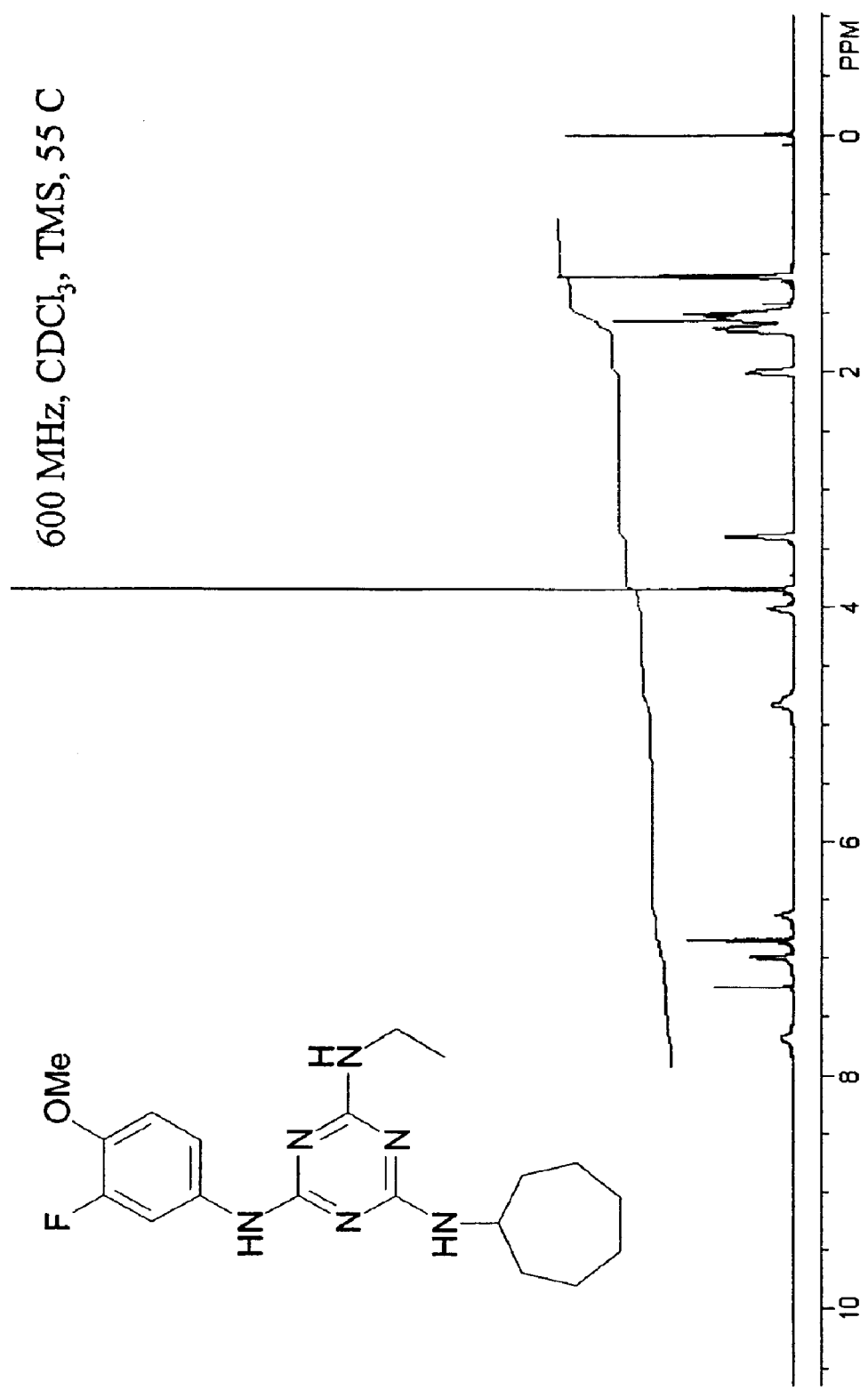
FIG. 6. $^1$H NMR of N-Cycloheptyl-N'-ethyl-N''-(3-fluoro-4-methoxy-phenyl)-[1,3,5]triazine-2,4-diamine.
Figure 7:
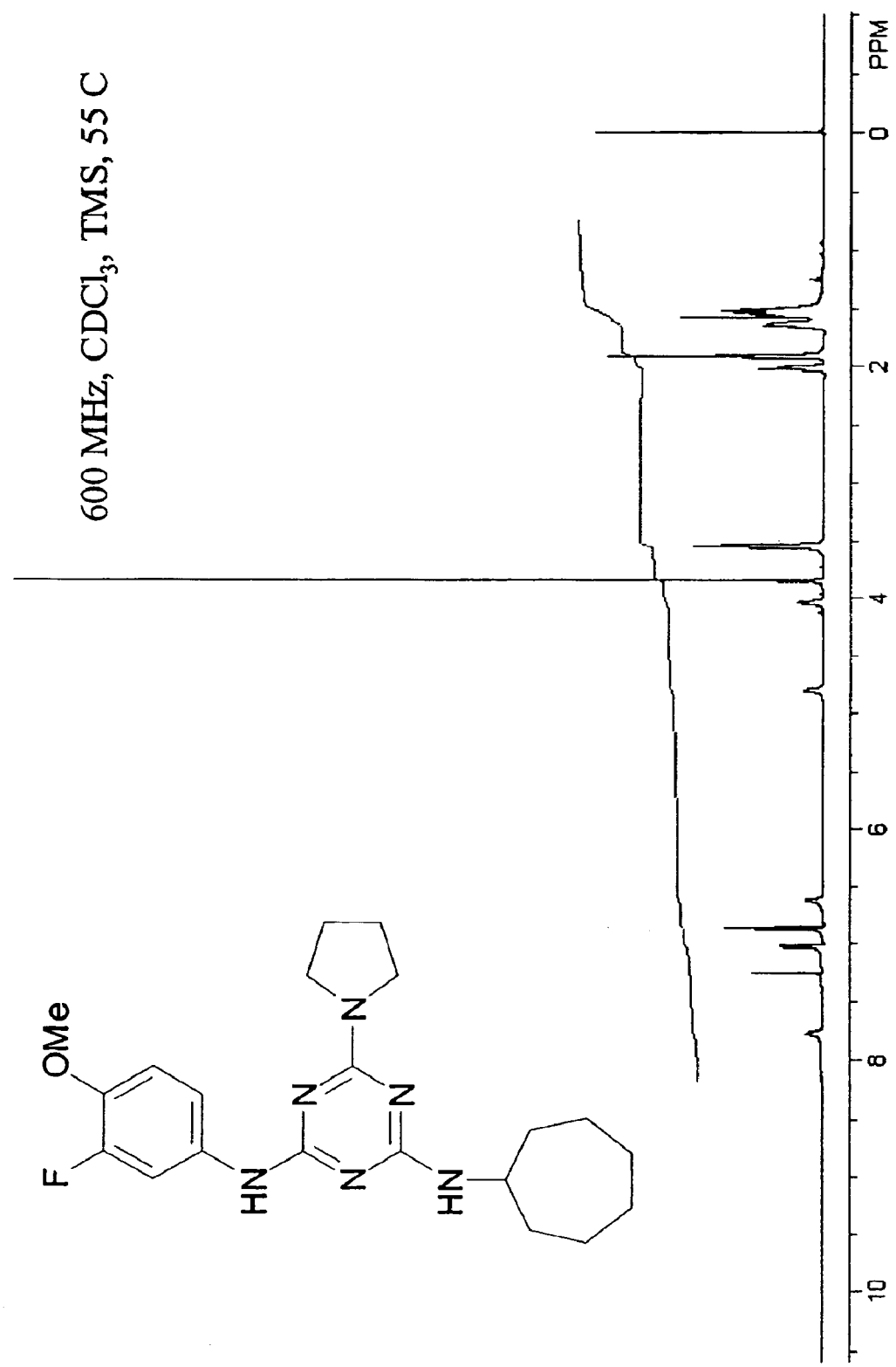
FIG. 7. $^1$H NMR of N-Cycloheptyl-N'-(3-fluoro-4-methoxy-phenyl)-6-pyrrolidin-1-yl-[1,3,5]triazine-2,4-diamine.
Figure 8:
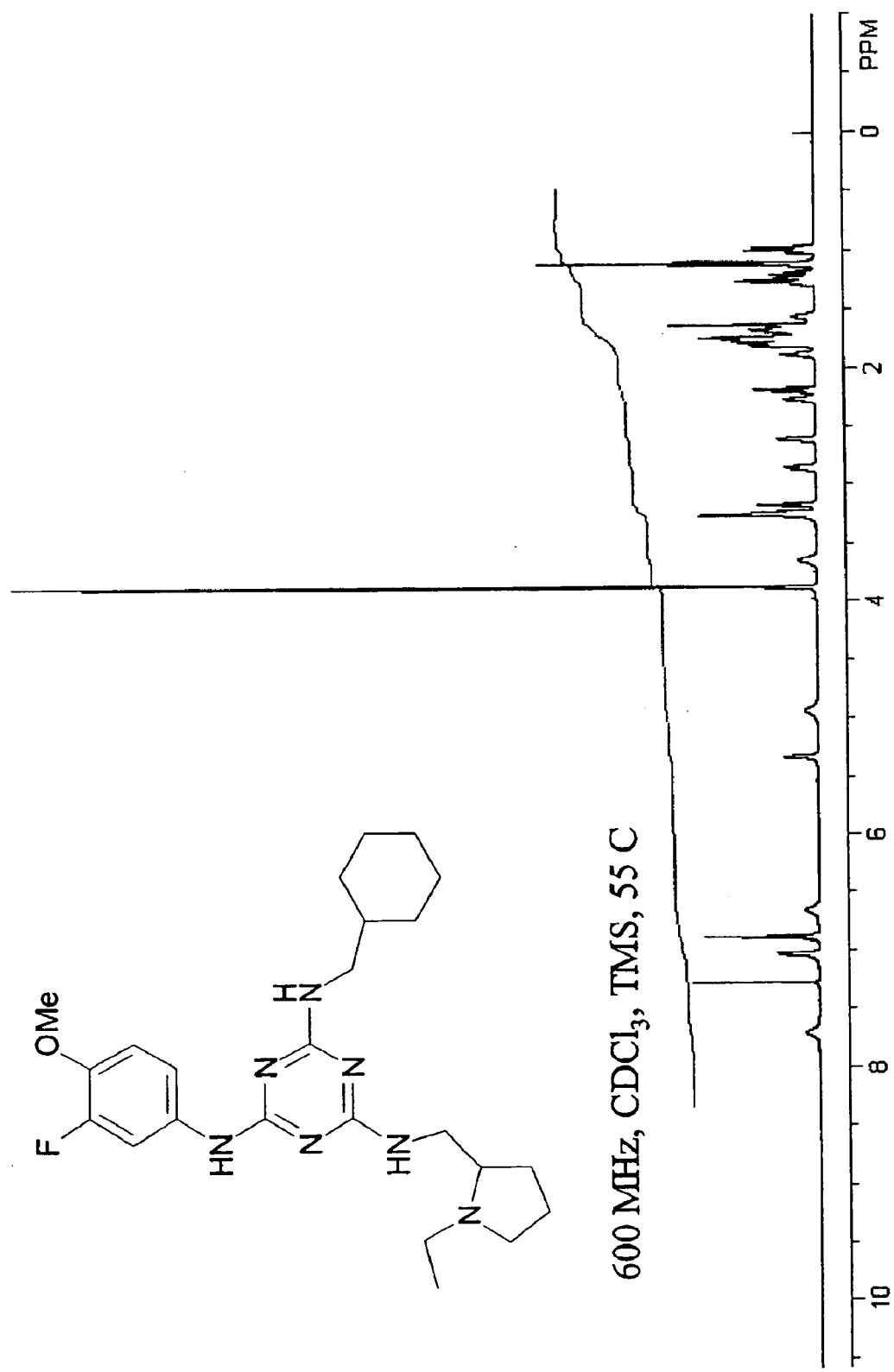
FIG. 8. $^1$H NMR of N-Cyclohexylmethyl-N'-(1-ethyl-pyrrolidin-2-ylmethyl)-N''-(3-fluoro-4-methoxy-phenyl)-[1,3,5]triazine-2,4,6-triamine.
Figure 9:
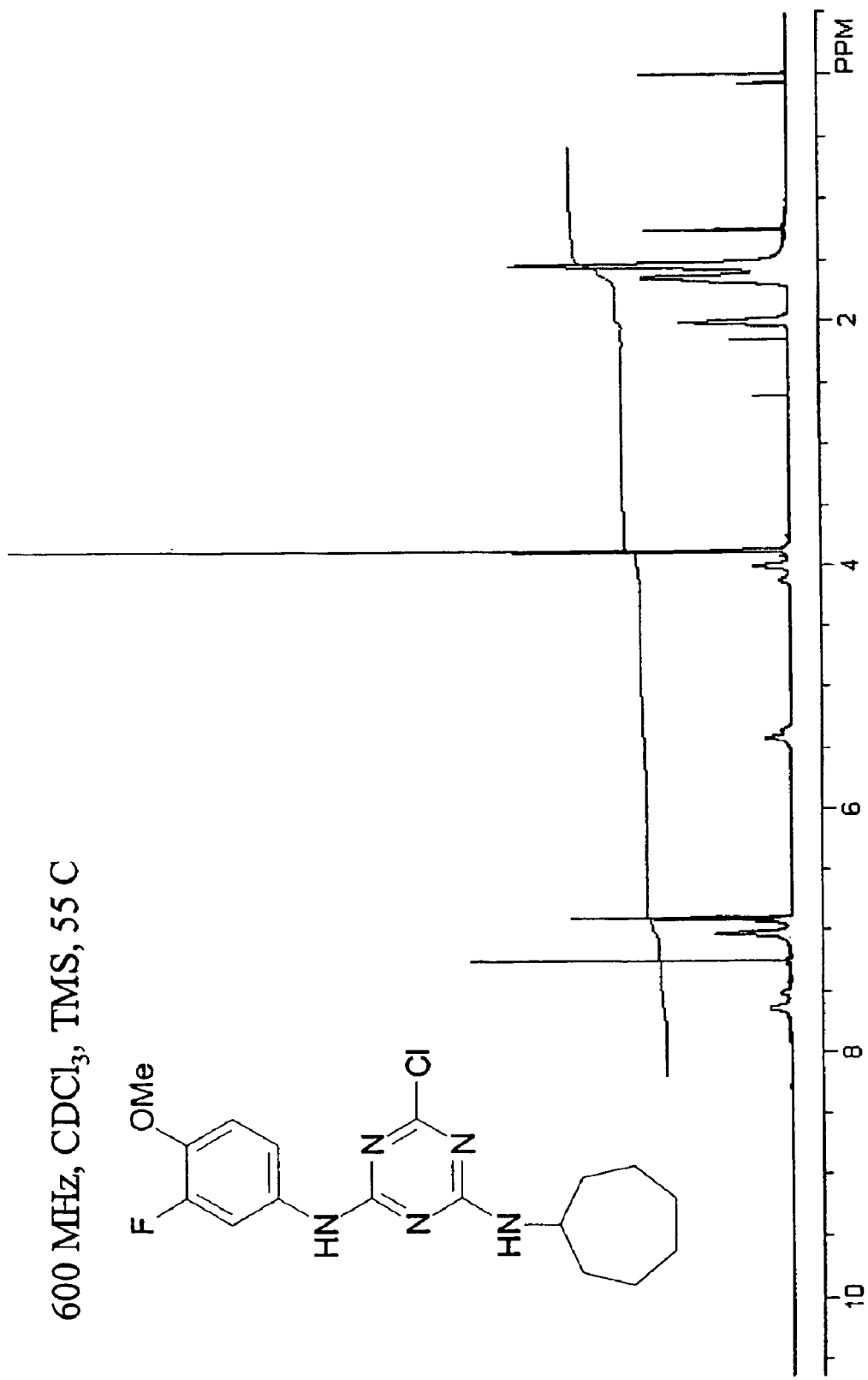
FIG. 9. $^1$H NMR of 6-Chloro-N-cycloheheptyl-N'-(3-fluoro-4-methoxy-phenyl)-[1,3,5]triazine-2,4-diamine.
Figure 10:
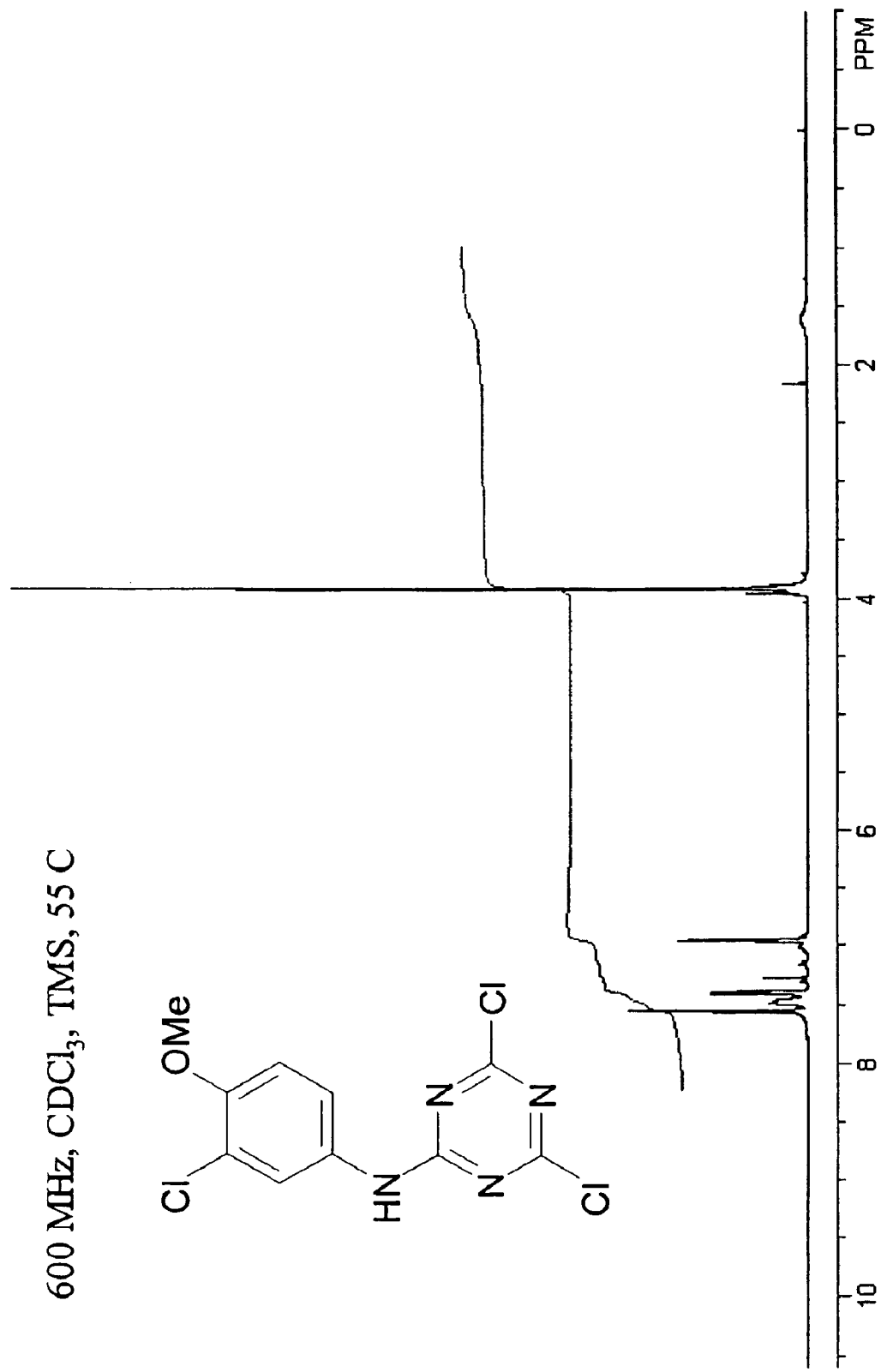
FIG. 10. $^1$H NMR of (3-Chloro-4-methoxy-phenyl)-(4,6-dichloro-[1,3,5]triazin-2-yl)-amine.
Figure 11:
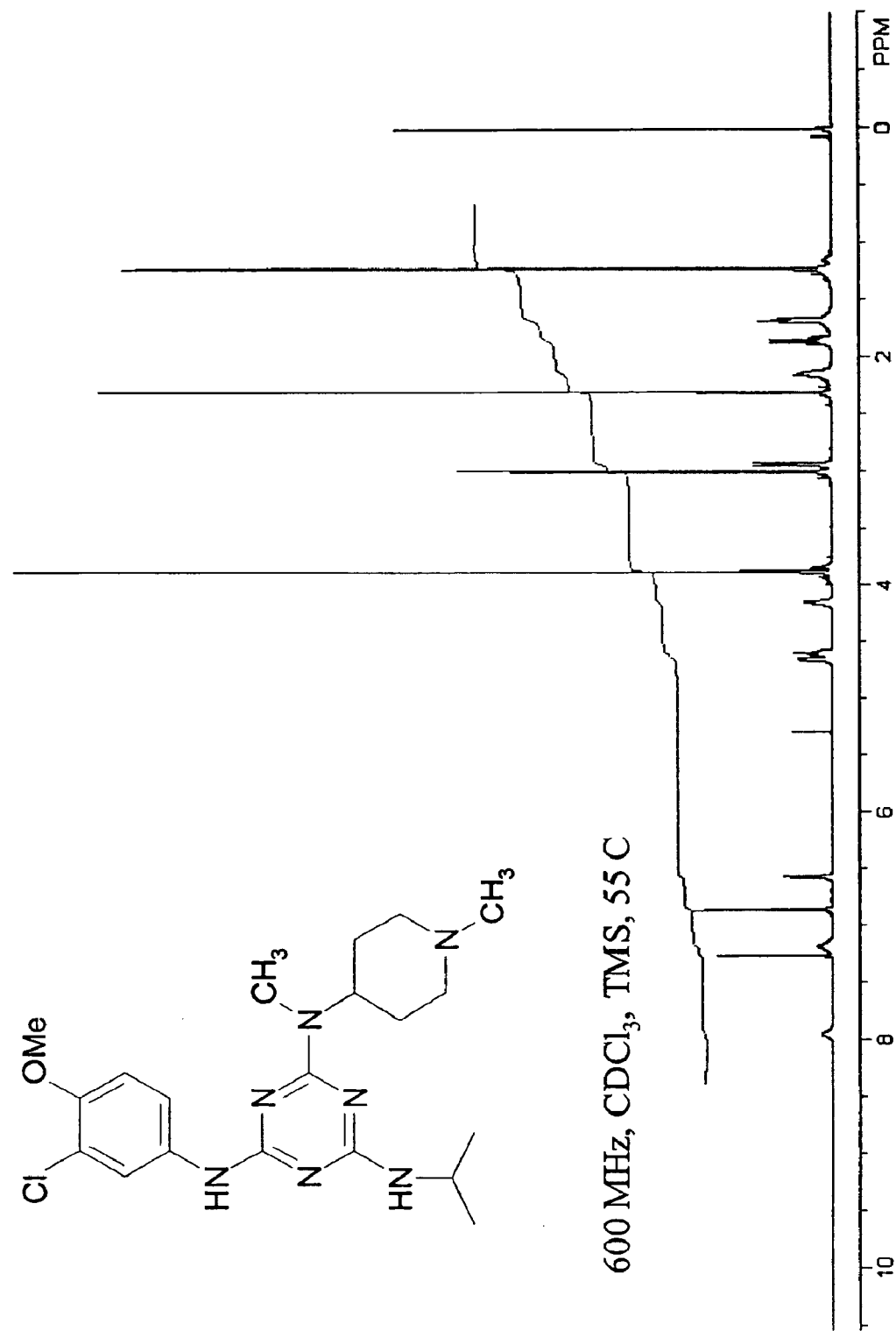
FIG. 11. $^1$H NMR of N-(3-Chloro-4-methoxy-phenyl)-N'-isopropyl-N'''-methyl-N''-(1-methyl-piperidin-4-yl)-[1,3,5]triazine-2,4,6-triamine.
Figure 12:
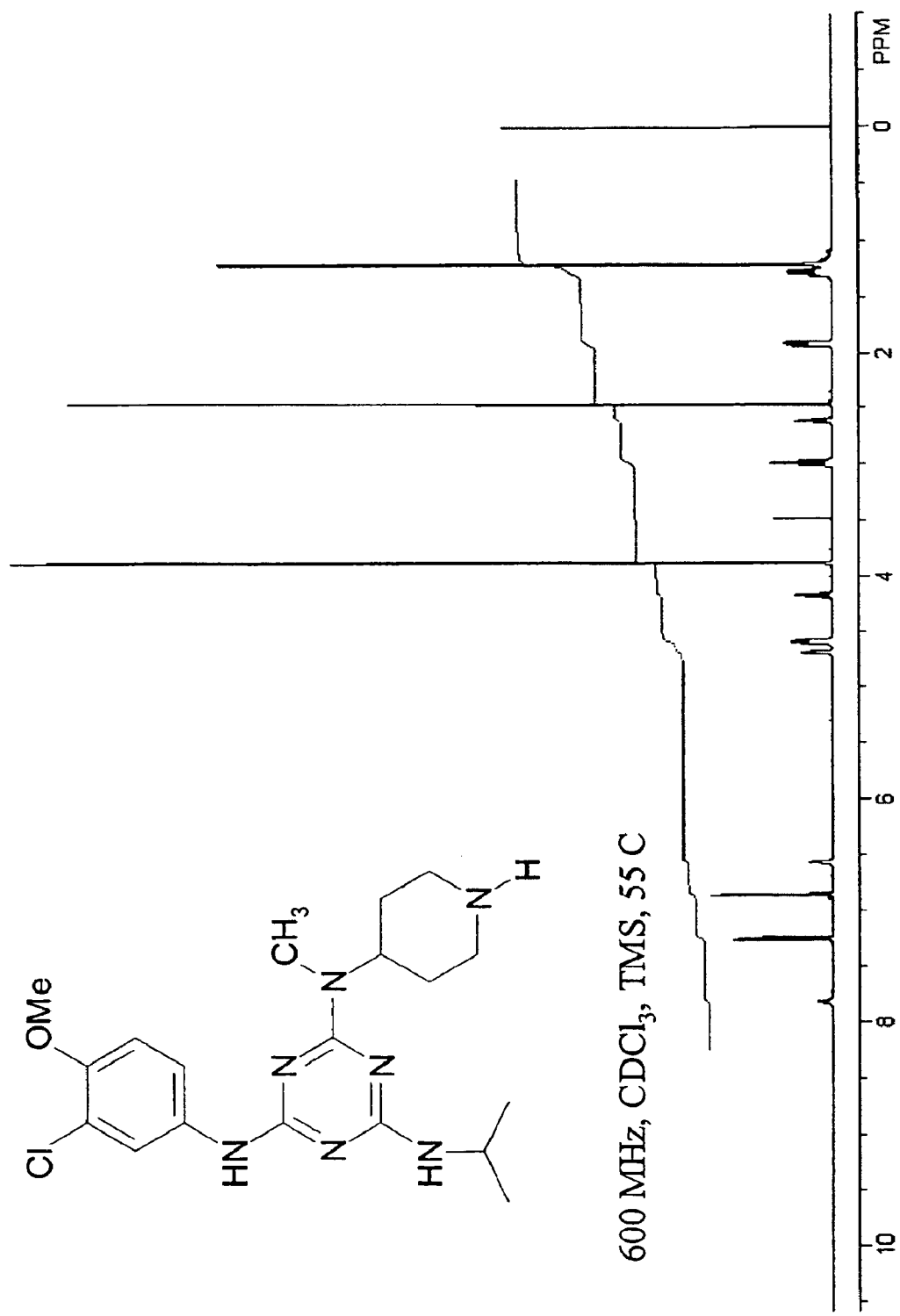
FIG. 12. $^1$H NMR of N2-(3-chloro-4-methoxy-phenyl)-N4-isopropyl-N6-methyl-N6-piperidin-4-yl-1,3,5-triazine-2,4,6-triamine.
Figure 13:
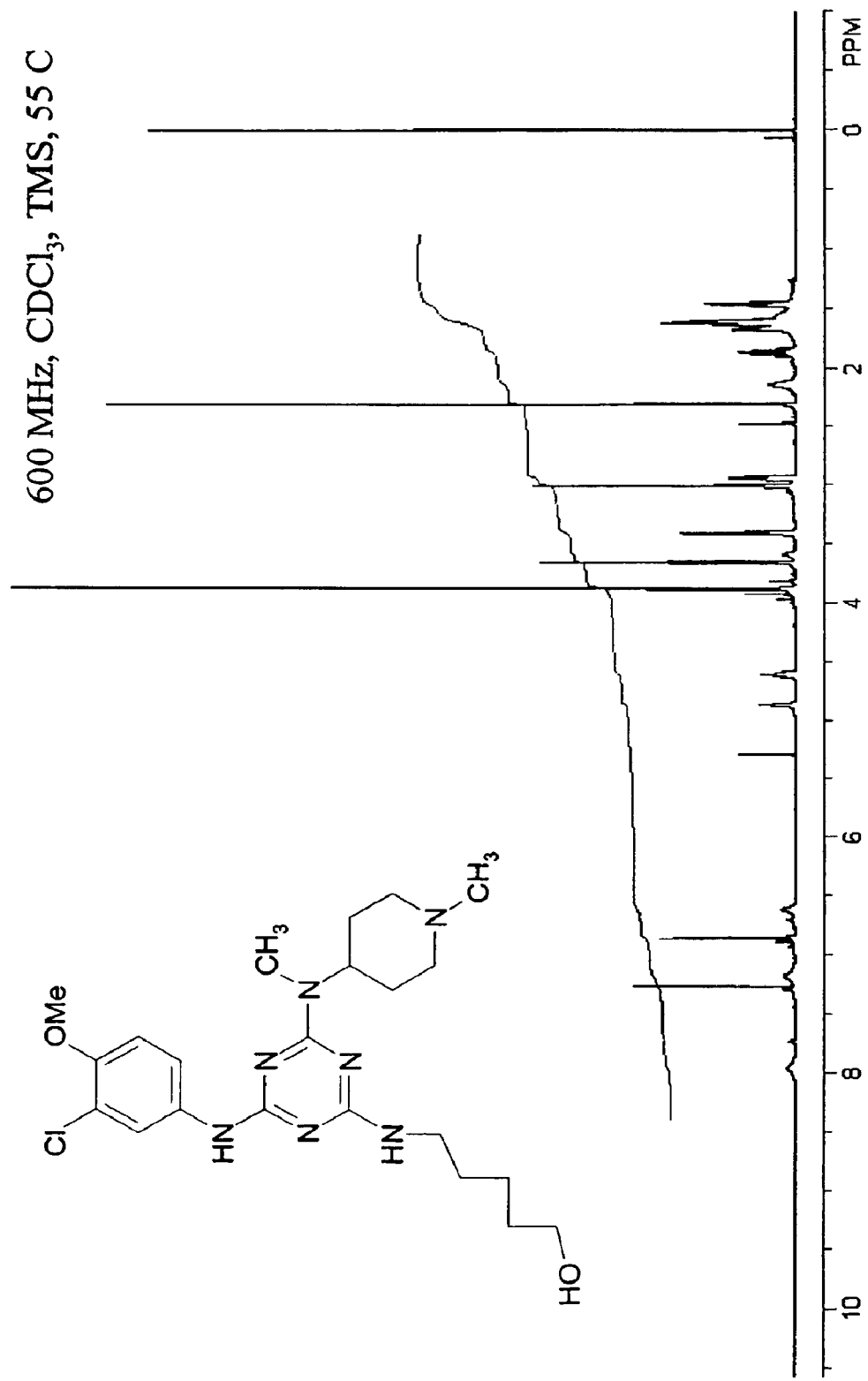
FIG. 13. $^1$H NMR of 5-{4-(3-Chloro-4-methoxy-phenylamino)-6-[methyl-(1-methyl-piperidin-4-yl)-amino]-[1,3,5]triazin-2-ylamino}-pentan-1-ol.
Figure 14:
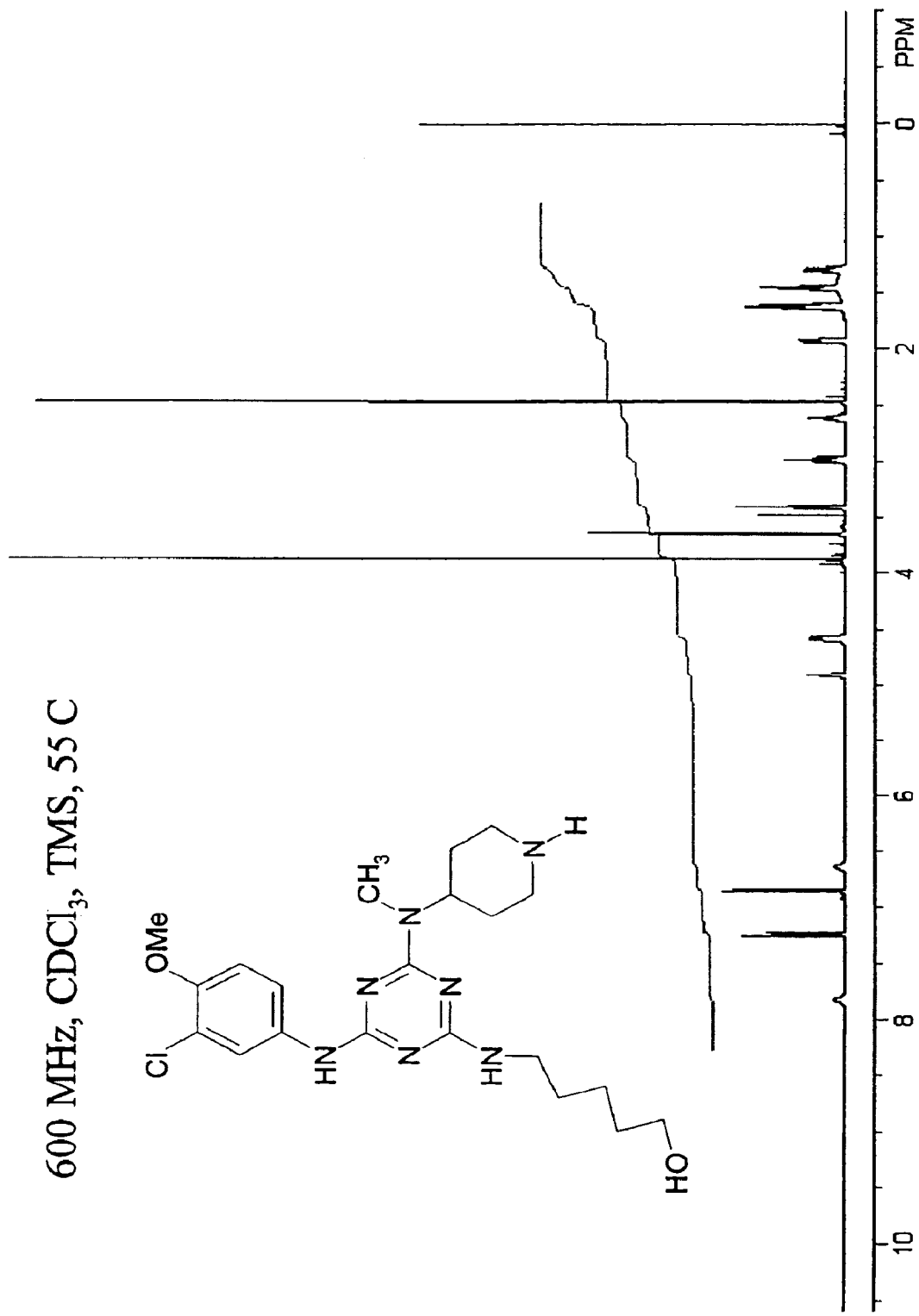
FIG. 14. $^1$H NMR of 5-[4-(3-chloro-4-methoxy-phenylamino)-6-(methyl-piperidin-4-yl-amino)-1,3,5-triazin-2-ylamino]-pentan-1-ol.
Figure 15:
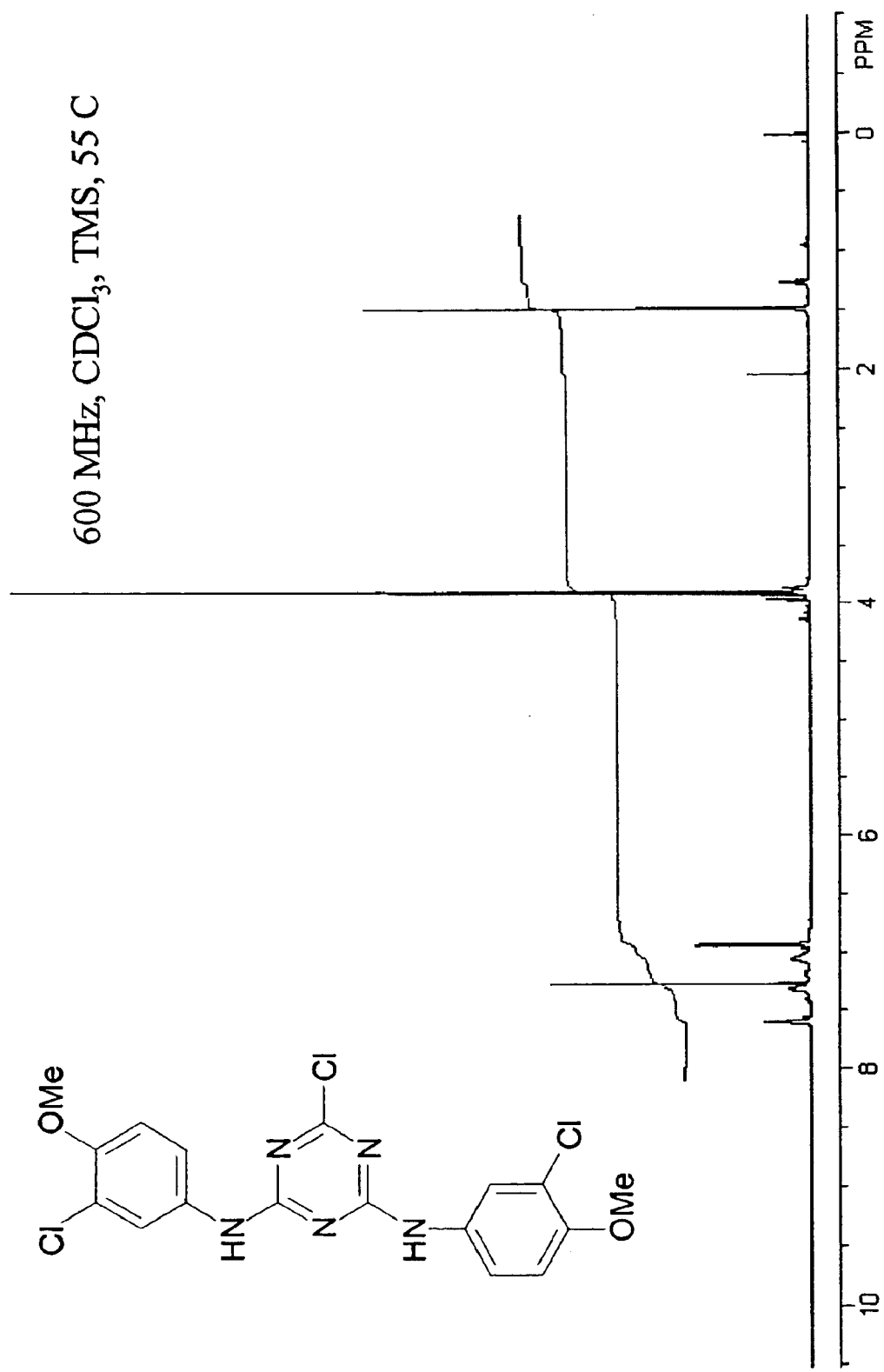
FIG. 15. $^1$H NMR of 6-Chloro-N,N''-bis-(3-chloro-4-methoxy-phenyl)-[1,3,5]triazine-2,4-diamine.
Figure 16:
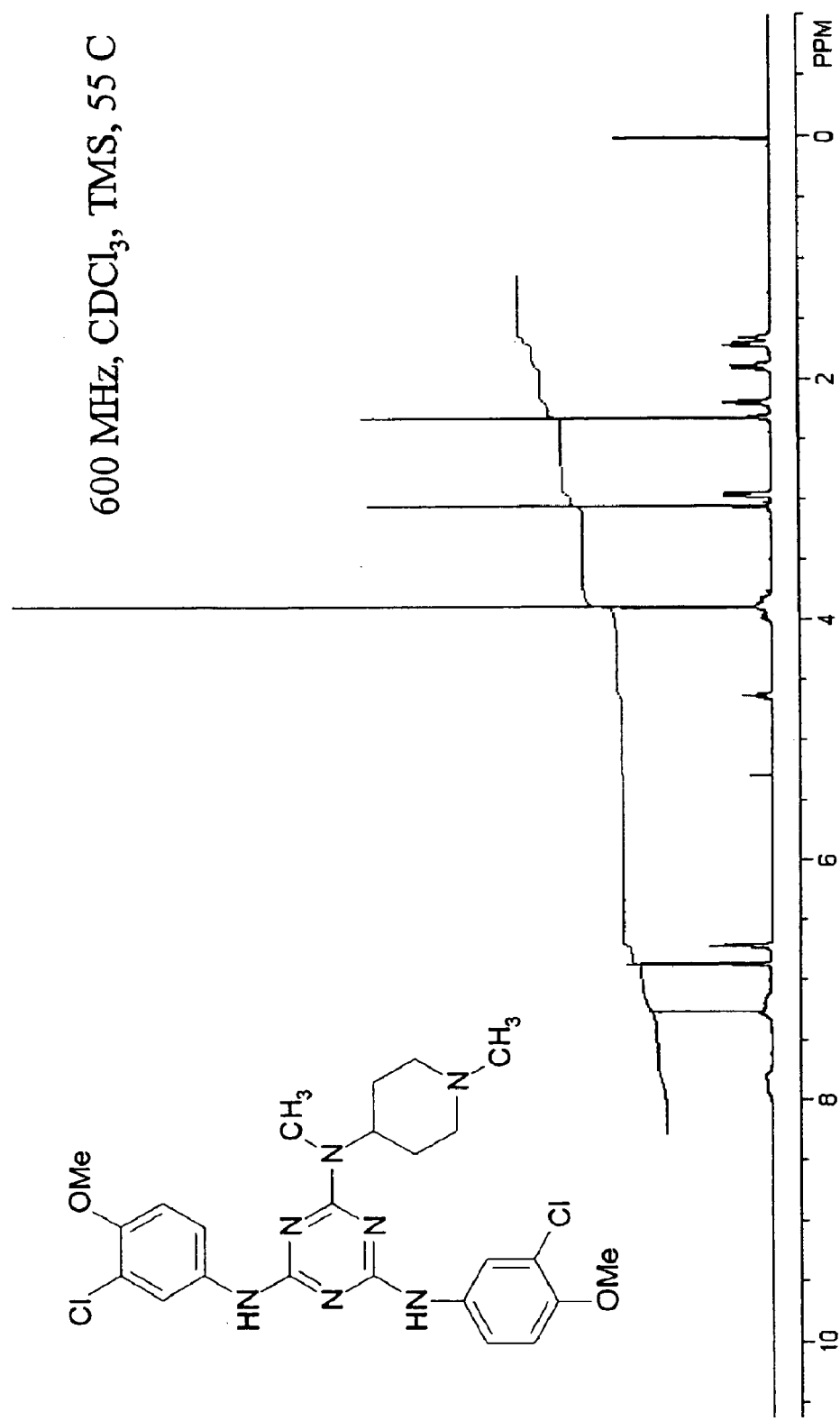
FIG. 16. $^1$H NMR of N,N'-Bis-(3-chloro-4-methoxy-phenyl)-N'''-methyl-N''-(4-methyl-cyclohexyl)-[1,3,5]triazine-2,4,6-triamine.
Figure 17:
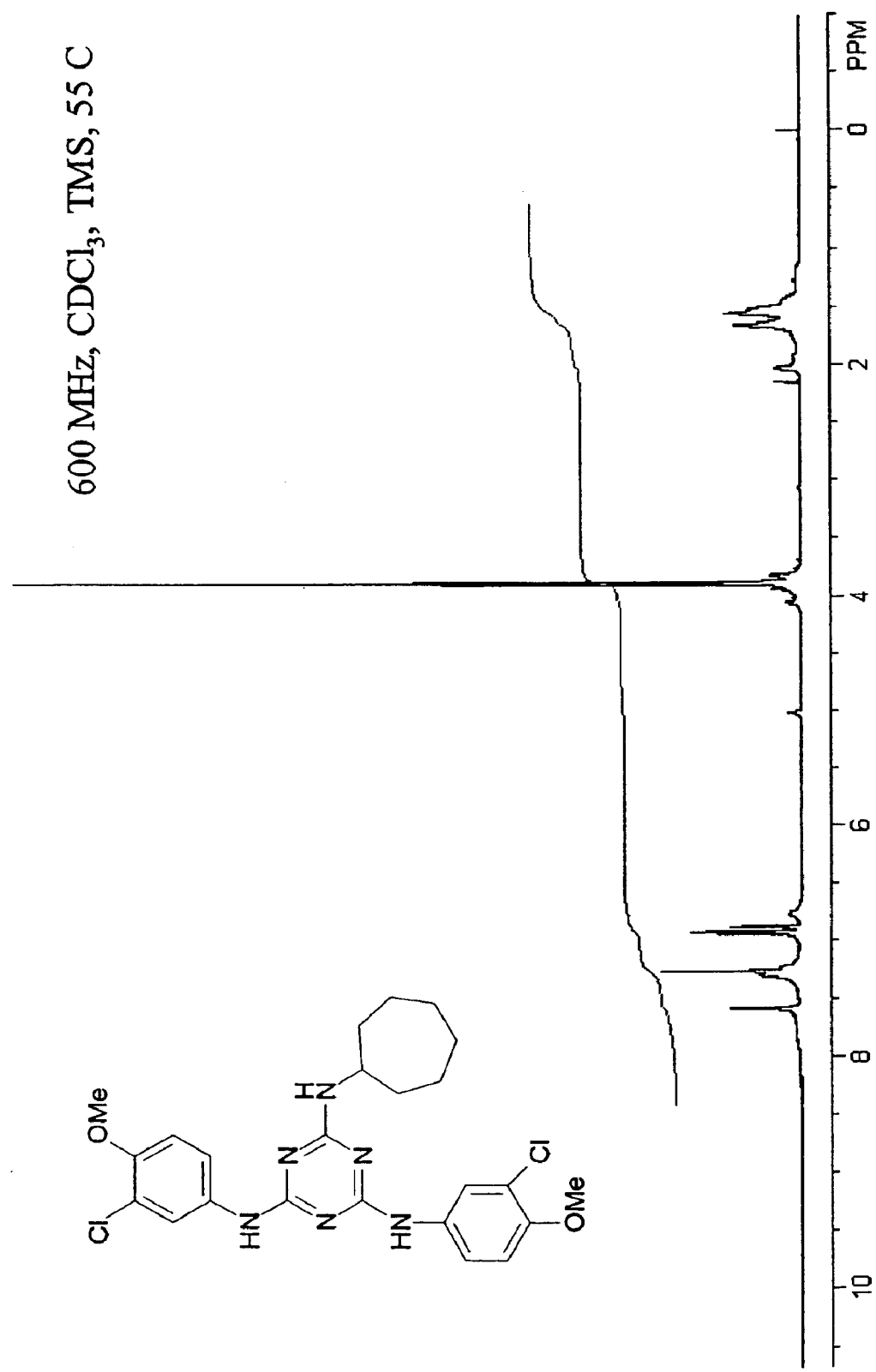
FIG. 17. $^1$H NMR of N,N'-Bis-(3-chloro-4-methoxy-phenyl)-N''-cycloheptyl-[1,3,5]triazine-2,4,6-triamine.
Figure 18:
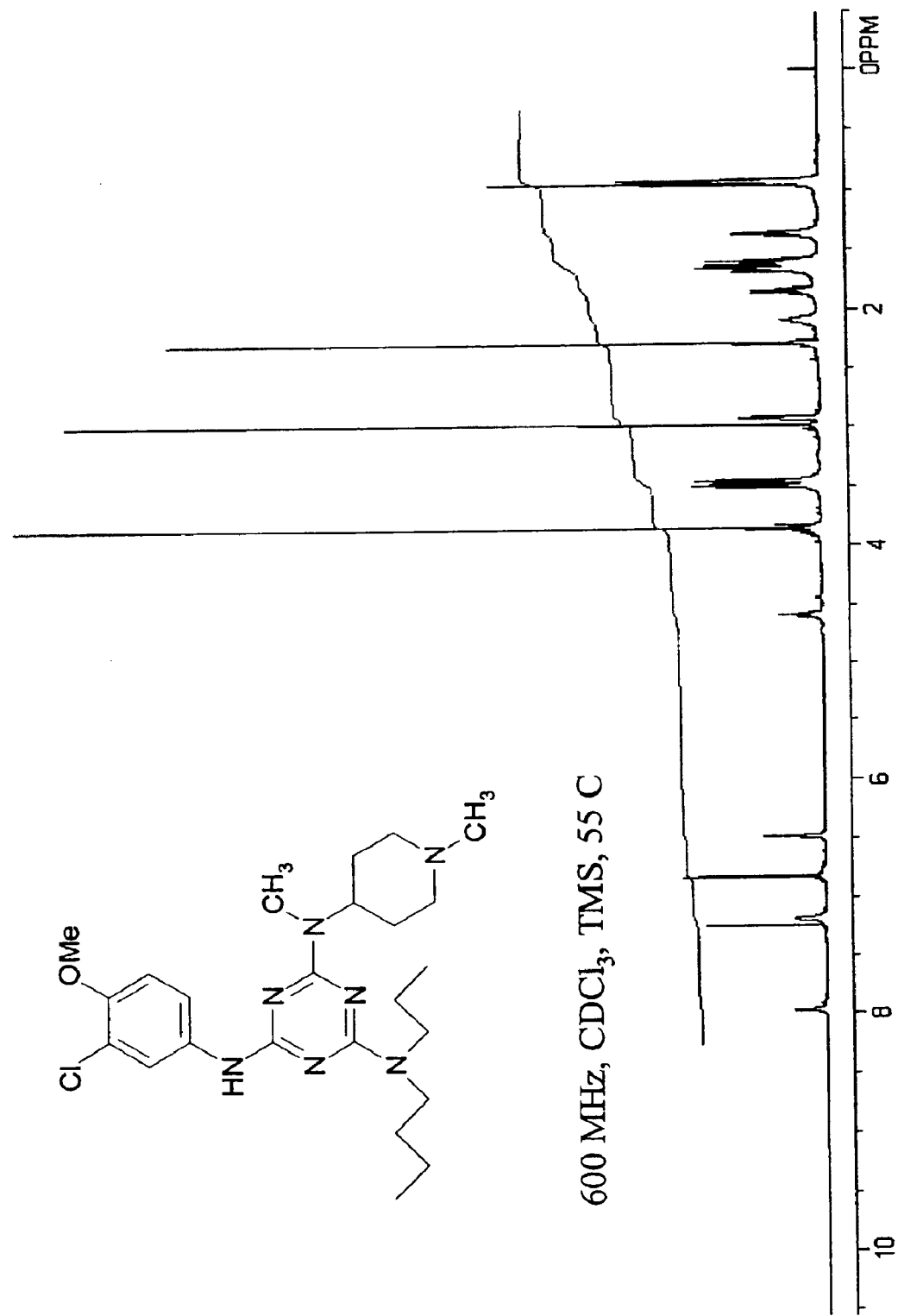
FIG. 18. $^1$H NMR of N-Butyl-N'-(3-chloro-4-methoxy-phenyl)-N'''-(1-methyl-piperidin-4-yl)-N-propyl-[1,3,5]triazine-2,4,6-triamine.
Figure 19:
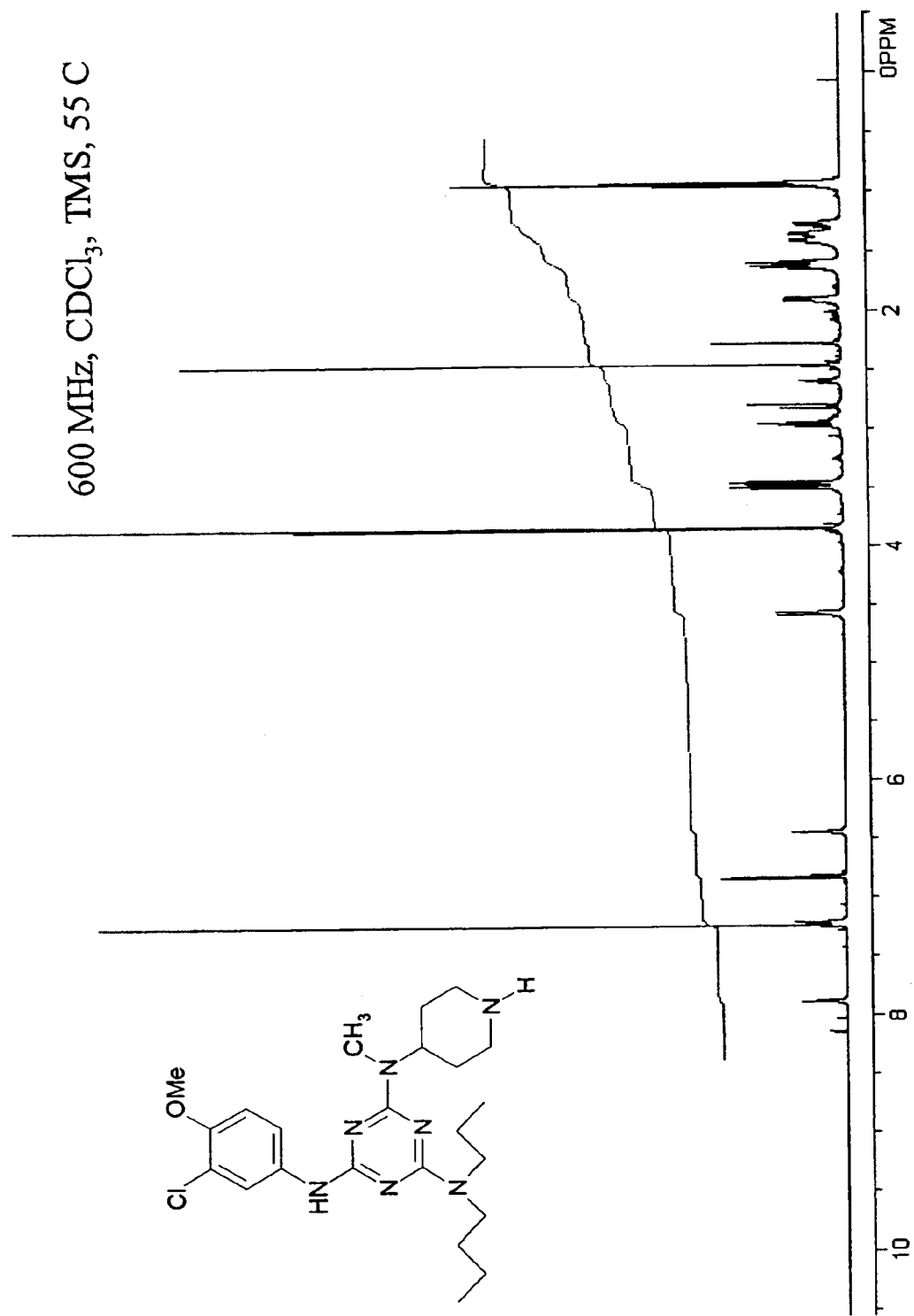
FIG. 19. $^1$H NMR of N2-Butyl-N4-(3-chloro-4-methoxy-phenyl)-N6-methyl-N6-piperidin-4-yl-N2-propyl-1,3,5-triazine-2,4,6-triamine.
Figure 20:
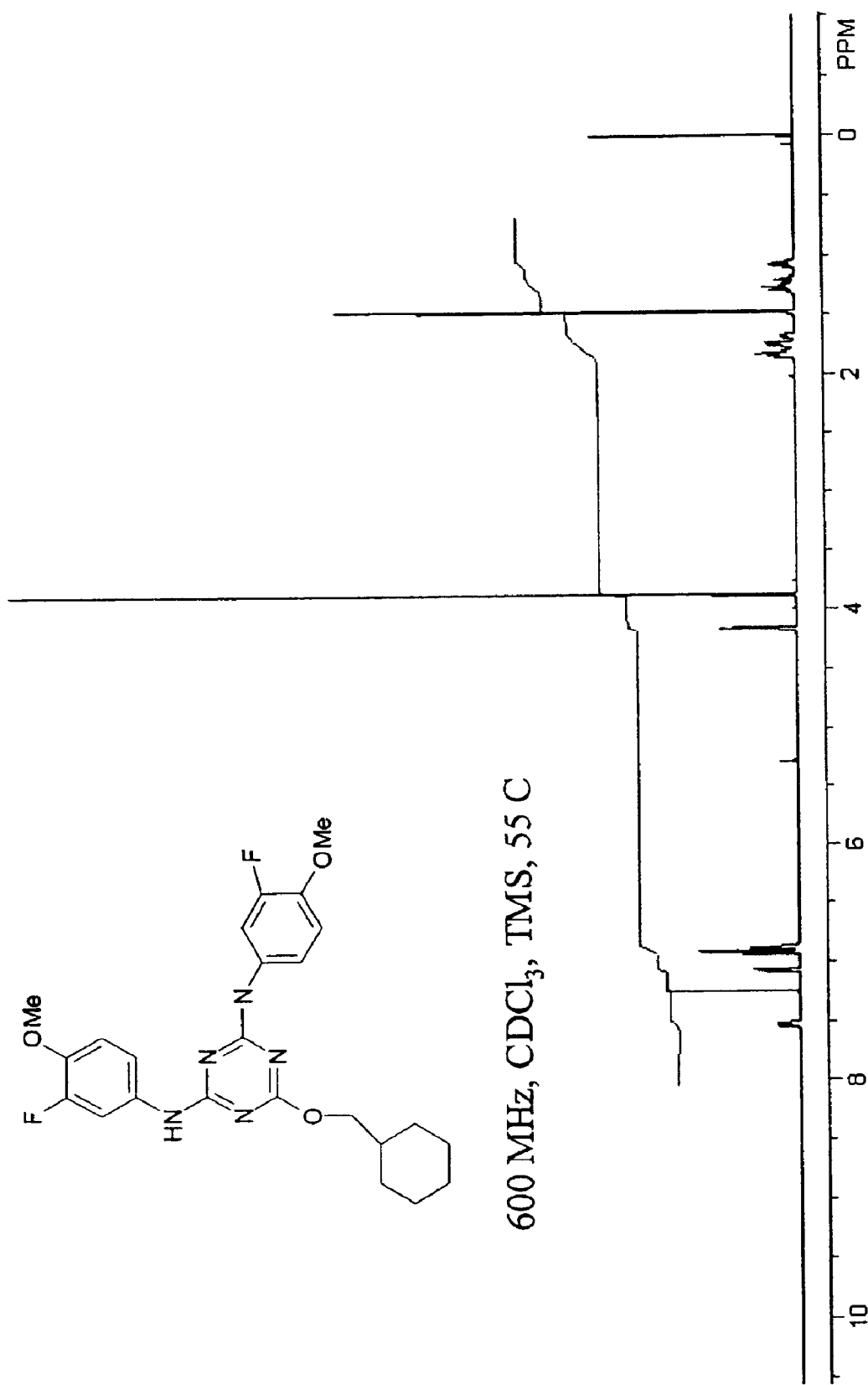
FIG. 20. $^1$H NMR of 6-Cyclohexylmethoxy-N,N'-bis-(3-fluoro-4-methoxy-phenyl)-1,3,5-triazine-2,4-diamine.
Figure 21:
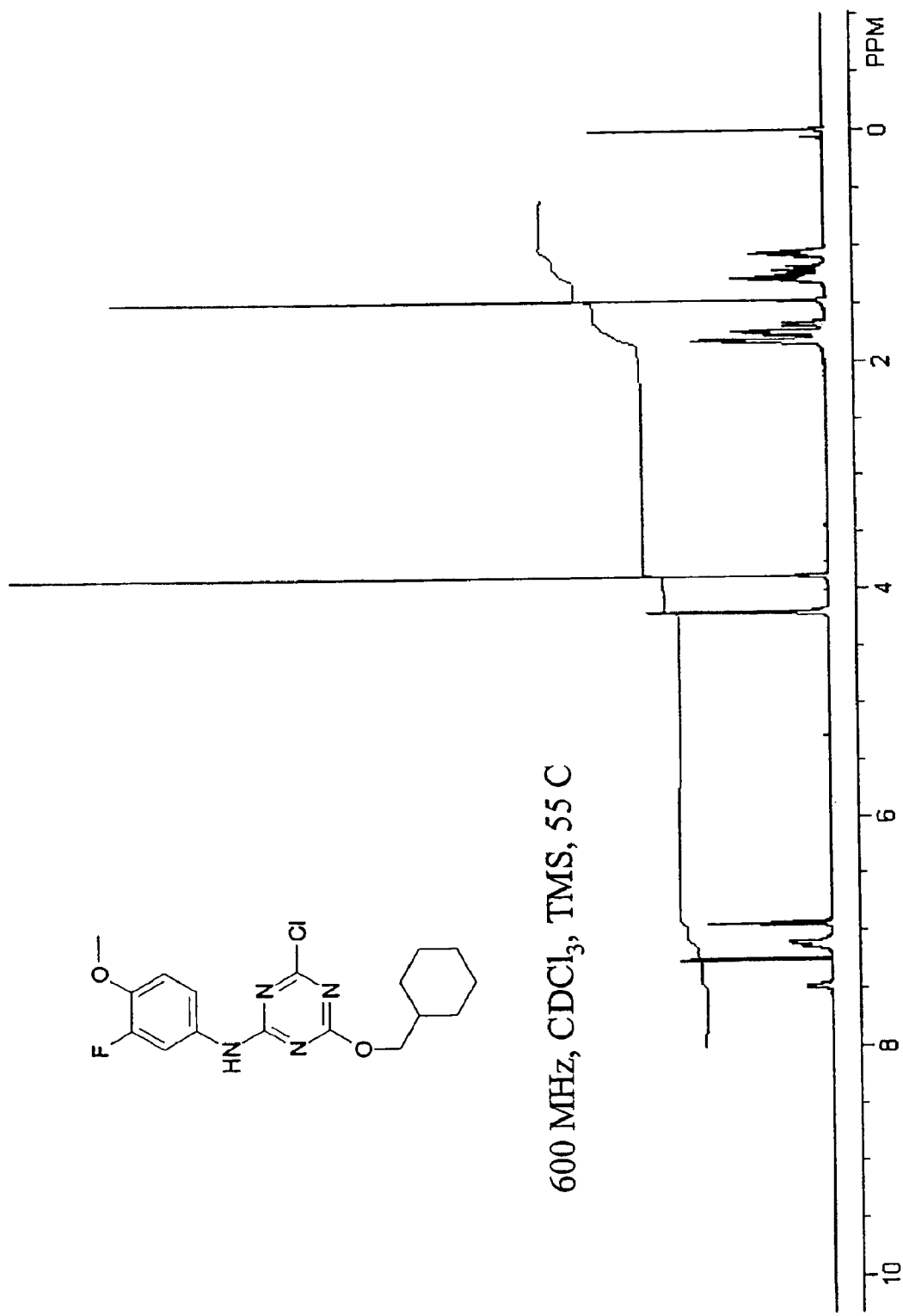
FIG. 21. $^1$H NMR of (4-Chloro-6-cyclohexylmethoxy-[1,3,5]triazin-2-yl)-(3-fluoro-4-methoxy-phenyl)-amine.
Figure 22:
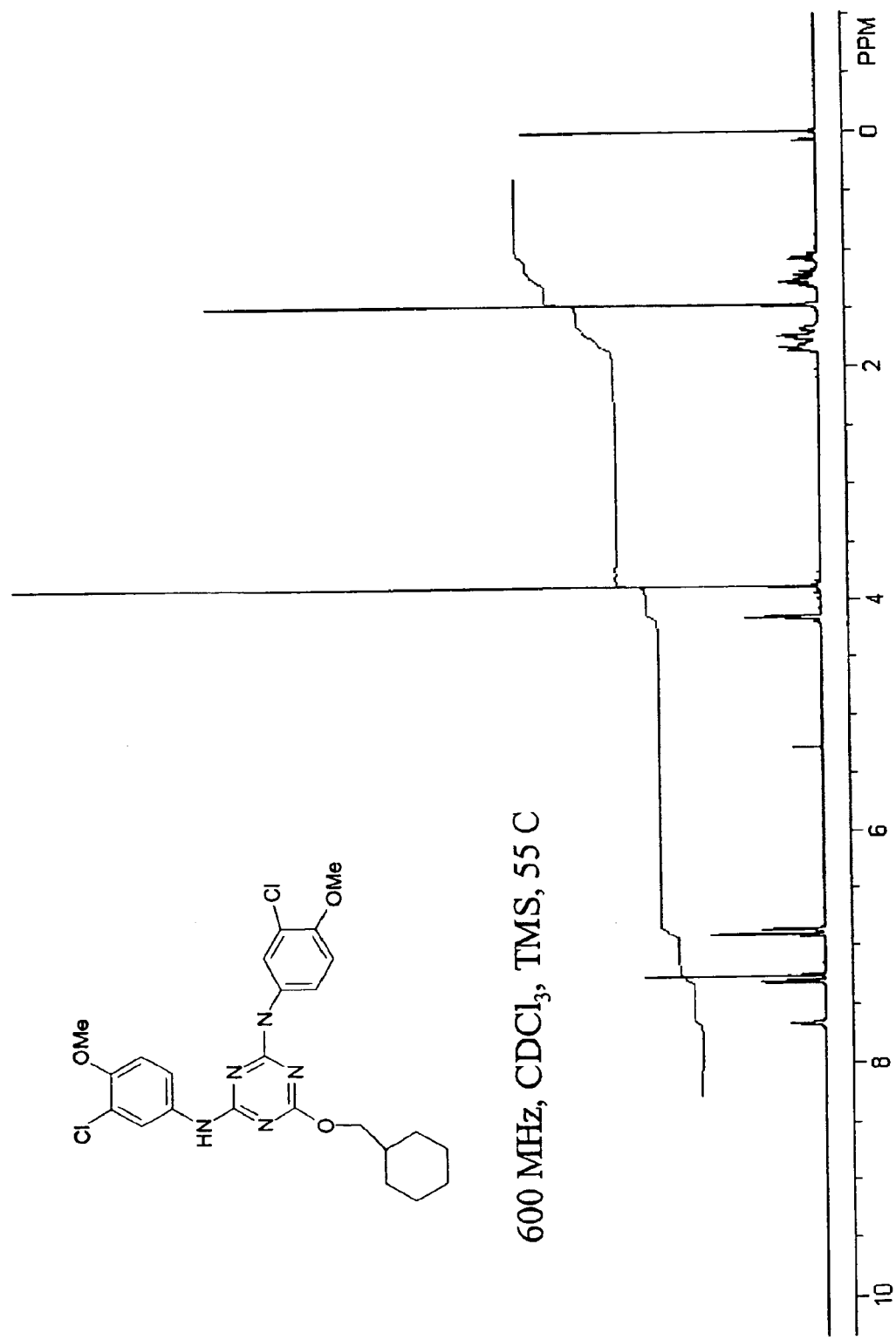
FIG. 22. $^1$H NMR of N,N'-Bis-(3-chloro-4-methoxy-phenyl)-6-cyclohexylmethoxy-1,3,5-triazine-2,4-diamine.
Figure 23:
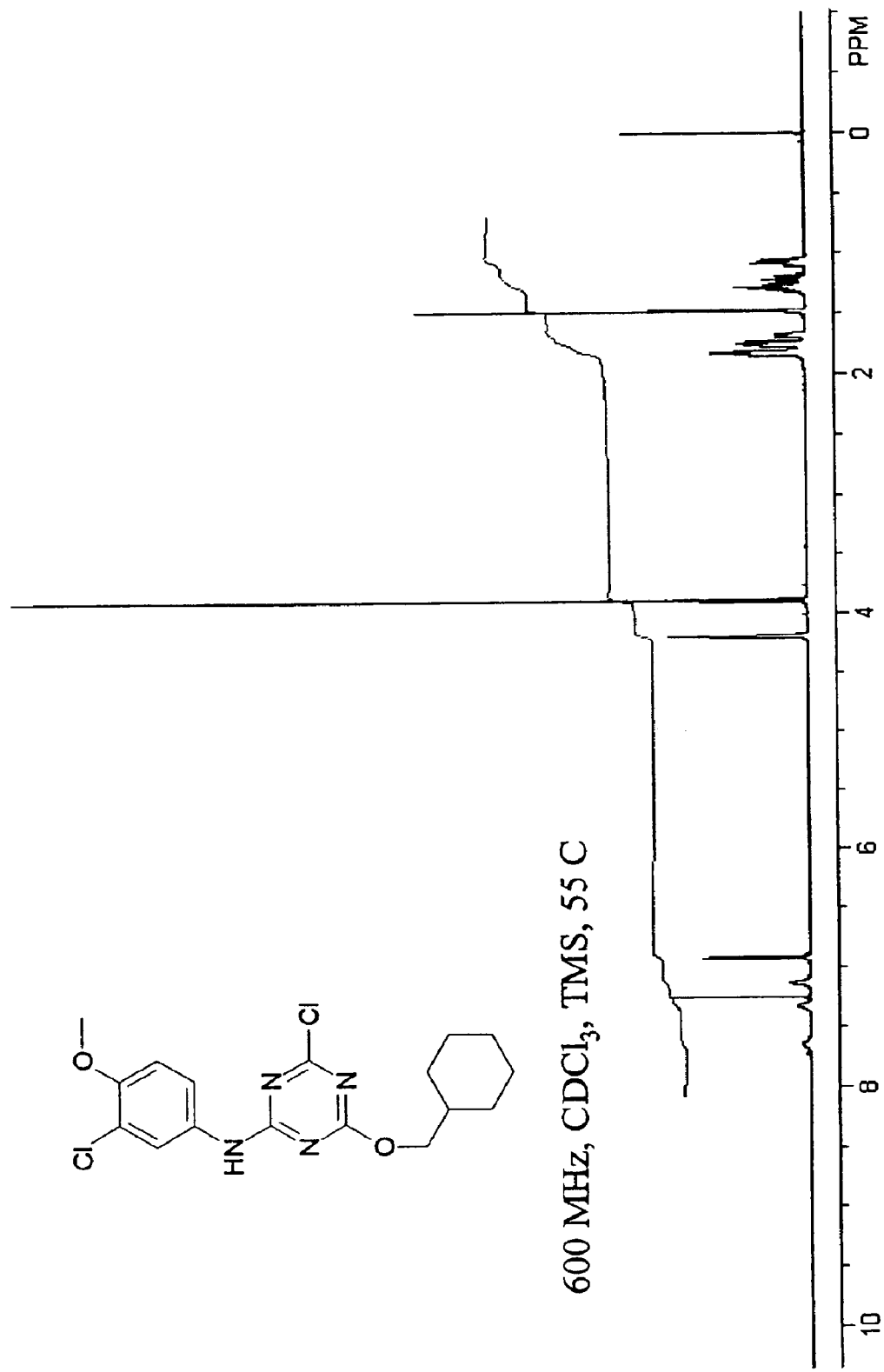
FIG. 23. $^1$H NMR of (4-Chloro-6-cyclohexylmethoxy-[1,3,5]triazin-2-yl)-(3-chloro-4-methoxy-phenyl)-amine.
Figure 24:
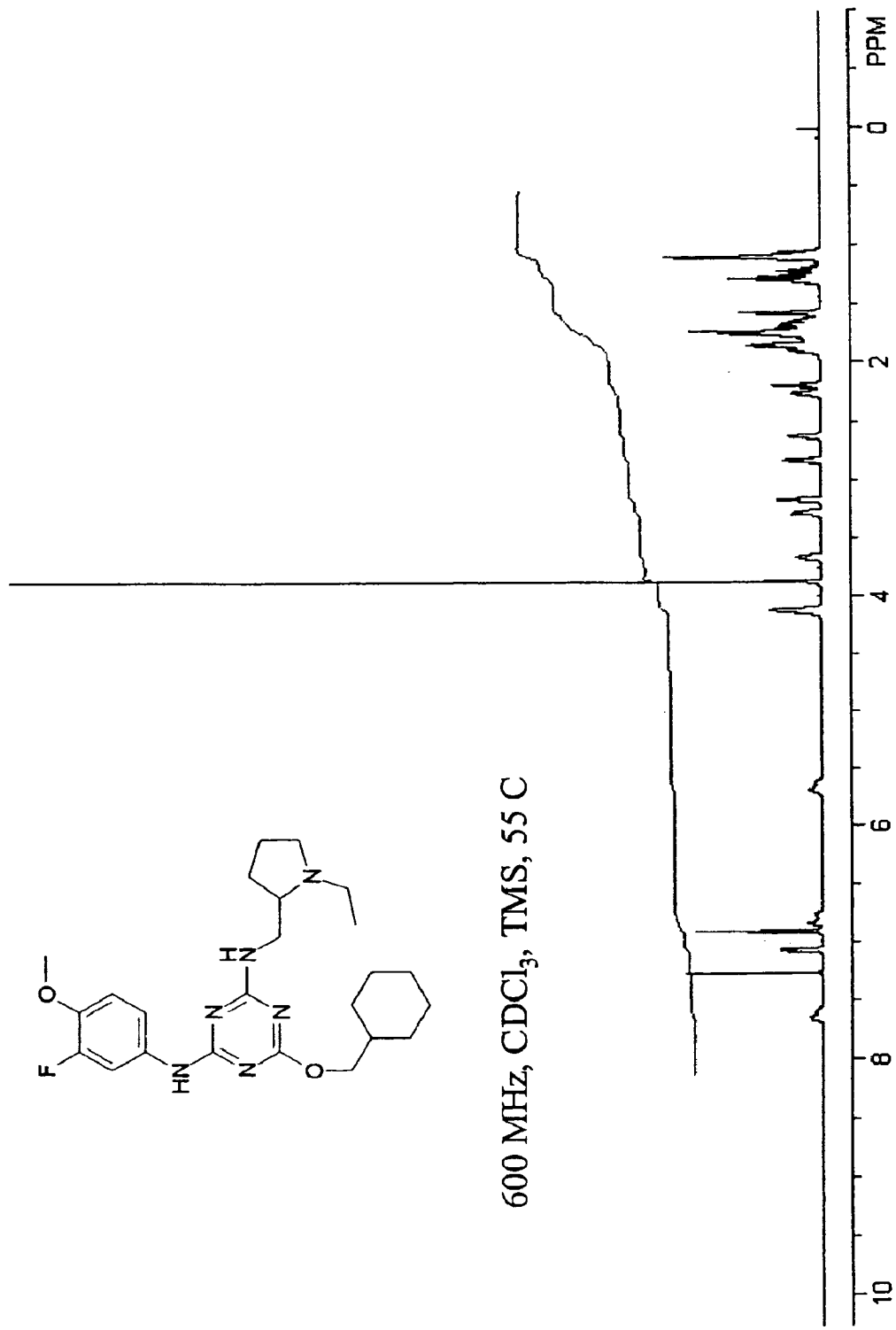
FIG. 24. $^1$H NMR of 6-Cyclohexylmethoxy-N-(1-ethyl-pyrrolidin-2-ylmethyl)-N'-(3-fluoro-4-methoxy-phenyl)-[1,3,5]triazine-2,4-diamine.
Figure 25:
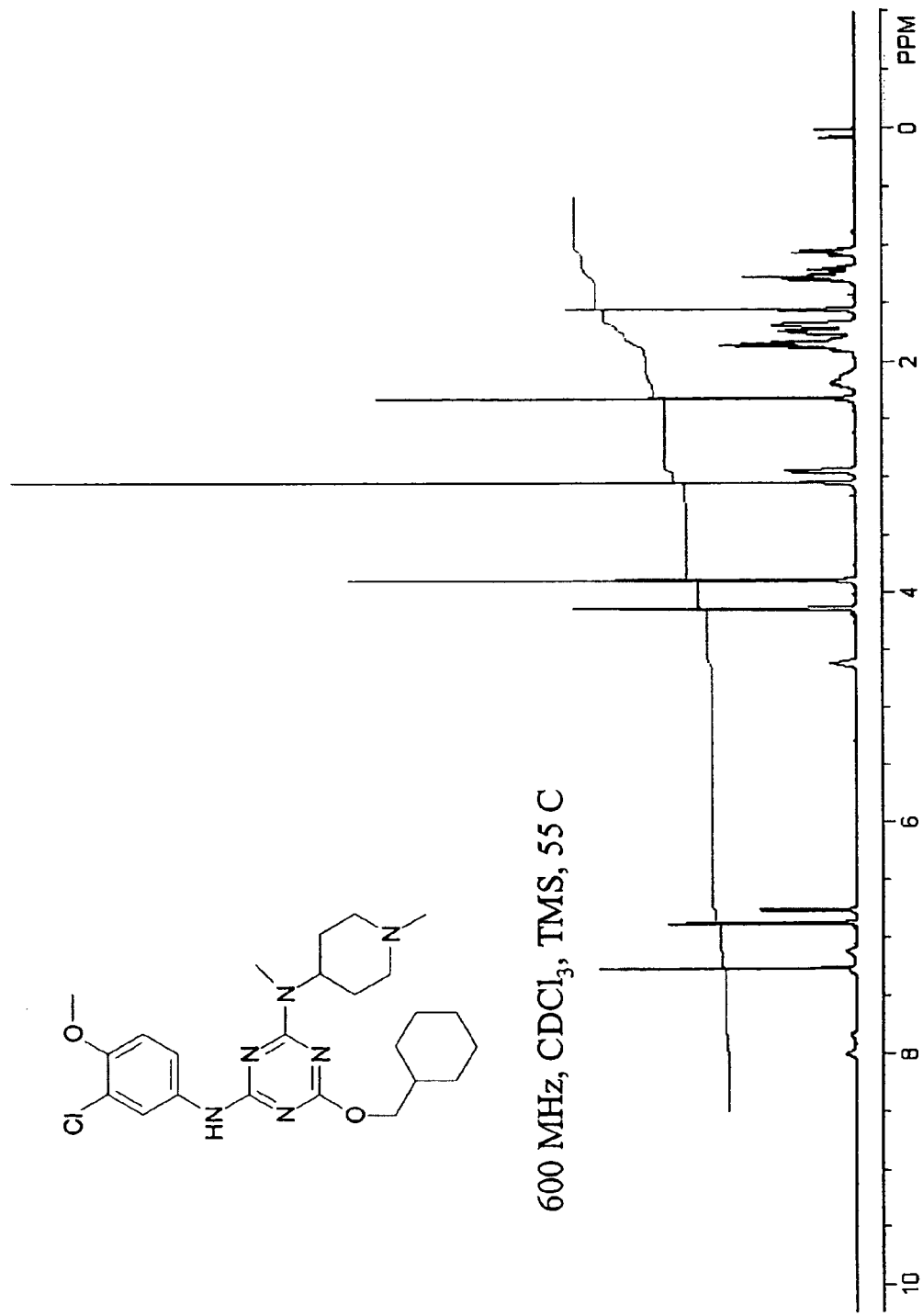
FIG. 25. $^1$H NMR of N-(3-Chloro-4-methoxy-phenyl)-6-cyclohexylmethoxy-N'-methyl-N'-(1-methyl-piperidin-4-yl)-[1,3,5]triazine-2,4-diamine.
Figure 26:
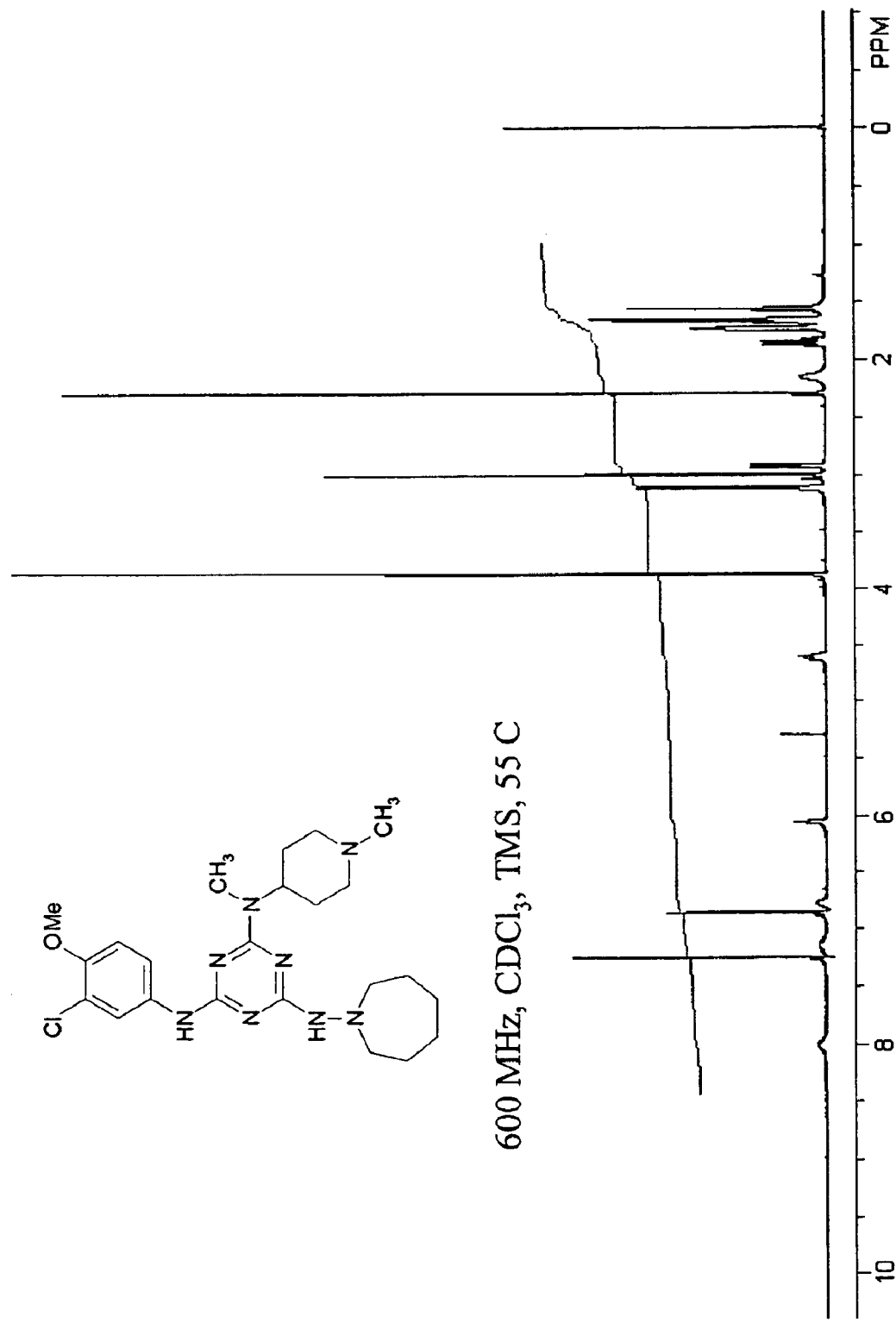
FIG. 26. ¹H NMR of N-Azepan-1-yl-N'-(3-chloro-4-methoxy-phenyl)-N"-(1-methyl-piperidin-4-yl)-[1,3,5]triazine-2,4,6-triamine.
Figure 27:
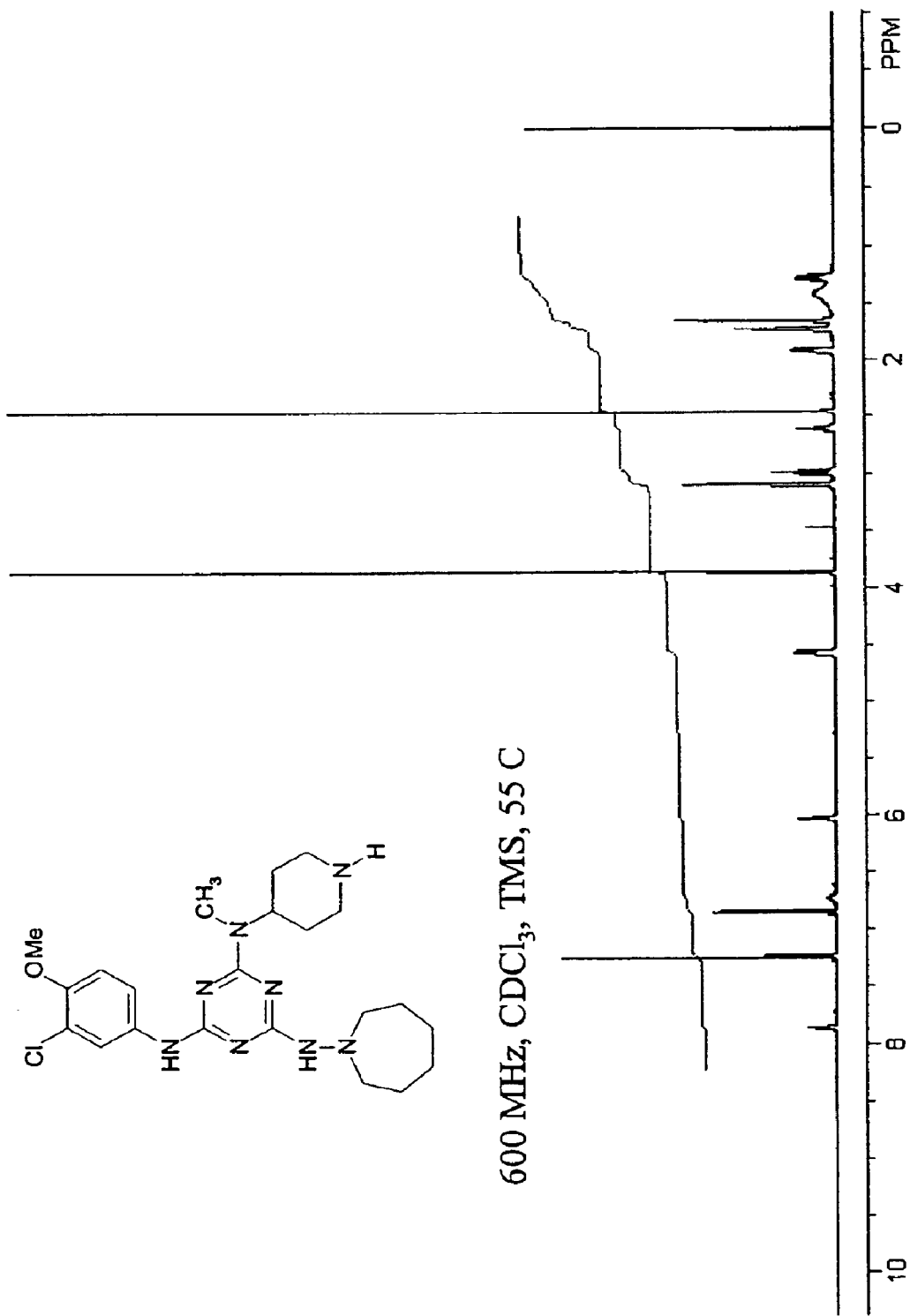
FIG. 27. ¹H NMR of N4-(3-chloro-4-methoxy-phenyl)-N6-methyl-N2-perhydro-azepin-1-yl-N6-piperidin-4-yl-1,3,5-triazine-2,4,6-triamine.
Figure 28:
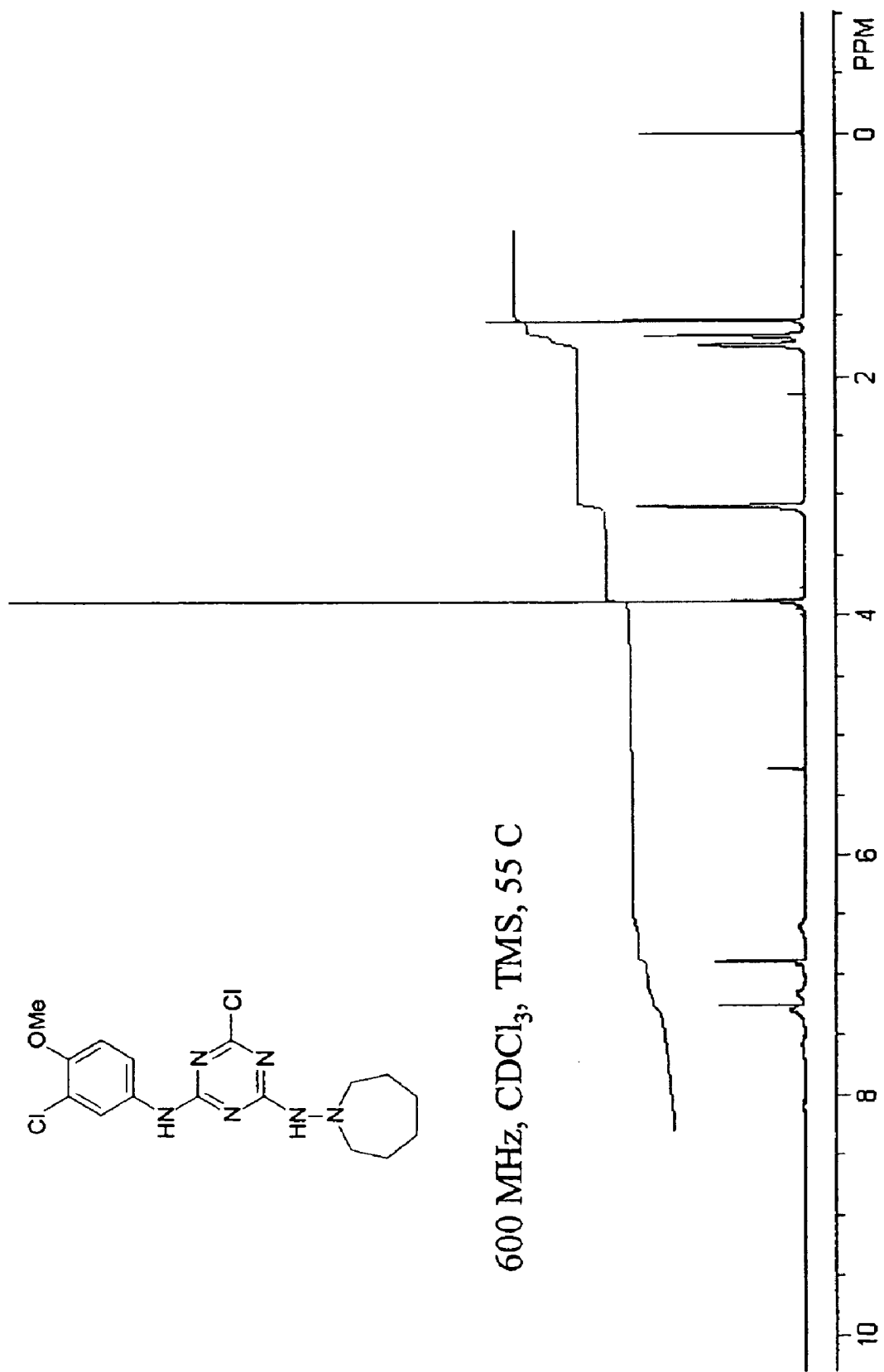
FIG. 28. ¹H NMR of N-Azepan-1-yl-6-chloro-N'-(3-chloro-4-methoxy-phenyl)-[1,3,5]triazine-2,4-diamine.
Figure 29:
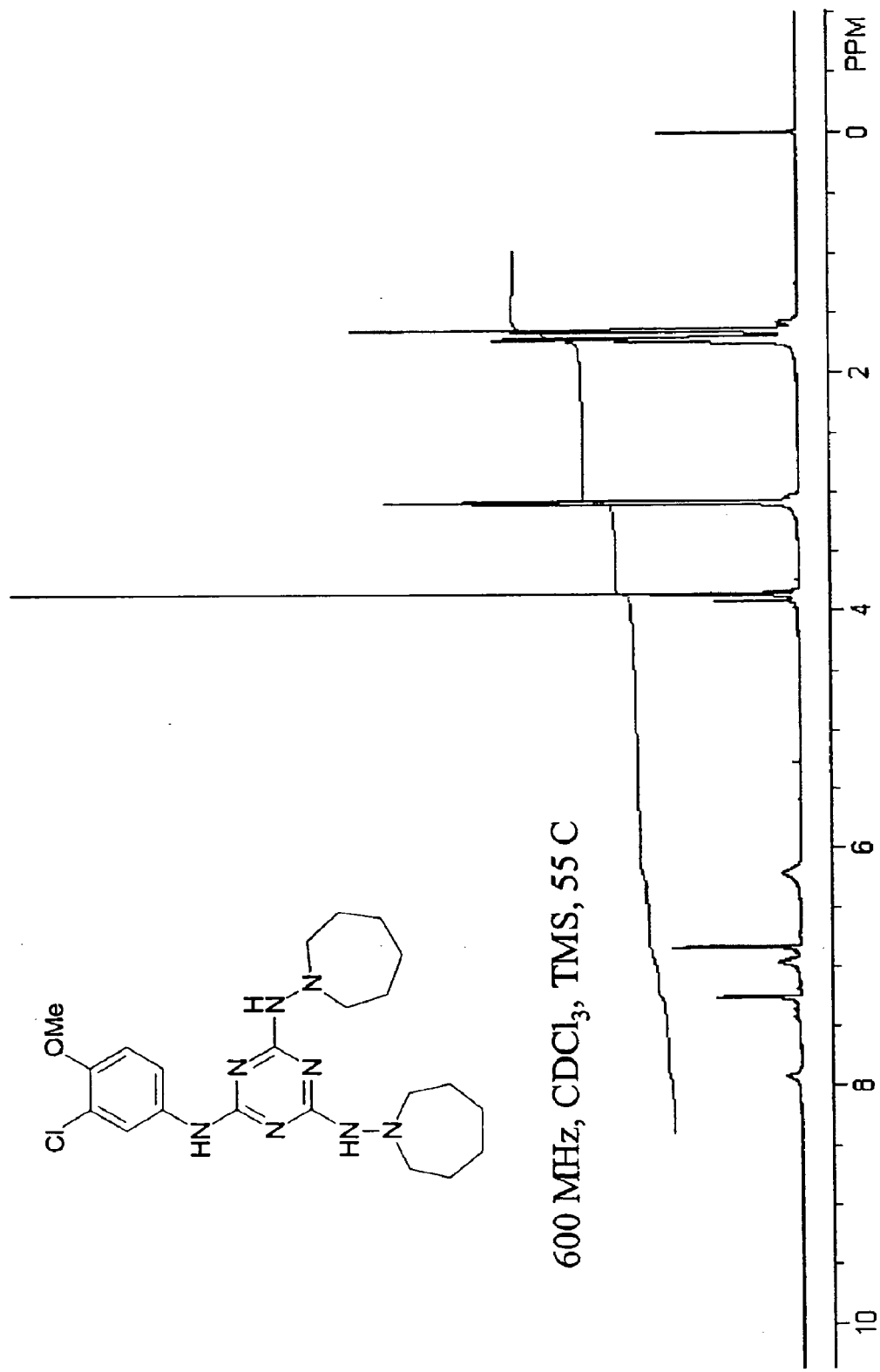
FIG. 29. ¹H NMR of N"-(3-chloro-4-methoxy-phenyl)-N,N'-bis-perhydro-azepin-1-yl-1,3,5-triazine-2,4,6-triamine.
Figure 30:
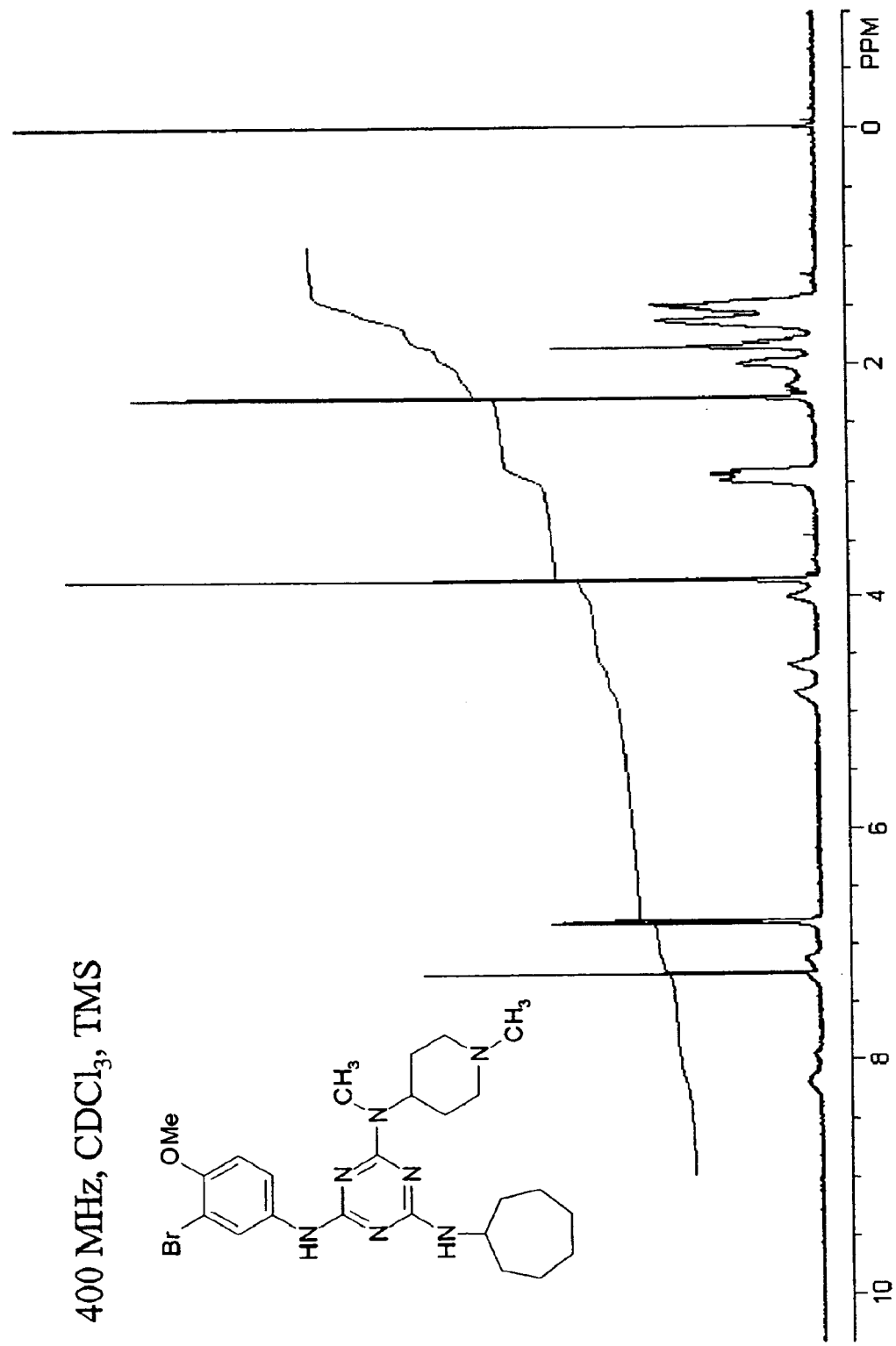
FIG. 30. ¹H NMR of N-(3-Bromo-4-methoxy-phenyl)-N'-cycloheptyl-N"'-methyl-N"-(1-methyl-piperidin-4-yl)-[1,3,5]triazine-2,4,6-triamine.
Figure 31:
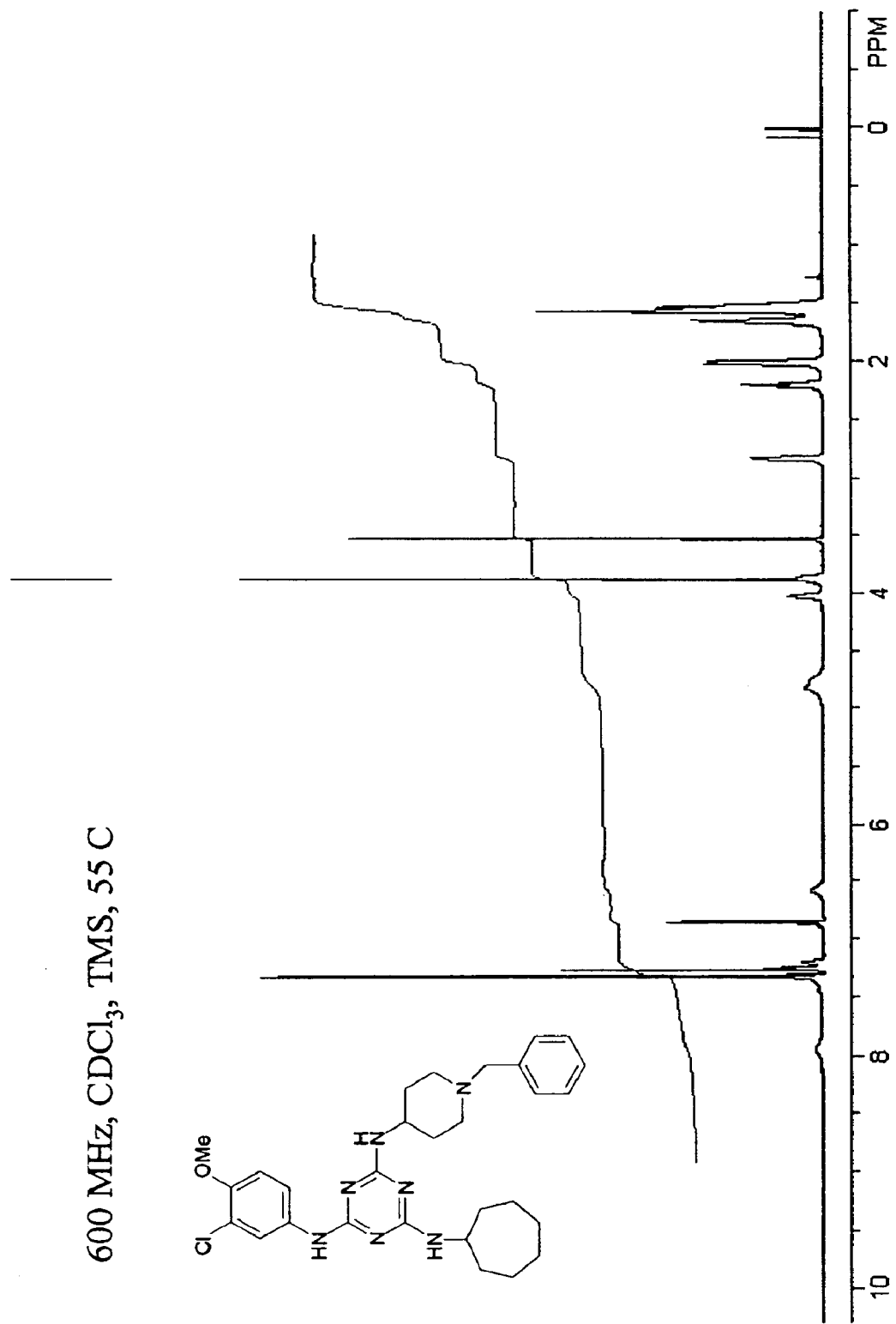
FIG. 31. ¹H NMR of N-(1-benzyl-piperidin-4-yl)-N'-(3-chloro-4-methoxy-phenyl)-N"-cycloheptyl-[1,3,5]-2,4,6-triamine.
Figure 32:
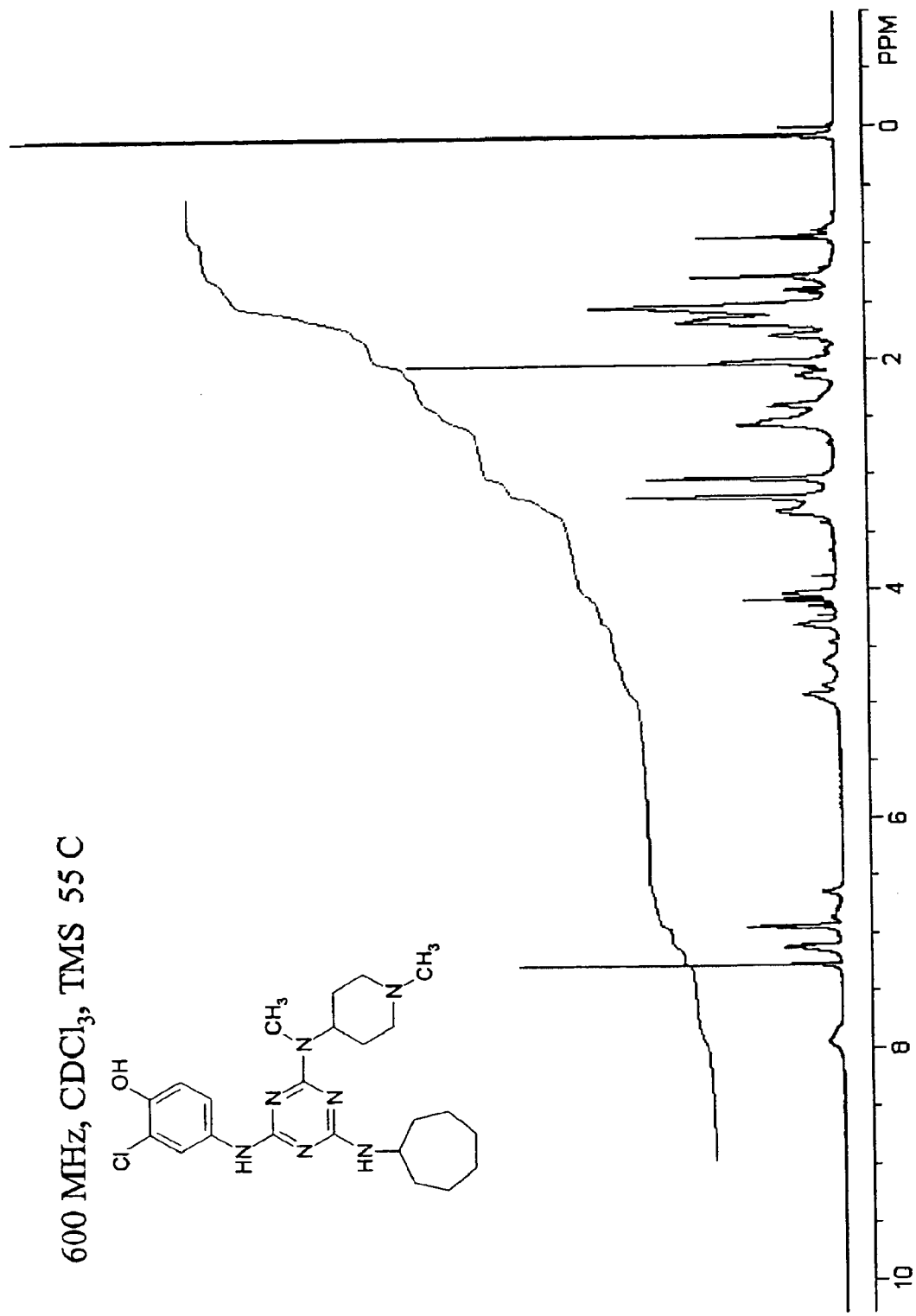
FIG. 32. ¹H NMR of 2-chloro-4-{4-cycloheptylamino-6-[methyl-(1-methyl-piperidin-4-yl-amino]-1,3,5-triazin-2-ylamino}-phenol.
Figure 33:
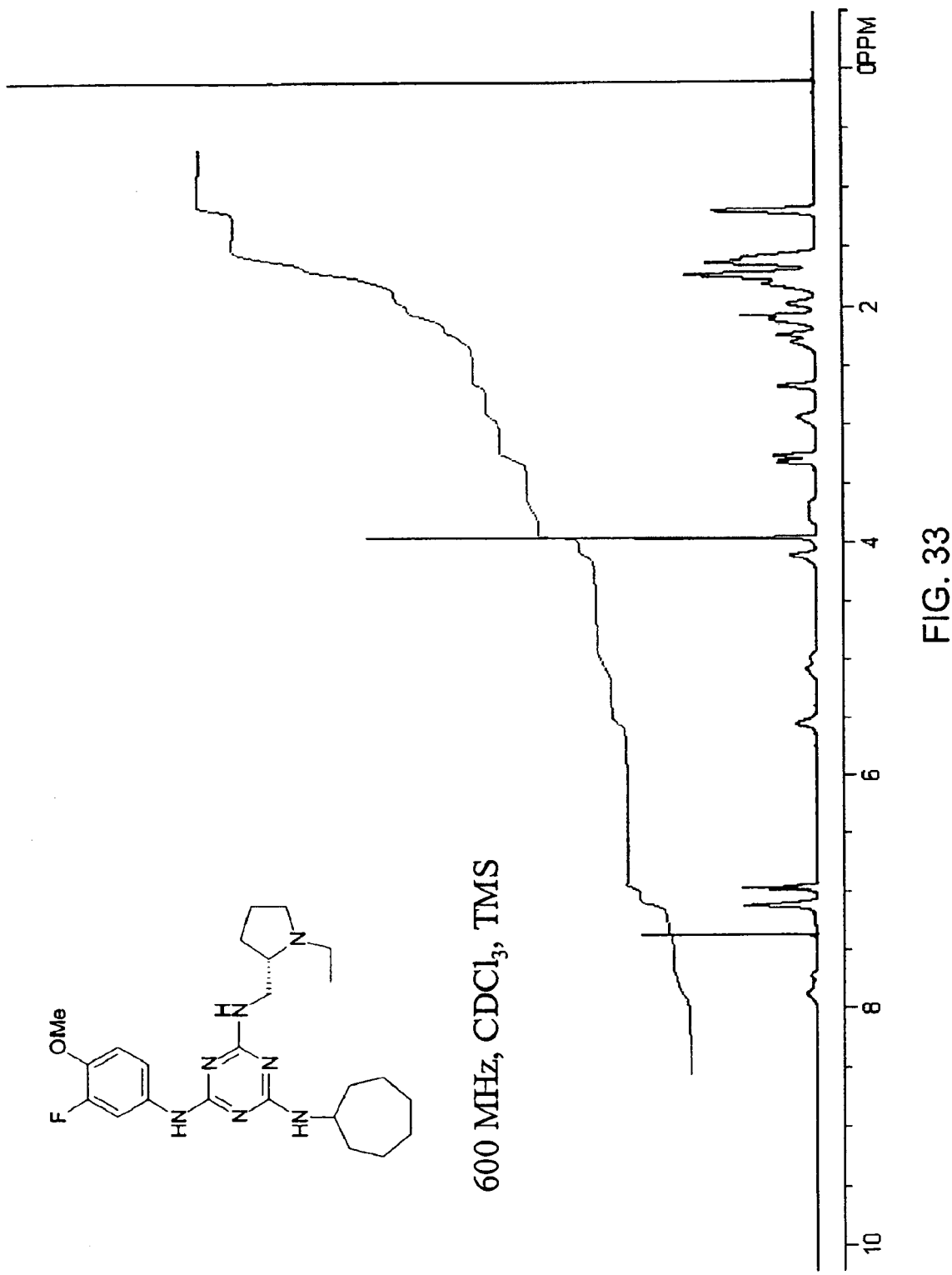
FIG. 33. ¹H NMR of N2-cycloheptyl-N4-((S)-1-ethyl-pyrrolidin-2-ylmethyl)-N6-(3-fluoro-4-methoxyphenyl)-1,3,5-triazine-2,4,6-triamine.
Figure 34:
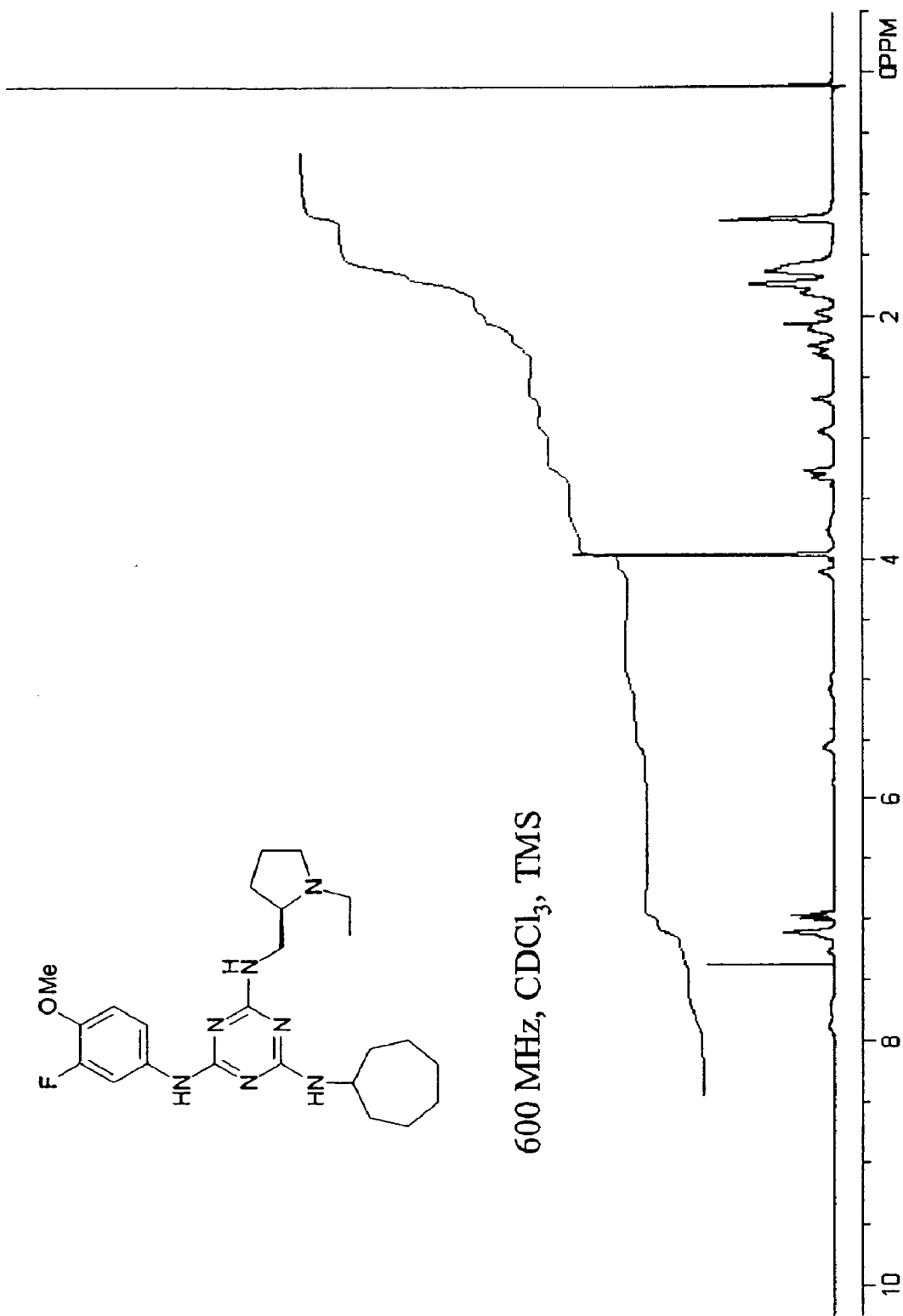
FIG. 34. ¹H NMR of N2-cycloheptyl-N4-((R)-1-ethyl-pyrrolidin-2-ylmethyl)-N6-(3-fluoro-4-methoxyphenyl)-1,3,5-triazine-2,4,6-triamine.
Figure 35:
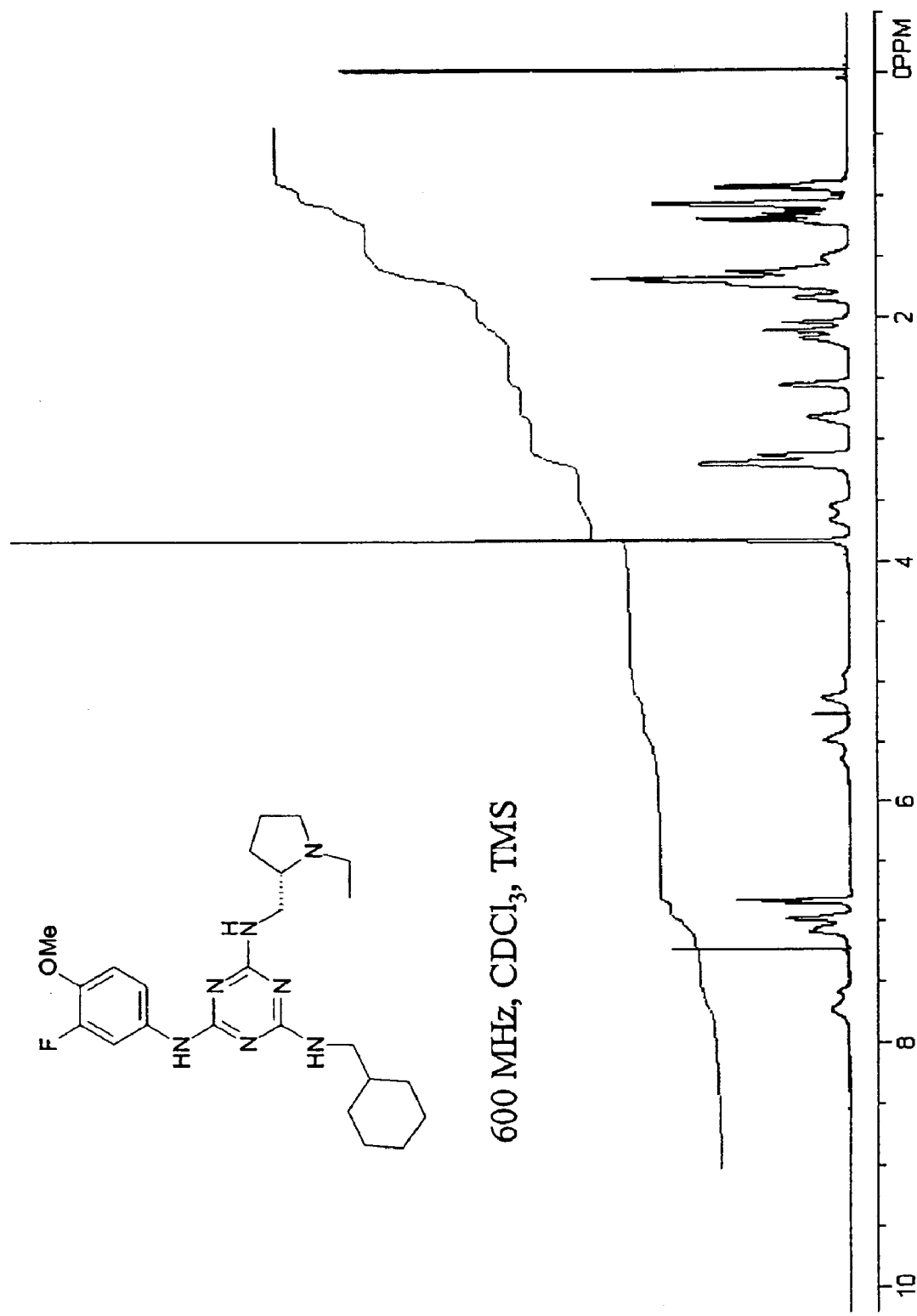
FIG. 35. ¹H NMR of N2-cyclohexylmethyl-N4-((S)-1-ethyl-pyrrolidin-2-ylmethyl)-N6-(3-fluoro-4-methoxyphenyl)-1,3,5-triazine-2,4,6-triamine.
Figure 36:
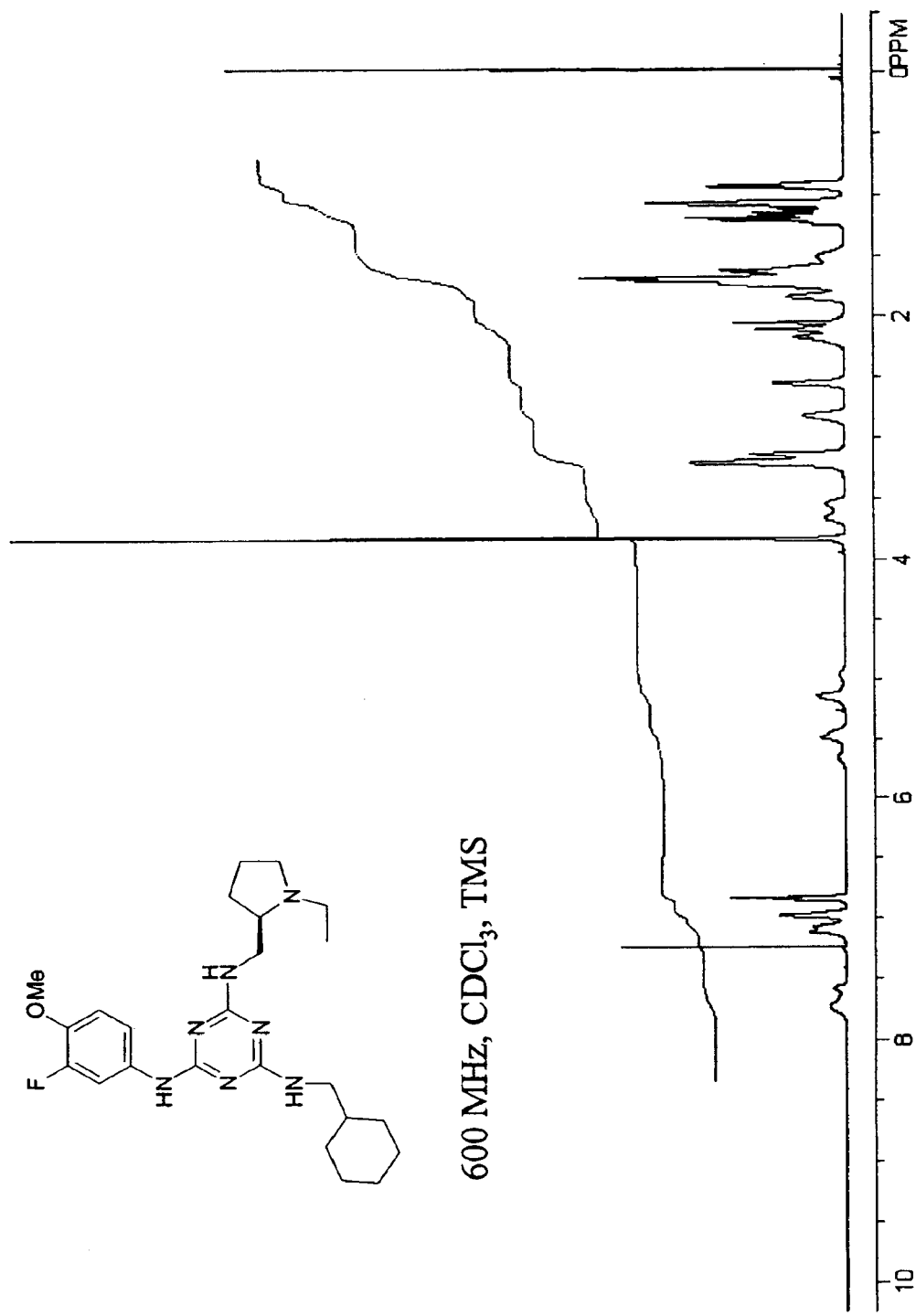
FIG. 36. ¹H NMR of N2-cyclohexylmethyl-N4-((R)-1-ethyl-pyrrolidin-2-ylmethyl)-N6-(3-fluoro-4-methoxyphenyl)-1,3,5-triazine-2,4,6-triamine.
Figure 37:
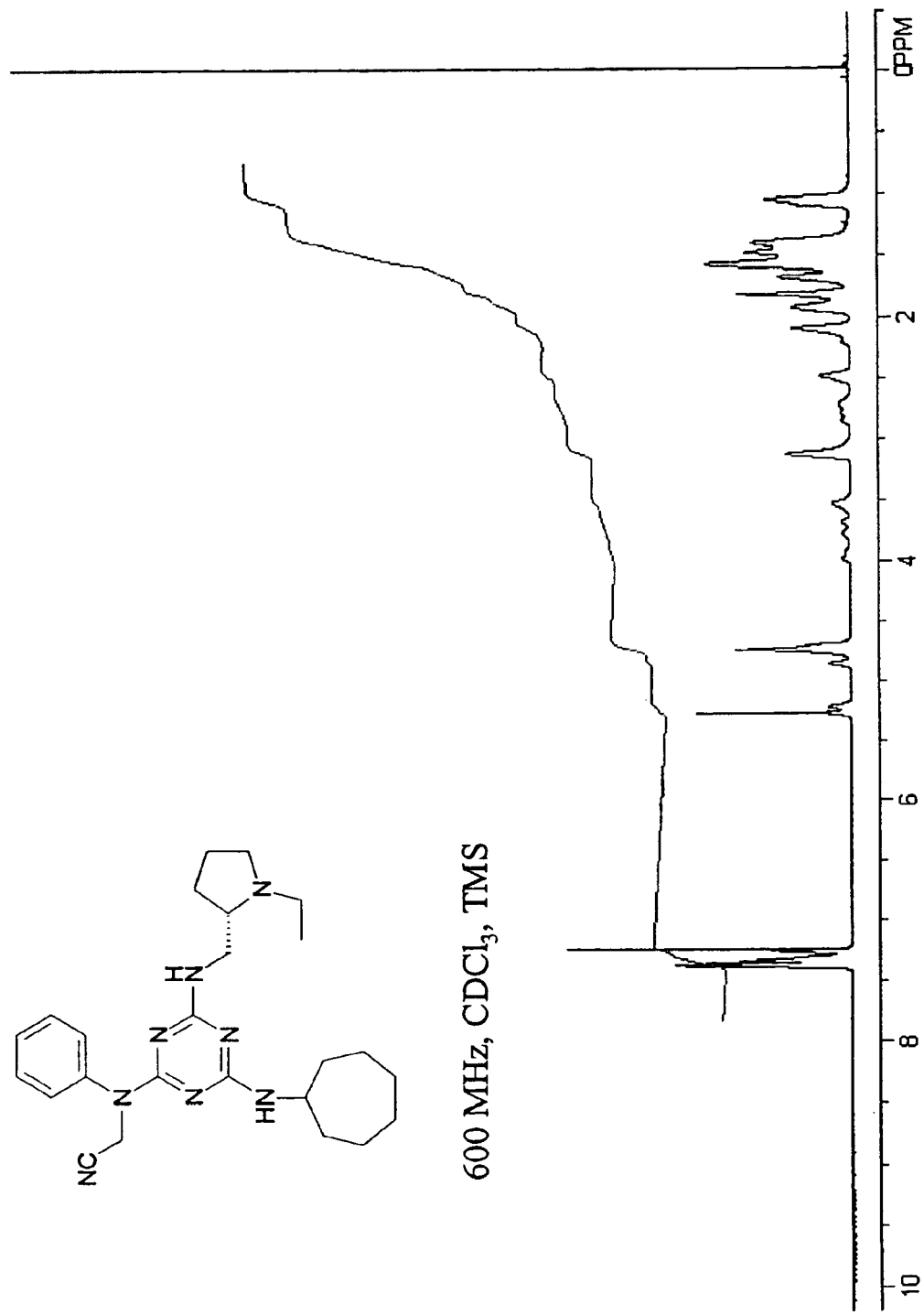
FIG. 37. ¹H NMR of ({4-cycloheptylamino-6-[((S)-1-ethyl-pyrrolidin-2-ylmethyl)-amino]-1,3,5-triazin-2-yl}-phenyl-amino)-acetonitrile.
Figure 38:
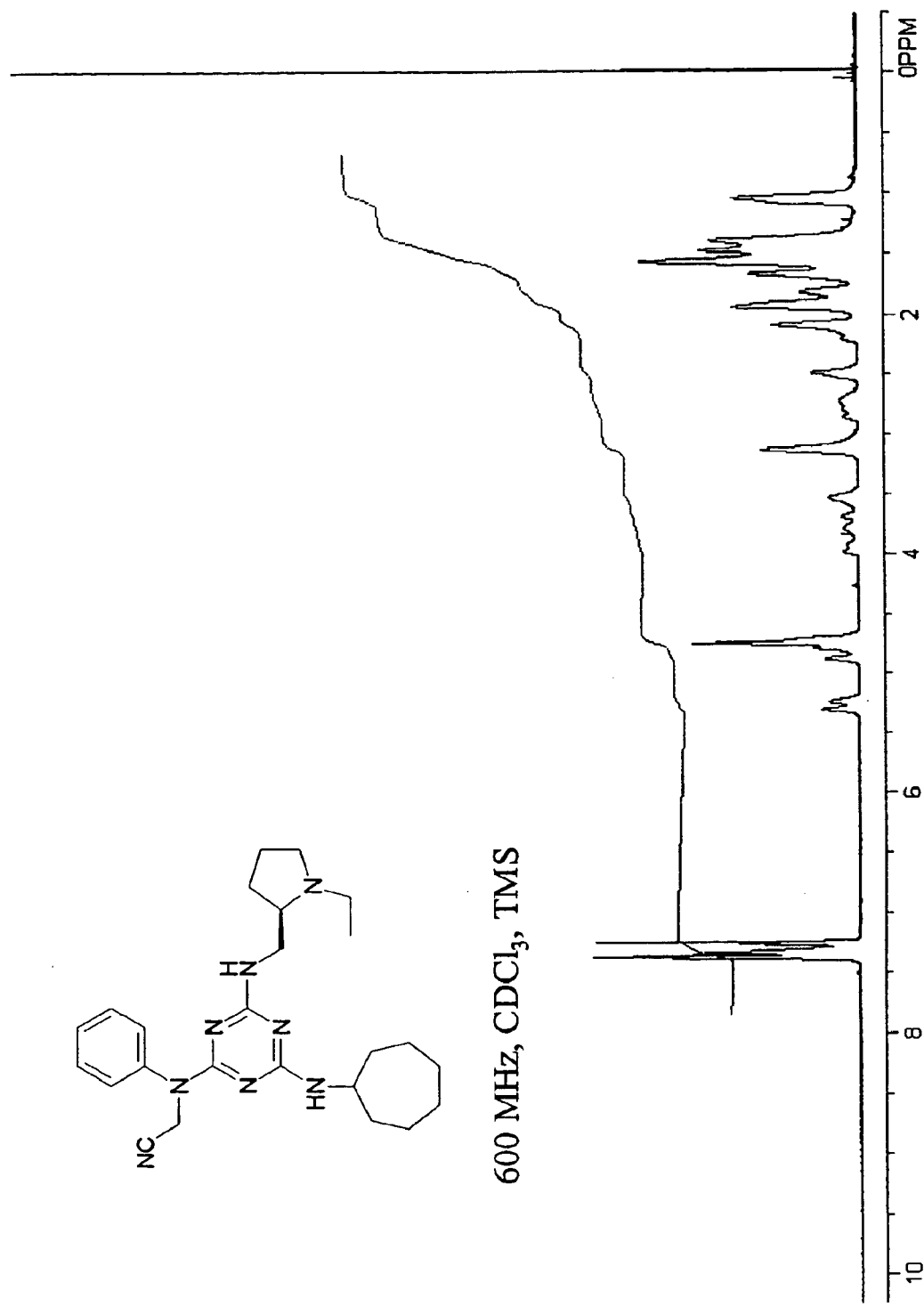
FIG. 38. ¹H NMR of ({4-cycloheptylamino-6-[((R)-1-ethyl-pyrrolidin-2-ylmethyl)-amino]-1,3,5-triazin-2-yl}-phenyl-amino)-acetonitrile.
Figure 39:
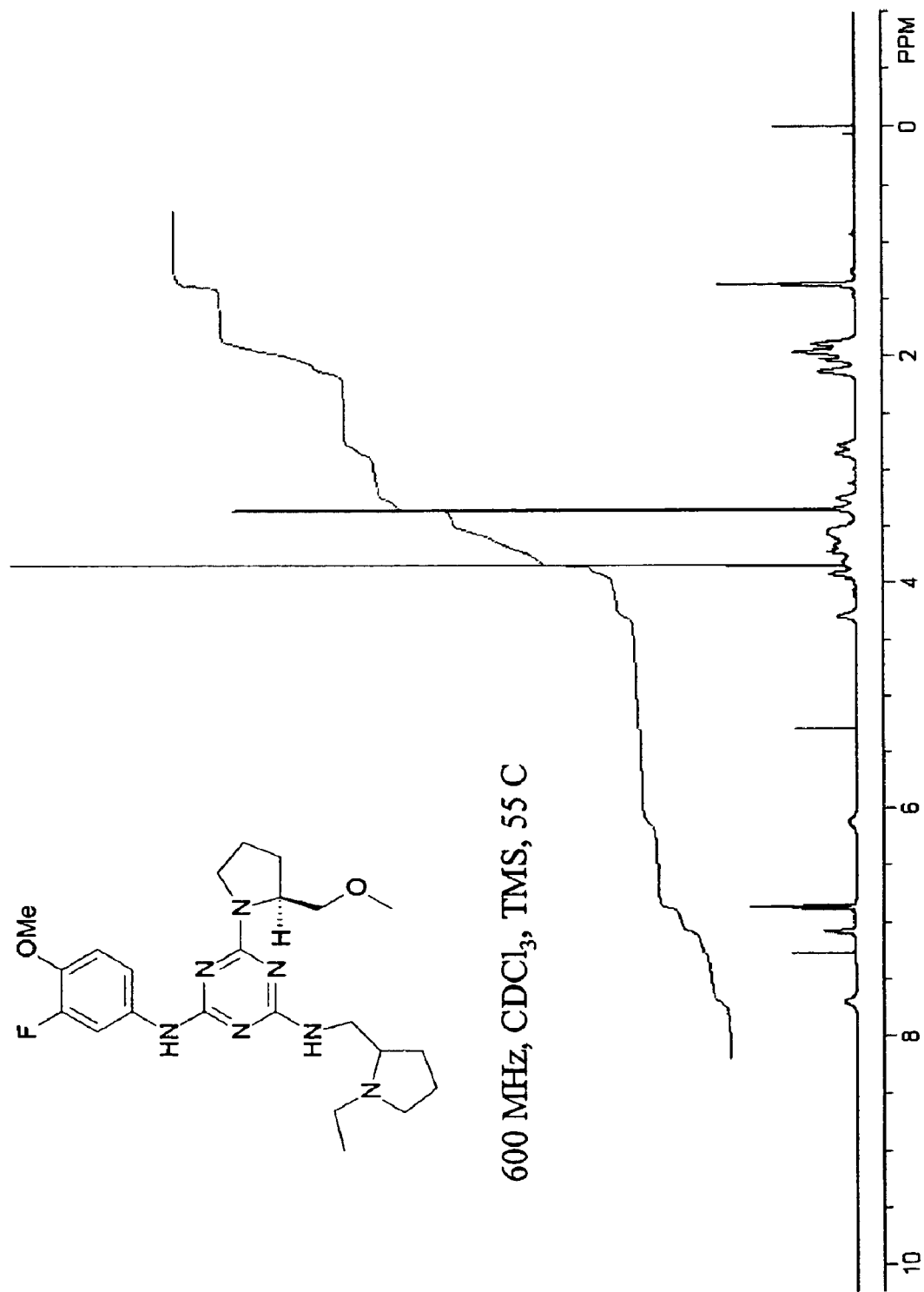
FIG. 39. ¹H NMR of N2-[(1-ethyl-2-pyrrolidinyl]-N4-(3-fluoro-4-methoxyphenyl)-6-[(S)-2-(methoxymethyl)-1-pyrrolidinyl]-1,3,5-triazine-2,4-diamine.
Figure 40:
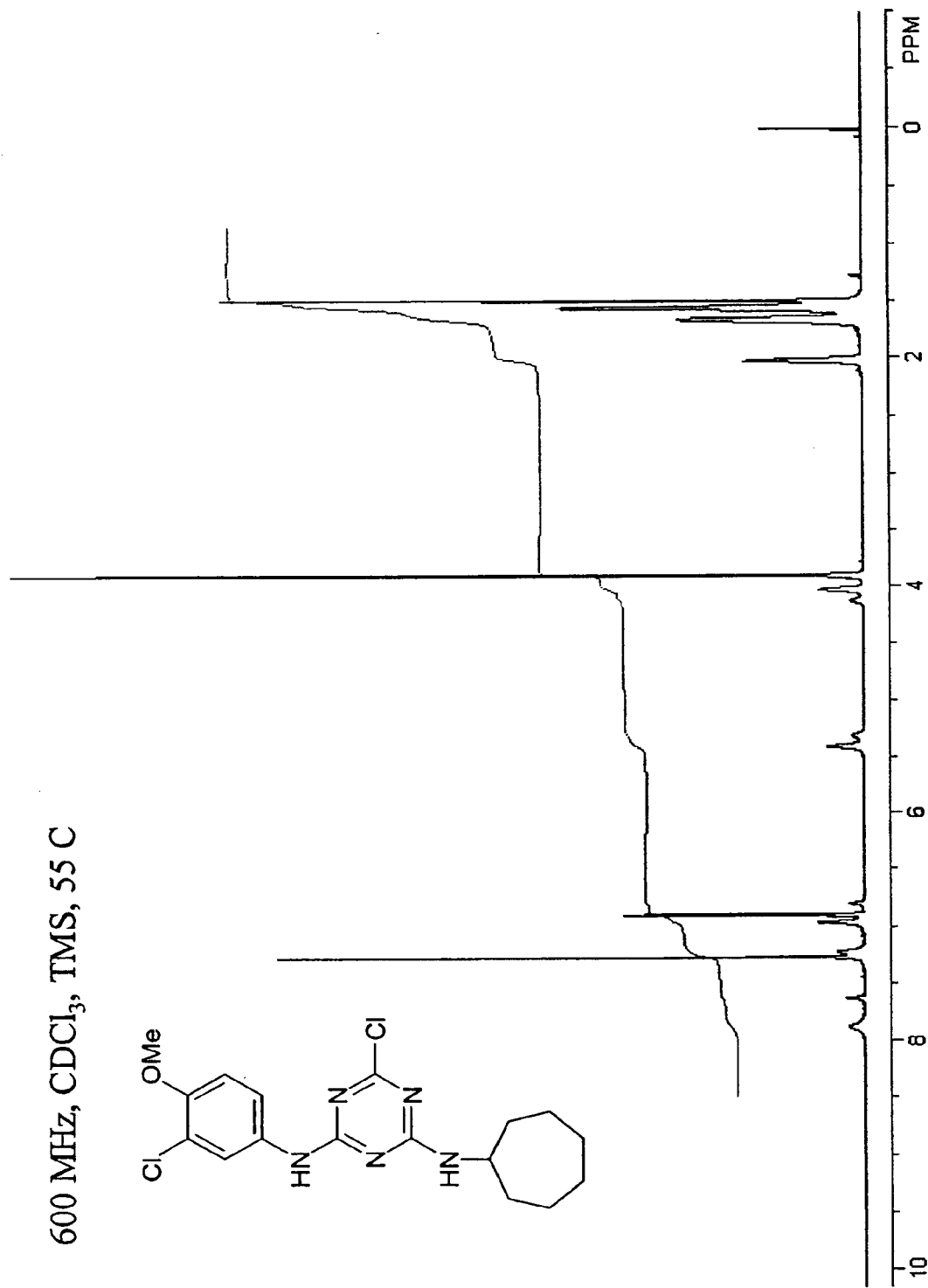
FIG. 40. ¹H NMR of 6-Chloro-N-(3-chloro-4-methoxyphenyl)-N'-cycloheptyl-[1,3,5]triazine-2,4-diamine.
Figure 41:
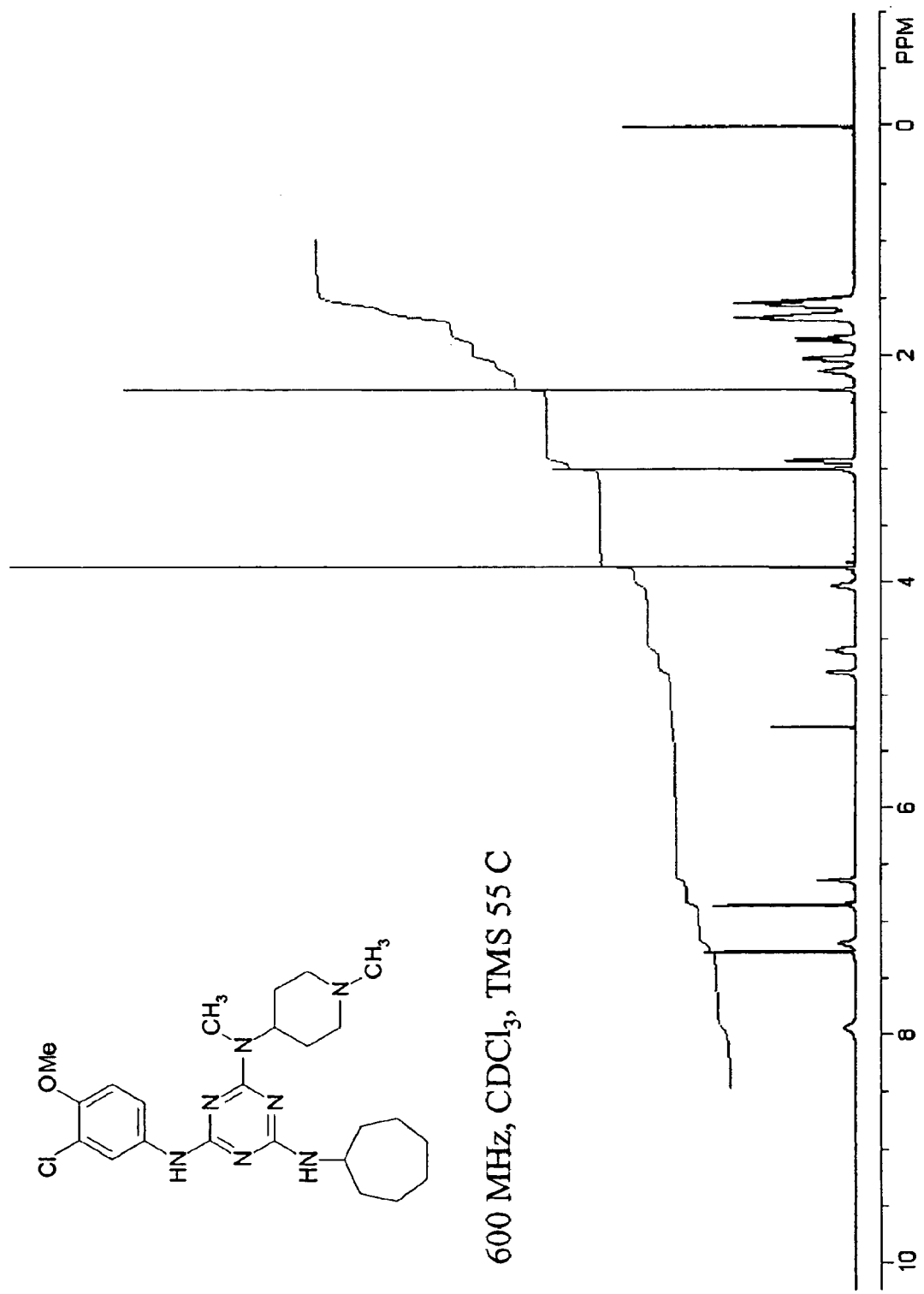
FIG. 41. ¹H NMR of N-(3-Chloro-4-methoxy-phenyl)-N'-cycloheptyl-N"'-methyl-N'-(1-methyl-piperidin-4-yl)-[1,3,5]triazine-2,4,6-triamine.
Figure 42:
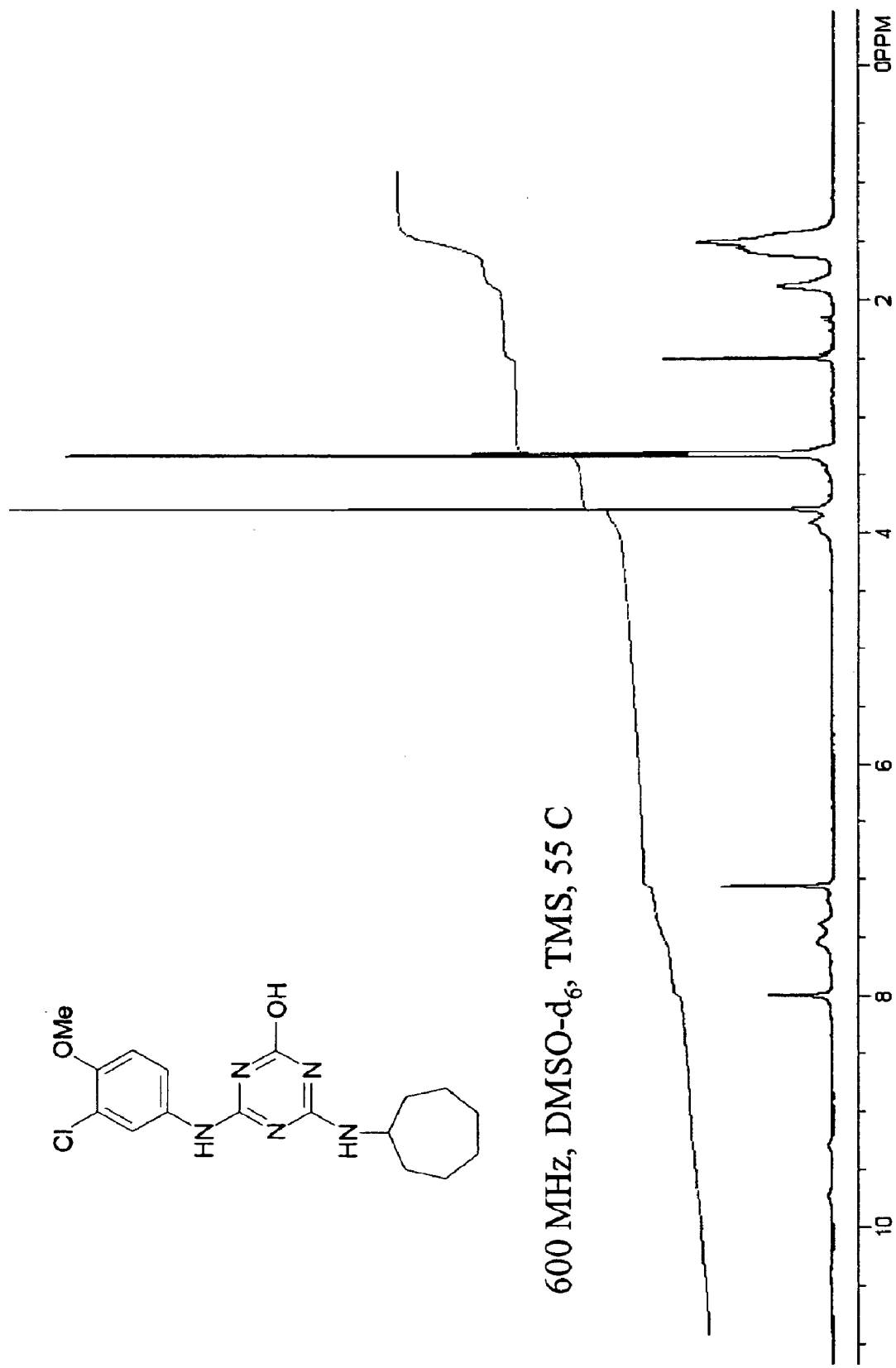
FIG. 42. ¹H NMR of 4-(3-Chloro-4-methoxy-phenylamino)-6-cycloheptylamino-1,3,5-triazin-2-ol.
Figure 43:
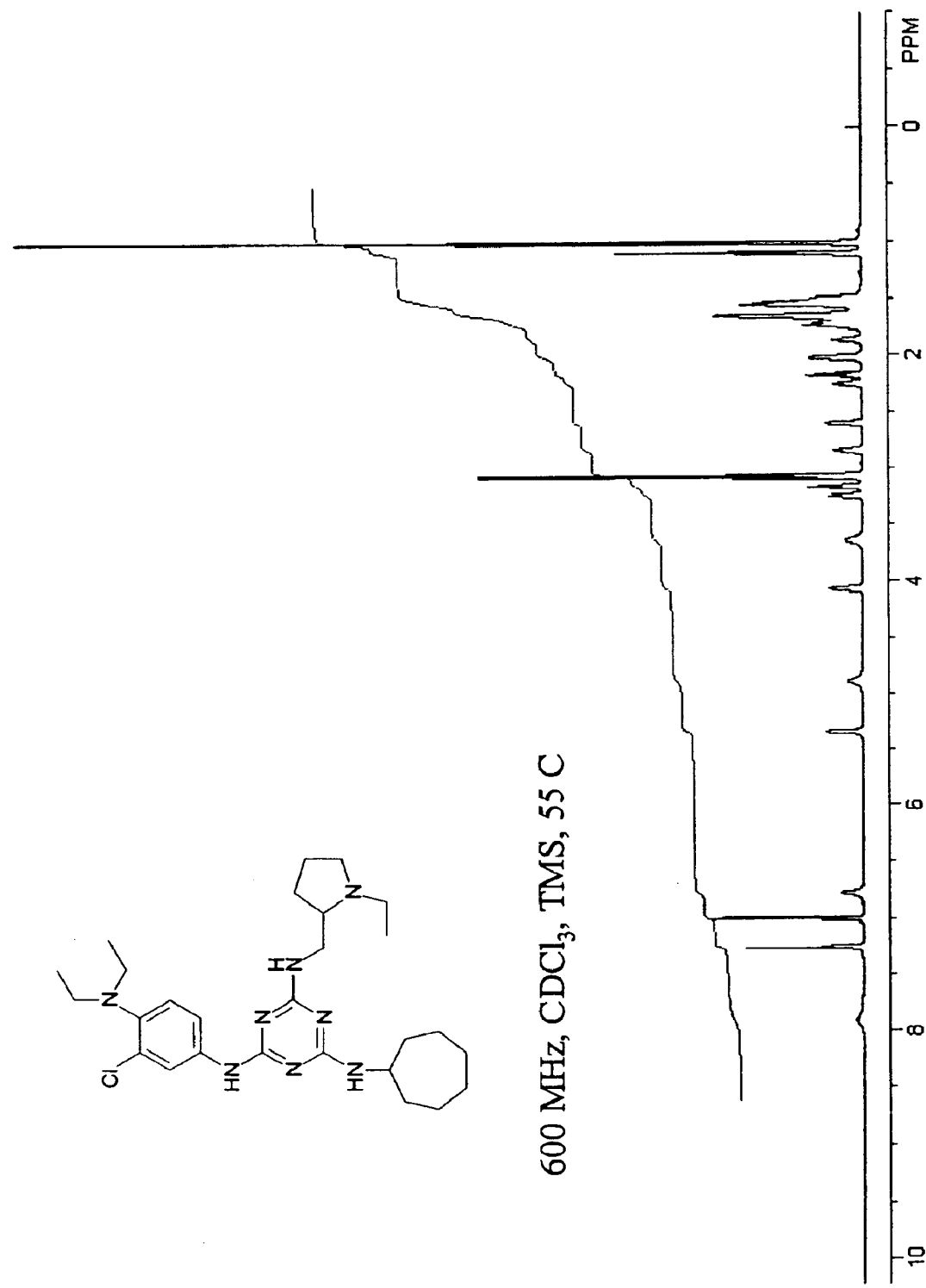
FIG. 43. ¹H NMR of N2-(3-chloro-4-diethylamino-phenyl)-N4-cycloheptyl-N6-(1-ethyl-pyrrolidin-2-ylmethyl)-1,3,5-triazine-2,4,6-triamine.
Figure 44:
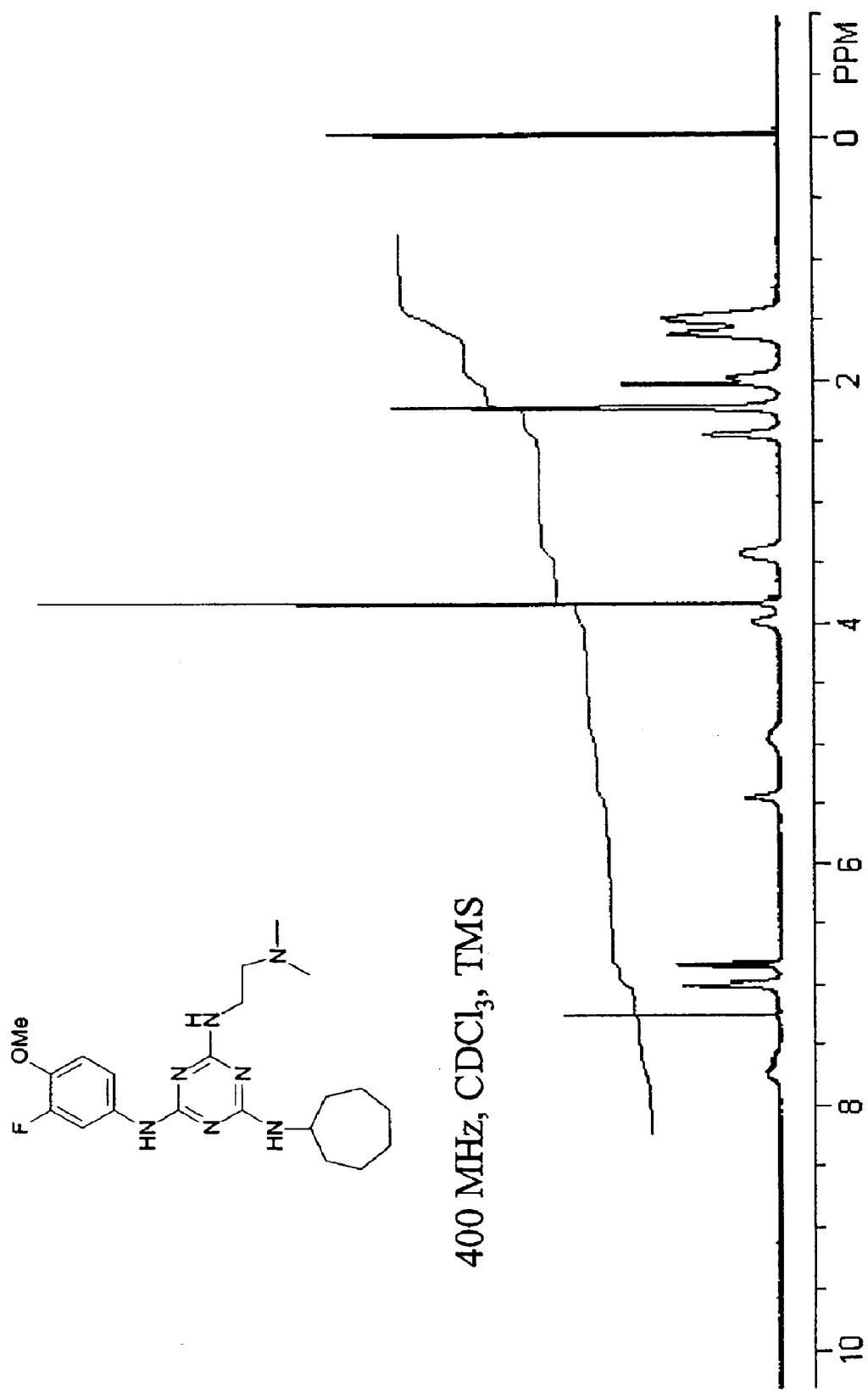
FIG. 44. ¹H NMR of N2-cycloheptyl-N4-(2-dimethylamino-ethyl)-N6-(3-fluoro-4-methoxy-phenyl)-1,3,5-triazine-2,4,6-triamine.
Figure 45:
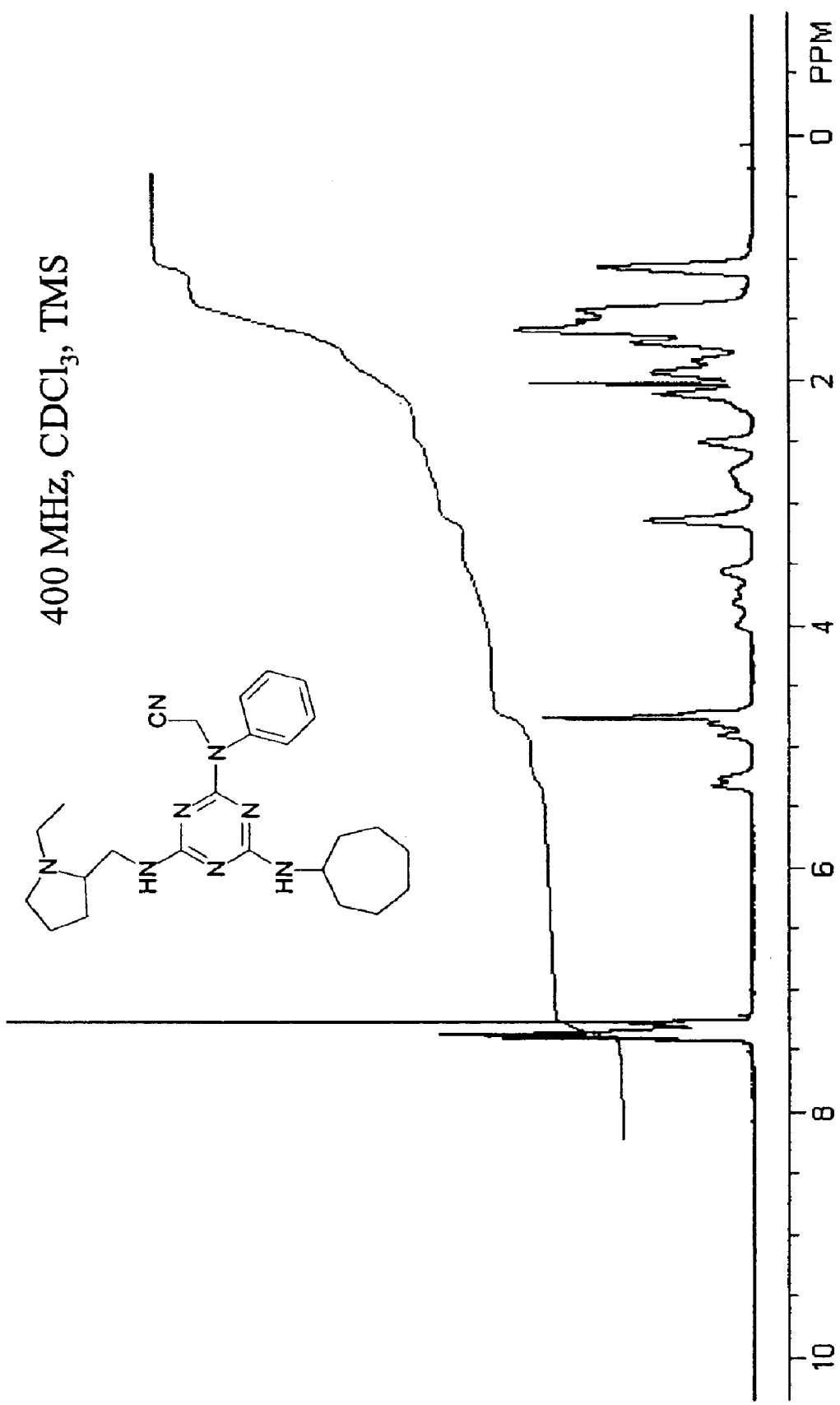
FIG. 45. ¹H NMR of ({4-cycloheptylamino-6-[1-ethyl-pyrrolidin-2-ylmethyl)-amino]-1,3,5-triazin-2-yl}-phenyl-amino)-acetonitrile.
Figure 46:
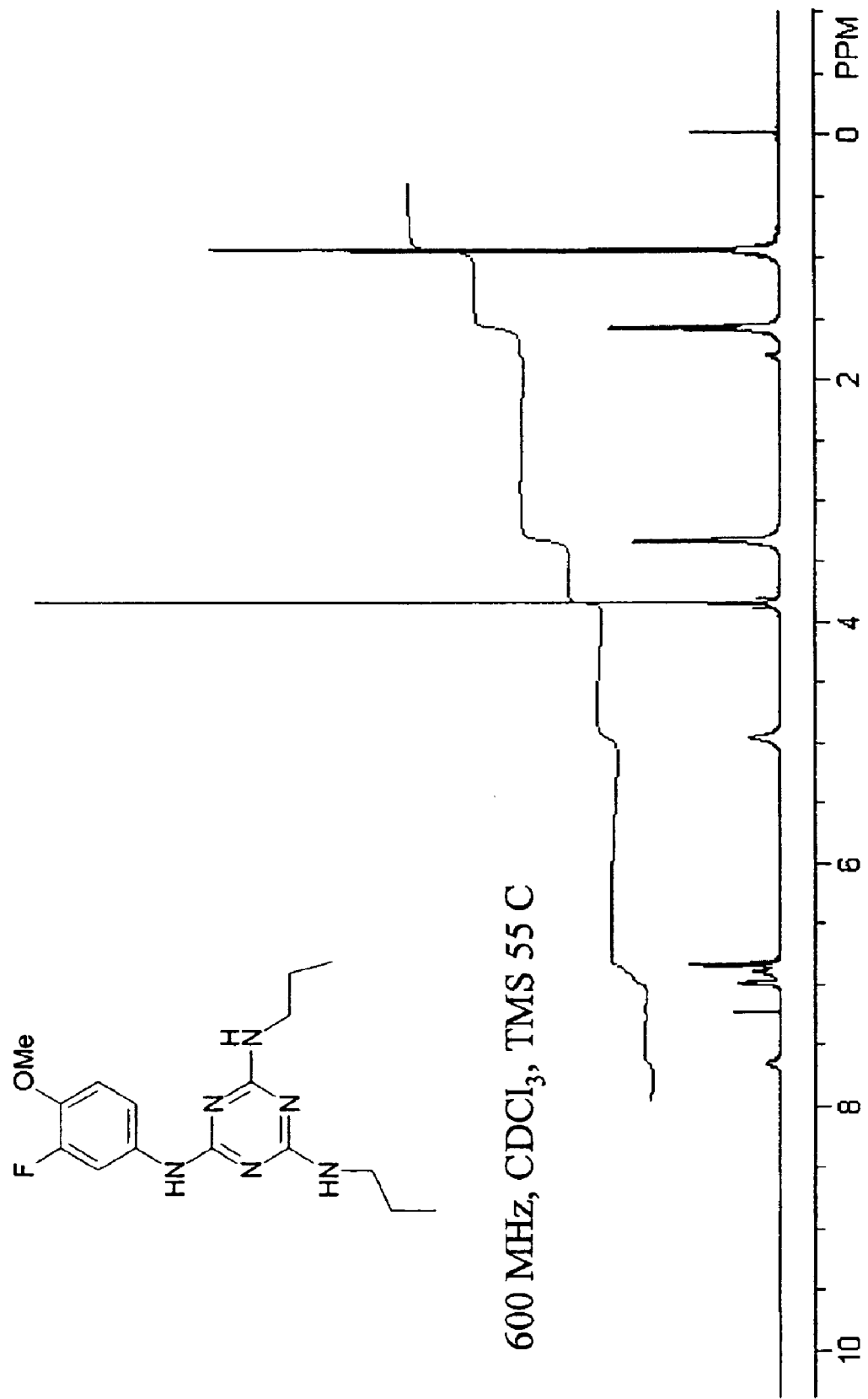
FIG. 46. ¹H NMR of N,N'-di-n-propyl-N"-(3-fluoro-4-methoxy-phenyl)-1,3,5-triazine-2,4,6-triamine.
Figure 47:
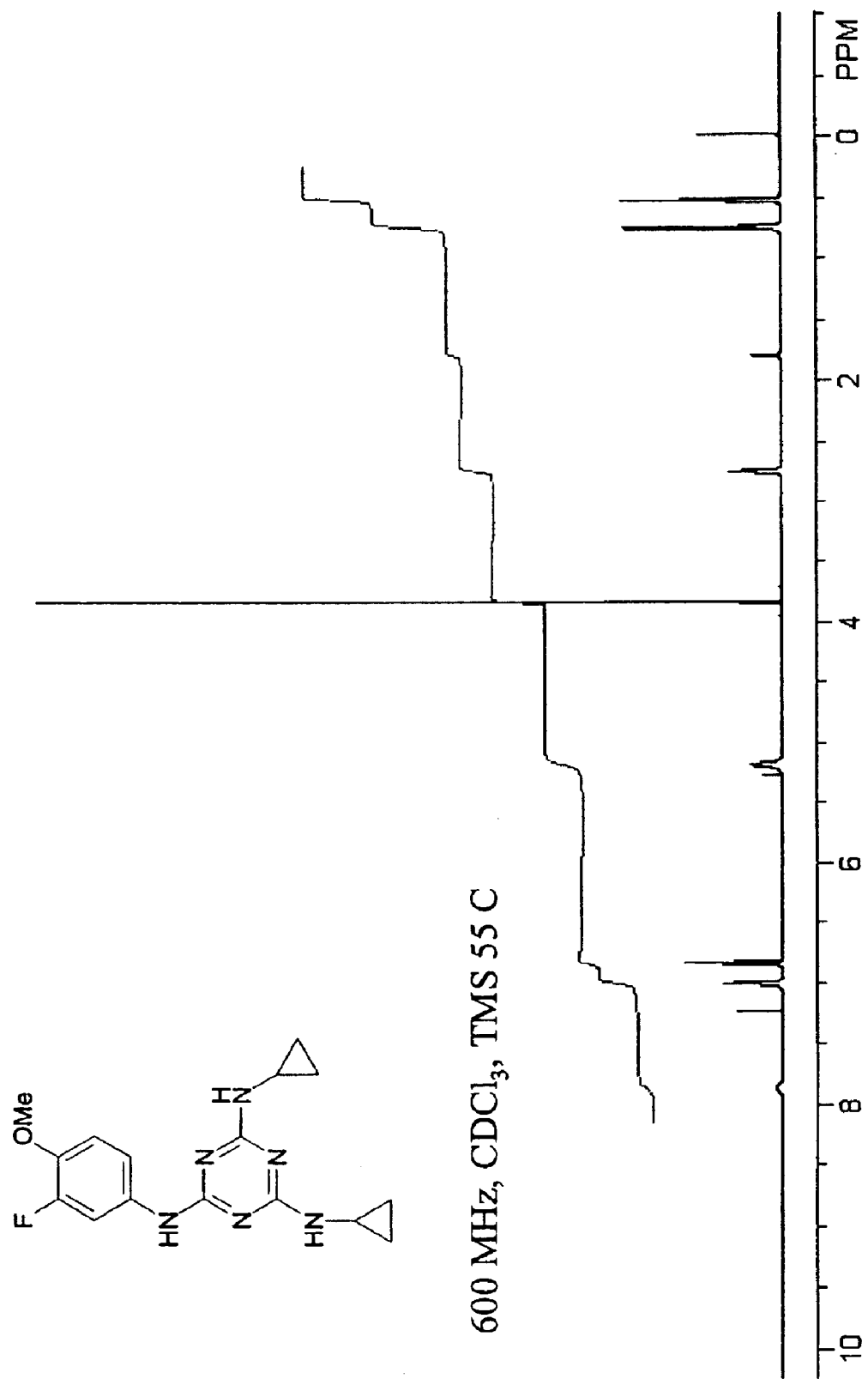
FIG. 47. ¹H NMR of N,N'-dicyclopropyl-N"-(3-fluoro-4-methoxy-phenyl)-1,3,5-triazine-2,4,6-triamine.
Figure 48:
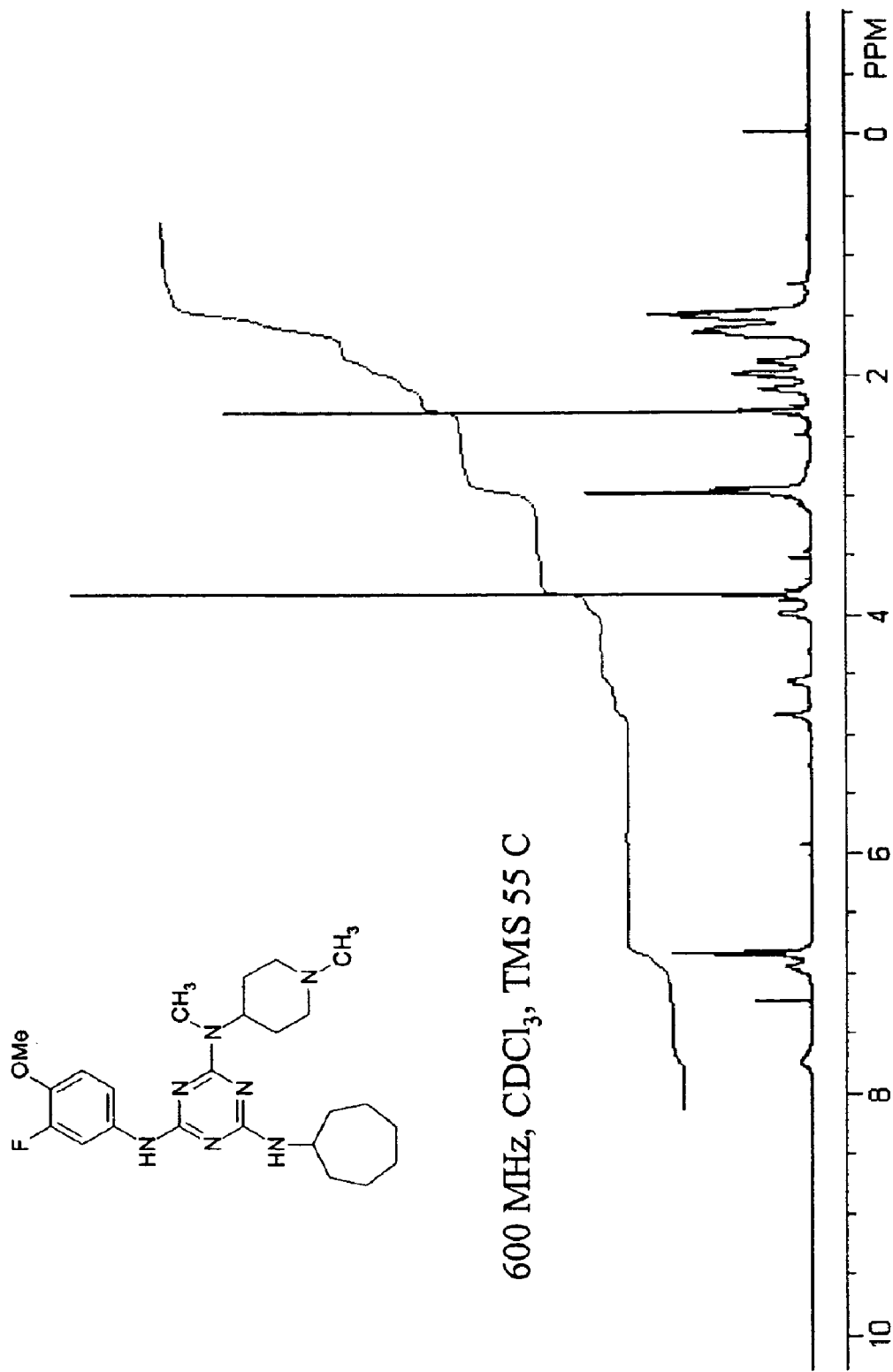
FIG. 48. ¹H NMR of N2-Cycloheptyl-N4-(3-fluoro-4-methoxy-phenyl)-N6-methyl-N6-(1-methyl-piperidin-4-yl)-1,3,5-triazine-2,4,6-triamine.
Figure 49:
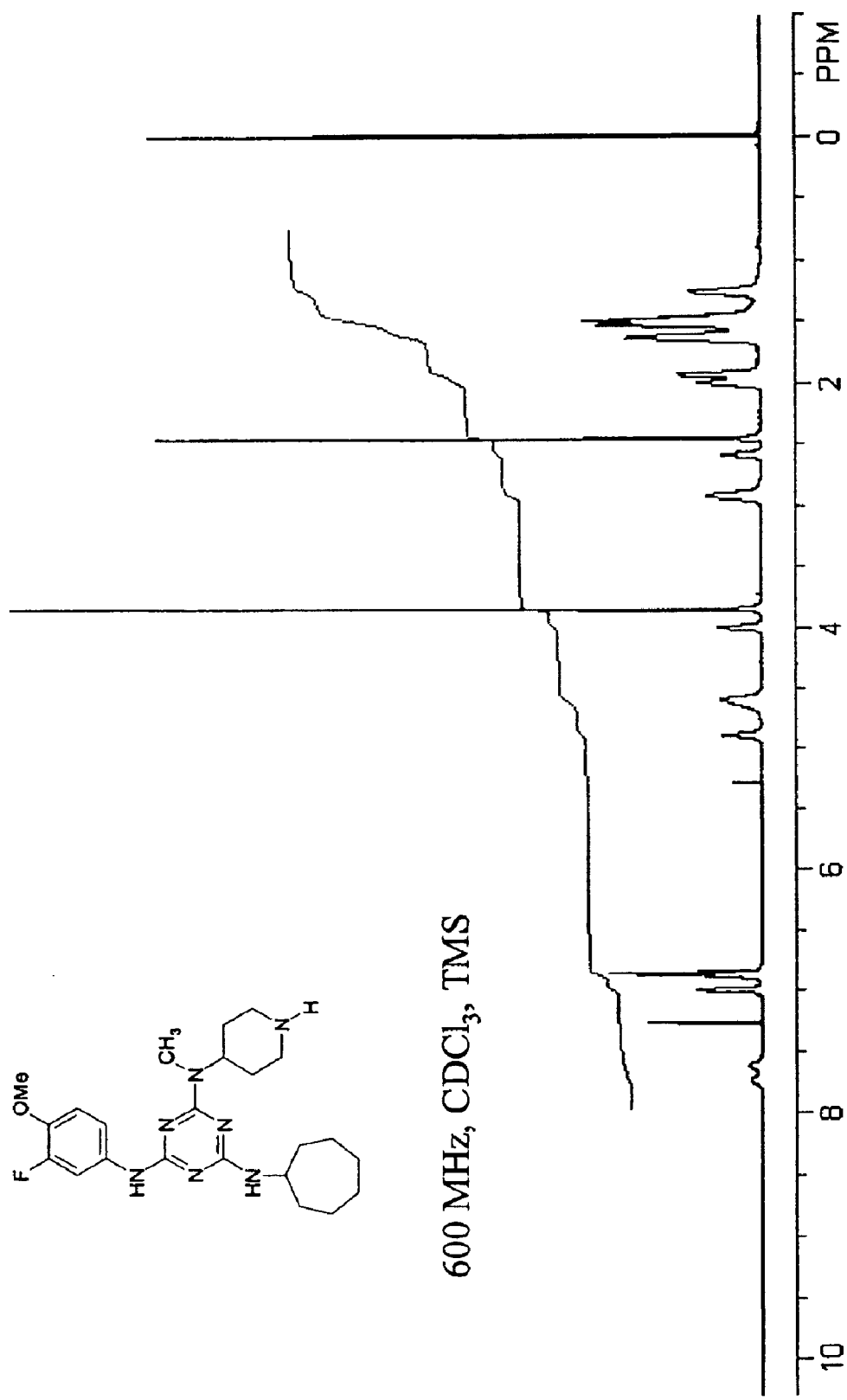
FIG. 49. ¹H NMR of N2-Cycloheptyl-N4-(3-fluoro-4-methoxy-phenyl)-N6-methyl-N6-piperidin-4-yl-1,3,5-triazine-2,4,6-triamine.
Figure 50:
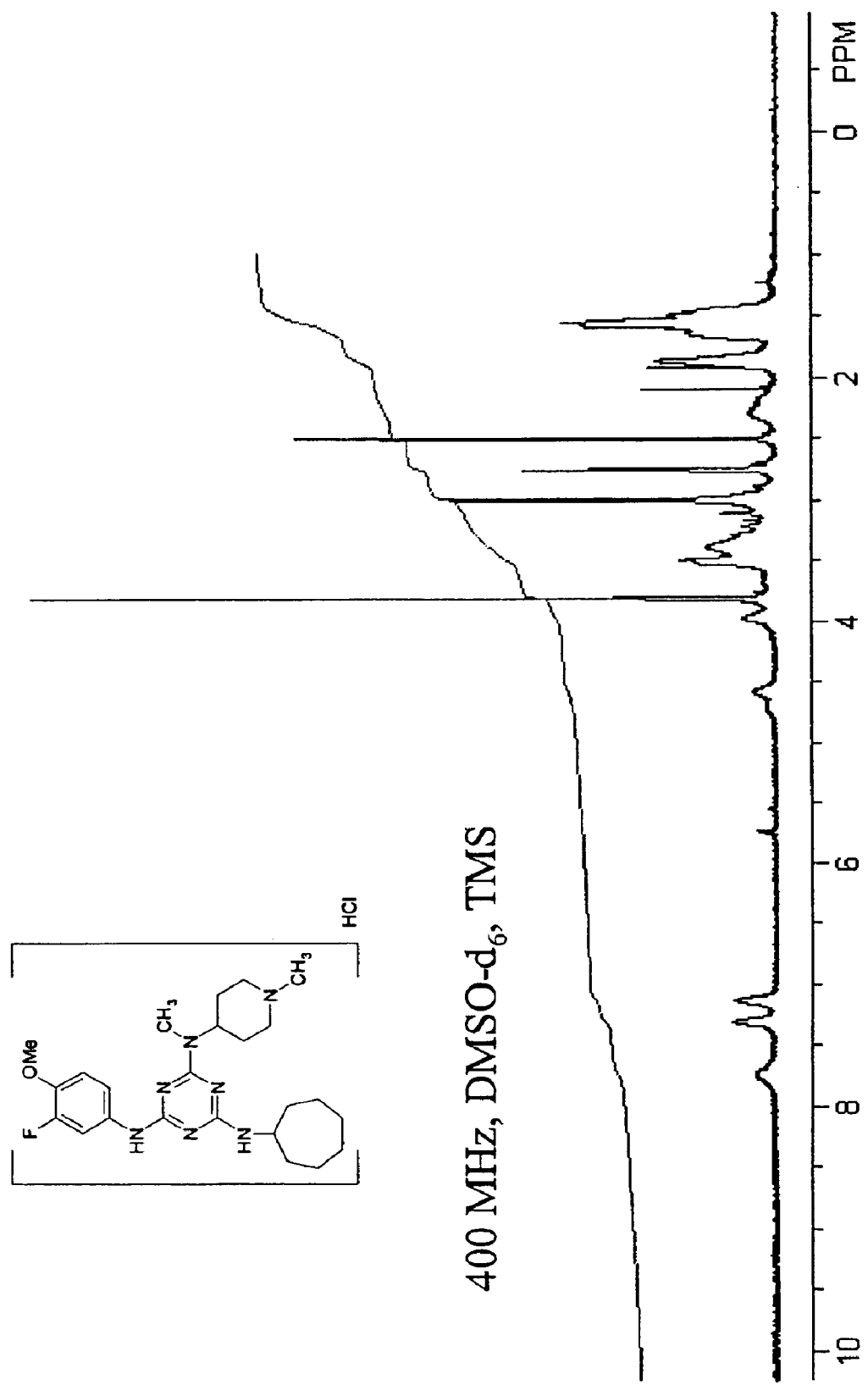
FIG. 50. ¹H NMR of N2-cycloheptyl-N4-(3-fluoro-4-methoxyphenyl)-N6-methyl-N6-(1-methyl-piperidin-4-yl)-1,3,5-triazine-2,4,6-triamine, hydrogen chloride salt.
Figure 51:
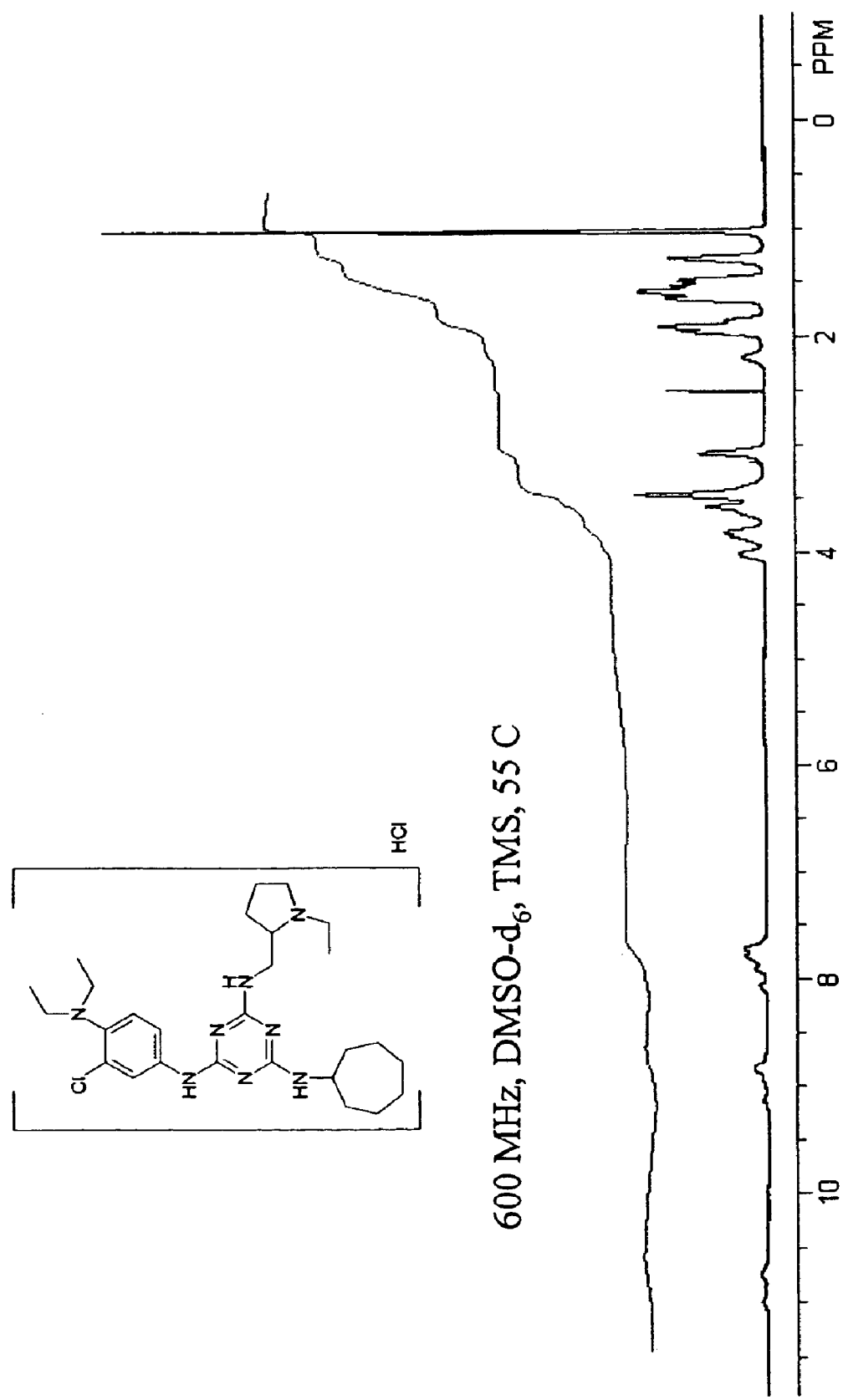
FIG. 51. ¹H NMR of N2-(3-chloro-4-diethylamino-phenyl)-N4-cycloheptyl-N6-(1-ethyl-pyrrolidin-2-ylmethyl)-1,3,5-triazine-2,4,6-triamineS42-63 hydrogen chloride salt.
Figure 52:
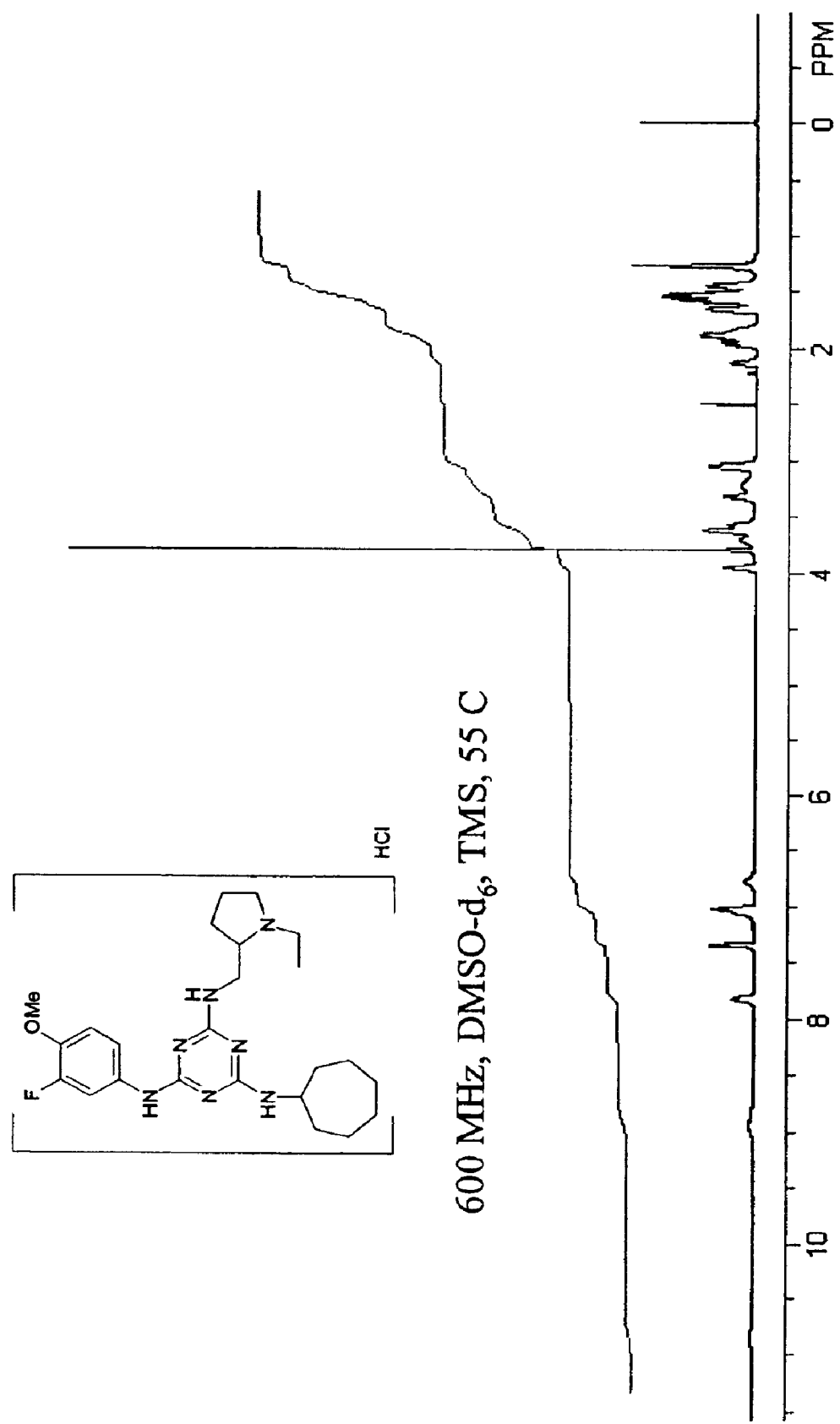
FIG. 52. ¹H NMR of N2-cycloheptyl-N4-(1-ethyl-pyrrolidin-2-ylmethyl)-N6-(3-fluoro-4-methoxyphenyl)-1,3,5-triazine-2,4,6-triamine hydrogen chloride salt.

It is to be understood that this invention is not limited to the particular methodology, protocols, cell lines, constructs, and reagents described herein and as such may vary. It is also to be understood that the terminology used herein is for the purpose of describing particular embodiments only, and is not intended to limit the scope of the present invention which will be limited only by the appended claims.

All publications and patents mentioned herein are incorporated herein by reference for the purpose of describing and disclosing, for example, the constructs and methodologies that are described in the publications, which might be used in connection with the presently described invention. The publications discussed above and throughout the text are provided solely for their disclosure prior to the filing date of the present application. Nothing herein is to be construed as an admission that the inventors are not entitled to antedate such disclosure by virtue of prior invention.

I. Description of Compounds

In one aspect, the present invention encompasses novel organic compounds that are generally described as $N^2$, $N^4$, $N^6$-tris(amino)-1,3,5-triazines which are represented by the names in Table 1 and the structural formulas in the remaining Tables 2 and following. Representative compounds of this invention can be described by the general structural formula below, where $N^A$, $N^B$ and $N^C$ are pendant substituted amino groups attached to 1,3,5-triazines at the 2, 4 and 6 positions.

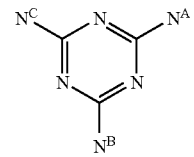

Thus, the typical compound encompassed by the present invention includes triazine compounds comprising the following structure:

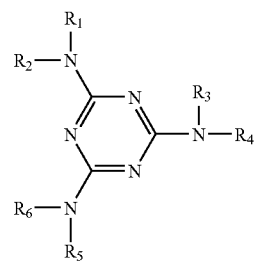

In this typical embodiment, each pendant $NR_1R_2$, $NR_3R_4$, and $NR_5R_6$ amino group can represent a primary, secondary, or tertiary amine when bonded to the triazine core, including a cyclic secondary amide substitutent (for example a pyrrolidin-N-yl group), and a range of other substituents as described herein. Compositions in accordance with the present invention also comprise analogs of the tris(amino) compounds, for example, compounds that are prepared as intermediate compounds in the synthesis of the tris(amino) triazine compounds indicated above, or compounds that represent a partially substituted trizaine core. Many of the syntheses of triazine compounds of this invention typically use cyanuric chloride $C_3N_3Cl_3$ as a starting compound, therefore intermediate species such as bis(amino) chlorotriazine compounds, or amino diclorotriazine compounds shown below, where $N^A$ and $N^B$ are pendant substituted amino groups as described above, are also encompassed by this invention.

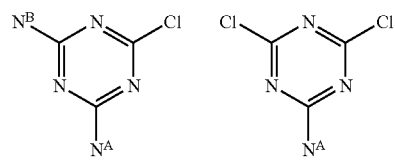

Compositions in accordance with the present invention also comprise analogs of the tris(amino) triazine compounds indicated above, including compounds that are isolated as byproducts in the synthesis of the tris(amino) triazine compounds, a general formula of which is shown below, where E=O or S. An example of such a compound is a bis(amino)alkoxy triazine compound.

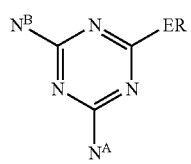

In general terms, the compounds and compositions in accordance with the present invention comprise analogs of the tris(amino) triazine compounds of the following general structure:

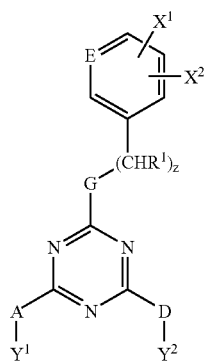

or an ene, a diene, a triene, or an yne derivative thereof; a saturated derivative thereof; a stereoisomer thereof; or a salt thereof;

wherein:

$R^1$ is in each occurrence independently selected from —H; alkyl, cycloalkyl, alkenyl, cycloalkenyl, cycloalkadienyl, alkynyl, aralkyl, aralkenyl, aralkynyl, heteroalkyl, alkoxy, alkylthio, alkylamino, or dialkylamino, each of which having up to 12 carbon atoms and including linear or branched derivatives thereof, cyclic derivatives thereof, substituted derivatives thereof, heteroatom derivatives thereof, or heterocyclic derivatives thereof, aryl; heteroaryl; aryloxy; arylthio; halogen; or amino;

G is selected from $NR^1$ or O;

E is selected from CH or N;

z is an integer from 0 to 3;

$X^1$ is selected from $R^1$, $NR^1_3{}^+$, CN, $NO_2$, $CO_2R^1$, $C(O)NR^1_2$, $CH=CR^1_2$, $C\equiv CR^1$, $C(O)R^1$, $SO_2R^1$, $SO_2OR^1$, or $NC(O)R^1$, or $X^1$ and $X^2$ together is a fused aryl, pyridine, dioxane, pyrrole, pyrrolidine, furan, or thiophene ring; with the proviso that the $R^1$ moiety of the $C(O)R^1$ substituent in the $X^1$ position excludes amino or dialkylamino when $X^1$ is $C(O)R^1$;

$X^2$ is selected from $R^1$; $CX_xH_{3-x}$, wherein X is a halogen and x is an integer from 0 to 3; $OR^1$; $SR^1$; $NR^1_2$; CN; $C(O)OR^1$; $NC(O)R^1$; 4-morpholinyl; 4-methyl-1-piperazinyl; $OR^2$, wherein $R^2$ is selected from $CH_2OCH_3$, $CH_2OCH_2OCH_3$, $CH_2OCH_2CH_2OCH_3$, $CH_2SCH_3$, or $C(O)R^1$; $SR^3$, wherein $R^3$ is selected from $CH_2OCH_3$, $CH_2OCH_2CH_2OCH_3$, $CH_2OCH_2CH(CH_3)_2$, $CH_2NHC(O)CH_3$, or $SR^1$; OM or SM, wherein M is selected from Li, Na, K, Mg, or Ca;

$AY^1$ is halogen, or A is selected from $NR^1$ or O, and

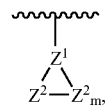

$Y^1$ is selected from $R^1$; $CR^4{}_3$; $NR^4{}_2$; $OR^4$; or $SR^4$;

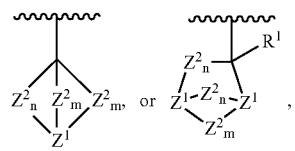

wherein n is an integer from 0 to 8, m is an integer from 1 to 8, $Z^1$ is independently selected from $CR^1$ or N, $Z^2$ is independently selected from $CR^1_2$, $NR^1$, O, or S, with the proviso that two O or S atoms are not located adjacent to each other, and the proviso that no more than two $Z^2$ moieties are $NR^1$;

$R^4$ is in each occurrence independently selected from linear or branched alkyl, cycloalkyl, cycloalkenyl, cycloalkadienyl, alkenyl, alkynyl, aralkyl, aralkenyl, aralkynyl, heteroalkyl, alkoxy, alkylthio, alkylamino, or dialkylamino, each of which having up to 10 carbon atoms, —H, aryl, heteroaryl, aryloxy, arylthio, halogen, amino, $NR^1_2$-substituted derivatives thereof, $OR^1$-substituted derivatives thereof, $SR^1$-substituted derivatives thereof, or halogen-substituted derivatives thereof; and $DY^2$ is halogen, or D is selected from $NR^1$ or O wherein $R^1$ is defined as above, and $Y^2$ is selected from $R^1$,

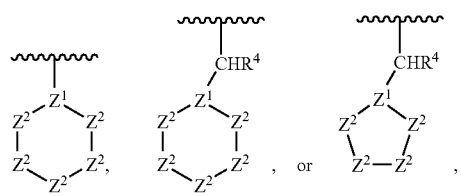

wherein $Z^1$ is independently selected from N or $CR^4$ and $Z^2$ is independently selected as defined above, with the proviso that two O or S atoms are not located adjacent to each other, and with the proviso that no more than two $Z^2$ moieties are $NR^1$. The compounds of the present invention according to this general description do not include those that encompass the unique combination of substituents that would provide the following compounds:

N-Cycloheptyl-N'-methyl-N''-(1-methyl-piperidin-4-yl)-N'''-naphthalen-2-yl-[1,3,5]triazine-2,4,6-triamine;

N-Cycloheptyl-N'-(3-fluoro-4-methoxy-phenyl)-N''-methyl-N'''-(1-methyl-piperidin-4-yl)-[1,3,5]triazine-2,4,6-triamine;

[4-(4-Benzyl-piperazin-1-yl)-6-morpholin-4-yl-[1,3,5]triazin-2-yl]-(4-methoxy-phenyl)-amine;

N-Cycloheptyl-6-morpholin-4-yl-N'-naphthalen-2-yl-[1,3,5]triazine-2,4-diamine;

N-Cycloheptyl-N'-(3-fluoro-4-methoxy-phenyl)-6-morpholin-4-yl-[1,3,5]triazine-2,4-diamine;

N-Cycloheptyl-6-morpholin-4-yl-N'-phenyl-[1,3,5]triazine-2,4-diamine;

N-Cycloheptyl-N'-(4-methoxy-phenyl)-6-morpholin-4-yl-[1,3,5]triazine-2,4-diamine;

N-Benzyl-N'-cycloheptyl-N''-(4-methoxy-phenyl)-N-methyl-[1,3,5]triazine-2,4,6-triamine;

N-(2-[1,3]Dioxolan-2-yl-ethyl)-N'-methyl-N'-(1-methyl-piperidin-4-yl)-N"-naphthalen-2-yl-[1,3,5]triazine-2,4,6-triamine; or N-Cyclopropyl-N'-methyl-N'-(1-methyl-piperidin-4-yl)-N"-naphthalen-2-yl-[1,3,5]triazine-2,4,6-triamine.

Because this invention encompass compounds that represent saturated derivatives of the above general structure, and compounds that include various states of unsaturation (for example, -ene, -diene, -triene, and -yne derivatives of the above compounds), then the aryl or pyridyl ring shown in the general formula above can be partially or completed hydrogenated in this invention. As a result, the $C_5E$ ring in the above structure can represent a cyclohexyl or piperidynl ring that is $X^1$ and $X^2$ substituted. In general terms, $X^1$ usually, but not always, represent an electron withdrawing group such as halide or nitro, while $X^2$ usually, but not always, represents an electron donating group such as alkoxide or amino.

As indicated in the general structure above, $AY^1$ and $DY^2$ typically represent an $NR^1$ moiety (where $R^1$ is defined above), in which case these substituents constitute a portion of amino or substituted amino group and therefore, the compound itself constitutes a triazine. In this case, $Y^1$ and $Y^2$ may be selected from a wide range of substituents, including, but not limited to, cycloalkyl with up to 10 carbon atoms;

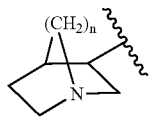

wherein n is from 1 or 2;

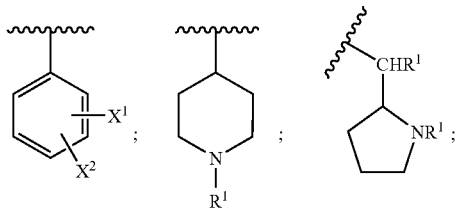

linear or branched alkyl with up to 10 carbon atoms; $CH_2R^1$; $(CHR^1)_xNR^1_2$ wherein x is 1–6; $CH_2R^1$; $(CHR^1)_xOR^1$ wherein x is from 1 to 6;

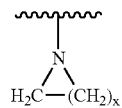

wherein x is from 3 to 5;

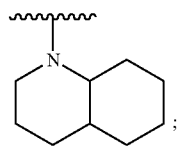

$CH_2CF_3$; $(CHR^1)_xZ^1$ wherein x is from 1 to 6 and $Z^1$ is selected from $NR^1_2$,

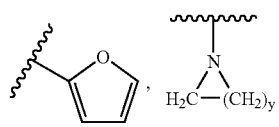

wherein y is from 3 to 5,

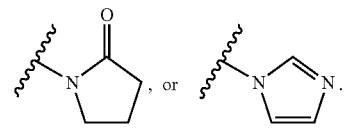

In these examples, $R^1$ is independently selected as defined above. These are merely representative examples of the definitions of the $Y^1$ and $Y^2$ substitutents, and are not intended to be exclusive.

It is also noted that $AY^1$ together, and $DY^2$ together, can also represent a wide range of chemical moieties bonded to the triazine core such as halide or secondary amino groups such as

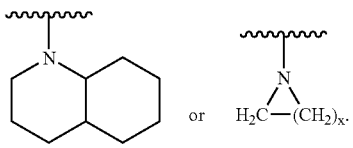

In the latter cases, the amino substituent groups are termed secondary amino groups, however upon bonding to the triazine core, the amino nitrogens become tertiary amine moieties. Examples of $AY^1$ together and $DY^2$ together include, but are not limited to: halide;

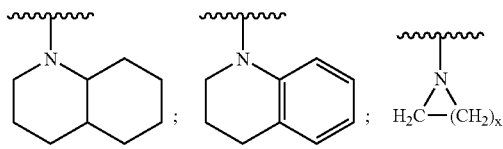

wherein x is from 3 to 5;

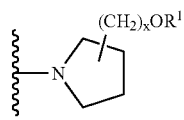

wherein x is from 0 to 6;

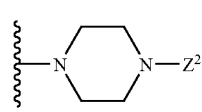

wherein $Z^2$ is selected from $R^1$,

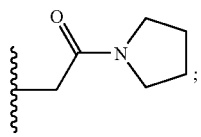

$C(O)R^1$, $C(O)OR^1$, pyridinyl, aryl,

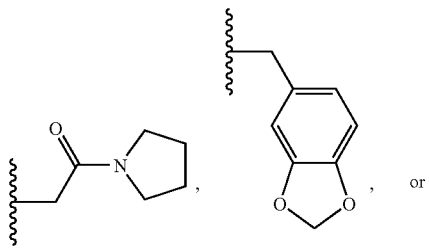 or

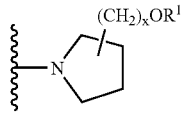

wherein x is from 0 to 6, and wherein $R^1$ is independently defined above. These are also merely representative examples of ions of these substitutents, and are not intended to be exclusive.

Representative compounds in accordance with the present invention are presented in Table 1. This table is not intended to be exclusive of the compounds of the present invention, but rather exemplary of the triazine compounds that are encompassed by this invention.

TABLE 1

| COMPOUND NUMBER | COMPOUND NAME |
|---|---|
| 1 | $N^2$-(4-bromo-1-naphthyl)-$N^4$-cycloheptyl-$N^6$-[(1-ethyl-2-pyrrolidinyl)methyl]-1,3,5-triazine-2,4,6-triamine |
| 2 | $N^2$-(4-chloro-1-naphthyl)-$N^4$-cycloheptyl-$N^6$-[(1-ethyl-2-pyrrolidinyl)methyl]-1,3,5-triazine-2,4,6-triamine |
| 3 | $N^2$-cycloheptyl-$N^4$-[(1-ethyl-2-pyrrolidinyl)methyl]-$N^6$-(3-quinolinyl)-1,3,5-triazine-2,4,6-triamine |
| 4 | $N^2$-cycloheptyl-$N^4$-[(1-ethyl-2-pyrrolidinyl)methyl]-$N^6$-(6-quinolinyl)-1,3,5-triazine-2,4,6-triamine |
| 5 | $N^2$-cycloheptyl-$N^4$-[(1-ethyl-2-pyrrolidinyl)methyl]-$N^6$-(8-quinolinyl)-1,3,5-triazine-2,4,6-triamine |
| 6 | $N^2$-cycloheptyl-$N^4$-[(1-ethyl-2-pyrrolidinyl)methyl]-$N^6$-[1-(2-naphthyl)ethyl]-1,3,5-triazine-2,4,6-triamine |
| 7 | $N^2$-cycloheptyl-$N^4$-(3,4-dichlorophenyl)-$N^6$-[(1-ethyl-2-pyrrolidinyl)methyl]-1,3,5-triazine-2,4,6-triamine |
| 8 | $N^2$-cycloheptyl-$N^4$-(3,4-difluorophenyl)-$N^6$-[(1-ethyl-2-pyrrolidinyl)methyl]-1,3,5-triazine-2,4,6-triamine |
| 9 | $N^2$-cycloheptyl-$N^4$-[(1-ethyl-2-pyrrolidinyl)methyl]-$N^6$-[4-(trifluoromethoxy)phenyl]-1,3,5-triazine-2,4,6-triamine |
| 10 | $N^2$-cycloheptyl-$N^4$-[(1-ethyl-2-pyrrolidinyl)methyl]-$N^6$-(4-fluorophenyl)-1,3,5-triazine-2,4,6-triamine |
| 11 | 4-[(4-cycloheptylamino)-6-{[(1-ethyl-2-pyrrolidinyl)methyl]amino}-1,3,5-triazin-2-yl)-amino]benzonitrile |
| 12 | $N^2$-(4-chlorophenyl)-$N^4$-cycloheptyl-$N^6$-[(1-ethyl-2-pyrrolidinyl)methyl]-1,3,5-triazine-2,4,6-triamine |
| 13 | $N^2$-(4-bromophenyl)-$N^4$-cycloheptyl-$N^6$-[(1-ethyl-2-pyrrolidinyl)methyl]-1,3,5-triazine-2,4,6-triamine |
| 14 | Ethyl 4-[(4-(cycloheptylamino)-6-{[(1-ethyl-2-pyrrolidinyl)methyl]amino}-1,3,5-triazin-2-yl)-amino]benzoate |
| 15 | $N^2$-(1,1'-biphenyl-4-yl)-$N^4$-cycloheptyl-$N^6$-[(1-ethyl-2-pyrrolidinyl)methyl]-1,3,5-triazine-2,4,6-triamine |
| 16 | $N^2$-cycloheptyl-$N^4$-[(1-ethyl-2-pyrrolidinyl)methyl]-$N^6$-(3-fluorophenyl)-1,3,5-triazine-2,4,6-triamine |
| 17 | $N^2$-(3-chlorophenyl)-$N^4$-cycloheptyl-$N^6$-[(1-ethyl-2-pyrrolidinyl)methyl]-1,3,5-triazine-2,4,6-triamine |
| 18 | $N^2$-(3-bromophenyl)-$N^4$-cycloheptyl-$N^6$-[(1-ethyl-2-pyrrolidinyl)methyl]-1,3,5-triazine-2,4,6-triamine |
| 19 | Ethyl 3-[(4-(cycloheptylamino)-6-{[(1-ethyl-2-pyrrolidinyl)methyl]amino}-1,3,5-triazin-2-yl)-amino]benzoate |
| 20 | $N^2$-cycloheptyl-$N^4$-[(1-ethyl-2-pyrrolidinyl)methyl]-$N^6$-(2-fluorophenyl)-1,3,5-triazine-2,4,6-triamine |
| 21 | $N^2$-(2-chlorophenyl)-$N^4$-cycloheptyl-$N^6$-[(1-ethyl-2-pyrrolidinyl)methyl]-1,3,5-triazine-2,4,6-triamine |
| 22 | $N^2$-(2-bromophenyl)-$N^4$-cycloheptyl-$N^6$-[(1-ethyl-2-pyrrolidinyl)methyl]-1,3,5-triazine-2,4,6-triamine |
| 23 | $N^2$-(1,3-benzodioxol-5-yl)-$N^4$-cycloheptyl-$N^6$-[(1-ethyl-2-pyrrolidinyl)methyl]-1,3,5-triazine-2,4,6-triamine |

TABLE 1-continued

| COMPOUND NUMBER | COMPOUND NAME |
|---|---|
| 24 | $N^2$-cycloheptyl-$N^4$-(2,3-dihydro-1,4-benzodioxin-6-yl)-$N^6$-[(1-ethyl-2-pyrrolidinyl)methyl]-1,3,5-triazine-2,4,6-triamine |
| 25 | $N^2$-cycloheptyl-$N^4$-[4-(dimethylamino)phenyl]-$N^6$-[(1-ethyl-2-pyrrolidinyl)methyl]-1,3,5-triazine-2,4,6-triamine |
| 26 | $N^2$-[3-chloro-4-(diethylamino)phenyl]-$N^4$-cycloheptyl-$N^6$-[(1-ethyl-2-pyrrolidinyl)methyl]-1,3,5-triazine-2,4,6-triamine |
| 27 | $N^2$-cycloheptyl-$N^4$-[(1-ethyl-2-pyrrolidinyl)methyl]-$N^6$-[4-(4-morpholinyl)phenyl]-1,3,5-triazine-2,4,6-triamine |
| 28 | $N^2$-cycloheptyl-$N^4$-[(1-ethyl-2-pyrrolidinyl)methyl]-$N^6$-[4-(4-methyl-1-piperazinyl)phenyl]-1,3,5-triazine-2,4,6-triamine |
| 29 | N-{4-[(4-(cycloheptylamino)-6-{[(1-ethyl-2-pyrrolidinyl)methyl]amino}-1,3,5-triazin-2-yl)-amino]phenyl}acetamide |
| 30 | N-{3-[(4-(cycloheptylamino)-6-{[(1-ethyl-2-pyrrolidinyl)methyl]amino}-1,3,5-triazin-2-yl)-amino]phenyl}acetamide |
| 31 | $N^2$-cycloheptyl-$N^4$-[(1-ethyl-2-pyrrolidinyl)methyl]-$N^6$-(3-methoxyphenyl)-1,3,5-triazine-2,4,6-triamine |
| 32 | $N^2$-cycloheptyl-$N^4$-(4-ethoxyphenyl)-$N^6$-[(1-ethyl-2-pyrrolidinyl)methyl]-1,3,5-triazine-2,4,6-triamine |
| 33 | $N^2$-cycloheptyl-$N^4$-[(1-ethyl-2-pyrrolidinyl)methyl]-$N^6$-[4-(methylthio)phenyl]-1,3,5-triazine-2,4,6-triamine |
| 34 | $N^2$-cycloheptyl-$N^4$-[(1-ethyl-2-pyrrolidinyl)methyl]-$N^6$-(2-pyridinyl)-1,3,5-triazine-2,4,6-triamine |
| 35 | $N^2$-cycloheptyl-$N^4$-[(1-ethyl-2-pyrrolidinyl)methyl]-$N^6$-(2-methylphenyl)-1,3,5-triazine-2,4,6-triamine |
| 36 | $N^2$-cycloheptyl-$N^4$-[(1-ethyl-2-pyrrolidinyl)methyl]-$N^6$-(4-phenoxyphenyl)-1,3,5-triazine-2,4,6-triamine |
| 37 | $N^2$-cycloheptyl-$N^4$-[(1-ethyl-2-pyrrolidinyl)methyl]-$N^6$-(3-methylphenyl)-1,3,5-triazine-2,4,6-triamine |
| 38 | $N^2$-cycloheptyl-$N^4$-[(1-ethyl-2-pyrrolidinyl)methyl]-$N^6$-(4-methylphenyl)-1,3,5-triazine-2,4,6-triamine |
| 39 | 2-[(4-(cycloheptylamino)-6-{[(1-ethyl-2-pyrrolidinyl)methyl]amino}-1,3,5-triazin-2-yl)-amino]-4-methyl-3-thiophenecarboxamide |
| 40 | $N^2$-(4-chlorophenyl)-$N^4$-cycloheptyl-$N^6$-[(1-ethyl-2-pyrrolidinyl)methyl]-$N^2$-methyl-1,3,5-triazine-2,4,6-triamine |
| 41 | 3-[(4-(cycloheptylamino)-6-{[(1-ethyl-2-pyrrolidinyl)methyl]amino}-1,3,5-triazin-2-yl)-(phenyl)amino]propanenitrile |
| 42 | $N^2$-cycloheptyl-$N^4$-[(1-ethyl-2-pyrrolidinyl)methyl]-$N^6$-(4-methoxyphenyl)-$N^6$-methyl-1,3,5-triazine-2,4,6-triamine |
| 43 | $N^2$-cycloheptyl-$N^4$-(2,4-difluorophenyl)-$N^6$-[(1-ethyl-2-pyrrolidinyl)methyl]-$N^4$-methyl-1,3,5-triazine-2,4,6-triamine |
| 44 | [(4-(cycloheptylamino)-6-{[(1-ethyl-2-pyrrolidinyl)methyl]amino}-1,3,5-triazin-2-yl)(phenyl)amino]acetonitrile |
| 45 | $N^2$-(3-chlorophenyl)-$N^4$-cycloheptyl-$N^6$-[(1-ethyl-2-pyrrolidinyl)methyl]-$N^2$-methyl-1,3,5-triazine-2,4,6-triamine |
| 46 | $N^2$-cycloheptyl-$N^4$-[(1-ethyl-2-pyrrolidinyl)methyl]-$N^6$-methyl-$N^6$-[2-(trifluoromethyl)phenyl]-1,3,5-triazine-2,4,6-triamine |
| 47 | $N^2$-cycloheptyl-$N^4$-[(1-ethyl-2-pyrrolidinyl)methyl]-$N^6$-methyl-$N^6$-[4-(trifluoromethoxy)phenyl]-1,3,5-triazine-2,4,6-triamine |
| 48 | $N^2$-(3-chloro-4-methoxyphenyl)-$N^4$-cycloheptyl-$N^6$-[(1-ethyl-2-pyrrolidinyl)methyl]-1,3,5-triazine-2,4,6-triamine |
| 49 | N-benzoyl-4-[(4-(cycloheptylamino)-6-{[(1-ethyl-2-pyrrolidinyl)methyl]amino}-1,3,5-triazin-2-yl)-amino]benzenesulfonamide |
| 50 | $N^2$-cycloheptyl-$N^4$-[(1-ethyl-2-pyrrolidinyl)methyl]-$N^6$-(2-naphthyl)-1,3,5-triazine-2,4,6-triamine |
| 51 | $N^2$-ethyl-$N^4$-[(1-ethyl-2-pyrrolidinyl)methyl]-$N^6$-(3-fluoro-4-methoxyphenyl)-1,3,5-triazine-2,4,6-triamine |
| 52 | $N^2$-(tert-butyl)-$N^4$-[(1-ethyl-2-pyrrolidinyl)methyl]-$N^6$-(3-fluoro-4-methoxyphenyl)-1,3,5-triazine-2,4,6-triamine |
| 53 | $N^2$-benzyl-$N^4$-[(1-ethyl-2-pyrrolidinyl)methyl]-$N^6$-(3-fluoro-4-methoxyphenyl)-1,3,5-triazine-2,4,6-triamine |
| 54 | $N^2$-cyclooctyl-$N^4$-[(1-ethyl-2-pyrrolidinyl)methyl]-$N^6$-(3-fluoro-4-methoxyphenyl)-1,3,5-triazine-2,4,6-triamine |
| 55 | $N^2$-cyclohexyl-$N^4$-[(1-ethyl-2-pyrrolidinyl)methyl]-$N^6$-(3-fluoro-4-methoxyphenyl)-1,3,5-triazine-2,4,6-triamine |
| 56 | $N^2$-cyclopentyl-$N^4$-[(1-ethyl-2-pyrrolidinyl)methyl]-$N^6$-(3-fluoro-4-methoxyphenyl)-1,3,5-triazine-2,4,6-triamine |
| 57 | $N^2$-[(1-ethyl-2-pyrrolidinyl)methyl]-$N^4$-(3-fluoro-4-methoxyphenyl)-6-(1-pyrrolidinyl)-1,3,5-triazine-2,4-diamine |
| 58 | $N^2$-[(1-ethyl-2-pyrrolidinyl)methyl]-$N^4$-(3-fluoro-4-methoxyphenyl)-$N^6$-hexahydro-1H-azepin-1-yl-1,3,5-triazine-2,4-diamine |
| 59 | $N^2$-[(1-ethyl-2-pyrrolidinyl)methyl]-$N^4$-(3-fluoro-4-methoxyphenyl)-$N^6$-octahydro-1(2H)-quinolinyl-1,3,5-triazine-2,4-diamine |

TABLE 1-continued

| COMPOUND NUMBER | COMPOUND NAME |
|---|---|
| 60 | $N^2$-[(1-ethyl-2-pyrrolidinyl)methyl]-$N^4$-(3-fluoro-4-methoxyphenyl)-$N^6$-(4-methylcyclohexyl)-1,3,5-triazine-2,4,6-triamine |
| 61 | $N^2$-(1-ethyl-pyrrolidin-2-ylmethyl]-$N^4$-(3-fluoro-4-methoxyphenyl)-6-((S)-2-methoxymethyl-pyrrolidin-1-yl)-1,3,5-triazine-2,4-diamine |
| 62 | $N^2$-[(1-ethyl-2-pyrrolidinyl)methyl]-$N^4$-(3-fluoro-4-methoxyphenyl)-6-(4-methyl-1-piperazinyl)-1,3,5-triazine-2,4-diamine |
| 63 | 6-(4-acetyl-1-piperazinyl)-$N^2$-[(1-ethyl-2-pyrrolidinyl)methyl]-$N^4$-(3-fluoro-4-methoxyphenyl)-1,3,5-triazine-2,4-diamine |
| 64 | Ethyl 4-{4-{[[(1-ethyl-2-pyrrolidinyl)methyl]amino}-$N^6$-[(3-fluoro-4-methoxyphenyl)amino]-1,3,5-triazin-2-yl}-1-piperazinecarboxylate |
| 65 | $N^2$-(cyclohexylmethyl)-$N^4$-[(1-ethyl-2-pyrrolidinyl)methyl]-$N^6$-(3-fluoro-4-methoxyphenyl)-1,3,5-triazine-2,4,6-triamine |
| 66 | $N^2$-[(1-ethyl-2-pyrrolidinyl)methyl]-$N^4$-(3-fluoro-4-methoxyphenyl)-$N^6$-(2-furylmethyl)-1,3,5-triazine-2,4,6-triamine |
| 67 | $N^2$-[(1-ethyl-2-pyrrolidinyl)methyl]-$N^4$-(3-fluoro-4-methoxyphenyl)-$N^6$-(2,2,2-trifluoroethyl)-1,3,5-triazine-2,4,6-triamine |
| 68 | $N^2$-[2-(dimethylamino)ethyl]-$N^4$-[(1-ethyl-2-pyrrolidinyl)methyl]-$N^6$-(3-fluoro-4-methoxyphenyl)-1,3,5-triazine-2,4,6-triamine |
| 69 | $N^2$-[(1-ethyl-2-pyrrolidinyl)methyl]-$N^4$-(3-fluoro-4-methoxyphenyl)-$N^6$-{4-[2-oxo-2-(1-pyrrolidinyl)ethyl]-1-piperazinyl}-1,3,5-triazine-2,4-diamine |
| 70 | $N^2,N^4$-bis[(1-ethyl-2-pyrrolidinyl)methyl]-$N^6$-(3-fluoro-4-methoxyphenyl)-1,3,5-triazine-2,4,6-triamine |
| 71 | $N^2$-[(1-ethyl-2-pyrrolidinyl)methyl]-$N^4$-(3-fluoro-4-methoxyphenyl)-$N^6$-[2-(1-piperidinyl)ethyl]-1,3,5-triazine-2,4,6-triamine |
| 72 | $N^6$-[4-(1,3-benzodioxol-5-ylmethyl)-1-piperazinyl]-$N^2$-[(1-ethyl-2-pyrrolidinyl)methyl]-$N^4$-(3-fluoro-4-methoxyphenyl)-1,3,5-triazine-2,4-diamine |
| 73 | $N^2$-[(1-ethyl-2-pyrrolidinyl)methyl]-$N^4$-(3-fluoro-4-methoxyphenyl)-$N^6$-[4-(2-pyridinyl)-1-piperazinyl]-1,3,5-triazine-2,4-diamine |
| 74 | 1-[3-({4-{[(1-ethyl-2-pyrrolidinyl)methyl]amino}-6-[(3-fluoro-4-methoxyphenyl)amino]-1,3,5-triazin-2-yl}amino)propyl]-2-pyrrolidinone |
| 75 | $N^2$-[(1-ethyl-2-pyrrolidinyl)methyl]-$N^4$-(3-fluoro-4-methoxyphenyl)-$N^6$-[3-(1H-imidazol-1-yl)propyl]-1,3,5-triazine-2,4,6-triamine |
| 76 | $N^2$-cycloheptyl-$N^4$-ethyl-$N^6$-(3-fluoro-4-methoxyphenyl)-1,3,5-triazine-2,4,6-triamine |
| 77 | $N^2$-(tert-butyl)-$N^4$-cycloheptyl-$N^6$-(3-fluoro-4-methoxyphenyl)-1,3,5-triazine-2,4,6-triamine |
| 78 | $N^2$-benzyl-$N^4$-cycloheptyl-$N^6$-(3-fluoro-4-methoxyphenyl)-1,3,5-triazine-2,4,6-triamine |
| 79 | $N^2$-cycloheptyl-$N^4$-cyclooctyl-$N^6$-(3-fluoro-4-methoxyphenyl)-1,3,5-triazine-2,4,6-triamine |
| 80 | $N^2$-cycloheptyl-$N^4$-cyclohexyl-$N^6$-(3-fluoro-4-methoxyphenyl)-1,3,5-triazine-2,4,6-triamine |
| 81 | $N^2$-cycloheptyl-$N^4$-cyclopentyl-$N^6$-(3-fluoro-4-methoxyphenyl)-1,3,5-triazine-2,4,6-triamine |
| 82 | $N^2$-cycloheptyl-$N^4$-(3-fluoro-4-methoxyphenyl)-6-(1-pyrrolidinyl)-1,3,5-triazine-2,4-diamine |
| 83 | $N^2$-cycloheptyl-$N^4$-(3-fluoro-4-methoxyphenyl)-6-hexahydro-1H-azepin-1-yl-1,3,5-triazine-2,4-diamine |
| 84 | $N^2$-cycloheptyl-$N^4$-(3-fluoro-4-methoxyphenyl)-6-octahydro-1(2H)-quinolinyl-1,3,5-triazine-2,4-diamine |
| 85 | $N^2$-cycloheptyl-$N^4$-(3-fluoro-4-methoxyphenyl)-$N^6$-(4-methylcyclohexyl)-1,3,5-triazine-2,4,6-triamine |
| 86 | $N^2$-cycloheptyl-$N^4$-(3-fluoro-4-methoxyphenyl)-6-[(2S)-2-(methoxymethyl)-1-pyrrolidinyl]-1,3,5-triazine-2,4-diamine |
| 87 | $N^2$-cycloheptyl-$N^4$-(3-fluoro-4-methoxyphenyl)-6-(4-methyl-1-piperazinyl)-1,3,5-triazine-2,4-diamine |
| 88 | 6-(4-acetyl-1-piperazinyl)-$N^2$-cycloheptyl-$N^4$-(3-fluoro-4-methoxyphenyl)-1,3,5-triazine-2,4-diamine |
| 89 | ethyl-4-{4-(cycloheptylamino)-6-[(3-fluoro-4-methoxyphenyl)amino]-1,3,5-triazin-2-yl}-1-piperazinecarboxylate |
| 90 | $N^2$-cycloheptyl-$N^4$-(cyclohexylmethyl)-$N^6$-(3-fluoro-4-methoxyphenyl)-1,3,5-triazine-2,4,6-triamine |
| 91 | $N^2$-cycloheptyl-$N^4$-(3-fluoro-4-methoxyphenyl)-$N^6$-(2-furanylmethyl)-1,3,5-triazine-2,4,6-triamine |
| 92 | $N^2$-cycloheptyl-$N^4$-(3-fluoro-4-methoxyphenyl)-$N^6$-(2,2,2-trifluoroethyl)-1,3,5-triazine-2,4,6-triamine |
| 93 | $N^2$-cycloheptyl-$N^4$-[2-(dimethylamino)ethyl]-$N^6$-(3-fluoro-4-methoxyphenyl)-1,3,5-triazine-2,4,6-triamine |
| 94 | $N^2$-cycloheptyl-$N^4$-(3-fluoro-4-methoxyphenyl)-6-{4-[2-oxo-(1-pyrrolidinyl)ethyl]-1-piperazinyl}-1,3,5-triazine-2,4-diamine |
| 95 | $N^2$-cycloheptyl-$N^4$-[(1-ethyl-2-pyrrolidinyl)methyl]-$N^6$-(3-fluoro-4-methoxyphenyl)-1,3,5-triazine-2,4,6-triamine |

TABLE 1-continued

| COMPOUND NUMBER | COMPOUND NAME |
|---|---|
| 96 | $N^2$-cycloheptyl-$N^4$-(3-fluoro-4-methoxyphenyl)-$N^6$-[2-(1-piperidinyl)ethyl]-1,3,5-triazine-2,4,6-triamine |
| 97 | 6-[4-(1,3-benzodioxol-5-ylmethyl)1-piperazinyl]-$N^2$-cycloheptyl-$N^4$-(3-fluoro-4-methoxypenyl)-1,3,5-triazine-2,4-diamine |
| 98 | $N^2$-cycloheptyl-$N^4$-(3-fluoro-4-methoxyphenyl)-6-[4-(2-pyridinyl)-1-piperazinyl]-1,3,5-triazine-2,4-triamine |
| 99 | 1-[3-({4-(cycloheptylamino)-6-[(3-fluoro-4-methoxyphenyl)amino]-1,3,5-triazin-2-yl}amino)propyl]-2-pyrrolidinone |
| 100 | $N^2$-cycloheptyl-$N^4$-(3-fluoro-4-methoxyphenyl)-$N^6$-[3-(1H-imidazol-1-yl)propyl]-1,3,5-triazine-2,4,6-triamine |
| 101 | (3-Chloro-4-methoxy-phenyl)-(4,6-dichloro-[1,3,5]triazin-2-yl)-amine |
| 102 | 6-Chloro-N-(3-chloro-4-methoxy-phenyl)-N'-cyclohexylmethyl-[1,3,5]triazine-2,4-diamine |
| 103 | N-(3-Chloro-4-methoxy-phenyl)-N'-cyclohexylmethyl-N''-methyl-N''-(1-methyl-piperidin-4-yl)-[1,3,5]triazine-2,4,6-triamine |
| 104 | 6-Chloro-N-(3-chloro-4-methoxy-phenyl)-N'-(1-propyl-butyl)-[1,3,5]triazine-2,4-diamine |
| 105 | N-(3-Chloro-4-methoxy-phenyl)-N'-methyl-N'-(1-methyl-piperidin-4-yl)-N''-(1-propyl-butyl)-[1,3,5]triazine-2,4,6-triamine |
| 106 | N-(3-Chloro-4-methoxy-phenyl)-N'-isopropyl-N''-methyl-N''-(1-methyl-piperidin-4-yl)-[1,3,5]triazine-2,4,6-triamine |
| 107 | $N^2$-(3-chloro-4-methoxy-phenyl)-$N^4$-isopropyl-$N^6$-methyl-$N^6$-piperidin-4-yl-1,3,5-triazine-2,4,6-triamine |
| 108 | 5-{4-(3-Chloro-4-methoxy-phenylamino)-6-[methyl-(1-methyl-piperidin-4-yl)-amino]-[1,3,5]triazin-2-ylamino}-pentan-1-ol |
| 109 | 5-[4-(3-chloro-4-methoxy-phenylamino)-6-(methyl-piperidin-4-yl-amino)-1,3,5-triazin-2-ylamino]-pentan-1-ol |
| 110 | N-Butyl-6-chloro-N'-(3-chloro-4-methoxy-phenyl)-N-propyl-[1,3,5]triazine-2,4-diamine |
| 111 | N-Butyl-N'-(3-chloro-4-methoxy-phenyl)-N''-methyl-N''-(1-methyl-piperidin-4-yl)-N-propyl-[1,3,5]triazine-2,4,6-triamine |
| 112 | $N^2$-Butyl-$N^4$-(3-chloro-4-methoxy-phenyl)-$N^6$-methyl-$N^6$-piperidin-4-yl-$N^2$-propyl-1,3,5-triazine-2,4,6-triamine |
| 113 | 2,4-Dichloro-6-cyclohexylmethoxy-[1,3,5]triazine |
| 114 | (4-Chloro-6-cyclohexylmethoxy-[1,3,5]triazin-2-yl)-(3-fluoro-4-methoxy-phenyl)-amine |
| 115 | 6-Cyclohexylmethoxy-N,N'-bis-(3-fluoro-4-methoxy-phenyl)-1,3,5-triazine-2,4-diamine |
| 116 | 6-Cyclohexylmethoxy-N-(1-ethyl-pyrrolidin-2-ylmethyl)-N'-(3-fluoro-4-methoxy-phenyl)-[1,3,5]triazine-2,4-diamine |
| 117 | (4-Chloro-6-cyclohexylmethoxy-[1,3,5]triazin-2-yl)-(3-chloro-4-methoxy-phenyl)-amine |
| 118 | N,N'-Bis-(3-chloro-4-methoxy-phenyl)-6-cyclohexylmethoxy-1,3,5-triazine-2,4-diamine |
| 119 | N-(3-Chloro-4-methoxy-phenyl)-6-cyclohexylmethoxy-N'-methyl-N'-(1-methyl-piperidin-4-yl)-[1,3,5]triazine-2,4-diamine |
| 120 | 6-Chloro-N,N''-bis-(3-chloro-4-methoxy-phenyl)-[1,3,5]triazine-2,4-diamine |
| 121 | N,N'-Bis-(3-chloro-4-methoxy-phenyl)-N''-methyl-N''-(1-methyl-piperidin-4-yl)-[1,3,5]triazine-2,4,6-triamine |
| 122 | N,N'-Bis-(3-chloro-4-methoxy-phenyl)-N''-cycloheptyl-[1,3,5]triazine-2,4,6-triamine |
| 123 | N-(3-Bromo-4-methoxy-phenyl)-N'-cycloheptyl-N''-methyl-N''-(1-methyl-piperidin-4-yl)-[1,3,5]triazine-2,4,6-triamine |
| 124 | (4,6-Dichloro-[1,3,5]triazin-2-yl)-(3-fluoro-4-methoxy-phenyl)-amine |
| 125 | 6-Chloro-N-cyclohexylmethyl-N'-(3-fluoro-4-methoxy-phenyl)-[1,3,5]triazine-2,4-diamine |
| 126 | N-Cyclohexylmethyl-N'-(1-ethyl-pyrrolidin-2-ylmethyl)-N''-(3-fluoro-4-methoxy-phenyl)-[1,3,5]triazine-2,4,6-triamine |
| 127 | 6-Chloro-N-cycloheheptyl-N'-(3-fluoro-4-methoxy-phenyl)-[1,3,5]triazine-2,4-diamine |
| 128 | N-Cycloheptyl-N'-(3-fluoro-4-methoxy-phenyl)-6-pyrrolidin-1-yl-[1,3,5]triazine-2,4-diamine |
| 129 | N-Cycloheptyl-N'-ethyl-N''-(3-fluoro-4-methoxy-phenyl)-[1,3,5]triazine-2,4-diamine |
| 130 | N-Cycloheptyl-N'-(1-ethyl-pyrrolidin-2-ylmethyl)-N''-(3-fluoro-4-methoxy-phenyl)-[1,3,5]triazine-2,4,6-triamine |
| 131 | 2-[4-chloro-6-(3-chloro-4-methoxy-phenylamino)-[1,3,5]triazin-2-ylamino]-propane-1,3-diol |
| 132 | 2-{4-(3-chloro-4-methoxy-phenylamino)-6-[methyl-(1-methyl-piperidin-4-yl)-amino]-[1,3,5]triazin-2-ylamino}-propane-1,3-diol |
| 133 | 6-Chloro-N-(3-chloro-4-methoxy-phenyl)-N'-cycloheptyl-[1,3,5]triazine-2,4-diamine |
| 134 | N-(1-benzyl-piperidin-4-yl)-N'-(3-chloro-4-methoxy-phenyl)-N''-cycloheptyl-[1,3,5]-2,4,6-triamine |

TABLE 1-continued

| COMPOUND NUMBER | COMPOUND NAME |
|---|---|
| 135 | $N^2$-(3-chloro-4-methoxy-phenyl)-$N^4$-cycloheptyl-$N^6$-piperidin-4-yl-1,3,5-triazine-2,4,6-triamine |
| 136 | $N^2$-(3-chloro-4-methoxy-phenyl)-$N^4$-cycloheptyl-$N^6$-(1-ethyl-pyrrolidin-2-ylmethyl)-1,3,5-triazine-2,4,6-triamine |
| 137 | N-(3-Chloro-4-methoxy-phenyl)-N'-cycloheptyl-N''-methyl-N''-(1-methyl-piperidin-4-yl)-[1,3,5]triazine-2,4,6-triamine |
| 138 | 2-chloro-4-{4-cycloheptylamino-6-[methyl-(1-methyl-piperidin-4-yl-amino]-1,3,5-triazin-2-ylamino}-phenol |
| 139 | $N^2$-cycloheptyl-$N^4$-((S)-1-ethyl-pyrrolidin-2-ylmethyl)-$N^6$-(3-fluoro-4-methoxyphenyl)-1,3,5-triazine-2,4,6-triamine |
| 140 | $N^2$-cycloheptyl-$N^4$-((R)-1-ethyl-pyrrolidin-2-ylmethyl)-$N^6$-(3-fluoro-4-methoxyphenyl)-1,3,5-triazine-2,4,6-triamine |
| 141 | $N^2$-cyclohexylmethyl-$N^4$-((S)-1-ethyl-pyrrolidin-2-ylmethyl)-$N^6$-(3-fluoro-4-methoxyphenyl)-1,3,5-triazine-2,4,6-triamine |
| 142 | $N^2$-cyclohexylmethyl-$N^4$-((R)-1-ethyl-pyrrolidin-2-ylmethyl)-$N^6$-(3-fluoro-4-methoxyphenyl)-1,3,5-triazine-2,4,6-triamine (42, Scheme 23) |
| 143 | ({4-cycloheptylamino-6-[((S)-1-ethyl-pyrrolidin-2-ylmethyl)-amino]-1,3,5-triazin-2-yl}-phenyl-amino)-acetonitrile (43, Scheme 24) |
| 144 | ({4-cycloheptylamino-6-[((R)-1-ethyl-pyrrolidin-2-ylmethyl)-amino]-1,3,5-triazin-2-yl}-phenyl-amino)-acetonitrile |
| 145 | $N^2$-[(1-ethyl-2-pyrrolidinyl]-$N^4$-(3-fluoro-4-methoxyphenyl)-6-[(S)-2-(methoxymethyl)-1-pyrrolidinyl]-1,3,5-triazine-2,4-diamine |
| 146 | $N^2$-(3-chloro-4-methoxy-phenyl)-$N^4$-cycloheptyl-$N^6$-methyl-$N^6$-piperidin-4-yl-1,3,5-triazine-2,4,6-triamine |
| 147 | 4-(3-Chloro-4-methoxy-phenylamino)-6-cycloheptylamino-1,3,5-triazin-2-ol |
| 148 | N-(1-Aza-bicyclo[2.2.2]oct-3-yl)-N'-(3-chloro-4-methoxy-phenyl)-N''-)1-ethyl-pyrrolidin-2-ylmethyl)-[1,3,5]triazine-2,4,6-triamine |
| 149 | $N^2$-(3-chloro-4-diethylamino-phenyl)-$N^4$-cycloheptyl-$N^6$-(1-ethyl-pyrrolidin-2-ylmethyl)-1,3,5-triazine-2,4,6-triamine |
| 150 | $N^2$-cycloheptyl-$N^4$-(2-dimethylamino-ethyl)-$N^6$-(3-fluoro-4-methoxy-phenyl)-1,3,5-triazine-2,4,6-triamine |
| 151 | ({4-cycloheptylamino-6-[1-ethyl-pyrrolidin-2-ylmethyl)-amino]-1,3,5-triazin-2-yl}-phenyl-amino)-acetonitrile |
| 152 | N-Azepan-1-yl-6-chloro-N'-(3-chloro-4-methoxy-phenyl)-[1,3,5]triazine-2,4-diamine |
| 153 | N''-(3-chloro-4-methoxy-phenyl)-N,N'-bis-perhydro-azepin-1-yl-1,3,5-triazine-2,4,6-triamine |
| 154 | N-Azepan-1-yl-N'-(3-chloro-4-methoxy-phenyl)-N''-(1-methyl-piperidin-4-yl)-[1,3,5]triazine-2,4,6-triamine |
| 155 | $N^4$-(3-chloro-4-methoxy-phenyl)-$N^6$-methyl-$N^2$-perhydro-azepin-1-yl-$N^6$-piperidin-4-yl-1,3,5-triazine-2,4,6-triamine |
| 156 | N,N'-di-n-propyl-N''-(3-fluoro-4-methoxy-phenyl)-1,3,5-triazine-2,4,6-triamine |
| 157 | N,N'-dicyclopropyl-N''-(3-fluoro-4-methoxy-phenyl)-1,3,5-triazine-2,4,6-triamine |
| 158 | $N^2$-Cycloheptyl-$N^4$-(3-fluoro-4-methoxy-phenyl)-$N^6$-methyl-$N^6$-(1-methyl-piperidin-4-yl)-1,3,5-triazine-2,4,6-triamine |
| 159 | $N^2$-Cycloheptyl-$N^4$-(3-fluoro-4-methoxy-phenyl)-$N^6$-methyl-$N^6$-piperidin-4-yl-1,3,5-triazine-2,4,6-triamine |
| 160 | $N^2$-cycloheptyl-$N^4$-(3-fluoro-4-methoxyphenyl)-$N^6$-methyl-$N^6$-(1-methyl-piperidin-4-yl)-1,3,5-triazine-2,4,6-triamine, hydrogen chloride salt |
| 161 | [N-(3-Chloro-4-methoxy-phenyl)-N'-cycloheptyl-N''-methyl-N''-(1-methyl-piperidin-4-yl)-[1,3,5]trizaine-2,4,6-triamine, hydrogen chloride salt |
| 162 | $N^2$-(3-chloro-4-diethylamino-phenyl)-$N^4$-cycloheptyl-$N^6$-(1-ethyl-pyrrolidin-2-ylmethyl)-1,3,5-triazine-2,4,6-triamine |
| 163 | $N^2$-(3-chloro-4-diethylamino-phenyl)-$N^4$-cycloheptyl-$N^6$-(1-ethyl-pyrrolidin-2-ylmethyl)-1,3,5-triazine-2,4,6-triamine hydrogen chloride salt |
| 164 | $N^2$-cycloheptyl-$N^4$-(1-ethyl-pyrrolidin-2-ylmethyl)-$N^6$-(3-fluoro-4-methoxyphenyl)-1,3,5-triazine-2,4,6-triamine hydrogen chloride salt |
| 165 | $N^2$-(cyclohexylmethyl)-$N^4$-[(1-ethyl-2-pyrrolidinyl)methyl]-$N^6$-(4-fluoro-3-methoxyphenyl)-1,3,5-triazine-2,4,6-triamine hydrogen chloride salt |
| 166 | ({4-cycloheptylamino-6-[(1-ethyl-pyrrolidin-2-ylmethyl)-amino]-1,3,5-triazin-2-yl}-phenyl-amino)-acetonitrile hydrogen chloride salt |
| 167 | $N^2$-cycloheptyl-$N^4$-(3-fluoro-4-methoxy-phenyl)-$N^6$-methyl-$N^6$-(1-methyl-piperidin-4-yl)-1,3,5-triazine-2,4,6-triamine maleate salt |
| 168 | $N^2$-cycloheptyl-$N^4$-(3-fluoro-4-methoxy-phenyl)-$N^6$-methyl-$N^6$-(1-methyl-piperidin-4-yl)-1,3,5-triazine-2,4,6-triamine citrate salt |
| 169 | $N^2$-cycloheptyl-$N^4$-(3-fluoro-4-methoxy-phenyl)-$N^6$-methyl-$N^6$-(1-methyl-piperidin-4-yl)-1,3,5-triazine-2,4,6-triamine succinate salt |

TABLE 1-continued

| COMPOUND NUMBER | COMPOUND NAME |
|---|---|
| 170 | N-(3-Bromo-4-methoxy-phenyl)-N'-cycloheptyl-N''-methyl-N''-(1-methyl-piperidin-4-yl)-[1,3,5]triazine-2,4,6-triamine hydrogen chloride salt |

In general terms, the compositions in accordance with the present invention also comprise tris(amino) triazine compounds of the following structure:

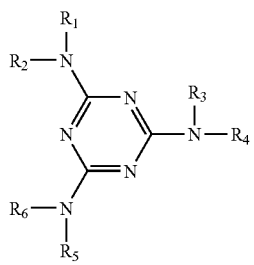

wherein $R_1$ to $R_6$ represent H, alkyl, aryl, alkenyl, alkynyl, aralkyl, aralkenyl, aralkynyl, cycloalkyl, cycloalkenyl, heteroalkyl, heteroaryl, halide, alkoxy, aryloxy, alkylthio, arylthio, silyl, siloxy, amino, alkylamino, dialkylamino and the like, including straight or branched chain derivatives thereof, cyclic derivatives thereof, substituted derivatives thereof, heteroatom derivatives thereof, heterocyclic derivatives thereof, functionalized derivatives thereof, salts thereof, isomers thereof, or combinations thereof.

For example, a typical substituent $R_1$ to $R_6$ is a substituted alkyl, in which the substituent is a heterocyclic derivative. Examples of nitrogen-containing heterocyclic moieties include, but are not limited to groups such as pyridinyl (derived from pyridine, bonded through a ring carbon), piperidinyl (derived from piperidine and bonded through the ring nitrogen atom or a ring carbon), and pyrrolidinyl (derived from pyrrolidine and bonded through the ring nitrogen atom or a ring carbon).

Examples of substituted or functionalized derivatives of $R_1$ to $R_6$ include, but are not limited to, moieties containing substituents such as acyl, formyl, hydroxy, acyl halide, amide, amino, azido, acid, alkoxy, aryloxy, halide, carbonyl, ether, ester, thioether, thioester, nitrile, alkylthio, arylthio, sulfonic acid and salts thereof, thiol, alkenyl, alkynyl, nitro, imine, imide, alkyl, aryl, combinations thereof, and the like. Moreover, in the case of alkylated derivatives of the recited moieties, the alkyl substitutent may be pendant to the recited chemical moiety, or used for bonding to the amine nitrogen through the alkyl substituent.

Examples of chemical moieties $R_1$ to $R_6$ of the present invention further include, but are not limited to: H; methyl; ethyl; propyl; butyl; pentyl; hexyl; heptyl; octyl; ethenyl; propenyl; butenyl; ethynyl; propynyl; butynyl; cyclobutyl; cyclopentyl; cyclohexyl; cyclobutenyl; cyclopentenyl; cyclohexenyl; phenyl; tolyl; xylyl; benzyl; naphthyl; pyridinyl; furanyl; tetrahydro-1-napthyl; piperidinyl; indolyl; indolinyl; pyrrolidinyl; 2-(methoxymethyl) pyrrolidinyl; piperazinyl; quinolinyl; quinolyl; alkylated-1,3-dioxolane; triazinyl; morpholinyl; phenyl pyrazolyl; indanyl; indonyl pyrazolyl; thiadiazolyl; rhodaninyl; thiolactonyl; dibenzofuranyl; benzothiazolyl; homopiperidinyl; thiazolyl; quinonuclidinyl; isoxazolidinonyl; any isomers, derivatives, or substituted analogs thereof; or any substituted or unsubstituted chemical groups such as alcohol, ether, thiol, thioether, tertiary amine, secondary amine, primary amine, ester, thioester, carboxylic acid, diol, diester, acrylic acid, acrylic ester, methionine ethyl ester, benzyl-1-cysteine ethyl ester, imine, aldehyde, ketone, amide, or diene.

Further examples of chemical moieties $R_1$ to $R_6$ of this invention include, but are not limited to, the following species or substituted or alkylated derivatives of the following species, covalently bonded to the amine nitrogen: furan; tetrahydrofuran; indole; piperazine; pyrrolidine; pyrrolidinone; pyridine; quinoline; anthracene; tetrahydroquinoline; naphthalene; pyrazole; imidazole; thiophene; pyrrolidine; morpholine; and the like. One feature of the recited species or substituted or alkylated derivatives of these species, is that they may be covalently bonded to the amine nitrogen in any fashion, including through the pendant substituent or alkyl group, through the heteroatom as appropriate, or through a ring atom as appropriate, as understood by one of ordinary skill in the art.

The chemical moieties $R_1$ to $R_6$ of the present invention also include, but are not limited to, cyclic alkanes and alkenes and include bridged and non-bridged rings. Examples of bridged rings include, but are not limited to, groups such as norbornyl; norbonadienyl, adamantyl; 6-azabicyclo[3.2.1]octanyl; 3-azabicyclo[2.2.2]octanyl, and the like.

In one embodiment of the present invention, $NR_1R_2$, $NR_3R_4$, or $NR_5R_6$ are derived from a cyclic secondary amine. Examples of a cyclic amino chemical moiety of the present invention include, but are not limited to piperidine; 4-benzyl-piperidine; 3-piperidinemethanol; morpholine; 4-piperidinopiperidine; 1-(2-amino-methyl)-piperazine; decahydroquinoline; 1,2,3,4-tetrahydro-pyridoindole (either amine moiety); 3-amino-5-phenyl pyrazole; 3-aminopyrazole; histidinol; hexamethyleimine; 4-hydroxypiperidine; 2-piperidinemethanol; 1,3,3-trimethyl-6-azabicyclo[3.2.1]octane; 3-pyrrolidinol; 1-methylpiperazine; 2-ethyl-piperidine; 1,2,3,4-tetrahydroisoquinoline; 3-aminopyrrolidine; 2,6-dimethylmorpholine; 2,3,4-tetrahydroisoquinoline; 1,2,3,4-tetrahydroquinoline; 1-(2-methoxyphenyl) piperazine; 2,6-dimethylpiperazine (either amine moiety); iminodibenzyl; 5-methoxytryptamine; 4,4'-bipiperidine; 1-(2-hydroxyethyl) piperazine; 4-methylpiperidine; and the like.

Importantly, the general structure of the present invention encompasses all states of saturation of the substitutents shown, such as all ene, diene, triene, and yne derivatives of any substitutent. The general structure also encompasses all conformational isomers, regioisomers, and stereoisomers that may arise from a particular set of substitutents. The general structure also encompasses all enantiomers, diastereomers, and other optical isomers whether in enantiomeric or racemic forms, or mixtures of stereoisomers.

Preparation of the Focused Library of Compounds

Many of the compounds of this invention were prepared in a parallel synthetic procedure according to the methods described below. Examples of compounds prepared by the parallel synthesis techniques are provided in Table 2. These preparations involve reacting the individual amine compounds (monomers) with cyanuric chloride, which are also presented in Table 2, along with the chemical structures of compounds prepared by the parallel synthesis methods.

A library of compounds was synthesized according to the present invention to afford substituted $N^2,N^4,N^6$-tris(amino)-1,3,5-triazines, as follows. The design of the compound library was based primarily on structure 95 shown below. That is, the design of the $N^2,N^4,N^6$-tris(amino) triazines was focused so that only one of the pendant amino groups ($N^A$, $N^B$, or $N^C$ in the structure above) was changed during each synthesis, while the other two groups were held constant. The combination of the specific amines employed produced a library of compounds of novel composition. Initially, the library was developed using methyl-(1-methyl-piperidin-4-yl)-amine, holding the cycloheptyl and m-fluoroanisidyl groups constant (in structure 95 below). The synthesis of the triazines around methyl-(1-methyl-piperidin-4-yl)-amine was not optimized, and the amine was subsequently replaced with (1-ethyl-pyrrolidin-2-yl)-methylamine which provided a more tractable synthesis.

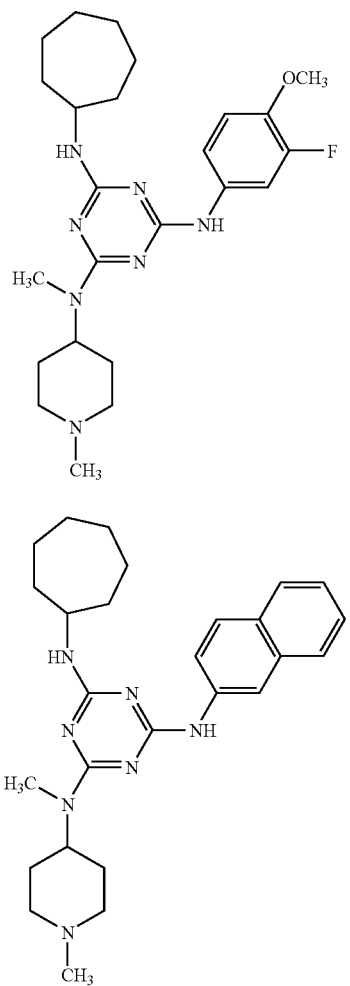

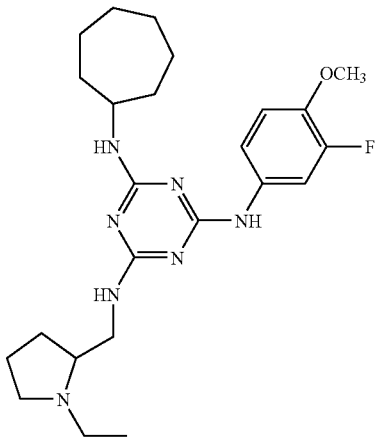

The library of $N^2,N^4,N^6$-tris(amino)-1,3,5-triazines was prepared based on the strategy of changing only one pendant amino group per synthesis, and based on the parent structure 95 shown above. The library was divided into three subgroups: Libraries I, II, and III (shown in Table 2). Library I includes compounds having unchanged $N^B$ and $N^C$ groups but different $N^A$ groups (6). The pendant amino group $N^A$ was changed according to the specific examples listed below. Library II includes compounds having unchanged $N^A$ and $N^C$ groups and different $N^B$ groups (7). Pendant amino group $N^B$ was changed according to the specific examples listed below. Library III includes compounds having unchanged $N^A$ and $N^B$ groups and different $N^C$ groups (8). The pendant amino group $N^C$ was changed according to the specific examples listed below.

The $N^2,N^4,N^6$-tris(amino)-1,3,5-triazine compound structures that are presented in Tables 2 and following were generated using ISIS-Draw™ version 2.4.0.20, and were generated with the option to display unspecified hydrogen atoms if not shown, however, not all hydrogen atoms were displayed in the structures shown. In all structures presented in any text, table, scheme or figure herein, any hydrogen atoms that are required for any atom to attain its usual valence, whether a carbon atom or a heteroatom, should be inferred if it is not specifically indicated in a structure.

One method of preparation of the compounds is shown in the scheme below. The compounds were prepared by reacting cyanuric chloride sequentially with monomers of primary or secondary amines to afford the desired 1,3,5-triazine derivatives [1,2,3,4]. Thus, the amine starting compounds that are used to react with cyanuric chloride are termed "monomers." The $N^2,N^4,N^6$-tris(amino-substituted)-1,3,5-triazines were prepared without the need for purification between each step of the synthesis, and the final product was isolated by standard procedures. Purification was accomplished using flash column chromatography as needed. It is within the skill of the art of organic synthesis to prepare, isolate and purify these organic compounds described herein, and to modify the syntheses shown. For example, it is possible to synthesize the compounds of the present invention by using an excess of any monomers of primary or secondary amines in any of the three steps shown in Scheme 1, such that the excess monomer, serves as both substituent for the triazine core, as well as a base, in which case i-Pr$_2$NEt base can be excluded.

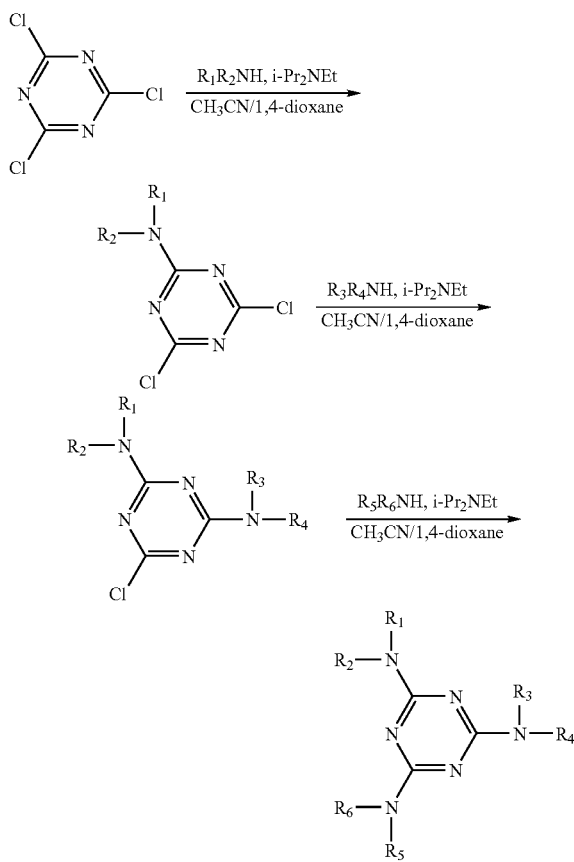

The pendant amino groups can be substituted by functional groups depicted as $R_1$ to $R_6$ groups in Scheme 1. The degree of functionality of a pendant amino group is determined by the structure and complexity of the amine monomer, and will affect the overall molecular diversity of the $N^2,N^4,N^6$-tris(amino-substituted)-1,3,5-triazines. A wide range of amine monomers may be used in this invention. Once bonded to the triazine core, the pendant amino groups can be described as secondary or tertiary substituted, depending on the degree of substitution at the nitrogen atom.

Table 2 presents charts of $N^2,N^4,N^6$-tris(amino)-1,3,5-triazine compounds of Libraries I–III of this invention, respectively, along with the amine precursor monomers used in the preparation of the compounds. General procedures and synthetic procedures are detailed in Example 1–5. The sequence in which each monomer is added in Scheme 1 is also presented in Table 2, where Monomer 1 is added first, Monomer 2 added second, and Monomer 3 is added third. While not intending to be bound by the following statement, it is believed that this order of addition is significant, because each synthetic stop necessarily involves the reaction of a monomer with a different triazine precursor. That is, monomer 1 reacts with cyanuric chloride, monomer 2 reacts with an amino dichloro(triazine), and monomer 3 reacts with a diamino chloro(triazine), as shown in Scheme 1. Thus, the order in which the monomers are employed is based on the general synthetic principle that the relative nucleophilicity and/or basicity of monomers 1–3 used in the synthetic scheme should generally increase from monomer 1 to monomer 3. This strategy permits the most nucleophilic and/or basic amine monomer to be reacted with the more sterically congested and presumably less-reactive diamino chloro (triazine), where its greater reactivity may assist the reaction proceeding to completion. In some cases, more than one order of monomer addition will provide the desired product, but the reaction sequences provided in Table 2 represents the optimum synthetic methods presently known.

Note that only in a general sense do the substituents indicated as $N^A$, $N^B$, and $N^C$ in the general structures above correspond with the actual $N^2,N^4,N^6$-nomenclature of the $N^2,N^4,N^6$-tris(amino)triazines. Because the order in which $N^2$, $N^4$, and $N^6$ substituents are assigned a 2-, 4-, or 6-position on the triazine core is dependent on the name of each amino group in the molecule, it is not always true that one particular amino group always appears as an $N^2$, $N^4$, or $N^6$ substituent, even when only a single substituent is being permuted at one position. For example, many of the compounds of Table 2 contain both cycloheptyl amino and 3-fluoro-4-methoxyphenyl amino groups, yet these groups take on different 2-, 4-, or 6-positions as a function of the name of the third substituent on the triazine core. As a result, the syntheses are discussed in terms of permuting amino groups at one pendant $N^A$, $N^B$, or $N^C$ position (rather than $N^2$, $N^4$, or $N^6$ position) in the structure above, while maintaining the other amino groups constant. Further, note that the compound names used in the Tables, Claims and specification were typically generated using Beilstein's Autonom™ 4.01.188, as well as the earlier CD "stand-alone" version of Beilstein's Autonom™, Autonom 2000. Typically, the compound names generated in this fashion were used, regardless of whether the compound name is an IUPAC, CAS, Beilstein, or other nomenclature. In each case however, the names unambiguously identify the compound specified.

A. Amino Groups Derived from Monomer 1

The sequence of monomer reaction with the triazine core, shown in Scheme 1, is Monomer 1, Monomer 2, and Monomer 3, added in that order. Thus, an amino dichloro (triazine) is formed from Monomer 1 and cyanuric chloride. For the first pendant amino group derived from Monomer 1 and cyanuric chloride, the Monomer 1 amine used and proposed included primarily, but not always, aryl amines, specifically phenyl, naphthyl, naphthylalkyl, quinolinyl, heteroaryl derivatives, and the like.

Specific examples of Monomer 1 used to produce the first pendant amino group in $N^2,N^4,N^6$-tris(amino-substituted)-1,3,5-triazines, and their [*Chemical Abstract Registry* numbers] include, but are not limited to, 4-chloroaniline [106-47-9], 3,4-ethylenedioxaniline [22013-33-8], 4-bromoanline [106-40-1], ethyl 4-aminobenzoate [94-09-7], 4-fluoro-aniline [371-40-4], 4-aminobiphenyl [92-67-1], 3-fluoroaniline [372-19-0], 2-aminonaphthalene [91-59-8], 3-chloroaniline [108-42-9], 4-morpholinoaniline [2524-67-6], 3-bromoaniline [591-19-5], 4'-aminoacetanilide [122-80-5], ethyl 3-aminobenzoate [582-33-2] m-aminoacetanilide [102-28-3], 2-fluoroaniline [348-54-9], m-anisidine [536-90-3], 2-chloroaniline [[95-51-2], p-phenetidine [156-43-4], 2-bromoaniline [615-36-1], 4-(methylthio)aniline [104-96-1], 3,4-(methylendioxy) aniline [14268-66-7], 2-aminopyridine [504-29-0], o-toluidine [95-53-4], 2,4-difluoro-N-methylaniline [138564-16-6], 4-phenoxyaniline [139-59-3], N-phenylglycinonitrile [3009-97-0], m-toluidine [108-44-1], 3-chloro-N-methylaniline [7006-52-2], p-toluidine 106-49-0], 2-(methylamino) benzotrifluoride, 4-chloro-N-methylaniline [932-96-7], 4-aminobenzonitrile [873-74-5], 3-anilinopropionitrile, [1075-76-9], tetracaine [94-24-6], N-methyl-p-anisidine [5961-59-1], 3-chloro-p-anisidine [5345-54-0], sulfabenzamide [127-71-9], 3-aminoquinoline [580-17-6], 1-amino-4-bromonaphthalene [2298-07-9], 6-aminoquinoline [580-15-

4] 1-amino-4-chloronaphthalene, [4684-12-2] 8-aminoquinoline [578-66-5], S-(−)-1-(2-naphthyl)-ethylamine [3082-62-0], 3,4-dichloroaniline [95-76-1], 3,4-difluoroaniline [3863-11-4], N-methyl-4-(trifluoromethoxy)aniline [41419-59-4], 4-(trifluoromethoxy)aniline [461-82-5], 2-amino-4-methylthiophene-3-carboxamide [4651-97-2], NN-diethyl-N'-phenethylenediamine [1665-59-4],1-(4-amino-phenyl)-4-methylpiperazine hydrochloride [94520-33-9], 2-chloro-N',N'-diethyl-1,4-phenylenediamine monohydrochloride [196938-07-5] 2-(dimethylamino)ethyl 4-aminobenzoate [11012-47-2], N,N-dimethyl-1,4-phenylenediamine [1665-95-4].

B. Amino Groups Derived from Monomer 2

The reaction of Monomer 2 with a preformed amino dichloro(triazine) provides an intermediate diamino chloro (triazine) in the synthesis of $N^2,N^4,N^6$-tris(amino-substituted)-1,3,5-triazines. Thus, for bonding the second pendant amino group to the triazine core, the Monomer 2 amine used and proposed included amines, specifically alkyl ($C_1$–$C_{12}$, straight chain or branched), cycloalkyl ($C_3$–$C_{10}$ ring size), azacyclo ($C_2$–$C_{10}$), and benzyl amine derivatives. The ring of the cycloalkyl and azacycloamine, and phenyl ring of the benzyl derivatives can be optionally substituted with one or more moieties, or a combination of moieties, such as, alkyl, alkenyl, alkynyl, phenyl, benzyl, halo, cyano, nitro, hydroxy, thioxy, alkoxy, aryloxy, haloalkyloxy, alkylthio, arylthio, amino, alkyl amino, aryl amino, acyl, carboxyl, amido, sulfonamido, sulfonyl, sulfate, sulfonic acid, morpholino, thiomorpholino, piperazinyl, pyridyl, thienyl, furanyl, pyrroyl, pyrazoyl, phosphate, phosphonic acid, phosphonate and the like. These groups can be represented in protected or unprotected forms used in standard organic synthesis.

In addition, any monomer described that has a stereocenter includes its enantiomers, diastereomers, and optical isomers whether in enantiomeric or racemic forms, or mixtures of stereoisomers. This is to include all of the 1,3,5-triazine derivatives and their stereoisomers presented herein that are formed as a result of using optically active, scalemic or racemic monomers.

Specific examples of Monomer 2 used to attach the second pendant amino group in the synthesis of $N^2,N^4,N^6$-tris(amino-substituted)-1,3,5-triazines, and their corresponding [Chemical Abstract Registry numbers] include, but are not limited to, ethylamine [75-04-07], cyclohexanemethylamine [3128-02-8] tert-butylamine [75-64-9], furfurylamine [617-89-0], benzylamine [100-46-9], 2,2,2-trifluroethylamine [753-90-2], cyclooctylamine [5452-37-9N,N-dimethylethylenediamine cyclohexylamine [108-91-8], cyclopentylamine [1003-03-8], 1-(2-aminoethyl)-piperidine [26116-12-1], 1-acetylpiperazine [13096-96-3], pyrrolidine [123-75-1], 1-piperonylpiperazine [32231-06-4], hexamethyleneimine [111-49-9], 1-(2-pyridyl)piperazine [34803-66-2], decahydroquinoline (cis/trans)[2051-28-7], 1-methylpiperazine [109-01-3], 1-(3-aminopropyl)-imidazole [5036-48-6], ethyl 1-piperazine carboxylate [120-43-4], 4-methylcyclohexylamine (cis/trans)[6321-23-9], 1-(3-aminopropyl)-2-pyrrolidine [7663-77-6], 2-(aminomethyl)-ethy-lpyrrolidine [26116-12-1], (+)-S-2-(methoxymethyl) pyrrolidine [63126-47-6], 1-(pyrrolidineo carbonylmethyl) piperazine [339890-45-4].

C. Amino Groups Derived from Monomer 3

The reaction of Monomer 3 with a preformed diamino chloro(triazine) provides the final step in the synthesis of $N^2$, $N^4$, $N^6$-tris(amino-substituted)-1,3,5-triazines. Thus, for bonding the third pendant amino group to the triazine core, the Monomer 3 used and proposed consisted of amines, specifically alkyl ($C_1$–$C_{12}$, straight chain or branched), cycloalkyl ($C_3$–$C_{10}$ ring size), azacyclo ($C_2$–$C_{10}$), and benzyl amine derivatives. The ring of these cycloalkyl-, azacycloamine, and phenyl ring of the benzyl derivatives can be optionally substituted with one or more moieties, or a combination of moieties such as groups as alkyl, alkenyl, alkynyl, phenyl, benzyl, halo, cyano, nitro, hydroxy, thioxy, alkoxy, aryloxy, haloalkyloxy, alkylthio, arylthio, amino, alkyl amino, aryl amino, acyl, carboxyl, amido, sulfonamido, sulfonyl, sulfate, sulfonic acid, morpholino, thiomorpholino, piperazinyl, pyridyl, thienyl, furanyl, pyrroyl, pyrazoyl, phosphate, phosphonic acid, phosphonate and the like.

In addition, any monomer described that has a stereocenter includes its enantiomers, diastereomers, and optical isomers whether in enantiomeric or racemic forms, or mixtures of stereoisomers. This is to include all of the 1,3,5-triazine derivatives and their stereoisomers presented herein that are formed as a result of using optically active, scalemic or racemic monomers.

Specific examples of Monomer 3 used to attach the third pendant amino group in the synthesis of $N^2,N^4,N^6$-tris(amino-substituted)-1,3,5-triazines, and their corresponding [Chemical Abstract Registry numbers] used in the synthesis of the $N^2$, $N^4$, $N^6$-tris(amino-substituted)-1,3,5-triazine derivatives include, but are not limited to, ethylamine [75-04-07], cyclohexanemethylamine [3128-02-08], tert-butylamine [75-64-9], furfurylamine [617-89-0], benzylamine [100-46-9], 2,2,2-trifluroethylamine [753-90-2], cyclooctylamine [5452-37-9], N,N-dimethylethylenediamine, cyclohexylamine [108-91-8], cyclopentylamine [1003-03-8], 1-(2-aminoethyl)-piperidine, [26116-12-1], 1-acetylpiperazine [13096-96-3], pyrrolidine [123-75-1], 1-piperonylpiperazine [32231-06-4], hexamethyleneimine [111-49-9], 1-(2-pyridyl)piperazine [34803-66-2], decahydroquinoline (cis/trans)[2051-28-7], 1-methylpiperazine [109-01-3], 1-(3-aminopropyl)-imidazole [5036-48-6], ethyl 1-piperazine carboxylate [120-43-4], 4-methylcyclohexylamine (cis/trans)[6321-23-9], 1-(3-aminopropyl)-2-pyrrolidine [7663-77-6], 2-(aminomethyl)-ethyl-pyrrolidine [26116-12-1], (+)-S-2-(methoxymethyl) pyrrolidine [63126-47-6], 1-(pyrrolidineocarbonylmethyl) piperazine [339890-45-4].

In addition to the parallel synthetic procedures used to prepare the compounds of Table 2, Table 1 also provides other exemplary triazine compounds of the present invention, which were synthesized individually rather than using parallel syntheses. The complete preparation and properties of these compounds are presented in the Examples, where details of the synthetic procedures used are provided. The synthetic procedures for these compounds involve both the substitution of chloride groups on cyanuric chloride, as well as various chemical modifications of these groups once bonded to the trizine core. In particular, this invention also encompasses salts of the neutral triazine compounds, as provided in the Examples and the Tables.

In another aspect of this invention, compounds of the present invention include, but are not limited to, those having the following formula:

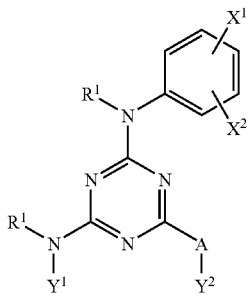

or an ene, a diene, a triene, or an yne derivative thereof; a saturated derivative thereof; a stereoisomer thereof; or a salt thereof;

wherein:

$R^1$ is in each occurrence independently selected from —H; linear or branched alkyl with up to 10 carbon atoms; or cycloalkyl with up to 10 carbon atoms;

$X^1$ is selected from m-F, m-Cl, m-Br, m-I, m-CN, m-NO$_2$, m-SO$_2$R$^1$, or m-SO$_2$OR$^1$, or $X^1$ and $X^2$ together is a fused benzene, pyridine, or dioxane ring;

$X^2$ is selected from p-OR$^1$, p-SR$^1$, p-NR$^1$$_2$, p-OM, or p-SM, wherein M is selected from Li, Na, K, Mg, or Ca;

$Y^1$ is selected from cycloalkyl with up to 10 carbon atoms; linear or branched alkyl with up to 10 carbon atoms; CH$_2$R$^2$, wherein R$^2$ is a cycloalkyl with up to 10 carbon atoms; or

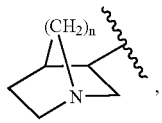

wherein n is 1 or 2;

AY$^2$ is selected from a halogen or OR$^1$, or

A is NR$^1$ and y$^2$ is selected from R$^1$,

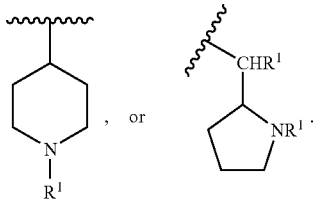

Compositions comprising compounds of this formula are also encompassed by the present invention, as well as mixtures or combinations of compounds of this formula.

In a further aspect of this invention, compounds of the present invention include, but are not limited to, those having the following formula:

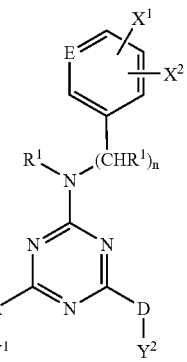

or an ene, a diene, a triene, or an yne derivative thereof; a saturated derivative thereof; a stereoisomer thereof; or a salt thereof;

wherein:
$R^1$ is in each occurrence independently selected from —H; linear or branched alkyl with up to 10 carbon atoms; cycloalkyl with up to 10 carbon atoms; or aryl;
E is CH or N;
n is an integer from 0 to 3;
$X^1$ is selected from —H, m-F, m-Cl, m-Br, m-I, m-CN, m-NO$_2$, m-SO$_2$R$^1$, or m-SO$_2$OR$^1$, or $X^1$ and $X^2$ together is a fused benzene or pyridine ring;
$X^2$ is selected from —H, o-Cl, o-Br, p-OR$^1$, p-SR$^1$, p-NR$^1$$_2$, p-F, p-Cl, p-Br, p-CF$_3$, p-C(O)OR$^1$, p-OM, or p-SM, wherein M is selected from Li, Na, K, Mg, or Ca;
A is selected from NR$^1$ or O, wherein Y$^1$ is selected from cycloalkyl with up to 10 carbon atoms, linear or branched alkyl with up to 10 carbon atoms, or

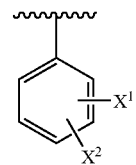

when A is NR$^1$, and wherein Y$^1$ is selected from R$^1$ or CH$_2$R$^1$ when A is O; or AY$^1$ is selected from a halogen,

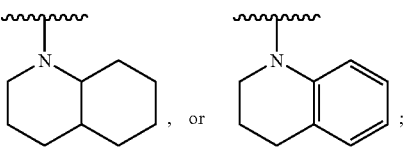

and
DY$^2$ is a halogen, or D is NR$^1$ and Y$^2$ is selected from

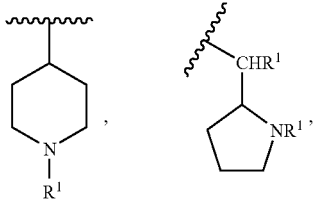

or (CHR$^1$)$_x$NR$^1$$_2$, wherein x is an integer from 1 to 6.

Compositions comprising compounds of this formula are also encompassed by the present invention, as well as mixtures or combinations of compounds of this formula.

In yet another aspect of this invention, compounds of the present invention include, but are not limited to, those having the following formula:

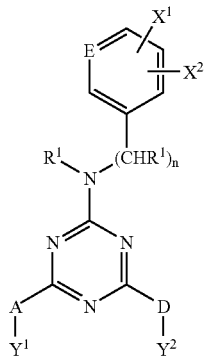

or an ene, a diene, a triene, or an yne derivative thereof, a saturated derivative thereof, a stereoisomer thereof, or a salt thereof;

wherein:

$R^1$ is in each occurrence independently selected from —H; linear or branched alkyl with up to 10 carbon atoms; cycloalkyl with up to 10 carbon atoms; aryl; or $(CH_2)_xCN$, wherein x is an integer from 0 to 6;

E is CH or N;

n is an integer from 0 to 3;

$X^1$ is selected from —H, m-F, m-Cl, m-Br, m-I, m-CN, m-NO$_2$, m-SO$_2$R$^1$, M-SO$_2$OR$^1$, m-NC(O)R$^1$, or o-F, or $X^1$ and $X^2$ together is a fused benzene, pyridine, or dioxane ring;

X2 is selected from —H, o-Cl, o-Br, o-CF$_3$, o-R$^1$, p-OR$^1$, p-SR$^1$, p-NR$^1_2$, p-F, p-Cl, p-Br, p-CF$_3$, p-CN, p-C(O)OR$^1$, p-NC(O)R$^1$, p-(4-morpholinyl), or p-(4-methyl-1-piperazinyl);

AY$^1$ is a halogen, or A is NR$^1$ or O and Y$^1$ is selected from cycloalkyl with up to 10 carbon atoms, cycloalkyl with up to 10 carbon atoms substituted with R$^1$, linear or branched alkyl with up to 10 carbon atoms, CH$_2$R$^1$, (CHR$^1$)$_y$OR$^1$, wherein y is an integer from 1 to 6,

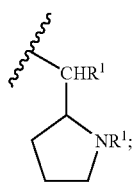

or AY$^1$ together are

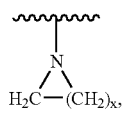

wherein x is an integer from 3 to 5; and

DY$^2$ is a halogen, or D is NR$^1$ and Y$^2$ is selected from

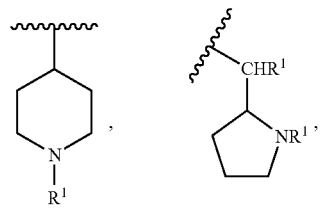

cycloalkyl with up to 10 carbon atoms, cycloalkyl with up to 10 carbon atoms substituted with R$^1$, linear or branched alkyl with up to 10 carbon atoms, CH$_2$R$^1$,

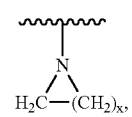

wherein x is an integer from 3 to 5,

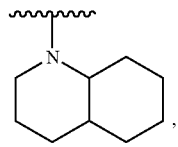

CH$_2$CF$_3$, (CHR$^1$)$_z$Z$^1$, wherein z is an integer from 1 to 6, and Z$^1$ is selected from NR$^1_2$,

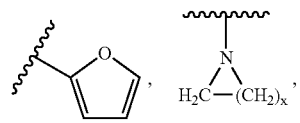

wherein x is an integer from 3 to 5,

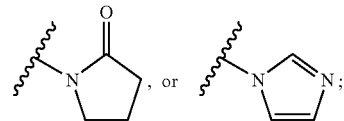

or NY$^2$R$^1$ together is selected from

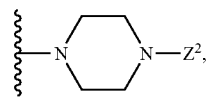

wherein Z$^2$ is selected from R$^1$, C(O)R$^1$, C(O)OR$^1$, pyridinyl, aryl,

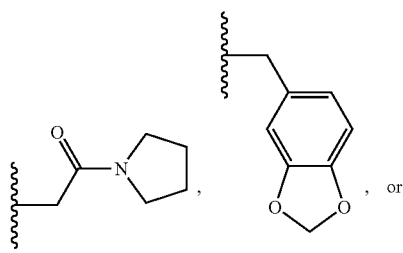

-continued

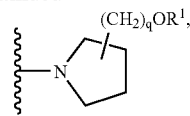

wherein q is an integer from 0 to 6.

Compositions comprising compounds of this formula are also encompassed by the present invention, as well as mixtures or combinations of compounds of this formula.

As an additional aspect of this invention includes compounds of the present invention include, but are not limited to, those having the following formula:

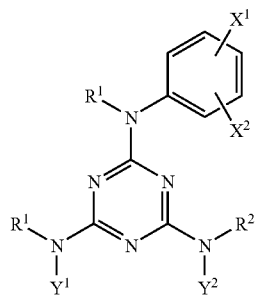

or an ene, a diene, a triene, or an yne derivative thereof; a saturated derivative thereof; a stereoisomer thereof; or a salt thereof;

wherein:

$R^1$ is in each occurrence independently selected from —H; linear or branched alkyl with up to 10 carbon atoms; or cycloalkyl with up to 10 carbon atoms;

$X^1$ is selected from H, r-F, m-Cl, m-Br, m-I, m-CN, m-NO$_2$, m-SO$_2$R$^1$, or m-SO$_2$OR$^1$;

$X^2$ is selected from o-R$^1$, p-OR$^1$, p-SR$^1$, p-NR$^1{}_2$, p-OM, or p-SM, wherein M is selected from Li, Na, K, Mg, or Ca;

$Y^1$ is selected from cycloalkyl with up to 10 carbon atoms or

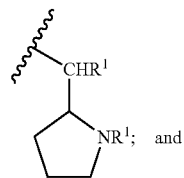

$Y^2$ is selected from linear or branched alkyl with up to 10 carbon atoms, cycloalkyl with up to 10 carbon atoms, or

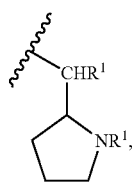

and $R^2$ is —H; or NY$^2$R$^2$ together is selected from

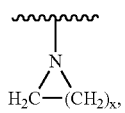

wherein x is an integer from 3 to

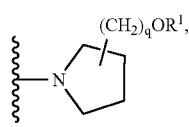

wherein q is an integer from 0 to 6, or

wherein $Z^2$ is selected from $R^1$ or

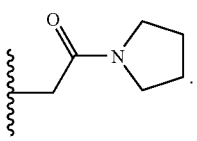

Compositions comprising compounds of this formula are also encompassed by the present invention, as well as mixtures or combinations of compounds of this formula.

In still another aspect of this invention, compounds of the present invention include, but are not limited to, those having the following structural formula:

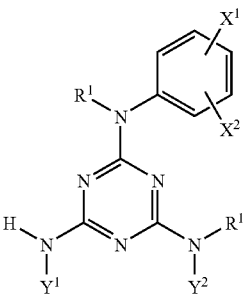

or an ene, a diene, a triene, or an yne derivative thereof; a saturated derivative thereof; a stereoisomer thereof; or a salt thereof;

wherein:

$R^1$ is in each occurrence independently selected from —H; linear or branched alkyl with up to 10 carbon atoms; or cycloalkyl with up to 10 carbon atoms;

$X^1$ is in each occurrence independently selected from —H, m-F, m-Cl, m-Br, m-I, m-CN, m-NO$_2$, m-SO$_2$R$^1$, or m-SO$_2$OR$^1$;

$X^2$ is in each occurrence independently selected from o-CH$_3$, p-OR$^1$, p-SR$^1$, p-NR$^1{}_2$, or p-OM or p-SM, wherein M is selected from Li, Na, K, Mg, or Ca;

$Y^1$ is selected from cycloalkyl with up to 10 carbon atoms;

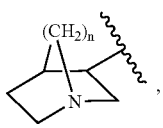

wherein n is 1 or 2; or

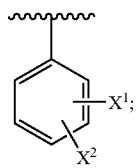

and
$Y^2$ is selected from

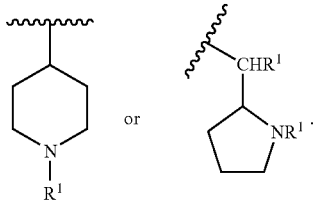

Compositions comprising compounds of this formula are also encompassed by the present invention, as well as mixtures or combinations of compounds of this formula.

These compounds and compositions presented above are not intended to be limiting, but merely representative of the chemical structures and formulas encompassed by the present invention.

Pharmaceutically Acceptable Salts

For the proposed $N^2,N^4,N^6$-tris(amino-substituted)-1,3,5-triazines, the terms "non-toxic, pharmaceutically acceptable salt" or "pharmaceutically acceptable salt" refer to a salt or complex of the 1,3,5-triazine compounds that retain or enhance the biologically activity of the compounds described in this invention. Examples of salts are those that are derived from the interaction of the 1,3,5-triazine compounds or derivatives and an inorganic (mineral acids) or organic acid, as well as compounds derived from deprotonating an amine nitrogen of the triamine derivatives.

Examples of inorganic acids include, but are not limited to, hydrochloric acid, hydrobromic acid, hydroiodic acid, hydrofluoric acid, nitric acid, nitrous acid, perchloric acid, chloric acid, hypochlorous acid, chlorous acid, phosphoric acid, sulfuric acid, sulfurous acid, and carbonic acid. Examples of organic acids include, but are not limited to acetic acid, benzene sulfonic acid, benzoic acid, butanoic acid, camphorsulfonic acid, citric acid, ethane sulfonic acid, fumaric acid, glutaric acid, 2-hydroxy acetic acid acids (derivatives where alkyl group is c=3–7 and hydroxy group is located accordingly), 2-hydroxy alkyl sulfonic acids (derivatives where alkyl group is c=3–7 and hydroxy group is located accordingly), lactic acid, maleic acid, malic acid malonic, methane sulfonic acid, naphthalene sulfonic acid, oxalic acid, palmitic acid, propanoic acid, phthalic acid, pyruvic acid, salicylic acid, stearic acid, succinic acid, tartaric acid, p-toluene sulfonic acid, and amino acids (e.g., alanine, N-acetylglycine, arginine, aspartic acid, glutamic acid, glycine, lysine, and phenylalanine).

Examples of salts described here include compounds that derive from a deprotonation reaction of an amine nitrogen of the triamine derivatives with a strong base, to form an amido salt, compound or complex. For example, these compounds include those that are derived from the interaction or chemical reaction of the 1,3,5-triazine compounds or derivatives acting as a Bronsted or Lewis acid and an inorganic or organic base to form an ionic and/or complexed species Examples of inorganic bases, include but not limited to, metallic bases or organometallic bases such as alkyllithiums or metal hydrides, where there is a metallic counterion include, but are not limited to, aluminum, barium, calcium, lithium, magnesium, potassium sodium, and zinc.

Examples of organic bases include, but are not limited to, alky and aryl amines as well as ammonia. Included in this description are salts formed from the combination or interaction/reaction of inorganic acids (e.g., Lewis acids) and metallic counterions and the 1,3,4-triazine compounds or derivatives acting as a Bronsted or Lewis base resulting in the formation of ionic and/or complexed species For all salts and complexes as described above, these are to include hydrated or solvated forms of the compounds.

Additionally, this invention also encompasses salts of these triazine derivatives that are non-toxic and pharmaceutically acceptable, such as quaternary ammonium salts, for example $[-N^+R_2R']X^-$, where the R and R' groups represent hydrogen or an organic group (such as alkyl, alkenyl, alkynyl, aryl, and the like) and the X group is a counter ion (halogen, hydroxide, alkoxide, thioalkoxide, or conjugate base of an organic or inorganic acid). For all salts and complexes as described above, these are to include hydrated or solvated forms of the compounds.

In another aspect, compounds and compositions in accordance with the present invention comprise analogs of the tris(amino) triazene compounds of the following general structure Ib:

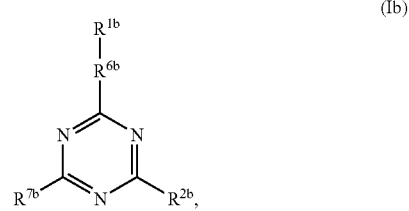

(Ib)

wherein:
$R^{1b}$ is selected from

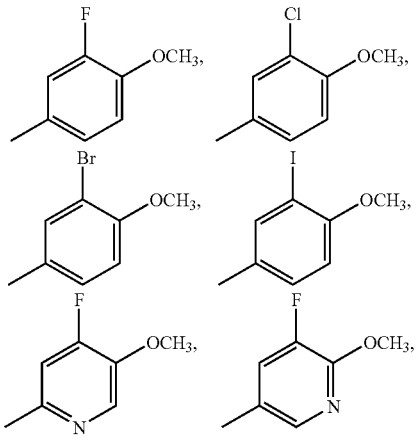

-continued
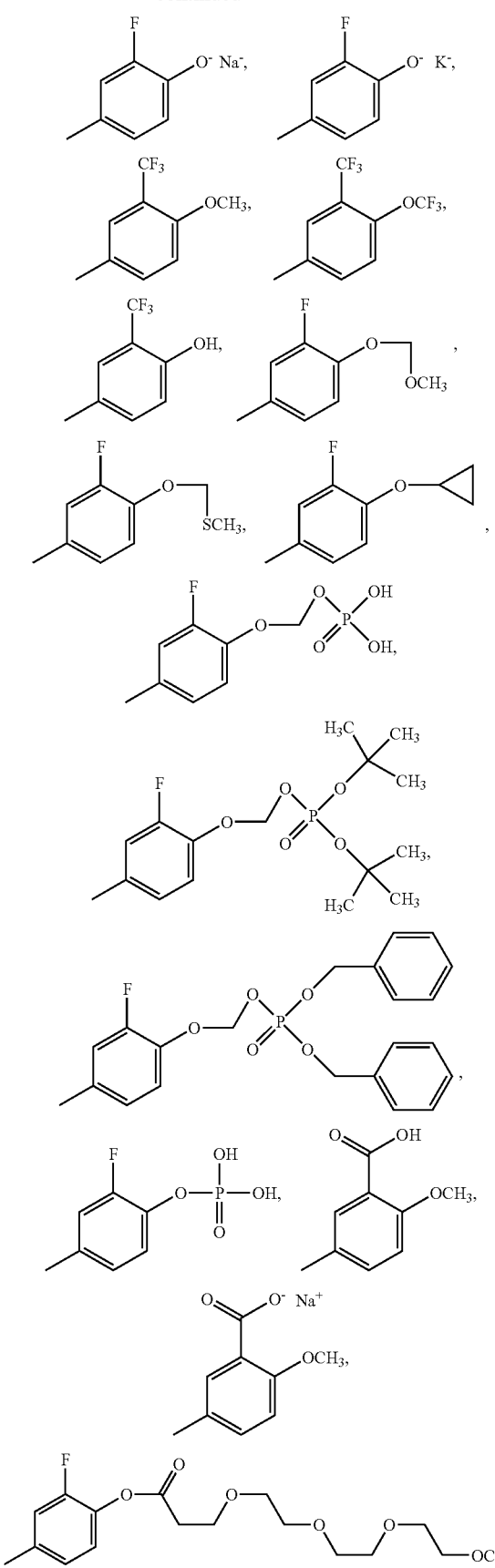
-continued
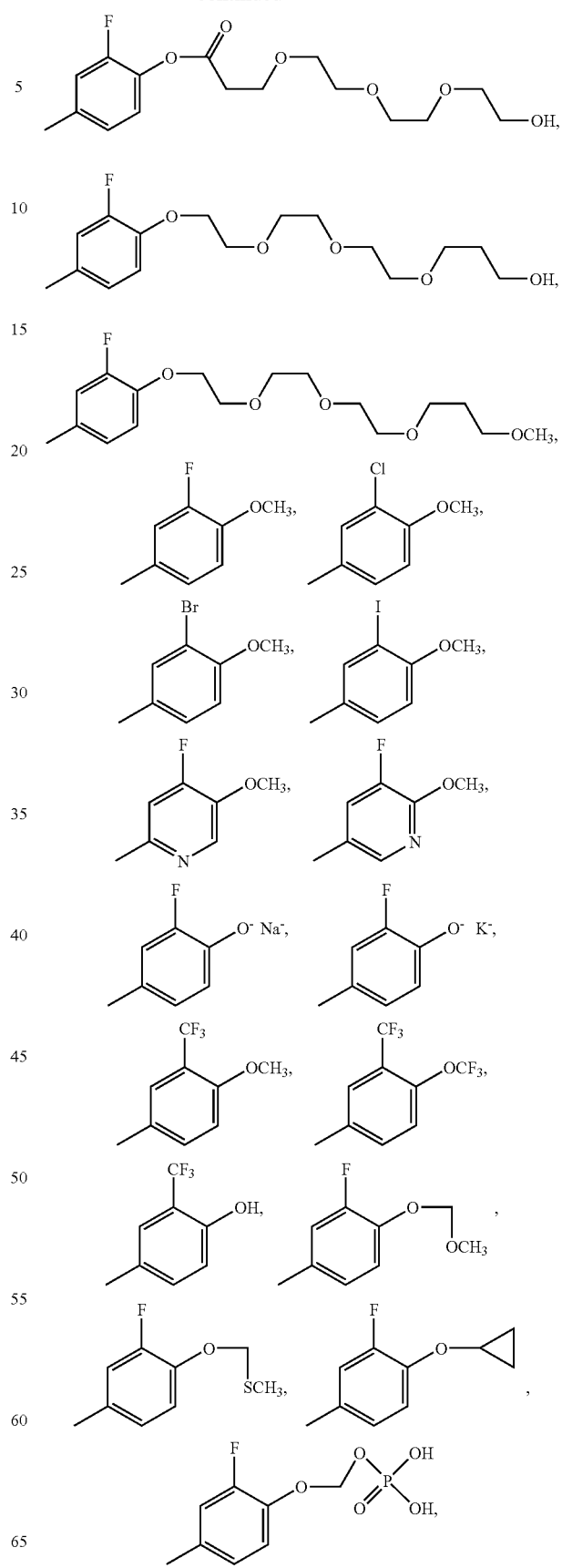

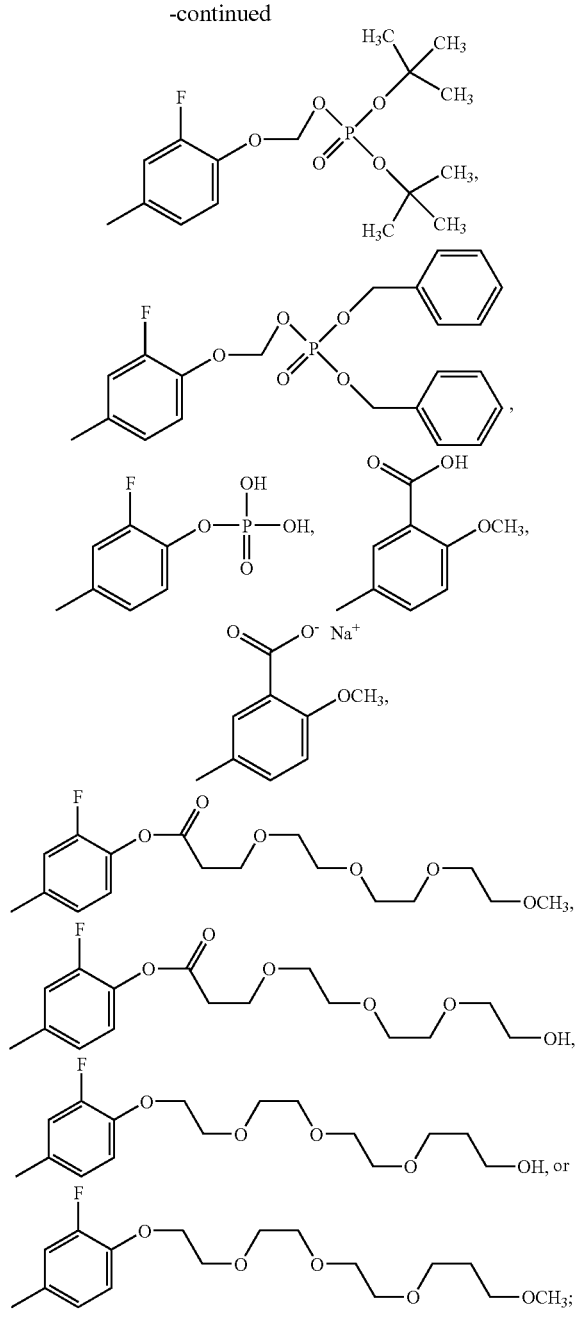
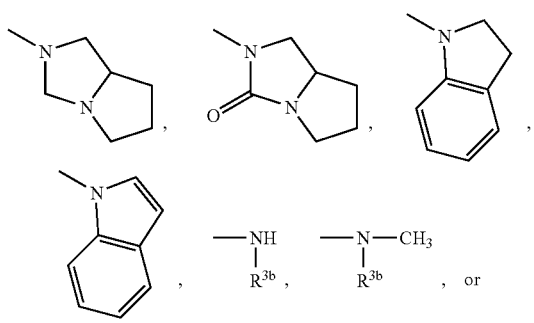
$R^{2b}$ is selected from
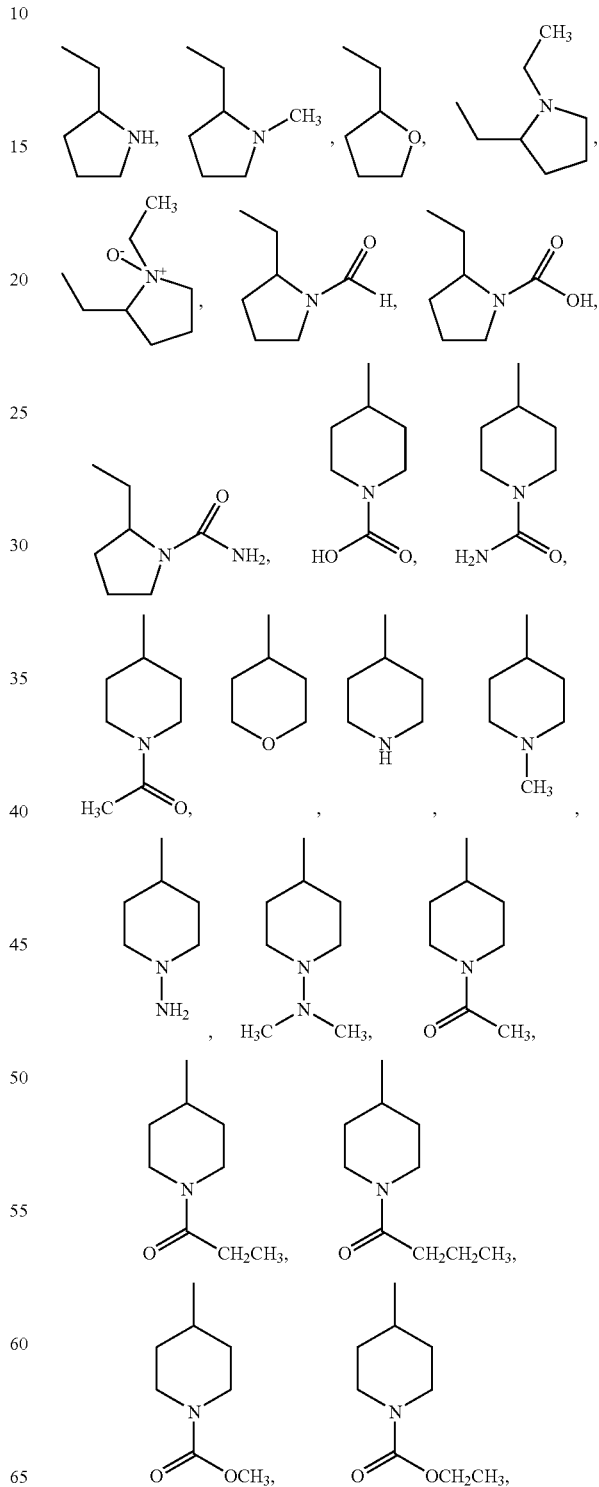
—O—$R^{3b}$;
$R^{3b}$ is selected from

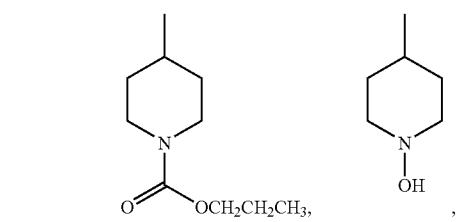
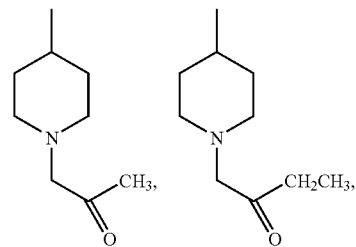
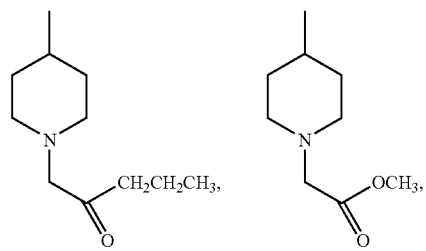
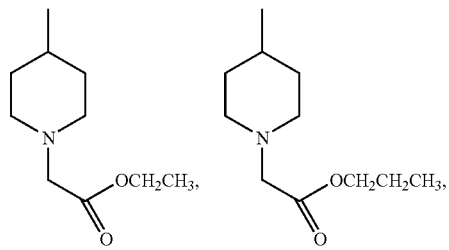
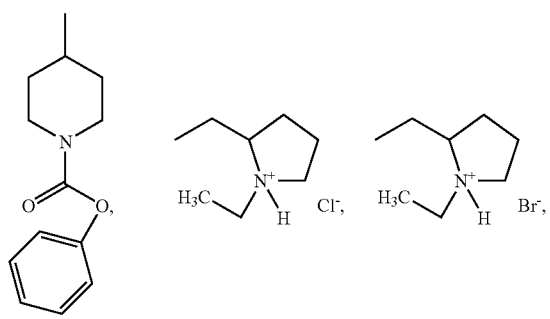
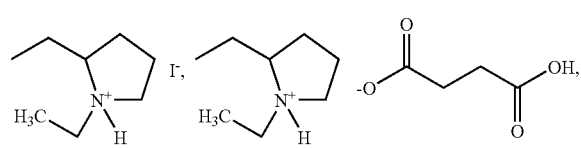
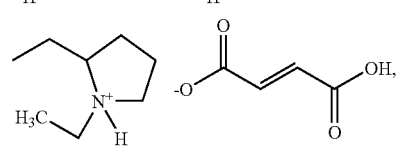
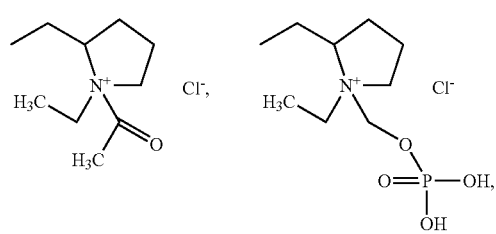
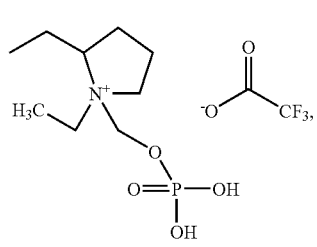
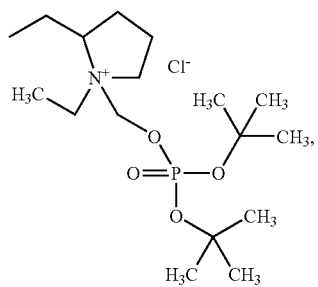
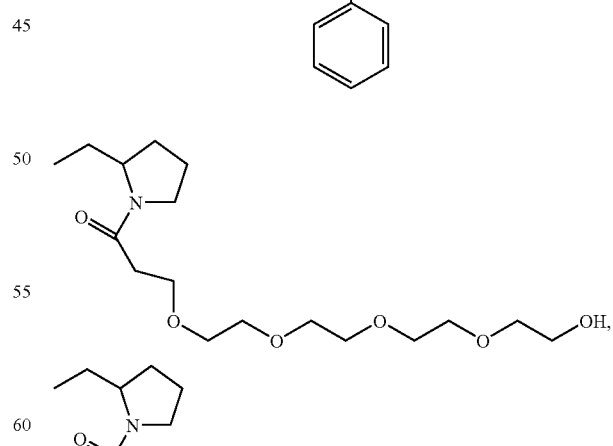
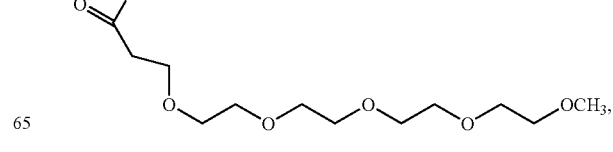

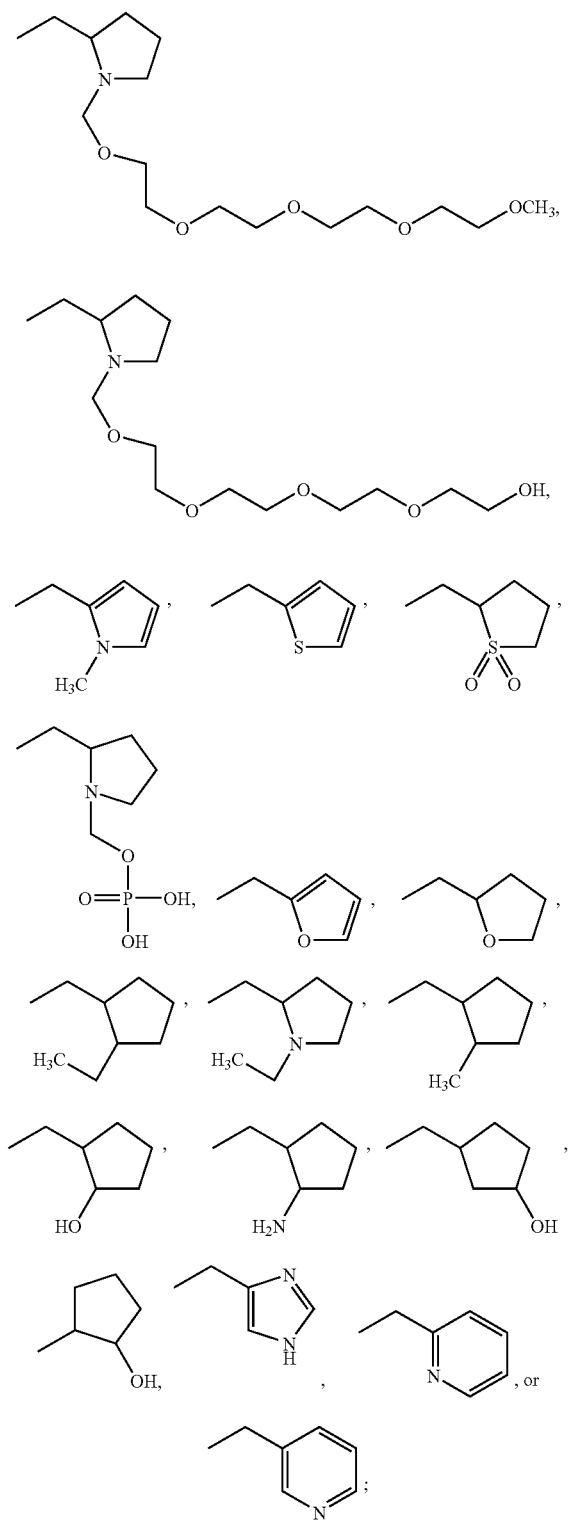
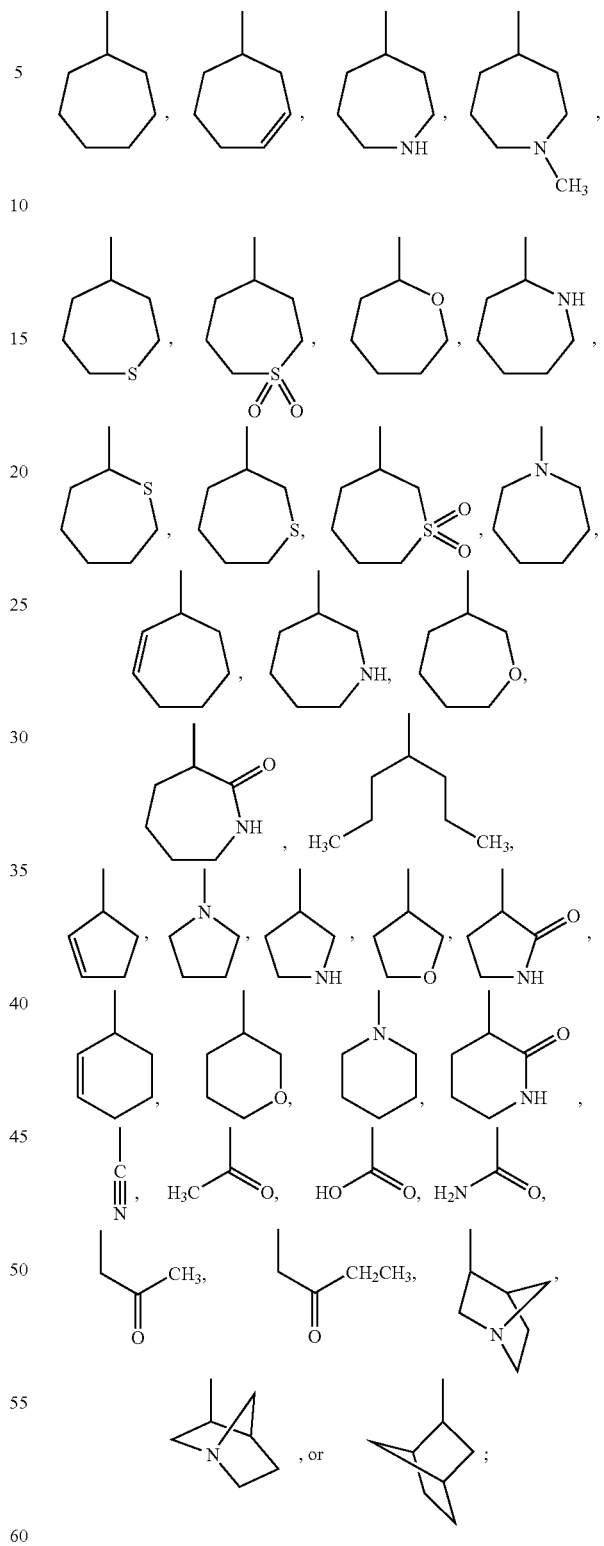
$R^{4b}$ is selected from —H, —CH$_3$, —CH$_2$CH$_3$, or —CH$_2$CH$_2$CH$_3$;
$R^{5b}$ is selected from
$R^{6b}$ is selected from
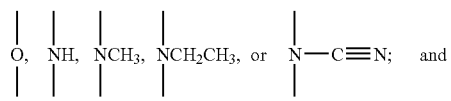
and $R^{7b}$ is selected from

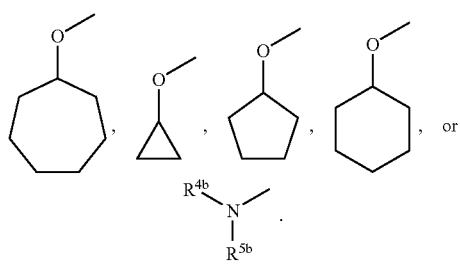

Compositions comprising compounds of this formula are also encompassed by the present invention, as well as mixtures or combinations of compounds of this formula.

In another aspect, compounds and compositions in accordance with the present invention comprise analogs of the tris(amino) triazene compounds of the following general structure IIb:

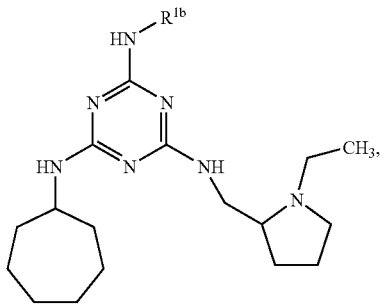

(IIb)

wherein $R^{1b}$ is selected from

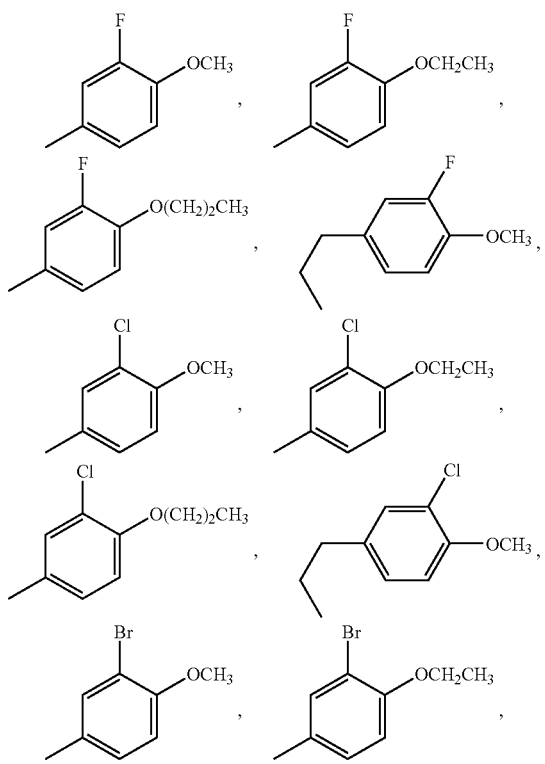

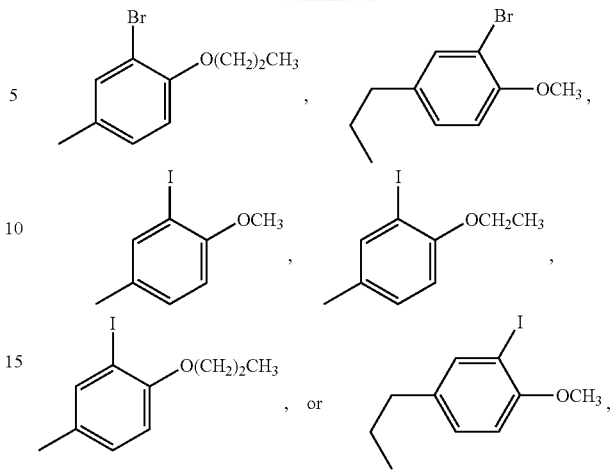

Compositions comprising compounds of this formula are also encompassed by the present invention, as well as mixtures or combinations of compounds of this formula.

In another aspect, compounds and compositions in accordance with the present invention comprise analogs of the tris(amino) triazene compounds of the following general structure IIIb:

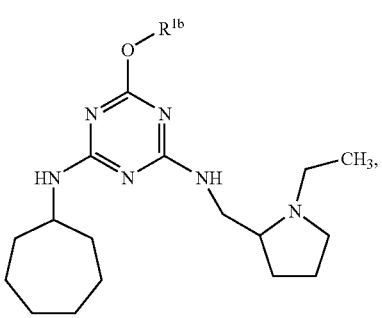

(IIIb)

wherein $R^{1b}$ is selected from

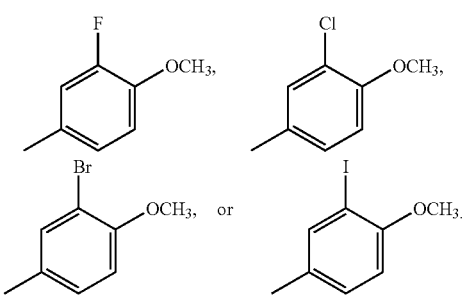

Compositions comprising compounds of this formula are also encompassed by the present invention, as well as mixtures or combinations of compounds of this formula.

In another aspect, compounds and compositions in accordance with the present invention comprise analogs of the tris(amino) triazene compounds of the following general structure IVb:

(IVb)

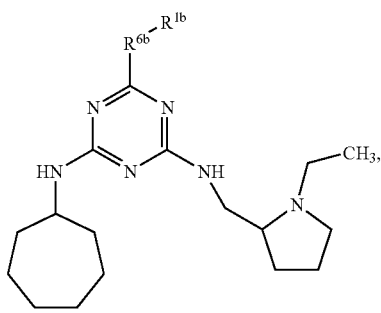

wherein R^{1b} is selected from

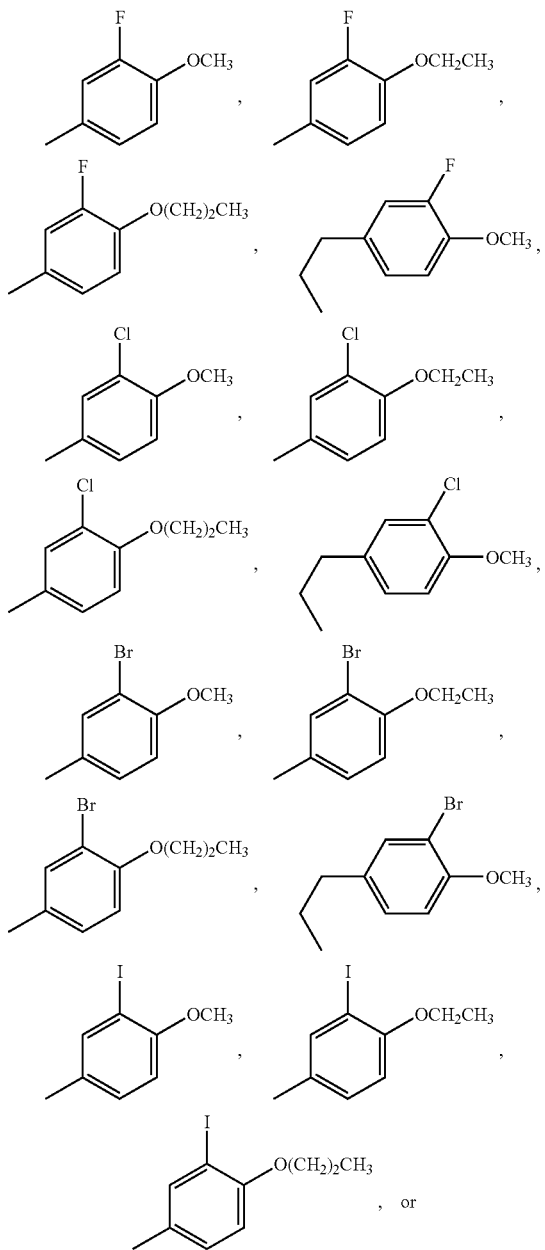

, or

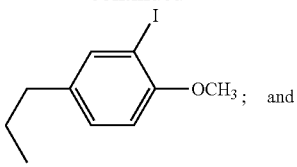

; and

R^{6b} is selected from

Compositions comprising compounds of this formula are also encompassed by the present invention, as well as mixtures or combinations of compounds of this formula.

In another aspect, compounds and compositions in accordance with the present invention comprise analogs of the tris(amino) triazene compounds of the following general structure Vb:

(Vb)

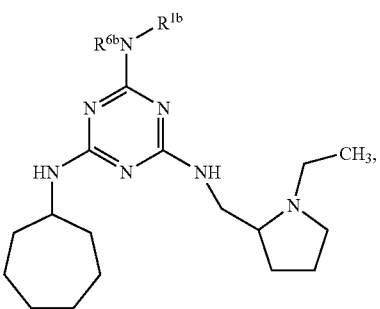

wherein R^{1b} is selected from

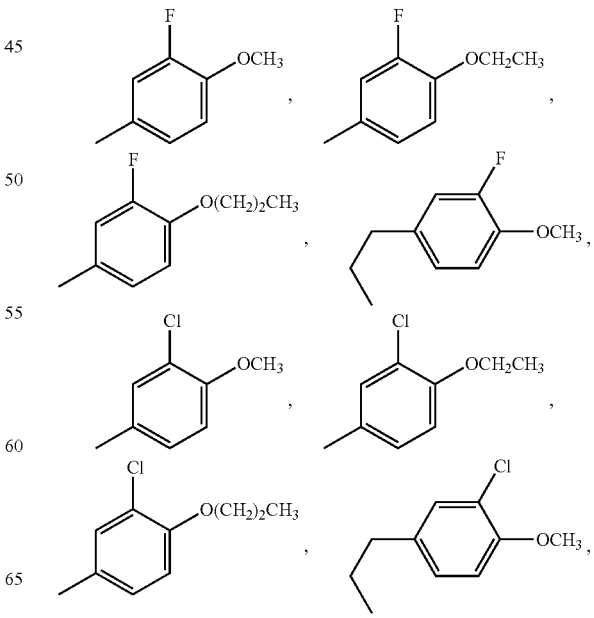

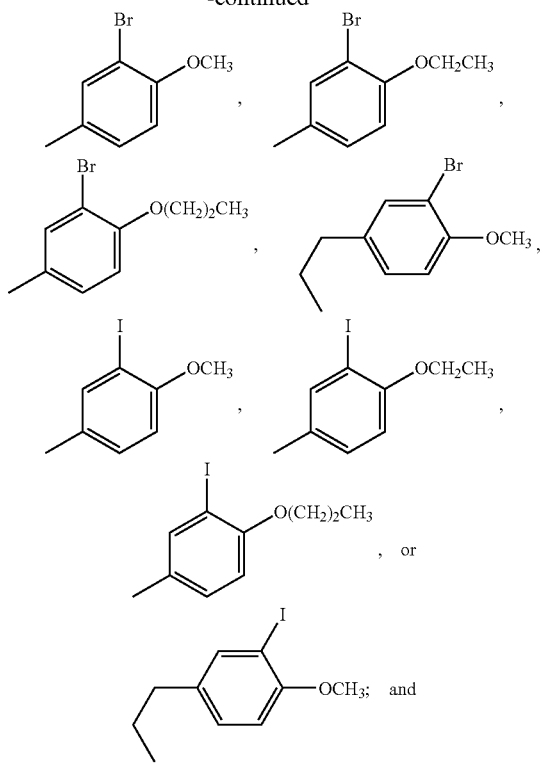

$R^{6b}$ is selected from —H, —CH$_3$, —CH$_2$CH$_3$, or —C≡N.

Compositions comprising compounds of this formula are also encompassed by the present invention, as well as mixtures or combinations of compounds of this formula.

In another aspect, compounds and compositions in accordance with the present invention comprise analogs of the tris(amino) triazene compounds of the following general structure VIb:

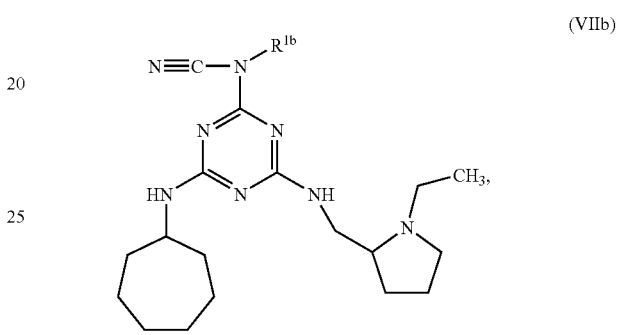
(VIb)

wherein $R^{1b}$ is selected from

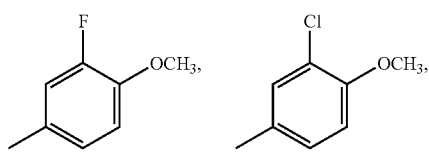

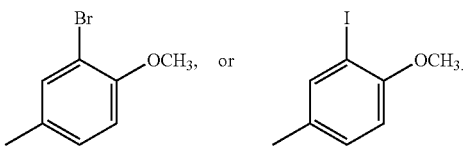

Compositions comprising compounds of this formula are also encompassed by the present invention, as well as mixtures or combinations of compounds of this formula.

In another aspect, compounds and compositions in accordance with the present invention comprise analogs of the tris(amino) triazene compounds of the following general structure VIIb:

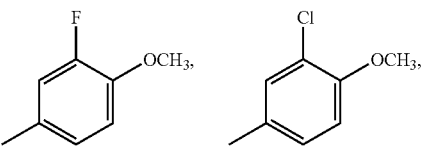
(VIIb)

wherein $R^{1b}$ is selected from

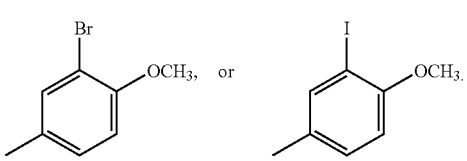

Compositions comprising compounds of this formula are also encompassed by the present invention, as well as mixtures or combinations of compounds of this formula.

In another aspect, compounds and compositions in accordance with the present invention comprise analogs of the tris(amino) triazene compounds of the following general structure VIIb:

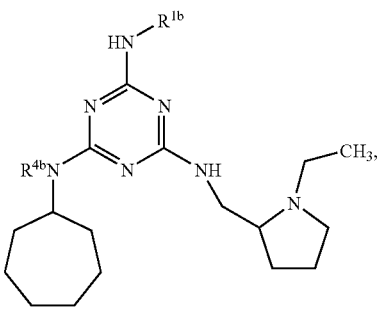
(VIIIb)

wherein $R^{1b}$ is selected from

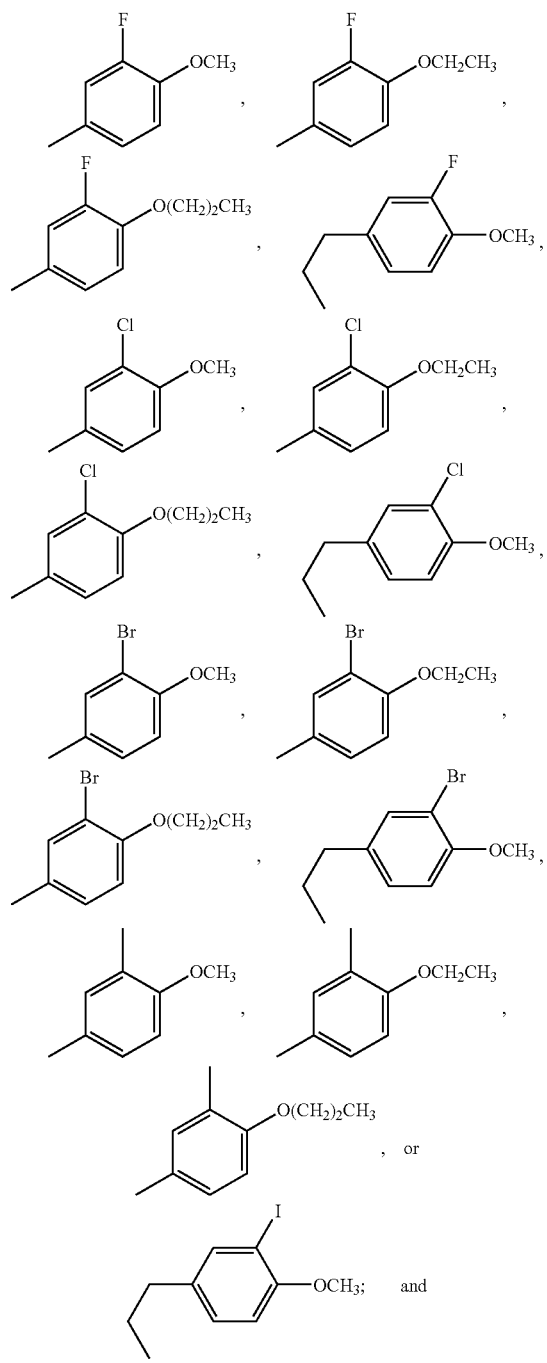

$R^{4b}$ is selected from —H, —CH$_3$, —CH$_2$CH$_3$, or —CH$_2$CH$_2$CH$_3$.

Compositions comprising compounds of this formula are also encompassed by the present invention, as well as mixtures or combinations of compounds of this formula.

In another aspect, compounds and compositions in accordance with the present invention comprise analogs of the tris(amino) triazene compounds of the following general structure IXb:

(IXb)

wherein $R^{5b}$ is selected from

Compositions comprising compounds of this formula are also encompassed by the present invention, as well as mixtures or combinations of compounds of this formula.

In another aspect, compounds and compositions in accordance with the present invention comprise analogs of the tris(amino) triazene compounds of the following general structure Xb:

(Xb)
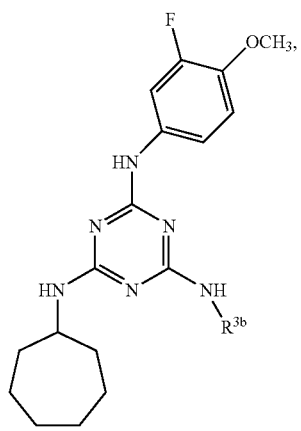
wherein R³ᵇ is selected from
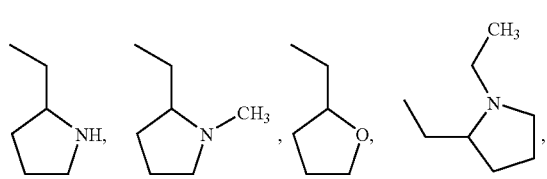
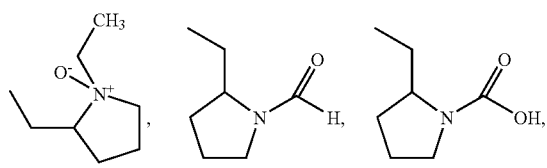
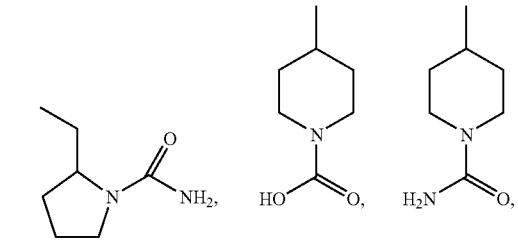
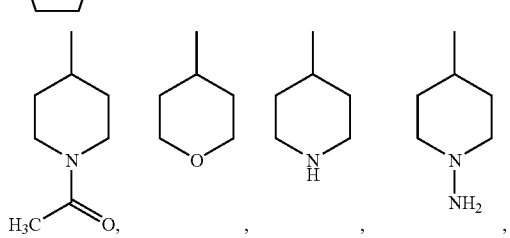
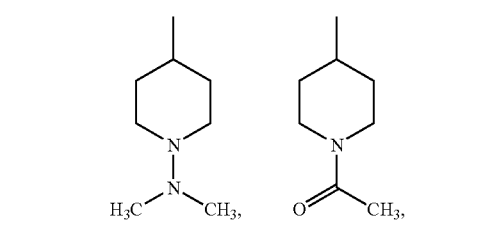
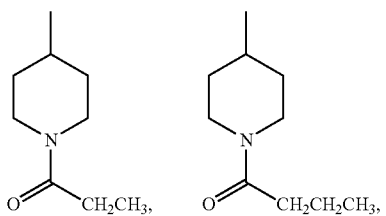
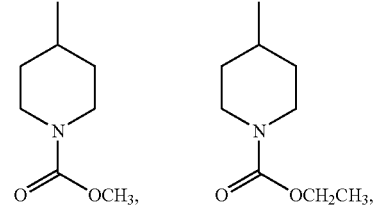
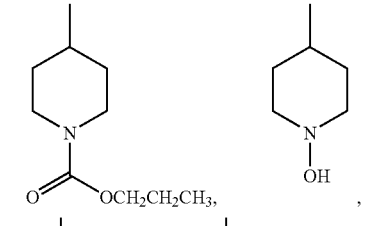
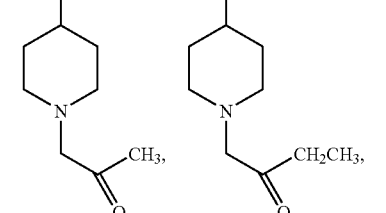
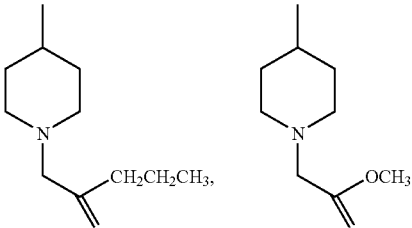
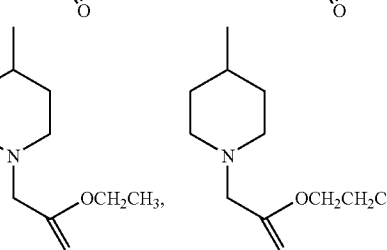
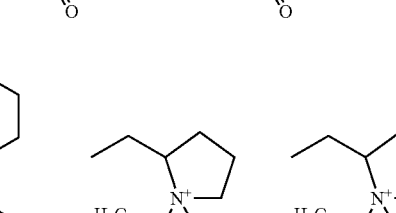
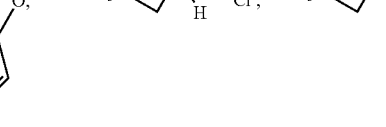

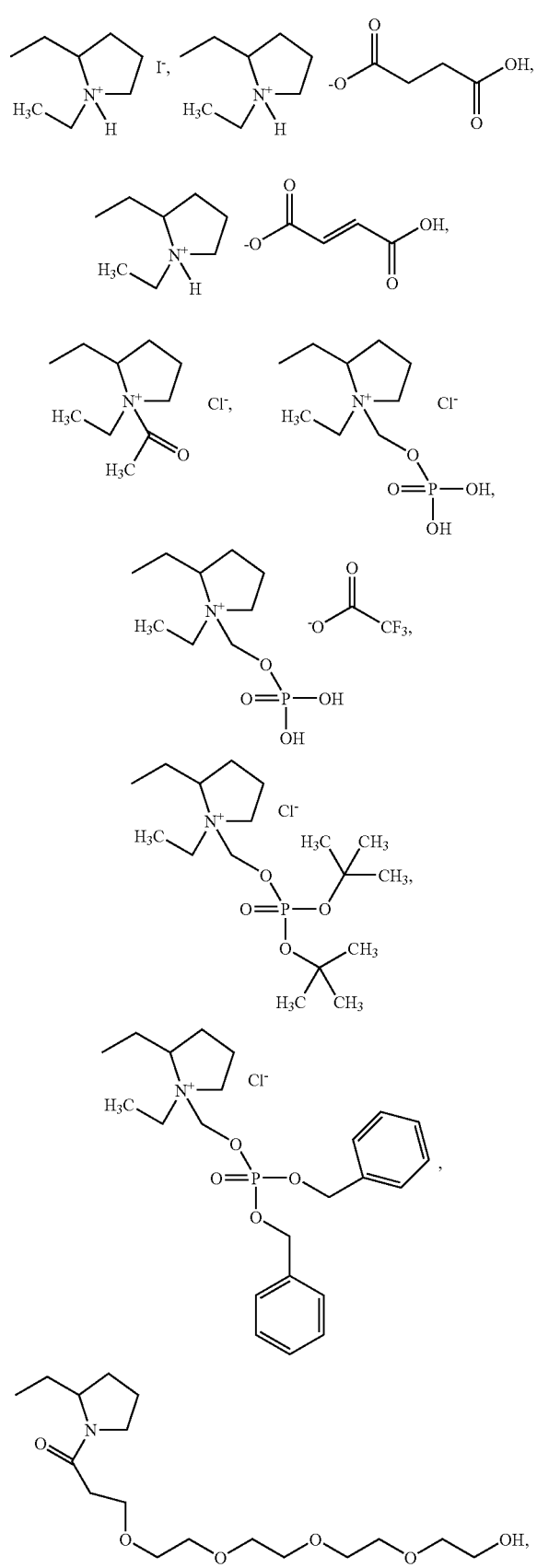
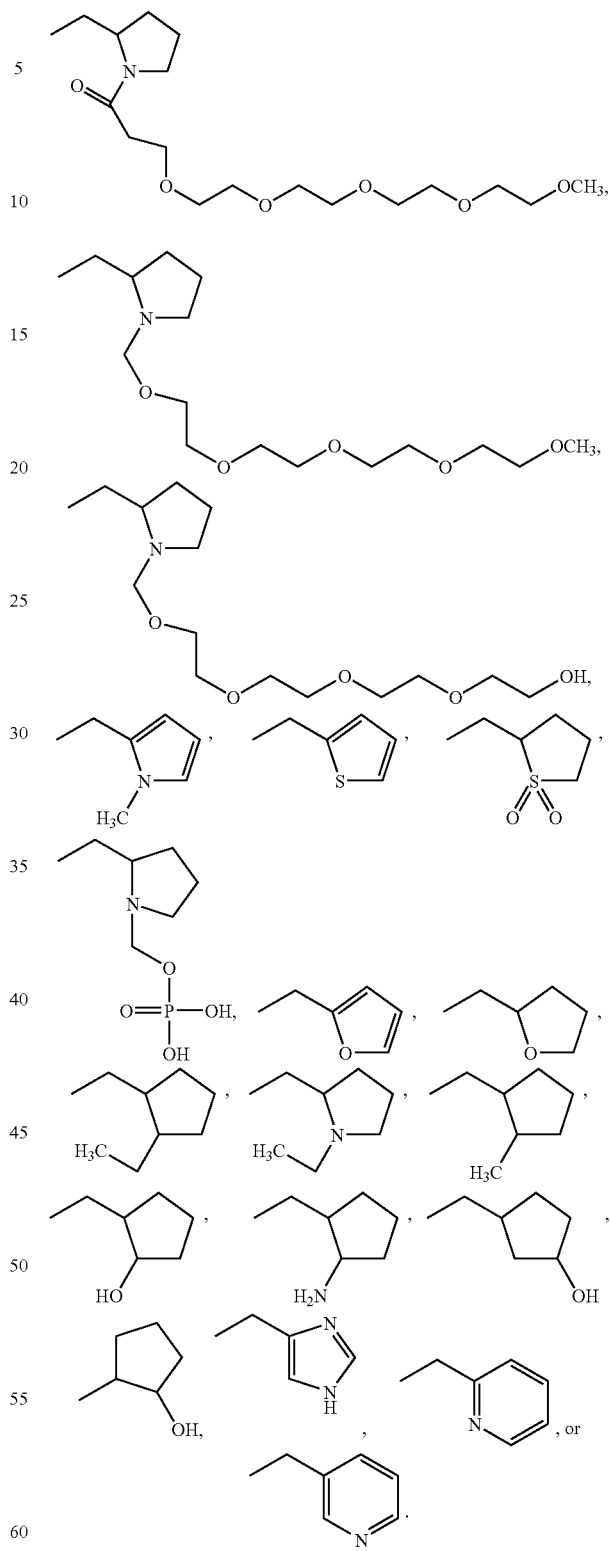
Compositions comprising compounds of this formula are also encompassed by the present invention, as well as mixtures or combinations of compounds of this formula.
In another aspect, compounds and compositions in accordance with the present invention comprise analogs of the tris(amino) triazene compounds of the following general structure XIb:
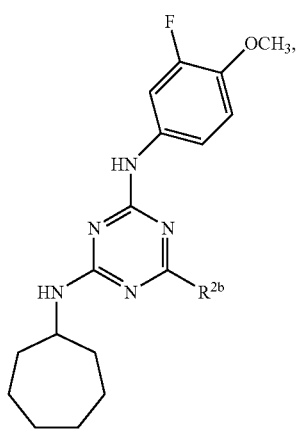 (XIb)
wherein $R^{2b}$ is selected from
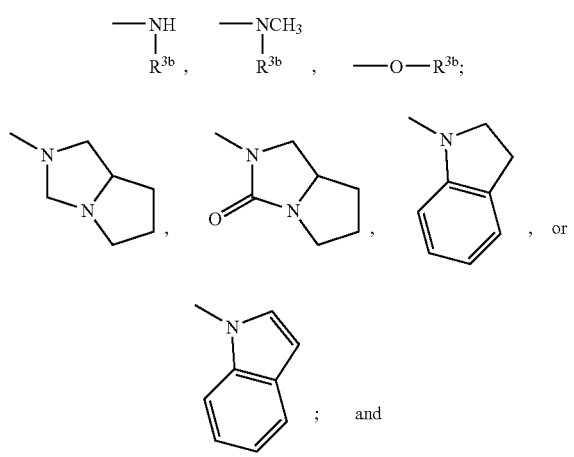
and $R^{3b}$ is selected from
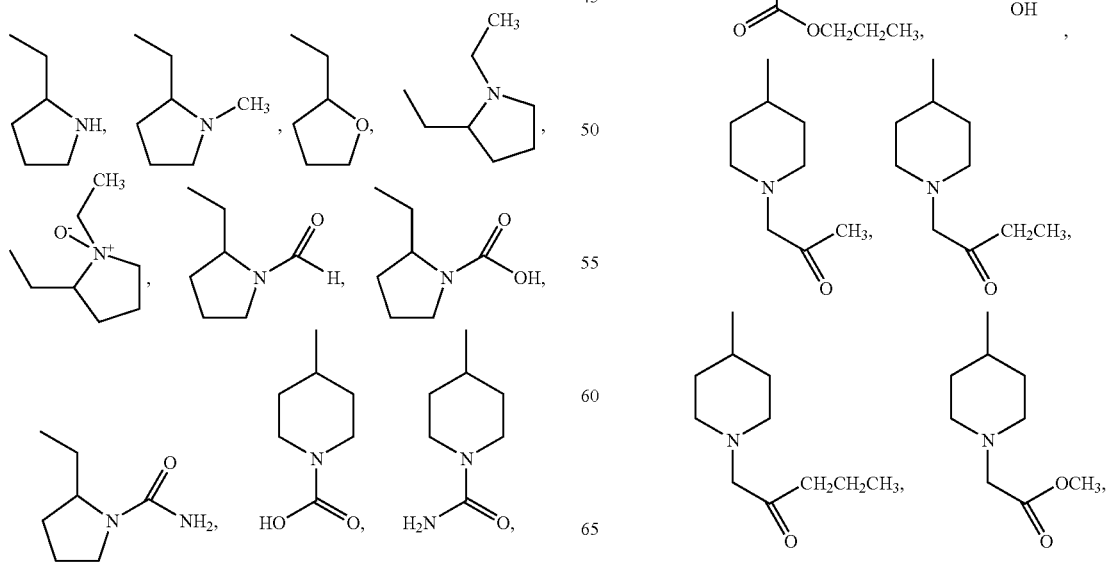
-continued
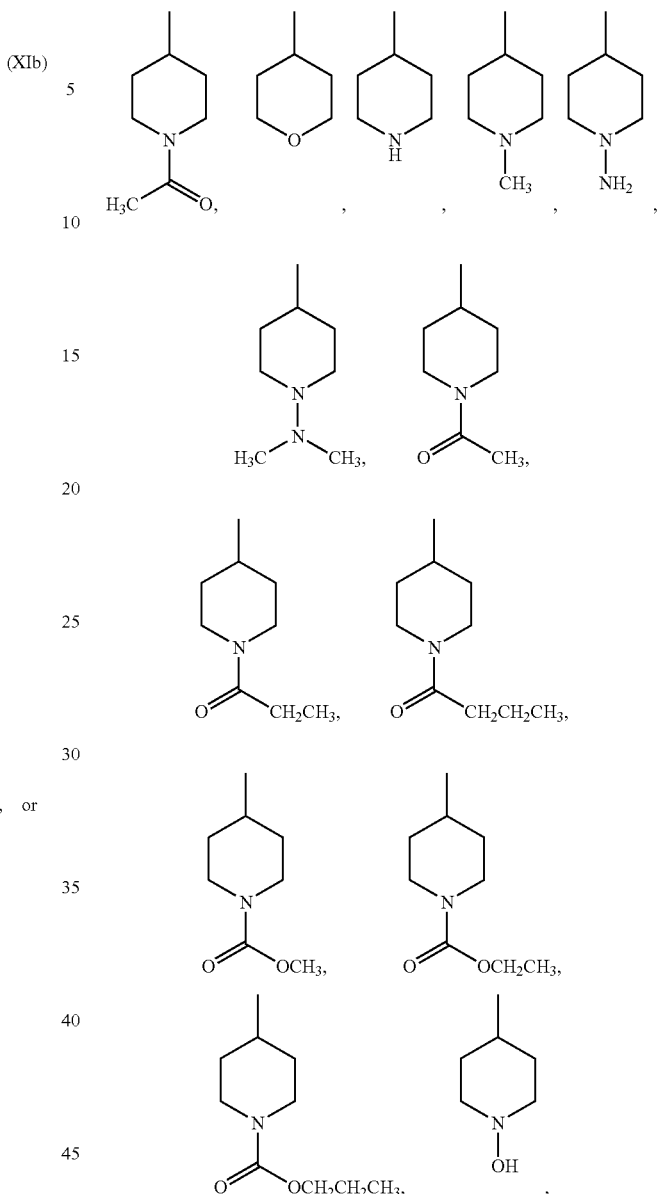
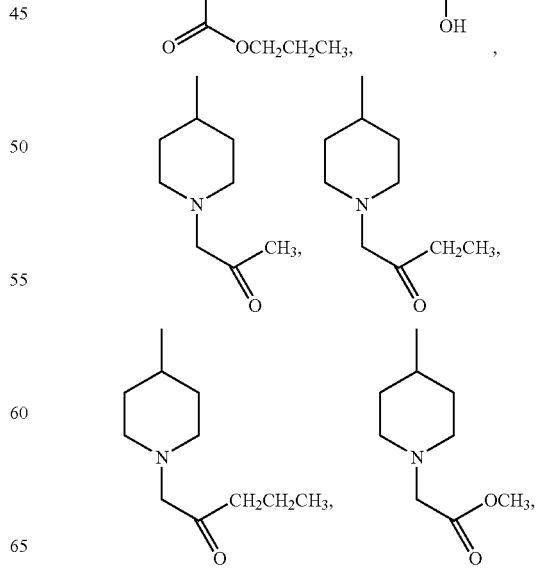

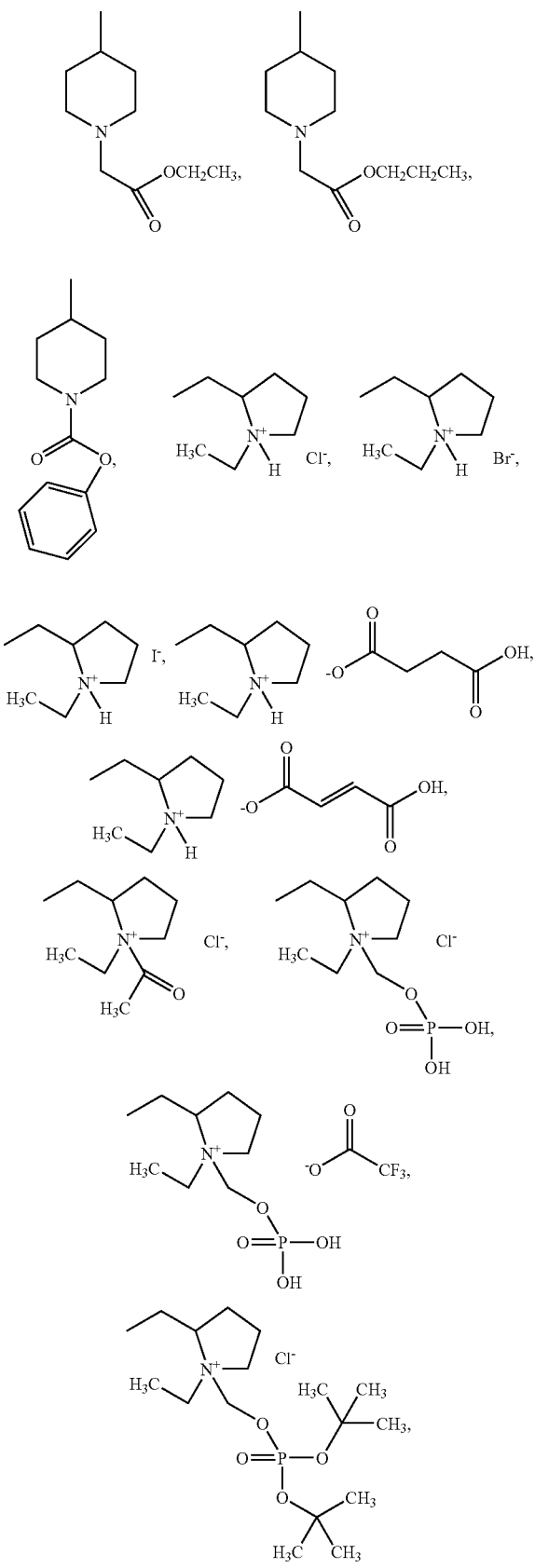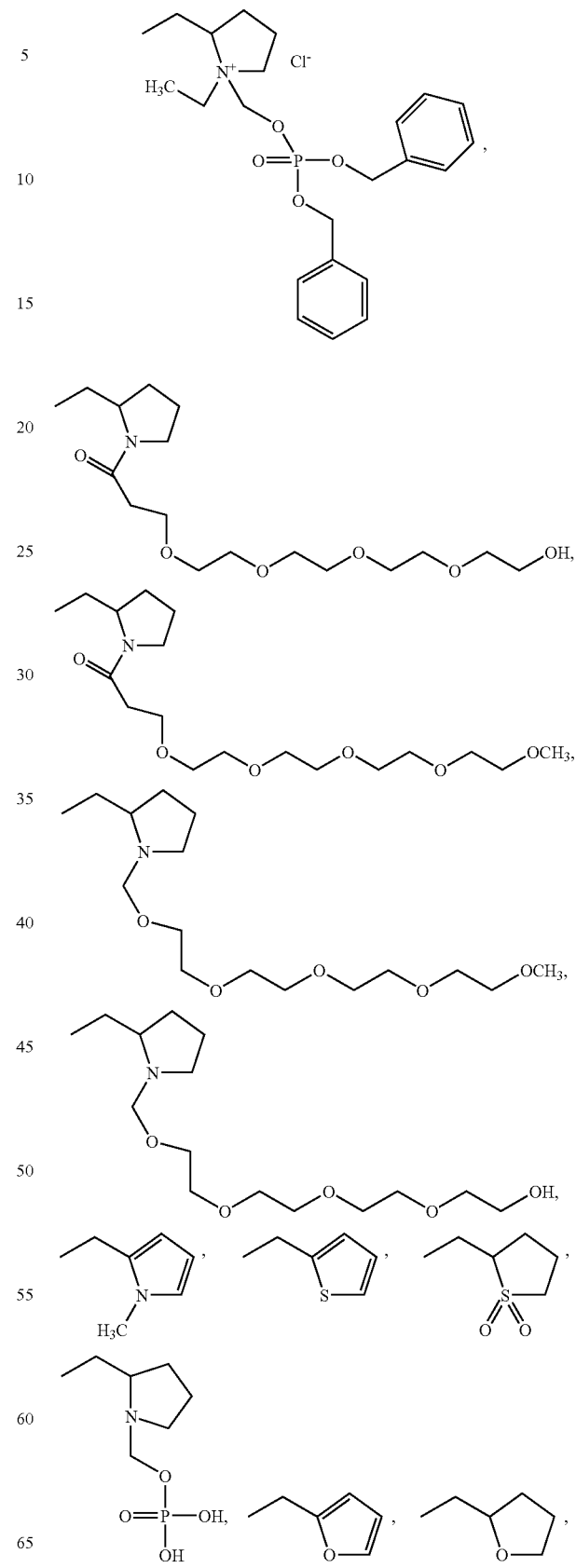

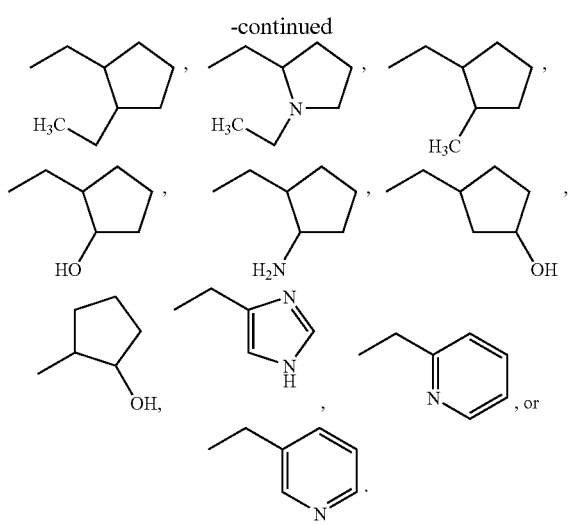

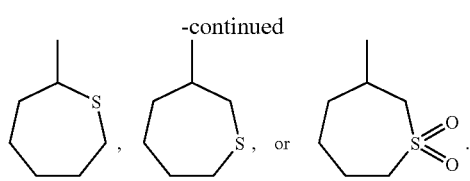

Compositions comprising compounds of this formula are also encompassed by the present invention, as well as mixtures or combinations of compounds of this formula.

In another aspect, compounds and compositions in accordance with the present invention comprise analogs of the tris(amino) triazene compounds of the following general structure XIIb:

(XIIb)

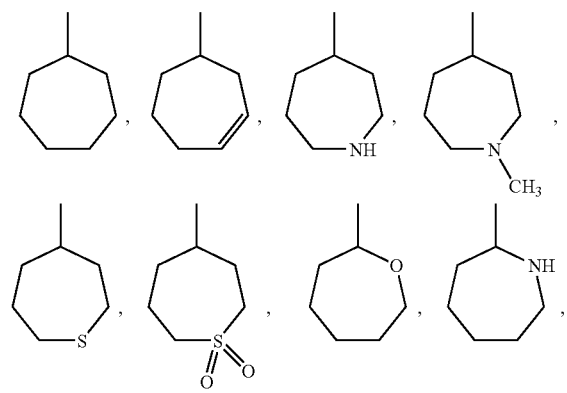

wherein $R^{5b}$ is selected from

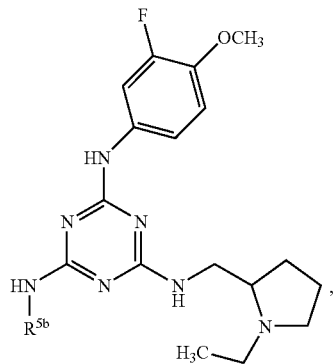

In another aspect, compounds and compositions in accordance with the present invention comprise analogs of the tris(amino) triazene compounds of the following general structure XIIIb:

(XIIIb)

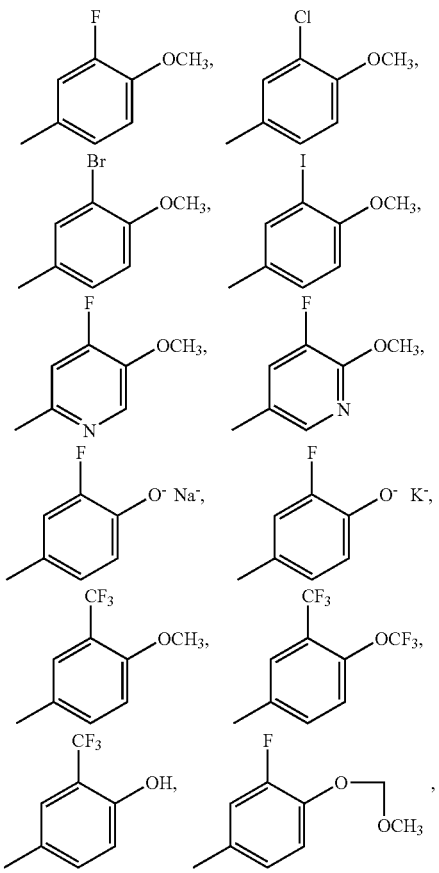

wherein $R^{1b}$ is selected from

-continued

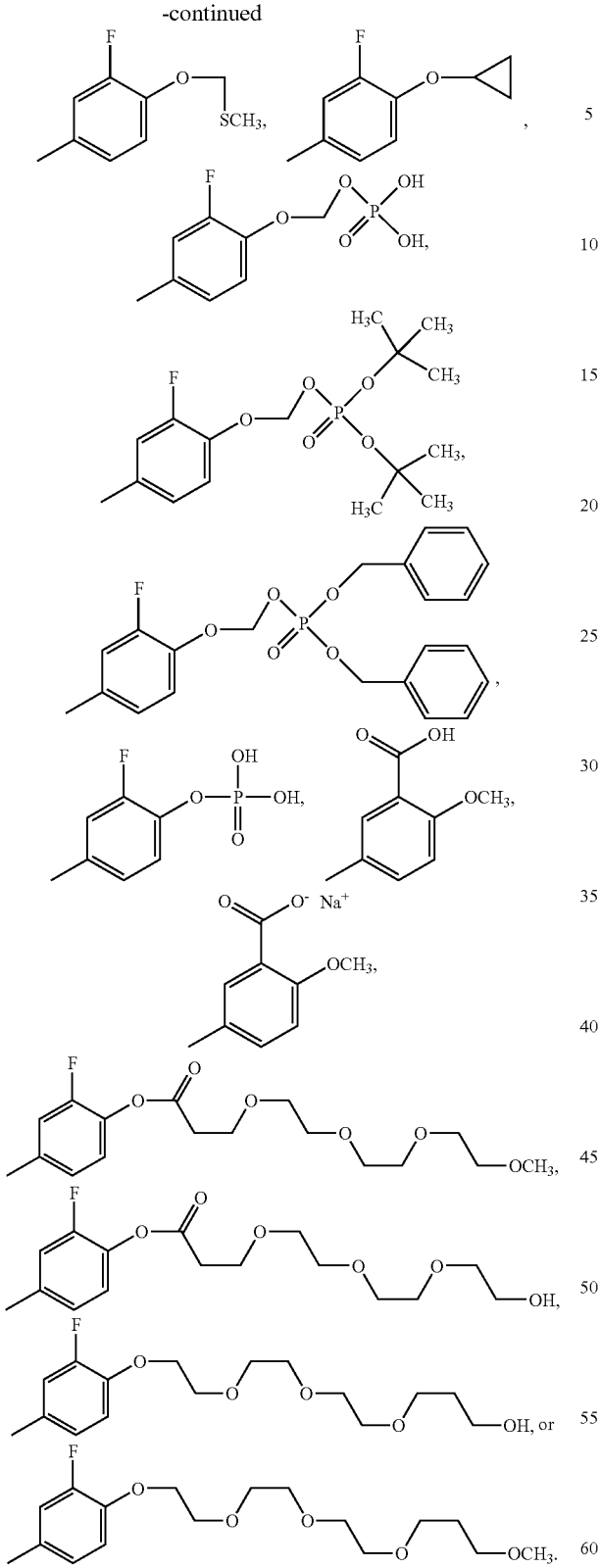

Compositions comprising compounds of this formula are also encompassed by the present invention, as well as mixtures or combinations of compounds of this formula.

In another aspect, compounds and compositions in accordance with the present invention comprise analogs of the tris(amino) triazene compounds of the following general structure XIVb:

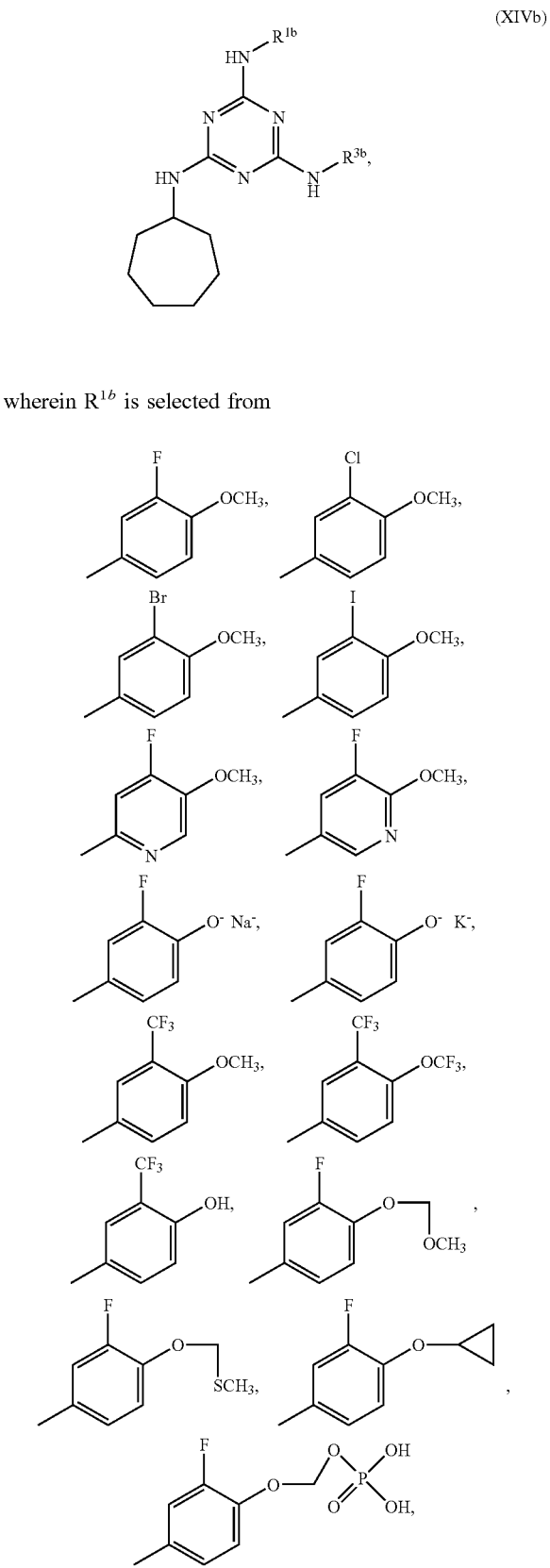

wherein $R^{1b}$ is selected from

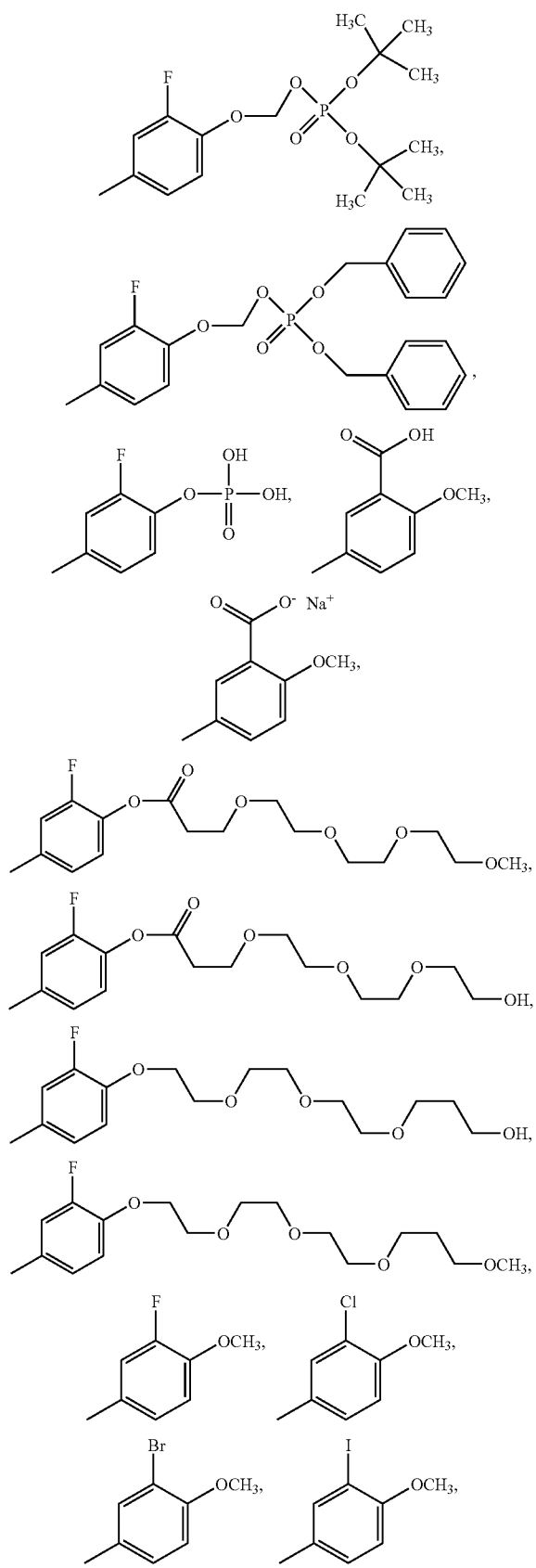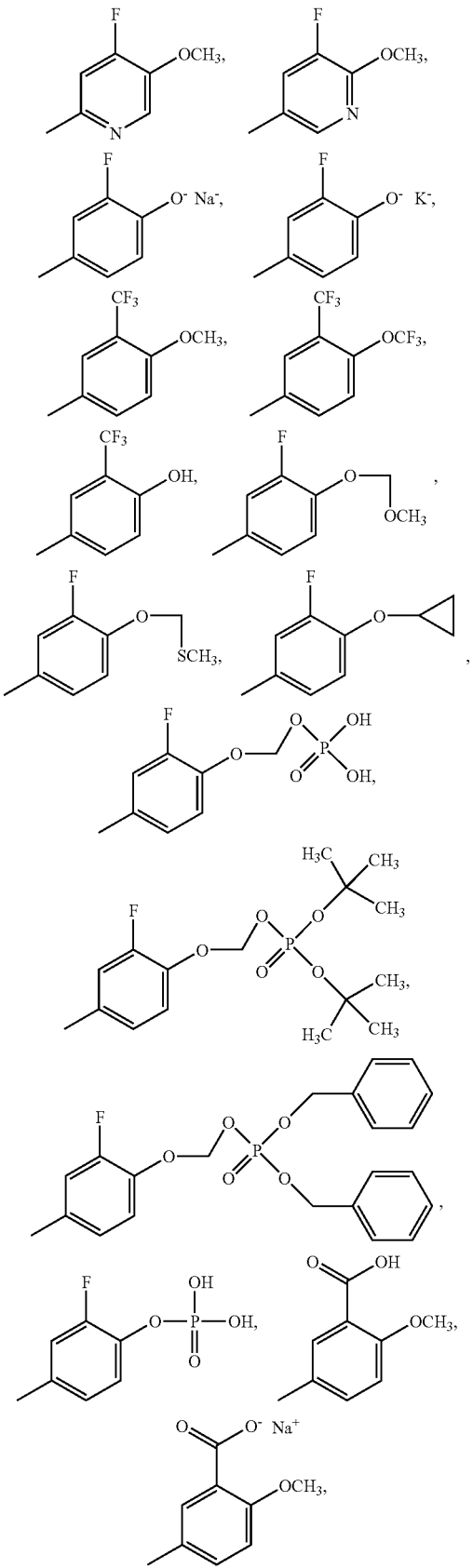

-continued
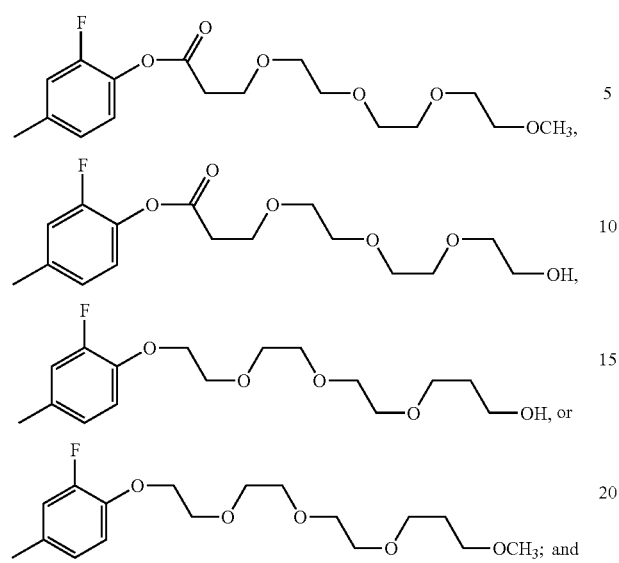
R<sup>3b</sup> is selected from
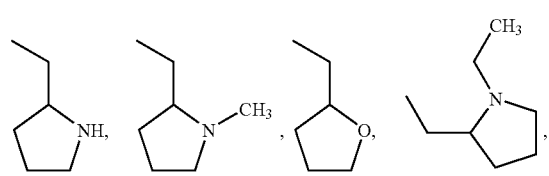
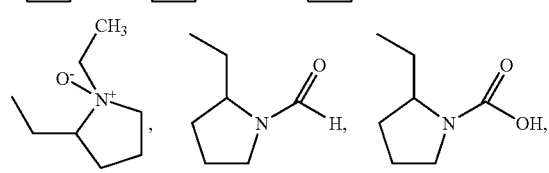
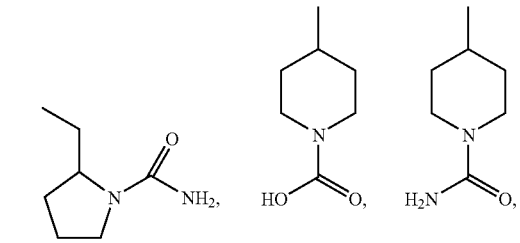
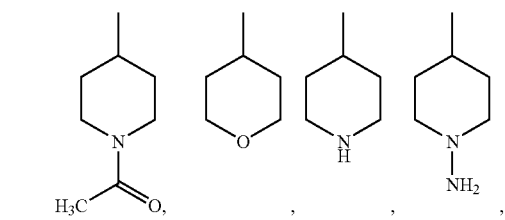
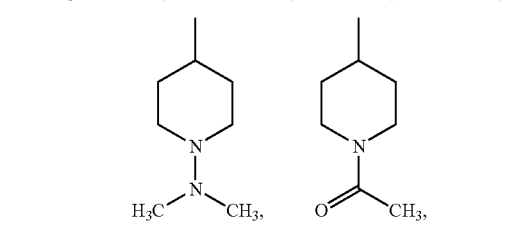
-continued
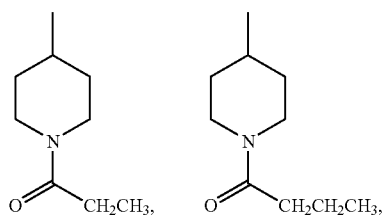
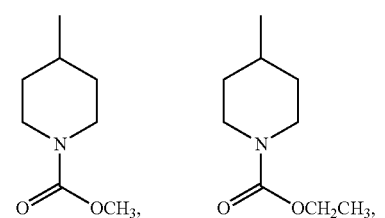
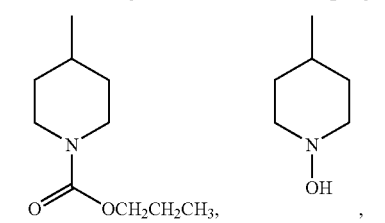
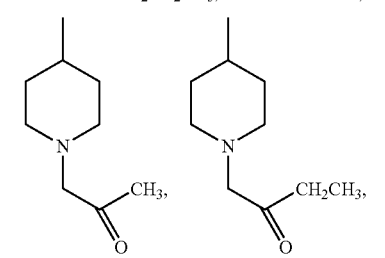
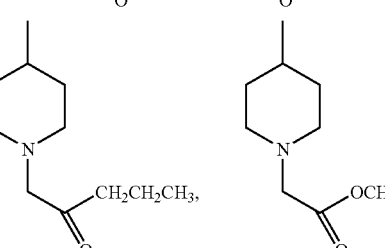
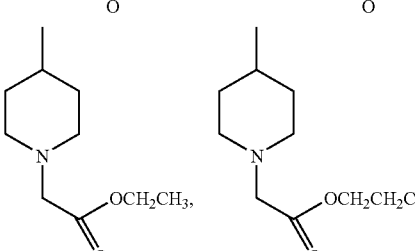
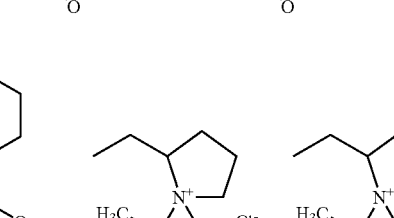
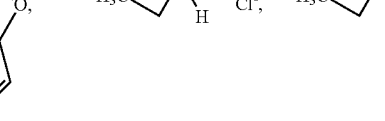

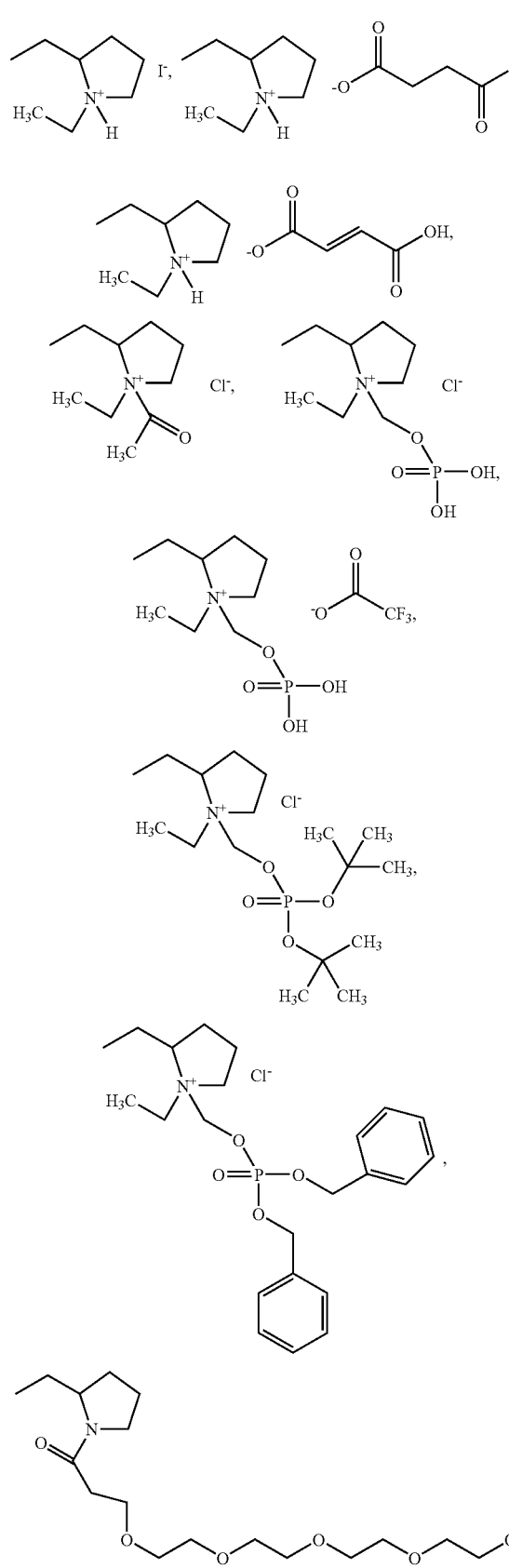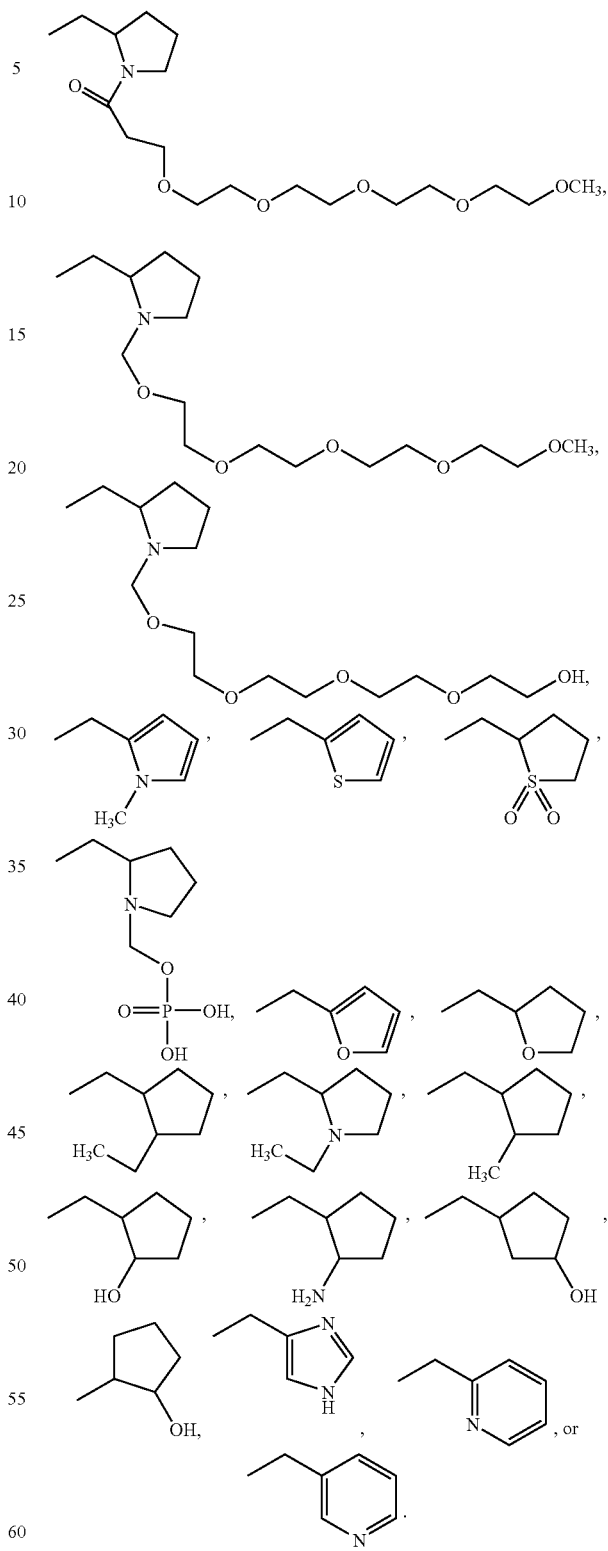
Compositions comprising compounds of this formula are also encompassed by the present invention, as well as mixtures or combinations of compounds of this formula.
In another aspect, compounds and compositions in accordance with the present invention comprise analogs of the tris(amino) triazene compounds of the following general structure XVb:

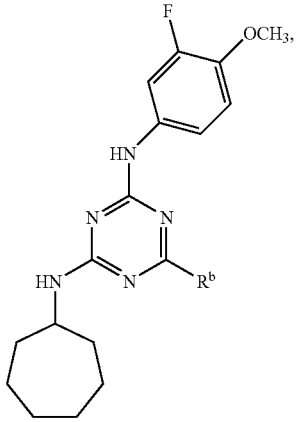
(XVb)

wherein $R^{8b}$ is selected from

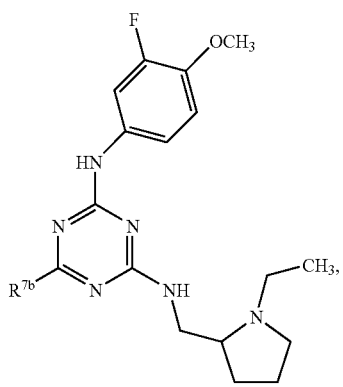

Compositions comprising compounds of this formula are also encompassed by the present invention, as well as mixtures or combinations of compounds of this formula.

In another aspect, compounds and compositions in accordance with the present invention comprise analogs of the tris(amino) triazene compounds of the following general structure XVIb:

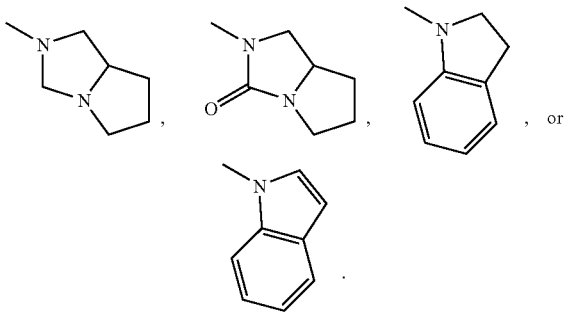
(XVIb)

wherein $R^{7b}$ is selected from

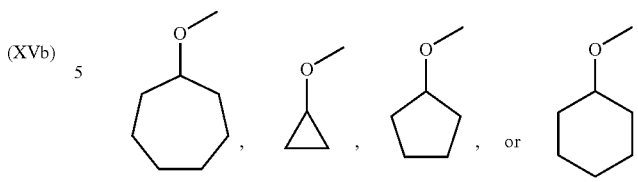

Compositions comprising compounds of this formula are also encompassed by the present invention, as well as mixtures or combinations of compounds of this formula.

Table 1B presents further exemplary compounds of the present invention. The inclusion of compounds in this table is not to be seen as limiting, rather compounds are provided in this table by way of example.

Additionally, compounds in accordance with the present invention include the compounds listed in Table 1E. Again, these compounds, which are discussed in the Examples provided herein, are to be considered as exemplary.

TABLE 1E

Representative Compounds According to the Present Invention

| COMPOUND NUMBER | COMPOUND NAME |
| --- | --- |
| E1 | 4-Benzyloxy-3-chloro-phenylamine, |
| E2 | N-(4-Benzyloxy-3-chloro-phenyl)-N'-cycloheptyl-N''-(1-methyl-piperidin-4-yl)-[1,3,5]triazine-2,4,6-triamine, |
| E3 | N-(4-benzyloxy-3-chloro-phenyl)-N'-cycloheptyl-N''-methyl-N''-piperidin-4-yl-[1,3,5]triazine-2,4,6-triamine, |
| E4 | 4-[4-Cycloheptylamino-6-(methyl-piperidin-4-yl-amino)-[1,3,5]triazin-2-ylamino]-phenol, |
| E5 | 4-{4-Cycloheptylamino-6-[methyl-(1-methyl-piperidin-4-yl)-amino]-1,3,5]triazin-2-ylamino}-phenol, |
| E6 | 2-Chloro-4-(4,6-dichloro-[1,3,5]triazin-2-ylamino)-phenol, |
| E7 | 2-Chloro-4-(4-chloro-6-cycloheptylamino-[1,3,5]triazin-2-ylamino)-phenol, |
| E8 | N-(1-Benzyl-piperidin-4-yl)-N'-(3-fluoro-4-methoxy-phenyl)-N''-cycloheptyl-[1,3,5]triazine-2,4,6-diamine, |
| E9 | N-Cycloheptyl-N'-(4-methoxy-phenyl)-N''-piperidin-4-yl-[1,3,5]triazine-2,4,6-triamine, |
| E10 | 6-Chloro-N-cyclopropyl-N'-(3-fluoro-4-methoxy-phenyl)-[1,3,5]triazine-2,4-diamine, |
| E11 | N-Cyclopropyl-N'-(3-flouro-4-methoxy-phenyl)-N''-methyl-N''-(1-methyl-piperidin-4-yl)-[1,3,5]triazine-2,4,6-triamine, |
| E12 | N-Cyclopropyl-N'-(1-ethyl-pyrrolidin-2-ylmethyl)-N''-(3-fluoro-4-methoxy-phenyl)-[1,3,5]triazine-2,4,6-triamine, |
| E13 | 6-Chloro-N-(3-chloro-4-methoxy-phenyl)-N'-cyclopropyl-[1,3,5]triazine-2,4-diamine |
| E14 | N-Cyclopropyl-N'-(3-chloro-4-methoxy-phenyl)-N''-methyl-N''-(1-methyl-piperidin-4-yl)-[1,3,5]triazine-2,4,6-triamine, |
| E15 | 6-Chloro-N,N'-bis-(3-fluoro-4-methoxy-phenyl)-[1,3,5]triazine-2,4-diamine, |
| E16 | N-(1-Ethyl-pyrrolidin-2-ylmethyl)-N',N''-bis-(3-fluoro-4-methoxy-phenyl)-[1,3,5]triazine-2,4,6-triamine, |
| E17 | 1-[4-(3-chloro-4-methoxyanilino)-cycloheptyl amino-1,3,5-triazin-2-yl]-2-azoloamymethanol, |
| E18 | $N^2$-(3-chloro-4-methoxyphenyl)-$N^4$-cycloheptyl-6-(4-methylpiperzino)-1,3,5-triazine-4,2-diamine, |
| E19 | 3-[4-(3-chloro-4-methoxyanilino)-6-cycloheptylamino-1,3,5-triazin-2-yloxy]-2-ethyl-4H-4-pyranone, |
| E20 | 1-[3-{4-(3-chloro-4-methoxyanilino)-6-cycloheptylamino-1,3,5-triazine-2-yloxy}piperidino]-1-ethanone, |
| E21 | $N^2$-(3-chloro-4-methoxyphenyl)-$N^4$-cyclohepty-6-isopropoxy-1,3,5-triazine-2,4-diamine, |
| E22 | $N^2$-(3-chloro-4-methoxyphenyl)-$N^4$-cycloheptyl-6-(2-azolanylmethoxy)-1,3,5-triazine-2,4-diamine, |
| E23 | 1-[4-(3-chloro-4-methoxy-phenylamino)-6-cycloheptylamino-[1,3,5]triazine-2-yl]-piperidin-3-ol], |
| E24 | 1-[4-(3-chloro-4-methoxy-phenylamino)-6-cycloheptylamino-[1,3,5]triazine-2-yl]-piperidin-4-ol], |

TABLE 1E-continued

Representative Compounds According to the Present Invention

| COMPOUND NUMBER | COMPOUND NAME |
|---|---|
| E25 | $N^2$-(3-chloro-4-methoxyphenyl)-$N^4$-cycloheptyl-6-(1-methyl-2-azolanylmethoxy)-1,3,5-triazine-2,4-diamine, |
| E26 | $N^2$-(3-chloro-4-methoxyphenyl)-$N^4$-cycloheptyl-6-(1-methyl-4-piperidyloxy)-1,3,5-triazine-2,4-diamine, |
| E27 | $N^2$-(3-chloro-4-methoxyphenyl)-$N^4$-cycloheptyl-6-(1,4-thiazinan-4-yl)-1,3,5-triazine-4,2-diamine, |
| E28 | $N^2$-(3-chloro-4-methoxyphenyl)-$N^4$-cycloheptyl-6-(2-fluorophenoxy)-1,3,5-triazine-4,2-diamine, |
| E29 | $N^2$-(3-chloro-4-methoxyphenyl)-$N^4$-cycloheptyl-6-[2-(2-fluorophenoxy) ethoxy]-1,3,5-triazine-4,2-diamine, |
| E30 | $N^2$-(3-chloro-4-methoxyphenyl)-$N^4$-cycloheptyl-6-(6-methyl-2-pyryl methoxy]-1,3,5-triazine-4,2-diamine, |
| E31 | N-(3-chloro-4-methoxyphenyl)-N'-cycloheptyl-N''-methyl-N''-(1-methyl piperidin-4-yl)[1,3,5]triazine-2,4,6-triamine, HCl salt, |
| E32 | 6-methoxy-N-(3-Chloro-4-methoxy phenyl)-N'-cyclo heptyl-[1,3,5] triazine-2,4 diamine, |
| E33 | 6-ethoxy-N-(3-Chloro-4-methoxy phenyl)-N'-cyclo heptyl-[1,3,5] triazine-2,4 diamine, |
| E34 | 6-isopropoxy-N-(3-Chloro-4-methoxy phenyl)-N'-cyclo heptyl-[1,3,5] triazine-2,4 diamine. |

III. Antiproliferative Activities

One embodiment of the present invention comprises methods and compositions comprising the compounds of the present invention for the treatment and prevention of conditions or diseases that have as an aspect of the disease or condition, unwanted cellular proliferation occurring or are the result of cellular proliferation. For example, many vascular diseases, such as cardiovascular diseases, organ transplant sequellae, vascular occlusive conditions including, but not limited to, neointimal hyperplasia, restenosis, transplant vasculopathy, cardiac allograft vasculopathy, atherosclerosis, and arteriosclerosis, are caused by or have collateral damage due to unwanted cellular proliferation. Smooth muscle cell (SMC) hyperplasia is a major event in the development of atherosclerosis and is also responsible for the significant number of failure rates following vascular procedures such as angioplasty and coronary artery bypass surgery, particularly due to restenosis. Proliferation of arterial wall SMC in response to local injury is a major feature of many vascular proliferative disorders. Neointimal hyperplasia is commonly seen after various forms of vascular injury and a major component of the vein graft's response to harvest and surgical implantation into high-pressure arterial circulation. Proliferation of SMC in response to local injury is a major feature of vascular proliferative disorders such as atherosclerosis and restenosis after angioplasty.

One aspect of the present invention relates to methods and compositions for the treatment and prevention of smooth muscle cell (SMC) proliferation, preferably comprising compositions and compounds having cellular antiproliferative activity. These compounds and compositions comprising such compounds are referred to as antiproliferative compounds or compositions. At least one activity of one or more of these compounds is that the compound has the activity of effecting the synthesis of proteoglycans including induction and synthesis of proteoglycans and active fragments of proteoglycans. Thus, one aspect of the activity of one or more of the compounds and compositions of the present invention comprise molecules that induce HSPG production and that regulate SMC (smooth muscle cell) proliferation.

Compounds of the present invention that have at least the activity of effecting cellular proliferation are shown in TABLE 3. The compounds shown in this Table have the activity of effecting cellular proliferation as measured by the assays taught herein. The inclusion of compounds in the categories of the Tables disclosed herein are not to be seen as limiting, in that compounds included in such Tables have at least the activity shown for inclusion in the Table and may have more or other activities. Nor are the Tables to be seen as limiting in that these are the only compounds disclosed herein that have that activity, representative compounds are shown in the Tables that have at least that particular activity for inclusion in the Table. One or more compounds disclosed herein have at least an activity that has utility in treatment of disease states.

Examples of compounds that show at least this activity and utility are shown in the following structure:

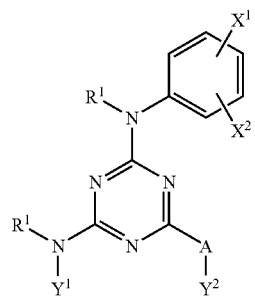

or an ene, a diene, a triene, or an yne derivative thereof; a saturated derivative thereof; a stereoisomer thereof; or a salt thereof;

wherein:

$R^1$ is in each occurrence independently selected from —H; linear or branched alkyl with up to 10 carbon atoms; or cycloalkyl with up to 10 carbon atoms;

$X^1$ is selected from m-F, m-Cl, m-Br, m-I, m-CN, m-$NO_2$, m-$SO_2R^1$, or m-$SO_2OR^1$, or $X^1$ and $X^2$ together is a fused benzene, pyridine, or dioxane ring;

$X^2$ is selected from p-$OR^1$, p-$SR^1$, p-$NR^1_2$, p-OM, or p-SM, wherein M is selected from Li, Na, K, Mg, or Ca;

$Y^1$ is selected from cycloalkyl with up to 10 carbon atoms; linear or branched alkyl with up to 10 carbon atoms; $CH_2R^2$, wherein $R^2$ is a cycloalkyl with up to 10 carbon atoms; or

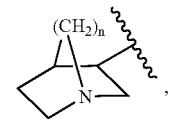

wherein n is 1 or 2;

$AY^2$ is selected from a halogen or $OR^1$, or

A is $NR^1$ and $Y^2$ is selected from $R^1$,

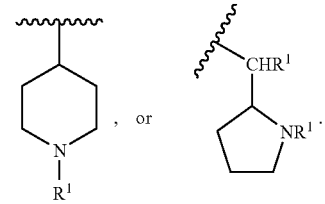

Further examples of compounds that show at least this activity and utility are presented in Table 3, where compound activity is also presented. The activity scale used in Table 3 as follows (numbers are inclusive): "+++" represents $IC_{50}$ of less than about 3 μM; "++" represents $IC_{50}$ of between about 3 and about 7 μM; and "+" represents $IC_{50}$ of greater than about 7 μM. In addition, compounds, to include compositions thereof, encompassed within the scope of structures Ib–XVIb, respectively, or listed in Tables 1B and 1E may be likewise employed in this embodiment and/or aspect of the present invention. Further, any hydrogen atoms that are required for any atom to attain its usual valence in a structure presented in Table 3, whether a carbon atom or a heteroatom, should be inferred if it is not specifically indicated.

In addition to the above compounds, the following compounds and compositions comprising these compounds are active in an anti-proliferation assay (Perlecan). These compounds and compositions comprising these compounds are, among other things, generally useful for treating cardiovascular disorders associated with proliferative activity. Specifically, these compounds include $N^2$-cycloheptyl-$N^4$-(3-fluoro-4-methoxyphenyl)-$N^6$-methyl-$N^6$-(1-methyl-piperidin-4-yl)-1,3,5-triazine-2,4,6-triamine, and $N^2$-cycloheptyl-$N^4$-methyl-$N^4$-(1-methyl-piperidin-4-yl)-$N^6$-naphthalen-2-yl-1,3,5-triazine-2,4,6-triamine. Using the same activity scale used in Table 3, and discussed above, the first compound, $N^2$-cycloheptyl-$N^4$-(3-fluoro-4-methoxyphenyl)-$N^6$-methyl-$N^6$-(1-methyl-piperidin-4-yl)-1,3,5-triazine-2,4,6-triamine, is characterized as a compound exhibiting medium or moderate activity, while the second compound, $N^2$-cycloheptyl-$N^4$-methyl-$N^4$-(1-methyl-piperidin-4-yl)-$N^6$-naphthalen-2-yl-1,3,5-triazine-2,4,6-triamine, is characterized as a compound exhibiting high activity.

As used herein, when a proteoglycan is referred to, the entire molecule or fragments are included therein. For example, perlecan refers to the entire perlecan molecule or fragments thereof. Different fragments of perlecan may have the same or different effects on cells and the effects may be the same as or different from the effects that the entire perlecan molecule has on cells. These fragments and activities are contemplated in the present invention and compounds included in the present invention may have at least one activity that modulates or effects the fragments' activities or the entire molecule's activities. Although the discussion herein refers specifically to perlecans it is important to note that the compositions, methods, and assays described herein are equally applicable in the context of other proteoglycans, including HSPGs, and including but not limited to, chondroitan sulfates (e.g., A,B, and C), dermatan sulfates, syndecans and glypicans.

Methods for identifying the activity and screening for one or more of these compounds or molecules that induce synthesis of proteoglycans such as HSPG (heparan sulfate proteoglycan) are taught in U.S. patent application Ser. No. 10/091,357, which is incorporated herein in its entirety. Assays of effects of compounds in vivo are also taught in the incorporated references and are known to those skilled in the art. In general, methods comprise the addition of such compounds to assays and measurement of HSPG synthesis including, but not limited to, the production of syndecans, glypicans and perlecans, for example, syndecans 1, 2 and 4; and glypican-1. Other assays that can be used to determine the activity of the compounds of the present invention include other methods for measuring the induction of perlecan synthesis. For example, in one assay, perlecan is induced in cells by certain inducers, and the response is measured. Compounds of the present invention are then added to a replicate assay and the effect on perlecan induction is determined. Using such methods, compounds are determined that can either inhibit perlecan, elevate induction of perlecan, or that have no effect at all. Those compounds that are effective as therapeutic agents can then be used in animals, humans or patients with cellular proliferation disease aspects, such as vascular-associated diseases or SMC proliferation pathologies.

Another assay for determining compounds having SMC effects comprises adding a composition suspected of effecting SMC proliferation to smooth muscle cells in growth medium or serum-free medium. The change in cell proliferation can be measured by methods known to those skilled in the art, such as incorporation of labeled nucleotides into dividing cells' DNA, and compared to the proliferation of cells which are not treated with the compound. Other measurements include directly determining levels of HSPG synthesis by measuring the amount or change in amount of HSPG such as with ELISA for HSPGs, and compared to the amount of HSPG synthesis in untreated cells. Other indirect or direct measurement are contemplated by the present invention and are known to those skilled in the art. For example, such methods include, but are not limited to, measurement of RNA levels, RT-PCR, Northern blotting, Western blotting promoter-based assays to identify compounds that affect one or more proteoglycans and assays for proteoglycan biological activity shown by recombinant proteins, partially purified proteins, or lysates from cells expressing proteoglycans in the presence or absence of compounds of interest.

An assay for identifying and determining an activity of one or more of the compounds of the present invention comprises identifying compounds that interact with the promoter regions of a gene, or interact and effect proteins that interact with the promoter region, and are important in the transcriptional regulation of the protein's expression. For example, if perlecan were the protein, in general, the method comprises a vector comprising regulatory sequences of the perlecan gene and an indicator region controlled by the regulatory sequences, such as an enzyme, in a promoter-reporter construct. The protein product of the indicator region is referred to herein as a reporter enzyme or reporter protein. The regulatory region of the sequence of perlecan comprises a range of nucleotides from approximately −4000 to +2000 wherein the transcription initiation site is +1, more preferably, from −2500 to +1200, most preferably, from −1500 to +800 relative to the transcription initiation site.

Cells are transfected with a vector comprising the promoter-reporter construct and then treated with one or more compositions comprising at least one compound of the present invention. For example, the transfected cells are treated with a composition comprising a compound suspected of effecting the transcription of perlecan and the level of activity of the perlecan regulatory sequences are compared to the level of activity in cells that were not treated with the compound. The level of activity of the perlecan regulatory sequences are determined by measuring the amount of the reporter protein or determining the activity of the reporter enzyme controlled by the regulatory sequences. An increase in the amount of the reporter protein or the reporter enzyme activity shows a stimulatory effect on perlecan, by positively effecting the promoter, whereas a decrease in the amount or the reporter protein or the reporter enzyme activity shows a negative effect on the promoter and thus, on perlecan.

Additionally, the present invention comprises methods and compositions that can be used with gene therapy methods and composition, such as those gene therapy methods comprising administering compositions comprising nucleic acids that effect the synthesis or expression of HSPGs, particularly perlecan. Such methods and compositions are taught in U.S. patent application Ser. No. 10/091,357, incorporated herein by reference.

The present invention comprises methods and compositions for mediating proteoglycan synthesis, expression and for the maintenance of SMC in a quiescent state. Methods and compositions of the present invention comprise treatment and prevention of vascular diseases and pathologies related to celluar proliferation, such as SMC proliferation. Such methods and compositions comprise methods for inhibition of smooth muscle cell (SMC) growth and proliferation, and for induction of quiescence in smooth muscle cells. Embodiments of the present invention comprise methods and compositions for inducing proteoglycan synthesis, particularly HSPG synthesis and expression including, but not limited to, the induction of HSPGs such as syndecans, glypicans and perlecans, and preferably perlecan synthesis and gene expression. Perlecan is a major extracellular HSPG in the blood vessel matrix. It interacts with extracellular matrix proteins, growth factors and receptors. Perlecan is also present in basement membranes other than blood vessels and in other extracellular matrix structures.

The activities of the compounds included in the present invention effect cells or tissues to increase the synthesis of proteoglycans by those cells or tissues or may act directly upon one or more proteoglycans to modulate the biological activity or to increase the biological stability of the proteoglycan itself, for example, of the protein perlecan. Activities also included herein are ones that increase the biosynthesis of one or more proteoglycans by increasing the transcription of the proteoglycan gene, increasing the biological stability of the proteoglycan mRNA or increasing the translation of proteoglycan mRNA into protein. Further activities include activities of compounds that can block or decrease the effects of agents or proteins that inhibit the activity of proteoglycans.

The present invention comprises methods and compositions for the treatment and prevention of smooth muscle cell proliferation, including vascular occlusive pathologies. Such methods comprise administration of compositions comprising compounds capable of inhibiting SMC proliferation, such as compositions comprising compounds disclosed herein that inhibit SMC proliferation. Administration of such compounds that are effective in inhibiting SMC proliferation are administered to humans and animals suspected of having or who have, for example, vasculopathy or who have undergone angioplasty or other procedures damaging to the endothelium. Effective amounts are administered to such humans and animals in dosages that are safe and effective, including, but not limited to, the ranges taught herein. Routes of administration include, but are not limited to, those disclosed herein. As disclosed herein, compositions comprising such compounds may be used in conjunction with other therapeutic agents or in methods comprising steps such as altered patient activities, including, but not limited to, changes in exercise or diet.

The compounds of the present invention are useful in the treatment or prophylaxis of at least one cardiovascular disease in a cell, tissue, organ, animal, or patient including, but not limited to, vascular occlusive lesions including atherosclerosis, transplant vasculopathy, cardiac allograft vasculopathy, restenosis, graft atherosclerosis after coronary transplantation, cardiac stun syndrome, myocardial infarction, congestive heart failure, stroke, ischemic stroke, hemorrhage, arteriosclerosis, atherosclerosis, restenosis, diabetic aterioscleroctic disease, hypertension, arterial hypertension, renovascular hypertension, syncope, shock, syphilis of the cardiovascular system, heart failure, cor pulmonale, primary pulmonary hypertension, cardiac arrhythmias, atrial ectopic beats, atrial flutter, atrial fibrillation (sustained or paroxysmal), post perfusion syndrome, cardiopulmonary bypass inflammation response, chaotic or multifocal atrial tachycardia, regular narrow QRS tachycardia, specific arrythmias, ventricular fibrillation, His bundle arrythmias, atrioventricular block, bundle branch block, myocardial ischemic disorders, coronary artery disease, angina pectoris, myocardial infarction, cardiomyopathy, dilated congestive cardiomyopathy, restrictive cardiomyopathy, valvular heart diseases, endocarditis, pericardial disease, cardiac tumors, aordic and peripheral aneuryisms, aortic dissection, inflammation of the aorta, occulsion of the abdominal aorta and its branches, peripheral vascular disorders, occulsive arterial disorders, peripheral atherlosclerotic disease, thromboangitis obliterans, functional peripheral arterial disorders, Raynaud's phenomenon and disease, acrocyanosis, erythromelalgia, venous diseases, venous thrombosis, varicose veins, arteriovenous fistula, lymphederma, lipedema, unstable angina, reperfusion injury, post pump syndrome, ischemia-reperfusion injury, and the like. Such methods can optionally comprise administering an effective amount of a composition or pharmaceutical composition comprising at least one compound to a cell, tissue, organ, animal or patient in need of such modulation, treatment or therapy.

Proteoglycan-associated diseases that are treatable with the compounds of the present invention include, but are not limited to, hereditary multiple exostosis, mucopolysaccharidosis types I–III and VII, commonly known as Hurler's Syndrome, Hunter's Syndrome, Sanfilippo's Syndrome and Sly's Syndrome respectively, Alzheimer's disease, Simpson-Golabi-Behmel syndrome, fibroblast growth factor related disorders, herpes simplex virus, dengue fever, Parkinson's disease, renal disease, muscular dystrophy, Schwarts-Jampel syndrome, proteinuric glomerulopathies, myotonia and skeletal dysplasia, kyphoscoliosis, dyssegmental dysplasia, Silverman-Handmaker type, chondrodysplasia, periodontitis, rheumatoid and osteoarthritis, Gerstmann-Straussler syndrome, Creutzfeldt-Jakob disease, scrapie, carcinomas, Happle syndrome, macular dystrophy, bone diseases, corneal diseases, leukocyte-mediated disease, collagen fibril assembly disorder and coronary heart disease and other vascular disorders.

IV. Glycosidase Modulation Activity

The present invention also comprises methods and compositions comprising compounds described herein that have an activity associated with modulation of glycosidase enzymes and thus, effecting the substrates for such enzymes. Glycosidase enzymes and their activity with their substrates, such as proteoglycans or glycated proteins, are aspects of a variety of diseases such as vascular conditions, including those conditions discussed supra, proteoglycan-associated diseases, supra, associated diseases with vascular components, including but not limited to, kidney disease, ischemic heart disease, cardiovascular disease, generalized vascular disease, proliferative retinopathy, and macroangeopathy, inflammatory diseases and metastatic diseases such as cancer, cellular proliferative conditions, and solid and blood borne tumors or other oncological conditions. Compounds described herein that have an activity that effects the concentrations of substrates of glycosidase enzymes are used in methods of treatment of such vascular, inflammatory, metastatic and systemic diseases.

An aspect of the present invention comprises methods and compositions for the modulation of enzymes, such as glycosaminoglycan degrading enzymes, which effect or are effected by proteoglycan levels, amount or activity. For example, the present invention comprises methods and compositions comprising compounds that modulate enzymes including but not limited to, heparanase, chondroitanase, heparan sulfate endoglycosidase, heparan sulfate exoglycosidase, polysaccharide lyases, keratinase, hyauronidase, glucanase, amylase, glycosidases, or other proteoglycan degrading enzymes are useful for the treatment of conditions such as diabetic vasculopathy, cancer, inflammatory diseases, autoimmune diseases and cardiovascular diseases. For example, the present invention comprises methods and compositions of compounds that inhibit, impair or down-regulate the activity of proteoglycan degrading enzymes.

Proteoglycans such as HSPG are important components of the subendothelial extracellular matrix and the basement membrane of blood vessels. Rosenberg et al., 99 J. CLIN. INVEST. 2062–70 (1997). Basement membranes are continuous sheets of extracellular matrix composed of collagenous and noncollagenous proteins and proteoglycans that separate parenchymal cells from underlying interstitial connective tissue. They have characteristic permeabilities and play a role in maintaining tissue architecture.

In addition to HSPGs, the basal lamina consists predominantly of a complex network of adhesion proteins, fibronectin, laminin, collagen and vitronectin. Wight et al., 6 CURR. OPIN. LIPIDOL. 326–334 (1995). Heparan sulfate (HS) is an important structural component of the basal lamina. Each of the adhesion proteins interacts with HS side chains of HSPGs within the matrix. Thus, HSPGs function as a barrier to the extravasation of metastatic and inflammatory cells. Cleavage of HS by the endoglycosidase heparanase produced by metastatic tumor cells and inflammatory cells destroys the filtering properties of the lamina. In addition, the degradation of the HS may assist in the disassembly of the extracellular matrix and thereby facilitate cell migration by allowing blood bome cells to escape into the bloodstream. Vlodavsky et al., 12 INVASION METASTASIS 112–127 (1992).

Heparanase activity has been described in a number of tissues and cell types including liver, placenta, platelets, fibroblasts, neutrophils, activated T and B-lymphocytes, monocytes, and endothelial cells (7–16). Nakajima et al., (31) CANCER LETT. 277–283 (1986); Nakajima et al., 36 J. CELL. BIOCHEM. 157–167 (1988); Ricoveri et al., 46 CANCER RES. 3855–3861 (1986); Gallagher et al., 250 BIOCHEM. J. 719–726 (1988); Dempsey et al., 10 GLYCOBIOLOGY 467 (2000); Goshen et al., 2 MOL. HUM. REPROD. 679 (1996); Parish et al., 76 IMMUNOL CELL BIOL. 104–113 (1998); Gilat et al., 181 J. EXP. MED. 1929–1934 (1995); Graham, et al., 39 BIOCHEM. MOL. BIOL. INT. 56371 (1996); Pillarisetti et al., 270 J.BIOL.CHEM. 29760–29765 (1995). An important process in tissue invasion by blood-borne tumor cells and white cells involves their passage through the vascular endothelial cell layer and subsequent degradation of the underlying basal lamina or basement membranes and extracellular matrix with a battery of secreted proteases and glycosidases. Nakajinia et al., 220 SCIENCE 611–613 secreted proteases and glycosidases. Nakajinia et al., 220 SCIENCE 611–613 (1983); Vlodavsky et al.,12 INVASION METASTASIS 112–127 (1992). of animal and human tumor cell lines. Nakajima et al., 31 CANCER LETT. 277–283 (1986); Nakajima et al., 212 PROG CLIN BIOL RES. 113–122 (1986); Freeman et al., 325 BIOCHEM. J. 229–237 (1997); Vlodavsky et al., 5 NAT. MED. 793–802 (1999); Hulett et al., 5 NAT MED. 803–809 (1999). It is also known to regulate growth factor activity. Many growth factors remain bound to heparan sulfate in storage form and are disassociated by heparanase during angiogenesis, improving the survival rate of cancer cells.

Serum heparanase levels in rats were higher by more than an order of magnitude after injection of the rats with highly metastatic mammary adenocarcinoma cells. In addition, heparanase activity in the sera of rats bearing MTLn3 tumors correlated well with the extent of the metastases. Moreover, serum/urine heparanase activity in cancer patients was shown to be 2–4 fold increased in particular where tissue metastases were present. Because the cleavage of HS appears to be essential for the passage of metastatic tumor cells and leukocytes through basement membranes, studies of heparanase inhibitors provides the potential of developing a novel and highly selective class of anti-metastatic and anti-inflammatory drugs.

The present invention comprises methods and compositions comprising compounds that modulate heparanase activity or the activity of other glycosidases, including, but not limited to enzymes with glycosaminoglycan activity such as chondroitinase, heparan sulfate endoglycosidase, heparan sulfate exoglycosidase, polysaccharide lyases, keratinase, hyaluranidase, glucanase, and amylase. Compounds of the present invention that have at least the activity of modulating glycosidase enzyme activity are shown in TABLE 6. The compounds shown in this Table have the activity of modulating glycosidase enzyme activity as measured by the assays taught herein. The inclusion of compounds in the categories of the Tables disclosed herein are not to be seen as limiting, in that compounds included in such Tables have at least the activity shown for inclusion in the Table and may have more or other activities. Nor are the Tables to be seen as limiting in that these are the only compounds disclosed herein that have that activity, representative compounds are shown in the Tables that have at least that particular activity for inclusion in the Table. One or more compounds disclosed herein have at least an activity that has utility in treatment of disease states.

Examples of compounds that show at least this activity and utility are shown in the following formula:

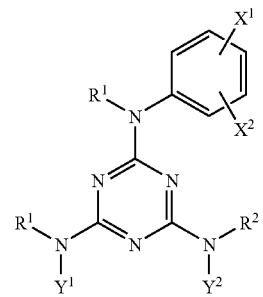

or an ene, a diene, a triene, or an yne derivative thereof; a saturated derivative thereof; a stereoisomer thereof; or a salt thereof, wherein:

$R^1$ is in each occurrence independently selected from —H; linear or branched alkyl with up to 10 carbon atoms; or cycloalkyl with up to 10 carbon atoms;

$X^1$ is selected from H, m-F, m-Cl, m-Br, m-I, m-CN, m-NO$_2$, m-SO$_2$R$^1$, or m-SO$_2$OR$^1$;

$X^2$ is selected from o-R$^1$, p-OR$^1$, p-SR$^1$, p-NR$^1{}_2$, p-OM, or p-SM, wherein M is selected from Li, Na, K, Mg, or Ca;

$Y^1$ is selected from cycloalkyl with up to 10 carbon atoms or

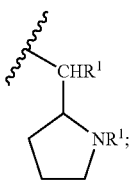

and $Y^2$ is selected from linear or branched alkyl with up to 10 carbon atoms, cycloalkyl with up to 10 carbon atoms, or

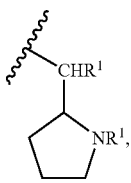

and $R^2$ is —H; or $NY^2R^2$ together is selected from

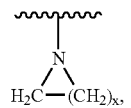

wherein x is an integer from 3 to 5,

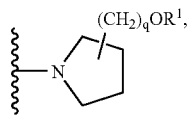

wherein q is an integer from 0 to 6, or

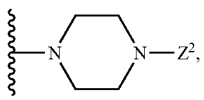

wherein $Z^2$ is selected from $R^1$ or

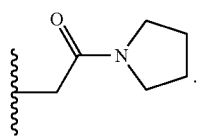

Further examples of compounds that show at least this activity and utility are presented in Table 6, where compound activity is also shown. The activity scale used in Table 6 is as follows (numbers are inclusive): "+++" represents between about 70 and about 100% inhibition; "++" represents between about 30 and about 40% inhibition; and "+" indicates between 0 and about 30% inhibition, all at 5 μM compound concentration. In addition, compounds, to include compositions thereof, encompassed within the scope of structures Ib–XVIb, respectively, or listed in Tables 1B and 1E may be likewise employed in this embodiment and/or aspect of the present invention. Also note that any hydrogen atoms that are required for any atom to attain its usual valence in a structure presented in Table 6, whether a carbon atom or a heteroatom, should be inferred if it is not specifically indicated.

Compounds or compositions comprising such compounds that are effective in modulating glycosidase enzyme activity are useful in treating and/or preventing cancer including, but not limited to, malignant and non-malignant cell growth, leukemia, acute leukemia, acute lymphoblastic leukemia (ALL), B-cell, T-cell or FAB ALL, acute myeloid leukemia (AML), chromic myclocytic leukemia (CML), chronic lymphocytic leukemia (CLL), hairy cell leukemia, myelodyplastic syndrome (MDS), a lymphoma, Hodgkin's disease, a malignamt lymphoma, non-hodgkin's lymphoma, Burkitt's lymphoma, multiple myeloma, Kaposi's sarcoma, colorectal carcinoma, pancreatic carcinoma, nasopharyngeal carcinoma, malignant histiocytosis, paraneoplastic syndrome/hypercalcemia of malignancy, solid tumors, adenocarcinomas, sarcomas, malignant melanoma, hemangioma, metastatic disease, cancer related bone resorption, cancer related bone pain, and the like.

In another aspect of the present invention, the compounds disclosed herein are useful in modulating heparanase activity or the activity of other glycosidases as a means for treating and preventing autoimmune diseases. Generally autoimmune disease results when (1) the immune system mistakenly identifies a cell surface molecule on normal tissue as a foreign molecule (2) the synthesis and secretion of chemokines, cytokines and lymphokines is not shut down after the eradication of the disease or (3) the immune system overreacts to the apparent infection and destroys vast quantities of surrounding normal tissue.

To be effective in an immune response, the immune effector cells must bind to the luminal/apical surface of the blood vessel walls. This is accomplished through the interaction of adhesion molecules on the immune effector cells with their locally upregulated cognate receptors on the endothelial cells lining the vasculature near the site of infection. After binding to the apical surface and before entering the inflamed tissue, the immune effector cells must breach the basement membrane (BM) and extracellular matrix (ECM) that surround the basal portion of the blood vessels and give the vessels their shape and strength. The BM and ECM consists of structural proteins embedded in a fiber meshwork consisting mainly of complex carbohydrate containing structures (glycosaminoglycans), of which the main constituent is heparin sulfate proteoglycan (HSPG). In order to breach this barrier the immune effector cell must weaken or destroy it, which is accomplished through the local secretion of proteases and heparanase(s).

Thus, the inhibition of heparanase or the activity of other glycosidases using the compounds of the present invention finds utitlity in treating arthritis and other autoimmune diseases. More specifically, the compounds of the present invention are useful in the treatment or prophylaxis of at least one autoimmune-related disease in a cell, tissue, organ, animal, or patient including, but not limited to, rheumatoid arthritis, juvenile rheumatoid arthritis, systemic onset juvenile rheumatoid arthritis, psoriatic arthritis, ankylosing spondilitis, gastric ulcer, seronegative arthropathies, osteoarthritis, inflammatory bowel disease, ulcerative colitis, systemic lupus erythematosis, antiphospholipid syndrome, iridocyclitis/uveitis/optic neuritis, idiopathic pulmonary fibrosis, systemic vasculitis/wegener's granulomatosis, sarcoidosis, orchitis/vasectomy reversal procedures, allergic/atopic diseases, asthma, allergic rhinitis, eczema, allergic contact dermatitis, allergic conjunctivitis, hypersensitivity pneumonitis, transplants, organ transplant rejection, graft-versus-host disease, systemic inflammatory response syndrome, sepsis syndrome, gram positive sepsis, gram negative sepsis, culture negative sepsis, fungal sepsis, neutropenic fever, urosepsis, meningococcemia, trauma/hemorrhage, burns, ionizing radiation exposure, acute pancreatitis, adult respiratory distress syndrome, rheumatoid arthritis, alcohol-induced hepatitis, chronic inflammatory pathologies, Crohn's pathology, sickle cell anemia, diabetes, nephrosis, atopic diseases, hypersensitivity reactions, allergic rhinitis, hay fever, perennial rhinitis, conjunctivitis, endometriosis, asthma, urticaria, systemic anaphalaxis, dermatitis, pernicious anemia, hemolytic disease, thrombocytopenia, graft rejection of any organ or tissue, kidney transplant rejection, heart transplant rejection, liver transplant rejection, pancreas transplant rejection, lung transplant rejection, bone marrow transplant (BMT) rejection, skin allograft rejection, cartilage transplant rejection, bone graft rejection, small bowel transplant rejection, fetal thymus implant rejection, parathyroid transplant rejection, xenograft rejection of any organ or tissue, allograft rejection, anti-receptor hypersensitivity reactions, Graves disease, Raynoud's disease, type B insulin-resistant diabetes, asthma, myasthenia gravis, -meditated cytotoxicity, type III hypersensitivity reactions, POEMS syndrome (polyneuropathy, organomegaly, endocrinopathy, monoclonal gammopathy, and skin changes syndrome), polyneuropathy, organomegaly, endocrinopathy, monoclonal gammopathy, skin changes syndrome, anti-phospholipid syndrome, pemphigus, scleroderma, mixed connective tissue disease, idiopathic Addison's disease, autoimmune hemolytic anemia, autoimmune hepatitis, idiopathic pulmonary fibrosis, scleroderma, diabetes mellitus, chronic active hepatitis, vitiligo, vasculitis, post-MI cardiotomy syndrome, type IV hypersensitivity, contact dermatitis, hypersensitivity pneumonitis, allograft rejection, granulomas due to intracellular organisms, drug sensitivity, metabolic/idiopathic, Wilson's disease, hemachromatosis, alpha-1-antitrypsin deficiency, diabetic retinopathy, hashimoto's thyroiditis, osteoporosis, hypothalamic-pituitary-adrenal axis evaluation, primary biliary cirrhosis, thyroiditis, encephalomyelitis, cachexia, cystic fibrosis, neonatal chronic lung disease, chronic obstructive pulmonary disease (COPD), familial hematophagocytic lymphohistiocytosis, dermatologic conditions, psoriasis, alopecia, nephrotic syndrome, nephritis, glomerular nephritis, acute renal failure, hemodialysis, uremia, toxicity, preeclampsia, ankylosing spondylitis, Behcet's disease, bullous pemphigoid, cardiomyopathy, celiac sprue-dermatitis, chronic fatigue immune dysfunction syndrome (CFIDS), chronic inflammatory demyelinating polyneuropathy, Churg-Strauss syndrome, cicatricial pemphigoid, CREST syndrome, cold agglutinin disease, discoid lupus, essential mixed cryoglobulinemia, fibromyalgia-fibromyositis, Graves' disease, Guillain-Barré, Hashimoto's thyroiditis, idiopathic thrombocytopenia purpura (ITP), IgA nephropathy, insulin dependent diabetes, juvenile arthritis, lichen planus, meniere's disease, multiple sclerosis, pemphigus vulgaris, polyarteritis nodosa, Cogan's syndrome, polychondritis, polyglandular syndromes, polymyalgia rheumatica, polymyositis and dermatomyositis, primary agammaglobulinemia, Raynaud's phenomenon, Reiter's syndrome, rheumatic fever, Sjeögren's syndrome, stiff-man syndrome, Takayasu arteritis, temporal arteritis/giant cell arteritis, Wegener's granulomatosis; okt3 therapy, anti-cd3 therapy, cytokine therapy, chemotherapy, radiation therapy (e.g., including but not limited to asthenia, anemia, cachexia, and the like), chronic salicylate intoxication, and the like.

Compounds having heparanase activity inhibition, that are effective for example, in treatment of cancer and autoimmune disease, can be determined using assays such as those disclosed in U.S. patent application Ser. No. 09/952,648, which is incorporated herein in its entirety. Such assays, which are used for measurement of cellular and enzymatic activities, both qualitatively and quantitatively, and in methods for diagnosing metastases, metastatic potential and inflammatory states, are performed with and without the addition of at least one of the compounds of the present invention to determine the activity of the compound. Existing heparanase assays are taught in Goshen et al., 2 MOL. HUM. REPROD. 679–84 (1996); Nakajima et al., 31 CANCER LETT. 277–83 (1986); and Viodasky et al., 12 INVASION METASTASIS 112–27 (1992); Freeman and Parish, 325 BIOCHEM. J. 229–37 (1997); Kahn and Newman, 196 ANAL. BIOCHEM. 373–76 (1991). Solid-phase heparanase assays have also been developed where chemically and biosynthetically radiolabeled heparin and HS chains were attached to a solid support, with release of radiolabel from the solid support being a measure of enzyme activity. Assays using such procedures are taught in U.S. Pat. No. 4,859,581, which is entirely expressly herein incorporated by reference.

In general, a preferred assay comprises attaching one of a binding partner to a substrate for the enzyme to be measured, forming the substrate-binding partner. Incubation with a sample comprising the enzyme to be measured allows for activity by the enzyme to be measured in a reaction mixture. A portion or the whole reaction mixture, depending on the amount needed, is then mixed with the complementary binding partner, so that the binding partners are bound together. This is the first binding reaction. After incubating to allow for binding, washings are performed. A complementary binding partner, complementary to the first binding partner attached to the substrate, is added. This complementary binding partner may or may not be the same as the first complementary binding partner. This is the second binding reaction. The complementary binding partner in the second binding reaction is labeled in a manner that is detectable. For example, the complementary binding partner is labeled with an enzyme that causes a detectable color change when the appropriate reaction conditions exist. The difference between the activity of the enzyme in the presence of a compound and the absence of compound is used to determine the activity of the compound.

An example of a heparanase assay comprises the following steps. A composition comprising biotin-HS (heparan sulfate) is mixed with a biological sample such as a tumor sample, bodily fluid, or other fluid suspected of having heparanase activity, to form a reaction mixture. This sample may be pretreated to remove contaminating or reactive substances such as endogenous biotin. A control portion for this reaction mixture does not contain a compound of the present invention, whereas a test portion contains one or more compounds disclosed herein. After incubation, an aliquot or portion of the reaction mixture portions is removed and placed in a biotin-binding plate. The biotin-binding plate comprises any means for binding biotin, preferably to a solid surface. See WO 02/23197, which is entirely expressly incorporated herein by reference. After washing with buffers, a streptavidin-enzyme conjugate is added to the biotin-binding plate. Reagents for the enzyme are added to form a detectable color product. For example, a decrease in color formation, from a known standard, indicates there was heparanase activity in the sample. The difference between the activity of the enzyme in the presence of a compound and the absence of compound is used to determine the activity of the compound.

Using the above assays or those taught in the Examples herein, the amount of enzyme activity in a sample can be determined and the activities of compounds of the present invention can be determined. For example, a composition comprising a compound of the present invention is added to a known amount of heparanase either before or during the incubation of the heparanase and its substrate-binding partner. If the compound alters the activity of the heparanase, the assay methods of the present invention will show a change in the amount of detectable label. Such assays are used for high throughput determination of the activity of compounds. See WO 02/23197, which is entirely expressly incorporated herein by reference.

The activities of the compounds included in the present invention modulate the activity of glycosidases, either positively or negatively, include effects on the glycosidases either directly or indirectly. The compounds may modulate the synthesis of glycosidases by cells or tissues or may act directly upon one or more glycosidases to modulate the biological activity or the biological stability of the enzyme itself, for example, heparanase. Activities also included herein are ones that increase the biosynthesis of one or more glycosidases by increasing the transcription of the glycosidase gene, increasing the biological stability of the glycosidase mRNA or increasing the translation of glycosidase mRNA into protein. Further activities include activities of compounds that can block or decrease the effects of agents or proteins that inhibit the activity of glycosidases. Additionally, activities are included that effect the substrates for the glycosidases, such as those discussed supra in relation to proteoglycans, or effect the binding parameters of the enzyme with its substrate, cofactors or stimulatory or inhibitory factors.

The present invention comprises methods and compositions for the treatment and prevention of diseases or conditions that present or result from glycosidase activity. Such methods comprise administration of compositions comprising compounds capable of modulating heparanase activity, such as compositions comprising compounds disclosed herein that inhibit heparanase activity. Administration of such compounds that are effective in modulating heparanase activity are administered to humans and animals suspected of having or who have, for example, inflammatory conditions, autoimmune disease or diabetic vasculopathy. Effective amounts are administered to such humans and animals in dosages that are safe and effective, including, but not limited to, the ranges taught herein. Routes of administration include, but are not limited to, those disclosed herein. As disclosed herein, compositions comprising such compounds may be used in conjunction with other therapeutic agents or in methods comprising steps such as altered patient activities.

V. Inflammation Modulation

An embodiment of the present invention comprises methods and compositions comprising compounds of the present invention for the treatment and prevention of conditions or diseases that have as an aspect of the disease or condition, inflammation. An aspect of the present invention is directed to methods and compositions comprising compounds that are effective in inhibiting inflammation, particularly inflammation associated with the accumulation or presence of glycated proteins or AGE. The activity of modulating inflammation includes, but is not limited to, inhibiting inflammation and/or its associated cell activation by glycated proteins or AGE, blocking the glycation of proteins, blocking AGE interactions with receptors, blocking AGE-induced signaling or signaling-associated inflammatory responses, cytokine induction, synthesis or release, AGE formation or AGE cross-linking.

The present invention also provides compositions for and methods of treatment of biological conditions including, but not limited to, vascular complications of type I and type II diabetic-induced vasculopathies, other vasculopathies, microangiopathies, renal insufficiency, Alzheimer's syndrome, and inflammation-induced diseases such as atherosclerosis. Other inflammatory related diseases include, but are not limited to, inflammatory diseases of the joint such as rheumatoid arthritis, osteoarthritis, autoimmune diseases such as those taught supra, streptococcal cell-wall induced arthritis, adjuvant-induced arthritis, bursitis; inflammatory diseases of the thyroid such as acute, subacute and chronic thyroiditis, pelvic inflammatory disease, hepatitis; inflammatory bowel diseases such as Crohn's disease and colitis; neuroinflammatory diseases such as multiple sclerosis, abscess, meningitis, encephalitis, and vasculitis; inflammatory diseases of the heart such as myocarditis, chronic obstructive pulmonary disease, atherosclerosis, pericarditis; inflammatory diseases of the skin such as acute inflammatory dermatoses (urticaria (hives), spongiotic dermatitis, erythema multiforme (em minor), Stevens-Johnson syndrome (sjs, em major), toxic epidermal necrolysis (ten) and chronic inflammatory dermatoses (psoriasis, lichen planus, discoid lupus erythematosus, acne vulgaris); inflammatory diseases of the eye such as uveitis, allergic conjunctivitis, corneal inflammation, intraocular inflammation, iritis; laryngitis and asthma.

The compounds of the present invention have utility in inhibiting inflammation and/or its associated cell activation by glycated proteins or AGE. Pharmacological inhibition of AGE-induced cell activation provides the basis for therapeutic intervention in many diseases, notably in diabetic complications and Alzheimer's disease. Therapeutic approaches for inhibition of AGE-induced inflammation include, but are not limited to, blocking the glycation of proteins, blocking AGE interactions with receptors and blocking AGE-induced signaling or signaling-associated inflammatory responses.

At least one activity of some of the compounds of the present invention is to block AGE effects by inhibiting AGE-induced signaling. The sequence of these signaling events leading to inflammation are not clear, but inhibition of these signaling events leads to reduced or no inflammatory results. Compounds that block AGE-induced up-regulation of inflammatory molecules were determined using screening assays. Other aspects of the present invention comprise methods and compositions comprising compounds that block glycated protein-induced inflammation. Some compounds may effect AGE formation or AGE cross-linking.

At least one activity of some of the compounds of the present invention is to block AGE effects by inhibiting reactions with receptors of AGE and such activities are also contemplated by the methods of the present invention for treatment of related pathologies. For example, RAGE, a known receptor for AGE, is a therapeutic target. Blocking RAGE inhibited AGE-induced inflammation. Prior to use of the compounds of the present invention, the multiple functions of RAGE and possible long term side effects of accumulated AGE in plasma, have prevented this method of treatment from being implemented. However, using the methods and compositions of the present invention, more specific inhibitory compounds can be used for treatments and overcome the current problems with treatments that target receptors.

Compounds of the present invention that have at least the activity of modulating inflammation activity are shown in TABLE 5. The compounds shown in this Table have the activity of modulating inflammation activity as measured by the assays taught herein. The inclusion of compounds in the categories of the Tables disclosed herein are not to be seen as limiting, in that compounds included in such Tables have at least the activity shown for inclusion in the Table and may have more or other activities. Nor are the Tables to be seen as limiting in that these are the only compounds disclosed herein that have that activity, representative compounds are shown in the Tables that have at least that particular activity for inclusion in the Table. One or more compounds disclosed herein have at least an activity that has utility in treatment of disease states.

Examples of compounds that show at least this activity and utility are shown in the following formula:

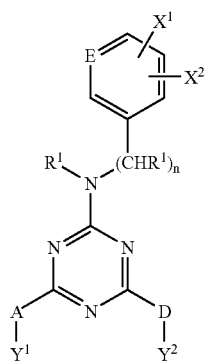

or an ene, a diene, a triene, or an yne derivative thereof; a saturated derivative thereof; a stereoisomer thereof; or a salt thereof;

wherein:

$R^1$ is in each occurrence independently selected from —H; linear or branched alkyl with up to 10 carbon atoms; cycloalkyl with up to 10 carbon atoms; aryl; or $(CH_2)_xCN$, wherein x is an integer from 0 to 6;

E is CH or N;

n is an integer from 0 to 3;

$X^1$ is selected from —H, m-F, m-Cl, m-Br, m-I, m-CN, m-NO$_2$, m-SO$_2$R$^1$, m-SO$_2$OR$^1$, m-NC(O)R$^1$, or o-F, or $X^1$ and $X^2$ together is a fused benzene, pyridine, or dioxane ring;

$X^2$ is selected from —H, o-Cl, o-Br, o-CF$_3$, o-R$^1$, p-OR$^1$, p-SR$^1$, p-NR$^1_2$, p-F, p-Cl, p-Br, p-CF$_3$, p-CN, p-C(O)OR$^1$, p-NC(O)R$^1$, p-(4-morpholinyl), or p-(4-methyl-1-piperizinyl);

$AY^1$ is a halogen, or A is $NR^1$ or O and $Y^1$ is selected from cycloalkyl with up to 10 carbon atoms, cycloalkyl with up to 10 carbon atoms substituted with $R^1$, linear or branched alkyl with up to 10 carbon atoms, $CH_2R^1$, $(CHR^1)_yOR^1$, wherein y is an integer from 1 to 6,

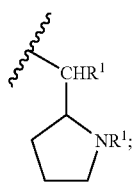

or $AY^1$ together are

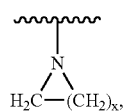

wherein x is an integer from 3 to 5; and $DY^2$ is a halogen, or D is $NR^1$ and $Y^2$ is selected from

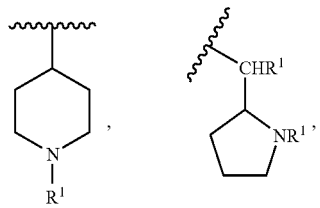

cycloalkyl with up to 10 carbon atoms, cycloalkyl with up to 10 carbon atoms substituted with $R^1$, linear or branched alkyl with up to 10 carbon atoms, $CH_2R^1$,

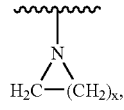

wherein x is an integer from 3 to 5,

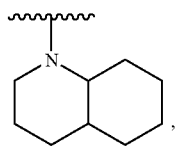

$CH_2CF_3$, $(CHR^1)_zZ^1$, wherein z is an integer from 1 to 6, and $Z^1$ is selected from $NR^1_2$,

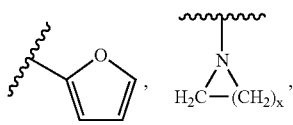

wherein x is an integer from 3 to 5,

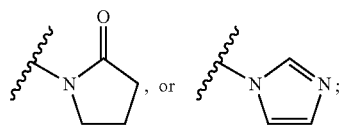

or $NY^2R^1$ together is selected from

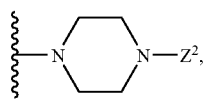

wherein $Z^2$ is selected from $R^1$, $C(O)R^1$, $C(O)OR^1$, pyridinyl, aryl,

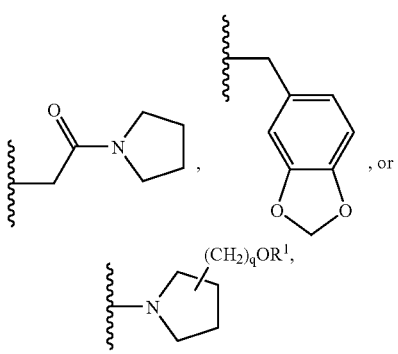

wherein q is an integer from 0 to 6.

Further examples of compounds that show at least this activity and utility are presented in Table 5, where compound activity is also shown. The activity scale used in Table 5 is as follows (numbers are inclusive): "++++" represents between 0 and about 25% of IL6 production compared to cells that did not receive compound (or per cent of control IL6 production); "+++" represents between about 25 and about 50% of control IL6 production; "++" represents between about 50 and about 75% of control IL6 production; and "+" represents between about 75 and 100% of control IL6 production. The note "n.d." indicates that the activity of the compound was not determined in the given assay. Further note that any hydrogen atoms that are required for any atom to attain its usual valence in a structure presented in Table 5, whether a carbon atom or a heteroatom, should be inferred if it is not specifically indicated.

In addition to the above compounds, the compounds shown in Table 7, and compositions comprising these compounds, also exhibit the activity of modulating inflammation activity as measured by the assays taught herein. The activity scale used in Table 7 is as follows (numbers are inclusive): "+++" represents between about 85 to 100% inhibition of IL6 production in the presence of AGE or TNF, as compared to cells that did not receive any compound; "++" represents between about 65 and about 85% inhibition of IL6 production in the presence of AGE or TNF; and "+" represents between about 50 and about 65% inhibition of IL6 production in the presence of AGE or TNF. In addition, compounds, to include compositions thereof, encompassed within the scope of structures Ib–XVIb, respectively, or listed in Tables 1B and 1E may be likewise employed in this embodiment and/or aspect of the present invention. As before, the inclusion of compounds in the categories of the Tables disclosed herein are not to be seen as limiting, in that compounds included in such Tables have at least the activity shown for inclusion in the Tables and may have more or other activities. Nor are the Tables to be seen as limiting in that these are the only compounds disclosed herein that have that activity, representative compounds are shown in the Tables that have at least that particular activity for inclusion in the Table. One or more compounds disclosed herein have at least an activity that has utility in treatment of disease states.

Enhanced formation and accumulation of glycated proteins and AGE are thought to play a major role in the pathogenesis of diabetic complications, and atherosclerosis, leading to the development of a range of diabetic complications including nephropathy, retinopathy and neuropathy. There is ample in vivo evidence that suggests that diabetes-related complications can be reduced by 1) preventing glycation of proteins, 2) by breaking the cross-links in glycated proteins or 3) by blocking glycated protein interaction with receptors. Despite the importance of AGE in the pathogenesis of diabetic microangiopathies, there are no currently available medications known to block AGE formation.

Endothelium is the target organ of damage in diabetes. See Laight et al., 15 DIABETES METAB. RES. REV. 274–82 (1999); Stehouwer et al., 34 CARDIOVASC. 55–68 (1997). Up-regulation of molecules involved in endothelial leads to endothelial dysfunction and vasculopathy. See Stehouwer et al., 34 CARDIOVASC. 55–68 (1997); Libby, 247 J. INTERN. MED. 349–58 (2000); Van Lente, 293 CLINICA. CHIMICA. ACTA. 31–52 (2000).

IL-6 is a pro-inflammatory cytokine that is known to play a key role in the pathogenesis of diabetes and atherosclerosis. See Horii et al., 39 KIDNEY INT. SUPPL. 71–5 (1993); Huber et al., 19 ARTERIOSCLER. THROMB. VASC. BIOL. 2364–67 (1999); Shikano et al., 85 NEPHRON 81–5 (2000); Pickup et al., 291–300 (2000). IL-6 also promotes the growth of renal mesangial cells thus contributing to nephropathy. See Kado et al., 36 ACTA. DIABETOL. 67–72 (1999). healthy controls (3.48+/−3.29 pg/ml vs 0.784+/−0.90 pg/ml, mean+/−SD). In addition the urinary IL-6 level is a good indicator of diabetic nephropathy. Serum IL-6 is useful in the evaluation of atherosclerosis and nephropathy.

MCP-1, another pro-inflammatory cytokine is found highly expressed in human atherosclerotic lesions and postulated to play a central in monocyte recruitment into the arterial wall and developing lesions. See Libby, 247 J. INTERN. MED. 349–58 (2000). Recent results show that MCP-1 is also a key pathogenic molecule in diabetic nephropathy. See Eitner et al., 51 KIDNEY INT. 69–78 (1997); Banba et al. 58 KIDNEY INT. 684–90 (2000). Glycated albumin stimulates endothelial production of IL-6 and MCP-1. The effects of glycated albumin on IL-6 production are comparable to that of TNFα, a known inducer of IL-6. These cytokines are known to be factors in vascular diseases.

The activity of the compounds of the present invention in inhibiting glycated protein- and AGE-induced inflammation can be determined using the assays described herein and in U.S. patent application Ser. No. 10/026,335, which is herein incorporated in its entirety. Such assays comprise measurement of the specific activity of biological components involved in a known cellular response. The assays provide a measurable response in which the activity of the compounds is determined. One assay comprises measurement of the effects of compounds on an inflammatory response by cells to the presence of a stimulating agent. Yet another assay comprises endothelial cells that are stimulated by the addition of a glycated protein, the stimulating agent. The endothelial cells respond by producing specific cytokines. The amount of cytokines produced are determined by measurement protocols known to those skilled in the art. The compounds of the present invention are then added to the assay and the production of cytokines is measured. From the comparison of the assay without the compound with the assay with the compound, the biological effect of the compound can be determined. The compound may have an inhibitory effect, a stimulatory effect, or no effect at all.

The amount and type of cytokine produced can be determined using immunological methods, such as ELISA assays. The methods of the present invention are not limited by the type of assay used to measure the amount of cytokine produced, and any methods known to those skilled in the art and later developed can be used to measure the amount of cytokines produced in response to the stimulating agent and to the compound having unknown activity.

An aspect of the present invention comprises methods and compositions for the treatment of diseases, preconditions or pathologies associated with inflammatory cytokines and other inflammation related molecules including, but not limited to IL-6, VCAM-1, AGE-induced MCP-1, (monocyte chemoattractant protein 1), heme oxygenase, insulin-like growth factor, selectins, IP-10, MIG and I-TAC, NF-κB, IL-1β (interleukin 1β), IL-11 (interleukin 11), m-CSF (macrophage colony stimulating factor), fibrinogen, TNF-α (tumor necrosis factor α), adhesion molecules, selecting, VCAM-1 (Vascular Cell Adhesion Molecule-1), CRP (C-reactive protein), and PAI-1 (plasminogen activator inhibitor-1). Examples of such diseases include the pathogenesis of atherosclerosis and the development of diabetic vasculopathy in type II diabetes. For example, affecting the activity or level of TNFα is a key mediator of tissue damage following acute or chronic inflammatory reactions. The present invention contemplates providing compositions and methods that modulate the effects of cytokines and inflammatory molecules such as TNFα, IL-6, VCAM-1, IP-10, MIG, I-TAC and AGE-induced MCP-1, and treat the associated diseases, acute or chronic conditions, preconditions and pathologies.

Assays for determining the activity of compounds capable of modulating inflammation include those taught in U.S. patent application Ser Nos. 10/026,335 and 09/969,013, which are both expressly incorporated by reference. In general, once the baseline response to the stimulating agent for the production of cytokines by the endothelial cells is established, thus comprising the control levels for the screening assay, the methods comprise addition of compounds of the present invention. The effect of the compound on the baseline response is determined by comparing the amount of cytokine produced in the presence of the stimulating agent and the amount of cytokine produced in the presence of the stimulating agent and the compound of the present invention. In a preferred method, compounds that have inhibitory effects on the inflammation of the cells in the presence of glycated albumin are then used as therapeutic agents. One or more compounds may be added to the screening assay. Combinations or mixtures of compounds can be added. Different amounts and formulations of the compounds are added to determine the effects on the screening assay. The screening assay may also be used to determine stimulatory compounds or compounds that have no effects in the assay.

The present invention comprises methods and compositions for the treatment and prevention of disease, conditions and pathologies associated with inflammation. Such methods comprise administration of compositions comprising compounds capable of modulating the activity of molecules associated with inflammation such as AGE or cytokines or other cellular factors, including release rates or activity, and include compositions comprising compounds disclosed herein with inflammation modulating activity. Administration of such compounds that are effective in modulating inflammation are administered to humans and animals suspected of having or who have inflammatory diseases, for example, diabetic-induced vasculopathies, autoimmune diseases, renal insufficiency, Alzheimer's syndrome, and inflammation-induced diseases such as atherosclerosis. Effective amounts are administered to such humans and animals in dosages that are safe and effective, including, but not limited to, the ranges taught herein. Routes of administration include, but are not limited to, those disclosed herein. As disclosed herein, compositions comprising such compounds may be used in conjunction with other therapeutic agents or in methods comprising steps such as altered patient activities, including, but not limited to, changes in exercise or diet.

VI. Cytotoxic Activity

An embodiment of the present invention comprises methods and compositions comprising compounds that have at least the activity of causing cellular death or a cessation of cellular activity, referred to herein as cytotoxic activity. This activity can be used in methods for in vitro or in vivo cytotoxicity. For example, compounds having this activity can be selectively delivered to an area within a living organism to selectively kill cells in that area. Such methods are using in treating hyperproliferative cells, such as cancers, or other unwanted cellular growth or cellular activities. One aspect of the invention provides compositions comprising compounds that nonselectively kill cells. Another aspect of the invention provides compounds that selectively kill cells, for example, cells that have a particular cellular marker or other identifying characteristic such as metabolic rate or uptake of a particular compound, such as sodium, calcium or thymidine.

The present invention also provides compositions for and methods of treatment of biological conditions including, but not limited to, conditions for which cytotoxic activity is a treatment. For example, the compositions and methods for providing compounds that have at least the activity of cytotoxicity are useful in the treatment or prophylaxis of at least one hyperproliferative disease in a cell, tissue, organ, animal, or patient including, but not limited to, malignant and non-malignant cell growth, leukemia, acute leukemia, acute lymphoblastic leukemia (ALL), B-cell, T-cell or FAB ALL, acute myeloid leukemia (AML), chromic myelocytic leukemia (CML), chronic lymphocytic leukemia (CLL), hairy cell leukemia, myclodyplastic syndrome (MDS), a lymphoma, Hodgkin's disease, a malignamt lymphoma, non-hodgkin's lymphoma, Burkitt's lymphoma, multiple myeloma, Kaposi's sarcoma, colorectal carcinoma, pancreatic carcinoma, nasopharyngeal carcinoma, malignant histiocytosis, paraneoplastic syndrome/hypercalcemia of malignancy, solid tumors, adenocarcinomas, sarcomas, malignant melanoma, hemangioma, metastatic disease, cancer related bone resorption, cancer related bone pain, and the like.

Compounds of the present invention that have at least the activity of cytotoxicity are shown in TABLE 4A and B. The compounds shown in this Table have the activity of cytotoxicty as measured by the assays taught herein. The inclusion of compounds in the categories of the Tables disclosed herein are not to be seen as limiting, in that compounds included in such Tables have at least the activity shown for inclusion in the Table and may have more or other activities. Nor are the Tables to be seen as limiting in that these are the only compounds disclosed herein that have that activity, representative compounds are shown in the Tables that have at least that particular activity for inclusion in the Table. One or more compounds disclosed herein have at least an activity that has utility in treatment of disease states.

Examples of compounds that show at least this activity and utility are shown in the following formula:

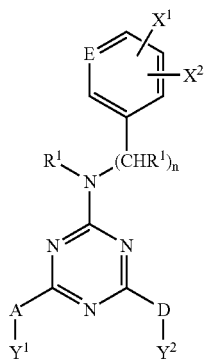

or an ene, a diene, a triene, or an yne derivative thereof; a saturated derivative thereof; a stereoisomer thereof, or a salt thereof;
wherein:
$R^1$ is in each occurrence independently selected from —H; linear or branched alkyl with up to 10 carbon atoms; cycloalkyl with up to 10 carbon atoms; or aryl;
E is CH or N;
n is an integer from 0 to 3;
$X^1$ is selected from —H, m-F, m-Cl, m-Br, m-I, m-CN, m-$NO_2$, m-$SO_2R^1$, or m-$SO_2OR^1$, or $X^1$ and $X^2$ together is a fused benzene or pyridine ring;
$X^2$ is selected from —H, o-Cl, o-Br, p-$OR^1$, p-$SR^1$, p-$NR^1_2$, p-F, p-Cl, p-Br, p-$CF_3$, p-C(O)$OR^1$, p-OM, or p-SM, wherein M is selected from Li, Na, K, Mg, or Ca;
A is selected from $NR^1$ or O, wherein $Y^1$ is selected from cycloalkyl with up to 10 carbon atoms, linear or branched alkyl with up to 10 carbon atoms, or

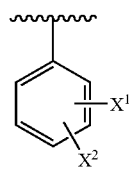

when A is $NR^1$, and wherein $Y^1$ is selected from $R^1$ or $CH_2R^1$ when A is O; or $AY^1$ is selected from a halogen,

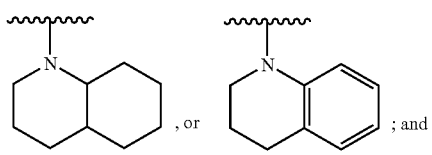

$DY^2$ is a halogen, or D is $NR^1$ and $Y^2$ is selected from

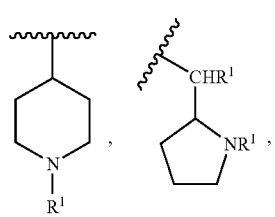

or $(CHR^1)_x,NR^1_2$, wherein x is an integer from 1 to 6.

Additional examples of compounds that show at least this activity and utility are shown in the following formula:

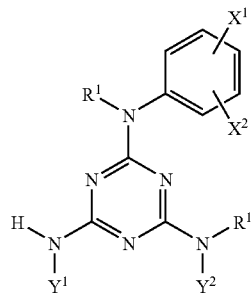

or an ene, a diene, a triene, or an yne derivative thereof; a saturated derivative thereof; a stereoisomer thereof; or a salt thereof;
wherein:
$R^1$ is in each occurrence independently selected from —H; linear or branched alkyl with up to 10 carbon atoms; or cycloalkyl with up to 10 carbon atoms;
$X^1$ is in each occurrence independently selected from —H, m-F, m-Cl, m-Br, m-I, m-CN, m-$NO_2$, m-$SO_2R^1$, or m-$SO_2OR^1$;
X2 is in each occurrence independently selected from o-$CH_3$, p-$OR^1$, p-$SR^1$, p-$NR^1_2$, or p-OM or p-SM, wherein M is selected from Li, Na, K, Mg, or Ca;
$Y^1$ is selected from cycloalkyl with up to 10 carbon atoms;

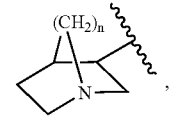

wherein n is 1 or 2; or

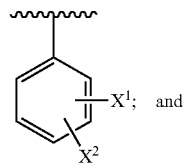

$Y^2$ is selected from

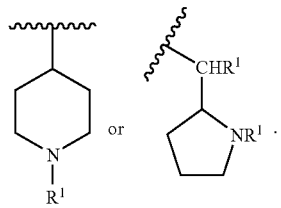

Further examples of compounds that show at least this activity and utility are presented in Tables 4A and 4B. The compound nomenclature of Tables 4A and 4B, as in the other tables presented herein, was generated using Autonom, where the name provided may be the Beilstein or CAS version of the chemical name. Note that any hydrogen atoms that are required for any atom to attain its usual valence in a structure presented in Tables 4A and 4B, whether a carbon atom or a heteroatom, should be inferred if it is not specifically indicated. In addition, compounds, to include compositions thereof, encompassed within the scope of structures Ib–XVIb, respectively, or listed in Tables 1B and 1E may be likewise employed in this embodiment and/or aspect of the present invention.

Assays for determining the activity of compounds capable of cytotoxic activity include those taught in herein and others that are well known in the art. In general, to determine if there is cytotoxic activity associated with a compound, cells of a particular type, in a growing stage or a quiescent stage, are treated with the compound of interest. Various parameters of cell death or cessation are used to measure the effects of the compound. For example, the amount of nucleic acid or protein synthesis can be measured or visual observation of the state of the cells, such as release from the substrate, can be used to measure the state of the cells.

The present invention comprises methods and compositions for the treatment and prevention of diseases or conditions that present or result from cellular proliferation or unwanted cellular growth or cellular activity. Such methods comprise administration of compositions comprising compounds capable of modulating cellular activity or causing cellular death or cessation of growth such as compositions comprising compounds disclosed herein that have cytotoxic activity. Administration of such compounds that are effective in cytotoxic activity are administered to humans and animals suspected of having or who have, for example, cancer, overactive tissues such as thyroid or hypothalamus, or cellular conditions where factors are released in unwanted amounts. Effective amounts are administered to such humans and animals in dosages that are safe and effective, including, but not limited to, the ranges taught herein. Routes of administration include, but are not limited to, those disclosed herein. As disclosed herein, compositions comprising such compounds may be used in conjunction with other therapeutic agents or in methods comprising steps such as altered patient activities.

Compound/Composition-Coated Medical Devices

The compounds of the present invention may be used alone or in combination with other agents along with delivery devices to effectively prevent and treat the diseases described herein, though particular applications are found in vascular disease, and in particular, vascular disease caused by injury and/or by transplantation. Though this example focuses on vascular disease, provision of the compounds of the present invention with medical devices for treatment of the diseases and conditions capable of being treated with the compounds is contemplated by the present invention.

Various medical treatment devices utilized in the treatment of vascular disease may ultimately induce further complications. For example, balloon angioplasty is a procedure utilized to increase blood flow through an artery and is the predominant treatment for coronary vessel stenosis. However, the procedure typically causes a certain degree of damage to the vessel wall, thereby creating new problems or exacerbating the original problem at a point later in time. Although other procedures and diseases may cause similar injury, exemplary embodiments of the present invention will be described with respect to the treatment of restenosis and related complications following percutaneous transluminal coronary angioplasty and other similar arterial/venous procedures, including the joining of arteries, veins and other fluid carrying conduits in other organs or sites of the body, such as the liver, lung, bladder, kidney, brain, prostate, neck and legs.

The local delivery of a compound of the present invention and, in some embodiments, along with other therapeutic agents, from a stent prevents vessel recoil and remodeling through the scaffolding action of the stent. The activity of compound provided, with or without other therapeutic agents, helps determine for which application, to treat which disease, the coated medical device is being administered. For example, compound-coated stents can prevent multiple components of neointimal hyperplasia or restenosis as well as reduce inflammation and thrombosis. Local administration of a compound of the present invention and other therapeutic agents to stented coronary arteries may also have additional therapeutic benefit. For example, higher tissue concentrations of the compounds of the present invention and other therapeutic agents may be achieved utilizing local delivery rather than systemic administration. In addition, reduced systemic toxicity may be achieved utilizing local delivery rather than systemic administration while maintaining higher tissue concentrations. In utilizing local delivery from a stent rather than systemic administration, a single procedure may suffice with better patient compliance. An additional benefit of combination therapeutic agent and/or compound therapy may be to reduce the dose of each of the therapeutic agents, thereby limiting toxicity, while still achieving a reduction in restenosis, inflammation and thrombosis. Local stent-based therapy is therefore a means of improving the therapeutic ratio (efficacy/toxicity) of anti-restenosis, anti-inflammatory, and anti-thrombotic therapeutic agents.

Although exemplary embodiments of the invention will be described with respect to the treatment of restenosis and other related complications, it is important to note that the local delivery of a compound of the present invention, alone or as part of a therapeutic agent combination, may be utilized to treat a wide variety of conditions utilizing any number of medical devices, or to enhance the function and/or life of the device. For example, intraocular lenses, placed to restore vision after cataract surgery is often compromised by the formation of a secondary cataract. The latter is often a result of cellular overgrowth on the lens surface and can be potentially minimized by combining one or more compounds of the present invention having activity that is effecting in preventing unwanted cellular growth with the device. Other medical devices that often fail due to tissue in-growth or accumulation of proteinaceous material in, on and around the device, such as shunts for hydrocephalus, dialysis grafts, colostomy bag attachment devices, ear drainage tubes, leads for pace makers and implantable defibrillators can also benefit from the combinations of the compounds of the present invention, possibly other pharmaceutical agents, and the devices. Other surgical devices, sutures, staples, anastomosis devices, vertebral disks, bone pins, suture anchors, hemostatic barriers, clamps, screws, plates, clips, vascular implants, tissue adhesives and sealants, tissue scaffolds, various types of dressings, bone substitutes, intraluminal devices, and vascular supports could also provide enhanced patient benefit using this compound-device combination approach. Essentially, any type of medical device may be coated in some fashion with at least one compound of the present invention, alone or as part of a therapeutic agent combination, which enhances treatment over the use of the device or therapeutic agent without combination with the compound.

As disclosed supra, the compounds of the present invention can be administered in combinational therapies with other therapeutic agents, and are not limited to only the other therapeutic agents disclosed herein. Thus, the present invention also contemplates, in addition to various medical devices, the coatings on these devices may be used to deliver a compound of the present invention in combination with other therapeutic agents. This illustrative list of therapeutic agents can be administered through pharmeutical means or in association with medical devices and such therapeutic agents include, but are not limited to, antiproliferative/antimitotic agents including natural products such as vinca alkaloids (e.g., vinblastine, vincristine, and vinorelbine), paclitaxel, epidipodophyllotoxins (e.g., etoposide, teniposide), antibiotics (dactinomycin (actinomycin D) daunorubicin, doxorubicin and idarubicin), anthracyclines, mitoxantrone, bleomycins, plicamycin (mithramycin) and mitomycin, enzymes (L-asparaginase which systemically metabolizes L-asparagine and deprives cells which do not have the capacity to synthesize their own asparagine); antiplatelet agents such as G(GP) IIb/IIIa inhibitors and vitronectin receptor antagonists; antiproliferative/antimitotic alkylating agents such as nitrogen mustards (mechlorethamine, cyclophosphamide and analogs, melphalan, chlorambucil), ethylenimines and meth-ylmelamines (hexamethylmelamine and thiotepa), alkyl sulfonates-busulfan, nirtosoureas (cannustine (BCNU) and analogs, streptozocin), trazenes-dacarbazinine (DTIC); antiproliferative/antimitotic antimetabolites such as folic acid analogs (methotrexate), pyrimidine analogs (fluorouracil, floxuridine, and cytarabine), purine analogs and related inhibitors (mercaptopurine, thioguanine, pentostatin and 2-chlorodeoxyadenosine (cladribine)); platinum coordination complexes (cisplatin, carboplatin), procarbazine, hydroxyurea, mitotane, aminoglutethimide; hormones (e.g. estrogen); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory; antisecretory (breveldin); anti-inflammatory agents such as adrenocortical steroids (cortisol, cortisone, fludrocortisone, prednisone, prednisolone, 6α-methylprednisolone, triamcinolone, betamethasone, and dexamethasone), non-steroidal agents (salicylic acid derivatives, i.e., aspirin; para-aminophenol derivatives, i.e., acetominophen; indole and indene acetic acids (indomethacin, sulindac, and etodalac), heteroaryl acetic acids (tolmetin, diclofenac, and ketorolac), arylpropionic acids (ibuprofen and derivatives), anthranilic acids (mefenamic acid, and meclofenamic acid), enolic acids (piroxicam, tenoxicam, phenylbutazone, and oxyphenthatrazone), nabumetone, gold compounds (auranofin, aurothioglucose, gold sodium thiomalate); immunosuppressives. (Cyclosporine, tacrolimus (FK-506), sirolimus (rapamycin), azathioprine, mycophenolate mofetil); angiogenic agents: vascular endothelial growth factor (VEGF), fibroblast growth factor (FGF); angiotensin receptor blockers; nitric oxide donors; anti-sense oligio-nucleotides and combinations thereof, cell cycle inhibitors, mTOR inhibitors, and growth factor signal transduction kinase inhibitors.

Although any number of stents may be utilized in accordance with the present invention, for simplicity, a limited number of stents will be described in exemplary embodiments of the present invention. The skilled artisan will recognize that any number of stents may be utilized in connection with the present invention. In addition, as stated above, other medical devices may be utilized. For example, though stents are described, sleeves outside the vessels are also contemplated, as are other medical devices that can provide a substrate for administration for at least one of the compounds of the present invention.

A stent is commonly used as a tubular structure left inside the lumen of a duct to relieve an obstruction. Typically, stents are inserted into the lumen in a non-expanded form and are then expanded autonomously, or with the aid of a second device in situ. A common method of expansion occurs through the use of a catheter-mounted, angioplasty balloon that is inflated within the stenosed vessel or body passageway in order to shear and disrupt the obstructions associated with the wall components of the vessel and to obtain an enlarged lumen.

A stent may resemble an expandable cylinder and may comprise a fenestrated structure for placement in a blood vessel, duct or lumen to hold the vessel, duct or lumen open, more particularly for protecting a segment of artery from restenosis after angioplasty. The stent may be expanded circumferentially and maintained in an expanded configuration that is circumferentially or radially rigid. The stent may be axially flexible and when flexed at a band, for example, the stent avoids any externally protruding component parts.

The stent may be fabricated utilizing any number of methods. For example, the stent may be fabricated from a hollow or formed stainless steel tube that may be machined using lasers, electric discharge milling, chemical etching or other means. The stent is inserted into the body and placed at the desired site in an unexpanded form. In one embodiment, expansion may be effected in a blood vessel by a balloon catheter, where the final diameter of the stent is a function of the diameter of the balloon catheter used. It should be appreciated that a stent in accordance with the present invention may be embodied in a shape-memory material including, for example, an appropriate alloy of nickel and titanium or stainless steel.

Structures formed from stainless steel may be made self-expanding by configuring the stainless steel in a predetermined manner, for example, by twisting it into a braided configuration. In this embodiment, after the stent has been formed it may be compressed so as to occupy a space sufficiently small as to permit its insertion in a blood vessel or other tissue by insertion means, wherein the insertion means include a suitable catheter, or flexible rod. Upon emerging from the catheter, the stent may be configured to expand into the desired configuration where the expansion is automatic or triggered by a change in pressure, temperature or electrical stimulation.

Furthermore, a stent may be modified to comprise one or more reservoirs. Each of the reservoirs may be opened or closed as desired. These reservoirs may be specifically designed to hold the compound or compound/therapeutic agent combination to be delivered. Regardless of the design of the stent, it is preferable to have the compound or compound/therapeutic agent combination dosage applied with enough specificity and a sufficient concentration to provide an effective dosage in the affected area. In this regard, the reservoir size in the bands is preferably sized to adequately apply the compound or compound/therapeutic agent combination dosage at the desired location and in the desired amount.

In an alternative embodiment, the entire inner and outer surface of the stent may be coated with the compound or compound/therapeutic agent combination in therapeutic dosage amounts. The coating techniques may vary depending on the compound or compound/therapeutic agent combination. Also, the coating techniques may vary depending on the material comprising the stent or other intraluminal medical device.

One or more compounds of the present invention and, in some instances, other therapeutic agents as a combination, may be incorporated onto or affixed to the stent in a number of ways. In one embodiment, the compound is directly incorporated into a polymeric matrix and sprayed onto the outer surface of the stent. The compound elutes from the polymeric matrix over time and enters the surrounding tissue. The compound preferably remains on the stent for at least three days up to approximately six months, and more preferably between seven and thirty days.

Any number of non-erodible polymers may be utilized in conjunction with the compound, and such polyermic compositions are well known in the art. In one embodiment, the polymeric matrix comprises two layers. The base layer comprises a solution of poly(ethylene-covinylacetate) and polybutylmethacrylate. The compound is incorporated into this base layer. The outer layer comprises only polybutylmethacrylate and acts as a diffusion barrier to prevent the compound from eluting too quickly. The thickness of the outer layer or topcoat determines the rate at which the compound elutes from the matrix. Essentially, the compound elutes from the matrix by diffusion through the polymer matrix. Polymers are permeable, thereby allowing solids, liquids and gases to escape therefrom. The total thickness of the polymeric matrix is in the range from about one micron to about twenty microns or greater. It is important to note that primer layers and metal surface treatments may be utilized before the polymeric matrix is affixed to the medical device. For example, acid cleaning, alkaline (base) cleaning, salinization and parylene deposition may be used as part of the overall process described above.

The poly(ethylene-co-vinylacetate), polybutylmethacrylate and compound solution may be incorporated into or onto the stent in a number of ways. For example, the solution may be sprayed onto the stent or the stent may be dipped into the solution. Other methods include spin coating and plasma polymerization. In one embodiment, the solution is sprayed onto the stent and then allowed to dry. In another embodiment, the solution may be electrically charged to one polarity and the stent electrically charged to the opposite polarity. In this manner, the solution and stent will be attracted to one another. In using this type of spraying process, waste may be reduced and more precise control over the thickness of the coat may be achieved.

Drug-coated stents are manufactured by a number of companies including Johnson & Johnson, Inc. (New Brunswick, N.J.), Guidant Corp. (Santa Clara, Calif.), Medtronic, Inc. (Minneapolis, Minn.), Cook Group Incorporated (Bloomington, Ind.), Abbott Labs., Inc. (Abbott Park, Ill.), and Boston Scientific Corp. (Natick, Mass.). See e.g., U.S. Pat. No. 6,273,913; U.S. Patent Application No. 20020051730; WO 02/26271; and WO 02/26139, each expressly entirely incorporated herein by reference.

Expression Profiles and Microarray Methods of Use

Other aspects of the present invention comprise compositions and methods for microarray devices. Such microarray devices and methods comprise a variety of microarrays that may be used, for example, to study and monitor gene expression in response to treatment with the compounds of the present invention. The microarrays may comprise nucleic acid sequences, carbohydrates or proteins that are determinative for specific cells, tissues, species, disease states, prognoses, disease progression, or any other combination of molecules that can be used to determine an effect of one or more of the compounds of the present invention For example, the microarrays of the present invention may be derived from, or representative of, for example, a specific organism or cell type, including human microarrays, vascular microarrays, inflammation microarrays, cancer microarrays, apoptosis microarrays, oncogene and tumor suppressor microarrays, cell-cell interaction microarrays, cytokine and cytokine receptor microarrays, blood microarrays, cell cycle microarrays, neuroarrays, mouse microarrays, and rat microarrays, or combinations thereof. In further embodiments, the microarrays may represent diseases including cardiovascular diseases, vasculopathic conditions, inflammatory diseases, autoimmune diseases, neurological diseases, immunological diseases, various cancers, infectious diseases, endocrine disorders, and genetic diseases.

Alternatively, the microarrays useful in assessing the efficacy of the compounds of the present invention may represent a particular tissue type including, but not limited to, heart, liver, prostate, lung, nerve, muscle, or connective tissue; preferably coronary artery endothelium, umbilical artery endothelium, umbilical vein endothelium, aortic endothelium, dermal microvascular endothelium, pulmonary artery endothelium, myometrium microvascular endothelium, keratinocyte epithelium, bronchial epithelium, mammary epithelium, prostate epithelium, renal cortical epithelium, renal proximal tubule epithelium, small airway epithelium, renal epithelium, umbilical artery smooth muscle, neonatal dermal fibroblast, pulmonary artery smooth muscle, dermal fibroblast, neural progenitor cells, skeletal muscle, astrocytes, aortic smooth muscle, mesangial cells, coronary artery smooth muscle, bronchial smooth muscle, uterine smooth muscle, lung fibroblast, osteoblasts, prostate stromal cells, or combinations thereof.

The present invention further contemplates microarrays comprising a gene expression profile comprising one or more polynucleotide sequences including complementary and homologous sequences, wherein said gene expression profile is generated from a cell type treated with a compound of the present invention and is selected from the group comprising coronary artery endothelium, umbilical artery endothelium, umbilical vein endothelium, aortic endothelium, dermal microvascular endothelium, pulmonary artery endothelium, myometrium microvascular endothelium, keratinocyte epithelium, bronchial epithelium, mammary epithelium, prostate epithelium, renal cortical epithelium, renal proximal tubule epithelium, small airway epithelium, renal epithelium, umbilical artery smooth muscle, neonatal dermal fibroblast, pulmonary artery smooth muscle, dermal fibroblast, neural progenitor cells, skeletal muscle, astrocytes, aortic smooth muscle, mesangial cells, coronary artery smooth muscle, bronchial smooth muscle, uterine smooth muscle, lung fibroblast, osteoblasts, and prostate stromal cells.

The present invention contemplates microarrays comprising one or more protein-binding agents, wherein a protein expression profile is generated from a cell type treated with a compound of the present invention and is selected from the group comprising coronary artery endothelium, umbilical artery endothelium, umbilical vein endothelium, aortic endothelium, dermal microvascular endothelium, pulmonary artery endothelium, myometrium microvascular endothelium, keratinocyte epithelium, bronchial epithelium, mammary epithelium, prostate epithelium, renal cortical epithelium, renal proximal tubule epithelium, small airway epithelium, renal epithelium, umbilical artery smooth muscle, neonatal dermal fibroblast, pulmonary artery smooth muscle, dermal fibroblast, neural progenitor cells, skeletal muscle, astrocytes, aortic smooth muscle, mesangial cells, coronary artery smooth muscle, bronchial smooth muscle, uterine smooth muscle, lung fibroblast, osteoblasts, and prostate stromal cells.

More specifically, the present invention contemplates methods for the reproducible measurement and assessment of the expression of specific mRNAs or proteins in, for example, a specific set of cells. One method combines and utilizes the techniques of laser capture microdissection, T7-based RNA amplification, production of cDNA from amplified RNA, and DNA microarrays containing immobilized DNA molecules for a wide variety of specific genes, including HSPGs such as perlecan, to produce a profile of gene expression analysis for very small numbers of specific cells. The desired cells are individually identified and attached to a substrate by the laser capture technique, and the captured cells are then separated from the remaining cells. RNA is then extracted from the captured cells and amplified about one million-fold using the T7-based amplification technique, and cDNA may be prepared from the amplified RNA. A wide variety of specific DNA molecules are prepared that hybridize with specific polynucleotides of the microarray, and the DNA molecules are immobilized on a suitable substrate. The cDNA made from the captured cells is applied to the microarray under conditions that allow hybridization of the cDNA to the immobilized DNA on the microarray. The expression profile of the captured cells is obtained from the analysis of the hybridization results using the amplified RNA or cDNA made from the amplified RNA of the captured cells, and the specific immobilized DNA molecules on the microarray. The hybridization results demonstrate, for example, which genes of those represented on the microarray as probes are hybridized to cDNA from the captured cells, and/or the amount of specific gene expression. The hybridization results represent the gene expression profile of the captured cells. The gene expression profile of the captured cells can be used to compare the gene expression profile of a different set of captured cells. For example, gene expression profiles may be generated from cells treated (and not treated) with a compound of the present invention. The similarities and differences provide useful information for determining the differences between the same cell type under different conditions, more specifically, the change in gene expression in response to treatment with a compound of the present invention.

The techniques used for gene expression analysis are likewise applicable in the context of protein expression profiles. Total protein may be isolated from a cell sample and hybridized to a microarray comprising a plurality of protein-binding agents, which may include antibodies, receptor proteins, small molecules, and the like. Using any of several assays known in the art, hybridization may be detected and analyzed as described above. In the case of fluorescent detection, algorithms may be used to extract a protein expression profile representative of the particular cell type. In this regard, the change in protein expression in response to treatment of cells with a compound of the present invention may be evaluated.

Thus, in one aspect, the present invention comprises at least one microarray corresponding to a population of genes isolated from a particular tissue or cell type in methods that is used to detect changes in gene transcription levels that result from exposing the selected tissue or cells to at least one compound of the present invention. In this embodiment, a biological sample derived from an organism, or an established cell line, may be exposed to at least one compound of the present invention in vivo or ex vivo. Thereafter, the gene transcripts, primarily mRNA, of the tissue or cells are isolated by methods well-known in the art. SAMBROOK ET AL., MOLECULAR CLONING: A LAB. MANUAL (2001). The isolated transcripts are then contacted with a microarray under conditions where the transcripts hybridize with a corresponding probe to form hybridization pairs. Thus, the microarray provides a model of the transcriptional responsiveness following exposure to at least one compound of the present invention. Such information can be used to determine therapeutic candidates. A hybridization signal may then be detected at each hybridization pair to obtain a gene expression profile.

Gene and/or protein expression profiles and microarrays may also be used to identify activating or non-activating compounds of a particular gene such as perlecan or other HSPG. Compounds that increase transcription rates or stimulate, maintain, or stabilize the activity of a protein are considered activating, and compounds that decrease rates or inhibit the activity of a protein are non-activating. Moreover, the biological effects of a compound may be reflected in the biological state of a cell. This state is characterized by the cellular constituents. One aspect of the biological state of a cell is its transcriptional state. The transcriptional state of a cell includes the identities and amounts of the constituent RNA species, especially mRNAs, in the cell under a given set of conditions. Thus, the gene expression profiles, microarrays, and algorithms discussed herein may be used to analyze and characterize the transcriptional state of a given cell or tissue following exposure to an activating or non-activating compound, specifically, a compound of the present invention.

Microarray techniques and methods for analyzing results are well known in the art. See U.S. Pat. Nos. 6,263,287; 6,239,209; 6,218,122; 6,197,599; 6,156,501; 5,874,219; 5,837,832; 5,700,637; 5,445,934; U.S. Patent Application Nos. 2001/0014461 A1; 2001/0039016 A1; 2001/0034023 A1; WO 01/94946; and WO 01/77668. See also, Haab et al., 2 GENOME BIOLOGY 1–12 (2001); Brown et al., 97 PROC. NATL. ACAD. SCI. USA 262–7 (2000); Getz et al., 97 PROC. NATL. ACAD. SCI. USA 12079–84 (2000); Harrington et al., 3 CURRENT OPINION MICROBIOL 285–91 (2000); Holter et al., 97 PROC. NATL. ACAD. SCI. USA 8409–14 (2000); MacBeath et al., 289 SCIENCE 1760–63 (2000); Duggan et al., 21 NATURE GENET 10–14 (1999); Lipshutz et al., 21 NATURE GENET 5–9 (1999); Eisen et al., 95 PROC. NATL. ACAD. SCI. USA 14863–68 (1998); Ermolaeva et al., 20 NATURE GENET. 19–23 (1998); Hacia et al., 26 NUCLEIC ACIDS RES. 3865–66 (1998); Lockhart et al., NUCLEIC ACIDS SYMP. SER. 11–12 (1998); Schena et al., 16 TRENDS BIOTECHNOL. 301–6 (1998); Shalon, 46 PATHOL. BIOL. 107–9 (1998); Welford et al., 26 NUCLEIC ACID RES. 3059–65 (1998); Blanchard et al., 11 BIOSENSORS BIOELECTRONICS 687–90 (1996); Lockhart et al., 14 NATURE BIOTECHNOL. 1675–80 (1996); Schena et al., 93 PROC. NATL. ACAD. SCI. USA 10614–19 (1996); Tomayo et al., 96 PROC. NATL. ACAD. SCI. USA 2907–12 (1996); Schena et al., 270 SCIENCE 467–70 (1995)

Database Creation, Database Access and Associated Methods of Use

Another embodiment of the present invention comprises a variety of methods for managing or using data related to the compounds, methods of making the compounds, methods of using and administering the compounds, and diagnosing, prognosing and following the outcomes associated with diseases in which the compounds are effective in treating. For example, methods for providing diagnostics and predictors relating to biomolecules including HSPGS, particularly, perlecan, are contemplated by the present invention. Also within the scope of this invention are methods providing diagnostics and predictors relating to the efficacy of the compounds of the present invention. The present invention further contemplates methods of providing expression profile databases, and methods for producing such databases, for normal and diseased tissues.

The expression profile database may be an internal database designed to include annotation information about the expression profiles generated to assess the effect of the compounds of the present invention and through other sources and methods. Such information may include, for example, the databases in which a given biomolecule was found, patient information associated with the expression profile, including age, cancer or tumor type or progression, information related to a compound of the present invention such as dosage and administration information, descriptive information about related cDNAs associated with the sequence, tissue or cell source, sequence data obtained from external sources, expression profiles for a given gene and the related disease state or course of disease, for example whether the expression profile relates to or signifies a particular disease state, and preparation methods. The expression profiles may be based on protein and/or polynucleotide microarray data obtained from publicly available or proprietary sources. The database may be divided into two sections: one for storing the sequences and related expression profiles and the other for storing the associated information. This database may be maintained as a private database with a firewall within the central computer facility. However, this invention is not so limited and the expression profile database may be made available to the public.

The database may be a network system connecting the network server with clients. The network may be any one of a number of conventional network systems, including a local area network (LAN) or a wide area network (WAN), as is known in the art (e.g., Ethernet). The server may include software to access database information for processing user requests, and to provide an interface for serving information to client machines. The server may support the World Wide Web and maintain a website and Web browser for client use. Client/server environments, database servers, and networks are well documented in the technical, trade, and patent literature.

Through the Web browser, clients may construct search requests for retrieving data from, for example, a microarray database and an expression profile database. For example, the user may "point and click" to user interface elements such as buttons, pull down menus, and scroll bars. The client requests may be transmitted to a Web application that formats them to produce a query that may be used to gather information from the system database, based, for example, on microarray or expression data obtained by the client, and/or other phenotypic or genotypic information. Specifically, the client may submit expression data based on microarray expression profiles obtained from a patient treated with a compound of the present invention and use the system to obtain a diagnosis based on that information based on a comparison by the system of the client expression data with the expression data contained in the database. By way of example, the system compares the expression profiles submitted by the client with expression profiles contained in the database and then provides the client with diagnostic information based on the best match of the client expression profiles with the database profiles. Thus, in one aspect, the comparison of expression profiles aids the clinician in determining the effectiveness of treatment with a compound of the present invention. Based on such a comparison, the clinician may alter or adjust the treatment regimen.

In addition, the website may provide hypertext links to public databases such as GenBank and associated databases maintained by the National Center for Biotechnology Information (NCBI), part of the National Library of Medicine as well as, any links providing relevant information for gene expression analysis, genetic disorders, scientific literature, and the like. Information including, but not limited to, identifiers, identifier types, biomolecular sequences, common cluster identifiers (GenBank, Unigene, Incyte template identifiers, and so forth) and species names associated with each gene, is contemplated.

The present invention also provides a system for accessing and comparing bioinformation, specifically expression profiles and other information which is useful in the context of the compositions and methods of the present invention. In one embodiment, the computer system may comprise a computer processor, suitable memory that is operatively coupled to the computer processor, and a computer process stored in the memory that executes in the computer processor and which comprises a means for matching an expression profile of a biomolecular sequence from a patient with expression profile and sequence identification information of biomolecular sequences in a database. More specifically, the computer system is used to match an expression profile generated from a biological sample treated with a compound of the present invention with expression profile and other information in a database.

Furthermore, the system for accessing and comparing information contained in biomolecular databases comprises a computer program comprising computer code providing an algorithm for matching an expression profile generated from a patient, for example, treated with a compound of the present invention, with expression profile and sequence identification information of biomolecular sequences in a biomolecular database.

The present invention contemplates, in one embodiment, the use of a Graphical User Interface ("GUI") for the access of expression profile information stored in a biomolecular database. In a specific embodiment, the GUI may be composed of two frames. A first frame may contain a selectable list of biomolecular databases accessible by the user. When a biomolecular database is selected in the first frame, a second frame may display information resulting from the pair-wise comparison of the expression profile database with the client-supplied expression profile as described above, along with any other phenotypic or genotypic information.

The second frame of the GUI may contain a listing of biomolecular sequence expression information and profiles contained in the selected database. Furthermore, the second frame may allow the user to select a subset, including all of the biomolecular sequences, and to perform an operation on the list of biomolecular sequences. In one embodiment, the user may select the subset of biomolecular sequences by selecting a selection box associated with each biomolecular sequence. In another embodiment, the operations that may be performed include, but are not limited to, downloading all listed biomolecular sequences to a database spreadsheet with classification information, saving the selected subset of biomolecular sequences to a user file, downloading all listed biomolecular sequences to a database spreadsheet without classification information, and displaying classification information on a selected subset of biomolecular sequences.

If the user chooses to display classification information on a selected subset of biomolecular sequences, a second GUI may be presented to the user. In one embodiment, the second GUI may contain a listing of one or more external databases used to create the expression profile databases as described above. Furthermore, for each external database, the GUI may display a list of one or more fields associated with each external database. In yet another embodiment, the GUI may allow the user to select or deselect each of the one or more fields displayed in the second GUI. In yet another embodiment, the GUI may allow the user to select or deselect each of the one or more external databases.

The methods of the present application further relate to the commercial and other uses of the compositions and methodologies of the present invention. In one aspect, the methods include the marketing, sale, or licensing of the compositions and methodologies of the present invention in the context of providing consumers, i.e., patients, medical practitioners, medical service providers, researchers, and pharmaceutical distributors and manufacturers, with expression profile databases including, in particular, databases produced in accordance with the use of the compounds of the present invention.

In another embodiment, the methods of the present invention include establishing a distribution system for distributing the pharmaceutical compositions of the present invention for sale, and may optionally include establishing a sales group for marketing the pharmaceutical composition. Yet another aspect of the present invention provides a method of conducting target discovery comprising identifying, by one or more of the above drug discovery methods, a test compound, as described above, which modulates the level of expression of a gene or the activity of a gene product such as perlecan; conducting therapeutic profiling of agents identified, or further analogs thereof, for efficacy and toxicity in animals; and optionally formulating a pharmaceutical composition including one or more of the agents identified as having an acceptable therapeutic profile; and optionally licensing or selling, the rights for further drug development of said identified agents.

Pharmaceutical Compositions

In addition to the compounds disclosed herein, the pharmaceutical compositions of the present invention can further comprise at least one of any suitable auxiliary such as, but not limited to, diluent, binder, stabilizer, buffers, salts, lipophilic solvents, preservative, adjuvant or the like. Pharmaceutically acceptable auxiliaries are preferred. Examples and methods of preparing such sterile solutions are well known in the art and can be found in well known texts such as, but not limited to, REMINGTON'S PHARMACEUTICAL SCIENCES (Gennaro, Ed., 18th Edition, Mack Publishing Co. (1990)). Pharmaceutically acceptable carriers can be routinely selected that are suitable for the mode of administration, solubility and/or stability of the compound.

Pharmaceutical excipients and additives useful in the present invention include, but are not limited to, proteins, peptides, amino acids, lipids, and carbohydrates (e.g., sugars, including monosaccharides, di-, tri-, tetra-, and oligosaccharides; derivatized sugars such as alditols, aldonic acids, esterified sugars and the like; and polysaccharides or sugar polymers), which can be present singly or in combination, comprising alone or in combination in ranges of 1–99.99% by weight or volume. Exemplary protein excipients include serum albumin such as human serum albumin (HSA), recombinant human albumin (rHA), gelatin, casein, and the like. Representative amino acid components, which can also function in a buffering capacity, include alanine, glycine, arginine, betaine, histidine, glutamic acid, aspartic acid, cysteine, lysine, leucine, isoleucine, valine, methionine, phenylalanine, aspartame, and the like.

Carbohydrate excipients suitable for use in the present invention include, for example, monosaccharides such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol, sorbitol (glucitol), myoinositol and the like.

The pharmaceutical compositions comprising the compounds of the present invention can also include a buffer or a pH adjusting agent. Typically, the buffer is a salt prepared from an organic acid or base. Representative buffers include organic acid salts such as salts of citric acid, ascorbic acid, gluconic acid, carbonic acid, tartaric acid, succinic acid, acetic acid, or phthalic acid; Tris, tromethamine hydrochloride, or phosphate buffers.

Additionally, pharmaceutical compositions of the invention can include polymeric excipients/additives such as polyvinylpyrrolidones, ficolls (a polymeric sugar), dextrates (e.g., cyclodextrins, such as 2-hydroxypropyl-β-cyclodextrin), polyethylene glycols, flavoring agents, antimicrobial agents, sweeteners, antioxidants, anti-static agents, surfactants (e.g., polysorbates such as "TWEEN 20" and "TWEEN 80"), lipids (e.g., phospholipids, fatty acids), steroids (e.g., cholesterol), and chelating agents (e.g., EDTA). These and additional known pharmaceutical excipients and/or additives suitable for use in the present invention are known in the art, e.g., as listed in REMINGTON: THE SCIENCE & PRACTICE OF PHARMACY ($19^{th}$ ed., Williams & Williams (1995)) and PHYSICIAN'S DESK REFERENCE ($52^{nd}$ ed., Medical Economics (1998)), the disclosures of which are expressly entirely incorporated herein by reference.

Pharmaceutical Compositions for Oral Administration

For oral administration in the form of a tablet or capsule, a compound may be combined with an oral, non-toxic pharmaceutically acceptable inert carrier such as ethanol, glycerol, water and the like. Moreover, when desired or necessary, suitable binders, lubricants, disintegrating agents, and coloring agents may also be incorporated into the mixture. Suitable binders include, without limitation, starch; gelatin; natural sugars such as glucose or beta-lactose; corn sweeteners; natural and synthetic gums such as acacia, tragacanth, or sodium alginate, carboxymethylcellulose; polyethylene glycol; waxes and the like. Lubricants used in these dosage forms include, without limitation, sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil emulsion and as a bolus, etc.

A tablet may be made by compression or molding, optionally with one or more accessory ingredients. Compressed tablets may be prepared by compressing, in a -suitable machine, the active ingredient in a free-flowing form such as a powder or granules, optionally mixed with a binder, lubricant, inert diluent, preservative, surface active or dispersing agent. Molded tablets may be made by molding, in a suitable machine, a mixture of the powdered compound moistened with an inert liquid diluent. The tablets may be optionally coated or scored and may be formulated so as to provide a slow or controlled release of the active ingredient therein.

In addition, the combinations may be incorporated into biodegradable polymers allowing for sustained release of the compound, the polymers being implanted in the vicinity of where drug delivery is desired, for example, at the site of restenosis. The biodegradable polymers and their uses are described, for example, in detail in Brem et al., 74 J. NEUROSURG. 441–46 (1991). Suitable examples of sustained-release compositions include semipermeable matrices of solid hydrophobic polymers containing a compound of the present invention, which matrices are in the form of shaped articles, e.g., films, or microcapsules. Examples of sustained-release matrices include polyesters, hydrogels (for example, poly(2-hydroxyethylmethacrylate), or poly(vinylalcohol)), polylactides (U.S. Pat. No. 3,773,919), copolymers of L-glutamic acid and y ethyl-L-glutamate, non-degradable ethylene-vinyl acetate, degradable lactic acid-glycolic acid copolymers such as the LUPRON DEPOT® (Tap Pharmaceuticals, Inc., Chicago, Ill.) (injectable microspheres composed of lactic acid glycolic acid copolymer and leuprolide acetate), and poly-D-(−)-3-hydroxybutyric acid.

Pharmaceutical Compositions for Parenteral Administration

Formulations suitable for parenteral administration include aqueous and non-aqueous sterile injection solutions which may contain anti-oxidants, buffers, bacteriostats and solutes that render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze-dried (lyophilized) condition requiring only the addition of the sterile liquid carrier, for example, water for injections, immediately prior to use. Extemporaneous injection solutions and suspensions may be prepared from sterile powders, granules and tablets of the kind previously described.

For parenteral administration, sterile suspensions and solutions are desired. Isotonic preparations which generally contain suitable preservatives are employed when intravenous administration is desired. The pharmaceutical compositions may be administered parenterally via injection of a formulation consisting of the active ingredient dissolved in an inert liquid carrier. The term "parenteral," as used herein, includes, but is not limited to, subcutaneous injections, intravenous, intramuscular, intraperitoneal injections, or infusion techniques. Acceptable liquid carriers include, for example, vegetable oils such as peanut oil, cotton seed oil, sesame oil and the like, as well as organic solvents such as solketal, glycerol formal and the like. The formulations may be prepared by dissolving or suspending the active ingredient in the liquid carrier such that the final formulation contains from about 0.005% to 30% by weight of the active ingredient, i.e., a compound of the present invention.

Pharmaceutical Compositions for other Routes of Administration

Formulations suitable for topical administration in the mouth include lozenges comprising the ingredients in a flavored basis, usually sucrose and acacia or tragacanth; pastilles comprising the active ingredient in an inert basis such as gelatin and glycerin, or sucrose and acacia; and mouthwashes comprising the compound to be administered in a suitable liquid carrier. The liquid forms may include suitably flavored suspending or dispersing agents such as the synthetic and natural gums, for example, tragacanth, acacia, methyl-cellulose and the like.

Formulations for rectal administration may be presented as a suppository with a suitable base comprising, for example, cocoa butter or a salicylate.

Formulations suitable for vaginal administration may be presented as pessaries, tamports, creams, gels, pastes, foams or spray formulations containing in addition to the active ingredient such carriers as are known in the art to be appropriate.

The compounds may also be entrapped in microcapsules prepared, for example, by coacervation techniques or by interfacial polymerization, for example, hydroxymethylcellulose or gelatin-microcapsules and poly (methylmethacylate) microcapsules, respectively, in colloidal drug delivery systems (for example, liposomes, albumin microspheres, microemulsions, nano-particles and nanocapsules) or in macroemulsions. REMINGTON'S PHARMACEUTICAL SCIENCES (A. Osol ed., 16th ed. (1980)).

In a specific embodiment, the compounds disclosed herein are formulated as liposomes. Liposomes containing a compound of the present invention are prepared by methods known in the art. See, e.g., U.S. Pat. Nos. 5,013,556; 4,485,045; 4,544,545; WO 97/38731; Epstein et al., 82 PROC. NATL. ACAD. SCI. USA 3688 (1985); and Hwang et al., 77 PROC. NATL. ACAD. SCI. USA 4030 (1980). The compounds of the present invention can also be administered in the form of liposome delivery systems such as small unilamellar vesicles, large unilamellar vesicles, and multilamellar vesicles. Liposomes can be formed from a variety of phospholipids such as cholesterol, stearylamine or phophatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropylmethacrylamidephenol, polyhydroxyethylaspartamidephenol, or polyethyleneoxidepolylysine substituted with palmitoyl residue.

Pharmaceutically Acceptable Preservatives

The present invention provides stable formulations as well as preserved solutions and formulations containing a preservative as well as multi-use preserved formulations suitable for pharmaceutical or veterinary use, comprising at least one compound disclosed herein in a pharmaceutically acceptable formulation. Formulations in accordance with the present invention may optionally contain at least one known preservative. Preservatives include, but are not limited to, phenol, m-cresol, p-cresol, o-cresol, chlorocresol, benzyl alcohol, phenylmercuric nitrite, phenoxyethanol, formaldehyde, chlorobutanol, magnesium chloride (e.g., hexahydrate), alkylparaben (methyl, ethyl, propyl, butyl and the like), benzalkonium chloride, benzethonium chloride, sodium dehydroacetate and thimerosal, or mixtures thereof in an aqueous diluent. Any suitable concentration or mixture can be used as known in the art, such as 0.001–5%, or any range or value therein. Non-limiting examples include, no preservative, 0.1–2% m-cresol, 0.1–3% benzyl alcohol, 0.001–0.5% thimerosal, 0.001–2.0% pheno, 0.0005–1.0% alkylparaben(s), and the like.

Other excipients, e.g., isotonicity agents, buffers, antioxidants, preservative enhancers, can be optionally added to the diluent. An isotonicity agent such as glycerin, is commonly used at known concentrations. A physiologically tolerated buffer is preferably added to provide improved pH control. The formulations can cover a wide range of pHs, such as from about pH 4 to about pH 10, specifically, a range from about pH 5 to about pH 9, and more specifically, a range of about 6.0 to about 8.0. In one aspect, the formulations of the present invention have pH between about 6.8 and about 7.8. Suitable buffers include phosphate buffers, for example, sodium phosphate and phosphate buffered saline (PBS).

Other additives, such as a pharmaceutically acceptable solubilizers like Tween 20 (polyoxyethylene (20) sorbitan monolaurate), Tween 40 (polyoxyethylene (20) sorbitan monopalmitate), Tween 80 (polyoxyethylene (20) sorbitan monooleate), Pluronic F68 (polyoxyethylene polyoxypropylene block copolymers), and PEG (polyethylene glycol) or non-ionic surfactants such as polysorbate 20 or 80 or poloxamer 184 or 188, Pluronic® polyls, other block co-polymers, and chelators such as EDTA and EGTA can optionally be added to the pharmaceutical compositions to reduce aggregation. These additives are particularly useful if a pump or plastic container is used to administer the pharmaceutical composition. The presence of pharmaceutically acceptable surfactant mitigates the propensity for the composition to aggregate.

During any of the processes for preparation of the compounds of the present invention, it may be necessary and/or desirable to protect sensitive or reactive groups on any of the molecules concerned. This may be achieved by means of conventional protecting groups, such as those described in PROTECTIVE GROUPS IN ORGANIC CHEMISTRY (1973); and GREENE AND WUTS, PROTECTIVE GROUPS IN ORGANIC SYNTHESIS (1991). The protecting groups may be removed at a convenient subsequent stage using methods known from the art.

Routes of Administration

The invention further relates to the administration of at least one compound disclosed herein by the following routes, including, but not limited to oral, parenteral, subcutaneous, intramuscular, intravenous, intrarticular, intrabronchial, intraabdominal, intracapsular, intracartilaginous, intracavitary, intracelial, intracelebellar, intracerebroventricular, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, bolus, vaginal, rectal, buccal, sublingual, intranasal, iontophoretic means, or transdermal means.

Pulmonary/Nasal Administration

There are a several desirable features of an inhalation device for administering a compound of the present invention. For example, delivery by the inhalation device is reliable, reproducible, and accurate. For pulmonary administration, at least one pharmaceutical composition is delivered in a particle size effective for reaching the lower airways of the lung or sinuses. The inhalation device can optionally deliver small dry particles, e.g. less than about 10 μm, preferably about 1–5 μm, for good respirability.

According to the invention, at least one pharmaceutical composition can be delivered by any of a variety of inhalation or nasal devices known in the art for administration of a therapeutic agent by inhalation. Devices capable of depositing aerosolized formulations in the sinus cavity or alveoli of a patient include metered dose inhalers, nebulizers, dry powder generators, sprayers, and the like. Other devices suitable for directing pulmonary or nasal administration are also known in the art.

All such devices can be used for the administration of a pharmaceutical composition in an aerosol. Such aerosols may comprise either solutions (both aqueous and non aqueous) or solid particles. Metered dose inhalers like the Ventoline metered dose inhaler, typically use a propellent gas and require actuation during inspiration. See, e.g.,WO 98/35888; WO 94/16970. Dry powder inhalers like Turbuhaler® (Astra), Rotahaler® (Glaxo), Diskus® (Glaxo), Spiros® inhaler (Dura), devices marketed by Inhale Therapeutics, and the Spinhaler® powder inhaler (Fisons), use breath-actuation of a mixed powder. See U.S. Pat. Nos. 5,458,135; 4,668,218; WO 97/25086; WO 94/08552; WO 94/06498; and EP 0 237 507, each entirely expressly incorporated herein by reference. Nebulizers like AERx®, Aradigm, the Ultravent® nebulizer (Mallinckrodt), and the Acorn II® nebulizer (Marquest Medical Products), the above references entirely expressly incorporated herein by reference, produce aerosols from solutions, while metered dose inhalers, dry powder inhalers, etc. generate small particle aerosols. These specific examples of commercially available inhalation devices are intended to be a representative of specific devices suitable for the practice of the invention, and are not intended as limiting the scope of the invention.

Formulations suitable for nasal administration, wherein the carrier is a solid, include a coarse powder having a particle size, for example, in the range of 20 to 500 microns which is administered in the manner in which snuff is administered, i.e., by rapid inhalation through the nasal passage from a container of the powder held close up to the nose. Suitable formulations, wherein the carrier is a liquid, for administration, as for example, a nasal spray or as nasal drops, include aqueous or oily solutions of the active ingredient.

A spray comprising a pharmaceutical composition of the present invention can be produced by forcing a suspension or solution of a compound disclosed herein through a nozzle under pressure. The nozzle size and configuration, the applied pressure, and the liquid feed rate can be chosen to achieve the desired output and particle size. An electrospray can be produced, for example, by an electric field in connection with a capillary or nozzle feed. Advantageously, particles of at least one compound delivered by a sprayer have a particle size in a range of about less than 1 μm to less than about 20 μm.

Pharmaceutical compositions of at least one of the compounds of the present invention suitable for use with a sprayer typically include a compound disclosed herein in an aqueous solution at a concentration of about 0.1 mg to about 100 mg of a compound disclosed herein per ml of solution or mg/gm, or any range or value therein, including, but not limited to, 0.01, 0.02, 0.03, 0.04, 0.05, 0.06, 0.07, 0.08, 0.09, 0.1, 0.2., 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 45, 50, 60, 70, 80, 90 or 100 mg/ml or mg/gm. The pharmaceutical composition can include agents such as an excipient, a buffer, an isotonicity agent, a preservative, a surfactant, or other known agents of pharmaceutical compositions.

A pharmaceutical composition of the present invention can be administered by a nebulizer such as a jet nebulizer or an ultrasonic nebulizer. Typically, in a jet nebulizer, a compressed air source is used to create a high-velocity air jet through an orifice. As the gas expands beyond the nozzle, a low-pressure region is created, which draws a solution of composition protein through a capillary tube connected to a liquid reservoir. The liquid stream from the capillary tube is sheared into unstable filaments and droplets as it exits the tube, creating the aerosol. A range of configurations, flow rates, and baffle types can be employed to achieve the desired performance characteristics from a given jet nebulizer. In an ultrasonic nebulizer, high-frequency electrical energy is used to create vibrational, mechanical energy, typically employing a piezoelectric transducer. This energy is transmitted to the formulation of composition protein either directly or through a coupling fluid, creating an aerosol including the composition protein. Advantageously, particles of the pharmaceutical composition delivered by a nebulizer have a particle size range of from about less than 1 μm to less than about 20 μm.

Pharmaceutical compositions comprising a compound of the present invention suitable for use with a nebulizer, either jet or ultrasonic, typically include a concentration of about 0.1 mg to about 100 mg of a compound disclosed herein per ml of solution or mg/gm, or any range or value therein including, but not limited to, the individual amounts disclosed for spray compositions. The pharmaceutical composition can include other pharmaceutical agents such as an excipient, a buffer, an isotonicity agent, a preservative, a surfactant, and those known in the art for use in nebulizer administration.

In a metered dose inhaler (MDI), a propellant, a compound of the present invention, and any excipients or other additives are contained in a cannister as a mixture including a liquefied, compressed gas. Actuation of the metering valve releases the mixture as an aerosol, preferably containing a particle size range of from about less than 1 μm to less than about 20 μm.

The desired aerosol particle size can be obtained by employing a formulation of a compound of the present invention produced by various methods known to those of skill in the art including, but not limited to, jet-milling, spray drying, critical point condensation, and the like. Suitable metered dose inhalers include those manufactured by 3M or Glaxo and employing a hydrofluorocarbon propellant.

Pharmaceutical compositions for use with a metered-dose inhaler device will generally include a finely divided powder containing a compound disclosed herein as a suspension in a non-aqueous medium, for example, suspended in a propellant with the aid of a surfactant. The propellant can be any conventional material employed for this purpose such as chlorofluorocarbon, a hydrochlorofluorocarbon, a hydrofluorocarbon, or a hydrocarbon including trichlorofluoromethane, dichlorodifluoromethane, dichlorotetrafluoroethanol and 1,1,1,2-tetrafluoroethane, HFA-134a (hydrofluroalkane-134a), HFA-227 (hydrofluroalkane-227), or the like. In one embodiment, the propellant is a hydrofluorocarbon. The surfactant can be chosen to stabilize the compound of the present invention as a suspension in the propellant, to protect the active agent against chemical degradation, and the like. Suitable surfactants include sorbitan trioleate, soya lecithin, oleic acid, or the like. In some cases solution aerosols are preferred using solvents such as ethanol. One of ordinary skill in the art will recognize that the methods of the present invention can be achieved by pulmonary administration of a compound disclosed herein via devices not described herein.

For absorption through mucosal surfaces, the compositions and methods of the present invention for administering a compound disclosed herein include an emulsion comprising a plurality of submicron particles, a mucoadhesive macromolecule, a bioactive peptide, and an aqueous continuous phase, which promotes absorption through mucosal surfaces by achieving mucoadhesion of the emulsion particles. See, e.g., U.S. Pat. No. 5,514,670. Mucous surfaces suitable for application of the emulsions of the present invention can include corneal, conjunctival, buccal, sublingual, nasal, vaginal, pulmonary, abdominal, intestinal, and rectal routes of administration. Pharmaceutical compositions for vaginal or rectal administration such as suppositories, can contain as excipients, for example, polyalkyleneglycols, vaseline, cocoa butter, and the like. Pharmaceutical composition s for intranasal administration can be solid and contain excipients, for example, lactose or can be aqueous or oily solutions of nasal drops. For buccal administration, excipients include sugars, calcium stearate, magnesium stearate, pregelinatined starch, and the like. See, e.g., U.S. Pat. No. 5,849,695.

In another embodiment, the pharmaceutical compositions of the present invention may be administered via transdermal routes using forms of transdermal skin patches well known to those of ordinary skill in that art. For transdermal administration, a compound of the present invention is encapsulated in a delivery device such as a liposome or polymeric nanoparticles, microparticle, microcapsule, or microspheres (referred to collectively as microparticles unless otherwise stated). A number of suitable devices are known, including microparticles made of synthetic polymers such as polyhydroxy acids such as polylactic acid, polyglycolic acid and copolymers thereof, polyorthoesters, polyanhydrides, and polyphosphazenes, and natural polymers such as collagen, polyamino acids, albumin and other proteins, alginate and other polysaccharides, and combinations thereof. See, e.g., U.S. Pat. No. 5,814,599. To be administered in the form of a transdermal delivery system, the dosage administration may be, for example, continuous rather than intermittent throughout the dosage regimen.

Formulations suitable for topical administration to the skin may be presented as ointments, creams, gels and pastes comprising the ingredient to be administered in a pharmaceutical acceptable carrier. A preferred topical delivery system is a transdermal patch comprising a compound of the present invention.

Topical compositions containing a compound of the present invention may be admixed with a variety of carrier materials well known in the art including alcohols, aloe vera gel, allantoin, glycerine, vitamin A and E oils, mineral oil, PPG2 myristyl propionate and the like to form, for example, alcoholic solutions, topical cleansers, cleansing creams, skin gels, skin lotions, and shampoos in cream or gel formulations. Examples of such carriers and methods of formulation may be found in REMINGTON'S PHARMACEUTICAL SCIENCES (1990). Pharmaceutical formulations may contain from about 0.005% to about 10% by weight of the active ingredient. In one embodiment, the pharmaceutical formulations contain from about 0.01% to 5% by weight of the compound of the present invention.

It can be sometimes desirable to deliver the compounds of the present invention to the subject over prolonged periods of time, for example, for periods of one week to one year from a single administration. Certain medical devices may be employed to provide a continuous intermittent or on demand dosing of a patient. The devices may be a pump of diffusion apparatus, or other device containing a reservoir of drug and optionally diagnostic or monitoring components to regulate the delivery of the drug. Various slow-release, depot or implant dosage forms can be utilized. For example, a dosage form can contain a pharmaceutically acceptable non-toxic salt of compound disclosed herein that has a low degree of solubility in body fluids, for example, (a) an acid addition salt with a polybasic acid such as phosphoric acid, sulfuric acid, citric acid, tartaric acid, tannic acid, pamoic acid, alginic acid, polyglutamic acid, naphthalene mono- or di-sulfonic acids, polygalacturonic acid, and the like; (b) a salt with a polyvalent metal cation such as zinc, calcium, bismuth, barium, magnesium, aluminum, copper, cobalt, nickel, cadmium and the like, or with an organic cation formed from e.g., N,N'-dibenzyl-ethylenediamine or ethylenediamine; or (c) combinations of (a) and (b) e.g., a zinc tannate salt. Additionally, the compounds of the present invention or, preferably, a relatively insoluble salt such as those just described, can be formulated in a gel, for example, an aluminum monostearate gel with, e.g., sesame oil, suitable for injection. Exemplary salts include, but are not limited to, zinc salts, zinc tannate salts, pamoate salts, and the like. Another type of slow-release depot formulation for injection would contain the compound or salt dispersed or encapsulated in a slow degrading, non-toxic, non-antigenic polymer such as a polylactic acid/polyglycolic acid polymer, for example, as described in U.S. Pat. No. 3,773,919. The compounds or relatively insoluble salts thereof such as those described above can also be formulated in cholesterol matrix silastic pellets, particularly for use in animals. Additional slow-release, depot or implant formulations, e.g., gas or liquid liposomes are known in the literature. See, e.g., U.S. Pat. No. 5,770,222; SUSTAINED AND CONTROLLED RELEASE DRUG DELIVERY SYSTEMS (1978).

Other examples include provision of the compounds of the present invention to be administered by sustained release delivery system containing a biodegradable composition. The biodegradable composition may be composed of a biodegradable, water-coagulable, non-polymeric material and a biocompatible, non-toxic organic solvent that is miscible to dispersible in an aqueous medium. The delivery system may be implanted at an implant site causing the solvent to dissipate, disperse or leach from the composition into surrounding tissue fluid through a resulting microporous matrix.

As used herein, the term "implant site" is meant to include a site, in or on which the non-polymeric composition is applied. Implantation or implant site can also include the incorporation of the pharmaceutical composition comprising at least one compound of the present invention with a solid device. For example, the pharmaceutical composition is incorporated into a coating on a stent that is implanted into a subject. Additionally, other solid or biodegradeable materials can be used as a substrate on which the pharmaceutical composition is applied. The coated material, comprising the pharmaceutical composition is then implanted, inserted or is adjacent to the subject or patient. The term "biodegradable" means that the non-polymeric material and/or matrix of the implant will degrade over time by the action of enzymes, by simple or enzymatically catalyzed hydrolytic action and/or by other similar mechanisms in the human body. By "bioerodible," it is meant that the implant matrix will erode or degrade over time due, at least in part, to contact with substances found in the surrounding tissue fluids, cellular action, and the like. By "bioabsorbable," it is meant that the non-polymeric matrix will be broken down and absorbed within the human body, for example, by a cell, a tissue, and the like.

Non-polymeric materials that can be used in the composition generally are those that are biocompatible, substantially insoluble in water and body fluids, and biodegradable and/or bioerodible. The non-polymeric material is capable of being at least partially solubilized in a water-soluble organic solvent. The non-polymeric materials are also capable of coagulating or solidifying to form a solid implant matrix. The non-polymeric material is combined with a compatible and suitable organic solvent to form a composition that has the desired consistency ranging from watery to viscous to a spreadable putty or paste.

Suitable organic solvents are those that are biocompatible, pharmaceutically-acceptable, and will at least partially dissolve the non-polymeric material. The organic solvent has a solubility in water ranging from miscible to dispersible. Optionally, a pore-forming agent can be included in the composition to generate additional pores in the implant matrix. The pore-forming agent can be any organic or inorganic, pharmaceutically-acceptable substance that is substantially soluble in water or body fluid, and will dissipate from the coagulating non-polymeric material and/or the solid matrix of the implant into surrounding body fluid at the implant site.

The compounds of the present invention are capable of providing a local or systemic biological, physiological or therapeutic effect in the body of an animal. In formulating some pharmaceutical compositions described herein, the compound is preferably soluble or dispersible in the non-polymeric composition to form a homogeneous mixture, and upon implantation, becomes incorporated into the implant matrix. As the solid matrix degrades over time, the compound is capable of being released from the matrix into the adjacent tissue fluid, and to the pertinent body tissue or organ, either adjacent to or distant from the implant site, preferably at a controlled rate. The release of the compound from the matrix may be varied, for example, by the solubility of the compound in an aqueous medium, the distribution of the compound within the matrix, the size, shape, porosity, and solubility and biodegradability of the solid matrix. See e.g. U.S. Pat. No. 5,888,533. The amounts and concentrations of ingredients in the composition administered to the patient will generally be effective to accomplish the task intended.

Compounds of the present invention may be administered by bioactive agent delivery systems containing microparticles suspended in a polymer matrix. The microparticles may be microcapsules, microspheres or nanospheres currently known in the art. The microparticles should be capable of being entrained intact within a polymer that is or becomes a gel once inside a biological environment. The microparticles can be biodegradable or non-biodegradable. Many microencapsulation techniques used to incorporate a bioactive agent into a microparticle carrier are taught in the art. See e.g. U.S. Pat. Nos. 4,652,441; 5,100,669; 4,438,253; and 5,665,428.

A preferred polymeric matrix will be biodegradable and exhibit water solubility at low temperature and will undergo reversible thermal gelation at physiological mammalian body temperatures. The polymeric matrix is capable of releasing the substance entrained within its matrix over time and in a controlled manner. The polymers are gradually degraded by enzymatic or non-enzymatic hydrolysis in aqueous or physiological environments. See e.g. U.S. Pat. No. 6,287,588.

Compounds of the present invention may be administered by a drug delivery composition comprising microparticles containing at least one chemotherapeutic agent and at least one chemosensitizer suspended in a polymer matrix. The microparticles may be microcapsules, microspheres or nanospheres currently known in the art. The microparticles should be biodegradable and stable in physiological environments. The microparticles also permit diffusion of the chemotherapeutic agent and chemosensitizer from the core through the matrix at a predetermined release rate. Ionic chemotherapeutic agents are suitable for use in the delivery composition of the invention. Ionic chemosensitizers are suitable for use in the delivery composition of the invention. The drug delivery compositions may be delivered to a target site through a variety of known routes of administration. Dosages of the chemotherapeutic agent and chemosensiti The drug delivery compositions may be delivered to a target site through a variety of known routes of administration. Dosages of the chemotherapeutic agent and chemosensitizer incorporated in the drug delivery composition will depend on individual needs, the desired effect and on the chosen route of administration. See e.g. WO 98/50018.

Dosage Determinations

In general, the compounds disclosed herein may be used alone or in concert with other therapeutic agents at appropriate dosages defined by routine testing in order to obtain optimal efficacy while minimizing any potential toxicity. The dosage regimen utilizing a compound of the present invention may be selected in accordance with a variety of factors including type, species, age, weight, sex, medical condition of the patient; the severity of the condition to be treated; the route of administration; the renal and hepatic function of the patient; and the particular compound employed. A physician or veterinarian of ordinary skill can readily determine and prescribe the effective amount of the drug required to prevent, counter, or arrest the progress of the condition.

Optimal precision in achieving concentrations of drug within the range that yields maximum efficacy with minimal toxicity may require a regimen based on the kinetics of the compound's availability to one or more target sites. Distribution, equilibrium, and elimination of a drug may be considered when determining the optimal concentration for a treatment regimen. The dosages of a compound disclosed herein may be adjusted when combined to achieve desired effects. On the other hand, dosages of these various therapeutic agents may be independently optimized and combined to achieve a synergistic result wherein the pathology is reduced more than it would be if either agent were used alone.

In particular, toxicity and therapeutic efficacy of a compound disclosed herein may be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effect is the therapeutic index and it may be expressed as the ratio $LD_{50}/ED_{50}$. Compounds exhibiting large therapeutic indices are preferred except when cytotoxicity of the compound is the activity or therapeutic outcome that is desired. Although compounds that exhibit toxic side effects may be used, a delivery system can target such compounds to the site of affected tissue in order to minimize potential damage to uninfected cells and, thereby, reduce side effects. Generally, the compounds of the present invention may be administered in a manner that maximizes efficacy and minimizes toxicity.

Data obtained from cell culture assays and animal studies may be used in formulating a range of dosages for use in humans. The dosages of such compounds lies preferably within a range of circulating concentrations that include the $ED_{50}$ with little or no toxicity. The dosage may vary within this range depending upon the dosage form employed and the route of administration utilized. For any compound used in the methods of the invention, the therapeutically effective dose may be estimated initially from cell culture assays. A dose may be formulated in animal models to achieve a circulating plasma concentration range that includes the $IC_{50}$ (the concentration of the test compound that achieves a half-maximal inhibition of symptoms) as determined in cell culture. Such information may be used to accurately determine useful doses in humans. Levels in plasma may be measured, for example, by high performance liquid chromatography.

Moreover, the dosage administration of the pharmaceutical compositions of the present invention may be optimized using a pharmacokinetic/pharmacodynamic modeling system. For example, one or more dosage regimens may be chosen and a pharmacokinetic/pharmacodynamic model may be used to determine the pharmacokinetic/pharmacodynamic profile of one or more dosage regimens. Next, one of the dosage regimens for administration may be selected which achieves the desired pharmacokinetic/pharmacodynamic response based on the particular pharmacokinetic/pharmacodynamic profile. See WO 00/67776, which is entirely expressly incorporated herein by reference.

Methods are known in the art for determining effective doses for therapeutic and prophylactic purposes for the disclosed pharmaceutical compositions or the disclosed drug combinations, whether or not formulated in the same composition. For therapeutic purposes, the term "jointly effective amount," as used herein, means that amount of each active compound or pharmaceutical agent, alone or in combination, that elicits the biological or medicinal response in a tissue system, animal or human that is being sought by a researcher, veterinarian, medical doctor or other clinician, which includes alleviation of the symptoms of the disease or disorder being treated. For prophylactic purposes (i.e., inhibiting the onset or progression of a disorder), the term "jointly effective amount" refers to that amount of each active compound or pharmaceutical agent, alone or in combination, that inhibits in a subject the onset or progression of a disorder as being sought by a researcher, veterinarian, medical doctor or other clinician. Thus, the present invention provides combinations of two or more therapeutic agents wherein, for example, (a) each therapeutic agent is administered in an independently therapeutically or prophylactically effective amount; (b) at least one therapeutic agent in the combination is administered in an amount that is sub-therapeutic or subprophylactic if administered alone, but is therapeutic or prophylactic when administered in combination with the second or additional therapeutic agents according to the invention; or (c) both therapeutic agents are administered in an amount that is subtherapeutic or sub-prophylactic if administered alone, but are therapeutic or prophylactic when administered together. Combinations of three or more therapeutic agents are analogously possible. Methods of combination therapy include coadministration of a single formulation containing all active agents; essentially contemporaneous administration of more than one formulation; and administration of two or more active agents separately formulated.

Dosages

More specifically, the pharmaceutical compositions may be administered in a single daily dose, or the total daily dosage may be administered in divided doses of two, three, or four times daily. In the case of oral administration, the daily dosage of the compositions may be varied over a wide range from about 0.0001 to about 1,000 mg per patient, per day. The range may more particularly be from about 0.001 mg/kg to 10 mg/kg of body weight per day, about 0.1–100 mg, about 1.0–50 mg or about 1.0–20 mg per day for adults (at about 60 kg).

The daily dosage of the pharmaceutical compositions may be varied over a wide range from about 0.01 to about 1000 mg per adult human per day. For oral administration, the pharmaceutical compositions are preferably provided in the form of tablets containing from about 0.1 mg to about 1000 mg of the compound or 0.1, 0.2, 0.5, 1.0, 2.0, 5.0, 10.0, 15.0, 100, 150, 200, 250, 300, 350, 400, 450, 500, 550, 600, 650, 700, 800, 900, or 1000 milligrams of the active compound for the symptomatic adjustment of the dosage to the patient to be treated. An effective amount of the drug is ordinarily supplied at a dosage level of from about 0.1 mg/kg to about 20 mg/kg of body weight per day. In one embodiment, the range is from about 0.2 mg/kg to about 10 mg/kg of body weight per day. In another embodiment, the range is from about 0.5 mg/kg to about 10 mg/kg of body weight per day. The compounds may be administered on a regimen of about 1 to about 10 times per day.

In the case of injections, it is usually convenient to give by an intravenous route in an amount of about 0.01–30 mg, about 0.1–20 mg or about 0.1–10 mg per day to adults (at about 60 kg). In the case of other animals, the dose calculated for 60 kg may be administered as well.

Doses of a compound of the present invention can optionally include 0.0001 to 1,000 mg/kg/administration, or 0.001 to 100.0 mg/kg/administration, from 0.01 to 10 mg/kg/administration, from 0.1 to 10 mg/kg/administration, including 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 and/or 100–500 mg/kg/administration or any range, value or fraction thereof, or to achieve a serum concentration of 0.1, 0.5, 0.9, 1.0, 1.1, 1.2, 1.5, 1.9, 2.0, 2.5, 2.9, 3.0, 3.5, 3.9, 4.0, 4.5, 4.9, 5.0, 5.5, 5.9, 6.0, 6.5, 6.9, 7.0, 7.5, 7.9, 8.0, 8.5, 8.9, 9.0, 9.5, 9.9, 10, 10.5, 10.9, 11, 11.5, 11.9, 20, 12.5, 12.9, 13.0, 13.5, 13.9, 14.0, 14.5, 4.9, 5.0, 5.5., 5.9, 6.0, 6.5, 6.9, 7.0, 7.5, 7.9, 8.0, 8.5, 8.9, 9.0, 9.5, 9.9, 10, 10.5, 10.9, 11, 11.5, 11.9, 12, 12.5, 12.9, 13.0, 13.5, 13.9, 14, 14.5, 15, 15.5, 15.9, 16, 16.5, 16.9, 17, 17.5, 17.9, 18, 18.5, 18.9, 19, 19.5, 19.9, 20, 20.5, 20.9, 21, 22, 23, 24, 25, 26, 27, 28, 29, 30, 35, 40, 45, 50, 55, 60, 65, 70, 75, 80, 85, 90, 96, 100, 200, 300, 400, 500, 600, 700, 800, 900, 1000, 1500, 2000, 2500, 3000, 3500, 4000, 4500, and/or 5000 µg/ml serum concentration per single or multiple administration or any range, value or fraction thereof.

As a non-limiting example, treatment of humans or animals can be provided as a one-time or periodic dosage of a compound of the present invention 0.1 to 100 mg/kg such as 0.5, 0.9, 1.0, 1.1, 1.5, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 45, 50, 60, 70, 80, 90 or 100 mg/kg, per day, on at least one of day 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40, or alternatively or additionally, at least one of week 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, or 52, or alternatively or additionally, at least one of 1, 2, 3, 4, 5, 6, 7, 8, 9, 10, 11, 12, 13, 14, 15, 16, 17, 18, 19, or 20 years, or any combination thereof, using single, infusion or repeated doses.

Specifically, the pharmaceutical compositions of the present invention may be administered at least once a week over the course of several weeks. In one embodiment, the pharmaceutical compositions are administered at least once a week over several weeks to several months. In another embodiment, the pharmaceutical compositions are administered once a week over four to eight weeks. In yet another embodiment, the pharmaceutical compositions are administered once a week over four weeks.

More specifically, the pharmaceutical compositions may be administered at least once a day for about 2 days, at least once a day for about 3 days, at least once a day for about 4 days, at least once a day for about 5 days, at least once a day for about 6 days, at least once a day for about 7 days, at least once a day for about 8 days, at least once a day for about 9 days, at least once a day for about 10 days, at least once a day for about 11 days, at least once a day for about 12 days, at least once a day for about 13 days, at least once a day for about 14 days, at least once a day for about 15 days, at least once a day for about 16 days, at least once a day for about 17 days, at least once a day for about 18 days, at least once a day for about 19 days, at least once a day for about 20 days, at least once a day for about 21 days, at least once a day for about 22 days, at least once a day for about 23 days, at least once a day for about 24 days, at least once a day for about 25 days, at least once a day for about 26 days, at least once a day for about 27 days, at least once a day for about 28 days, at least once a day for about 29 days, at least once a day for about 30 days, or at least once a day for about 31 days.

Alternatively, the pharmaceutical compositions may be administered about once every day, about once every 2 days, about once every 3 days, about once every 4 days, about once every 5 days, about once every 6 days, about once every 7 days, about once every 8 days, about once every 9 days, about once every 10 days, about once every 11 days, about once every 12 days, about once every 13 days, about once every 14 days, about once every 15 days, about once every 16 days, about once every 17 days, about once every 18 days, about once every 19 days, about once every 20 days, about once every 21 days, about once every 22 days, about once every 23 days, about once every 24 days, about once every 25 days, about once every 26 days, about once every 27 days, about once every 28 days, about once every 29 days, about once every 30 days, or about once every 31 days.

The pharmaceutical compositions of the present invention may alternatively be administered about once every week, about once every 2 weeks, about once every 3 weeks, about once every 4 weeks, about once every 5 weeks, about once every 6 weeks, about once every 7 weeks, about once every 8 weeks, about once every 9 weeks, about once every 10 weeks, about once every 11 weeks, about once every 12 weeks, about once every 13 weeks, about once every 14 weeks, about once every 15 weeks, about once every 16 weeks, about once every 17 weeks, about once every 18 weeks, about once every 19 weeks, about once every 20 weeks.

Alternatively, the pharmaceutical compositions of the present invention may be administered about once every month, about once every 2 months, about once every 3 months, about once every 4 months, about once every 5 months, about once every 6 months, about once every 7 months, about once every 8 months, about once every 9 months, about once every 10 months, about once every 11 months, or about once every 12 months.

Alternatively, the pharmaceutical compositions may be administered at least once a week for about 2 weeks, at least once a week for about 3 weeks, at least once a week for about 4 weeks, at least once a week for about 5 weeks, at least once a week for about 6 weeks, at least once a week for about 7 weeks, at least once a week for about 8 weeks, at least once a week for about 9 weeks, at least once a week for about 10 weeks, at least once a week for about 11 weeks, at least once a week for about 12 weeks, at least once a week for about 13 weeks, at least once a week for about 14 weeks, at least once a week for about 15 weeks, at least once a week for about 16 weeks, at least once a week for about 17 weeks, at least once a week for about 18 weeks, at least once a week for about 19 weeks, or at least once a week for about 20 weeks.

Alternatively the pharmaceutical compositions may be administered at least once a week for about 1 month, at least once a week for about 2 months, at least once a week for about 3 months, at least once a week for about 4 months, at least once a week for about 5 months, at least once a week for about 6 months, at least once a week for about 7 months, at least once a week for about 8 months, at least once a week for about 9 months, at least once a week for about 10 months, at least once a week for about 11 months, or at least once a week for about 12 months.

Combination Therapy

In addition, co-administration or sequential administration of the compounds of the present invention and other therapeutic agents may be desirable, such as chemotherapeutic agents, immunosuppressive agents, cytokines, cytotoxic agents, nucleolytic compounds, radioactive isotopes, receptors, and pro-drug activating enzymes, which may be naturally occurring or produced by recombinant methods. The combined administration includes co-administration, using separate formulations or a single pharmaceutical formulation, and consecutive administration in either order, wherein preferably there is a time period while both (or all) active therapeutic agents simultaneously exert their biological activities.

The compounds of this invention may be administered in combination with at least one selected from the group consisting of an antirheumatic (e.g., methotrexate, auranofin, aurothioglucose, azathioprine, etanercept, gold sodium thiomalate, hydroxychloroquine sulfate, leflunomide, sulfasalzine), a muscle relaxant, a narcotic, a non-steroid anti-inflammatory drug (NSAID), an analgesic, an anesthetic, a sedative, a local anesthetic, a neuromuscular blocker, an anti-cancer, an antimicrobial (e.g., aminoglycoside, an antifungal, an antiparasitic, an antiviral, a carbapenem, cephalosporin, a flurorquinolone, a macrolide, a penicillin, a sulfonamide, a tetracycline, another antimicrobial), an anti-psoriatic, a corticosteriod, an anabolic steroid, a diabetes-related agent, a mineral, a nutritional, a thyroid agent, a vitamin, a calcium-related hormone, an antidiarrheal, an anti-tussive, an anti-emetic, an anti-ulcer, a laxative, an anticoagulant, an erythropieitin (e.g., epoetin alpha), a filgrastim (e.g., G-CSF, Neupogen), a sargramostim (GM-CSF, Leukine), an immunization, an immunoglobulin, an immunosuppressive (e.g., basiliximab, cyclosporine, daclizumab), a growth hormone, a hormone replacement drug, an estrogen receptor modulator, a mydriatic, a cycloplegic, an alkylating agent, an antimetabolite, a mitotic inhibitor, a radiopharmaceutical, an anti-depressant, anti-manic agent, an anti-psychotic, an anxiolytic, a hypnotic, a sympathomimetic, a stimulant, donepezil, tacrine, an asthma medication, a beta agonist, an inhaled steroid, a leukotriene inhibitor, a methylxanthine, a cromolyn, an epinephrine or analog thereof, dornase alpha (Pulmozyme), or a cytokine.

Such anti-cancer or antimicrobial compounds can also include toxin molecules that are associated, bound, co-formulated, co-administered or sequentially administered, in either order, with at least one of the compounds of the present invention. The toxin can optionally act to selectively kill the pathologic cell or tissue. The pathologic cell can be a cancer or other cell. Such toxins can be, but are not limited to, purified or recombinant toxin or toxin fragment comprising at least one functional cytotoxic domain of toxin, e.g., selected from at least one of ricin, diphtheria toxin, a venom toxin, or a bacterial toxin. The term toxin also includes both endotoxins and exotoxins produced by any naturally occurring, mutant or recombinant bacteria or viruses which may cause any pathological condition in humans and other mammals, including toxin shock, which can result in death. Such toxins may include, but are not limited to, enterotoxigenic *E. coli* heat-labile enterotoxin (LT), heat-stable enterotoxin (ST), *Shigella* cytotoxin, *Aeromonas* enterotoxins, toxic shock syndrome toxin-1 (TSST-1), Staphylococcal enterotoxin A (SEA), B (SEB), or C (SEC), Streptococcal enterotoxins and the like. Such bacteria include, but are not limited to, strains of a species of enterotoxigenic *E. coli* (ETEC), enterohemorrhagic *E. coli* (e.g., strains of serotype 0157:H7), *Staphylococcus* species (e.g., *Staphylococcus* aureus, *Staphylococcus pyogenes*), *Shigella* species (e.g., *Shigella dysenteriae, Shigella flexneri, Shigella boydii,* and *Shigella sonnei*), *Salmonella* species (e.g., *Salmonella typhi, Salmonella cholera-suis, Salmonella enteritidis*), *Clostridium* species (e.g., *Clostridium perfringens, Clostridium dificile, Clostridium botulinum*), *Camphlobacter* species (e.g., *Camphlobacter jejuni, Camphlobacter fetus*), *Heliobacter* species, (e.g., *Heliobacter pylori*), *Aeromonas* species (e.g., *Aeromonas sobria, Aeromonas hydrophila, Aeromonas caviae*), *Pleisomonas shigelloides, Yersina enterocolitica, Vibrios* species (e.g., *Vibrios cholerae, Vibrios parahemolyticus*), *Klebsiella* species, *Pseudomonas aeruginosa*, and *Streptococci*. See, e.g., Stein, ed., INTERNAL MEDICINE, 3rd ed., pp 1–13, Little, Brown and Co., Boston, (1990); Evans et al., eds., Bacterial Infections of Humans: Epidemiology and Control, 2d. Ed., pp 239–254, Plenum Medical Book Co., New York (1991); Mandell et al, Principles and Practice of Infectious Diseases, 3d. Ed., Churchill Livingstone, New York (1990); Berkow et al, eds., The Merck Manual, 16th edition, Merck and Co., Rahway, N.J., 1992; Wood et al, FEMS Microbiology Immunology, 76:121–134 (1991); Marrack et al, Science, 248:705–711 (1990), the contents of which references are incorporated entirely herein by reference.

More specifically, the compound of the present invention may be administered in combination with at least one immunosuppressive agent for use in, for example, treating or preventing a vascular occlusive conditions such as transplant vasculopathy. Suitable immunosuppressive agents include, but are not limited to, CellCept (Roche Labs.), Gengraf (Abbott Labs., Inc.), Micrhogam (Ortho-Clinical), Neoral (Novartis), Orthoclone OKT3 (Ortho-Biotech), Prograf (Fujisawa), Rapamune (Wyeth-Ayerst), Sandimmune (Novartis), Thymoglobulin (SangStat), Zenapax (Roche).

In one embodiment, the therapeutic agent administered simultaneously or sequentially, in either order and at various times with a compound of the present invention, comprises a chemotherapeutic agent. A "chemotherapeutic agent" is a compound useful in the treatment of cancer. Examples of chemotherapeutic agents include, but are not limited to, alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphaoramide and trimethylolomelamine; nitrogen mustards such as chlorambucil, chlornaphazine, cholophosphamide, estramustine, ifosfamide, mechlorethamine, mechlorethamine oxide hydrochloride, melphalan, novembiehin, phenesterine, prednimustine, trofosfamide, uracil mustard; nitroureas such as cannustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, chromoinycins, dactinomycin, daunorubicin, detorubicin, 6-diazo-5-oxo-L-norleucine, doxorubicin, epirubicin, esorubicin, idambicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, rnepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elfornithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK®; razoxane; sizofrran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxoids, e.g., paclitaxel (TAXOL®, Bristol-Myers Squibb Oncology, Princeton, N.J.) and doxetaxel (TAXOTERE®, Rhone-Poulenc Rorer, Antony, France); chlorambucil; gemeitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylornithine (DMFO); retinoic acid; esperamicins; capecitabine; and pharmaceutically acceptable salts, acids or derivatives of any of the above. Also included in this definition are anti-hormonal agents that act to regulate or inhibit hormone action on tumors such as anti-estrogens including for example tamoxifen, raloxifene, aromatase inhibiting 4(5)-imidazoles, 4 hydroxytamoxifen, trioxifene, keoxifene, onapristone, and toremifene (Fareston); and anti-androgens such as flutamide, nilutamide, bicalutamide, leuprolide, and goserelin; and pharmaceutically acceptable salts, acids or derivatives of any of the above.

In another embodiment, the therapeutic agent comprises a cytokine. The term "cytokine" is a generic term for proteins released by one cell population which act on another cell as intercellular mediators. Examples of such cytokines are lymphokines, monokines, and traditional polypeptide hormones. Included among the cytokines are growth hormones such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-α and -β; mullerian-inhibiting substance; mouse gonadotropin-associated peptide; inhibin; activin; vascular endothelial growth factor; integrin; thrombopoietin (TPO); nerve growth factors such as NGF-β; platelet growth factor; transforming growth factors (TGFs) such as TGF-α and TGF-β; insulin-like growth factor-I and -II; erythropoietin (EPO); osteoinductive factors; interferons such as interferon-α-β and -γ; colony stimulating factors (CSFs) such as macrophage-CSF (M-CSF); granulocyte-macrophage-CSF (GM-CSF); and granulocyte-CSF (GCSF); interleukins (ILs) such as IL-1, IL-1a, IL-2, IL-3, IL-4, IL-5, IL-6, IL-7, IL-8, IL-9, IL-11, IL-12, IL-15; a tumor necrosis factor such as TNF-α or TNF-β; and other polypeptide factors including LIF and kit ligand (KL). As used herein, the term cytokine includes proteins from natural sources or from recombinant cell culture and biologically active equivalents of the native sequence cytokines.

In another embodiment, the compounds of the present invention may be administered in combination with an anti-inflammatory agent including, but not limited to, adrenocortical steroids (cortisol, cortisone, fludrocortisone, prednisone, prednisolone, 6α-methylprednisolone, triamcinolone, betamethasone, and dexamethasone), non-steroidal agents (salicylic acid derivatives, i.e., aspirin; para-aminophenol derivatives, i.e., acetominophen; indole and indene acetic acids (indomethacin, sulindac, and etodalac), heteroaryl acetic acids (tolmetin, diclofenac, and ketorolac), arylpropionic acids (ibuprofen and derivatives), anthranilic acids (mefenamic acid, and meclofenamic acid), enolic acids (piroxicam, tenoxicam, phenylbutazone, and oxyphenthatrazone), nabumetone, gold compounds (auranofin, aurothioglucose, gold sodium thiomalate). Commercially available nonsteroidal anti-inflammatory drugs include, but are not limited to, Anaprox (Roche Labs.), Arthrotec (Searle), Cataflam (Novartis), Celebrex (Pfizer), , Clinoril (Merck), Dolobid (Merck), Feldene (Pfizer), Indocin (Merck), Lodine (Wyeth-Ayerst), Mobic (Boehringer Ingelheim), Motrin (McNeil Consumer), Naprosyn (Roche Labs.), Orudis (Wyeth-Ayerst), Oruvail (Wyeth-Ayerst), Ponstel (First Horizon), Relafen (GlaxoSmithKline), Tolectin (Ortho-McNeil), Toradol (Roche Labs., Inc.), Vioxx (Merck), Voltaren (Novartis), Advair (GlaxoSmithKline), Flovent (GlaxoSmithKline), Pulmicort (AstranZeneca), and Vanceril (Schering), Asacol (Procter & Gamble), Colazal (Salix), Dipentum (Pharmacia & Upjohn), and Rowasa (Solvay).

In yet another embodiment, the compounds of the present invention may be administered in combination with an antirheumatic agent. Commercially available antirheumatic agents include, but are not limited to, Anaprox (Roche Labs.), Arava (Aventic), Arthrotec (Searle), Azulfidine (Pharmacia & Upjohn), Cataflam (Novartis), Celebrex (Pfizer), Celestone (Schering), Cuprimine (Merck), Enbrel (Immunex), Feldene (Pfizer), Gengraf (Abbott), Indocin (Merck), Lodine (Wyeth-Ayerst), Naprosyn (Roche Labs.), Neoral (Novartis), Pediapred (Celltech), Prednisone (Roxanne), Remicade (Centocor), Solu-Medrol (Pharmacia & Upjohn), Triliate (Purdue Frederick), and Voltaren (Novartis).

Moreover, the compounds of the present invention may be used in combination with any cardiovascular agent including, but not limited to, adrenergic blockers such as Cardura (Pfizer), Dibenzyline (WellSpring), Hytrin (Abbott), Minipress (Pfizer), and Minizide (Pfizer); adrenergic stimulants such as Aldoclor (Merck), Aldomet (Merck), Aldoril (Merck), Catapres (Boehringer Ingelheim), Clorpres (Bertek), and Tenex (Robins); alpha/beta adrenergic blockers such as Coreg (GlaxoSmithKline), and Nornodyne (Schering); angiotensin converting enzyme inhibitors such as Accupril (Parke-Davis), Aceon (Solvay), Altace (Monarch), Captopril (Mylan), Enalaprilat (Baxter Anesthesia), Lotensin (Novartis), Mavik (Abbott), Monopril (Bristol-Myers Squibb), Prinivil (Merck), Univasc (Schwarz), Vaotec (Merck), and Zestril (AstraZeneca); angiotenisin converting enzyme inhibitors such as Lexxel (AstraZeneca), Lotrel (Novartis), Tarka (Abbott), Accuretic (Parke-Davis), Lotensin (Novartis), Prinzide (Merck), Uniretic (Schwarz), Vaeretic (Merck), and Zestoretic (AstraZeneca); angiotensin II receptor antagonists such as Atacand (AstraZeneca), Avapro (Briston-Myers Squibb), Cozaar (Merck), Diovan (Novartis), Micardis (Boehringer Ingelheim), and Teveten (Unimed); antiarrhythmics (Groups I–IV), antilipemic agents such as bile acid sequestrants, fibric acid derivatives, HMG-CoA reductase inhibitors, and nicotinic acid; Beta adrenergic blocking agents; calcium channel blockers; inotropic agents; vasodilators including coronoary vasodilators, natriuretic peptides, and peripheral vasodilators; and vasopressors.

In another aspect of the present invention, the therapeutic agent comprises a small molecule toxin, including maytansine, calicheamicin, trichothene, and CC 1065. In a specific embodiment, the therapeutic agent may comprise one more calicheamicin molecules. The calicheamicin family of antibiotics are capable of producing double-stranded DNA breaks at sub-picomolar concentrations. Structured analogues of calicheamicin are also known. See Hinman et al., 53 CANCER RESEARCH 3336–42 (1993); Lode et al., 58 CANCER RESEARCH 2925–28 (1998).

In yet another aspect of the present invention, the therapeutic agent may comprise one or more enzymatically active toxins and fragments thereof. Examples of such toxins include nonbinding active fragments of diphtheria toxin, diphtheria A chain, exotoxin A chain (from *Pseudomonas aeruginosa*), ricin A chain, abrin A chain, modeccin A chain, alpha-sarcin, dianthin proteins, *Phytolaca americana* proteins (PAPI, PAPAII, and PAP-S), *momordica charantia* inhibitor, curcin, crotin sapaonaria officinalis inhibitor, gelonin, mitogellin, restrictoein, phenomvcin, enomycin and the tricothecenes. See, e.g., WO 93/21232.

The present invention further contemplates therapeutic agents that have nucleolytic activity such as a ribonuclease and a deoxyribonuclease. In addition, a variety of radioactive isotopes are available for the production of radioconjugated binding partners. Examples include $Y^{90}$, $At^{222}$, $Ret^{86}$ $Re^{186}$, $Sm^{153}$, $Bi^{212}$, $P^{32}$ and radioactive isotopes of Lu.

In yet another aspect of the present invention, the at least one compound may be conjugated to a receptor, such as streptavidin, for utilization in tumor pretargeting. Briefly, the compound-receptor conjugate is administered to the patient and unbound conjugate is removed from circulation with a clearing agent. A ligand, such as biotin, which is conjugated to a cytotoxic agent is then administered.

Timing of Administration

In several embodiments of the present invention, a compound described herein is administered before or after administration of a second therapeutic agent. The administration of a compound may occur anytime from several minutes to several hours before the administration of the second therapeutic agent. The compound may alternatively be administered anytime from several hours to several days, possibly several weeks, and up to several months before the second therapeutic agent.

More specifically, a compound of the present invention may be administered at least about 1 minute, at least about minutes, at least about minutes, at least about minutes, at least about minutes, at least about 2 minutes, at least about 3 minutes, at least about 4 minutes, at least about 5 minutes, at least about 6 minutes, at least about 7 minutes, at least about 8 minutes, at least about 9 minutes, at least about 10 minutes, at least about 11 minutes, at least about 12 minutes, at least about 13 minutes, at least about 14 minutes, at least about 15 minutes, at least about 16 minutes, at least about 17 minutes, at least about 18 minutes, at least about 19 minutes, at least about 20 minutes, at least about 21 minutes, at least about 22 minutes, at least about 23 minutes, at least about 24 minutes, at least about 25 minutes, at least about 26 minutes, at least about 27 minutes, at least about 28 minutes, at least about 29 minutes, at least about 30 minutes, at least about 31 minutes, at least about 32 minutes, at least about 33 minutes, at least about 34 minutes, at least about 35 minutes, at least about 36 minutes, at least about 37 minutes, at least about 38 minutes, at least about 39 minutes, at least about 40 minutes, at least about 41 minutes, at least about 42 minutes, at least about 43 minutes, at least about 44 minutes, at least about 45 minutes, at least about 46 minutes, at least about 47 minutes, at least about 48 minutes, at least about 49 minutes, at least about 50 minutes, at least about 41 minutes, at least about 52 minutes, at least about 53 minutes, at least about 54 minutes, at least about 55 minutes, at least about 56 minutes, at least about 57 minutes, at least about 58 minutes, at least about 59 minutes, or at least about 60 minutes before or after the second therapeutic agent. Furthermore, a compound of the present invention may be administered at least about 1 hour, at least about 2 hours, at least about 3 hours, at least about 4 hours, at least about 5 hours, at least about 6 hours, at least about 7 hours, at least about 8 hours, at least about 9 hours, at least about 10 hours, at least about 11 hours, at least about 12 hours, at least about 13 hours, at least about 14 hours, at least about 15 hours, at least about 16 hours, at least about 17 hours, at least about 18 hours, at least about 19 hours, at least about 20 hours, at least about 21 hours, at least about 22 hours, at least about 23 hours, or at least about 24 hours before or after the second therapeutic agent.

Moreover, a compound of the present invention may be administered at least about 1 day, at least about 2 days, at least about 3 days, at least about 4 days, at least about 5 days, at least about 6 days, at least about 7 days, at least about 8 days, at least about 9 days, at least about 10 days, at least about 11 days, at least about 12 days, at least about 13 days, at least about 14 days, at least about 15 days, at least about 16 days, at least about 17 days, at least about 18 days, at least about 19 days, at least about 20 days, at least about 21 days, at least about 22 days, at least about 23 days, at least about 24 days, at least about 25 days, at least about 26 days, at least about 27 days, at least about 28 days, at least about 29 days, at least about 30 days or at least about 31 days before or after the administration of the second therapeutic agent.

In yet another aspect of the present invention, a compound of the present invention may be administered at least about 1 week, at least about 2 weeks, at least about 3 weeks, at least about 4 weeks, at least about 5 weeks, at least about 6 weeks, at least about 7 weeks, at least about 8 weeks, at least about 9 weeks, at least about 10 weeks, at least about 11 weeks, at least about 12 weeks, at least about 13 weeks, at least about 14 weeks, at least about 15 weeks, at least about 16 weeks, at least about 17 weeks, at least about 18 weeks, at least about 19 weeks, or at least about 20 weeks before or after the second therapeutic agent.

In a further aspect of the present invention, a compound of the present invention may be administered at least about one month, at least about two months, at least about three months, at least about four months, at least about five months, at least about six months, at least about seven months, at least about eight months, at least about nine months, at least about ten months, at least about eleven months, or at least about twelve months before or after the second therapeutic agent.

For convenience, the meaning of certain terms and phrases employed in the specification, examples, and appended claims are provided below.

Definitions

As used herein, the term "compound" includes both the singular and the plural, and includes any single entity or combined entities that have at least the activity disclosed herein and combinations, fragments, analogs or derivatives of such entities. Such entities include, but are not limited to, chemical elements, molecules, compounds, mixtures, emulsions, chemotherapeutic agents, pharmacological agents, hormones, antibodies, growth factors, cellular factors, nucleic acids, proteins, peptides, peptidomimetics, nucleotides, carbohydrates, and combinations, fragments, analogs or derivatives of such entities.

The term "phenylamine" refers to a primary or secondary benzeneamine, more commonly known as an aniline. The amino group on the aniline can be substituted with hydrogen, alkyl ($C_1$–$C_{12}$, straight chain or branched), cycloalkyl ($C_3$–$C_{10}$), or aryl substituted aryl groups. The phenyl ring of this aniline derivative can be optionally substituted with one or more functional groups, or a combination of functional groups such as alkyl, alkenyl, alkynyl, phenyl, benzyl, halo, cyano, nitro, hydroxy, thioxy, alkoxy, aryloxy, haloalkyloxy, alkylthio, arylthio, amino, alkyl amino, aryl amino, acyl, carboxyl, amido, sulfonamido, sulfonyl, sulfate, sulfonic acid, morpholino, piperazinyl, pyridyl, thienyl, furanyl, pyrroyl, pyrazoyl, phosphate, phosphonic acid, or phosphonate. If applicable, these groups can be represented in protected or unprotected forms used in standard organic synthesis.

The term "naphthylamine" refers to a primary or secondary α- or β-naphthylamine. The ring substructure in the naphthylamine can be optionally substituted with one or a combination of functional groups such as alkyl, alkenyl, alkynyl, phenyl, benzyl, halo, cyano, nitro, hydroxy, thioxy, alkoxy, aryloxy, haloalkyloxy, alkylthio, arylthio, amino, alkyl amino, aryl amino, acyl, carboxyl, amido, sulfonamido, sulfonyl, sulfate, sulfonic acid, morpholino, thiomorpholino, piperazinyl, pyridyl, thienyl, furanyl, pyrroyl, pyrazoyl, phosphate, phosphonic acid, phosphonate and the like. These groups can be represented in protected or unprotected forms used in standard organic synthesis.

The term "naphthylalkyl amine" refers to a primary or secondary α- and β-naphthylalkyl amine (for example, 2-α-naphthylethyl amine). The term "benzalkyl amine" refers to a primary or secondary benzylalkyl amine (for example, phenylethyl amine). These aryl alkyl substructures or compounds can be optically active or optically inactive. The aryl (ring) substructures of the naphthylalkyl and benzalkyl amines can be optionally subsituted with one or a combination of functional groups, such as alkyl, alkenyl, alkynyl, phenyl, benzyl, halo, cyano, nitro, hydroxy, thioxy, alkoxy, aryloxy, haloalkyloxy, alkylthio, arylthio, amino, alkyl amino, aryl amino, acyl, carbolyl, amido, sulfonamido, sulfonyl, sulfate, sulfonic acid, morpholino, piperazinyl, pyridyl, thienyl, furanyl, pyrroyl, pyrazoyl, phosphate, phosphonic acid, phosphonate and the like. If applicable these groups can be represented in protected or unprotected forms used in standard organic synthesis.

The term "quinolinyl amine" refers to primary or secondary quinolyl amines. These amines can be in optically active or inactive forms. The aryl (ring) substructure of the quinolyl amine can be optionally substituted with one a combination of functional groups such as alkyl, alkenyl, alkynyl, phenyl, benzyl, halo, cyano, nitro, hydroxy, thioxy, alkoxy, aryloxy, haloalkyloxy, alkylthio, arylthio, amino, alkyl amino, aryl amino, acyl, carboxyl, amido, sulfonamido, sulfonyl, sulfate, sulfonic acid, morpholino, thiomorpholino, piperazinyl, pyridyl, thienyl, furanyl, pyrroyl, pyrazoyl, phosphate, phosphonic acid, phosphonate and the like. These groups can be represented in protected or unprotected forms used in standard organic synthesis.

The term "heteroaryl amines" refers to pyrroles, pyrazoles, imidazoles, and indoles. The aryl (ring) substructure of the heteroaryl amine can be optionally substituted with one or a combination of functional groups such as alkyl, alkenyl, alkynyl, phenyl, benzyl, halo, cyano, nitro, hydroxy, thioxy, alkoxy, aryloxy, haloalkyloxy, alkylthio, arylthio, amino, alkyl amino, aryl amino, acyl, carboxyl, amido, sulfonamido, sulfonyl, sulfate, sulfonic acid, morpholino, thiomorpholino, piperazinyl, phosphate, phosphonic acid, or phosphonate. These groups can be represented in protected or unprotected forms used in standard organic synthesis.

The term "glycated protein," as used herein, includes proteins linked to glucose, either enzymatically or non-enzymatically, primarily by condensation of free epsilon-amino groups in the protein with glucose, forming Amadori adducts. Furthermore, glycated protein, as used herein, includes not only proteins containing these initial glycation products, but also glycation products resulting from further reactions such as rearrangements, dehydration, and condensations that form irreversible advanced glycation end products (AGE).

The term "polynucleotide" refers generally to polymeric forms of nucleotides of any length, either ribonucleotides or deoxynucleotides. Thus, this term includes, but is not limited to, single-stranded, double-stranded, or multi-stranded DNA or RNA. Polynucleotides may further comprise genomic DNA, cDNA, or DNA-RNA hybrids. Moreover, the polynucleotides of the present invention may be synthetically produced.

Polynucleotides may comprise chemically modified, biochemically modified, or derivatized nucleotides. For example, a polynucleotide may comprise, in part, modified nucleotides such as methylated nucleotides or nucleotide analogs. In other embodiments, polynucleotides may comprise sugars, caps, nucleotide branches, and linking groups such as fluororibose and thioate. In addition, the sequence of nucleotides may be interrupted by non-nucleotide components. Furthermore, a polynucleotide may be modified after polymerization to facilitate its attachment to other polynucleotides, proteins, metal ions, labeling components, or a solid support.

The backbone of the polynucleotide may comprise modified or substituted sugar and/or phosphate groups. Alternatively, the backbone of the polynucleotide may comprise a polymer of synthetic subunits such as phosphoramidites and thus may be an oligodeoxynucleoside phosphoramidate or a mixed phosphoramidate-phosphodiester oligomer. See Peyrottes et al., NUCL. ACIDS RES. (1996) 24:1841–1848, and Chaturvedi et al., NUCL. ACIDS RES. (1996) 24:2318–2323.

The term "homology", as used herein, refers to a degree of complementarity. There may be partial homology or complete homology (i.e., identity). A partially complementary sequence is one that at least partially inhibits an identical sequence from hybridizing to a target polynucleotide; it is referred to using the functional term "substantially homologous" The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous sequence or probe to the target sequence under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target sequence which lacks even a partial degree of complementarity (e.g., less than about 30% identity); in the absence of non-specific binding, the probe will not hybridize to the second non-complementary target sequence.

The term "gene" refers to a polynucleotide sequence that comprises coding sequences necessary for the production of a polypeptide or precursor, and may also include expression control sequences or other control or regulatory sequences. The polypeptide can be encoded by a full length coding sequence or by any portion of the coding sequence. The gene may be derived in whole or in part from any source known to those of ordinary skill in the art including a plant, a fungus, an animal, a bacterial genome or episome, eukaryotic, nuclear or plasmid DNA, cDNA, viral DNA, or chemically synthesized DNA. A gene may constitute an uninterrupted coding sequence or it may include one or more introns, bound by the appropriate splice junctions. Moreover, a gene may contain one or more modifications in either the coding or the untranslated regions that could affect certain properties of the polynucleotide or polypeptide, such as the biological activity or the chemical structure of the expression product, the rate of expression, or the manner of expression control. Such modifications include, but are not limited to, mutations, insertions, deletions, and substitutions of one or more nucleotides. In this regard, such modified genes may be referred to as variants of the native gene.

"Gene expression" refers to the process by which a polynucleotide sequence undergoes successful transcription and translation such that detectable levels of the nucleotide sequence are expressed as proteins or the polynucleotide sequence undergoes transcription, if RNA is copied from DNA, or replication if DNA is copied from DNA, such that the resulting nucleotide copies are detectable.

The term "gene expression profile" refers to a group of genes representing a particular cell or tissue type (e.g., neuron, coronary artery endothelium, or disease tissue) in any activation state. In one aspect, a gene expression profile is generated from cells exposed to a compound of the present invention. This profile may be compared to a gene expression profile generated from the same type of cell or tissue type prior to treatment with a compound of the present invention. Furthermore, a series of gene expression profiles may be generated from cells or tissues treated with a compound of the present invention, specifically, at different doses or a time-course to assess the effects of the compound. A gene expression profile is also known as a gene expression signature.

The term "differential expression" refers to both quantitative as well as qualitative differences in the temporal and tissue expression patterns of a gene. For example, a differentially expressed gene may have its expression activated or completely inactivated in normal versus disease conditions. Such a qualitatively regulated gene may exhibit an expression pattern within a given tissue or cell type that is detectable in either control or disease conditions, but is not detectable in both. "Differentially expressed polynucleotide," as used herein, refers to a polynucleotide sequence that uniquely identifies a differentially expressed gene so that detection of the differentially expressed polynucleotide in a sample is correlated with the presence of a differentially expressed gene in a sample.

Similarly, a differentially expressed protein may have its expression activated or completely inactivated in normal versus disease conditions. Such a qualitatively regulated protein may exhibit an expression pattern within a given tissue or cell type that is detectable in either control or disease conditions, but is not detectable in both. A "differentially expressed protein," as used herein, refers to an amino acid sequence that uniquely identifies a differentially expressed protein so that detection of the differentially expressed protein in a sample is correlated with the presence of a differentially expressed protein in a sample. "Cell type," as used herein, refers to a cell from a given source (e.g., tissue or organ), a cell in a given state of differentiation, or a cell associated with a given pathology or genetic makeup.

The term "polypeptide" refers to a polymeric form of amino acids of any length, which may include translated, untranslated, chemically modified, biochemically modified, and derivatized amino acids. A polypeptide may be naturally occurring, recombinant, or synthetic, or any combination of these. Moreover, the term "polypeptide," as used herein, refers to proteins, polypeptides, and peptides of any size, structure, or function. For example, a polypeptide may comprise a string of amino acids held together by peptide bonds. A polypeptide may alternatively comprise a long chain of amino acids held together by peptide bonds. Moreover, a polypeptide may also comprise a fragment of a naturally occurring protein or peptide. A polypeptide may be a single molecule or may be a multi-molecular complex. In addition, such polypeptides may have modified peptide backbones as well.

The term "polypeptide" further comprises immunologically tagged proteins and fusion proteins, including, but not limited to, fusion proteins with a heterologous amino acid sequence, fusion proteins with heterologous and homologous leader sequences, and fusion proteins with or without N-terminal methionine residues.

The term "protein expression" refers to the process by which a polynucleotide sequence undergoes successful transcription and translation such that detectable levels of the amino acid sequence or protein are expressed.

The term "protein expression profile" refers to a group of proteins representing a particular cell or tissue type (e.g., neuron, coronary artery endothelium, or disease tissue). In one aspect, a protein expression profile is generated from cells or tissues exposed to a compound of the present invention. This profile may be compared to a protein expression profile generated from the same type of cell or tissue prior to treatment with a compound of the present invention. Furthermore, a series of protein expression profiles may be generated from cells or tissues treated with a compound of the present invention, specifically, at different doses or a time-course to assess the effects of the compound. A protein expression profile is also known as a "protein expression signature."

As used herein, a "biomolecule" includes polynucleotides and polypeptides. Moreover, a "biomolecular sequence," as used herein, is a term that refers to all or a portion of a polynucleotide sequence. A biomolecular sequence may also refer to all or a portion of a polypeptide sequence. In the context of biomolecule, for example, perlecan, the term "functional equivalent" refers to a protein or polynucleotide molecule that possesses functional or structural characteristics that are substantially similar to all or part of the native perlecan protein or native perlecan-encoding polynucleotides. A functional equivalent of a native perlecan protein may contain modifications depending on the necessity of such modifications for a specific structure or the performance of a specific function. The term "functional equivalent" is intended to include the "fragments," "mutants," "derivatives," "alleles," "hybrids," "variants," "analogs," or "chemical derivatives" of native perlecan.

A "host cell," as used herein, refers to a microorganism, a prokaryotic cell, a eukaryotic cell or cell line cultured as a unicellular entity that may be, or has been, used as a recipient for a recombinant vector or other transfer of polynucleotides, and includes the progeny of the original cell that has been transfected. It is understood that the progeny of a single cell may not necessarily be completely identical in morphology or in genomic or total DNA complement as the original parent due to natural, accidental, or deliberate mutation.

In the context of immunoglobulins, the term "functional equivalent" refers to immunoglobulin molecules that exhibit immunological binding properties that are substantially similar to the parent immunoglobulin. As used herein, the term "immunological binding properties" refers to non-covalent interactions of the type which occur between an immunoglobulin molecule and an antigen for which the immunoglobulin is specific. Indeed, a functional equivalent of a monoclonal antibody immunoglobulin, for example, may inhibit the binding of the parent monoclonal antibody to its antigen. A functional equivalent may comprise F(ab')$_2$ fragments, F(ab) molecules, Fv fragments, single chain fragment variable displayed on phage (scFv), single domain antibodies, chimeric antibodies, or the like so long as the immunoglobulin exhibits the characteristics of the parent immunoglobulin.

As used herein, the term "isolated" refers to a polynucleotide, a polypeptide, an antibody, or a host cell that is in an environment different from that in which the polynucleotide, the polypeptide, the antibody, or the host cell naturally occurs. An isolated polynucleotide, polypeptide, antibody, or host cell is generally substantially purified.

As used herein, the term "substantially purified" refers to a compound that is removed from its natural environment and is at least about 60% to 99.9% free from other components, or is at least about 60% free, at least about 65% free, at least about 70% free, at least about 75% free, at least about 80% free, at least about 83% free, at least about 85% free, at least about 88% free, at least about 90% free, at least about 91% free, at least about 92% free, at least about 93% free, at least about 94% free, at least about 95% free, at least about 96% free, at least about 97% free, at least about 98% free, at least about 99% free, at least about 99.9% free, or at least about 99.99% free from other components with which it is naturally associated. For example, a composition containing A is "substantially free of" B when at least about 85% by weight of the total A+B in the composition is A. Alternatively, A comprises at least about 90% by weight of the total of A+B in the composition, further still, at least about 95% or even 99% by weight.

"Diagnosis," as used herein, generally includes a determination of a subject's susceptibility to a disease or disorder, a determination as to whether a subject is presently affected by a disease or disorder, a prognosis of a subject affected by a disease or disorder (e.g., identification of pre-metastatic or metastatic cancerous states, stages of cancer, or responsiveness of cancer to therapy), and therametrics (e.g., monitoring a subject's condition to provide information as to the effect or efficacy of therapy).

The term "biological sample" encompasses a variety of sample types obtained from or originating from an organism which may be used in diagnostic, monitoring, or other assays. The term encompasses blood, serum, plasma, cells, proteins, carbohydrates, nucleic acids, urine, nasal secretions, mucosal secretions, cellular fluid, cellular exudate and other liquid samples of biological origin, solid tissue samples such as a biopsy specimen, or tissue cultures or cells derived therefrom and the progeny thereof. The term specifically encompasses a clinical sample, and further includes cells in cell culture, cell supernatants, cell lysates, amniotic fluid, biological fluids, and tissue samples. The term also encompasses samples that have been manipulated in any way after procurement such as treatment with reagents, solubilization, or enrichment for certain components. The biological sample can be derived from the organism directly or can be collected from the environment.

The terms "individual," "subject," "host," and "patient" refer to any subject for whom diagnosis, treatment, or therapy is desired. In one embodiment, the individual, subject, host, or patient is a human. Other subjects may include, but are not limited to, animals including but not limited to, cattle, sheep, horses, dogs, cats, guinea pigs, rabbits, rats, primates, opossums and mice. Other subjects include species of bacteria, phages, cell cultures, viruses, plants and other eucaryotes, prokaryotes and unclassified organisms.

The terms "treatment," "treating," "treat," and the like are used herein to refer generally to obtaining a desired pharmacological and/or physiological effect. The effect may be prophylactic in terms of completely or partially preventing a disease or symptom thereof and/or may be therapeutic in terms of a partial or complete stabilization or cure for a disease and/or adverse effect attributable to the disease. "Treatment" as used herein covers any treatment of a disease in a subject, particularly a human, and includes: (a) preventing the disease or symptom from occurring in a subject which may be predisposed to the disease or symptom, but has not yet been diagnosed as having it; (b) inhibiting the disease symptom, i.e., arresting its development; or (c) relieving the disease symptom, i.e., causing regression of the disease or symptom.

The expression "therapeutically effective amount" refers to an amount of, for example, a compound disclosed herein, that is effective for preventing, ameliorating, treating or delaying the onset of a disease or condition.

A "prophylactically effective amount" refers to an amount of, for example, a compound disclosed herein that is effective for preventing a disease or condition.

A "liposome" is a small vesicle composed of various types of lipids, phospholipids and/or surfactant, which is useful for delivery of a drug to a subject, such as a mammal or other animal. The compounds of the present invention may be delivered by a liposome. The components of the liposome are commonly arranged in a bilayer formation, similar to the lipid arrangement of biological membranes. Liposome formulations, loading of liposomes and administration and delivery of liposomes are known in the art.

"Hybridization," broadly defined, refers to any process by which a polynucleotide sequence binds to a complementary sequence through base pairing. Hybridization conditions can be defined by, for example, the concentrations of salt or formamide in the prehybridization and hybridization solutions, or by the hybridization temperature, and are well known in the art. Hybridization can occur under conditions of various stringency. Hybridization may also refer to the binding of a protein-capture agent to a target protein under certain conditions, such as normal physiological conditions.

As understood herein, the term "activation" refers to any alteration of a signaling pathway or biological response including, for example, increases above basal levels, restoration to basal levels from an inhibited state, and stimulation of the pathway above basal levels.

The term "biological activity" refers to the biological behavior and effects of a protein or peptide. The biological activity of a protein may be affected at the cellular level and the molecular level. For example, an antisense oligonucleotide may prevent translation of a particular mRNA, thereby inhibiting the biological activity of the protein encoded by the mRNA. In addition, an antibody may bind to a particular protein and inhibit that protein's biological activity.

The term "oligonucleotide" as used herein refers to a polynucleotide sequence comprising, for example, from about 4 nucleotides (nt) to about 1000 nt. Oligonucleotides for use in the present invention are preferably from about 15 nt to about 150 nt, more preferably from about 150 nt to about 1000 nt in length. The oligonucleotide may be a naturally occurring oligonucleotide or a synthetic oligonucleotide. Oligonucleotides may be prepared by the phosphoramidite method (Beaucage and Carruthers, TETRAHEDRON LETT. (1981) 22:1859–1862), or by the triester method (Matteucci et al., J. AM. CHEM. SOC. (1981) 103:3185), or by other chemical methods known in the art.

The term "microarray" refers generally to the type of genes or proteins represented on a microarray by oligonucleotides (polynucleotide sequences) or protein-binding agents, and where the type of genes or proteins represented on the microarray is dependent on the intended purpose of the microarray (e.g., to monitor expression of human genes or proteins). The oligonucleotides or protein-binding agents on a given microarray may correspond to the same type, category, or group of genes or proteins. Genes or proteins may be considered to be of the same type if they share some common characteristics such as species of origin (e.g., human, mouse, rat); disease state (e.g., cancer); function (e.g., protein kinases, tumor suppressors); same biological process (e.g., apoptosis, signal transduction, cell cycle regulation, proliferation, differentiation). For example, one microarray type may be a "cancer microarray" in which each of the microarray oligonucleotides or protein-binding agents correspond to a gene or protein associated with a cancer. An "epithelial microarray" may be a microarray of oligonucleotides or protein-binding agents corresponding to unique epithelial genes or proteins. Similarly, a "cell cycle microarray" may be an microarray type in which the oligonucleotides or protein-binding agents correspond to unique genes or proteins associated with the cell cycle.

The term "detectable", one in sense, refers to a polynucleotide expression pattern which is detectable via the standard techniques of polymerase chain reaction (PCR), reverse transcriptase (RT)-PCR (RT-PCR), differential display, and Northern analyses, which are well known to those of skill in the art. Similarly, polypeptide expression patterns may be "detected" via standard techniques including immunoassays such as Western blots. In general, the term "detectable is used when a result of an action, such as addition of a compound in an assay step, is observable, particularly by physical means, such as a color change.

A "target gene" refers to a polynucleotide, often derived from a biological sample, to which an oligonucleotide probe is designed to specifically hybridize. It is either the presence or absence of the target polynucleotide that is to be detected, or the amount of the target polynucleotide that is to be quantified. The target polynucleotide has a sequence that is complementary to the polynucleotide sequence of the corresponding probe directed to the target. The target polynucleotide may also refer to the specific subsequence of a larger polynucleotide to which the probe is directed or to the overall sequence (e.g., gene or mRNA) whose expression level it is desired to detect.

A "target protein" refers to an polypeptide, often derived from a biological sample, to which a protein-capture agent specifically hybridizes or binds. It is either the presence or absence of the target protein that is to be detected, or the amount of the target protein that is to be quantified. The target protein has a structure that is recognized by the corresponding protein-capture agent directed to the target. The target protein or amino acid may also refer to the specific substructure of a larger protein to which the protein-capture agent is directed or to the overall structure (e.g., gene or mRNA) whose expression level it is desired to detect.

The term "complementary" refers to the topological compatibility or matching together of the interacting surfaces of a probe molecule and its target. The target and its probe can be described as complementary, and furthermore, the contact surface characteristics are complementary to each other. Hybridization or base pairing between nucleotides or nucleic acids, such as, for example, between the two strands of a double-stranded DNA molecule or between an oligonucleotide probe and a target are complementary.

The term "background" refers to non-specific binding or other interactions between, for example, polynucleotides, polypeptides, small molecules and polypeptides, or small molecules and polynucleotides. "Background" may also refer to the non-specific binding or other interactions in the context of assays including immunoassays.

In the context of microarrays, the term "background" refers to hybridization signals resulting from non-specific binding, or other interactions, between the labeled target polynucleotides and components of the oligonucleotide microarray (e.g., the oligonucleotide probes, control probes, the microarray support) or between target proteins and the protein-binding agents of a protein microarray. Background signals may also be produced by intrinsic fluorescence of the microarray components themselves. A single background signal may be calculated for the entire microarray, or a different background signal may be calculated for each target polynucleotide or target protein. The background may be calculated as the average hybridization signal intensity, or where a different background signal is calculated for each target gene or target protein. Alternatively, background may be calculated as the average hybridization signal intensity produced by hybridization to probes that are not complementary to any sequence found in the sample (e.g., probes directed to polynucleotides of the opposite sense or to genes not found in the sample such as bacterial genes where the sample is mammalian polynucleotides). The background can also be calculated as the average signal intensity produced by regions of the microarray which lack any probes or protein-binding agents at all.

A "small molecule" comprises a compound or molecular complex, either synthetic, naturally derived, or partially synthetic, composed of carbon, hydrogen, oxygen, and nitrogen, which may also contain other elements, and which may have a molecular weight of less than about 100 to about 15,000 Daltons, or less than about 15,000, less than about 14,000, less than about 13,000, less than about 12,000, less than about 11,000, less than about 10,000, less than about 9,000, less than about 8,000, less than about 7,000, less than about 6,000, less than about 5,000, less than about 4,000, less than about 3,000, less than about 2,000, less than about 1,000, less than about 900, less than about 800, less than about 700, less than about 600, less than about 500, less than about 400, less than about 300, less than about 200, or less than about 100.

The term "fusion protein" refers to a protein composed of two or more polypeptides that, although typically not joined in their native state, are joined by their respective amino and carboxyl termini through a peptide linkage to form a single continuous polypeptide. It is understood that the two or more polypeptide components can either be directly joined or indirectly joined through a peptide linker/spacer.

The term "normal physiological conditions" means conditions that are typical inside a living organism or a cell. Although some organs or organisms provide extreme conditions, the intra-organismal and intra-cellular environment normally varies around pH 7 (i.e., from pH 6.5 to pH 7.5), contains water as the predominant solvent, and exists at a temperature above 0° C. and below 50° C. The concentration of various salts depends on the organ, organism, cell, or cellular compartment used as a reference.

The term "cluster" refers to a group of clones or biomolecular sequences related to one another by sequence homology. In one example, clusters are formed based upon a specified degree of homology and/or overlap (e.g., stringency). "Clustering" may be performed with the sequence data. For instance, a biomolecular sequence thought to be associated with a particular molecular or biological activity in one tissue might be compared against another library or database of sequences. This type of search is useful to look for homologous, and presumably functionally related, sequences in other tissues or samples, and may be used to streamline the methods of the present invention in that clustering may be used within one or more of the databases to cluster biomolecular sequences prior to performing a method of the invention. The sequences showing sufficient homology with the representative sequence are considered part of a "cluster." Such "sufficient" homology may vary within the needs of one skilled in the art.

As used herein, the term "internal database" refers to a database maintained within a local computer network. It contains, for example, biomolecular sequences associated with a project. It may also contain information associated with sequences including, but not limited to, a library in which a given sequence is found and descriptive information about a likely gene associated with the sequence. The internal database may typically be maintained as a private database behind a firewall within an enterprise network. However, the invention is not limited to only this embodiment and an internal database could be made available to the public. The internal database may include sequence data generated by the same enterprise that maintains the database, and may also include sequence data obtained from external sources.

The term "external database," as understood herein, refers to a database located outside all internal databases. Typically, an enterprise network differing from the enterprise network maintaining the internal database will maintain an external database. The external database may be used, for example, to provide some descriptive information on biomolecular sequences stored in the internal database. In one embodiment, the external database is GenBank and associated databases maintained by the National Center for Biotechnology Information (NCBI), part of the National Library of Medicine.

As used herein and in the appended claims, the singular forms "a," "an," and "the" include plural reference unless the context clearly indicates otherwise. Thus, for example, reference to a "compound" is a reference to one or more such compounds and includes equivalents thereof known to those skilled in the art, and so forth.

Unless defined otherwise, all technical and scientific terms used herein have the same meaning as commonly understood to one of ordinary skill in the art to which this invention belongs. Although any methods, devices, and materials similar or equivalent to those described herein can be used in the practice or testing of the invention, the preferred methods, devices and materials are now described.

All publications and patents mentioned herein are incorporated herein by reference for the purpose of describing and disclosing, for example, the constructs and methodologies that are described in the publications, which might be used in connection with the presently described invention. The publications discussed above and throughout the text are provided solely for their disclosure prior to the filing date of the present application. Nothing herein is to be construed as an admission that the inventors are not entitled to antedate such disclosure by virtue of prior invention.

It is to be understood that this invention is not limited to the particular methodology, protocols, cell lines, constructs, and reagents described herein and as such may vary. It is also to be understood that the terminology used herein is for the purpose of describing particular embodiments only, and is not intended to limit the scope of the present invention which will be limited only by the appended claims.

EXAMPLES

The present invention is further illustrated by the following examples, which are not to be construed in any way as imposing limitations upon the scope thereof, but rather are illustrative only. On the contrary, it is to be clearly understood that resort may be had to various other embodiments, modifications, and equivalents thereof which, after reading the description herein, may suggest themselves to one of ordinary skill in the art without departing from the spirit of the present invention or the scope of the appended claims.

The following acronyms, abbreviations, terms and definitions have been used throughout the experimental section. Acronyms or abbreviations: DIEA (N,N-diisopropylethylamine), THF (tetrahydrofuran), HPLC (high performance liquid chromatography), TLC (thin layer chromatography), mp (melting point), rt (room temperature), aq (aqueous), min (minute), h (hr, hour), atm (atmosphere), conc. (concentrated), MS (mass spectroscopy/spectrometry), NMR (nuclear magnetic resonance), $R_f$ (TLC retention factor), and $R_t$ (HPLC retention time). NMR abbreviations: br (broad), apt (apparent), s (singlet), d (doublet), t (triplet), q (quartet), dq (doublet of quartets), dd (doublet of doublets), dt (doublet of triplets), m (multiplet).

Example 1

General Synthetic, Purification, Characterization, and Spectroscopic Procedures

General Synthetic Procedures. Room temperature is defined as an ambient temperature range, typically 20–25° C. An ice bath (crushed ice/water) temperature is defined as a range, typically −5 to 0° C. Temperature at reflux is defined as ±15° C. of the boiling point of the primary reaction solvent. Overnight is defined as a time range of 8–16 hours. Vacuum filtration (water aspirator) is defined as range of 5–15 mm Hg. Dried under vacuum is defined as using a high vacuum pump as a range of 0.1–5 mm Hg. Neutralization is defined as a typical acid-based neutralization method and measured to a pH 6–8 range using pH-indicating paper. Brine is defined as a saturated aqueous sodium chloride. Nitrogen atmosphere is defined as positive static pressure of nitrogen gas passed through a Drierite column with an oil bubbler system. Concentrated ammonium hydroxide is defined as an approximately 15 M solution.

All eluents for column or thin layer chromatography were prepared and reported as volume:volume (v:v) solutions, and HPLC eluent ratios are v:v ratios. Aqueous sodium hydroxide or sodium bicarbonate solutions were prepared as weight:volume (w:v) ratios. Aqueous hydrochloric acid solutions were prepared as v:v ratios.

The quantities of solvents and/or reagents used for reaction work-up or product isolation are those typically used by one trained in the art of organic chemical synthesis, and the quantity of these solvents and/or reagents used is determined based upon synthetic experience and appropriateness to the specific reaction. For example: 1) crushed ice quantity ranged from about 10–1000 g depending on reaction scale, 2) silica gel quantity used in column chromatography depended on material quantity, complexity of mixture, and size of chromatography column employed and ranged from about 5–1000 g, 3) extraction solvent volume ranged from about 10–500 mL depending on reaction size, 4) washes employed in compound isolation ranged from about 10–100 mL of solvent or aq reagent depending on scale of reaction 5) drying reagents (potassium carbonate, sodium carbonate or magnesium sulfate) ranged from about 5–100 g depending on the amount of solvent to be dried and its water content.

Melting points were measured against a mercury thermometer and are not corrected.

For column chromatography employing concentrated ammonium hydroxide as part of the mobile phase, the fractions collected from the column were dried over sodium sulfate, potassium carbonate or a mixture of both. Then the organic layer was filtered by gravity or vacuum to remove the drying agent prior to concentration/evaporation.

Flash Chromatography. In the Tables, "ISCO" indicates purification by flash chromatography as follows. Instrument: ISCO CombiFlashä Si 10x. Column: ISCO RediSep ä—Disposable Columns for Flash Chromatography (10 g of silica gel—normal phase—35–60 micron particle size (230–400 mesh)). Mobile Phase A: $CH_2Cl_2$; Mobile Phase B: 10% $NH_4OH$ in MeOH; Gradient: 0–10% B in 22 min, hold 10% B for 18 min; Fractions: 30 fractions collected per column, 1.5 min each. Flow rate: 8.93 mL/min. The salient fractions were analyzed by MS and TLC (90:9:1 $CH_2Cl_2$:MeOH:$NH_4OH$—$R_f$ range 0.15–0.45) and combined in barcoded, tared vials. The resulting solutions were sampled for LC/MS analysis, concentrated in vacuo and their masses and yields were determined as tabulated in the Tables.

If no additional purification was carried out after completion of the Parallel Synthesis, this is indicated as "None" in Table 2.

Analytical HPLC Procedures. Analytical HPLC procedures were carried out according in one of two specific methods, depending upon availability of instrumentation and sample requirements, as follows.

HPLC Method A. Column: Thomson Inst. Co. 4.6×50 mm C18 5 µm 60 A; Mobile Phase A: $H_2O$ with 0.1% TFA; Mobile Phase B: $CH_3CN$ with 0.1% TFA; Detection: UV 254 nm. Gradient 1: ELSD12MG; 10–90% B in 10 min, hold 90% B for 5 min; Flow: 1.0 mL/min. Gradient 2: ELSD5MG; 15–100% B in 5 min, hold 100% B for 3 min; Flow—2.0 mL/min.

HPLC Method B. Column: Thomson Inst. Co. 21×50 mm C18 5 µm 60 A; Mobile Phase A: $H_2O$ with 0.1% TFA; Mobile Phase B: $CH_3CN$ with 0.1% TFA; Detection: UV 254 nm. Gradient 1: MIC8MG; 0–100% B in 8 min, hold 100% B for 2 min; Flow: 0.5 mL/min. Gradient 2: MIC15MG; 10–90% B in 15 min, hold 90% B for 3 min; Flow: 0.5 mL/min.

Preparative HPLC Procedures. Preparative HPLC was carried as follows. Instrument: Gilson; Column: Thomson Inst. Co. 21.5×150 mm C18 5 µm 60 A; Mobile Phase A: $H_2O$; Mobile Phase B: $CH_3CN$; Gradient: 15–100% B in 10 min, hold 100% B for 5 min; Flow rate: 22 mL/min; Detection: UV 254 nm. The fractions containing the desired compounds were collected in barcoded, tared vials, sampled for LC/MS analysis, concentrated in vacuo and their masses and yields were determined as shown in the Tables.

Spectroscopic and other Instrumental Procedures.

NMR. The $^1H$ and $^{13}C$ NMR spectra described herein were obtained using Varian INOVA600 (600 MHz), Varian UNITY600 (600 MHz), or Varian 400 (400 MHz) spectrometers. Spectrometer field strength and NMR solvent used for a particular sample are indicated in the Examples, or on any NMR spectra actually shown as Figures. Typically, $^1H$ NMR chemical shifts are reported as δ values in parts per million (ppm) downfield from tetramethylsilane (TMS) (δ=0 ppm) as an internal standard, and $^{13}C$ NMR chemical shifts are reported in ppm downfield from TMS and referenced with respect to the $CDCl_3$ signal center line (δ=77.0 ppm). Solid or liquid samples were dissolved in an appropriate NMR solvent ($CDCl_3$ or DMSO-$d_6$), placed in a NMR sample tube, and data were collected according to the spectrometer instructional manuals. Most samples were analyzed in Variable Temperature mode, typically at about 55° C., though some data for some samples were collected with the probe at ambient temperature. NMR data were processed using NUTS: NMR Utility Transform Software (Lite Version-20011128) by Acorn NMR.

LC-MS. The Liquid Chromatography-Mass Spectrometry (LC-MS) instrumentation used to examine the compounds of the present invention was typically a quadrupole/time-of-flight mass spectrometer, with electrospray ionization (ESI). For example, the typical LC-MS instrumentation used was a Micromass Q-Tof using electrospray ionization (ESI). This instrument is a quadrupole/time-of-flight mass spectrometer capable of mass resolution up to m/z of about 7500. Samples were introduced in a direct injection mode by first dissolving and diluting the sample in methanol or acetonitrile and injecting the sample solution into the ESI source via a 10 µL loop Rheodyne injection valve. The carrier solvent was typically a mixture of 70% $CH_3CN$ or MeOH and 30% $H_2O$ (v:v), containing about 0.1% formic acid. Accurate mass analyses were performed in a similar fashion except for using a multipoint mass calibration with the same instrument under high mass resolution conditions. Samples were spiked with an appropriate internal mass reference compound, as known by one of ordinary skill, and analyzed as described above.

Example 2

General Methods for Parallel Synthesis

Examples 3–5 describe the synthetic procedures for the preparation of the "library" of $N^2,N^4,N^6$-tris(amino)-1,3,5-triazines which was prepared based on the strategy of changing only one pendant amino group per synthesis, and based on the parent structure 95 shown below, where each compound in the library contains two of the pendant groups in 95.

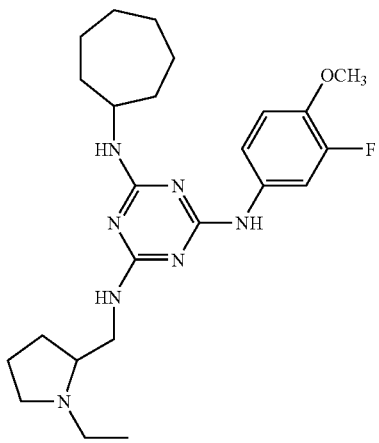

The library was divided into three subgroups, and all three subgroups are presented in Table 2. Library I (compounds 1–50) includes compounds having unchanged cycloheptylamino and [(1-ethyl-2-pyrrolidinyl)methyl]amino substituents, with various groups being permuted at the remaining triazine amino position, prepared by Method A as presented in Example 3. Library II (compounds 51–75) includes compounds having unchanged [(1-ethyl-2-pyrrolidinyl)methyl]amino and (3-fluoro-4-methoxyphenyl)amino substituents, with various groups being permuted at the remaining triazine amino position, prepared by Method B as presented in Example 4. Library III (Compounds 76–100) includes compounds having unchanged (3-fluoro-4-methoxyphenyl)amino and cycloheptylamino substituents, with various groups being permuted at the remaining triazine amino position, prepared by Method C as described in Example 5. Thus, the combination of the specific amines employed produced a library of compounds of novel composition. The sequence in which each monomer is added to form the compounds of the library is also presented in Table 2, because the Monomer 1 amine is added first, Monomer 2 amine added second, and Monomer 3 amine is added third.

Example 3

Parallel Synthetic Method A, for Library I Compounds

The following reaction scheme presents the general reagents and conditions for parallel synthetic method A used for the compounds of Table 2 which designate Method A.

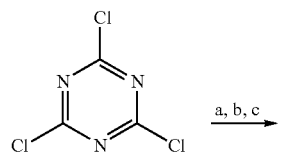

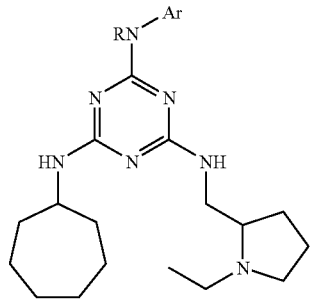

Reagents and conditions: (a) ArNHR, DIEA, CH$_3$CN/1,4-dioxane, −11 C., 1 h (b) cycloheptylamine, DIEA, CH$_3$CN/1,4-dioxane, rt, overnight (c) 2-(aminomethyl)-1-ethylpyrrolidine, DIEA, CH$_3$CN/1,4-dioxane, 80 C., 15

A stock solution of cyanuric chloride (0.542 M) in 1,4-dioxane was prepared and 1 mL of this solution (containing 100 mg or 0.542 mmol) was dispensed into each of 50 barcoded 40 mL vials. These solutions were cooled to about −11° C. (freezing) using a J-KEM block connected to a circulating cooler. Meanwhile, individual solutions of each aryl amine ArNHR (specified as Monomer 1 in Table 2, 0.542 mmol) and disopropylethylamine (DIEA) (77 mg/104 μL, 0.596 mmol) in 1 mL of CH$_3$CN were prepared. (For HCl salts, 204 μL DIEA (approx. 2.1 equiv) was used.) Over a period of about 1 h, the amine/DIEA solutions were added to the corresponding frozen cyanuric chloride solutions, one by one, with swirling. The resulting solutions were then shaken at about −11° C. for about 1 h and the reaction block was allowed to warm to room temperature over the next hour. The resulting 2-amino-4,6-dichlorotriazine solutions were carried to the next step without purification.

A stock solution of cycloheptylamine (1.08 M) and DIEA (1.19 M) in CH$_3$CN was prepared and 0.5 mL (containing 61 mg/69 μL, 0.542 mmol amine and 77 mg/104 μL, 0.596 mmol DIEA) was dispensed into each of the 40 mL vials from the first step. The vials were shaken on the J-KEM. block overnight at room temperature and placed in a freezer (about −14° C.) without purification until the next reaction.

A stock solution of 2-(aminomethyl)-1-ethylpyrrolidine (1.08 M) and DIEA (1.19 M) in CH$_3$CN was prepared and 0.5 mL (containing 69 mg/79 μL, 0.542 mmol amine and 77 mg/104 μL, 0.596 mmol DIEA) was dispensed into each of the 40 mL from the second step. The vials were then shaken on the J-KEM block at about 80° C. for about 15 h. The solutions were cooled to room temperature and taken to dryness in vacuo. The residues were then extracted with ethyl acetate and the extract was washed with brine. The aqueous layers were extracted a second time with ethyl acetate and the combined organic layers were dried over Na$_2$SO$_4$ and passed through a plug of Celite™ into barcoded, tared vials. After concentration in vacuo, masses were determined and yields were calculated, and the compounds were sampled for LC/MS analysis.

Example 4

Parallel Synthetic Method B, for Library II Compounds

The following reaction scheme presents the general reagents and conditions for parallel synthetic method B, used for the compounds of Table 2 which designate Method B.

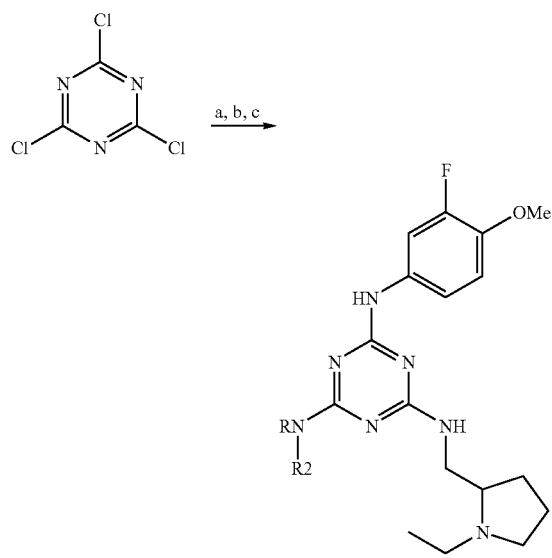

Reagents and conditions: (a) 3-fluoro-p-anisidine, DIEA, CH₃CN/1,4-dioxane, −20 C., 1 h (b) R₂NHR, DIEA, CH₃CN/1,4-dioxane, rt, overnight (c) 2-(aminomethyl)-1-ethylpyrrolidine, DIEA, CH₃CN/1,4-dioxane, 80 C, 15

In an oven-dried round bottom flask, a solution of cyanuric chloride (5.0 g, 27.1 mmol) in 1,4-dioxane (40 mL) was cooled to freezing in a CH₃CN/dry ice bath. To this frozen solution was added 40 mL of CH₃CN, followed by DIEA (3.85 g/5.19 mL, 29.8 mmol). A solution of 3-fluoro-p-anisidine (3.83 g, 27.1 mmol) in 10 mL of CH₃CN was then added slowly via syringe. The reaction mixture was stirred at about −20° C. for about 1 h and allowed to warm to room temperature over about 1 h. The resulting 2-amino-4,6-dichlorotriazine solution was carried to the next step without purification.

Fifty mL (13.5 mmol) of the prepared (4,6-dichloro-[1,3,5]triazin-2-yl)-(3-fluoro-4-methoxy-phenyl) amine solution was divided equally (2 mL or 0.54 mmol each) among 25 barcoded, 40 mL scintillation vials. Individual solutions of each R₂NHR amine (where R₂ indicates Monomer 2 in Table 2, 0.542 mmol) and DIEA (77 mg/104 VL, 0.596 mmol) in 0.5 mL of CH₃CN were prepared and added to the correspondingly labeled 40 mL vials. The resulting solutions were shaken on the J-KEM block overnight at room temperature and then placed in a freezer (about −14° C.) without purification until the next reaction.

A stock solution of 2-(aminomethyl)-1-ethylpyrrolidine (1.08 M) and DIEA (1.19 M) in CH₃CN was prepared and 0.5 mL (containing 69 mg/79 µL, 0.542 mmol amine and 77 mg/104 µL, 0.596 mmol DIEA) was dispensed into each of the 40 mL vials from the second step. The vials were shaken on the J-KEM block at about 80° C. for about 15 h. The solutions were cooled to room temperature and concentrated in vacuo. The residues were then extracted with ethyl acetate and the extract washed with brine. The aqueous layers were extracted a second time with ethyl acetate and the combined organic layers were dried over Na₂SO₄ and passed through a plug of Celite™ into barcoded, tared vials. After concentration in vacuo, masses were calculated and the compounds were sampled for LC/MS analysis.

Example 5

Parallel Synthetic Method C, for Library III Compounds

The following reaction scheme presents the general reagents and conditions for parallel synthetic method C, used for the compounds of Table 2 which designate Method C.

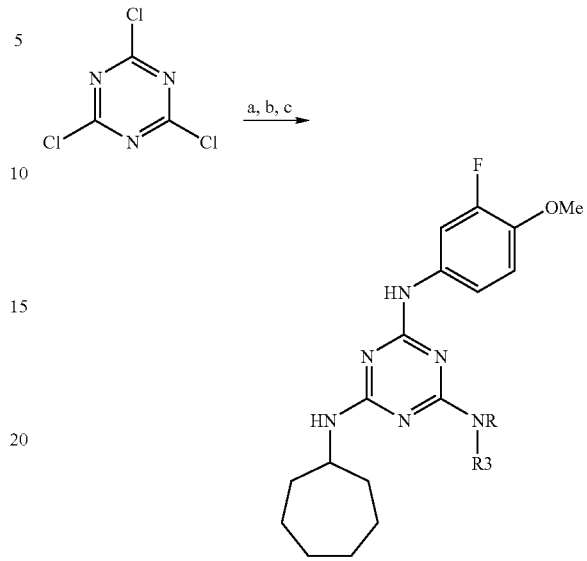

Reagents and conditions: (a) 3fluoro-p-anisidine, DIEA, CH₃CN/1,4-dioxane, −20 C., 1 h (b) cycloheptylamine, DIEA, CH₃CN/1,4-dioxane, rt, overnight (c) R₃NHR, DIEA, CH₃CN/1,4-dioxane, 80 C, 15

In an oven-dried round bottom flask, a solution of cyanuric chloride (5.0 g, 27.1 mmol) in 1,4-dioxane (40 mL) was cooled to freezing in a CH₃CN/dry ice bath. To this frozen solution was added 40 mL of CH₃CN, followed by DIEA (3.85 g/5.19 mL, 29.8 mmol). A solution of 3-fluoro p-anisidine (3.83 g, 27.1 mmol) in 10 mL of CH₃CN was then added slowly via syringe. The reaction mixture was stirred at about −20° C. for about 1h and allowed to warm to room temperature over 1 h. The resulting 2-amino-4,6-dichlorotriazine solution was carried to the next step without purification.

Fifty mL (13.5 mmol) of the prepared (4,6-dichloro-[1,3,5]triazin-2-yl)-(3-fluoro-4-methoxy-phenyl) amine solution was treated with a solution of cycloheptylamine (1.53 g/1.73 mL, 13.5 mmol) and DIFA (1.93 g/2.60 mL, 14.9 mmol) in CH₃CN (8 mL). The resulting solution was stirred overnight at room temperature and carried to the next step without purification.

The resulting 6-chloro-N-cycloheptyl-N'-(3-fluoro-4-methoxy-phenyl)-[1,3,5]triazine-2,4-diamine solution (13.5 mmol) was diluted up to 62.5 mL with CH₃CN and divided equally (2.5 mL or 0.54 mmol each) between 25 barcoded 40 mL scintillation vials. Individual solutions of each R₃NHR (where R₃ amine indicates Monomer 3 in Table 2, 0.542 mmol) and DIEA (77 mg/104 µL, 0.596 mmol) in 0.5 mL of CH₃CN were prepared and added to the correspondingly labeled 40 mL vial. The resulting solutions were shaken on the J-KEM block at about 80° C. for about 15 h. The solutions were cooled to room temperature and concentrated in vacuo. The residues were then extracted with ethyl acetate and the extract washed with brine. Each organic layer was dried over Na₂SO₄ and passed through a plug of Celite™ into a barcoded, tared vial. After concentration in vacuo, masses were calculated and the compounds were sampled for LC/MS analysis.

Example 6

Synthesis of 6-Chloro-N-(3-chloro-4-methoxy-phenyl)-N'-cyclohexylmethyl-[1,3,5]triazine-2,4-diamine (102)

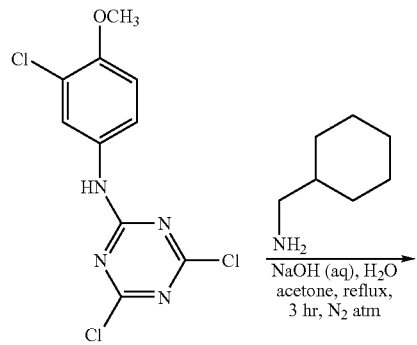

101

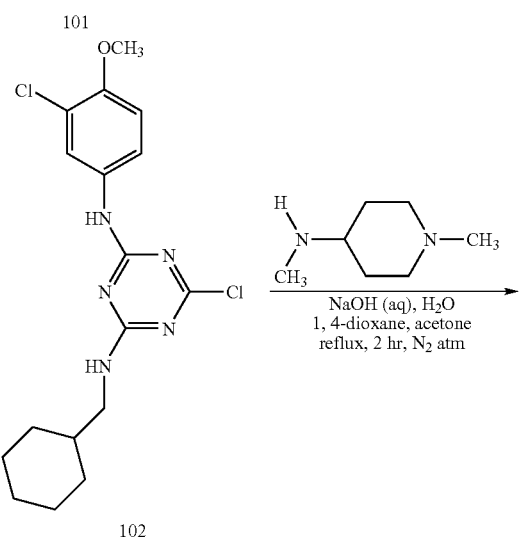

102

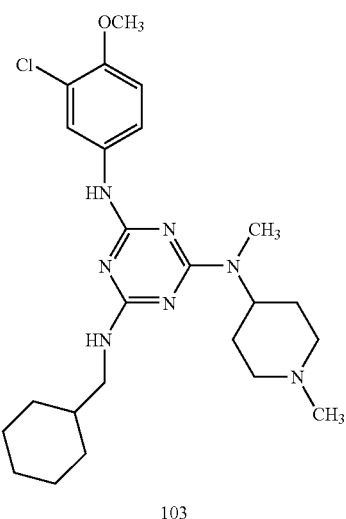

103

To a sample of 101 (0.3004 g, 1.0 mmol, prepared as indicated herein) dissolved in acetone (4 mL) was added a solution of cyclohexanemethylamine (0.13 mL, 1.0 mmol) in acetone (1 mL) followed by addition of a NaOHl solution (0.0448 g, 1.0 mmol dissolved in 1 mL of H₂O). The reaction mixture was allowed to stir at reflux for about 3 hours. The reaction mixture was then poured over crushed ice and neutralized with 10% HCl (aq) and 5% NaOH (aq). The resulting solid was collected by vacuum filtration, washed with water and dried overnight under vacuum to afford compound 102 (0.29 g, 76% recovery).

Example 7

Synthesis of N-(3-Chloro-4-methoxy-phenyl)-N'-cyclohexylmethyl-N''-methyl-N''-(1-methyl-piperidin-4-yl)-[1,3,5]triazine-2,4,6-triamine (103)

To a sample of 102 (0.286 g, 1.0 mmol) dissolved in 1,4-dioxane (4 mL) was added a solution of N-methyl-4 (methylamino)piperidine (0.15 mL, 1.0 mmol) in acetone (1 mL) followed by addition of a NaOH solution (0.0462 g, 1.0 mmol dissolved in 1 mL of H₂O). The reaction mixture was allowed to stir at about 80° C. for about 2 hours. The reaction mixture was poured over crushed ice and neutralized with 10% HCl (aq). The resulting solid was collected by vacuum filtration, washed with water and dried under vacuum overnight. Column chromatography (silica gel, 96:3:1 dichloromethane:methanol:conc. ammonium hydroxide) yielded a light purple solid 103 (41 mg, 9%), mp 84° C.; HPLC: YMC Pack Pro C18, 40:30:30 [KH₂PO₄ (0.01M, pH 3.2): CH₃OH: CH₃CN], 264 nm, $R_t$ 12.7 min, 97% purity); $^1$H NMR (600 MHz, CDCl₃, 55° C.) δ 7.98 (s, 1H), 7.18 (S, 1H), 6.85 (d, J=9 Hz, 1H), 6.58 (s, 1H), 4.89 (s, 1H), 4.58–4.62 (m, 1H), 3.87 (s, 3H), 3.25 (t, J=6.6 Hz, 2H), 3.05 (s, 3H), 2.94 (d, J=11.4 Hz, 2H), 2.31 (s, 3H), 2.15 (S, 2H), 1.86 (dq, J=12,4.2 Hz, 3H), 1.57–1.78 (m, 8H), 1.15–1.30 (m, 4H), 1.00 (dq, J=11.4, 3 Hz, 2H); MS (ESI): m/z 476 (37.7), 474 (M+H, 100), 410 (1.4).

Example 8

Synthesis of 6-Chloro-N-(3-chloro-4-methoxy-phenyl)-N'-(1-propyl-butyl)-[1,3,5]triazine-2,4-diamine (104)

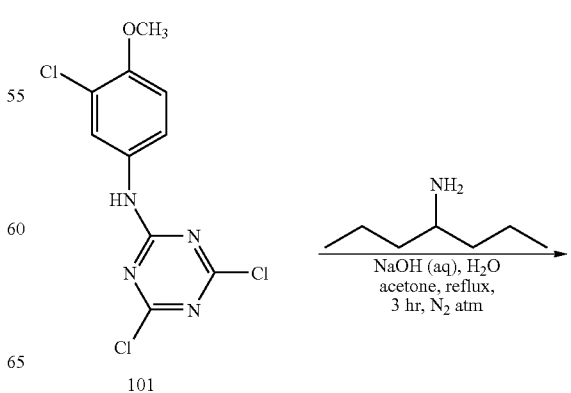

101

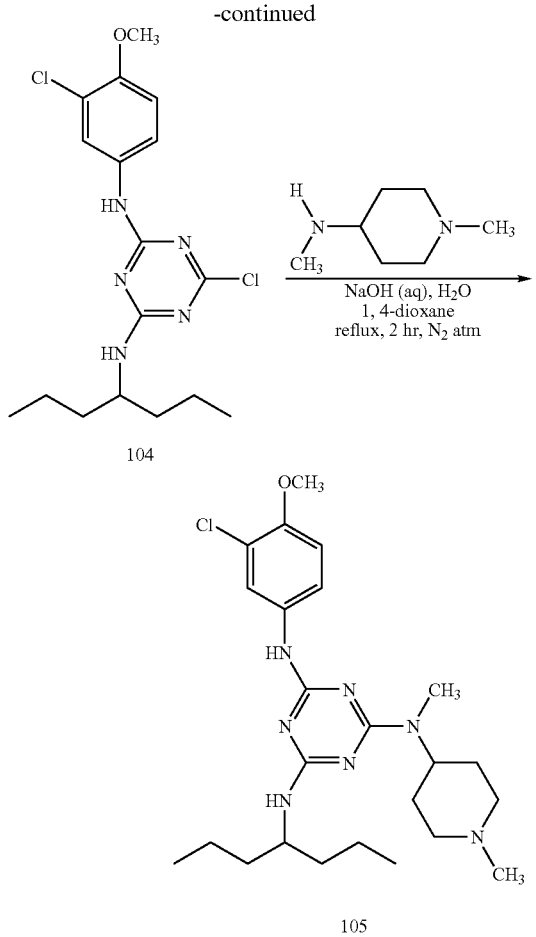

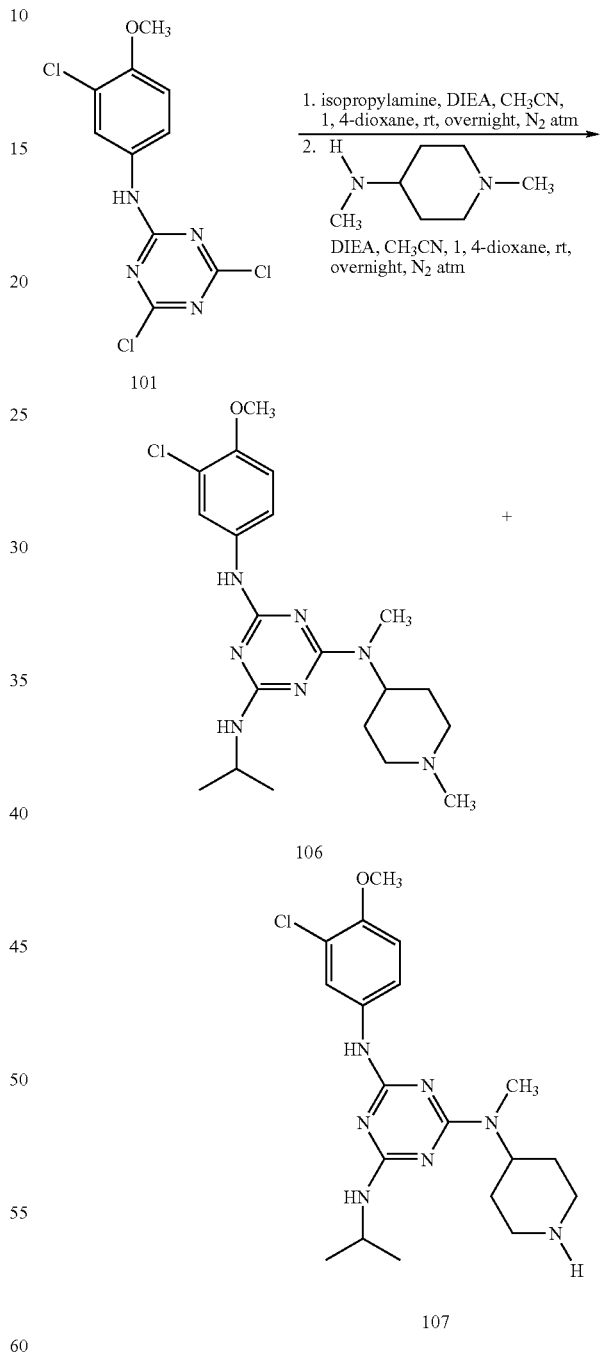

To a sample of 101 (0.3062 g, 1.0 mmol) dissolved in acetone (4 mL) was added a solution of 4-heptylamine (0.15 mL, 1.0 mmol) in acetone (1 mL) followed by addition of a NaOH solution (0.0410 g, 1 mmol dissolved in 1 mL of $H_2O$). The reaction mixture was allowed to stir at 30–50° C. for about 3 hours.

The reaction mixture was then poured over crushed ice and neutralized with 10% HCl (aq) and 5% NaOH (aq). The resulting solid was collected by vacuum filtration, washed with water and dried overnight under vacuum to afford 104 (0.363 g, 94% recovery).

Example 9

Synthesis of N-(3-Chloro-4-methoxy-phenyl)-N'-methyl-N'-(1-methyl-piperidin-4-yl)-N''-(1-propyl-butyl)-[1,3,5]triazine-2,4,6-triamine (105)

To a sample of 104 (0.363 g, 1.0 mmol) dissolved in 1,4-dioxane (6 mL) was added a solution of N-methyl-4 (methylamino)piperidine (0.15 mL, 1.0 mmol) in acetone (1 mL) followed by addition of a NaOH solution (0.0414 g, 1.0 mmol dissolved in 1 mL of $H_2O$). The reaction mixture was allowed to stir at about 80° C. for about 2 hours. The reaction mixture was poured over crushed ice and neutralized with 10% HCl (aq). The resulting solid was collected by vacuum filtration, washed with water and dried under vacuum overnight. Column chromatography (silica gel, 96:3:1 dichloromethane:methanol:conc. ammonium hydroxide) yielded light purple solid 105 (97 mg, 20%), mp 249° C. HPLC: YMC Pack Pro C18, 40:30:30 [$KH_2PO_4$ (0.01M, pH 3.2): $CH_3OH:CH_3CN$], 264 nm, $R_t$ 14.4 min, 98% purity; MS (ESI): m/z 476 (M+H, 100), 412 (2.9), 366 (2.8), 239 (1.9).

Example 10

Synthesis of N-(3-Chloro-4-methoxy-phenyl)-N'-isopropyl-N''-methyl-N''-(1-methyl-piperidin-4-yl)-[1,3,5]triazine-2,4,6-triamine (106)

To a sample of 101 (0.6157 g, 2.0 mmol) dissolved in anhydrous 1,4-dioxane (15 mL) was added a solution of isopropylamine (0.17 mL, 2.0 mmol) in anhydrous acetonitrile (1 mL) followed by addition of a N,N-diisopropylethylamine (DIEA) (0.38 mL, 2.2 mmol) in anhydrous acetonitrile (1 mL). The reaction mixture was allowed to stir at room temperature overnight under nitrogen. To this mixture was added DIEA (0.38 mL, 2.2 mmol) in anhydrous acetonitrile (1 mL) followed by addition of N-methyl-4(methylamino)piperidine (0.29 mL, 2.0 mmol) in anhydrous acetonitrile (1 mL). The reaction mixture was allowed to stir at reflux overnight under nitrogen. The reaction mixture was extracted 3 times with ethyl acetate. The combined organic layers were washed one time with brine solution and dried over anhydrous potassium carbonate. The organic layer was concentrated on a rotary evaporator and allowed to dry overnight under vacuum. Column chromatography (silica gel, 93:6:1 $CH_2Cl_2$:$CH_3OH$:conc. $NH_4OH$) yielded light brown solid 106 (271 mg, 32%); TLC (silica gel, 93:6:1 $CH_2Cl_2$:$CH_3OH$:conc. $NH_4OH$), $R_f$ 0.28; HPLC: Inertsil ODS-3V C18, 40:30:30 [$KH_2PO_4$ (0.01M, pH 3.2): $CH_3OH$:$CH_3CN$], 264 nm, $R_t$ 4.4 min, 84.8% purity; MS (ESI): mn/z 422 (26), 420 (M+H, 71.2), 378 (4.2), 231 (100), 211 (40.4), 118 (5.4).

Example 11

Synthesis of $N^2$-(3-chloro-4-methoxy-phenyl)-$N^4$-isopropyl-$N^6$-metyl-$N^6$-piperidin-4-yl-], 3, 5-triazine-2,4,6-triamine (107)

Compound 107 was isolated (0.159 g) as a by-product via column chromatography (silica gel, 93:6:1 $CH_2Cl_2$:$CH_3OH$:conc. $NH_4OH$); mp 129° C.; TLC (silica gel, 93:6:1 $CH_2Cl_2$:$CH_3OH$:conc. $NH_4OH$), $R_f$ 0.14; HPLC: Inertsil ODS-3V C18, 40:30:30 [$KH_2PO_4$ (0.01 M, pH 3.2): $CH_3OH$:$CH_3CN$], 264 nm, $R_t$ 4.4 min, 93.5% purity; MS (ESI): m/z 408 (17.2), 406 (M+H, 46.6), 375 (18.5), 245 (11.9), 224 (100), 204 (13.4).

Example 12

Synthesis of 5-{4-(3-Chloro-4-methoxy-phenylamino)-6-[methyl-(1-methyl-piperidin-4-yl)-amino]-[1,3,5]triazin-2-ylamino}-pentan-1-ol (108)

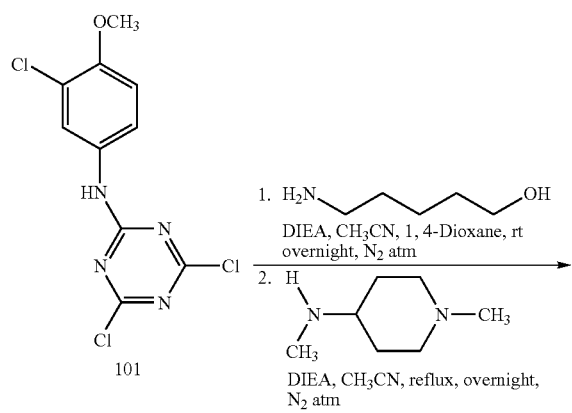

101

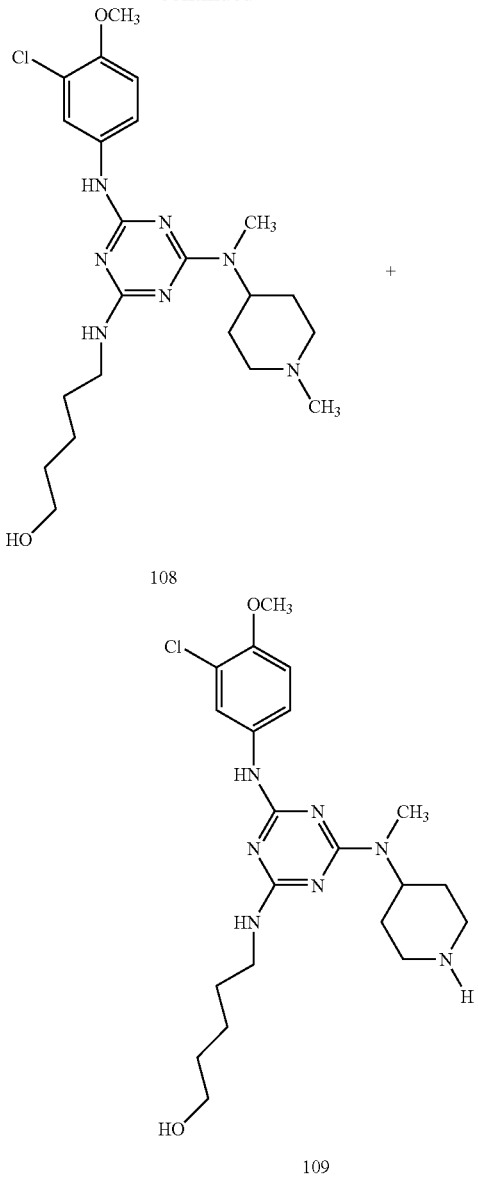

108

109

To a sample of 101 (1.5046 g, 5.0 mmol) dissolved in anhydrous 1,4-dioxane (30 mL) was added a solution of 5-amino-1-pentanol (0.5067 g, 5.0 mmol) in anhydrous acetonitrile (12 mL) followed by addition of N,N-diisopropylethylamine (DIEA) (0.95 mL, 5.5 mmol) in anhydrous acetonitrile (2 mL). The reaction mixture was allowed to stir at room temperature overnight under nitrogen. To the reaction mixture was added DIEA (0.95 mL, 5.5 mmol) in anhydrous acetonitrile (1 mL) followed by addition of N-methyl-4(methylamino)piperidine (0.73 mL, 5.0 mmol) in anhydrous acetonitrile (1 mL). The reaction mixture was allowed to stir at reflux overnight under nitrogen. The reaction mixture was extracted 3 times with ethyl acetate. The combined organic layers were washed one time with brine solution and dried over anhydrous potassium carbonate. The organic layer was concentrated on a rotary evaporator and allowed to dry overnight under vacuum. Column chromatography (silica gel, 90:9:1 $CH_2Cl_2$:$CH_3OH$:conc. $NH_4OH$) yielded light brown solid 108 (300 mg, 13%); TLC (silica gel, 90:9:1

CH$_2$Cl$_2$:CH$_3$OH:conc. NH$_4$OH), R$_f$ 0.22; HPLC: YMC Pack Pro C18, 40:30:30 [KH$_2$PO$_4$ (0.01M, pH 3.2): CH$_3$OH:CH$_3$CN], 264 nm, R$_t$ 3.5 min, 74.8% purity; MS (ESI): m/z 466 (24.2), 464 (M+H, 71.5), 378 (5.2), 253 (4.5), 244 (20.5), 233 (100), 216 (33.3), 196 (14.6), 118 (5.1).

Example 13

Synthesis of 5-[4-(3-chloro-4-methoxy-phenylamino)-6-(methyl-piperidin-4-yl-amino)-1,3,5-triazin-2-ylamino]-pentan-1-ol (109)

Compound 109 was isolated as a by-product (0.820 g) via column chromatography (silica gel, 90:9:1 CH$_2$Cl$_2$:CH$_3$OH:conc. NH$_4$OH), mp 101° C.; TLC (silica gel, 90:9:1 CH$_2$Cl$_2$:CH$_3$OH:conc. NOH), R$_f$ 0.08; HPLC: Inertsil ODS-3V C18, 40:30:30 [KH$_2$PO$_4$ (0.01M, pH 3.2): CH$_3$OH:CH$_3$CN], 264 nm, R$_t$ 3.6 min, 95.3% purity; MS (ESI): m/z 452 (13), 450 (M+H, 35.6), 419 (3.9), 267 (5.1), 246 (100), 226 (21.3), 209 (23.6), 118 (1.1).

Example 14

Synthesis of N-Butyl-6-chloro-N'-(3-chloro-4-methoxy-phenyl)-N-propyl-[1,3,5]triazine-2,4-diamine (110)

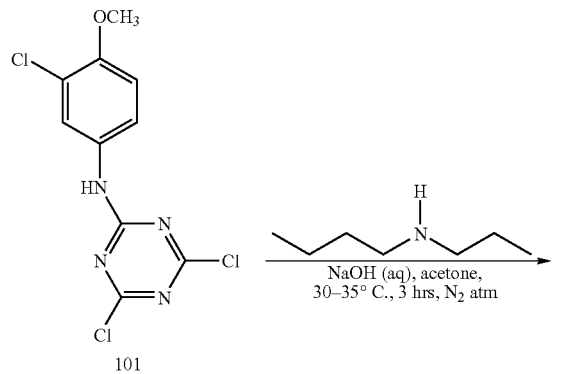

101

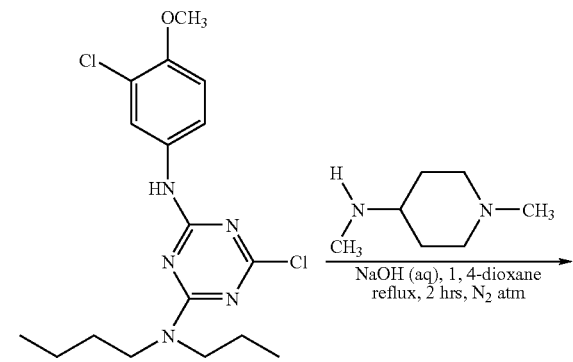

110

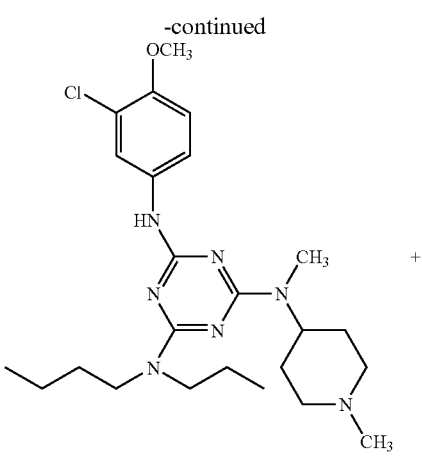

111

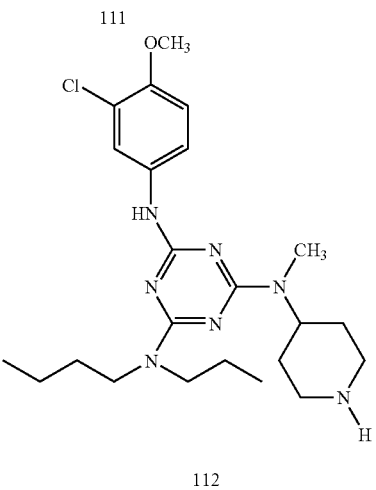

112

To a sample of 101 (1.5334 g, 5.0 mmol) dissolved in acetone (20 mL) was added a solution of N-propyl-butylamine (0.77 mL, 5.0 mmol) in acetone (1 mL) followed by the addition of NaOH (2.0 mL, 2.5 N, 5.0 mmol). The reaction mixture was allowed to stir at 30–35° C. for about 3 hours under nitrogen. The reaction mixture was extracted 3 times with dichloromethane; the combined organic layers were washed with brine solution and dried over potassium carbonate. The sample was concentrated on a rotary evaporator and the resulting oil was dried overnight under vacuum. Column chromatography (silica gel, 96:3:1 dichloromethane:methanol:conc. ammonium hydroxide) yielded light brown solid 110 (1.4 g, 77% recovery).

Example 15

Synthesis of N-Butyl-N'-(3-chloro-4-methoxy-phenyl)-N''-methyl-N''-(1-methyl-piperidin-4-yl)-N-propyl-[1,3,5]triazine-2,4,6-triamine (111)

To a sample of 110 (1.323 g, 3.4 mmol) dissolved in 1,4-dioxane (25 mL) was added a solution of N-methyl-4 (methylamino)piperidine (0.4 mL, 3.4 mmol) in 1,4-dioxane (1 mL) followed by the addition of NaOH (1.4 mL, 2.5 N, 3.4 mmol). The reaction mixture was allowed to stir at reflux for about 2 hours under nitrogen. The reaction mixture was extracted 3 times with dichloromethane; the combined organic layers were washed with brine and dried over potassium carbonate. The sample was concentrated on the rotary evaporator and the resulting solid was dried overnight under vacuum. Column chromatography (silica gel, 90:9:1 dichloromethane:methanol:conc. ammonium hydroxide) yielded light brown solid compound 111 (527 mg, 33%), mp 68° C.; TLC (silica gel, 90:9:1 $CH_2Cl_2:CH_3OH$: conc. $NH_4OH$), $R_f$ 0.46; HPLC: ODS-3V C18, 40:30:30 [$KH_2PO_4$ (0.01M, pH 3.2): $CH_3OH:CH_3CN$], 264 nm, $R_t$ 41.6 min, 90.8% purity); MS (ESI): m/z 476 (M+H, 28.5), 261 (20.2), 260 (52.8), 259 (100), 239 (18.6), 239 (50.6).

Example 16

Synthesis of $N^2$-Butyl-$N^4$-(3-chloro-4-methoxyphenyl)-$N^6$-methyl-$N^6$-piperidin-4-yl-$N^2$-propyl-1,3,5-triazine-2,4,6-triamine (112)

Compound 112 was isolated as a by-product via column chromatography, an oil (0.112 g); TLC (silica gel, 90:9:1 $CH_2Cl_2:CH_3OH$:conc. $NH_4OH$), $R_f$ 0.23; HPLC: ODS-3V C18, 40:30:30 [$KH_2PO_4$ (0.01M, pH 3.2): $CH_3OH:CH_3CN$], 265 nm, $R_t$ 41.4 min, 97.8% purity); MS (ESI): m/z 464 (11.6), 462 (M+H, 28.9), 431 (15.6), 273 (12.7), 253 (58.8), 252 (100), 232 (25.8), 157 (14.5).

Example 17

Synthesis of 2,4-Dichloro-6-cyclohexylmethoxy-[1,3,5]triazine (113)

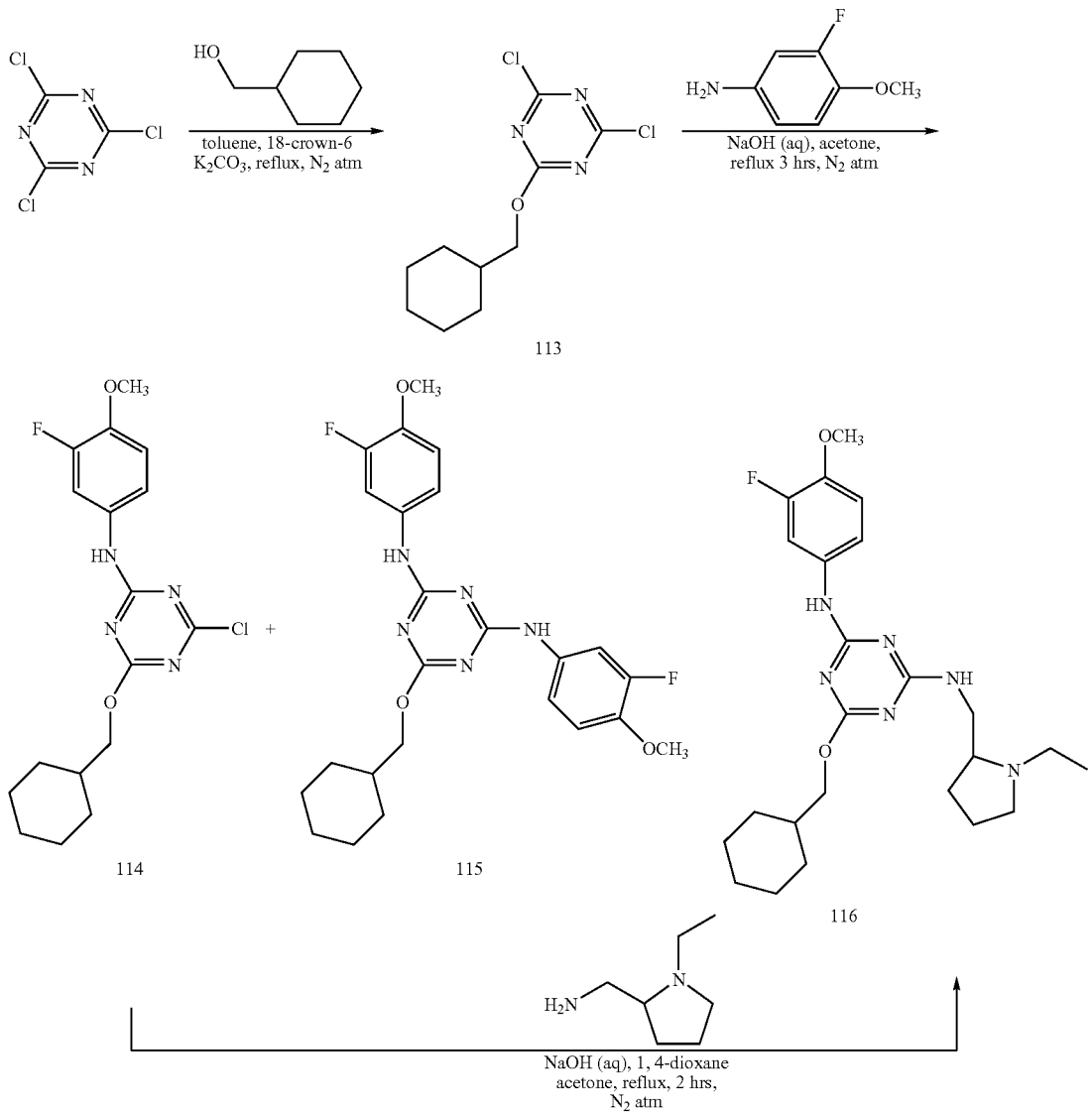

To cyanuric chloride (3.76 g, 20.0 mmol) dissolved in toluene (20 mL) was added potassium bicarbonate (2.80 g, 20.0 mmol) and 18-crown-6 (0.1614 g, 0.6 mmol) followed by dropwise addition of cyclohexylmethanol (2.5 mL, 20 mmol) in 15 mL of toluene (15 mL). The reaction mixture was allowed to stir at reflux for about 18 hours under nitrogen. The reaction mixture was passed through a plug of Celite and concentrated using a rotary evaporator and dried over night under vacuum to give 113 as an oil (5.212 g, 99% recovery).

Example 18

Synthesis of (4-Chloro-6-cyclohexylmethoxy-[1,3,5] triazin-2-yl)-(3-fluoro-4-methoxy-phenyl)-amine (114)

To a sample of 113 (1.011 g, 3.8 mmol) dissolved in acetone (20 mL) was added a solution of 3-fluoro-p-anisidine (0.541 g, 3.8 mmol) in acetone (10 mL) followed by addition of NaOH (1.52 mL, 2.5 N, 3.8 mmol) and water (3 mL). The reaction mixture was allowed to stir at reflux for about 3 hours under nitrogen. The reaction mixture was extracted 3 times with dichloromethane; the combined organic layers were washed with brine solution and dried over potassium carbonate. The sample was concentrated on a rotary evaporator and the resulting oil was dried overnight under vacuum. Column chromatography (silica gel, 70:30 hexanes: ethyl acetate) yielded light yellow solid compound 114 (0.581 g, 42%), mp 98° C.; TLC (silica gel, 30:70 ethyl acetate:hexanes), $R_f$ 0.36; MS (ESI): m/z 369 (39.1), 368 (22.1), 367 (M+H, 100), 273 (3.2), 271 (10.7).

Example 19

Synthesis of 6-Cyclohexylmethoxy-N,N'-bis-(3-fluoro-4-methoxy-phenyl)-1,3,5-triazine-2,4-diamine (115)

Compound 115 was obtained as a by-product (0.159 g) via column chromatography (silica gel, 70:30 hexanes:ethyl acetate), mp 181° C.; TLC (silica gel, 30:70 ethyl acetate:hexanes), $R_f$ 0.17; MS (ESI): m/z 472 (M+H, 100), 261 (1.5).

Example 20

Synthesis of 6-Cyclohexylmethoxy-N-(1-ethyl-pyrrolidin-2-ylmethyl)-N'-(3-fluoro-4-methoxy-phenyl)-[1,3,5]triazine-2,4-diamine (116)

To a sample of 114 (0.3004 g, 0.82 mmol) dissolved in 1,4-dioxane (15 mL) was added a solution of 2-(aminomethyl)-1-ethylpyrrolidine (0.12 mL, 0.82 mmol) in acetone (1 mL) followed by the addition of NaOH (0.33 mL, 2.5 N, 0.82 mmol) and water (1 mL). The reaction mixture was allowed to stir at reflux for about 2 hours under nitrogen. The reaction mixture was extracted 3 times with dichloromethane; the combined organic layers were washed with brine and dried over potassium carbonate. The sample was concentrated on the rotary evaporator and the resulting solid was dried overnight under vacuum. Column chromatography (silica gel, 93:6:1 dichloromethane:methanol:conc. ammonium hydroxide) yielded a light yellow solid, compound 116 (226 mg, 60%), mp 59° C.; HPLC: Inertsil ODS-3V C18, 40:30:30 [$KH_2PO_4$ (0.01M, pH 3.2): $CH_3OH:CH_3CN$], 264 nm, $R_t$ 10.5 min, 100% purity; $^1H$ NMR (600 MHz, CDCl$_3$, 55° C.) δ 7.65 (broad resonance, rotamers, 1H), 7.07 (br d, J=7.8 Hz, 1H), 6.90 (t, J=9 Hz, 1H) 6.84 (broad resonance, rotamers, 1H), 4.12 (s, 2H), 3.88 (S, 3H), 1.02 (s, 1H), 2.26 (apt sextet, J=6.6 Hz, 1H), 2.19 (q, J=9 Hz, 1H), 1.16–1.92 (m, 10H), 1.57 (s, 2H), 1.17–1.32 (m, 3H), 1.05–1.11 (m, 4H); MS (ESI): m/z 459 (M+H, 100), 363 (40.7), 223 (16.1), 202 (4.4), 138 (1.2).

Example 21

Synthesis of (4-Chloro-6-cyclohexylmethoxy-[1,3,5] triazin-2-yl)-(3-chloro-4-methoxy-phenyl)-amine (117)

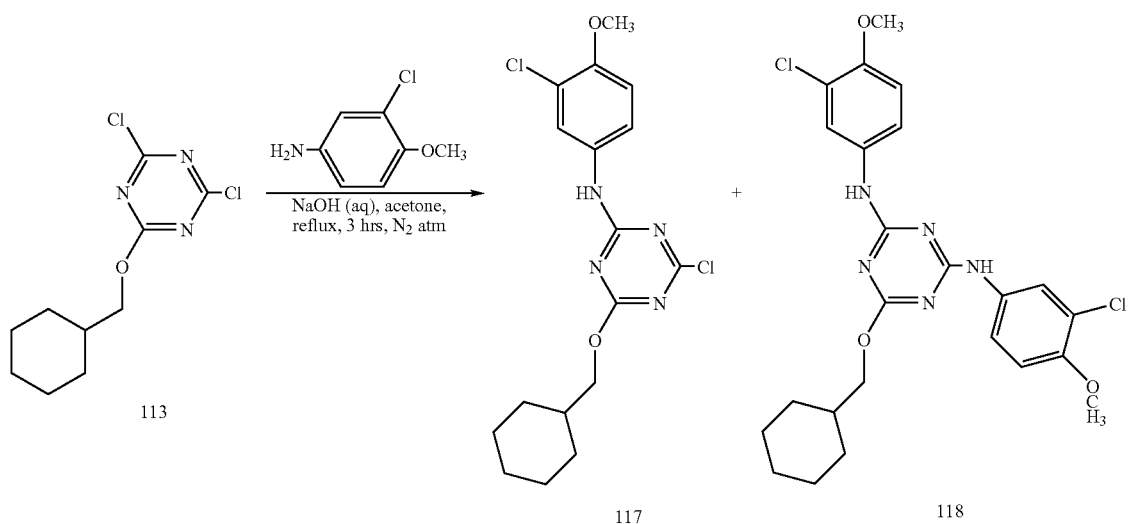

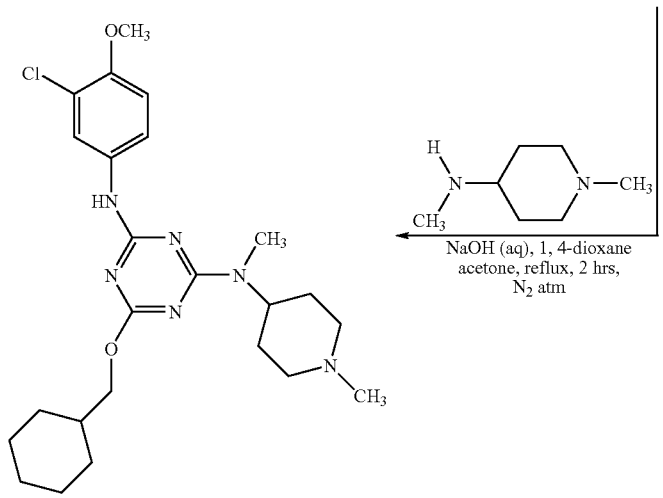

119

To a sample of compound 113 (1.012 g, 3.8 mmol) dissolved in acetone (20 mL) was added a solution of 3-chloro-p-anisidine (0.605 g, 3.8 mmol) in acetone (10 mL) followed by addition of NaOH (1.52 mL, 2.5 N, 3.8 mmol) and water (3 mL). The reaction mixture was allowed to stir at reflux for about 3 hours under nitrogen. The reaction mixture was extracted 3 times with dichloromethane; the combined organic layers were washed with brine and dried over potassium carbonate. The sample was concentrated on a rotary evaporator and the resulting oil was dried overnight under vacuum. Column chromatography (silica gel, 70:30 hexanes:ethyl acetate) yielded a light peach colored solid, compound 117 (0.547 g, 38%), mp 114° C.; TLC (silica gel, 30:70 ethyl acetate:hexanes), $R_f$ 0.44; MS (ESI): m/z 385 (74.3), 384, (22.9), 383 (M+H, 100), 287 (8.3).

Example 22

Synthesis of N,N'-Bis-(3-chloro-4-methoxy-phenyl)-6-cyclohexylmethoxy-1,3,5-triazine-2,4-diamine (118)

Compound 118 was obtained as a by-product (0.178 g) via column chromatography (silica gel, 70:30 hexanes:ethyl acetate), mp 188° C.; TLC (silica gel, 30:70 ethyl acetate:hexanes), $R_f$ 0.22; MS (ESI): m/z 504 (M+H, 100), 379 (1), 338 (1.3).

Example 23

Synthesis of N-(3-Chloro-4-methoxy-phenyl)-6-cyclohexylmethoxy-N'-methyl-N'-(1-methyl-piperidin-4-yl)-[1,3,5]triazine-2,4-diamine (119)

To a sample of 117 (0.3007 g, 0.78 mmol) dissolved in 1,4-dioxane (15 mL) was added a solution of 2-(aminomethyl)-1-ethylpyrrolidine (0.11 mL, 0.78 mmol) in acetone (1 mL) followed by the addition of NaOH (0.31 mL, 2.5 N, 0.78 mmol) and water (1 mL). The reaction mixture was allowed to stir at reflux for about 2 hours under nitrogen. The reaction mixture was extracted 3 times with dichloromethane; the combined organic layers were washed with brine solution and dried over potassium carbonate. The sample was concentrated on the rotary evaporator and the resulting solid was dried overnight under vacuum. Column chromatography (silica gel, 93:6:1 dichloromethane:methanol:conc. ammonium hydroxide) yielded light yellow solid compound 119 (159 mg, 43%), mp 140° C. HPLC: Inertsil ODS-3V C18, 40:30:30 [$KH_2PO_4$ (0.01M, pH 3.2): $CH_3OH:CH_3CN$], 264 nm, $R_t$ 15.2 min, 99.7% purity; MS (ESI): m/z 475 (M+H, 64.1), 379 (49.5), 231 (48.6), 210 (100), 190 (3.2).

Example 24

Synthesis of 6-Chloro-N,N''-bis-(3-chloro-4-methoxy-phenyl)-[1,3,5]triazine-2,4-diamine (120)

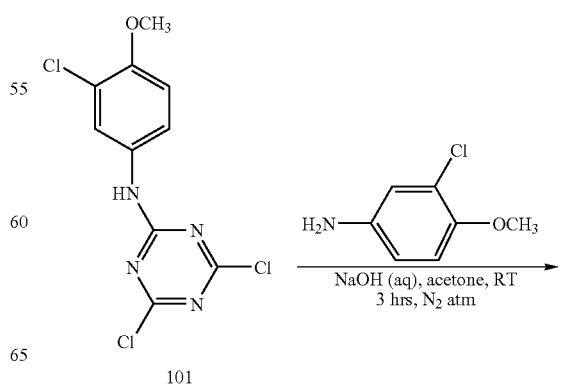

101

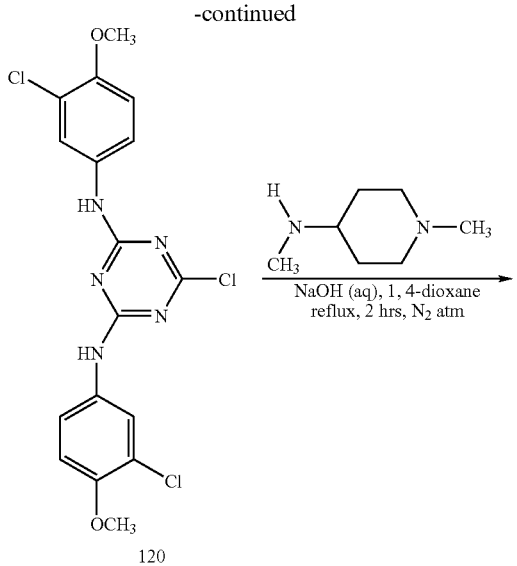

120

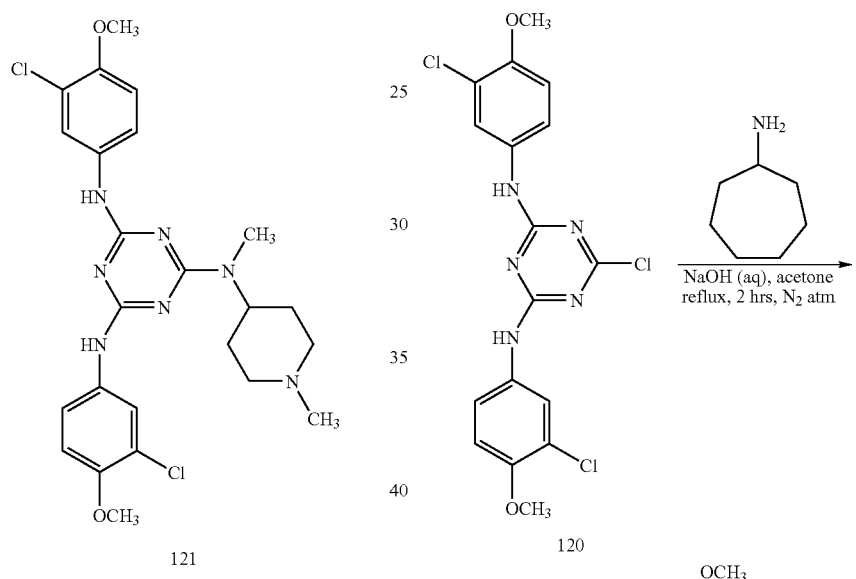

121

To a sample of 101 (3.0556 g, 10.0 mmol) dissolved in acetone (25 mL) was added a solution of 3-chloro-p-anisidine (1.6050 g, 10.0 mmol) in acetone (10 mL) followed by addition of NaOH (4.0 mL, 2.5 N, 10.0 mmol). The reaction mixture was allowed to stir at rt for about 3 hours under nitrogen. The reaction mixture was poured over crushed ice. The resulting solid was collected by vacuum filtration, washed with water and dried overnight under vacuum to give compound 120 (4.06 g, 95%), mp 213° C.; HPLC: Inertsil ODS-3V C18, 40:30:30 [KH$_2$PO$_4$ (0.01 M, pH 3.2):CH$_3$OH:CH$_3$CN], 264 nm, R$_t$ 70.0 min, 97.1% purity MS (ESI): m/z 427 (20.90), 426 (M+H, 99.6), 210 (100), 209 (22.2), 196 (55.3), 169 (25.4).

Example 25

Synthesis of N,N'-Bis-(3-chloro-4-methoxy-phenyl)-N''-methyl-N''-(4-methyl-cyclohexyl)-[1,3,5]triazine-2,4,6-triamine (121)

To a sample of compound 120 (1.5004 g, 3.5 mmol) dissolved in 1,4-dioxane (20 mL) was added a solution of N-methyl-4(methylamino)-piperidine (0.5 mL, 3.5 mmol) in 1,4-dioxane (1 mL) followed by the addition of NaOH (1.4 mL, 2.5 N, 3.5 mmol). The reaction mixture was allowed to stir at reflux for about 2 hours under nitrogen. The reaction mixture was poured over crushed ice and neutralized with 10% HCl (aq). The resulting solid was collected by vacuum filtration, washed with water and dried overnight under vacuum. Column chromatography (silica gel, 96:3:1 dichloromethane:methanol:conc. ammonium hydroxide) yielded a purple solid, compound 121 (487 mg, 27%), mp 130° C.; HPLC: Inertsil ODS-3V C18, 40:30:30 [KH$_2$PO$_4$ (0.01 M, pH 3.2):CH$_3$OH:CH$_3$CN], 264 mn, R$_t$ 8.1 min, 96% purity; $^1$H NMR (600 MHz, CDCl$_3$, 55° C.) δ 7.81–7.92 (broad resonance, 2H), 7.19–7.30 (broad resonance, 2H), 6.87 (d, J=9 Hz, 2H), 6.72 (s, 2H), 4.60–4.65 (m, 1H), 3.88 (s, 6H), 3.05 (s, 3H), 2.95 (d, J=12 Hz, 2H), 2.32 (s, 3H), 2.19 (t, J=11.4 Hz, 2H), 1.89 (dq, J=12.6, 3.6 Hz, 2H), 1.71 (apt d, J=11.4 Hz, 2H), 1.65 (s, 1H); MS (ESI): m/z 519 (28.3), 518 (M+H, 42.1), 261(71.9), 260 (100).

Example 26

Synthesis of N,N'-Bis-(3-chloro-4-methoxy-phenyl)-N''-cycloheptyl-[1,3,5]triazine-2,4,6-triamine (122)

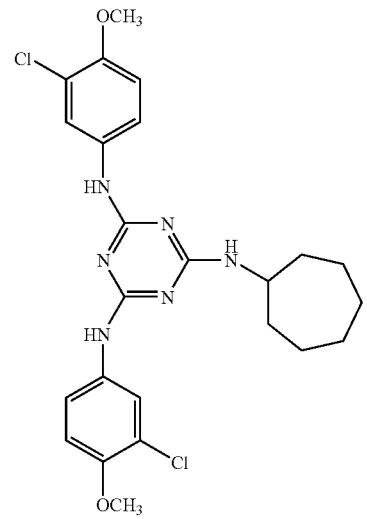

122

To a sample of 120 (1.5004 g, 3.5 mmol) dissolved in acetone (20 mL) was added a solution of cycloheptylamine (0.4 mL, 3.5 mmol) in acetone (1 mL) followed by the addition of NaOH (1.4 mL, 2.5 N, 3.5 mmol). The reaction mixture was allowed to stir at reflux for about 2 hours under nitrogen. The reaction mixture was poured over crushed ice and neutralized with 10% HCl (aq). The resulting solid was collected by vacuum filtration, washed with water and dried overnight under vacuum to give light purple solid compound 122 (1.5 g, 85%), mp 183° C.; HPLC: Inertsil ODS-3V C18, 40:30:30 [$KH_2PO_4$ (0.01 M, pH 3.2):$CH_3OH$:$CH_3CN$], 264 nm, $R_t$ 59 min, 96% purity; MS (ESI): m/z 503 (M+H, 29), 502 (100), 458 (24.2), 425 (17.9), 225 (5.7), 155 (11.3), 114 (27.6).

Example 27

Synthesis of N-(3-Bromo-4-methoxy-phenyl)-N'-cycloheptyl-N''-methyl-N''-(1-methyl-piperidin-4-yl)-[1,3,5]triazine-2,4,6-triamine (123)

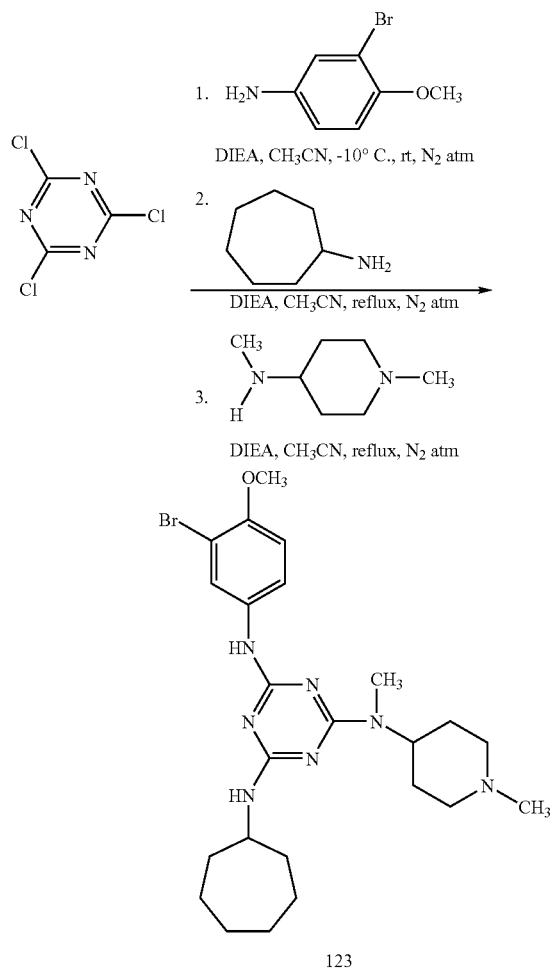

To cyanuric chloride (0.184 g, 1.0 mmol) dissolved in acetonitrile (3 mL) stirring at about −10° C., was added a solution of 3-bromo-p-anisidine (0.2019 g, 1.0 mmol) in acetonitrile followed by the addition of N,N-diisopropylethylamine (DIEA) (0.17 mL, 1.0 mmol) in acetonitrile. The reaction mixture was allowed to stir at about −10° C. for 1 hour under nitrogen. The reaction mixture was then warmed to room temperature and allowed to stir at room temperature for another hour under nitrogen. To the reaction mixture was added a solution of cyclohep-tylamine (0.13 mL, 1.0 mmol) in acetonitrile followed by addition of DIEA (0.17 mL, 1.0 mmol). The reaction mixture was allowed to stir at reflux overnight under nitrogen. To the reaction mixture was added N-methyl-4(methylamino)piperidine (0.13 mL, 1.0 mmol) in acetonitrile followed by the addition of DIEA (0.17 mL, 1.0 mmol). The reaction mixture was allowed to stir at reflux for overnight under nitrogen. The reaction mixture was extracted 3 times with ethyl acetate; the combined organic layers were washed with brine solution and dried over potassium carbonate. The sample was concentrated on the rotary evaporator and the resulting solid was dried overnight under vacuum. Column chromatography (silica gel, 90:9:1 methylene chloride:methanol:conc. ammonium hydroxide yielded 0.029 g (6%) of 123. $^1H$ NMR (400 MHz, $CDCl_3$) δ 7.97–8.19 (broad resonance, 1H), 7.12 (broad resonance, 1H), 6.78–6.80(m, 2H), 4.82 (br s, 1H), 4.58 (br s, 1H), 3.92 (br s, 1H), 3.84 (s, 3H), 2.90–2.98 (m, 5H), 2.29 (s, 3H), 2.17 (broad resonance, 2H), 1.99–2.24 (broad resonance, 4H), 1.72–1.85 (m, 3H), 1.42–1.62 (m, 11H); MS (ESI): m/z 520 (100), 518 (93.9), 458 (10.4), 424 (20.8), 422 (21.1), 261 (67.5), 260 (63.4), 213 (13.9), 212 (13.6).

Example 28

Synthesis of 6-Chloro-N-cyclohexylmethyl-N'-(3-fluoro-4-methoxy-phenyl)-[1,3,5]triazine-2,4-diamine (125)

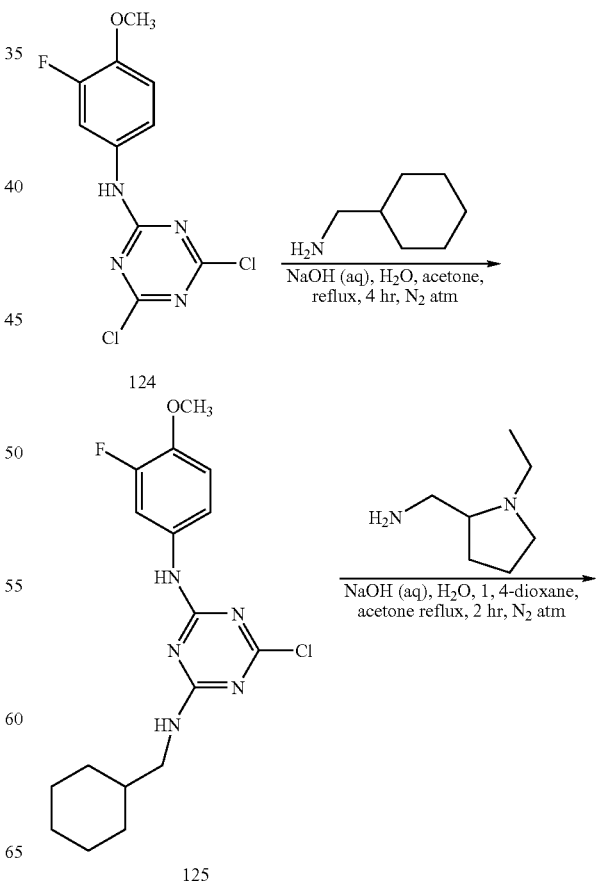

-continued

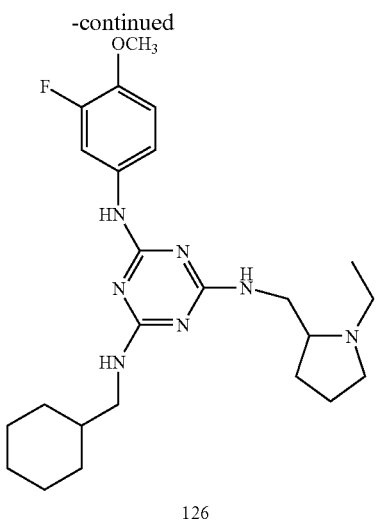

126

To a sample of 124 (40.02 g, 138.4 mmol, prepared as indicated herein) dissolved in acetone (300 mL) was added a solution of cyclohexanemethylamine (18.0 mL, 138.4 mmol) in acetone (30 mL) followed by addition of NaOH (55.4 mL, 2.5 N, 138.4 mmol) and 130 mL of water. The reaction mixture was allowed to stir at reflux for about 3 hours. The reaction mixture was then poured over crushed ice and neutralized with 10% HCl (aq) and 10% NaOH (aq). The resulting solid was collected by vacuum filtration, washed with water and dried overnight under vacuum. Recrystallization from ethyl acetate yielded a light yellow solid, compound 125 (32.93 g, 65%), mp 156° C.; HPLC: Inertsil ODS-3V C18, 40:10:50 [$KH_2PO_4$ (0.01M, pH 3.2):$CH_3OH$:$CH_3CN$], 264 nm, $R_t$ 47.9 min, 92% purity; MS (ESI): m/z 366 (M+H, 100).

Example 29

Synthesis of N-Cyclohexylmethyl-N'-(1-ethyl-pyrrolidin-2-ylmethyl)-N''-(3-fluoro-4-methoxy-phenyl)-[1,3,5]triazine-2,4,6-triamine (126)

To a sample of 125 (10.02 g, 27.3 mmol) dissolved in 1,4-dioxane (150 mL) was added a solution of 2-(aminomethyl)-1-ethylpyrrolidine (4.0 mL, 27.3 mmol) in acetone (10 mL) followed by addition of NaOH (11 mL, 2.5 N, 27.3 mmol) and 27 mL of water. The reaction mixture was allowed to stir at reflux for about 2 hours. The reaction mixture was extracted 3 times with dichloromethane; the combined organic layers were washed with brine and dried over potassium carbonate. The sample was concentrated on the rotary evaporator and the resulting solid was dried overnight under vacuum. Column chromatography (silica gel, 93:6:1 dichloromethane:methanol:conc. ammonium hydroxide) yielded a light yellow solid, compound 126 (7.014 g, 56%), mp 72° C.; HPLC: Inertsil ODS-3V C18, 40:30:30 [$KH_2PO_4$ (0.01M, pH 3.2):$CH_3OH$:$CH_3CN$], 264 nm, $R_t$ 8.5 min. 93.4% purity; MS (ESI): m/z 458 (M+H, 37.3), 362 (4), 250 (100), 230 (15.3), 229 (44.1).

Example 30

Synthesis of N-Cycloheptyl-N'-(3-fluoro-4-methoxy-phenyl)-6-pyrrolidin-1-yl-[1,3,5]triazine-2,4-diamine (128)

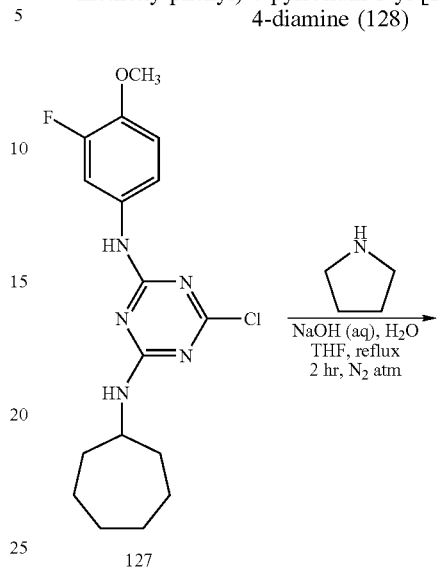

127

128

To a sample of compound 127 (13.24 g, 36.2 mmol, prepared as indicated herein) dissolved in THF (150 mL) was added a solution of pyrrolidine (3.0 mL, 36.2 mmol) in THF (10 mL) followed by addition of NaOH (14.5 mL, 2.5 N, 36.2 mmol) and 36 mL of water. The reaction mixture was allowed to stir at reflux for about 2.5 hours. The reaction mixture was extracted 3 times with dichloromethane; the combined organic layers were washed with brine and dried over potassium carbonate. The sample was concentrated on the rotary evaporator and the resulting solid was dried overnight under vacuum. Column chromatography (silica gel, 98:2 dichloromethane:methanol) yielded light yellow solid 128 (3.36 g, 23%), mp 79° C.; HPLC: Inertsil ODS-3V C18, 40:10:50 [$KH_2PO_4$ (0.01M, pH 3.2):$CH_3OH$:$CH_3CN$], 264 nm, $R_t$ 24.5 min, 95.5% purity; $^1$H NMR (600 MHz, $CDCl_3$, 55° C.) δ 7.77 (broad resonance, 1H), 7.01–7.03 (m, 1H), 6.86 (t, J=9 Hz, 1 H), 6.62 (s, 1H), 4.80 (s, 1H), 4.02–4.06 (m, 1H), 3.85 (s, 3H), 3.54 (s, 4 H), 1.99–2.03 (m, 2H), 1.91–1.93 (m, 3H), 1.47–1.66 (m, 11H); MS (ESI): m/z 402 (30.7), 401 (M+H, 100).

Example 31

Synthesis of (4,6-Dichloro-[1,3,5]triazin-2-yl)-(3-fluoro-4-methoxy-phenyl)-amine (124)

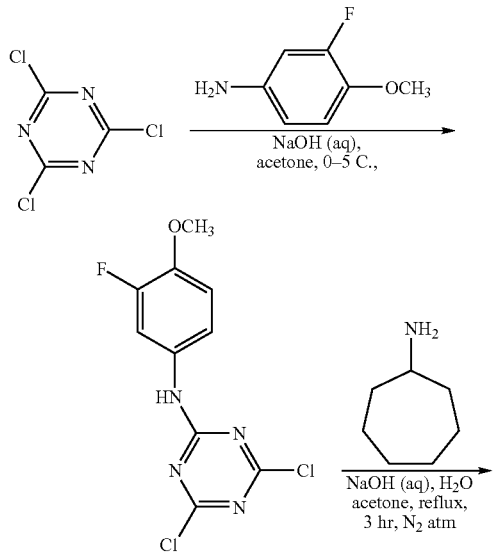

To cyanuric chloride (28.84 g, 156.0 mmol) dissolved in acetone (200 mL) stirring at approximately 0–5° C., was added a solution of 3-fluoro-p-anisidine (22.16 g, 156.0 mmol) in acetone (200 mL) followed by the addition of NaOH (63 mL, 2.5 N, 156.0 mmol). The reaction mixture was allowed to stir at approximately 0–5° C. for about 2 hours. The reaction mixture was then poured over crushed ice and neutralized with 10% HCl (aq) and 5% NaOH (aq). The resulting solid was collected by vacuum filtration, washed with water and dried overnight under vacuum. Column chromatography (silica gel, 70:30 hexane:ethyl acetate) yielded light yellow solid compound 124 (29.6 g, 66%); mp 134° C.; HPLC: Inertsil ODS-3V C18, 40:30:30 [$KH_2PO_4$ (0.01M, pH 3.2):$CH_3OH$:$CH_3CN$], 264 nm, $R_t$ 20.3 min, 97.7% purity.

Example 32

Synthesis of 6-Chloro-N-cycloheheptyl-N'-(3-fluoro-4-methoxy-phenyl)-[1,3,5]triazine-2,4-diamine (127)

To a sample of 124 (10.00 g, 34.6 mmol) dissolved in acetone (150 mL) was added a solution of cycloheptylamine (4.4 mL, 34.6 mmol) in acetone (20 mL) followed by addition of NaOH (13.8 mL, 2.5 N, 34.6 mmol) and 35 mL of water. The reaction mixture was allowed to stir at reflux for about 3 hours. The reaction mixture was extracted 3 times with dichloromethane; the combined organic layers were washed with brine and dried over potassium carbonate. The sample was concentrated on the rotary evaporator and the resulting solid was dried overnight under vacuum affording 127 (12.4 g, 98% recovery), mp 145° C.; HPLC: Inertsil ODS-3V C18, 40:30:30 [$KH_2PO_4$ (0.01M, pH 3.2):$CH_3OH$:$CH_3CN$], 264 nm, $R_t$ 104.8 min, 97.3% purity; $^1H$ NMR (600 MHz, CDCl3, 55° C.) δ 7.50–7.64 (m, 1H), 7.02–7.03 (br resonance, 2H), 6.90 (t, J=8.9 Hz, 1H), 5.35–5.41 (br resonance, 1H), 3.99 (br s, 1H), 4.12 (rotamer), 3.87 (s, 3H), 2.01 (br s, 2H), 1.42–1.67 (m, 11H).

Example 33

Synthesis of N-Cycloheptyl-N'-ethyl-N''-(3-fluoro-4-methoxy-phenyl)-[1,3,5]triazine-2,4-diamine (129)

To 127 (11.00 g, 30 mmol) dissolved in THF (150 mL) was added a solution of ethylamine hydrochloride (2.43 mL, 30 mmol) in THF (20 mL) followed by addition of NaOH (24 mL, 2.5 N, 60 mmol) and 30 mL of water. The reaction mixture was allowed to stir at reflux for about 2 hours. The reaction mixture was extracted 3 times with dichloromethane; the combined organic layers were washed with brine and dried over potassium carbonate. The sample was concentrated on the rotary evaporator and the resulting solid was dried overnight under vacuum. Column chromatography (silica gel, 98:2 dichloromethane:methanol) yielded a light yellow solid 129 (4.81 g, 43%), mp 84° C.; HPLC: Inertsil ODS-3V C18, 40:30:30 [$KH_2PO_4$ (0.01M, pH 3.2):$CH_3OH$:$CH_3CN$], 264 nm, $R_t$ 30.7 min, 94.2% purity; $^1H$ NMR (600 MHz, CDCl$_3$, 55° C.) δ 7.69 (s, 1H), 7.00 (br d, J=7.0 Hz, 1H), 6.86 (t, J=8.4 Hz, 1H), 6.64 (s, 1H), 4.79–4.83 (br resonance, 2H), 4.01–4.03 (m, 1H), 3.85 (s, 3H), 3.38–3.42 (m, 2H), 1.99–2.01 (m, 2H), 1.47–1.67 (m, 11H), 1.19 (t, J=7.2 Hz, 3H); MS (ESI): m/z 376 (29.5), 375 (M+H, 100).

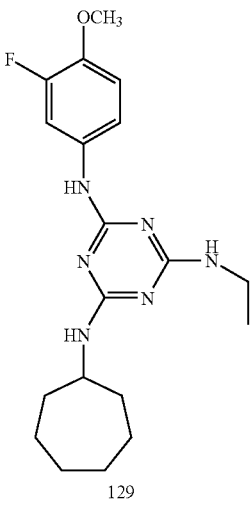

Example 34

Synthesis of N-Cycloheptyl-N'-(1-ethyl-pyrrolidin-2-ylmethyl)-N''-(3-fluoro-4-methoxy-phenyl)-[1,3,5]triazine-2,4,6-triamine (130)

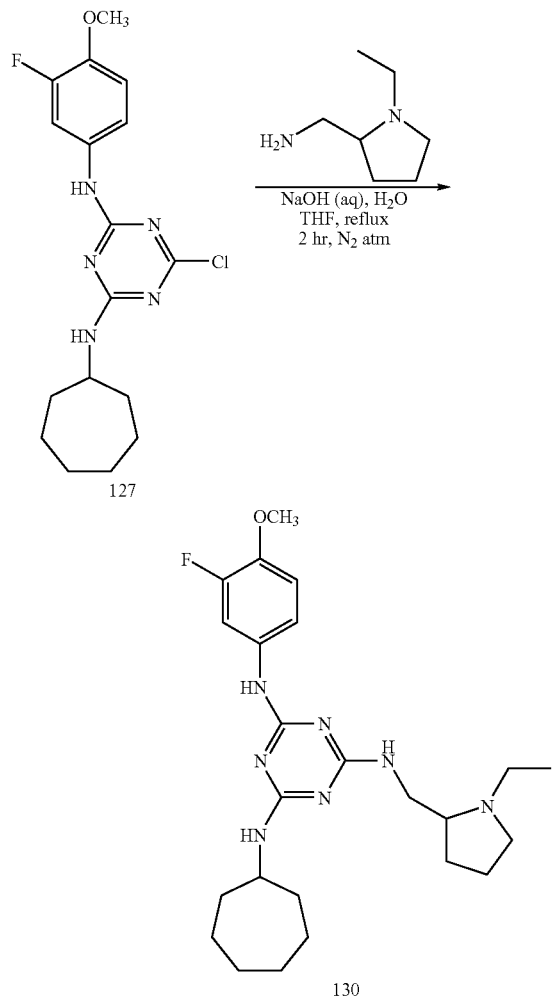

Example 35

Synthesis of 2-[4-chloro-6-(3-chloro-4-methoxy-phenylamino)-[1,3,5]triazin-2-ylamino]-propane-1,3-diol (131)

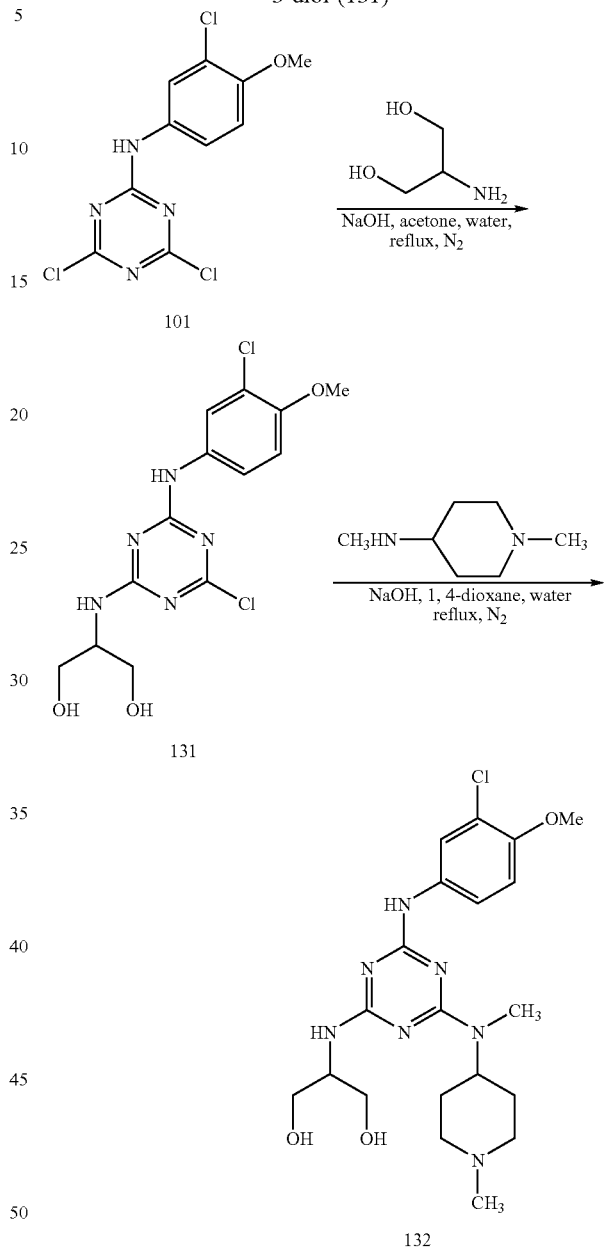

To 127 (5.009 g, 13.7 mmol) dissolved in THF (80 mL) was added a solution of 2-(aminomethyl)-1-ethylpyrrolidine (2.0 mL, 13.7 mmol) in THF (10 mL) followed by addition of NaOH (5.5 mL, 2.5 N, 13.7 mmol) and 13 mL of water. The reaction mixture was allowed to stir at reflux for about 2 hours under $N_2$ atm. The reaction mixture was extracted 3 times with dichloromethane; the combined organic layers were washed with brine and dried over potassium carbonate. The sample was concentrated on the rotary evaporator and the resulting solid was dried overnight under vacuum. Column chromatography (silica gel, 90:9:1 dichloromethane:methanol:conc. ammonium hydroxide) yielded a light yellow solid 130 (3.63 g, 58%), mp 76° C.; HPLC: Inertsil ODS-3V C18, 40:30:30 [$KH_2PO_4$ (0.01M, pH 3.2): $CH_3OH:CH_3CN$], 264 nm, $R_t$ 7.1 min, 97.1% purity; MS (ESI): m/z 459 (16.5), 458 (M+H, 48.7), 362 (31.3), 250 (100), 230 (22.8), 229 (62.7), 222 (17.2), 202 (34).

To 101 (0.6114 g, 2 mmol) dissolved in acetone (3 mL) was added 2-amino-propane-1,3-diol (0.1818 g, 2 mmol) dissolved in acetone (1 mL) and water (1 mL). Then water (1 mL) was added to the reaction mixture followed by 2.5 N NaOH (aq) (0.8 mL, 2 mmol). The reaction mixture was heated at reflux for 3 h under a $N_2$ atmosphere. The reaction mixture was diluted with ethyl acetate and washed 2× brine. The organic layer was separated, dried over anhydrous $K_2CO_3$, filtered, and concentrated under reduced pressure affording 0.634 g of a purple solid. The crude material was purified by silica gel flash column chromatography eluting with 100% ethyl acetate affording a colorless oil 131 (0.124 g, 18%); HPLC: Inertsil ODS-3V C18, 40:30:30 [$KH_2PO_4$ (0.01 M, pH 3.2):$CH_3OH:CH_3CN$], 264 nm, $R_t$ 5.7 min, 83.3% purity; MS (ESI): m/z 360 (M+H, 100), 338 (10.7), 183 (10.3)

Example 36

Synthesis of 2-{4-(3-chloro-4-methoxy-phenylamino)-6-[methyl-(1-methyl-piperidin-4-yl)-amino]-[1,3,5]triazin-2-ylamino}-propane-1,3-diol (132)

To 131 (0.979 g, 0.271 mmol) dissolved in 3 mL 1,4-dioxane was added methyl-4-(methylamino)piperidine (0.05 mL, 0.34 mmol) dissolved in 2 mL 1,4-dioxane followed by the addition of 2.5 N NaOH (aq) (0.11 mL, 0.275 mmol). The mixture was heated at reflux for 3 h 45 min, cooled to about room temperature, and then concentrated under reduced pressure. The resulting material was diluted with dichloromethane and filtered. The filtrate was then concentrated affording 56.5 mg of material. The crude material was purified by silica gel pipet column eluting with 100% methanol affording an white solid 132 (21.1 mg, 18%), mp 84° C.; MS (ESI): m/z 454 (34.7), 452 (M+H, 100), 422 (11.3), 248 (25.3), 247 (51.3), 157 (60.3), 129 (27.5).

Example 37

Synthesis of N-(1-benzyl-piperidin-4-yl)-N'-(3-chloro-4-methoxy-phenyl)-N''-cycloheptyl-[1,3,5]-2,4,6-triamine (134)

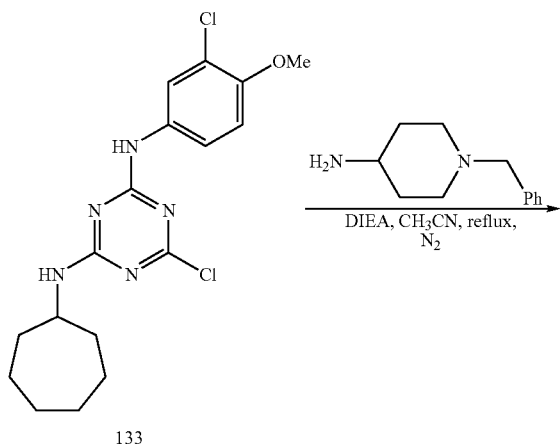

133

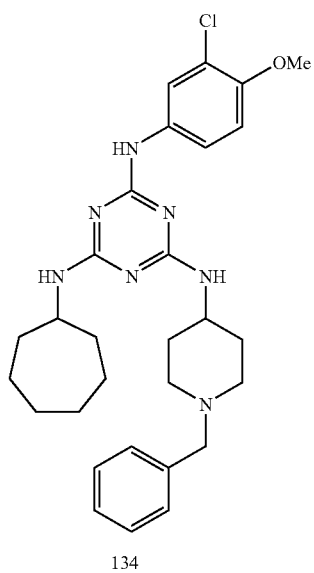

134

To 133 (0.1252 g, 0.382 mmol, prepared as indicated herein) dissolved in 3 mL acetonitrile was added N,N-diisopropyl ethyl amine (DIEA) (0.07 mL, 0.382 mL) followed by 4-amino-1-benzylamine (0.07 mL, 0.382 mmol). The mixture was refluxed overnight under a $N_2$ atmosphere. The reaction mixture was diluted with methylene chloride and washed with brine. The organic layer was separated, dried over $K_2CO_3$, filtered and concentrated under reduced pressure to afford 0.159 g of material. The crude material was purified by silica gel flash column chromatography eluting with 96:3:1 methylene chloride:methanol:conc. ammonium hydroxide and the collected fractions were dried over potassium carbonate, filtered and then concentrated under reduced pressure to afford 77 mg of product. A second column under similar conditions was completed to afford an additional 30 mg of material for a combined product 134 (103 mg, 50%); HPLC: Inertsil ODS-3V C18, 40:30:30 [$KH_2PO_4$ (0.01 M, pH 3.2):$CH_3OH$:$CH_3CN$], 264 nm, $R_t$ 13.7 min, 97.7% purity; MS (ESI): m/z 538 (15.4), 536 (38.2), 448 (19.3), 446 (49.3), 290 (41.4), 289 (84.6), 269 (100), 247 (4.4).

Example 38

Synthesis of $N^2$-(3-chloro-4-methoxy-phenyl)-$N^4$-cycloheptyl-$N^6$-piperidin-4-yl-1,3,5-triazine-2,4,6-triamine (135)

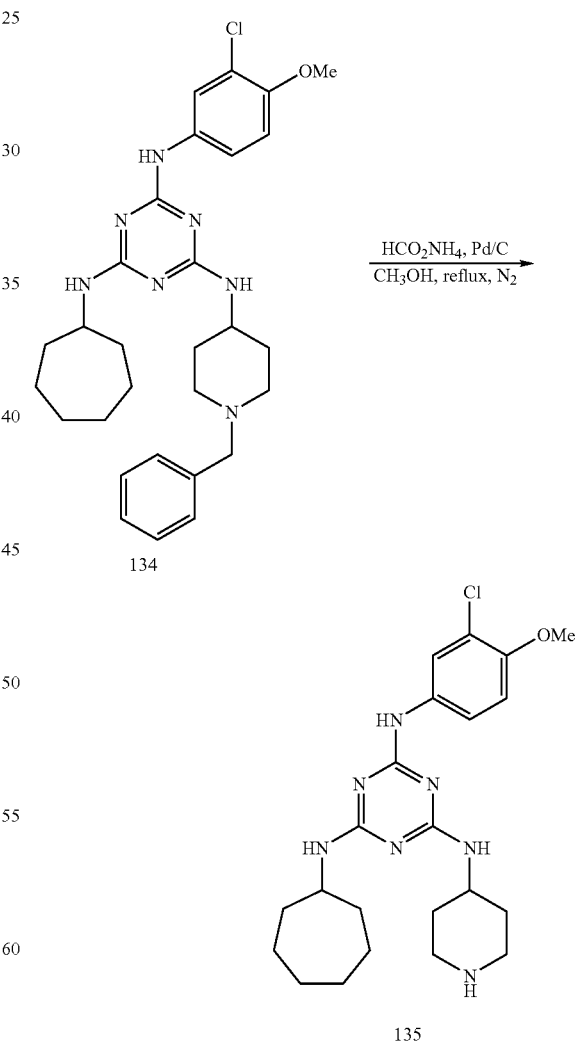

To 134 (0.0485 g, 0.0867 mmol) in 2 mL methanol was added 10% Pd/C (0.052 g) followed by ammonium formate (0.0646 g, 1.02 mmol). The mixture was heated at reflux for about 1.5 h under a $N_2$ atmosphere. The cooled reaction mixture was filtered by vacuum through Celite with a methylene chloride rinsing, and the filtrate concentrated under reduced pressure to afford 36 mg of material. The crude material was purified by silica gel flash chromatography eluting with 90:9:1 methylene chloride:methanol:conc. ammonium hydroxide, and the collected fractions were dried over potassium carbonate, filtered and then concentrated under reduced pressure to afford a solid 135 (20 mg, 51.8%), mp 167° C.; HPLC: Inertsil ODS-3V C18, 40:30:30 [$KH_2PO_4$ (0.01 M, pH 3.2):$CH_3OH$:$CH_3CN$], 264 nm, $R_t$ 4.6 min, 52.1% (another major peak at $R_t$ 7.3 min, 46.9%); MS (ESI): m/z 448 (4.4), 446 (12.5), 412 (22.7), 386 (2.3), 265 (32.9), 248 (42.6), 244 (56.2), 228 (37.1), 227 (100), 207 (6.9).

Example 39

Synthesis of $N^2$-(3-chloro-4-methoxy-phenyl)-$N^4$-cycloheptyl-$N^6$-(1-ethyl-pyrrolidin-2-ylmethyl)-1,3,5-triazine-2,4,6-triamine (136)

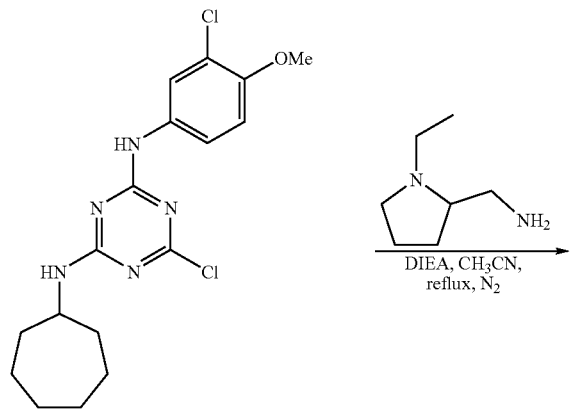

Example 40

Synthesis of 2-chloro-4-{4-cycloheptylamino-6-[methyl-(1-methyl-piperidin-4-yl-amino]-1,3,5-triazin-2-ylamino}-phenol (138)

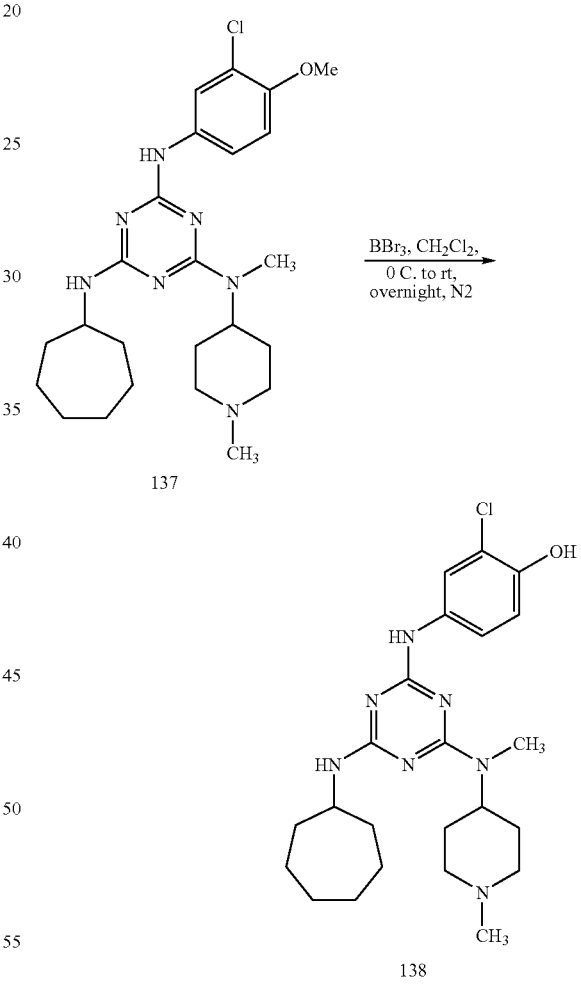

To 133 (0.1257 g, 0.382 mmol, prepared as indicated herein) dissolved in 3 mL acetonitrile was added DIEA (0.07 mL, 0.382 mL) followed by 2-(aminomethyl)-1-ethyl pyrrolidine (0.06 mL, 0.382 mmol). The mixture was refluxed overnight under a $N_2$ atmosphere. The reaction mixture was diluted with methylene chloride and washed with brine. The organic layer was separated, dried over $K_2CO_3$, filtered and concentrated under reduced pressure to afford 0.143 g of material. The crude material was purified by silica gel flash column chromatography eluting with 96:3:1 methylene chloride:methanol:conc. ammonium hydroxide and the collected fractions dried over approximately 1:1 potassium carbonate/sodium sulfate, filtered and then concentrated under reduced pressure to afford 77 mg of product. A second column under similar conditions was completed to afford an additional 30 mg of material for a combined 98 mg (54%) of a yellow colored solid 136, mp 69–70° C.; HPLC: YMC Pack Pro C18, 40:30:30 [$KH_2PO_4$ (0.01 M, pH 3.2): $CH_3OH$:$CH_3CN$], 264 nm, $R_t$ 12.9 min, 96.5% purity; MS (ESI): m/z 476 (16.3), 474 (42.9), 260 (15), 259 (44.2), 258 (100), 238 (56), 216 (5.3), 210 (9.2).

Under anhydrous conditions, 137 (0.1008 g, 0.21 mmol, prepared as described herein) in a dry round bottomed flask was dissolved in anhydrous methylene chloride (3 mL) under a $N_2$ atmosphere about 0° C. (ice/water bath) was added $BBr_3$ (2.1 mL, 2.1 mmol, 1 M in methylene chloride) slowly by syringe. The mixture was stirred for about 2 hours at about 0° C. and then quenched with water (5 mL). After standing overnight at rt, the mixture was diluted with ethyl acetate, water and 10% $NaHCO_3$ (aq), and the organic layer was separated then washed with brine. The organic layer was then dried over anhydrous sodium sulfate, filtered, and concentrated under reduced pressure to afford 0.648 g of material. The crude material was purified using silica gel flash column chromatography eluting with 100% methanol to afford of a white solid 138 (7 mg, 7%); HPLC: Inertsil ODS-3V C18, 40:30:30 [$KH_2PO_4$ (0.01 M, pH 3.2): $CH_3OH$:$CH_3CN$], 264 nm, $R_t$ 4.9 min, 90.3% purity; $^1H$ NMR (600 MHz, $CDCl_3$, 55° C.) (all resonances are broad) δ 7.93 (s, 1H), 7.13 (s, 1H), 6.91–6.92 (m 11H), 6.55 (s, 1H), 4.80 (s, 1H), 4.59 (s, 1H), 4.02 (s, 1H), 2.96–3.0 (m, 5H), 2.32 (s, 3H), 2.13 (s, 2H), 2.03 (s, 2H), 1.86–1.88 (m, 2H), 1.53–1.67 (m, 12H); MS (ESI): m/z 463 (12.4), 461 (27), 252 (59), 251 (100), 231 (32.3), 224 (1), 203 (9.8).

Example 41

Synthesis of $N^2$-cycloheptyl-$N^4$-((S)-1-ethyl-pyrrolidin-2-ylmethyl)-$N^6$-(3-fluoro-4-methoxyphenyl)-1,3,5-triazine-2,4,6-triamine (139)

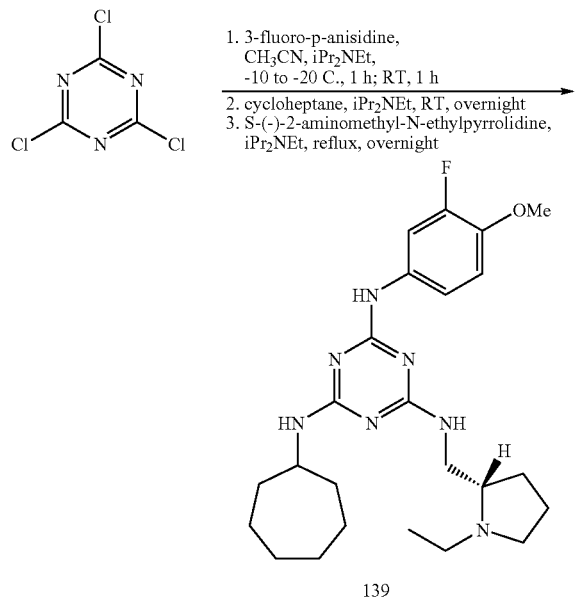

139

To a mixture of cyanuric chloride (0.368 g, 2 mmol) in $CH_3CN$ at approximately –10 to –20° C. was added 3-fluoro-p-anisidine (0.28 g, 2 mmol) in $CH_3CN$ followed by the addition of N,N-diisopropylethylamine (DIEA) (0.35 mL, 2 mmol) and stirred for an hour. The reaction mixture was then allowed to reach room temperature for an hour. The second step was continued without further purification. Cycloheptylamine (0.25 mL, 2 mmol) and DIEA (0.35 mL, 2 mmol) were added and the reaction mixture was stirred overnight at rt. The third step was also preceded without any further purification. S-(–)-2-aminomethyl-N-ethyl pyrrolidine (0.29 mL, 2 mmol) and DIEA (0.35 mL, 2 mmol) were added and the reaction mixture was refluxed overnight. The reaction mixture was diluted with ethyl acetate and washed with brine. The organic layer was separated and dried over potassium carbonate, filtered, and concentrated under reduced pressure affording 0.920 g crude material. The crude material was purified by column chromatography to yield a white solid 139 (0.550 g, 60%), mp 75–77° C.; HPLC: Inertsil ODS-3V C18, 40:30:30 [$KH_2PO_4$ (0.01M, pH 3.2): $CH_3OH$:$CH_3CN$], 264 nm, $R_t$ 7.9 min, 95.9% purity; MS (ESI): m/z 458 (M+H, 100).

Example 42

Synthesis of $N^2$-cycloheptyl-$N^4$-((R)-1-ethyl-pyrrolidin-2-ylmethyl)-$N^6$-(3-fluoro-4-methoxyphenyl)-1,3,5-triazine-2,4,6-triamine (140)

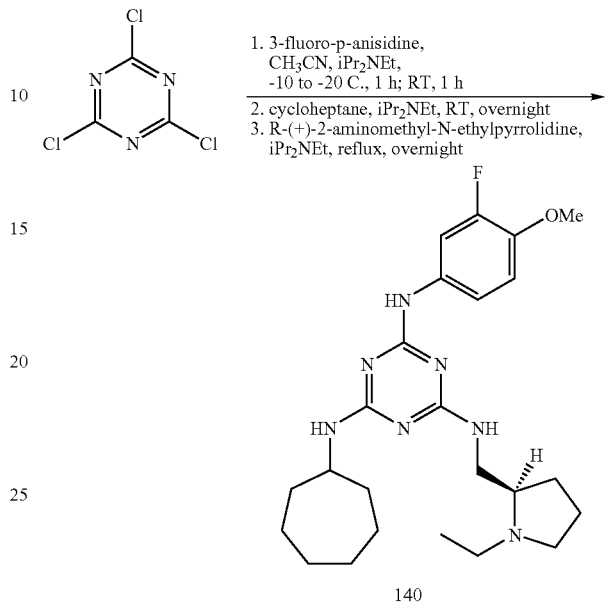

140

To a mixture of cyanuric chloride (0.368 g, 2 mmol) in $CH_3CN$ at about –10 to –20° C. was added 3-fluoro-p-anisidine (0.28 g, 2 mmol) in $CH_3CN$ followed by the addition of N,N-diisopropylethylamine (0.35 mL, 2 mmol) and stirred for an hour. The reaction mixture was then allowed to reach room temperature for an hour. Then cycloheptylamine (0.25 mL, 2 mmol) and DIEA (0.35 mL, 2 mmol) were added and the reaction mixture was stirred overnight at rt. To this reaction mixture R-(+)-2-aminomethyl-N-ethyl pyrrolidine (0.29 mL, 2 mmol) and DIEA (0.35 mL, 2 mmol) were added and the reaction mixture was refluxed overnight. The reaction mixture was diluted with ethyl acetate and washed with brine. The organic layer was separated and dried over potassium carbonate, filtered, and concentrated under reduced pressure affording 0.920 g crude material. The crude material was purified by column chromatography to yield a white solid 140 (0.500 g, 54.7%), mp 77–79° C.; HPLC: Inertsil ODS-3V C18, 40:30:30 [$KH_2PO_4$ (0.01 M, pH 3.2): $CH_3OH$:$CH_3CN$], 264 nm, $R_t$ 7.9 min, 74.3% purity; MS (ESI): m/z 458 (M+H, 100).

Example 43

Synthesis of $N^2$-cyclohexylmethyl-$N^4$-((S)-1-ethyl-pyrrolidin-2-ylmethyl)-$N^6$-(3-fluoro-4-methoxyphenyl)-1,3,5-triazine-2,4,6-triamine (141)

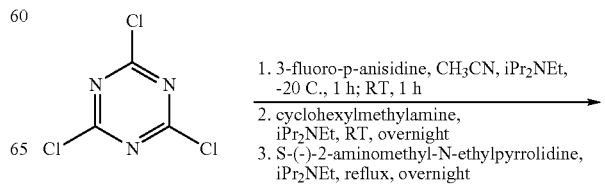

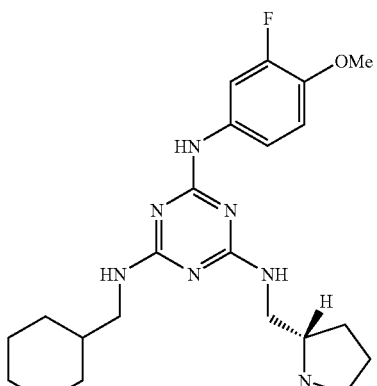

141

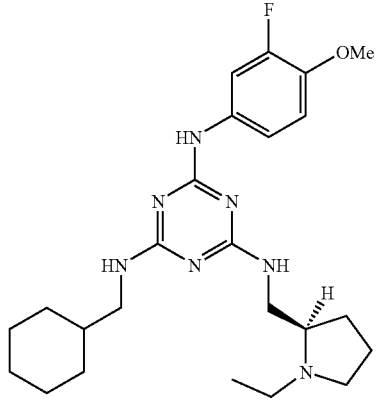

142

To a mixture of cyanuric chloride (0.368 g, 2 mmol) in CH₃CN at about −20° C. was added 3-fluoro-p-anisidine (0.28 g, 2 mmol) in CH₃CN followed by the addition of N,N-diisopropylethylamine (DIEA) (0.35 mL, 2 mmol) and stirred for about 1 hour. The reaction mixture was then stirred at room temperature for about 1 hour. Then, cyclohexylmethyl amine (0.26 mL, 2 mmol) and DIEA (0.35 mL, 2 mmol) were added and the reaction mixture was stirred overnight at RT. Then, S-(−)-2-aminomethyl-N-ethyl pyrrolidine (0.29 mL, 2 mmol) and DIEA (0.35 mL, 2 mmol) were added and the reaction mixture was refluxed overnight. The reaction mixture was diluted with ethyl acetate and washed with brine. The organic layer was separated and dried over sodium sulfate, filtered, and concentrated under reduced. The crude material was purified by column chromatography eluting with 96:3:1 methylene chloride:methanol:conc. ammonium hydroxide to yield a white solid 141 (0.400 g, 43.7%), mp 68–69° C.; HPLC: Inertsil ODS-3V C18, 40:30:30 [KH₂PO₄ (0.01 M, pH 3.2):CH₃OH:CH₃CN], 264 nm, $R_t$ 8.2 min, 97.1% purity; MS (ESI): m/z 458 (M+H, 100), 362 (2.8), 230 (85.4).

Example 44

Synthesis of N²-cyclohexylmethyl-N⁴-((R)-1-ethyl-pyrrolidin-2-ylmethyl)-N⁶-(3-fluoro-4-methoxyphenyl)-1,3,5-triazine-2,4,6-triamine (142)

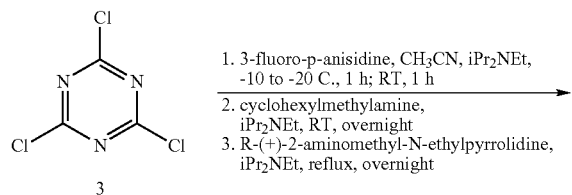

To a mixture of cyanuric chloride (0.368 g, 2 mmol) in CH₃CN at about −20° C. was added 3-fluoro-p-anisidine (0.28 g, 2 mmol) in CH₃CN followed by the addition of DIEA (0.35 mL, 2 mmol) and stirred for about 1 hour. The reaction mixture was then stirred at room temperature for about 1 hour. Then, cyclohexylmethyl amine (0.26 mL, 2 mmol) and DIEA (0.35 mL, 2 mmol) were added and the reaction mixture was stirred overnight at room temperature. Then, R-(+)-2-aminomethyl-N-ethyl pyrrolidine (0.29 mL, 2 mmol) and DIEA (0.35 mL, 2 mmol) were added and the reaction mixture was refluxed overnight. The reaction mixture was diluted with ethyl acetate and washed with brine. The organic layer was separated and dried over sodium sulfate, filtered, and concentrated under reduced pressure. The crude material was purified by column chromatography eluting with 96:3:1 methylene chloride:methanol:conc. ammonium hydroxide to give 142 (0.100 g, 10.9%), mp 66–67° C.; HPLC: Inertsil ODS-3V C18, 40:30:30 [KH₂PO₄ (0.01 M, pH 3.2):CH₃OH:CH₃CN], 264 nm, $R_t$ 8.2 min, 96.7% purity; ¹H NMR (600 MHz, CDCl₃) δ 7.58–7.73 (broad resonance, 1H), 7.07–7.11 (broad resonance, 1H), 6.82 (t, J=9 Hz, 1H), 5.49–5.65 (broad resonance, 1H), 4.96–5.13(broad resonance, 1H), 3.82 (s, 3H), 3.54–3.70 (broad resonance, 1H), 3.13–3.20 (br m, 4H), 2.81 (broad resonance, 1H), 2.54 (broad resonance, 1H), 2.05–2.18 (m, 2H), 2.01 (s, 1H), 1.50–1.83 (br m, 9H), 1.05–1.22 (m, 5H), 0.91 (apt q, J=11.4 Hz, 2H); MS (ESI): mn/z 458 (M+H, 100), 362 (3.8), 230 (99.8), 216 (1), 182 (1.1).

Example 45

Synthesis of ({4-cycloheptylamino-6-[((S)-1-ethyl-pyrrolidin-2-ylmethyl)-amino]-1,3,5-triazin-2-yl}-phenyl-amino)-acetonitrile (143)

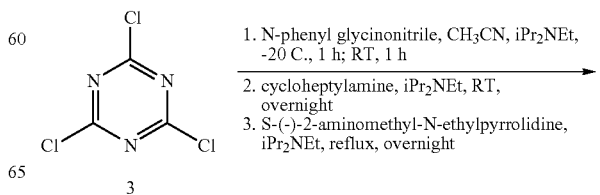

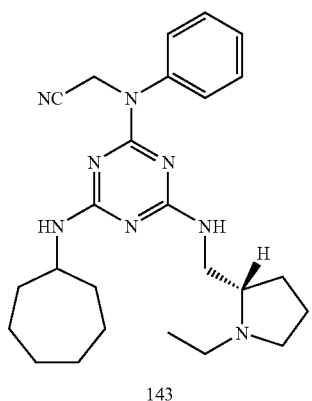

143

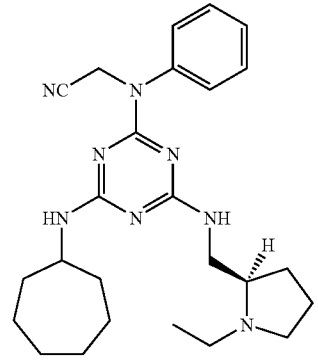

144

To a mixture of cyanuric chloride (0.368 g, 2 mmol) in CH$_3$CN at about −20° C. was added N-phenyl glycinonitrile (0.264 g, 2 mmol) in CH$_3$CN followed by the addition of DIEA (0.35 mL, 2 mmol) and stirred for about 1 hour. The reaction mixture was then stirred at room temperature for about 1 hour. Then, cycloheptylamine (0.25 mL, 2 mmol) and DIEA (0.35 mL, 2 mmol) were added and the reaction mixture was stirred overnight at rt. Then, S-(−)-2-aminomethyl-N-ethyl pyrrolidine (0.29 mL, 2 mmol) and DIEA (0.35 mL, 2 mmol) were added and the reaction mixture was refluxed overnight. The reaction mixture was diluted with ethyl acetate and washed with brine. The organic layer was separated and dried over sodium sulfate, filtered, and concentrated under reduced pressure. The crude material was purified by column chromatography eluting with 96:3:1 methylene chloride:methanol:conc. ammonium hydroxide to yield 143, (0.300 g, 33%) mp 53–55° C.; HPLC: Inertsil ODS-3V C18, 40:30:30 [KH$_2$PO$_4$ (0.01 M, pH 3.2):CH$_3$OH:CH$_3$CN], 264 nm, R$_t$ 6.9 min, 94.1% purity; MS (ESI): m/z 449 (M+H, 100), 381 (1.2), 353 (16.2), 226 (19.9), 225 (54.3), 212 (20.5), 177 (18.3), 164 (9.6).

To a mixture of cyanuric chloride (0.368 g, 2 mmol) in CH$_3$CN at about −20° C. was added N-phenyl glycinonitrile (0.264 g, 2 mmol) in CH$_3$CN followed by the addition of DIEA (0.35 mL, 2 mmol) and stirred for about 1 hour. The reaction mixture was then stirred at room temperature for about 1 hour. Then, cycloheptylamine (0.25 mL, 2 mmol) and DIEA (0.35 mL, 2 mmol) were added and the reaction mixture was stirred overnight at rt. Then, R-(+)-2-aminomethyl-N-ethyl pyrrolidine (0.29 mL, 2 mmol) and DIEA (0.35 mL, 2 mmol) were added and the reaction mixture was refluxed overnight. The reaction mixture was diluted with ethyl acetate and washed with brine. The organic layer was separated and dried over sodium sulfate, filtered, and concentrated under reduced pressure. The crude material was purified by column chromatography eluting with 96:3:1 methylene chloride:methanol:conc. ammonium hydroxide to yield 144, (0.300 g, 33%), mp 53–55° C.; HPLC: Inertsil ODS-3V C18, 40:30:30 [KH$_2$PO$_4$ (0.01 M, pH 3.2):CH$_3$OH:CH$_3$CN], 264 nm, R$_t$ 6.8 min, 92.6% purity; MS (ESI): m/z 449 (M+H, 100), 381 (1.4), 353 (11.8), 226 (13), 225 (33.1), 212 (15), 177 (13.5), 164 (7.8).

Example 47

Synthesis of N$^2$-[(1-ethyl-2-pyrrolidinyl]-N$^4$-(3-fluoro-4-methoxyphenyl)-6-[(S)-2-(methoxymethyl)-1-pyrrolidinyl]-1,3,5-triazine-2,4-diamine (145)

Example 46

Synthesis of ({4-cycloheptylamino-6-[((R)-1-ethyl-pyrrolidin-2-ylmethyl)-amino]-1,3,5-triazin-2-yl}-phenyl-amino)-acetonitrile (144)

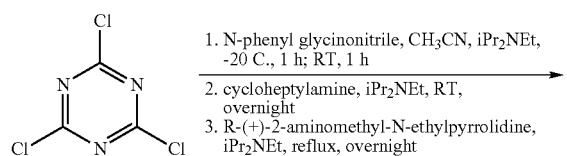

3

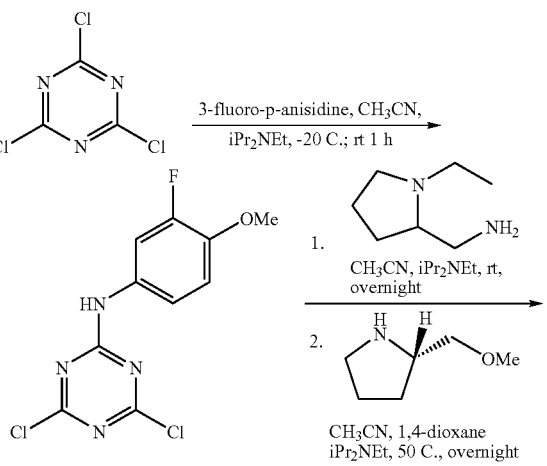

124

-continued

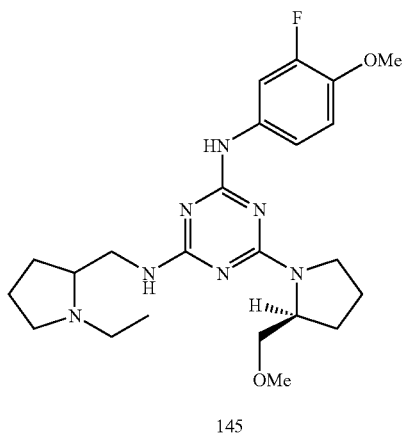

145

Cyanuric chloride (11.07 g, 60 mmol) was dissolved in 40 mL CH₃CN and was cooled to about −20° C. To this was added DIEA (11.5 mL, 60 mmol) followed by 3-fluoro-4-methoxyaninline (8.47 g, 60 mmol) in 20 mL CH₃CN (reaction froze). The reaction was allowed to warm to room temperature after about 1 hour at −20° C. TLC (2% CH₃OH/CH₂Cl₂) and mass spectroscopy indicated the presence of the compound 124. The reaction mixture was cooled to about 0° C. before adding DIEA (11.5 mL, 66 mmol). 2-Aminomethyl-1-ethylpyrrolidine (7.77 g, 60 mmol) in CH₃CN (10 mL) was added. The reaction was allowed to warm to rt and stirred overnight. Then DIEA (11.5 mL, 66 mmol) and S-(+)-2-methoxyethylpyrrolidine (6.91 g, 60 mmol) in 20 mL 1,4-dioxane were added. The reaction was heated at about 50° C. overnight. The solvent was removed in vacuo, and the resulting residue was purified by flash chromatography on silica gel packed in ethyl acetate. The front running impurities were removed and subsequently the eluent was increased in polarity to 10% CH₃OH:ethyl acetate. The material collected from the column was then dissolved in water and extracted in CH₂Cl₂ (4 times), dried over MgSO₄, and concentrated to dryness to give a brown solid 145 (9.7 g, 27.6% yield), 71–72° C.; HPLC: Inertsil ODS-3V C18, 40:30:30 [KH₂PO₄ (0.01M, pH 3.2): CH₃OH:CH₃CN], 264 nm, $R_t$ 5.37 min, 90.3% purity; ¹H NMR (600 MHz, CDCl₃, 55° C.) δ 7.69 (s, 1H), 7.08 (d, J=7.8 Hz, 1H), 6.86 (t, J=9 Hz, 1H), 4.29 (s, 1H), 3.90–3.96 (m, 1H), 3.84 (s, 3H), 3.63–3.81 (m, 6H), 3.35 (s, 3H), 3.23–3.25 (m, 1H), 2.85 (broad s, 1H), 2.78 (broad s 1H), 2.14 (broad s, 2H), 1.89–2.04 (m, 6H), 1.37 (apparent t, J=7.2 Hz, 3H); ¹³C NMR (150.8 MHz, CDCl₃, 55° C.) δ 165.8, 163.8 (2C), 152.3 (d, $J_{c-f}$=243.5 Hz), 143.0 (142.9, rotamer or diastereumer), 133.7 (133.67, rotamer or diastereomer), 115.0, 114.4, 109.1 (108.9, rotamer or diastereomer), 72.8, 66.6, 59.0, 57.0, 56.6, 53.7, 51.0, 46.8, 42.2, 28.4 (28.2, rotamer or diastereomer), 23.1 (23.0, rotamer or diastereomer), 10.9; MS (ESI) m/z 460.2 (M+H, 44.7), 251.1 (47.7), 235.1 (27.5), 231.1 (37.4), 230.6 (100), 214.6 (36.5).

Example 48

Synthesis of (3-Chloro-4-methoxy-phenyl)-(4,6-dichloro-[1,3,5]triazin-2-yl)-amine (101)

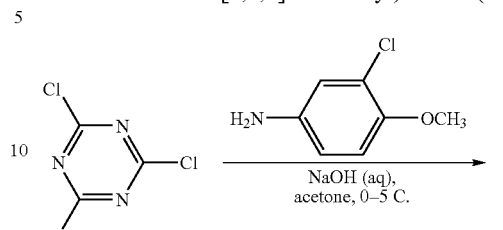

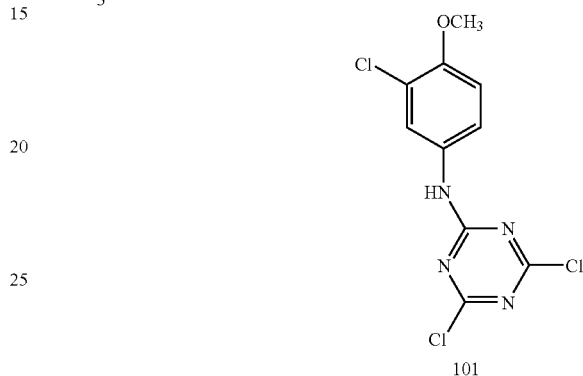

101

To cyanuric chloride (36.911 g, 200.0 mmol) dissolved in acetone (250 mL) stirring at approximately 0–5° C. (ice-water bath), was added a solution of 3-chloro-p-anisidine (31.528 g, 200.0 mmol) in acetone (150 mL) followed by the addition of NaOH solution (80 mL, 2.5 N, 200.0 mmol). The reaction mixture was allowed to stir at approximately 0–5° C. (ice-water bath) for about 1 hour. The reaction mixture was then poured over crushed ice and neutralized with 10% HCl (aq). The resulting solid was washed with water and dried overnight under vacuum to afford 101 (58.3 g, 96%), mp 165° C.; HPLC: YMC Pack Pro C18, 40:30:30 [KH₂PO₄ (0.01M, pH 3.2):CH₃OH:CH₃CN], 264 nm, $R_t$ 24.3 min, 97.8% purity); MS (ESI): m/z 305 (M+H, 100), 283 (26.3), 271 (26.9), 269 (75.2), 139 (16.2).

Example 49

Synthesis of 6-Chloro-N-(3-chloro-4-methoxy-phenyl)-N'-cycloheptyl-[1,3,5]triazine-2,4-diamine (133)

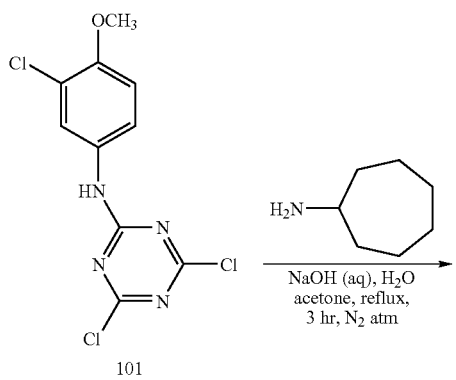

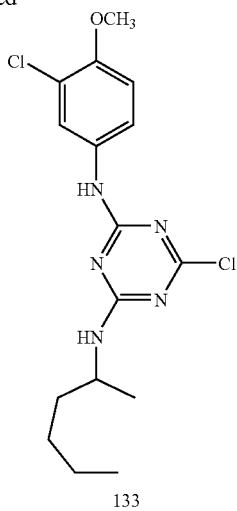

133

To a sample of compound 101 (20.02 g, 65.6 mmol) in acetone (200 mL) was added cycloheptylamine (8.3 mL, 65.5 mmol) in acetone (55 mL) slowly by addition funnel at rt. Then water (66 mL) was added followed by aqueous sodium hydroxide (26.2 mL, 2.5 N, 65.5 mmol) by addition funnel. The reaction mixture was heated at reflux under a nitrogen atmosphere for approximately 3 hours. The reaction was cooled, diluted with ethyl acetate, washed 1 time with water, and finally 1 time with brine. The organic layer was separated and dried over potassium carbonate/sodium sulfate. The organic layer was filtered and concentrated in vacuo. The product (24.13 g) was purified by flash column chromatography (silica gel, 1:4 ethyl acetate:hexanes). The fractions were combined and concentrated in vacuo to afford 133 as a pale yellow solid (17.66 g, 70.5%), mp 146° C.; HPLC: Inertsil ODS-3V C18, 40:10:50 [$KH_2PO_4$ (0.01M, pH 3.2):$CH_3OH$:$CH_3CN$], 264 nm, $R_t$ 58.8 min, 99.9% purity); MS (ESI): m/z 382 (M+H, 100), 241 (2.8), 226 (8.4), 139 (43.5), 116 (6).

Example 50

Synthesis of N-(3-Chloro-4-methoxy-phenyl)-N'-cycloheptyl-N''-methyl-N''-(1-methyl-piperidin-4-yl)-[1,3,5]triazine-2,4,6-triamine (137)

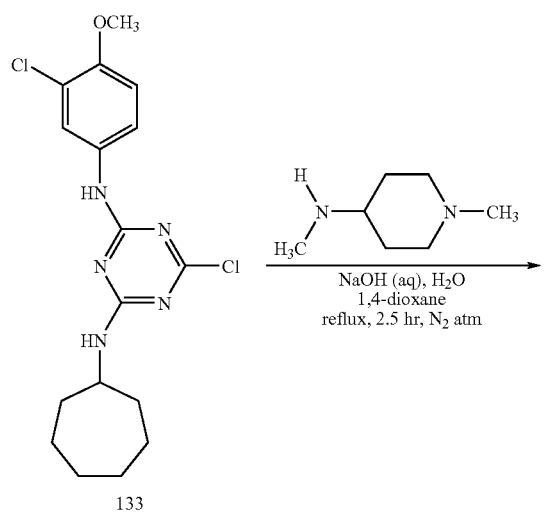

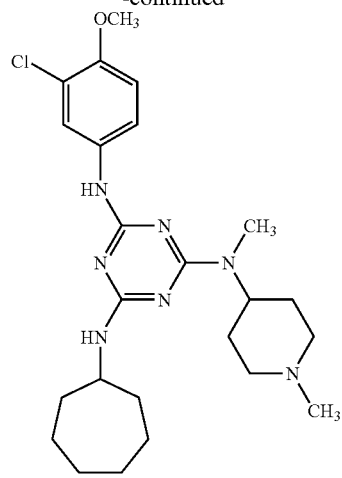

137

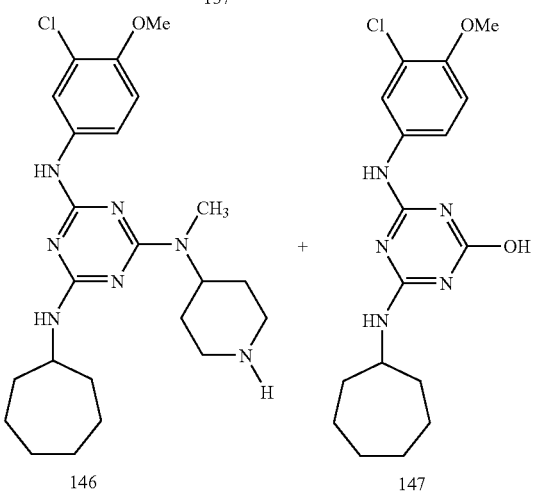

146               147

To 133 (10.014 g, 26.2 mmol) in 1,4-dioxane (80 mL) was added slowly methyl-(1-methyl-piperidin-4-yl)-amine (3.8 mL, 26.2 mmol) dissolved in 1,4-dioxane (15 mL) by addition funnel. Then aqueous sodium hydroxide (10.5 mL, 2.5 N, 26.2 mmol) was added by addition funnel followed by water (26 mL). The reaction mixture was heated at reflux for about 2.5 hours under a nitrogen atmosphere. The reaction was cooled and diluted with methylene chloride. The reaction mixture was filtered using vacuum and the white solid 147 removed. The filtrate was then washed 1 time with brine. The aqueous layer was back extracted 1 time with methylene chloride. The organic layers were combined and dried over potassium carbonate. The organic solution was filtered and concentrated in vacuo to afford the crude product (5.89 g). The crude reaction product was purified by flash column chromatography (silica gel) eluting with 96:3:1 methylene chloride:methanol:15 M ammonium hydroxide. The fractions were combined, dried over sodium sulfate/potassium carbonate, filtered, and concentrated in vacuo to afford 137 as a white solid (3.84 g, 30.9%), mp 104–105° C.; HPLC: YMC Pack Pro C18, 40:30:30 [$KH_2PO_4$ (0.01M, pH 3.2):$CH_3OH$:$CH_3CN$], 264 nm, $R_t$ 13.8 min, 97% purity); MS (ESI): m/z 474 (M+H, 41), 408 (2.3), 364 (2.8), 258 (13), 239 (14), 239 (47.5), 238 (100), 127 (5.3).

Example 51

Synthesis of N²-(3-chloro-4-methoxy-phenyl)-N⁴-cycloheptyl-N⁶-methyl-N⁶-piperidin-4-yl-1,3,5-triazine-2,4,6-triamine (146)

Compound 146 was isolated as a by-product via column chromatography (silica gel, 96:3:1 methylene chloride:methanol:conc. ammonium hydroxide, mp 114–116° C.; TLC (silica gel, 90:9:1, $CH_2Cl_2$:$CH_3OH$; conc. $NH_4OH$), $R_f$ 137 0.31 and $R_f$ 146 0.15; HPLC: Inertsil ODS-3V C18, 40:30:30 [$KH_2PO_4$ (0.01M, pH 3.2):$CH_3OH$:$CH_3CN$], 264 nm, $R_t$ 10.7 min, 91.1% purity); MS (ESI): m/z 460 (M+H, 25.4), 364 (17.9), 292 (2), 273 (17.1), 272 (37.9), 252 (44), 251 (100), 231 (2.2), 157 (10.54), 118 (2.8).

Example 52

Synthesis of 4-(3-Chloro-4-methoxy-phenylamino)-6-cycloheptylamino-1,3,5-triazin-2-ol (147)

Compound 147 was isolated as a by-product by vacuum filtration prior to isolation of 137, white solid, mp>310° C.; MS (ESI); m/z 727 ([2(363)+H], 1.2, 364 (M+H, 100).

Example 53

Synthesis of N-(1-Aza-bicyclo[2.2.2]oct-3-yl)-N'-(3-chloro-4-methoxy-phenyl)-N"-)1-ethyl-pyrrolidin-2-ylmethyl)-[1,3,5]triazine-2,4,6-triamine (148)

To 101 (3.056 g, 10.0 mmol) dissolved in anhydrous acetonitrile (30 mL) at about 0° C. was added a solution of 2-(aminomethyl)-1-ethylpyrrolidine (1.5 mL, 10.0 mmol) in anhydrous acetonitrile (5 mL) followed by addition of a DIEA (1.9 mL, 11.0 mmol). The reaction mixture was allowed to warm to room temperature and was stirred at room temperature overnight under nitrogen. Then DIEA (1.9 mL, 11 mmol) was added which was followed by addition of 3-aminoquinuclidine dihydrochloride (1.962 g, 10.0 mmol) in 1,4-dioxane (5 mL). The reaction mixture was allowed to stir at reflux overnight under nitrogen. The reaction mixture was extracted 2 times with dichloromethane and 1 time with ethyl acetate. The combined organic layers were washed one time with brine and dried over anhydrous potassium carbonate. The organic layer was with 20% HCl (aq). The aqueous layer was neutralized with 2.5 N NaOH (aq) and then extracted 3 times with ethyl acetate. The combined organic layers were washed 1 time with brine, dried over potassium carbonate, concentrated on a rotary evaporator and allowed to dry overnight under vacuum. Column chromatography (silica gel, 85:14:1 dichloromethane:methanol:conc. ammonium hydroxide) yielded a pale white solid 148 (100 mg, 2%), mp 83° C.; HPLC: Inertsil ODS-3V C18, 40:30:30 [$KH_2PO_4$ (0.01M, pH 3.2):$CH_3OH$:$CH_3CN$], 264 nm, $R_t$ 8.1 min, 71.2% purity); MS (ESI): m/z 488 (M+H, 18.7), 280 (100), 245 ([M+2H]++, 37.4), 236 (23.5).

Example 54

Synthesis of N²-(3-chloro-4-diethylamino-phenyl)-N⁴-cycloheptyl-N⁶-(1-ethyl-pyrrolidin-2-ylmethyl)-1,3,5-triazine-2,4,6-triamine (149)

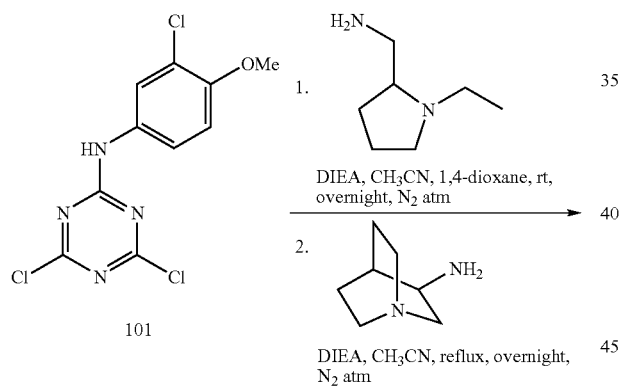

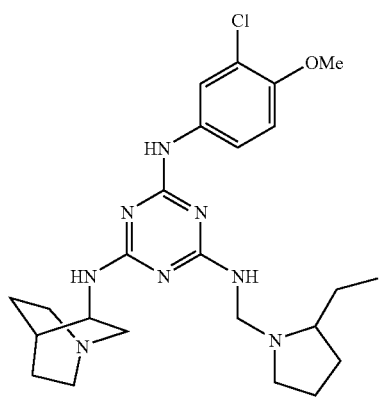

148

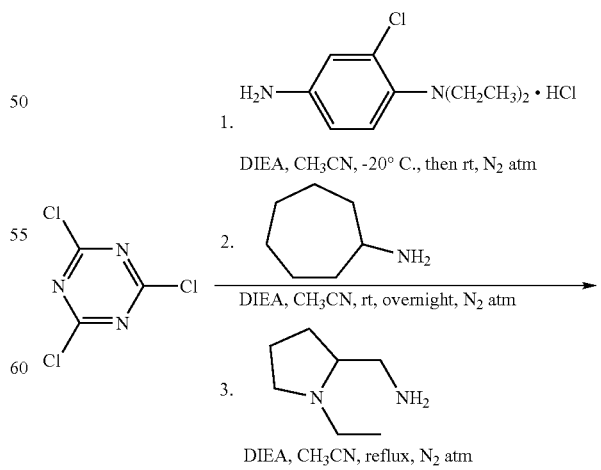

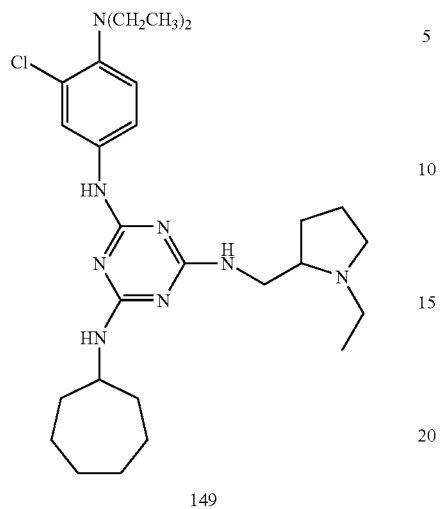

149

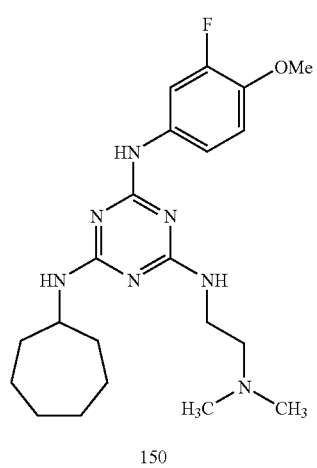

150

To a mixture of cyanuric chloride (1.8 g, 9.7 mmol) in CH₃CN at about −20° C. was added 2-chloro-N,N-diethyl phenylene-1,4-diamine hydrochloride (2.35 g, 10 mmol) in CH₃CN followed by the addition of N,N-diisopropylethylamine (DIEA) (1.75 mL, 10 mmol) and stirred for an hour. The reaction mixture was then allowed to reach room temperature for about 1 hour. Then cycloheptylamine (1.25 mL, 9.8 mmol) and DIEA (1.75 mL, 10 mmol) were added and the reaction mixture was stirred overnight at rt. Then, 2-(aminomethyl)-1-ethylpyrrolidine (1.45 mL, 10 mmol) and DIEA (1.75 mL, 10 mmol) were added and the reaction mixture was refluxed overnight. The reaction mixture was diluted with ethyl acetate and washed with brine. The organic layer was separated and dried over sodium sulfate, filtered, and concentrated under reduced pressure. The crude material was purified by column chromatography (silica gel) eluting with 96:3:1 methylene chloride:methanol:conc. ammonium hydroxide to yield 149 (0.800 g, 15%) as a white solid, mp 84–85° C.; HPLC: Inertsil ODS-3V C18, 40:30:30 [KH$_2$PO$_4$ (0.01 M, pH 3.2):CH₃OH:CH₃CN], 264 nm, R$_t$ 9.5 min, 96% purity; MS (ESI): m/z 515 (M+H, 9.4), 259 (16.8), 258 (55.1), 257 (100).

Cyanuric chloride (1.84 g, 10 mmol) in CH₃CN (20 mL) was cooled to about −10° C. was added 3-fluoro-p-anisidine (1.41 g, 10 mmol) followed by DIEA (1.8 mL, 10 mmol). The reaction was stirred for about 45 min then at room temperature for about 45 min under an N₂ atmosphere. Cycloheptylamine (1.26 mL, 10 mmol) was added followed by DIEA (1.8 mL, 10 mmol) and the reaction was stirred at room temperature overnight. N,N-dimethylethylenediamine (1.1 mL, 10 mmol) was added followed by DIEA (1.8 mL, 10 mmol) and the mixture was heated at reflux under N₂ overnight. The reaction was diluted with ethyl acetate, washed with brine, and dried over anhydrous K₂CO₃. The material (1.178 g) was purified by silica gel column chromatography to afford a solid 150 (1.178 g, 28%), mp 73–76° C.; HPLC: Inertsil ODS-3V C18, 40:30:30 [KH$_2$PO$_4$ (0.01M, pH 3.2):CH₃OH:CH₃CN], 264 nm, R$_t$ 10.8 min, 95.1% purity; MS (ESI): m/z 418 (M+H, 100), 373 (11.9), 322 (7.8), 277 (6.8), 162 (3.6).

Example 55

Synthesis of N²-cycloheptyl-N⁴-(2-dimethylamino-ethyl)-N⁶-(3-fluoro-4-methoxy-phenyl)-1,3,5-triazine-2,4,6-triamine (150)

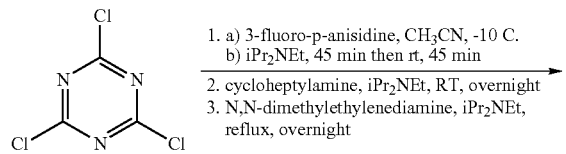

1. a) 3-fluoro-p-anisidine, CH₃CN, -10 C.
   b) iPr₂NEt, 45 min then rt, 45 min
2. cycloheptylamine, iPr₂NEt, RT, overnight
3. N,N-dimethylethylenediamine, iPr₂NEt, reflux, overnight Example 56

Synthesis of ({4-cycloheptylamino-6-[1-ethyl-pyrrolidin-2-ylmethyl)-amino]-1,3,5-triazin-2-yl}-phenyl-amino)-acetonitrile (151)

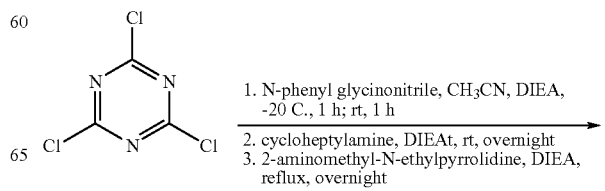

1. N-phenyl glycinonitrile, CH₃CN, DIEA, -20 C., 1 h; rt, 1 h
2. cycloheptylamine, DIEAt, rt, overnight
3. 2-aminomethyl-N-ethylpyrrolidine, DIEA, reflux, overnight

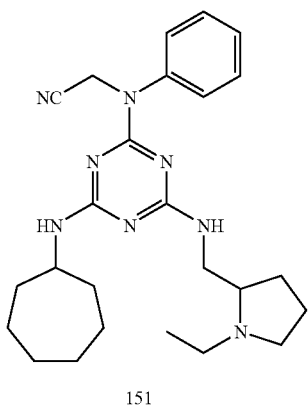

151

To cyanuric chloride (1.84 g, 10 mmol) in CH₃CN (20 mL) at about −10 to −20° C. was added DIEA (1.75 mL, 10 mmol) and N-phenyl glycinonitrile (1.3 g, 10 mmol), and stirred for about 1 hour. The reaction mixture was then allowed to reach room temperature for an hour. To this reaction mixture, DIEA (1.75 mL, 10 mmol) and cycloheptylamine (1.25 mL, 10 mmol) were added and the reaction mixture was stirred overnight at rt. Then, DIEA (1.75 mL, 10 mmol) and 2-aminomethyl-N-ethylpyrrolidine (1.45 mL, 10 mmol) were added and the reaction mixture was refluxed overnight. The reaction mixture was worked-up, isolated, and then purified by column chromatography (silica gel) eluting with 96:3:1 methylene chloride:methanol:conc. ammonium hydroxide to yield 151, (3 g, 66%), mp 52–54 ° C.; MS (ESI): m/z 449 (M+H, 100), 225 [(M+2H)²⁺, 22.3].

Example 57

Synthesis of N-Azepan-1-yl-6-chloro-N'-(3-chloro-4-methoxy-phenyl)-[1,3,5]triazine-2,4-diamine (152)

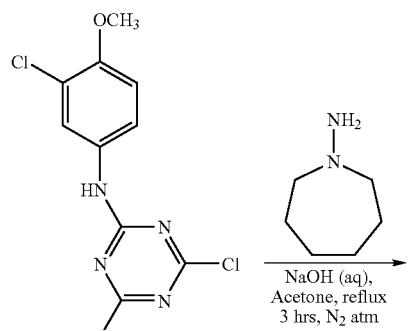

101

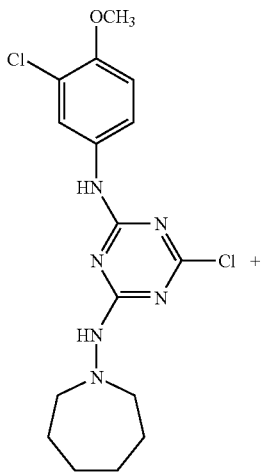

152

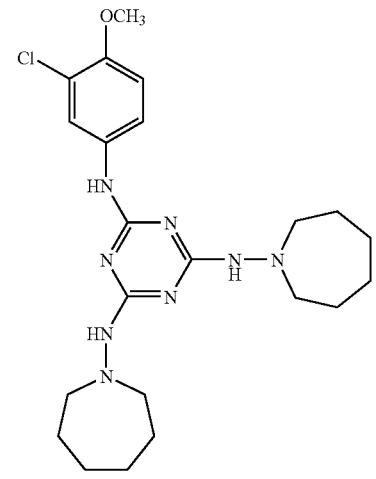

153

To 101 (6.03 g, 20.0 mmol) dissolved in acetone (75 mL) was added a solution of 1-aminohomopiperidine (2.3 mL, 20.0 mmol) in acetone (10 mL) followed by addition of NaOH (8.0 mL 2.5 N NaOH solution, 20.0 mmol) and 20 mL of water. The reaction mixture was allowed to stir at reflux overnight under nitrogen. The reaction mixture was extracted 3 times with dichloromethane; the combined organic layers were washed with brine and dried over potassium carbonate. The sample was concentrated on a rotary evaporator and the resulting oil was dried overnight under vacuum. Column chromatography (96:3:1 dichloromethane:methanol:conc. ammonium hydroxide) yielded a light purple solid 152 (1.2 g, 16%), mp 139° C.; TLC (silica gel, 96:3:1, CH₂Cl₂, CH₃OH, conc. NH₄OH), R$_f$ 0.31; HPLC: Inertsil ODS-3V C18, 40:30:30 [KH₂PO₄ (0.01M, pH 3.2):CH₃OH:CH₃CN], 264 nm, R$_t$ 52.5 min, 94.9% purity; MS (ESI): m/z 383 (M+H, 100).

Example 58

Synthesis of N''-(3-chloro-4-methoxy-phenyl)-N,N'-bis-perhydro-azepin-1-yl-1,3,5-triazine-2,4,6-triamine (153)

Compound 153 was isolated as a by-product (2.3 g) by column chromatography (silica gel, 96:3:1, CH₂Cl₂, CH$_3$OH, conc. NH$_4$OH), mp 199° C.; TLC (silica gel, 96:3:1, CH$_2$Cl$_2$, CH$_3$OH, conc. NH$_4$OH), R$_f$ 0.11; HPLC: Inertsil ODS 3V C18, 40:30:30 [KH$_2$PO$_4$ (0.01M, pH 3.2) :CH$_3$OH:CH$_3$CN], 264 nm, R$_t$ 15 min, 86% purity); MS (ESI): m/z 461 (M+H, 100), 366 (19.7), 365 (19.6), 232 (11), 231 (27.3).

Example 59

Synthesis of N-Azepan-1-yl-N'-(3-chloro-4-methoxy-phenyl)-N''-(1-methyl-piperidin-4-yl)-[1,3,5]triazine-2,4,6-triamine (154)

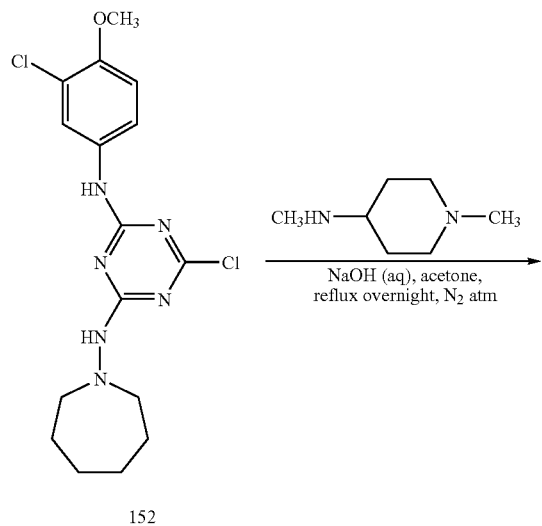

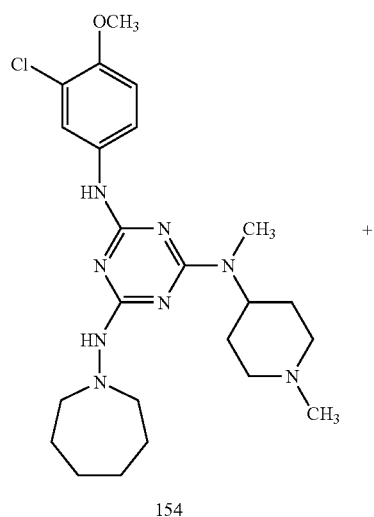

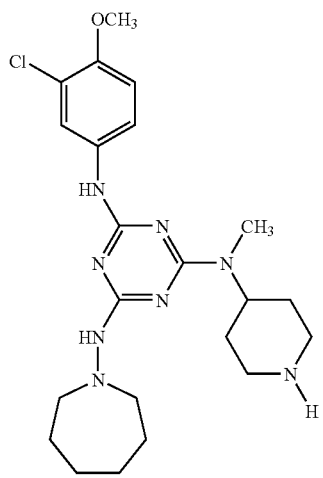

155

To 152 (0.2007 g, 0.5 mmol) dissolved in THF (10 mL) was added a solution of N-methyl-4(methylamino)piperidine (0.07 mL, 0.5 mmol) in THF (1 mL) followed by the addition of DIEA (1.0 mL, 0.55 mmol) in acetonitrile (1 mL). The reaction mixture was allowed to stir at reflux overnight under nitrogen. The reaction mixture was extracted 3 times with dichloromethane; the combined organic layers were washed with brine and dried over potassium carbonate. The sample was concentrated on a rotary evaporator and the resulting oil was dried overnight under vacuum. Column chromatography (90:9:1 dichloromethane:methanol:conc. ammonium hydroxide) yielded a light yellow solid 154 (65 mg, 27%), mp 100° C.; TLC (silica gel, 90:9:1 CH$_2$Cl$_2$:CH$_3$OH, conc. NH$_4$OH), R$_f$ 0.36; MS (ESI): m/z 475 (M+H, 23.2), 378 (11.6), 258 (68.9), 239 (52.2), 238 (100).

Example 60

Synthesis of N$^4$-(3-chloro-4-methoxy-phenyl)-N$^6$-methyl-N$^2$-perhydro-azepin-1-yl-N$^6$-piperidin-4-yl-1,3,5-triazine-2,4,6-triamine (155)

Compound 155 was obtained as a by product (50 mg) of the reaction via column chromatography (silica gel, 90:9:1 dichloromethane:methanol:conc. ammonium hydroxide), mp 81° C.; TLC (silica gel, 90:9:1 CH$_2$Cl$_2$:CH$_3$OH, conc. NH$_4$OH), R$_f$ 0.25; MS (ESI): m/z 461 (M+H, 20.3), 430 (2.8), 273 (11.8), 272 (25.5), 251 (100), 236 (4.6), 215 (4.7).

Example 61

Synthesis of N,N'-di-n-propyl-N''-(3-fluoro-4-methoxy-phenyl)-1,3,5-triazine-2,4,6-triamine (156)

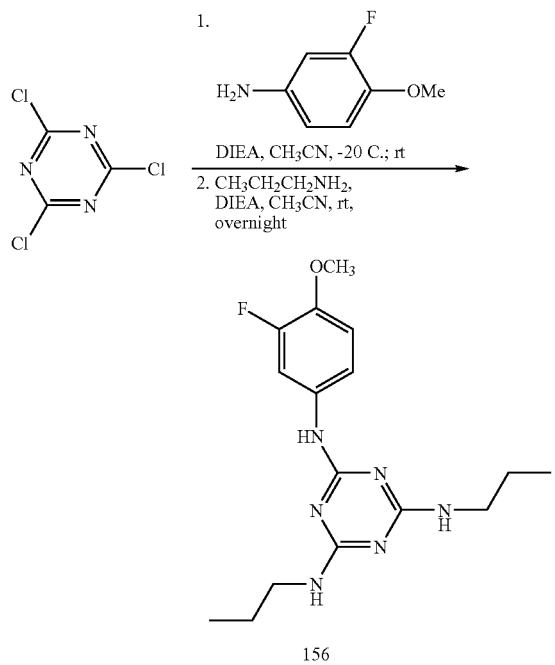

156

To cyanuric chloride (0.368 g, 2 mmol) in CH$_3$CN at about –20° C. was added 3-fluoro-p-anisidine (0.28 g, 2 mmol) in CH$_3$CN followed by the addition of DIEA (0.39 mL, 2.2 mmol) and stirred for about 1 hour. The reaction mixture was then stirred at room temperature for about 1 hour. Then n-propylamine (1.64 mL, 19.9 mmol) and DIEA (0.39 mL, 2.2 mmol) were added and the reaction mixture was stirred overnight at rt. The reaction mixture was worked up as usual, diluted with ethyl acetate and washed with brine. The organic layer was separated and dried over sodium sulfate, filtered, concentrated under reduced pressure, and compound 156 was purified by silica gel column chromatography. mp 53–55° C.; HPLC: Inertsil ODS-3V C18, 40:30:30 [KH$_2$PO$_4$ (0.01 M, pH 3.2):CH$_3$OH:CH$_3$CN], 264 nm, R$_t$ 12.6 min, 93.7% purity; MS (ESI): m/z 335 (M+H, 100), 331 (1.5), 126 (1).

Example 62

Synthesis of N,N'-dicyclopropyl-N''-(3-fluoro-4-methoxy-phenyl)-1,3,5-triazine-2,4,6-triamine (157)

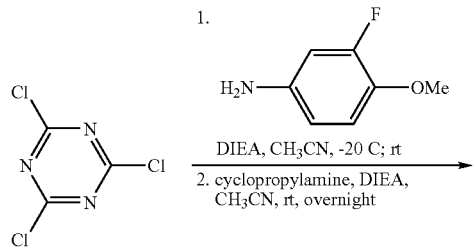

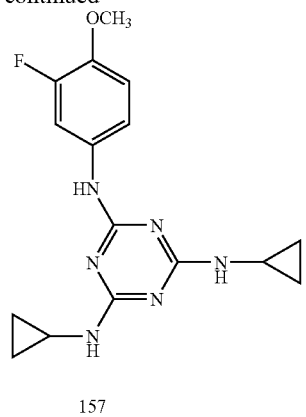

157

To cyanuric chloride (0.368 g, 2 mmol) in CH$_3$CN at about –20° C. was added 3-fluoro-p-anisidine (0.28 g, 2 mmol) in CH$_3$CN followed by the addition of DIEA (0.39 mL, 2.2 mmol) and stirred for about 1 hour. The reaction mixture was then stirred at room temperature for about 1 hour. Then cyclopropylamine (1.39 mL, 20 mmol) and DIEA (0.39 mL, 2.2 mmol) were added and the reaction mixture was stirred overnight at rt. The reaction mixture was worked up as usual, diluted with ethyl acetate and washed with brine. The organic layer was separated and dried over sodium sulfate, filtered, concentrated under reduced pressure, and compound 157 was purified by silica gel column chromatography (200 mg, 30%), mp 91–92° C.; HPLC: Inertsil ODS-3V C18, 40:30:30 [KH$_2$PO$_4$ (0.01 M, pH 3.2):CH$_3$OH:CH$_3$CN], 264 nm, R$_t$ 8.6 min, 99.1% purity; MS (ESI): m/z 331(M+H, 100), 305 (0.8), 151 (0.3).

Example 63

Synthesis of N$^2$-Cycloheptyl-N$^4$-(3-fluoro-4-methoxy-phenyl)-N$^6$-methyl-N$^6$-(1-methyl-piperidin-4-yl)-1,3,5-triazine-2,4,6-triamine (158)

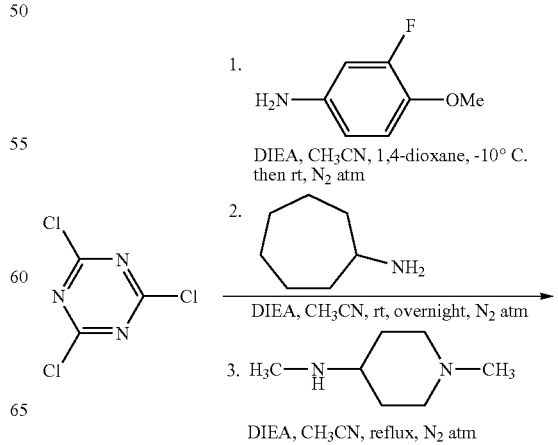

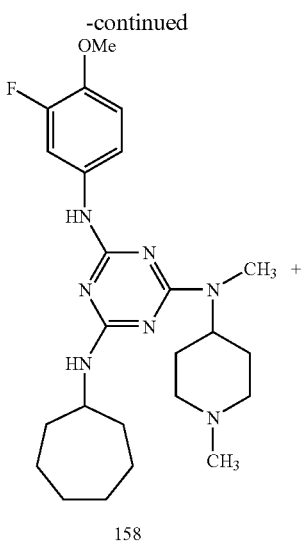

158

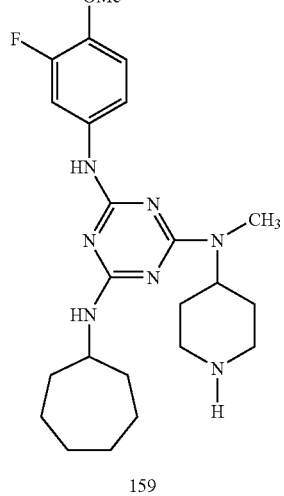

159

Example 64

Synthesis of $N^2$-Cycloheptyl-$N^4$-(3-fluoro-4-methoxy-phenyl)-$N^6$-methyl-$N^6$-piperidin-4-yl-1,3,5-triazine-2,4,6-triamine (159)

Compound 159 was isolated as a by-product (55 mg) by column chromatography (silica gel, 90:9:1 dichloromethane:methanol:conc. ammonium hydroxide); TLC (silica gel, 90:9:1, $CH_2Cl_2$, $CH_3OH$, conc. $NH_4OH$), $R_f$ 0.1); HPLC: Inertsil ODS-3V C18, 40:30:30 [$KH_2PO_4$ (0.01 M, pH 3.2):$CH_3OH$:$CH_3CN$], 264 nm, $R_t$ 8.3 min, 93.5% purity; MS (ESI): m/z 443 (M+H, 100).

Example 65

Synthesis of $N^2$-cycloheptyl-$N^4$-(3-fluoro-4-methoxyphenyl)-$N^6$-methyl-$N^6$-(1-methyl-piperidin-4-yl)-1,3,5-triazine-2,4,6-triamine, hydrogen chloride salt (160)

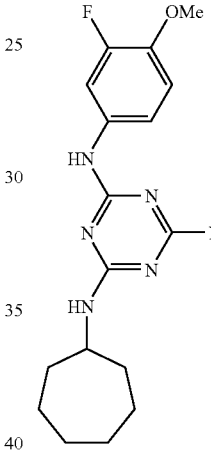

171

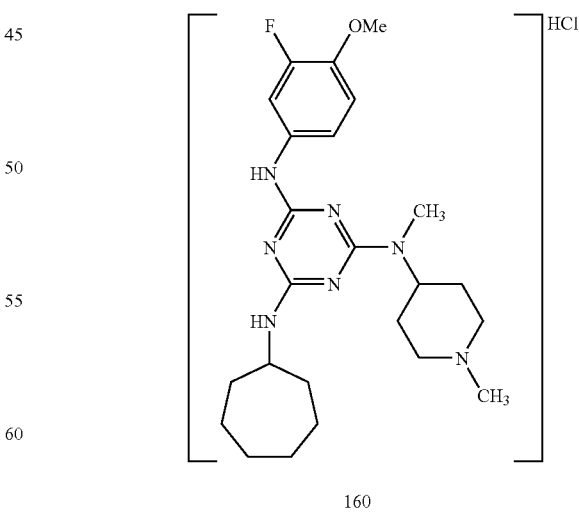

160

To cyanuric chloride (0.180 g, 1 mmol) in 1,4-dioxane (1 mL) at about −10 to −20° C. was added N,N-diisopropylethylamine (DIEA) (0.19 mL, 1 mmol) in $CH_3CN$ (1 mL) and 3-fluoro-p-anisidine (0.14 g, 1 mmol) in $CH_3CN$ (1 mL) and stirred for about 1 hour. The reaction mixture was then stirred at room temperature for about 1 hour. Then a solution of cycloheptylamine (0.13 mL, 1 mmol) and DIEA (0.19 mL, 1 mmol) in $CH_3CN$ (0.5 mL) was added and the reaction mixture was stirred overnight at rt. Then, N-methyl-4(methylamino)piperidine (0.15 mL, 1 mmol) and DIEA (0.19 mL, 1 mmol) in $CH_3CN$ (0.5 mL) were added and the reaction mixture was refluxed overnight. The reaction mixture was worked-up using saturated sodium bicarbonate, and brine. The organic layer was separated and dried over sodium sulfate, filtered, and concentrated under reduced pressure. The crude material was purified by column chromatography (silica gel, 90:9:1 dichloromethane:methanol:conc. ammonium hydroxide) to give 158 (0.130 g, 28%); TLC (silica gel, 90:9:1, $CH_2Cl_2$, $CH_3OH$, conc. $NH_4OH$), $R_f$ 0.26); $^1H$ NMR (600 MHz, $CDCl_3$, 55° C.) δ 7.74 (br s, 1H), 6.94 (br s, 1H), 6.81–6.84 (m, 2H), 4.83 (br resonance, 1H), 4.55 (s, 1H), 3.98 (s, 1H), 3.82 (s, 3H), 2.97 (s, 3H), 2.94 (br d, J=11.9 Hz, 2H), 2.29 (s, 3H), 2.06–2.10 (m, 2H), 1.93–1.97 (m, 2H), 1.84–1.90 (m, 2H), 1.44–1.66 (m, 12H).

To 171 in dry methanol (1 mL, prepared according to parallel synthesis Method C using the appropriate monomers, as disclosed herein) was added HCl (0.3 mL, 0.3 mmol, 1 M in diethyl ether) by syringe under a $N_2$ atmosphere. The mixture was stirred for 10 min at room temperature, concentrated and dried in vacuo overnight to give an off-white solid 160 (0.131 g) that is water soluble, mp 189–190° C. (at 160° C. sample turns brown); HPLC: Inertsil ODS-3V C18, 40:30:30 [$KH_2PO_4$ (0.01 M, pH 3.2):$CH_3OH$:$CH_3CN$], 264 nm, $R_t$ 7.3 min, 89.1% purity.

Example 66

Synthesis of [N-(3-Chloro-4-methoxy-phenyl)-N'-cycloheptyl-N''-methyl-N''-(1-methyl-piperidin-4-yl)-[1,3,5]trizaine-2,4,6-triamine (161)

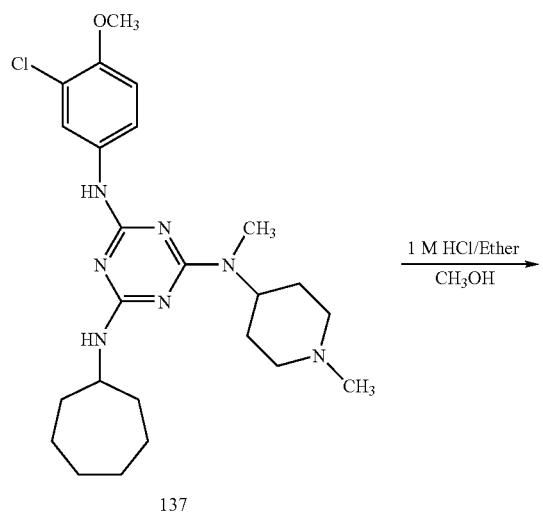

137

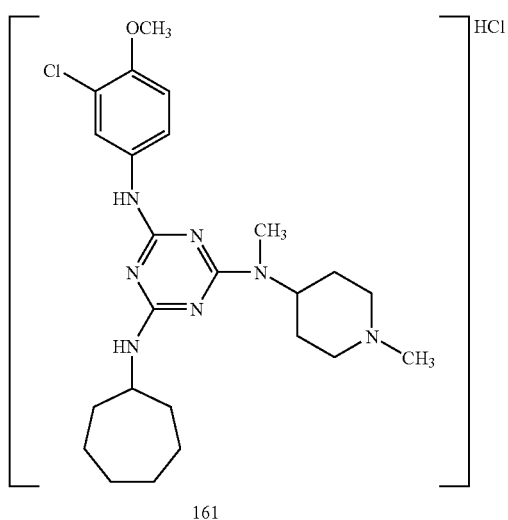

161

Example 67

Synthesis of $N^2$-(3-chloro-4-diethylamino-phenyl)-$N^4$-cycloheptyl-$N^6$-(1-ethyl-pyrrolidin-2-ylmethyl)-1,3,5-triazine-2,4,6-triamine hydrogen chloride salt (163)

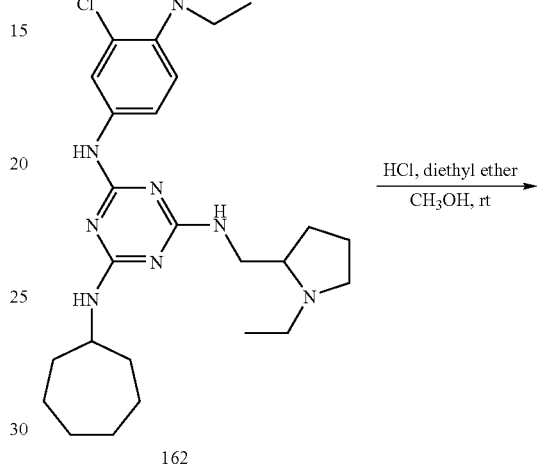

162

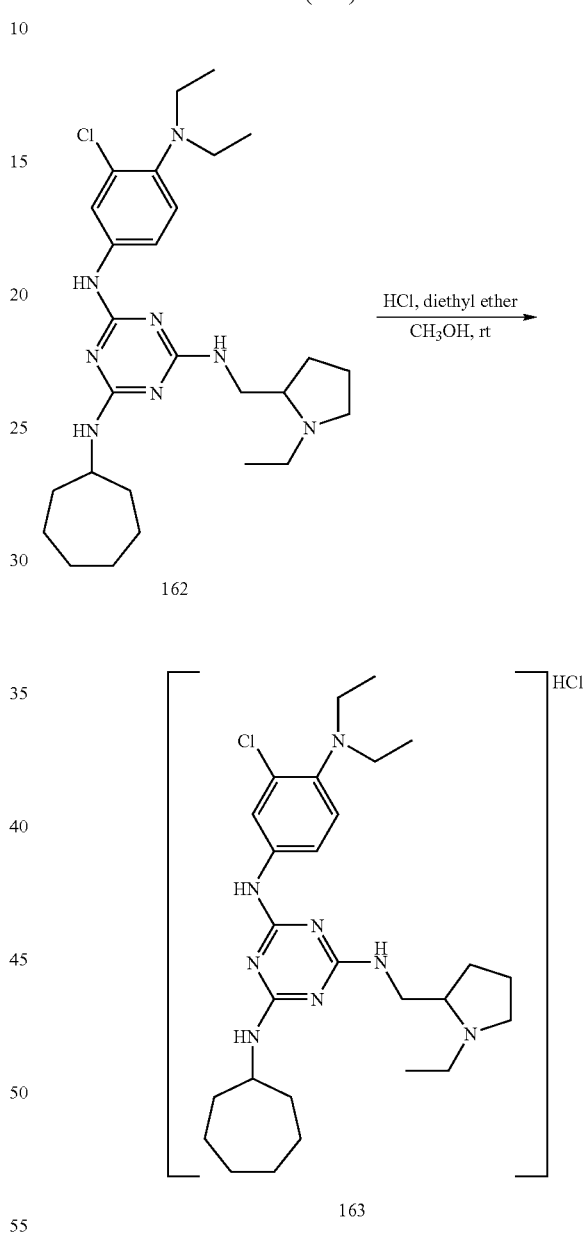

163

To 137 (0.473 g, 1.0 mmol) dissolved in methanol (5 mL) was added 1.0 M hydrochloric acid in diethyl ether (1.0 mL, 1 mmol). The reaction mixture was allowed to stir for about 1 hour at room temperature. The reaction mixture was then concentrated on a rotary evaporator. The resulting solid was dissolved in water, filtered and concentrated on the rotary evaporator. The sample was freeze dried under vacuum and a solid 161 (359.1 mg, 70%) was collected, mp 173–176° C.

To 162 (1.0 g, 2 mmol, prepared according to parallel synthesis method A with the appropriate monomers, as disclosed herein) in methanol (10 mL) was added HCl (2.5 mL, 2.5 mmol, 1 M) in diethyl ether and stirred. The reaction mixture was evaporated. It was then dissolved in water, filtered, evaporated in vacuo, and dried over night under vacuum to afford a solid 163 (1.1 g, 93%).

Example 68

Synthesis of $N^2$-cycloheptyl-$N^4$-(1-ethyl-pyrrolidin-2-ylmethyl)-$N^6$-(3-fluoro-4-methoxyphenyl)-1,3,5-triazine-2,4,6-triamine hydrogen chloride salt (164)

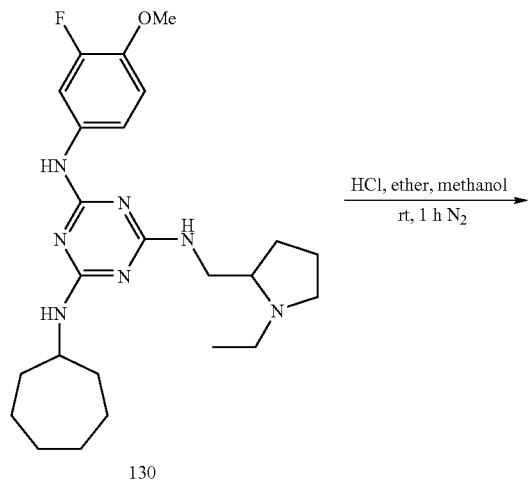

Example 69

Synthesis of $N^2$-(cyclohexylmethyl)-$N^4$-[(1-ethyl-2-pyrrolidinyl)methyl]-$N^6$-(4-fluoro-3-methoxyphenyl)-1,3,5-triazine-2,4,6-triamine hydrogen chloride salt (165)

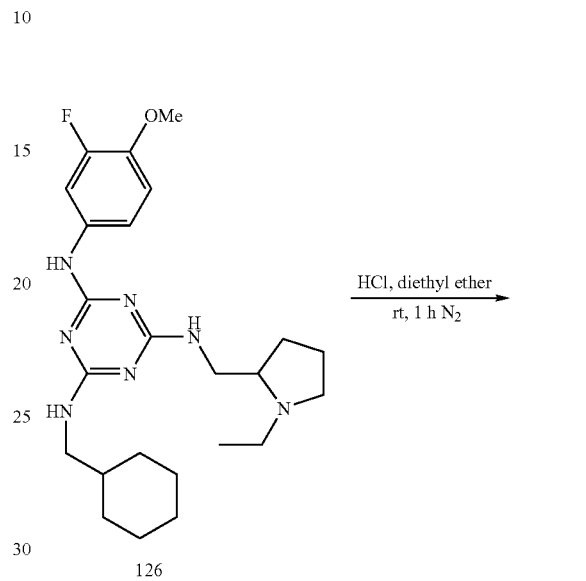

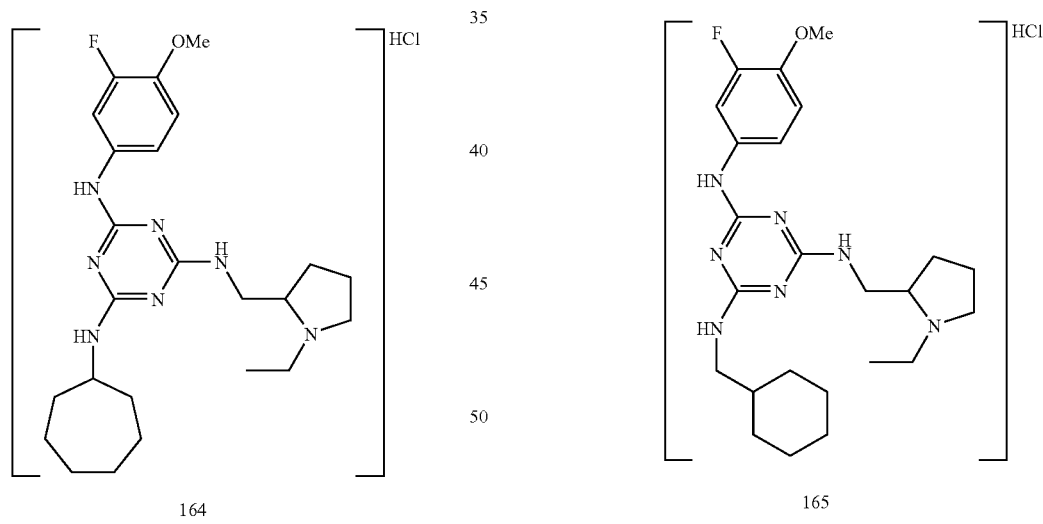

To 130 (2.285 g, 5 mmol) in dry methanol (10 mL) was added HCl (5 mL, 5 mmol, 1 M in diethyl ether) and stirred at room temperature for about 1 hour. The reaction was evaporated in vacuo, dissolved in water, filtered, evaporated and then dried under vacuum overnight to afford a solid 164 (2.396 g, 97%), mp 131–133° C.; HPLC: Inertsil ODS-3V C18, 40:30:30 [$KH_2PO_4$ (0.01 M, pH 3.2):$CH_3OH$:$CH_3CN$], 264 nm, $R_t$ 7.9 min, 98.2% purity.

To 136 (0.457 g, 1 mmol) in dry diethyl ether was added HCl (1 mL, 1 mmol, 1 M in diethyl ether). A precipitate formed immediately. The mixture was stirred at room temperature for about 1 hour, and then concentrated in vacuo. The resulting material was dissolved in water, filtered, evaporated, and dried overnight in vacuo to give a solid 165 (0.400 g, 81%), mp 85° C.; HPLC: Inertsil ODS-3V C18, 40:30:30 [$KH_2PO_4$ (0.01 M, pH 3.2):$CH_3OH$:$CH_3CN$], 264 nm, $R_t$ 8.2 min, 89.6% purity;

Example 70

Synthesis of ({4-cycloheptylamino-6-[(1-ethyl-pyrrolidin-2-ylmethyl)-amino]-1,3,5-triazin-2-yl}-phenyl-amino)-acetonitrile hydrogen chloride salt (166)

Example 71

Synthesis of $N^2$-cycloheptyl-$N^4$-(3-fluoro-4-methoxy-phenyl)-$N^6$-methyl-$N^6$-(1-methyl-piperidin-4-yl)-1,3,5-triazine-2,4,6-triamine maleate salt (167)

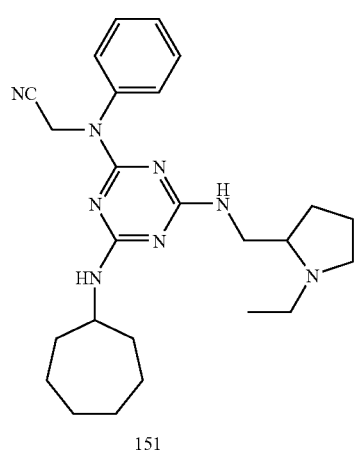

151

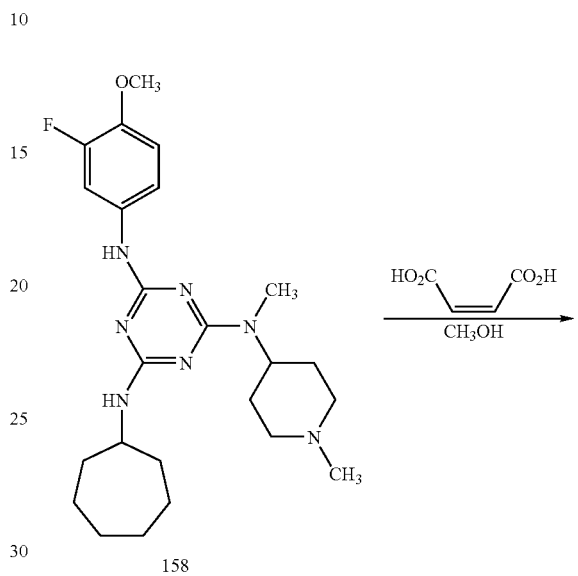

158

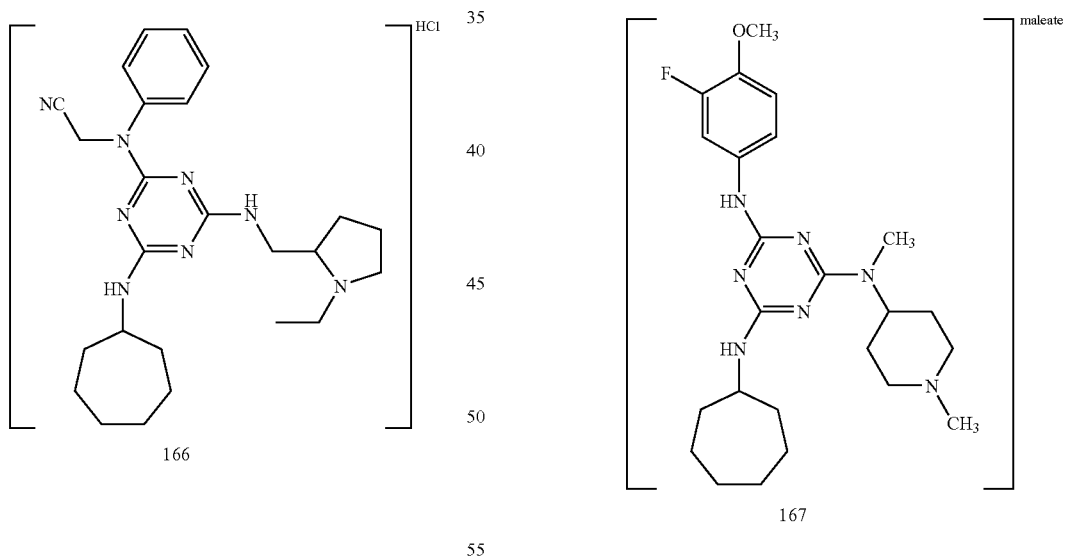

166        167

To 151 (0.448 g, 1 mmol) in dry diethyl ether (2 mL) was added HCl (1 mL, 1 mmol, 1 M in diethyl ether). The mixture was stirred at room temperature for about 1 hour, and then concentrated in vacuo. The resulting material was dissolved in water (5–10 mL), filtered, evaporated, and dried overnight under vacuum to give a solid 166 (0.418 g, 86%), mp 125–127° C.; HPLC: Inertsil ODS-3V C18, 40:30:30 [$KH_2PO_4$ (0.01 M, pH 3.2):$CH_3OH$:$CH_3CN$], 264 nm, $R_t$ 6.9 min, 73.4% purity.

Compounds 158 (100.3 mg, 0.219 mmol) and maleic acid (25.4 mg, 0.219 mmol) were dissolved in $CH_3OH$ (2 mL) and stirred at room temperature under a $N_2$ atmosphere for about 75 min. The reaction mixture was filtered through a cotton plug and concentrated in vacuo to afford a solid 167, 0.1239 g, mp 99–100° C. In a qualitative test, this material was water-soluble. HPLC: Inertsil ODS-3V C18, 40:30:30 [$KH_2PO_4$ (0.01M, pH 3.2):$CH_3OH$:$CH_3CN$], 264 nm, $R_t$ 7.7 min, 87.9% purity.

Example 72

Synthesis of $N^2$-cycloheptyl-$N^4$-(3-fluoro-4-methoxy-phenyl)-N'-methyl-$N^6$-(1-methyl-piperidin-4-yl)-1,3,5-triazine-2,4,6-triamine citrate salt (168)

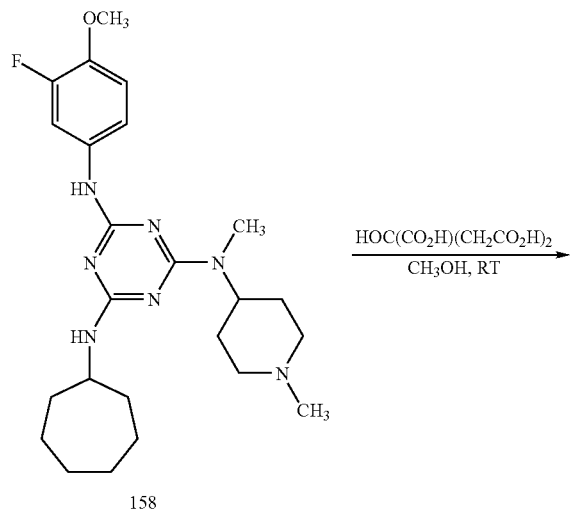

Example 73

Synthesis of $N^2$-cycloheptyl-$N^4$-(3-fluoro-4-methoxy-phenyl)-$N^6$-methyl-$N^6$-(1-methyl-piperidin-4-yl)-1,3,5-triazine-2,4,6-triamine succinate salt (169)

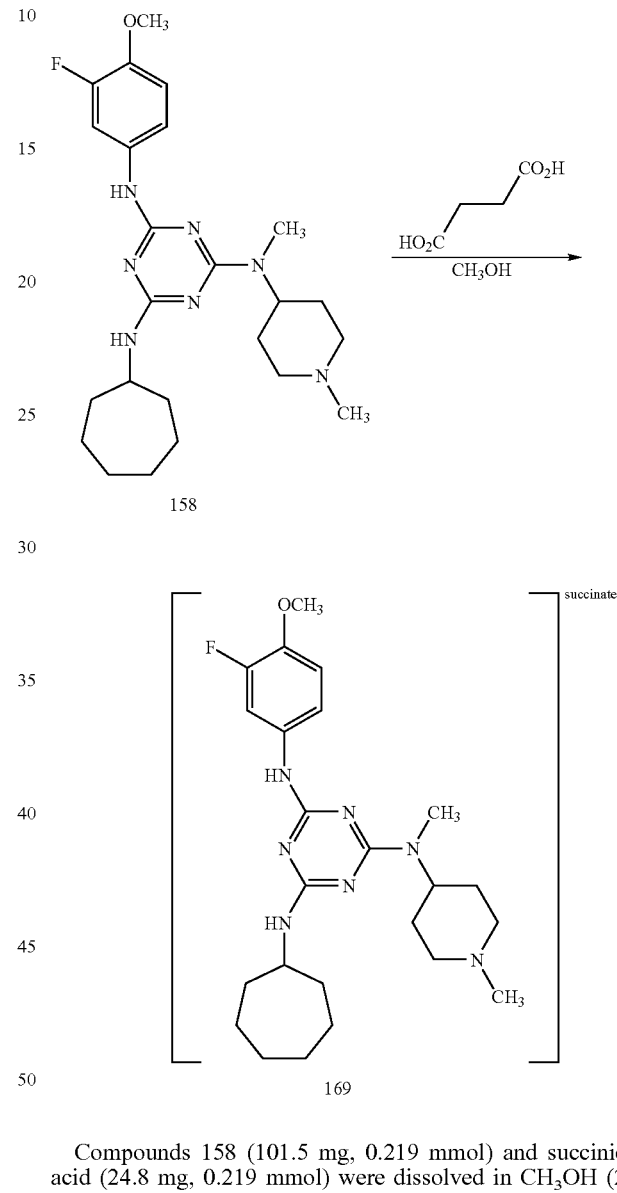

Compounds 158 (100 mg, 0.219 mmol) and citric acid (42.1 mg, 0.219 mmol) were dissolved in $CH_3OH$ (2 mL) and stirred at room temperature under a $N_2$ atmosphere for about 2 hours. The reaction mixture was filtered through a cotton plug and concentrated in vacuo to afford a solid 168 (0.1387 g), mp 125° C. In a qualitative test, this material was water insoluble. HPLC: Inertsil ODS-3V C18, 40:30:30 [$KH_2PO_4$ (0.01M, pH 3.2):$CH_3OH$:$CH_3CN$], 264 nm, $R_t$ 7.7 min, 90.1% purity.

Compounds 158 (101.5 mg, 0.219 mmol) and succinic acid (24.8 mg, 0.219 mmol) were dissolved in $CH_3OH$ (2 mL) and stirred at room temperature under a $N_2$ atmosphere for about 75 min. The reaction mixture was filtered through a cotton plug and concentrated in vacuo to afford a solid 169 (0.1248 g), mp 81° C. In a qualitative test, this material was water-soluble. HPLC: Inertsil ODS-3V C18, 40:30:30 [$KH_2PO_4$ (0.01M, pH 3.2):$CH_3OH$:$CH_3CN$], 264 nm, $R_t$ 7.6 min, 89.8% purity.

Example 74

Synthesis of N-(3-Bromo-4-methoxy-phenyl)-N'-cycloheptyl-N''-methyl-N''-(1-methyl-piperidin-4-yl)-[1,3,5]triazine-2,4,6-triamine hydrogen chloride salt (170)

To 123 (1.0 mmol) dissolved in methanol (5 mL) was added 1.0 M hydrochloric acid in diethyl ether (1.0 mL, 1 mmol). The reaction mixture was allowed to stir for about 1 hour at room temperature. The reaction mixture was then concentrated on a rotary evaporator. The resulting solid was dissolved in water, filtered and concentrated on the rotary evaporator. The sample was freeze dried under vacuum and a solid 170 (70%) was collected Example 75

Alternative Synthetic Route to Tris(amino) 1,3,5-Triazine Compounds

The following reaction scheme represents a proposed and alternative synthetic routes to 1,3,5-triazines.

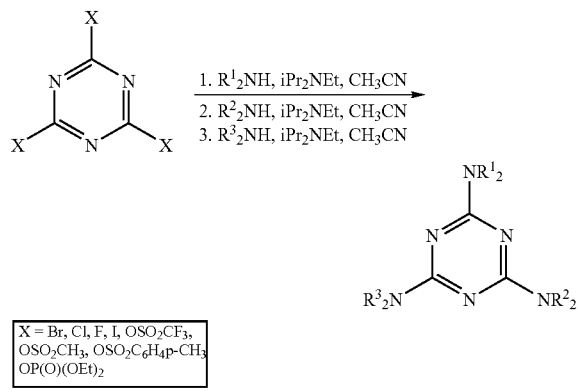

This scheme represents a modification of the synthetic route described in the patent to prepare the tris-amino substituted 1,3,5-triazines. Alternative leaving groups, X, could be used as compared to cyanuric chloride (X=Cl) in the $S_NAr$ reaction with a sequential addition of a nucleophilic amine in the presence of an acid (proton) scavenger to afford the tris-substituted 1,3,5-triazine with the desired combination of amino groups.

Example 76

Alternative Synthetic Route to Tris(amino) 1,3,5-Triazine Compounds

The following reaction scheme represents a proposed and alternative synthetic routes to 1,3,5-triazines.

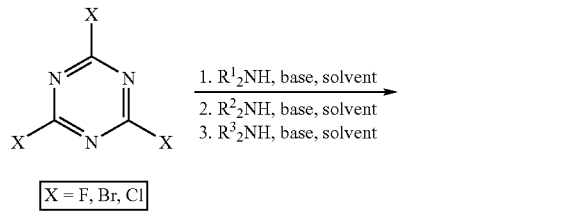

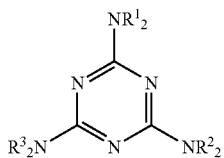

base = acid scavenger = $R_3N$, NaOH, KOH, $NaHCO_3$, $K_2CO_3$, $Na_2CO_3$, resin-$NR_2$, NaH, KH, RLi solvent = compatible with base = $CH_3CN$, THF, 1,4-dioxane, $Et_2O$, DMSO, DMF, $CH_2Cl_2$, $CHCl_3$, $ClCH_2CH_2Cl$, $C_6H_5CH_3$, $H_2O$ This scheme represents a modification of the synthetic route described in the patent text to prepare the tris-amino substituted 1,3,5-triazines. Bases, including excess amine reagent $R_2NH$, could be used as acid (proton) scavengers alternatively to the Hünig's base (i$Pr_2NEt$) used routinely in our procedure. These bases can include other organic tertiary amine bases or ionic, inorganic bases. One can use strong bases (NaH, KH, or RLi) to first deprotonate the amino monomer before addition to the cyanuric-X substrate. Additionally, one can use a solid supported base (e.g., resin-$NR_2$, a modified Hünig's base) as a proton scavenger. This potentially enables an easier isolation procedure and cleaner reaction products. Logically, one would use the appropriate solvent or combination of solvents that is compatible with the base of choice for this procedure.

Example 77

Alternative Synthetic Route to Tris(amino) 1,3,5-Triazine Compounds

The following reaction scheme represents a proposed and alternative synthetic routes to 1,3,5-triazines.

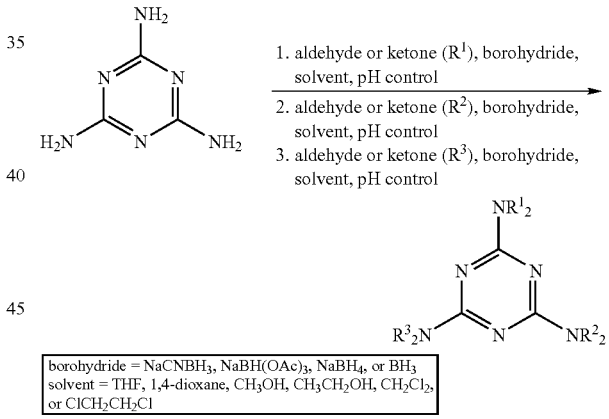

This scheme represents a modification of the synthetic route described in the patent to prepare the tris-amino substituted 1,3,5-triazines. Using melamine as the starting material, the method outlined would involve three sequential reductive amination procedures. With control of addition, temperature, and pH, the choice of aldehydes or ketone, one can prepare tris-amino substituted triazines with the desired combination of amino groups.

Example 78

Alternative Synthetic Route to Tris(amino) 1,3,5-Triazine Compounds

The following reaction scheme represents a proposed and alternative synthetic routes to 1,3,5-triazines.

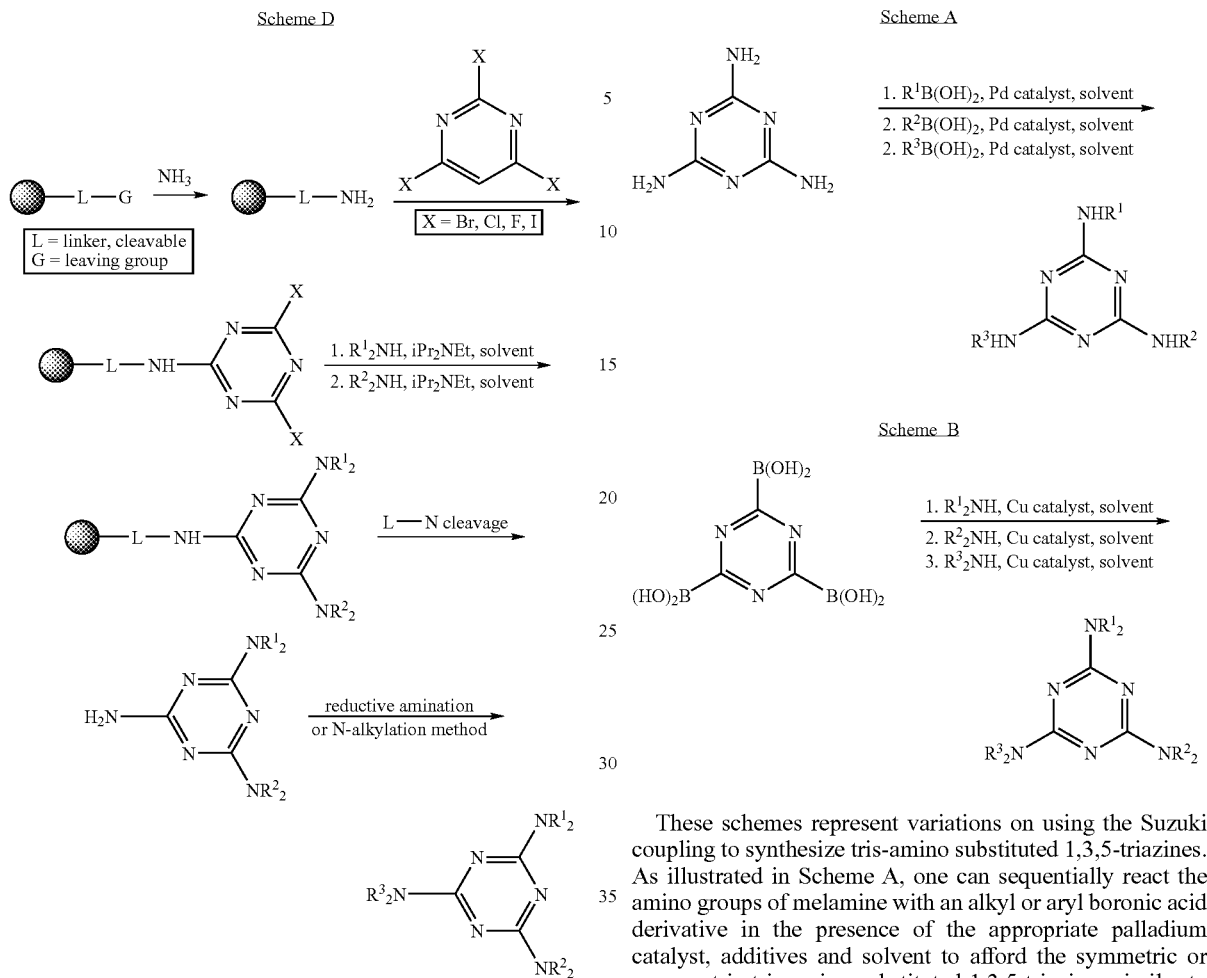

This scheme represents a solid phase synthetic approach to preparing symmetrically or asymmetrically substituted tris-amino substituted 1,3,5-triazines. The resin should possess a readily cleavable linker group (L) and a leaving group (G) for attachment of an amino group. The scheme outlines the synthesis by initially attaching a simple amino group, $NH_2$, by reacting the resin with ammonia. Using standard, $S_NAr$ chemistry for substitution of a perhalogenated 1,3,5-triazine, the triazine can be attached to the aminated resin. Sequential substitutions of the halogens on the triazine core with functionalized amines in the presence of an acid scavenger will produce the desired di-amino substituted 1,3,5-triazine. Cleavage of the triazine from the resin tether will afford the tris-amino substituted triazine product. The free $NH_2$ moiety of the triazine can be further alkylated or functionalized using standard chemistry such reductive amination or N-alkylation to give a completely functionalized tris-amino substituted 1,3,5-triazine.

Example 79

Alternative Synthetic Route to Tris(amino) 1,3,5-Triazine Compounds

The following reaction schemes (Schemes A and B) represent proposed and alternative synthetic routes to 1,3,5-triazines.

These schemes represent variations on using the Suzuki coupling to synthesize tris-amino substituted 1,3,5-triazines. As illustrated in Scheme A, one can sequentially react the amino groups of melamine with an alkyl or aryl boronic acid derivative in the presence of the appropriate palladium catalyst, additives and solvent to afford the symmetric or asymmetric tris-amino substituted 1,3,5-triazines similar to previously described examples. In Scheme B, a tris-boronic acid 1,3,5-triazine can be prepared from cyanuric chloride or bromide. This derivative can then be coupled with an aryl or alkyl amine, as illustrated in previous amine monomer descriptions, in the presence of the appropriate metal catalysts (e.g., Cu or Pd catalyst), additives and solvent to afford the symmetric or asymmetric tris-amino substituted 1,3,5-triazines.

Example 80

Proteoglycan Induction

Smooth muscle cells reach quiescence during serum starvation resulting in a blockade of DNA synthesis. To demonstrate the role of perlecan (proteoglycan example) in SMC quiescence, cells were starved by removing serum from the media. The cells used in this Example and the other examples herein were human aortic SMC, grown in basal medium supplemented with growth factors, bFGF and epidermal growth factor (EGF) (Clonetics, San Diego, Calif.).

SMC secretion of total PGs (proteoglycans) as well as perlecan were determined in the presence or absence of one or more compounds of the present invention. PGs were radiolabeled with ($^{35}$S)sulfate by incubating the cells with ($^{35}$S)sulfate for 2 to 6 hours. Media PGs were collected and purified by DEAE-cellulose chromatography. Cell-associated PGs were assessed by extracting cells with 50 mM Tris buffer pH 7.4 containing 4 M urea, 1% Triton X-100, 0.1 mM EDTA and 1 mM PMSF. Aqueous solutions of ($^{35}$S)sulfate and ($^3$H)leucine were from Amersham. Control cells have no added compounds whereas treated cells have one or more compounds of the present invention added.

To determine changes in PG levels, DEAE-cellulose chromatography was performed. A DEAE-cellulose column was equilibrated with 50 mM Tris buffer pH 7.4 containing 4 M urea, 0.1 M NaCl, 0.1 mM EDTA, 1 mM PMSF and 1% 3[(3-cholamidopropyl)dimethylammonio]-1-propanesulfonate (CHAPS). The column was washed with the same buffer and buffer containing 0.25 M NaCl and PG were eluted with the same buffer containing 0.5 M NaCl. Fractions containing radioactivity ($^{35}SO_4$) were pooled and dialyzed against MEM overnight and counted.

To determine the relative proportion of HSPG and chondroitin sulfate/dermatan sulfate proteoglycan (CS/DS PG), an aliquot of the pooled fraction was incubated in 50 mM sodium acetate buffer pH 5.2 with 1 unit/ml each of heparanase and heparitinase or with 0.5 units of chondroitin ABC lyase for 16 h at 37° C. Chondroitan ABC refers to different isomeric types of chondroitin, e.g. chondroitin A, chondroitin B, and chondroitin C. The reaction mixture was precipitated either with 0.5 volumes of 1% cetyl pyridinium chloride or with 3 volumes of ethanol to precipitate undigested glycosaminoglycans. Radioactivity in the supernatant and pellet was determined.

To determine changes in perlecan protein in response to the presence of a compound, cells were grown in serum-free or serum-containing media in the presence of ($^3$H)leucine for 24 h (steady state). Cells were plated at low density (8×10$^4$/well in 48 well plate, 30–40% confluency) and cultured for 24 h (hour). Wells were then replenished with fresh medium containing no serum or 10% fetal bovine serum (FBS). Following another 24 h incubation, cells were labeled with ($^3$H)thymidine for 6 h and radioactivity incorporated into the DNA was determined by trichloroacetic acid (TCA) precipitation of the cell lysate. ($^3$H)thymidine was from NEN. Purified PG (0.5 M eluate) were immunoprecipitated by incubation with an anti-perlecan antibody (100-fold diluted) followed by precipitation with Protein A-Sepharose. Immunoprecipitates were analyzed by 5% SDS-PAGE. Perlecan (Mr>550 kDa) was identified by autoradiography. Control cells have no added compound(s) whereas treated cells have one or more compounds of the present invention added.

Example 81

Inhibition of Smooth Muscle Cell Proliferation

Purified perlecan from SMC medium by DEAE-cellulose chromatography was obtained using methods in Example I, and was tested for its antiproliferative effects on SMC.

The addition of perlecan to serum-containing medium inhibited SMC growth by 70%. Sub-confluent SMC (40–50% confluence) were incubated in serum-free medium or 10% serum-containing medium with or without purified perlecan for 24 h. DNA synthesis was then determined by incubating cells for another 5 h in medium containing ($^3$H)thymidine. TCA precipitable (DNA) thymidine counts were determined and expressed as percentage of DNA synthesis in cells grown in 10% FBS.

This assay can be used to show the effect of a compound on perlecan directly by incubating the compound to perlecan first, then performing the assay. Alternatively, the cells can be pretreated with at least one compound of the present invention to show indirect effects. Control cells have no added compounds whereas treated cells have one or more compounds of the present invention added.

Example 82

Triazine Compounds in Smooth Muscle Cell Proliferation Assay

Human aortic smooth muscle cells (Clonetics) were used. Cells were grown in basal medium containing 5% fetal bovine serum supplemented with growth factors, basic fibroblast growth factor, epidermal growth factor and insulin. To determine the effects triazine compounds of the present invention had on SMC proliferation, cells were plated at low density (4000 cell per well in a 96 well plate) and cultured for 24 h. The cells were then serum starved for 24 h to induce quiescence. Fresh growth medium containing no compound or 10 µM compound was then added and further incubated for 24 h. Cell number was determined by using a cell proliferation assay kit (Celltiter96 AQ$_{ueous}$ from Promega).

Figure 53:
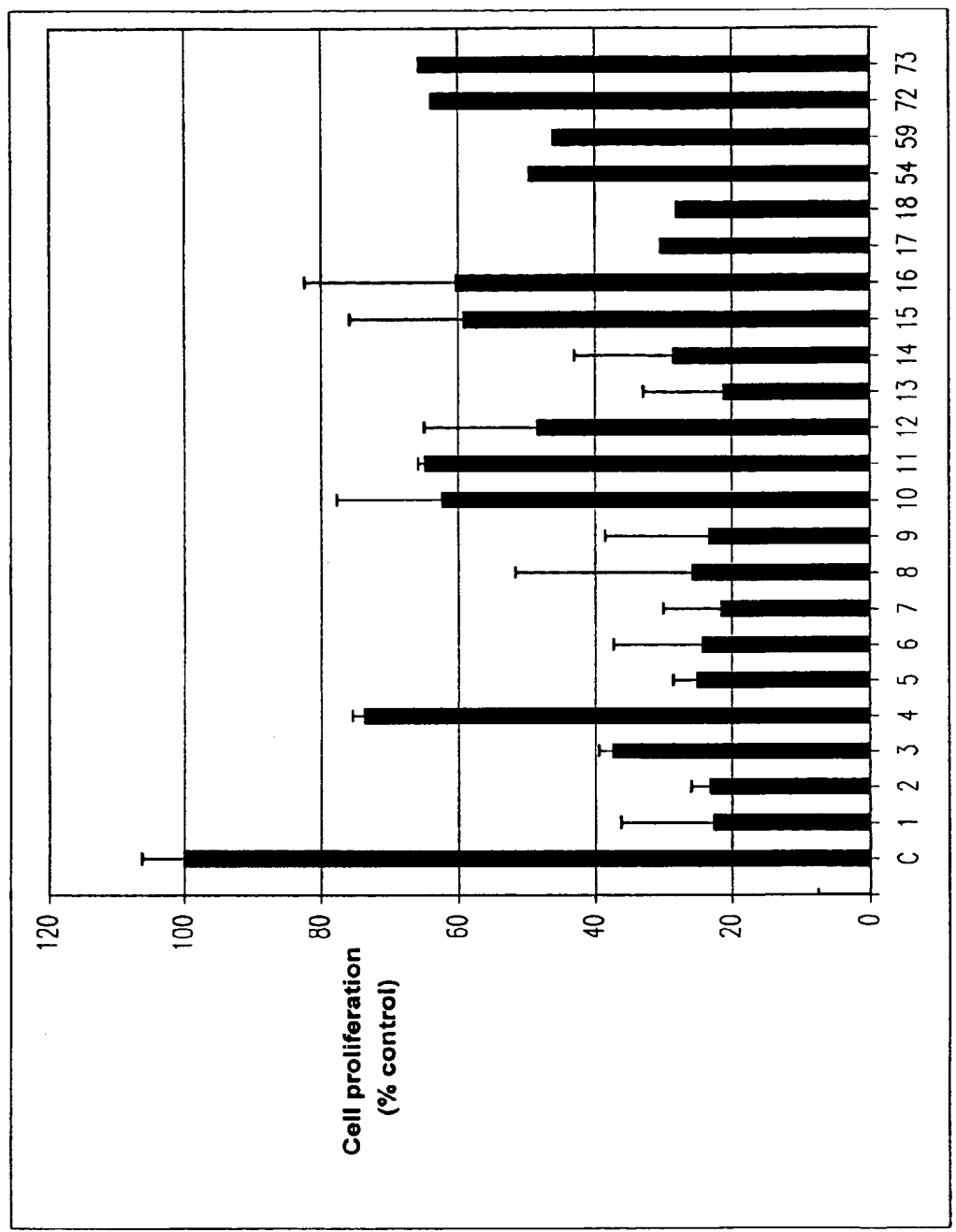
FIG. 53. Chart showing the effects of compounds in an assay where glycated human serum albumin (G-HSA) induces IL-6 production.

The effects of different triazine compounds on smooth muscle cell proliferation are shown in FIG. 53. Many of the triazine compounds inhibited SMC proliferation by greater than 70%.

Example 83

Induction and Measurement of Endothelial Heparanase Protein

Experiments were carried out on human microvascular endothelial cells (HMVEC) grown in 48-well plates (90% confluency). To induce heparanase activity, culture media was replaced with 200 µl Dulbecco's Modified Eagle's medium (DMEM) complemented with 1% bovine serum albumin (BSA) and with or without stimulants (5 ng/ml TGF-alpha, 1 ng/ml IL 1 alpha, 200 ng/ml VEGF or other stimulants, cytokines, or inducers as required). The secreted proteins were analyzed by SDS/PAGE and heparanase protein was detected by immunoblotting using polyclonal anti-human heparanase antibody. The changes of heparanase expression determined by densitometric analysis. The induction and measurement of endothelial heparanase protein reported in the Tables herein were carried out according to this Example.

Example 84

Preparation of Biotinylated HS

Heparan sulfate (HS) was biotinylated using biotin with extended spacer arms using succinimidyl-6-(biotinamido) hexanoate (NHS-LC-Biotin) obtained from Pierce. About 0.5 ml HS solution (2 mg/ml in NaHCO3, pH 8.5) was mixed with 0.05 ml of a freshly prepared solution of NHS-LC-Biotin in dimethyl sulfoxide. The mixture was incubated at room temperature for 1 hour. Unconjugated biotin was removed by centrifugation (10,000 RPM) through Microcon-3 filter (Millipore) followed by dilution with phosphate buffered saline (PBS). This procedure was repeated five times to ensure complete removal of free biotin. Unwanted aldehydes in the reaction were then quenched by incubation with one milliliter of Tris-glycine buffer(25 mM-183 mM, pH 8.3) at room temperature for 20 minutes. The mixture was subjected to three rounds of microfiltration as described above. Biotinylated HS (5 mg/ml in PBS) was aliquoted and stored at −20° C. To obtain maximum biotinylation, a 25-fold molar excess of biotin was used. Using HABA reagent, it was determined that the ratio of HS to biotin was 1:2.

The extent of biotinylation of HS was determined using Avidin-HABA (Pierce Chemical Co). The HABA assay can be used over a wide range of pH and salt concentrations. HABA (4-hydroxyazobenzene-2'-carboxylic acid) is a dye that binds to avidin and can serve as an indicator of unoccupied binding sites. Avidin combines stoichiometrically with biotin, making it possible to use any physiochemical differences between avidin and the avidin-biotin complex as the basis of a qualitative and quantitative assay method for either component.

When HABA binds to avidin, there is a large spectral change in the HABA dye. A new absorption band appears at 500 nm, which is characteristic of the quinoid form of the dye. The avidin-biotin complex does not bind HABA and because the dissociation constant of the complex is so low, the dye is stoichiometrically displaced by biotin. Consequently, the HABA assay can be the basis of both colorimetric and titrimetric assays. The amount of avidin can be calculated directly from the increased absorbance at 500 nm, or the dye may be used as an indicator in a spectrophotometric titration with biotin.

The absorption band that results from the avidin-HABA complex decreases proportionately when biotin is added. Since biotin has such a high affinity for avidin, it displaces the HABA dye. The unknown amount of biotin can be determined by preparing a standard curve using known amounts of biotin to displace the HABA which bound to avidin, and plotting against the absorbance at 500 mu.

HABA solution was prepared by adding 24.2 mg of HABA (Pierce) to 9.9 ml H20, and then adding 0.1 ml 1 M NaOH. Avidin-HABA reagent was prepared by adding 10 mg of avidin and 600 gl of HABA solution to 19.4 ml of phosphate buffered saline. To 1 ml of Avidin-HABA reagent in a cuvette, 100 µl of biotinylated HS was added, and the optical density was measured at 500 nm in a spectrophotometer. A standard curve was determined using known amounts of HABA. The decrease in optical density of the HABA following the addition of biotinylated HS was determined.

Example 85

Heparanase Assay

Biotin-labeled HS made as described above was digested with heparanase, under both control and treated conditions, and the reaction containing undegraded and degraded HS was bound to in a biotin-binding plate. Streptavidin, conjugated with an enzyme, was added to the binding plate. Quantitation of the color reaction measured the amount of available biotin binding sites. A decrease in color from a known amount reflects HS digestion by heparanase. Control conditions have no added compound of the present invention, and treated conditions have compounds of the present invention added.

A lyophilized powder of heparanase (heparanase III obtained from Seikagaku) containing 0.1 units of enzymatic activity was hydrated in 100 µl of Reaction Buffer (3.33 mM calcium acetate pH 7.0, containing 0.1 mg/ml BSA). This solution was then diluted to a working concentration of heparanase solution (0.01 micro-units to 1 milli-unit) in Reaction Buffer. Enzyme activity was defined by the manufacturer of the heparanase (Seikagaku) as follows: one unit of enzyme activity is defined as amount required to generate 1 micromole of hexuronic acid per minute. Biotin-HS was diluted to a desired concentration in Reaction Buffer.

To determine heparanase activity, 10 µl of heparanase solution, with or without at least one of the compounds of the present invention, was mixed with 200 µl of the biotin-HS substrate in a 96 well plate. The reaction was incubated at 43° C. for 1 hour. One hundred microliters of the reaction mixture was added to a hydrated biotin-binding plate (Chemicon) and incubated at 37° C. for 30 minutes. The biotin-binding plates were hydrated with 200 µl of 1× Assay Buffer (Chemicon). Wells were washed five times with 1× Assay Buffer and incubated with 100 µl of 1:3000 diluted Streptavidin-Enzyme Conjugate (Chemicon) for 30 minutes at 37° C. The wells were washed five times with 1× Assay Buffer and incubated for 20 minutes with 100 µl of Substrate Solution (Chemicon). Color development in the wells was assessed by measuring the optical density at 450 nm in a microplate reader (Labsystems, Muliskan Ascent model). Differences between the control and the treated conditions indicate the heparanase modulating activity of the added compound or compounds.

Example 86

AGE-induced Inflammatory Response Determined by IL-6 ELISA

Human aortic endothelial cells (HAEC, Clonetics) were cultured according to manufacturer in growth medium (Clonetics): basal medium containing human epidermal growth factor, hydrocortisone, vascular endothelial growth factor, heparin binding growth factor-B, long R3-insulin-like growth factor-1, ascorbic acid, gentamicin/amphotericin and 5% FBS. These cell were allowed to reach at least 90% confluency before subjected to experimental treatments. Glycated human serum albumin (G-HSA) was from US Biologicals. Tumor necrosis factor cc was from R&D Systems.

Endothelial cells were treated with control medium or medium containing 10 to 100 ng/ml TNF-α or 300 µg/ml glycated-HAS (treated cells or treatments) for 24 hrs, in control and compound-added duplicates, containing 10 µM compound. All treatments, compound-added and controls were carried out in serum free media containing 0.2% albumin. Media from all conditions were collected and used for IL-6 ELISA.

IL-6 ELISA was carried out using human IL-6 DuoSet ELISA development kit as described by manufacturer (R&D Systems). Mouse anti-human Il-6 was used as the capture antibody (2 ug/ml) and biotinylated goat anti-human IL-6 (200 ng/ml) was used as the detection antibody. Culture media were incubated with capture antibody (in 96 well) for 2 h at room temperature. Wells were washed three times with wash buffer (0.05% tween-20 in phosphate buffered saline (PBS) pH 7.4) followed by incubation with detection antibody for 2 h at room temperature. Following three washes wells were incubated with Streptavidin-HRP for 20 min. Color development was read at 450 nm in a Microplate reader.

Figure 54:
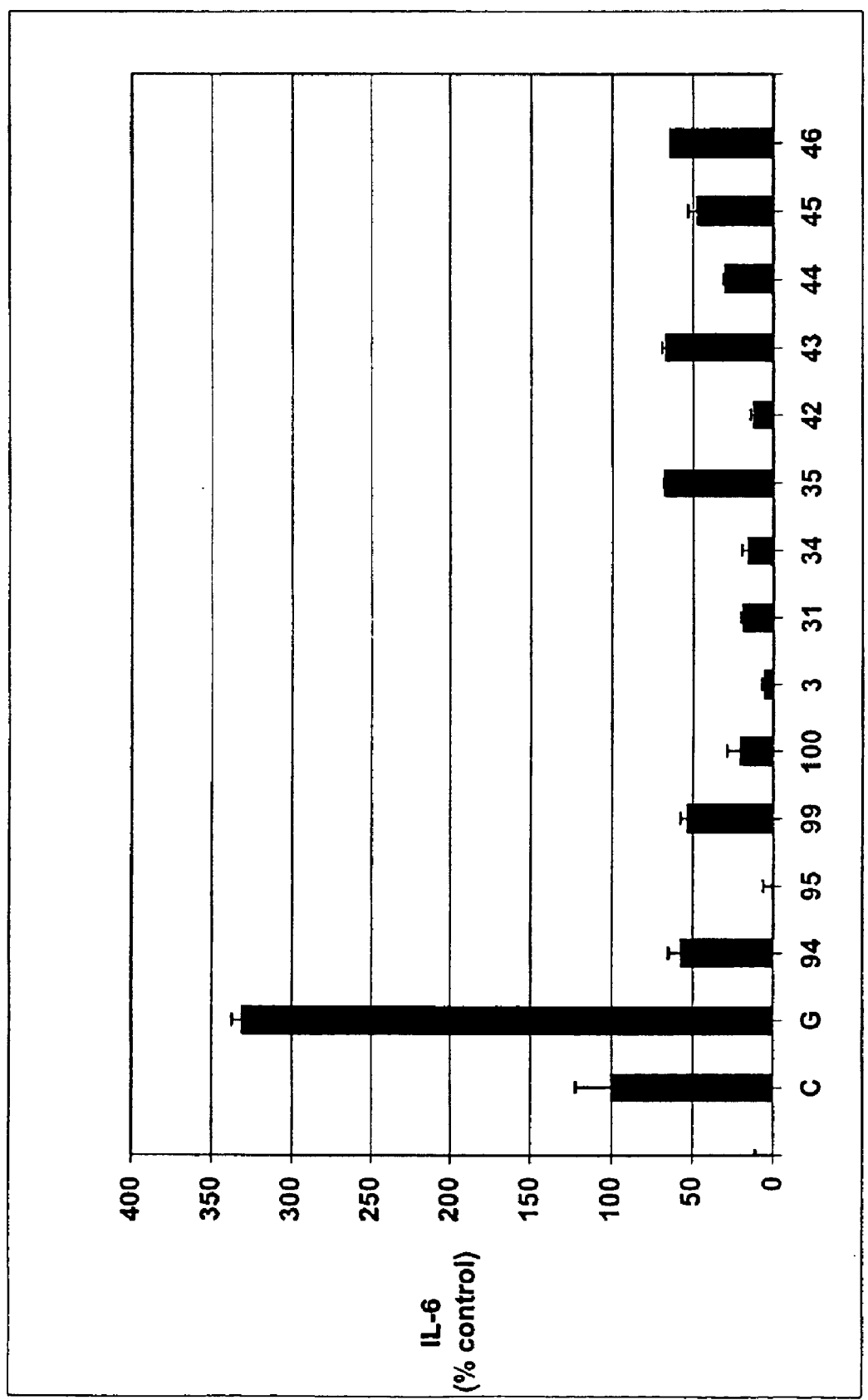
FIG. 54. Chart showing the effects of compounds in an antiproliferative assay.
Figure 55:
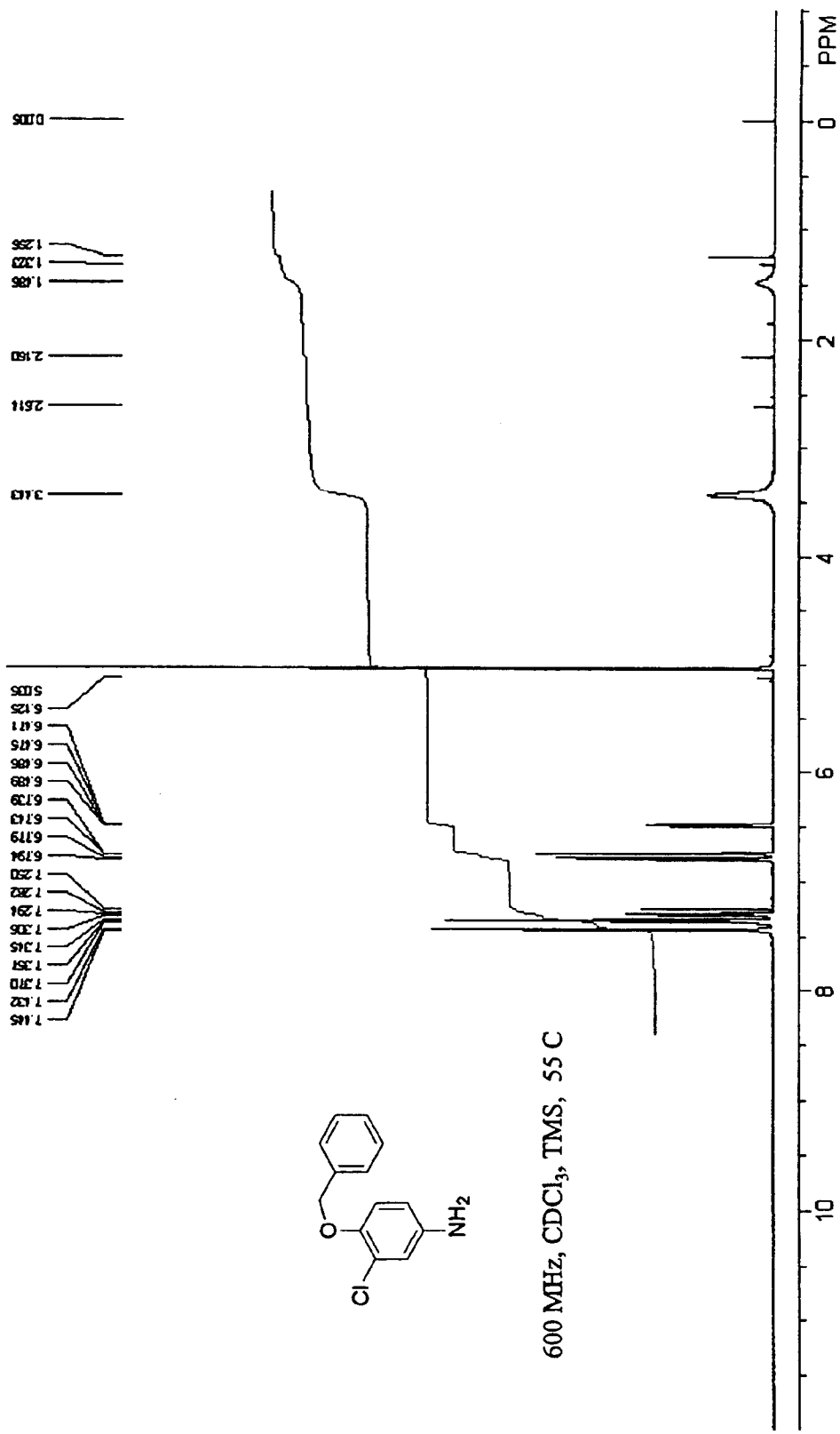
FIG. 55. ¹H NMR of 4-benzyloxy-3-chloro-phenylamine.
Figure 56:
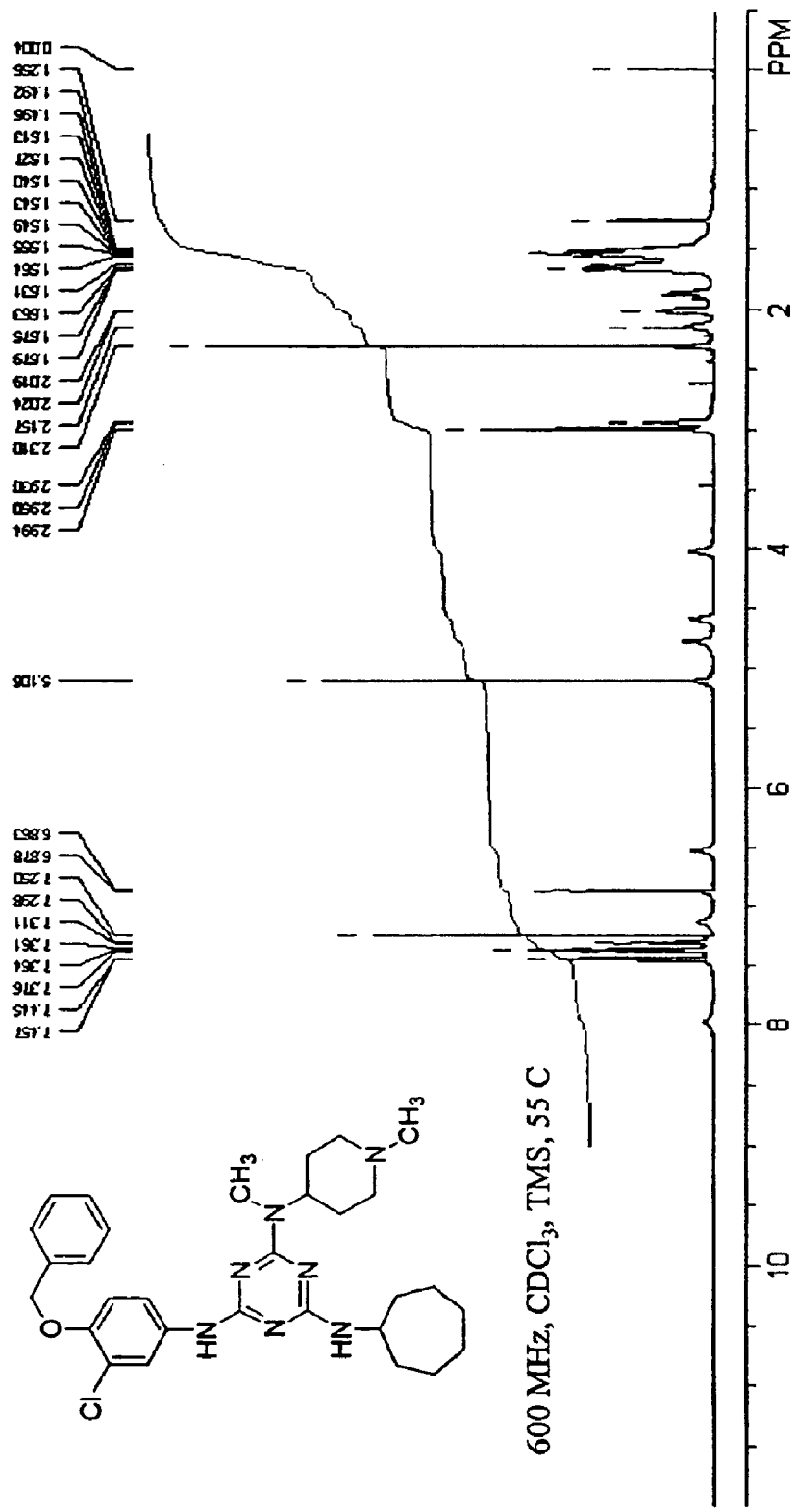
FIG. 56. ¹H NMR of N-(4-benzyloxy-3-chloro-phenyl)-N'-cycloheptyl-N"'-methyl-N"-(1-methyl-piperidin-4-yl)-[1,3,5]triazine-2,4,6-triamine.
Figure 57:
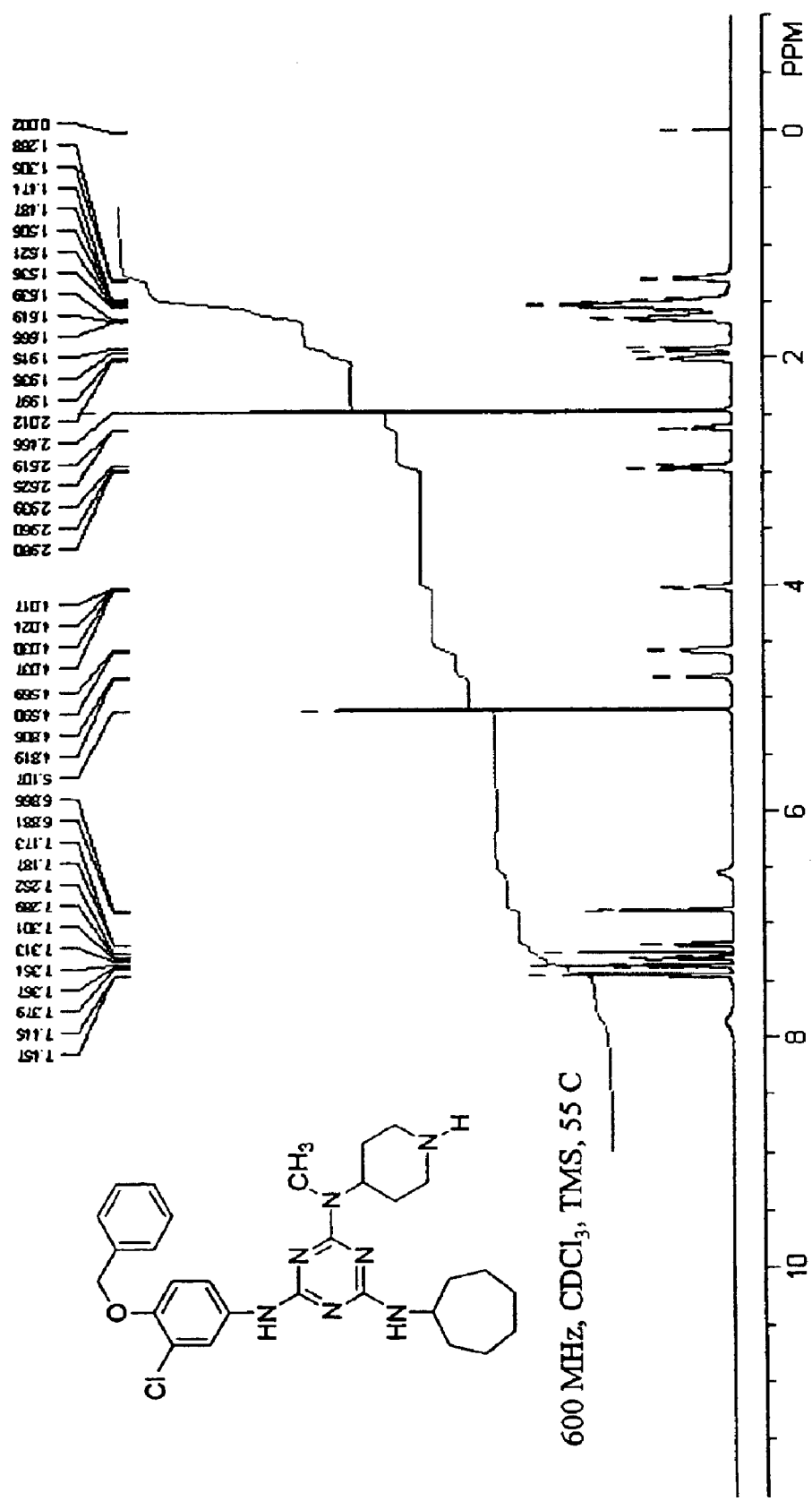
FIG. 57. ¹H NMR of N-(4-benzyloxy-3-chloro-phenyl)-N'-cycloheptyl-N"'-methyl-N'-piperidin-4-yl)-[1,3,5]triazine-2,4,6-triamine.
Figure 58:
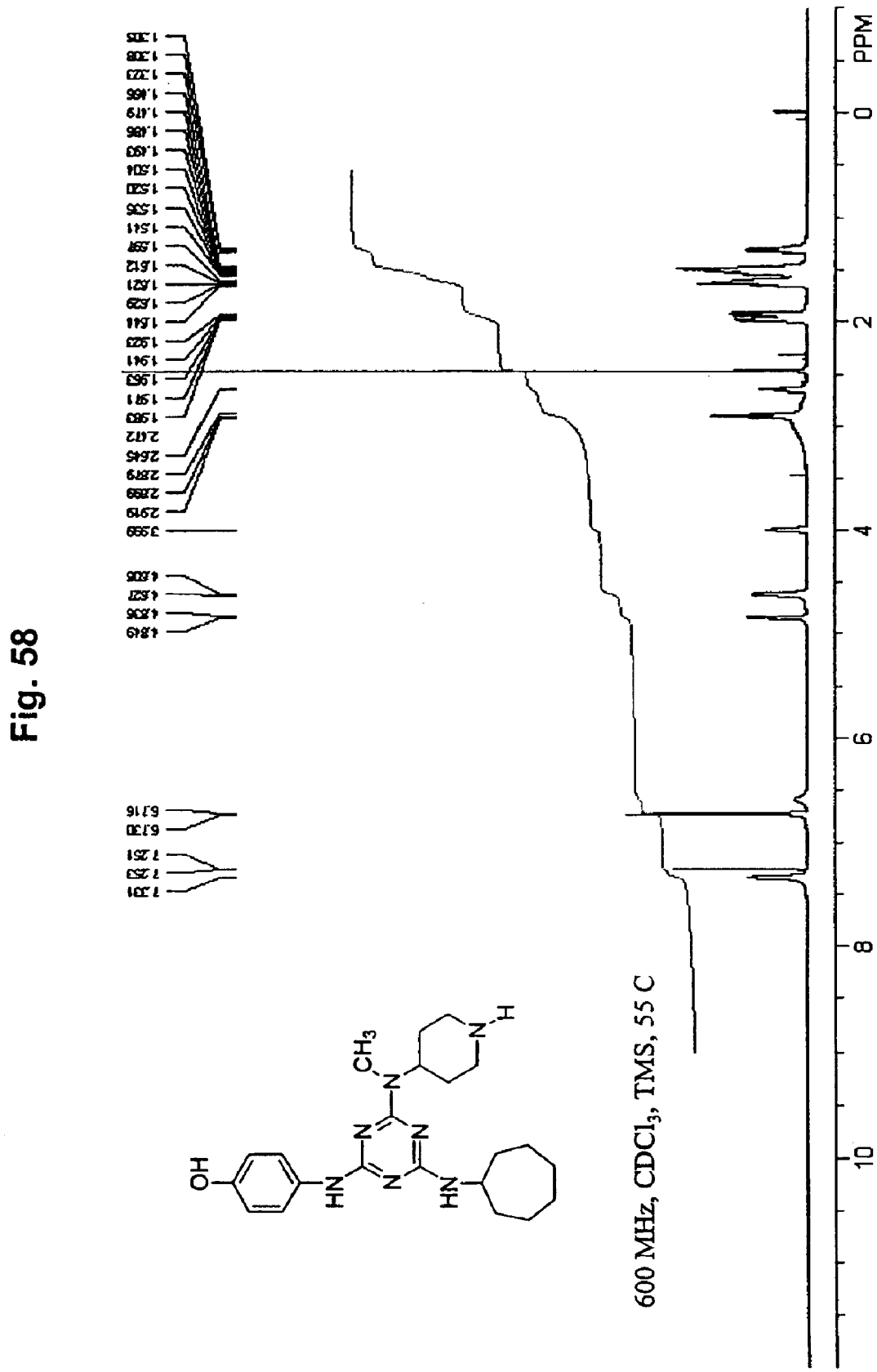
FIG. 58. ¹H NMR of 4-[4-cycloheptylamino-6-(methyl-piperidin-4-yl-amino)-[1,3,5]triazin-2-ylamino]-phenol.
Figure 59:
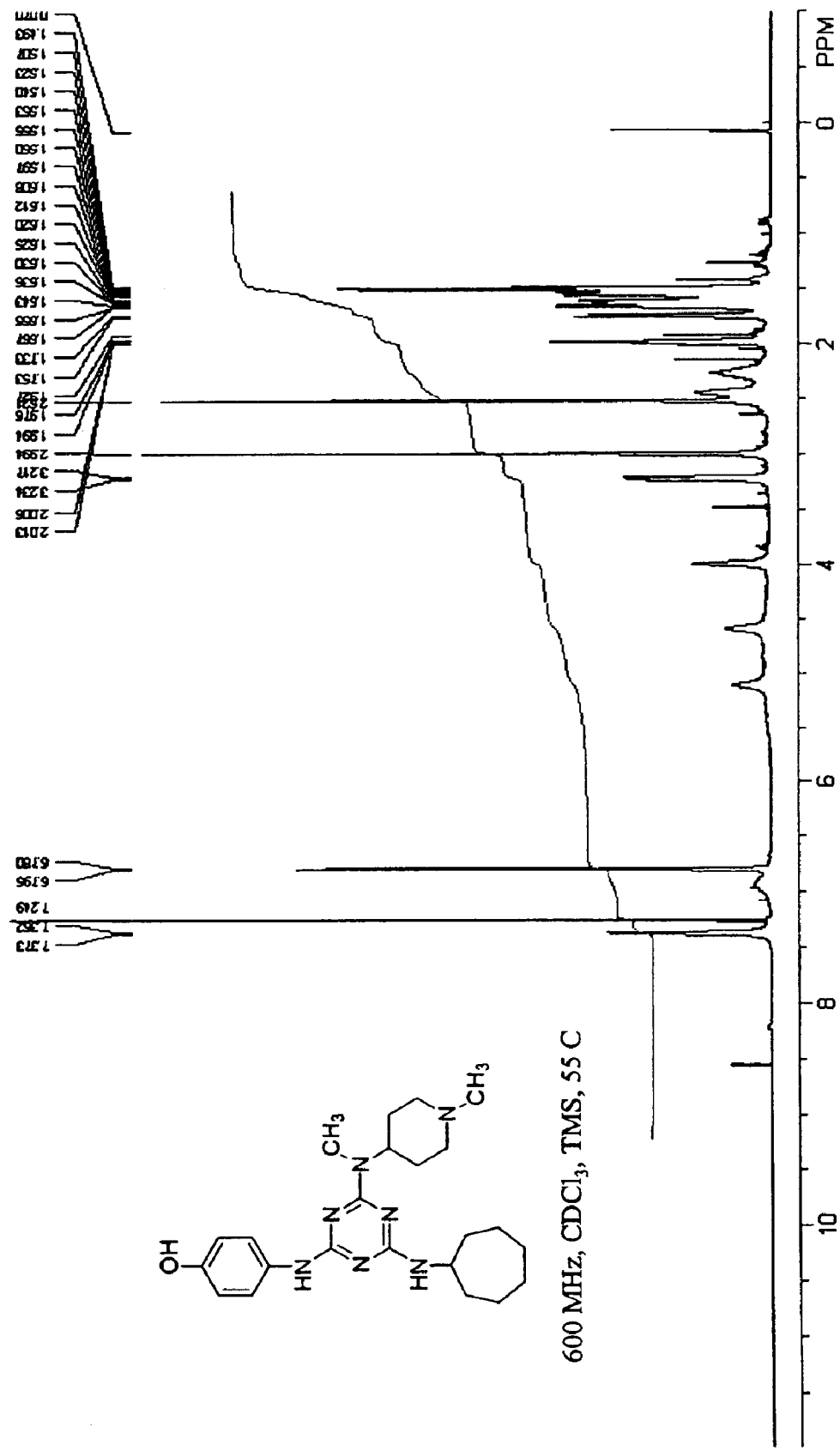
FIG. 59. ¹H NMR of 4-{4-cycloheptylamino-6-[methyl-(1-methyl-piperidin-4-yl)-amino]-[1,3,5-triazin-2-ylamino}-phenol.
Figure 60:
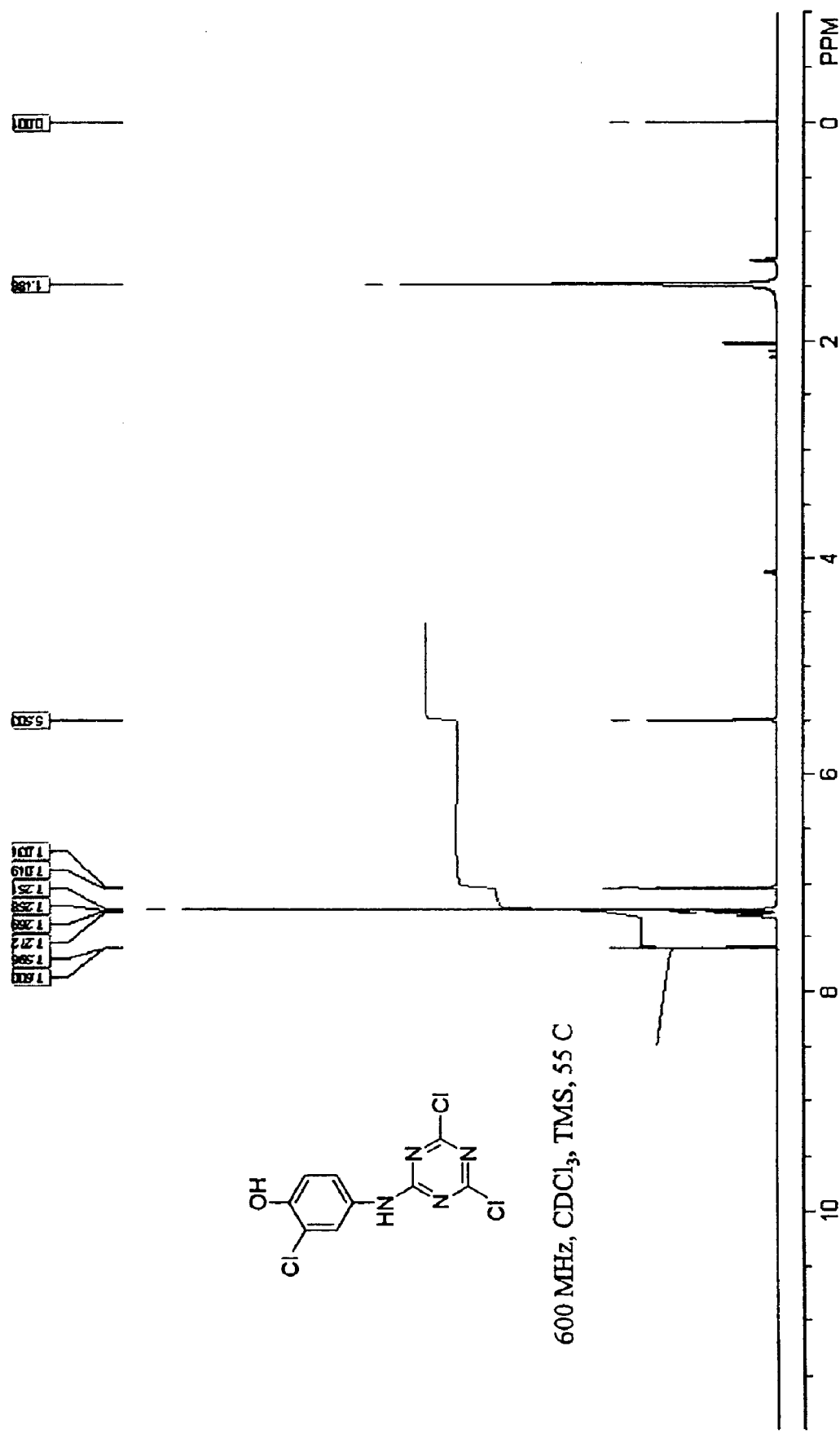
FIG. 60. ¹H NMR of 2-Chloro-4-(4,6-dichloro-[1,3,5]triazin-2-ylamino)-phenol.
Figure 61:
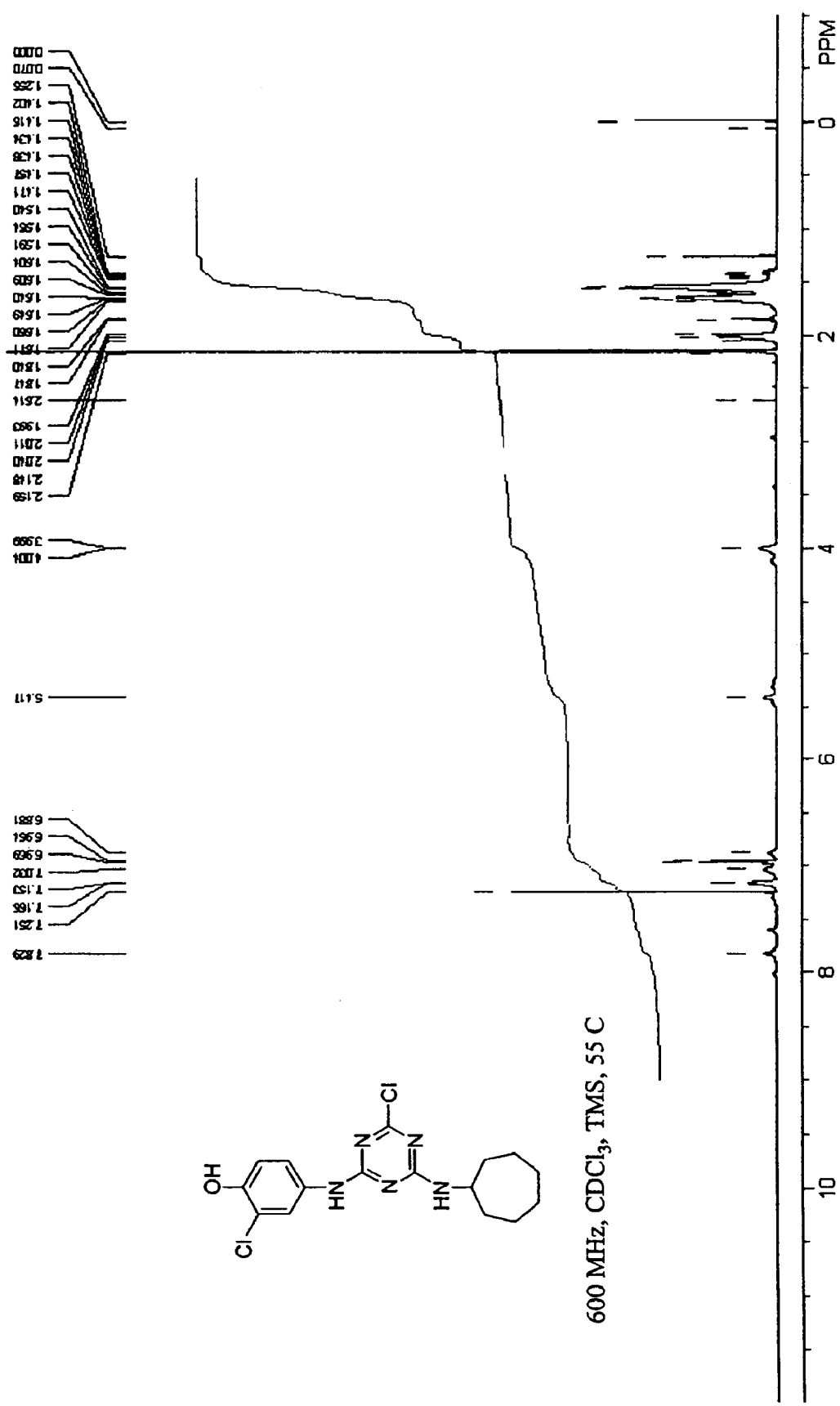
FIG. 61. ¹H NMR of 2-Chloro-4-(4-chloro-6-cycloheptylamino-[1,3,5]triazin-2-ylamino)-phenol.
Figure 62:
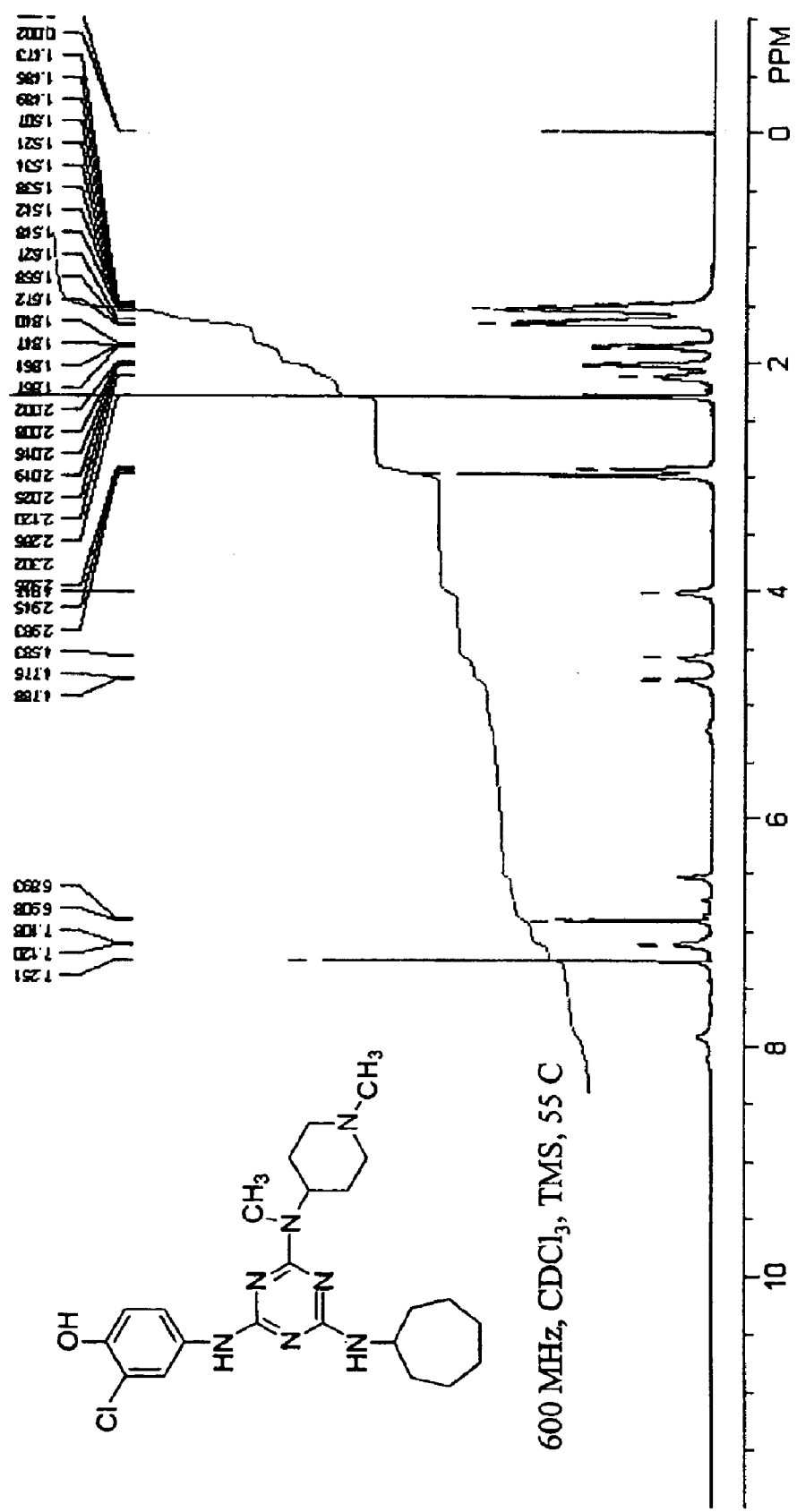
FIG. 62. ¹H NMR of 2-Chloro-4-{4-cycloheptylamino-6-[methyl-(1-methyl-piperidin-4-yl)-amino]-[1,3,5]triazin-2-ylamino}-phenol.
Figure 63:
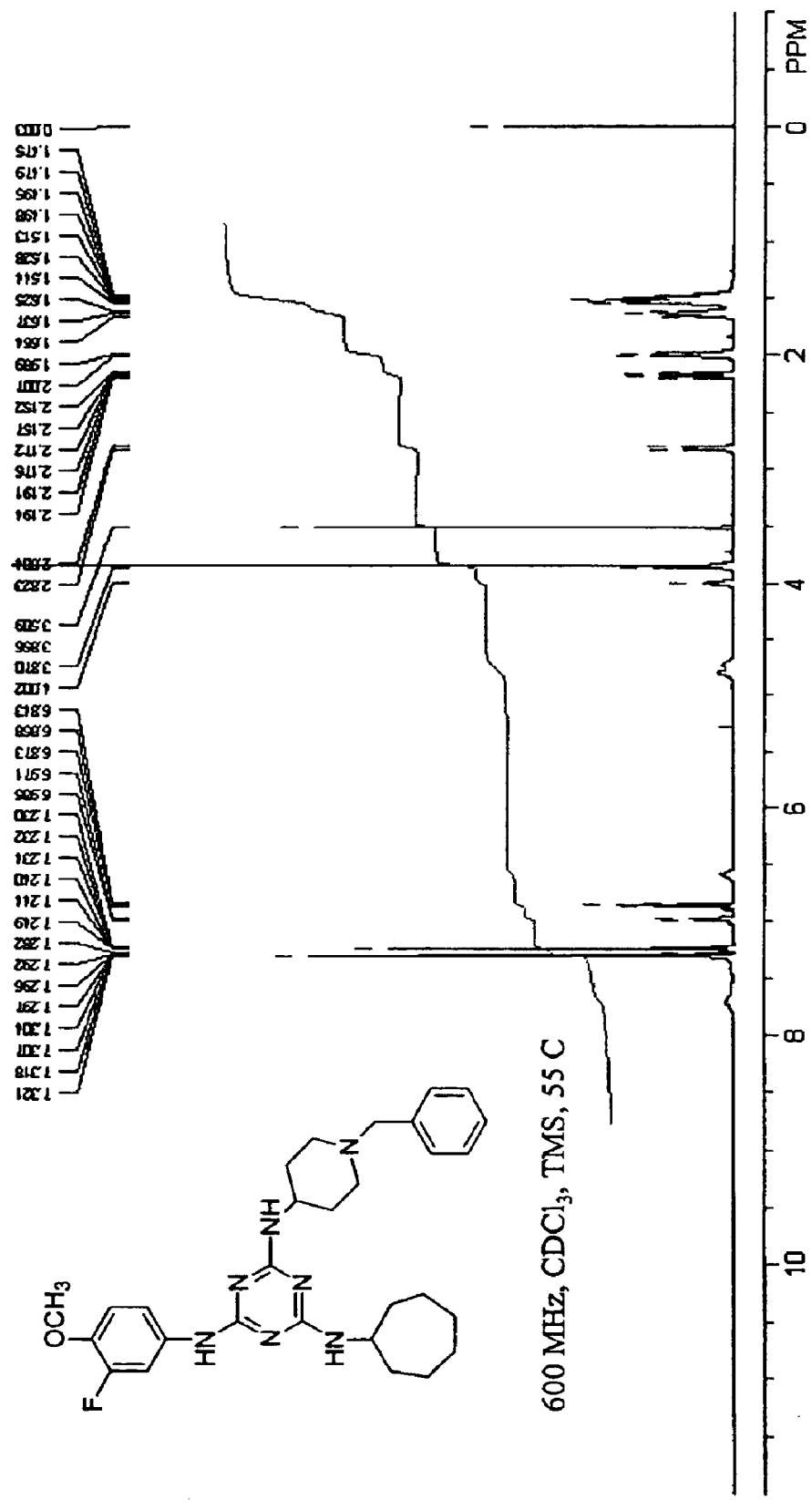
FIG. 63. ¹H NMR of N-(1-Benzyl-piperidin-4-yl)-N'-(3-fluoro-4-methoxy-phenyl)-N"-cycloheptyl-[1,3,5]triazine-2,4,6-diamine.
Figure 64:
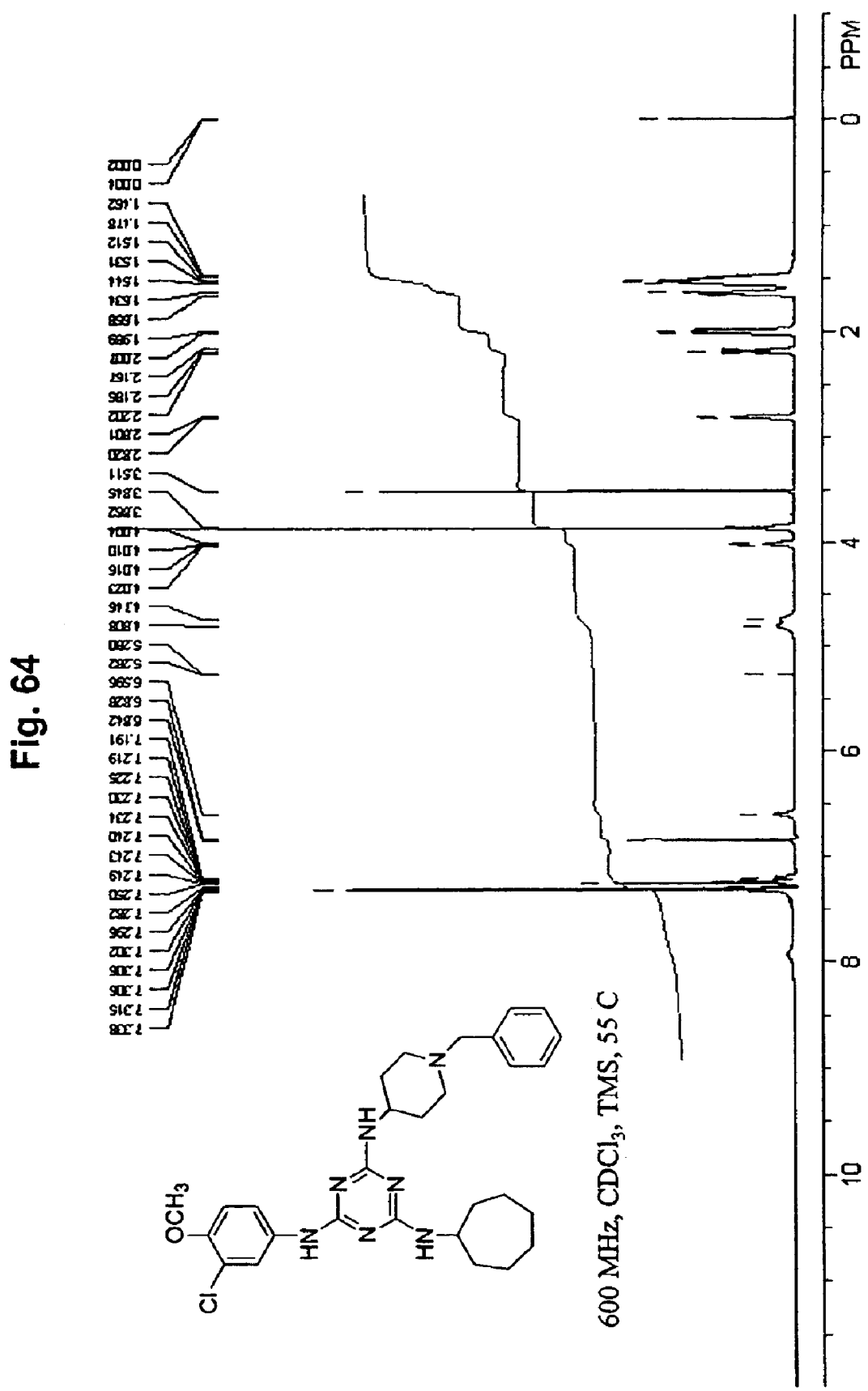
FIG. 64. ¹H NMR of N-(1-Benzyl-piperidin-4-yl)-N'-(3-chloro-4-methoxy-phenyl)-N"'-cycloheptyl-[1,3,5]triazine-2,4,6-diamine.
Figure 65:
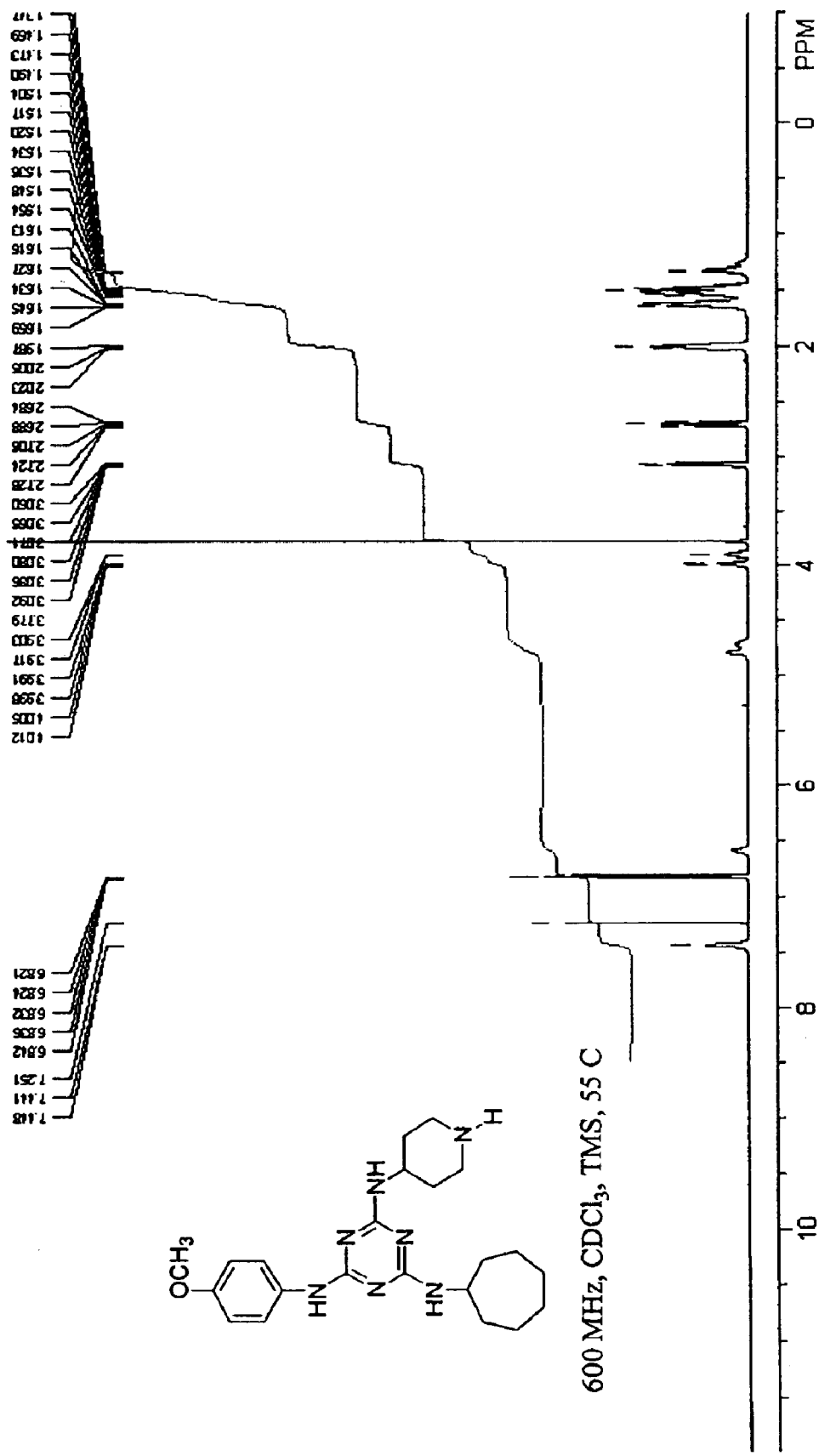
FIG. 65. ¹H NMR of N-Cycloheptyl-N'-(4-methoxy-phenyl)-N"-piperidin-4-yl-[1,3,5]triazine-2,4,6-triamine.
Figure 66:
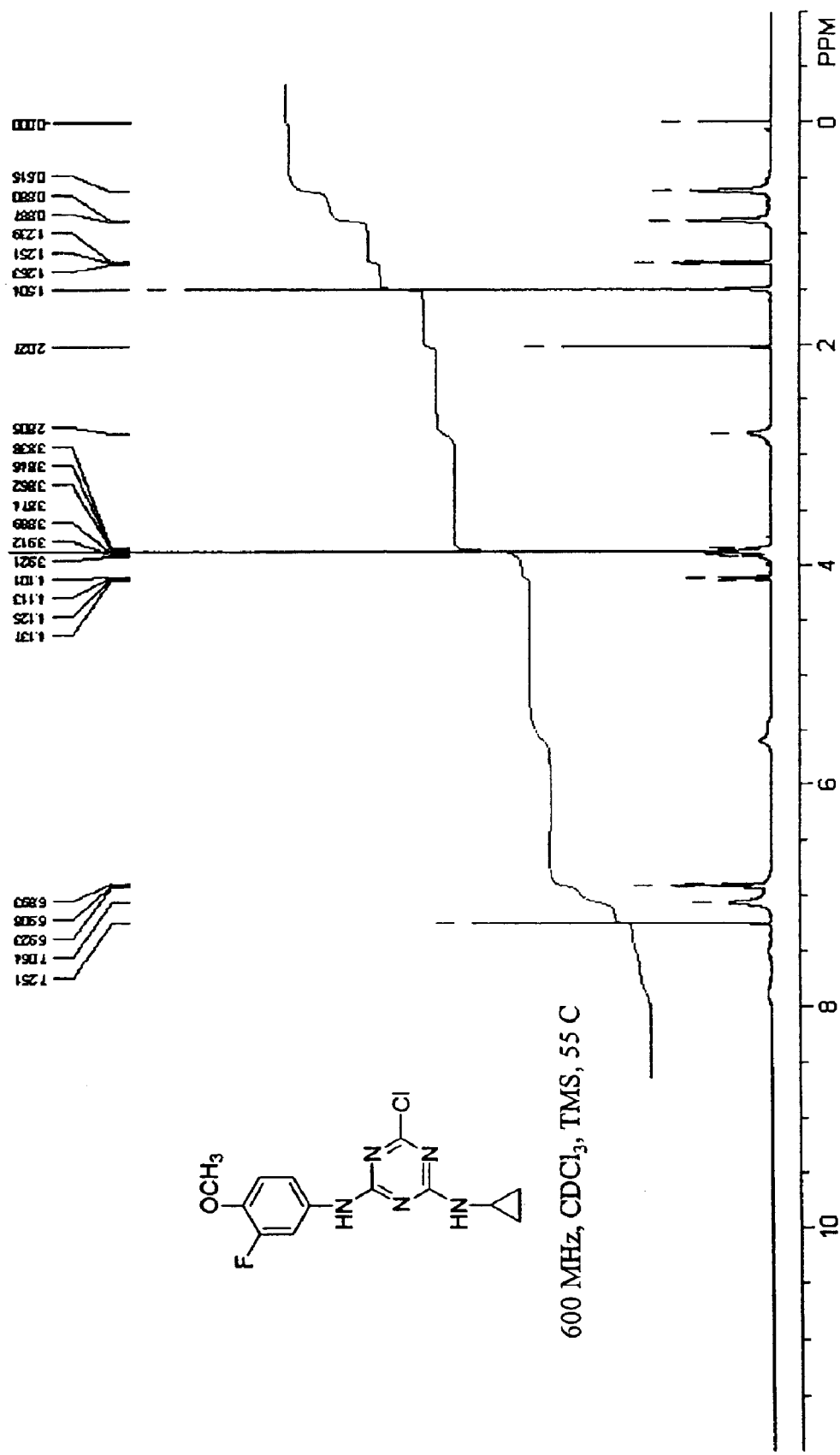
FIG. 66. ¹H NMR of 6-Chloro-N-cyclopropyl-N'-(3-fluoro-4-methoxy-phenyl)-[1,3,5]triazine-2,4-diamine.
Figure 67:
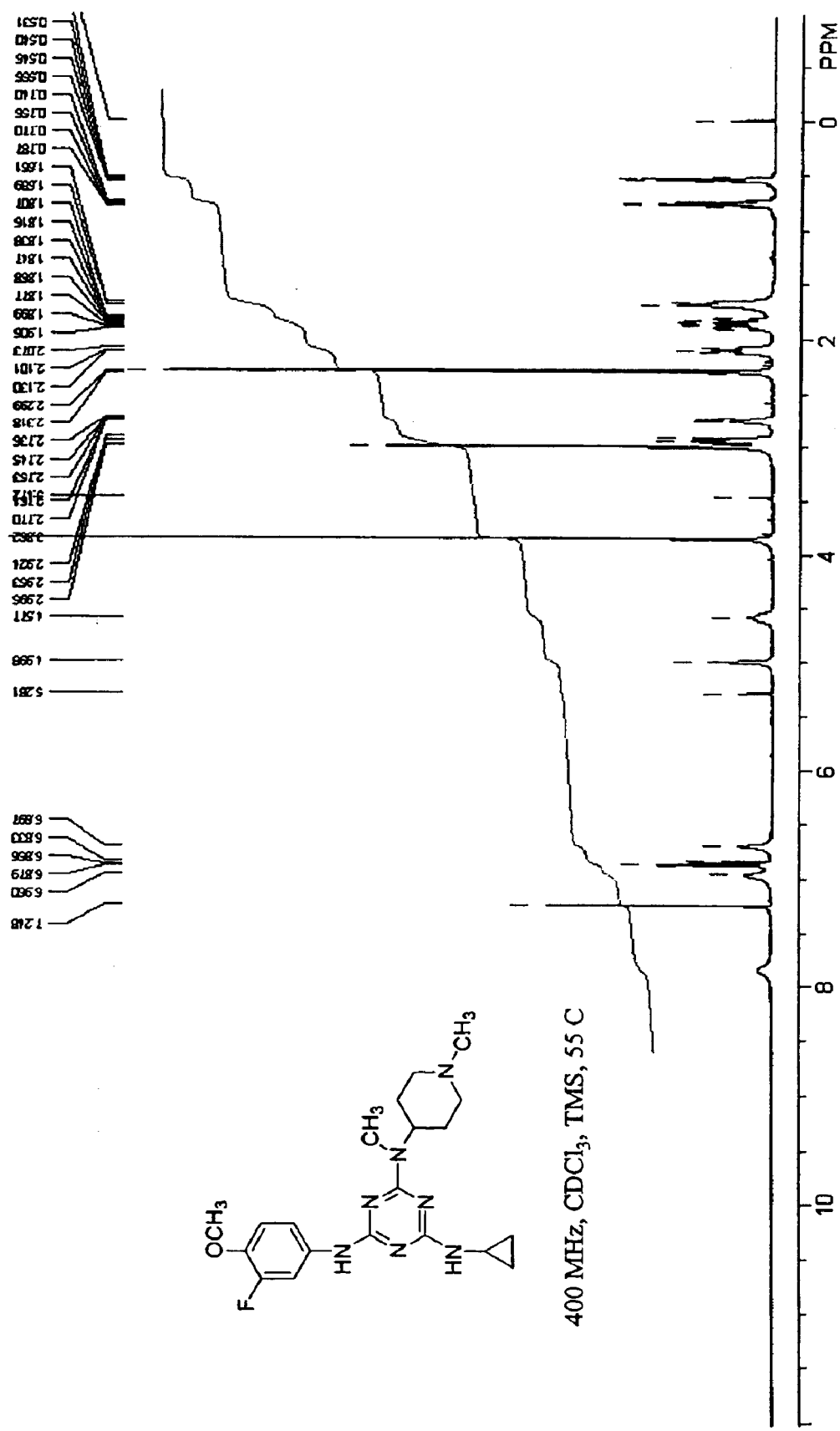
FIG. 67. ¹H NMR of N-Cyclopropyl-N'-(3-flouro-4-methoxy-phenyl)-N"'-methyl-N"-(1-methyl-piperidin-4-yl)-[1,3,5]triazine-2,4,6-triamine.
Figure 68:
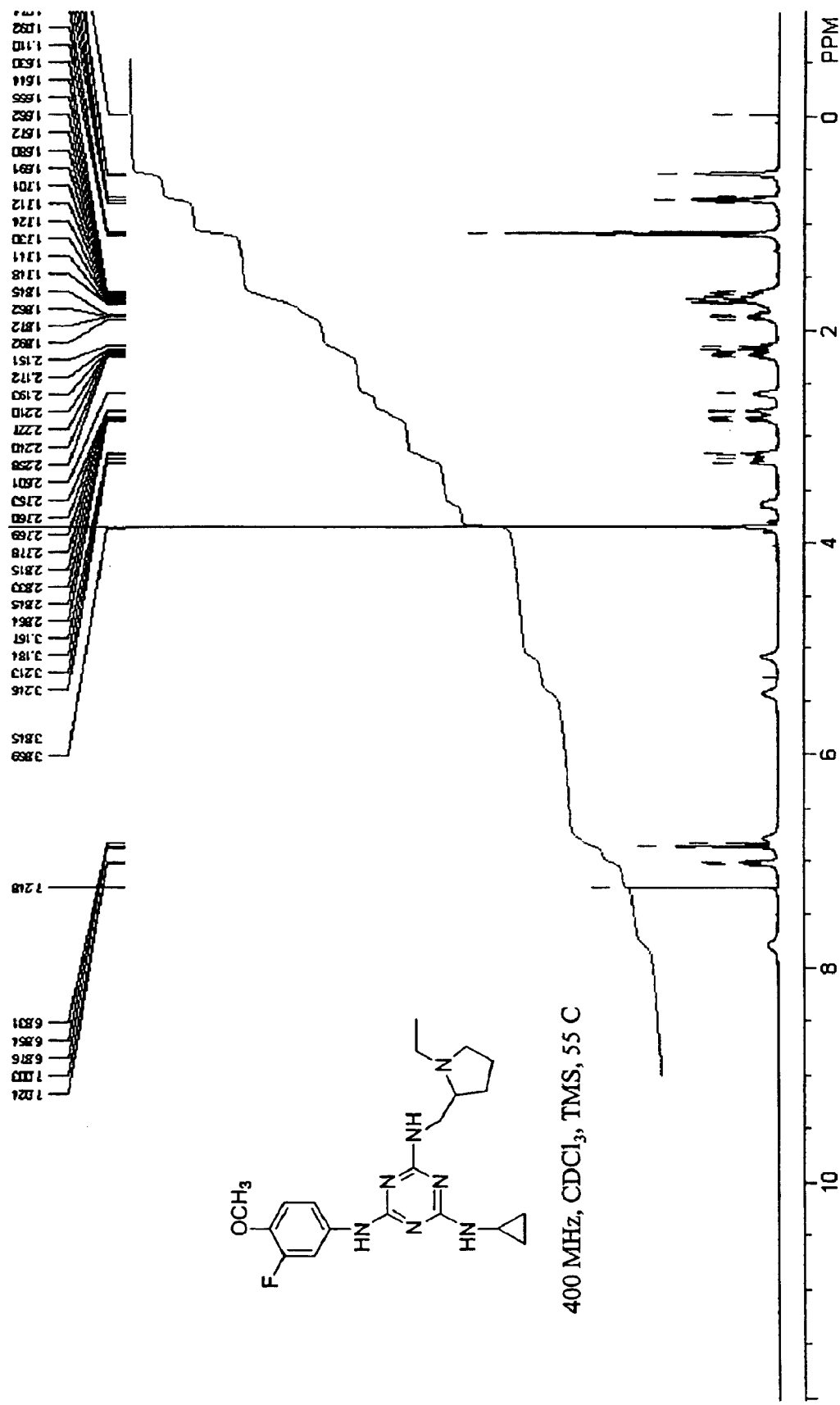
FIG. 68. ¹H NMR of N-Cyclopropyl-N'-(1-ethyl-pyrrolidin-2-ylmethyl)-N"-(3-fluoro-4-methoxy-phenyl)-[1,3,5]triazine-2,4,6-triamine.
Figure 69:
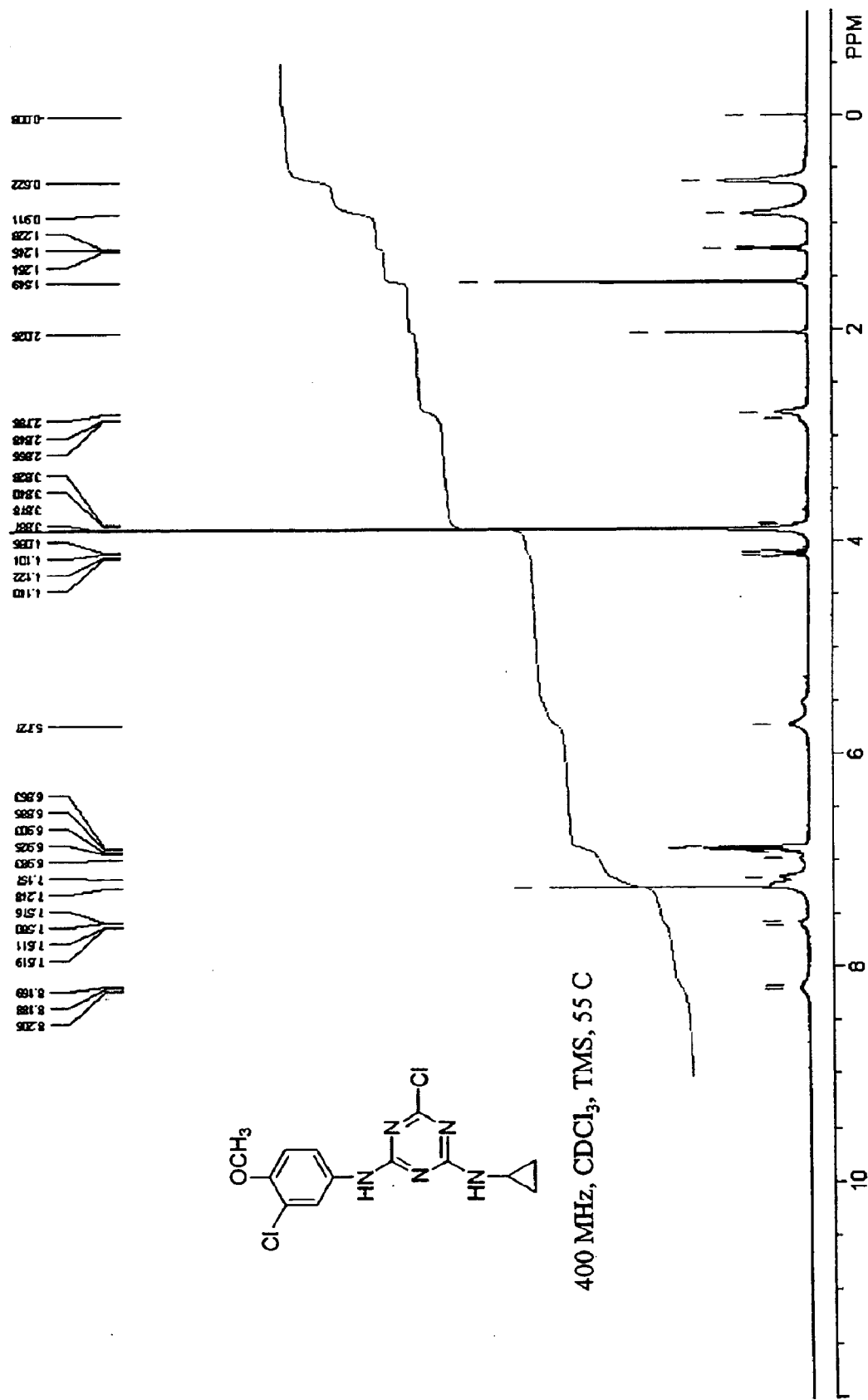
FIG. 69. ¹H NMR of 6-Chloro-N -(3-chloro-4-methoxy-phenyl)-N'-cyclopropyl-[1,3,5]triazine-2,4-diamine.
Figure 70:
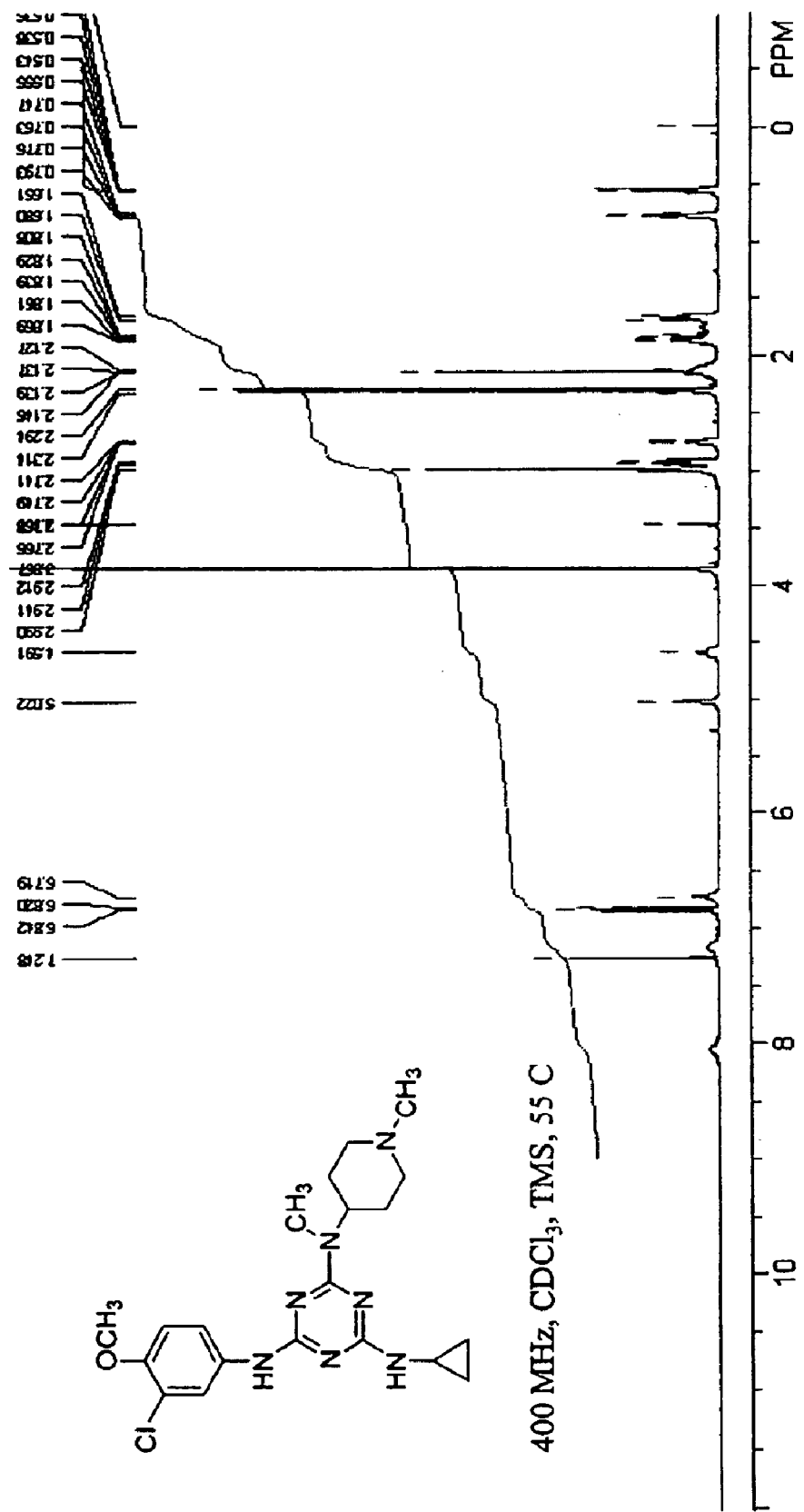
FIG. 70. ¹H NMR of N-Cyclopropyl-N'-(3-chloro-4-methoxy-phenyl)-N"'-methyl-"N-(1-methyl-piperidin-4-yl)-[1,3,5]triazine-2,4,6-triamine.
Figure 71:
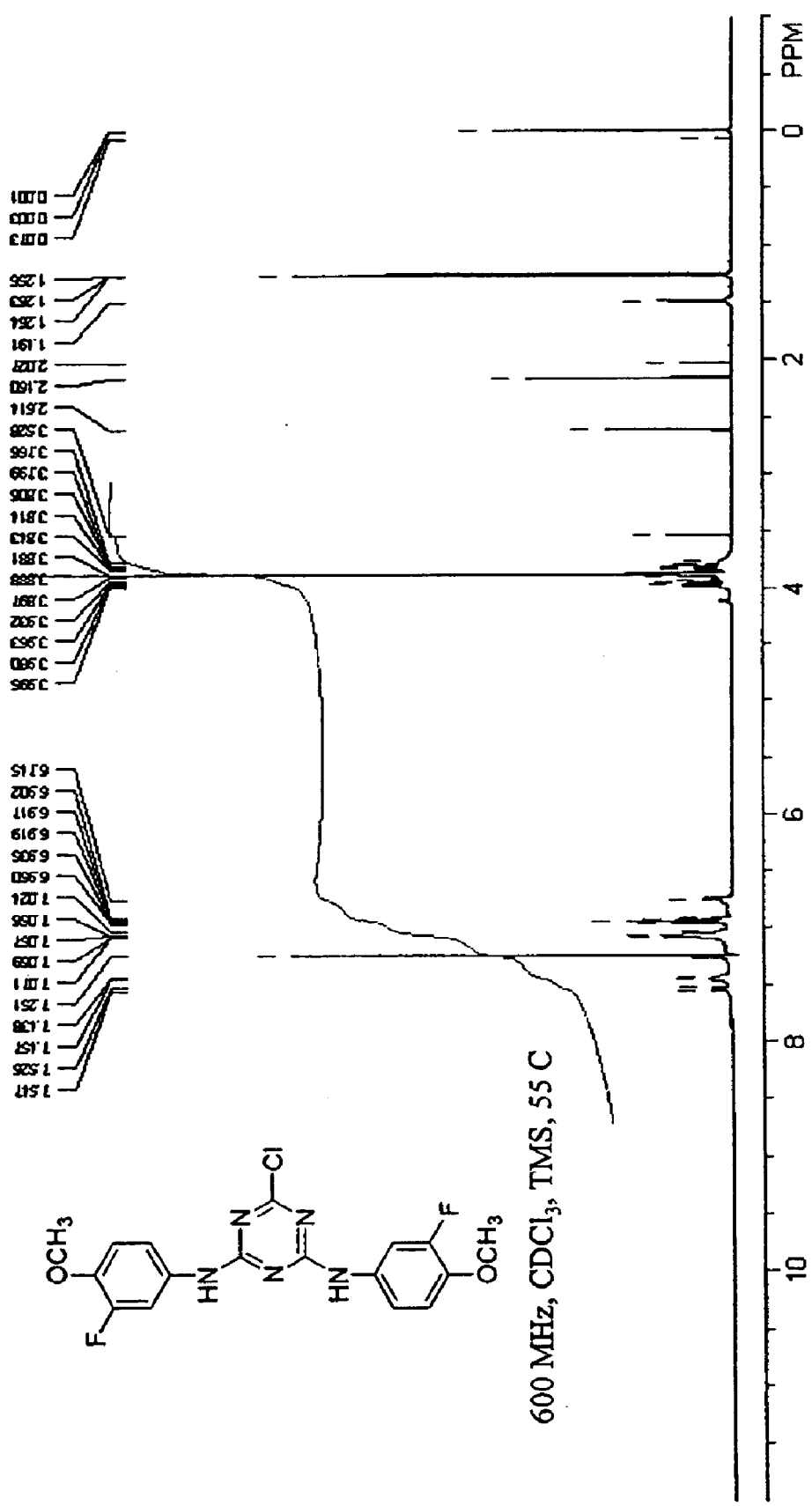
FIG. 71. ¹H NMR of 6-Chloro-N,N'-bis-(3-fluoro-4-methoxy-phenyl)-[1,3,5]triazine-2,4-diamine.
Figure 72:
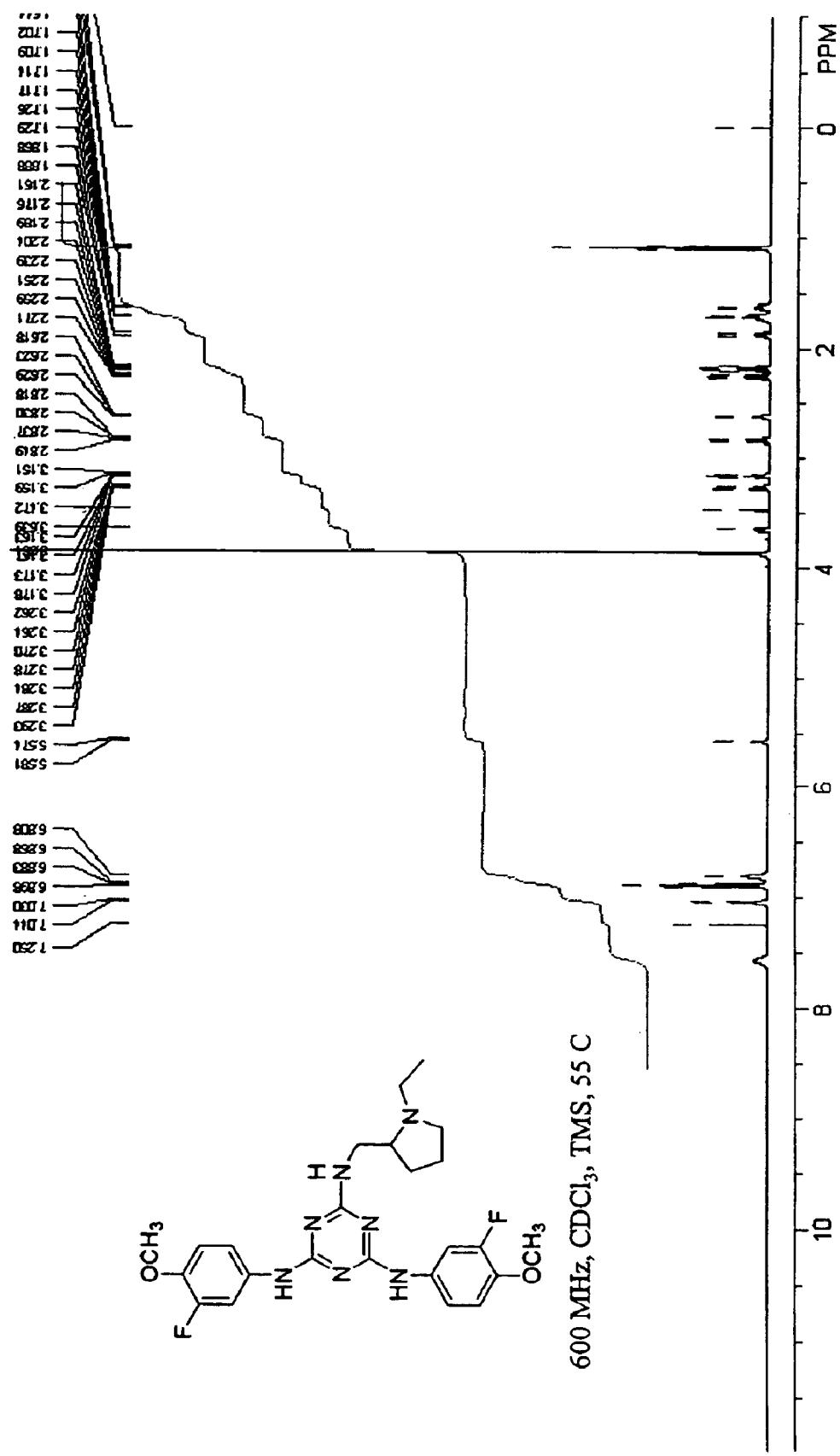
FIG. 72. ¹H NMR of N-(1-Ethyl-pyrrolidin-2-ylmethyl)-N',N"-bis-(3-fluoro-4-methoxy-phenyl)-[1,3,5]triazine-2,4,6-triamine.
Figure 74:
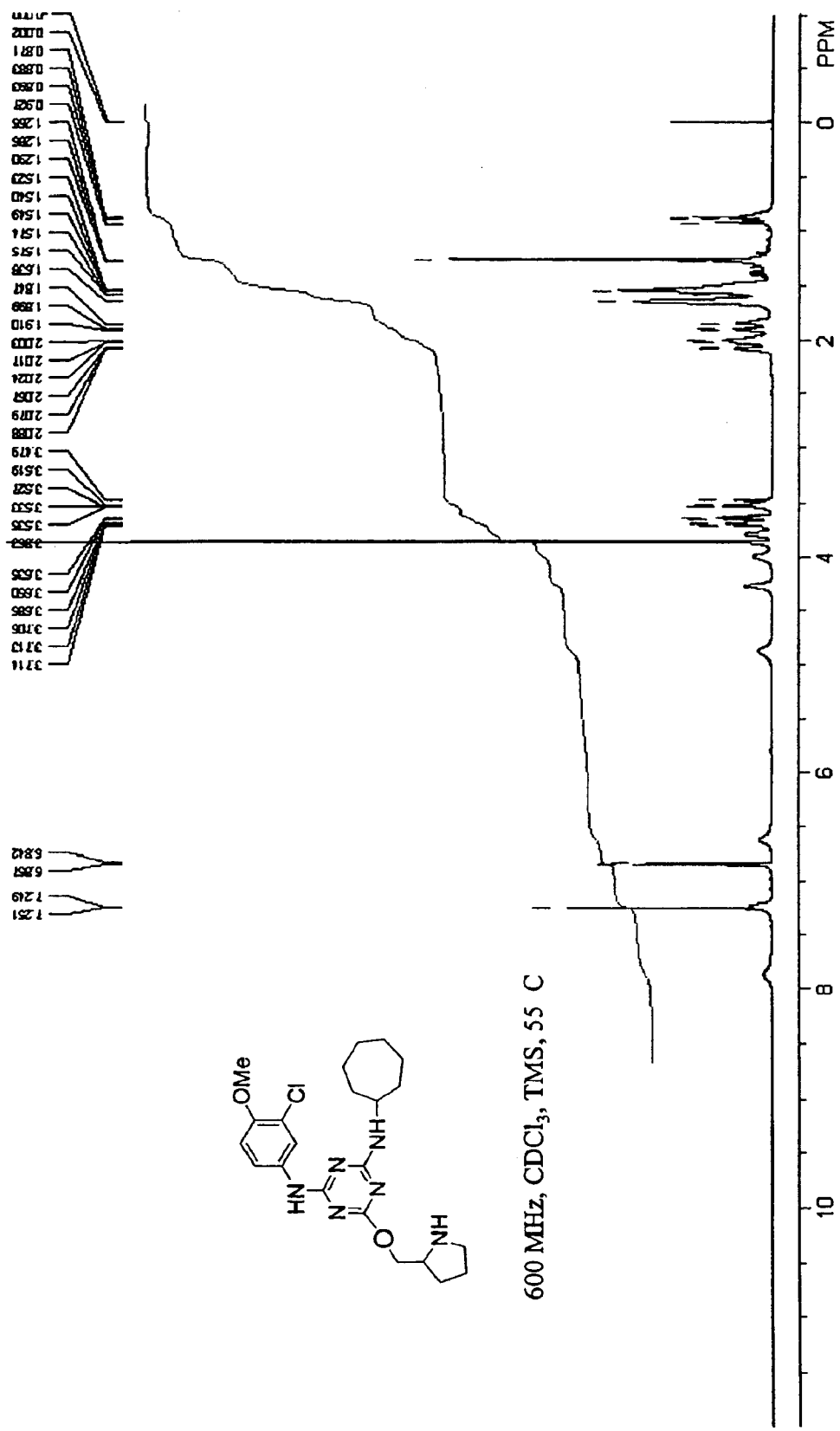
FIG. 74. ¹H NMR of $N^2$-(3-chloro-4-methoxyphenyl)-$N^4$-cycloheptyl-6-(2-azolanylmethoxy)-1,3,5-triazine-2,4-diamine.
Figure 75:
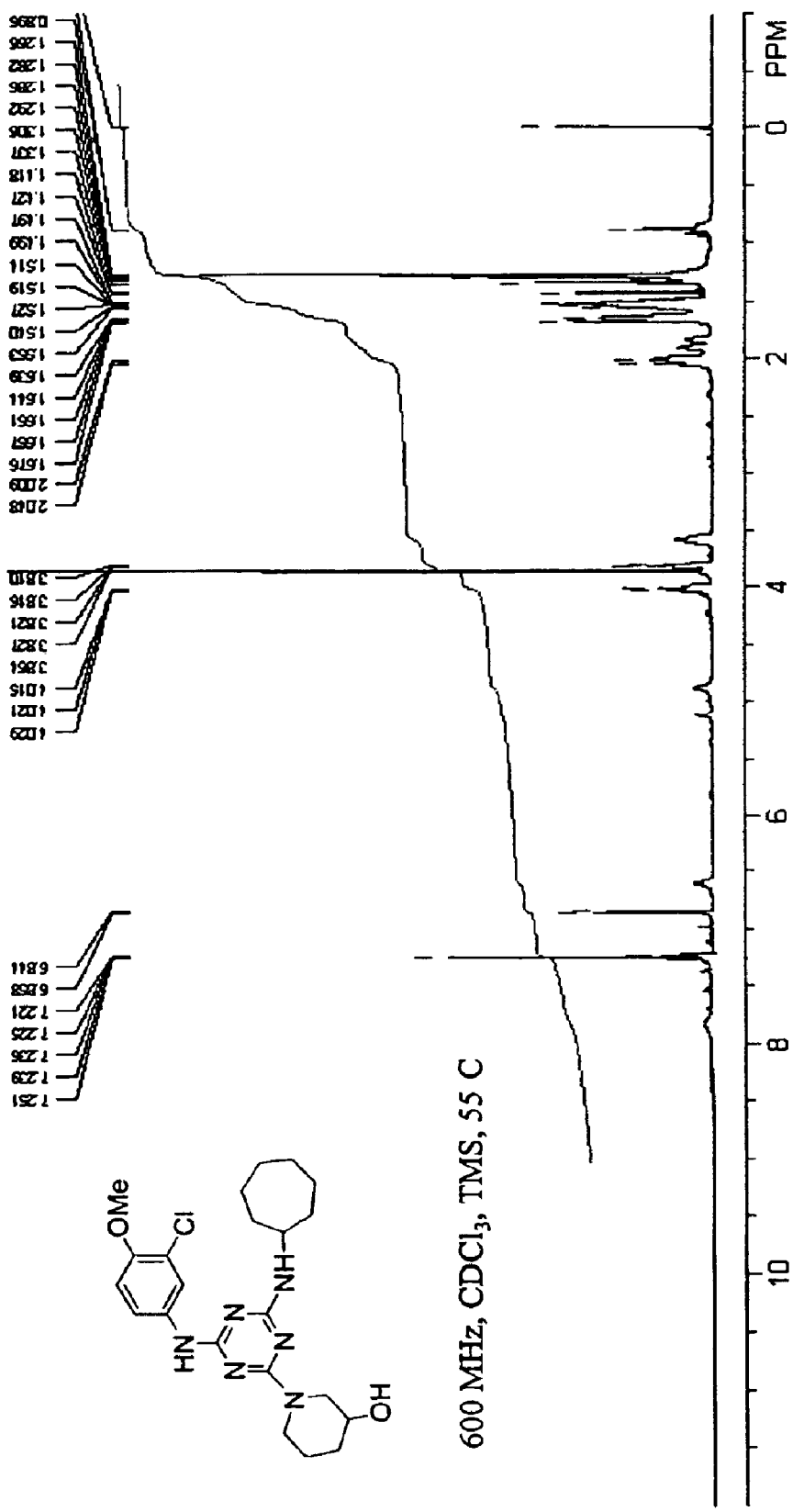
FIG. 75. ¹H NMR of 1-[4-(3-chloro-4-methoxyphenylamino)-6-cycloheptylamino-[1,3,5]triazine-2-yl]-piperidin-3-ol.
Figure 76:
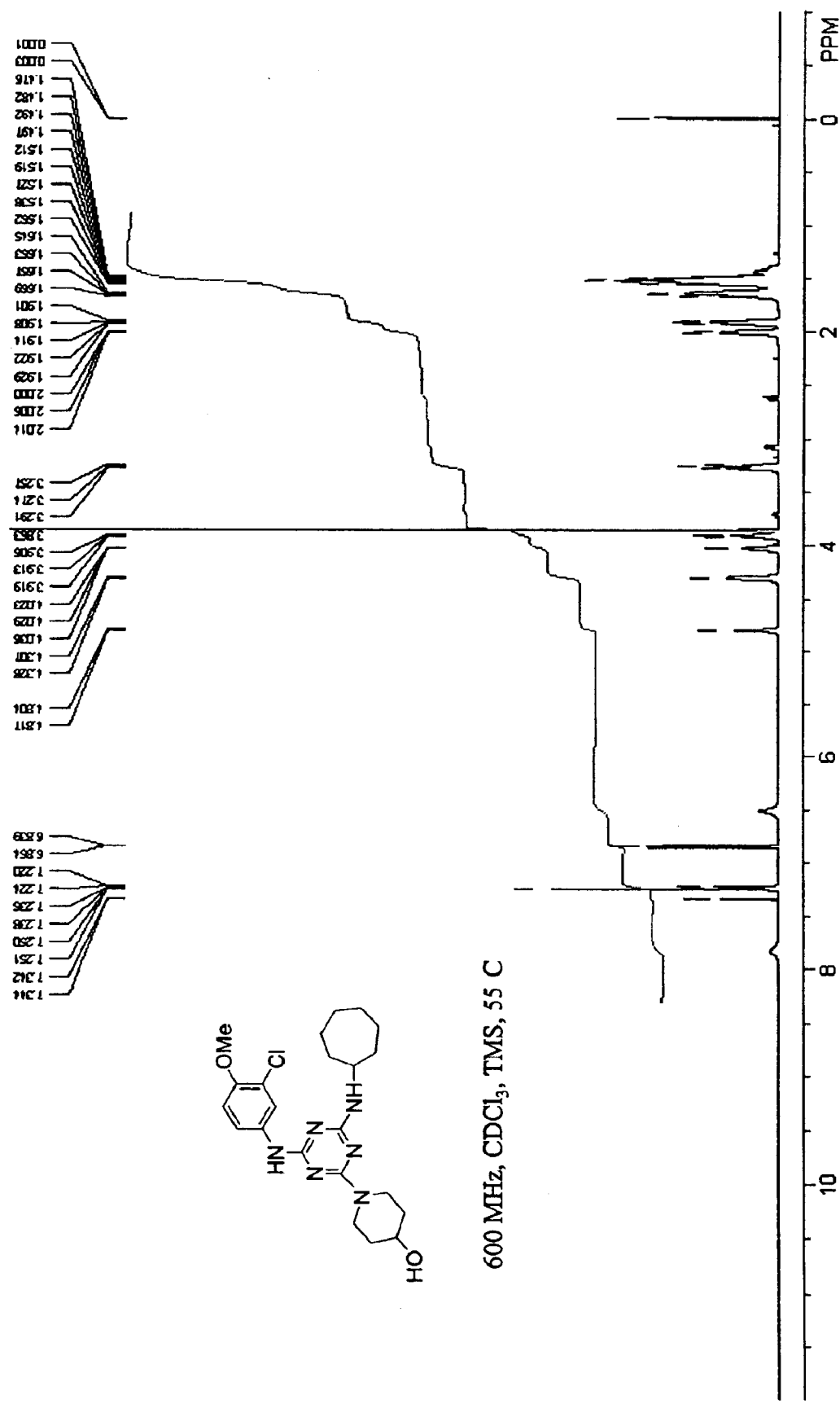
FIG. 76. ¹H NMR of 1-[4-(3-chloro-4-methoxyphenylamino)-6-cycloheptylamino-[1,3,5]triazine-2-yl]-piperidin-4-ol.
Figure 77:
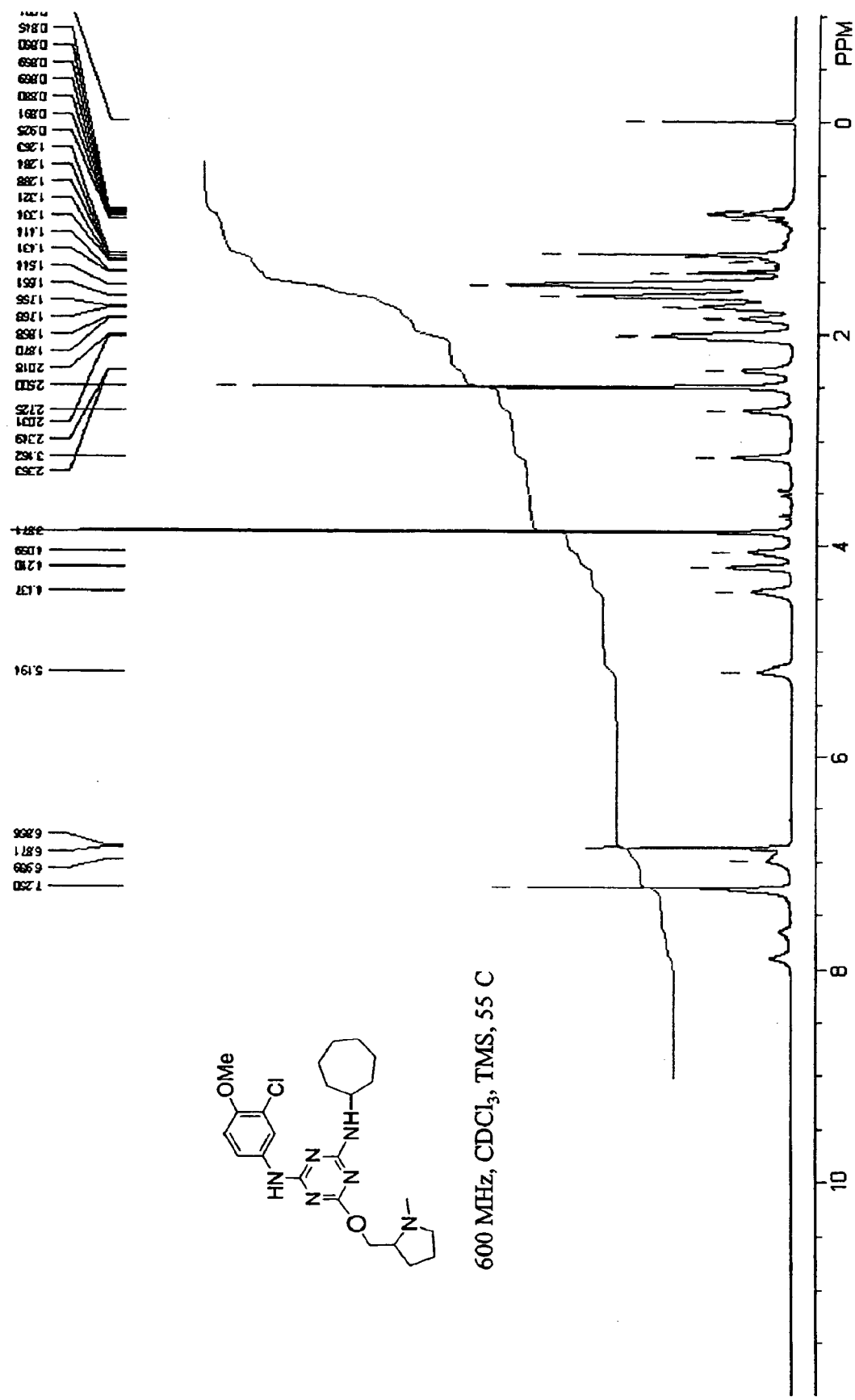
FIG. 77. ¹H NMR of $N^2$-(3-chloro-4-methoxyphenyl)-$N^4$-cycloheptyl-6-(1-methyl-2-azolanylmethoxy)-1,3,5-triazine-2,4-diamine.
Figure 78:
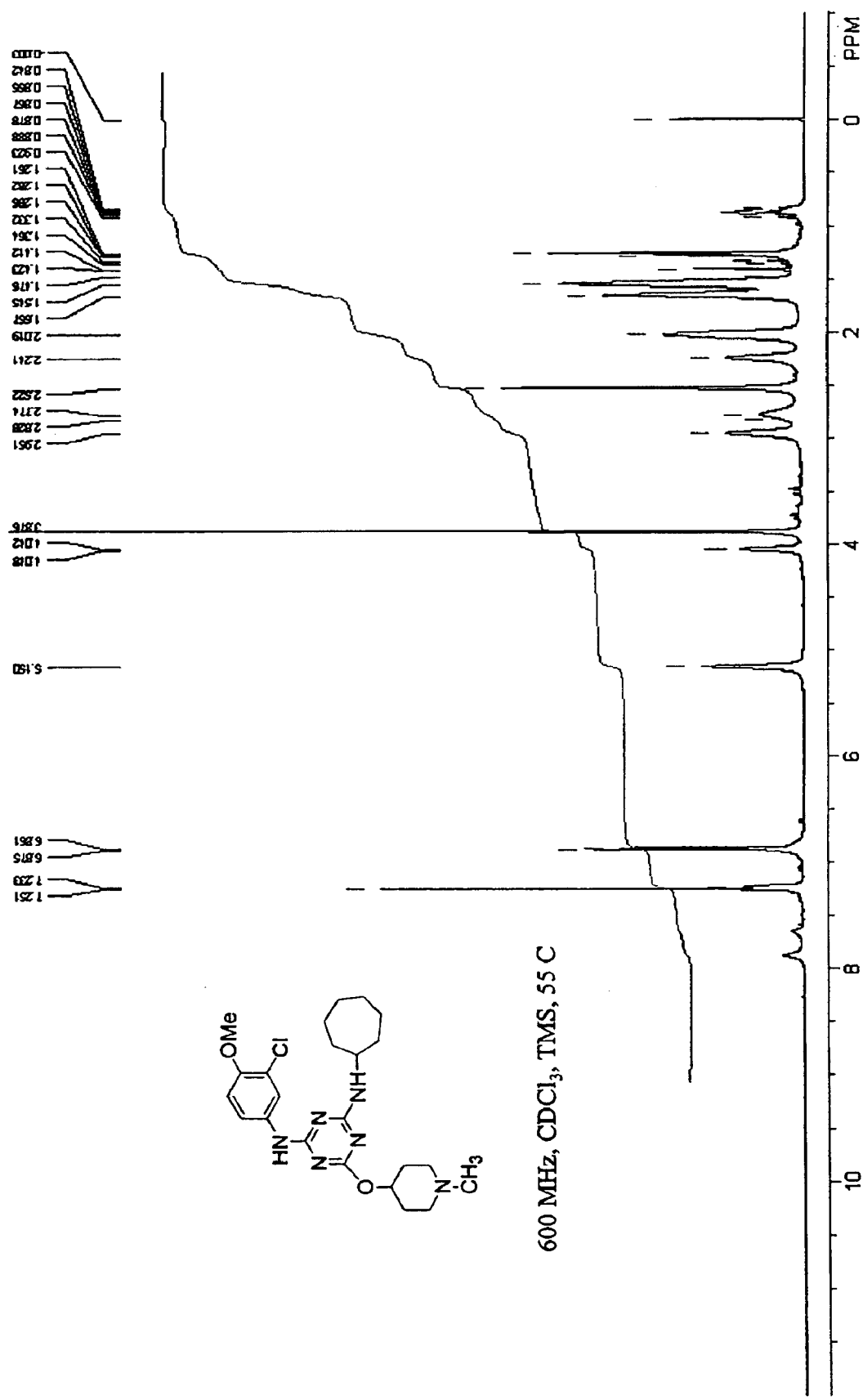
FIG. 78. ¹H NMR of $N^2$-(3-chloro-4-methoxyphenyl)-$N^4$-cycloheptyl-6-(1-methyl-4-piperidyloxy)-1,3,5-triazine-2,4-diamine.
Figure 79:
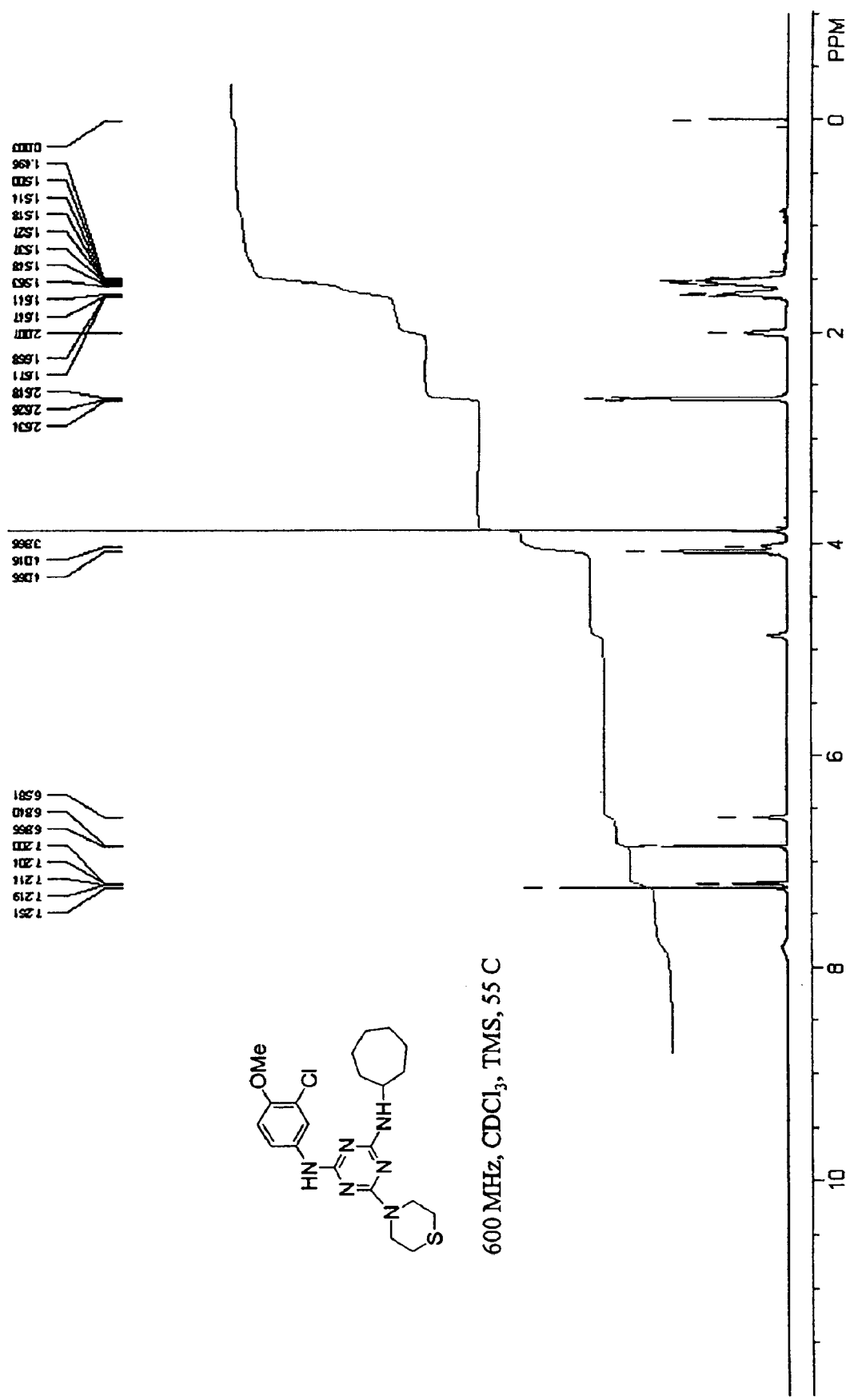
FIG. 79. ¹H NMR of $N^2$-(3-chloro-4-methoxyphenyl)-$N^4$-cycloheptyl-6-(1,4-thiazinan-4-yl)-1,3,5-triazine-4,2-diamine.
Figure 80:
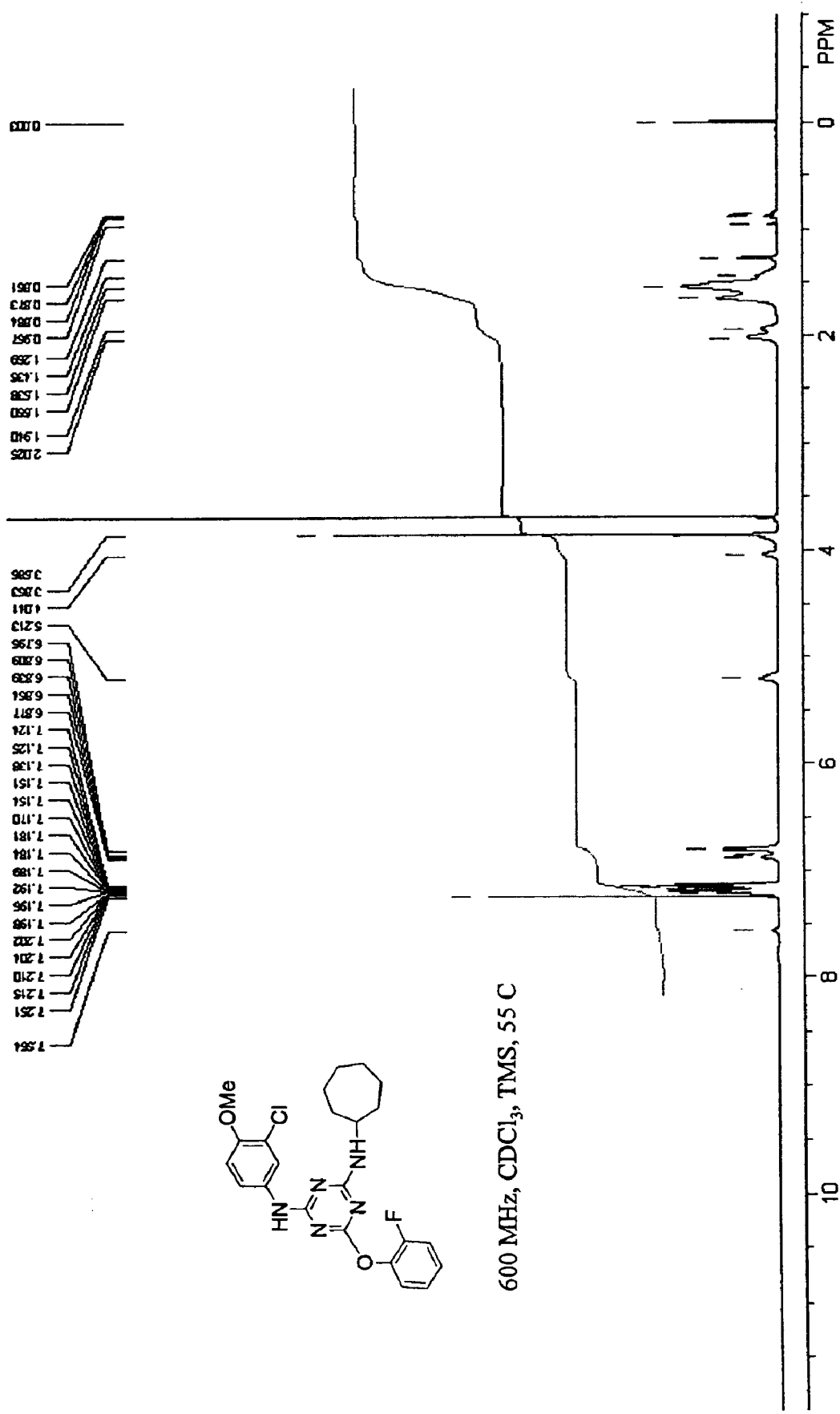
FIG. 80. ¹H NMR of $N^2$-(3-chloro-4-methoxyphenyl)-$N^4$-cycloheptyl-6-(2-fluorophenoxy)-1,3,5-triazine-4,2-diamine.
Figure 81:
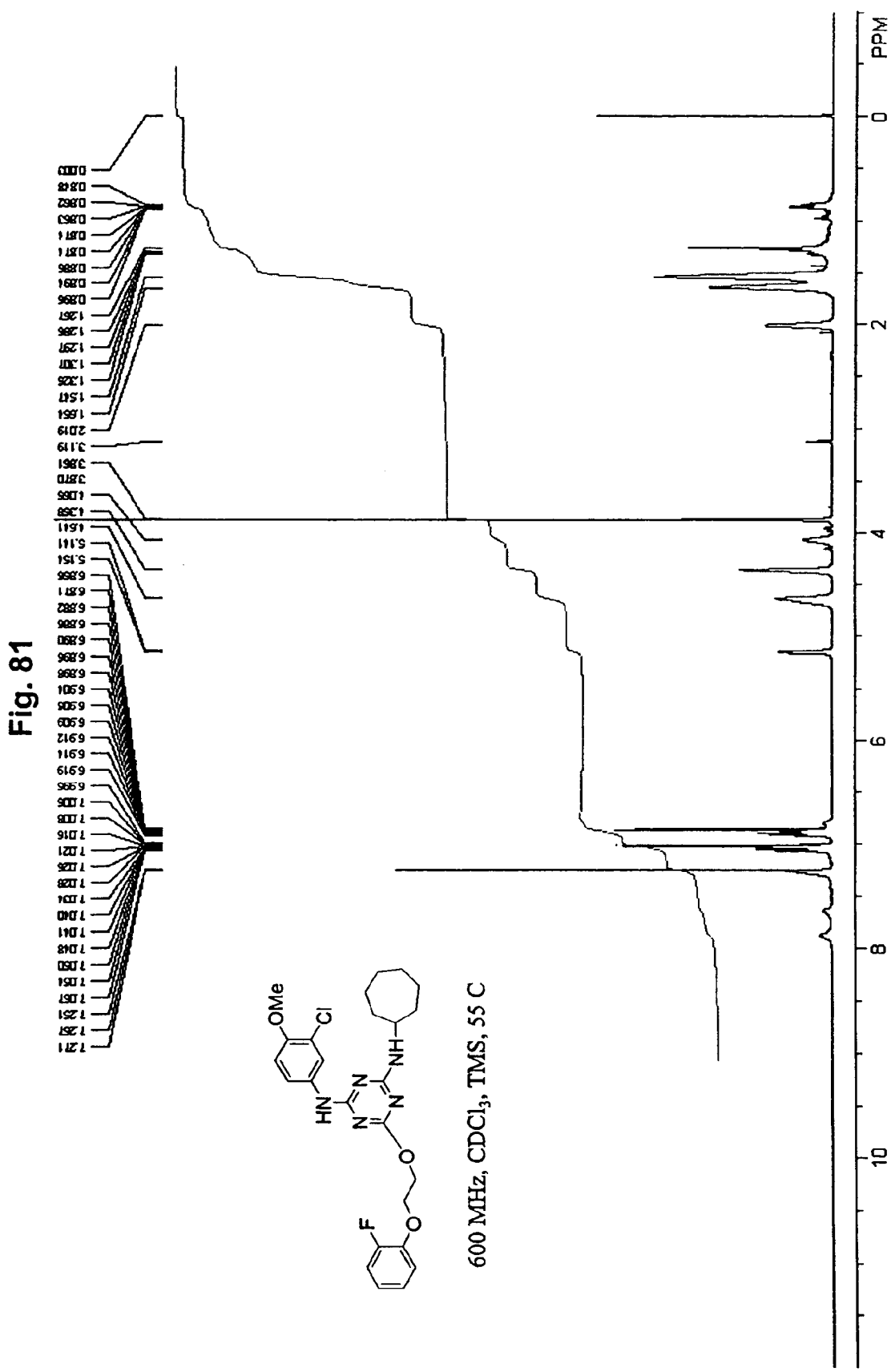
FIG. 81. ¹H NMR of $N^2$-(3-chloro-4-methoxyphenyl)-$N^4$-cycloheptyl-6-[2-(2-fluorophenoxy) ethoxy]-1,3,5-triazine-4,2-diamine.
Figure 82:
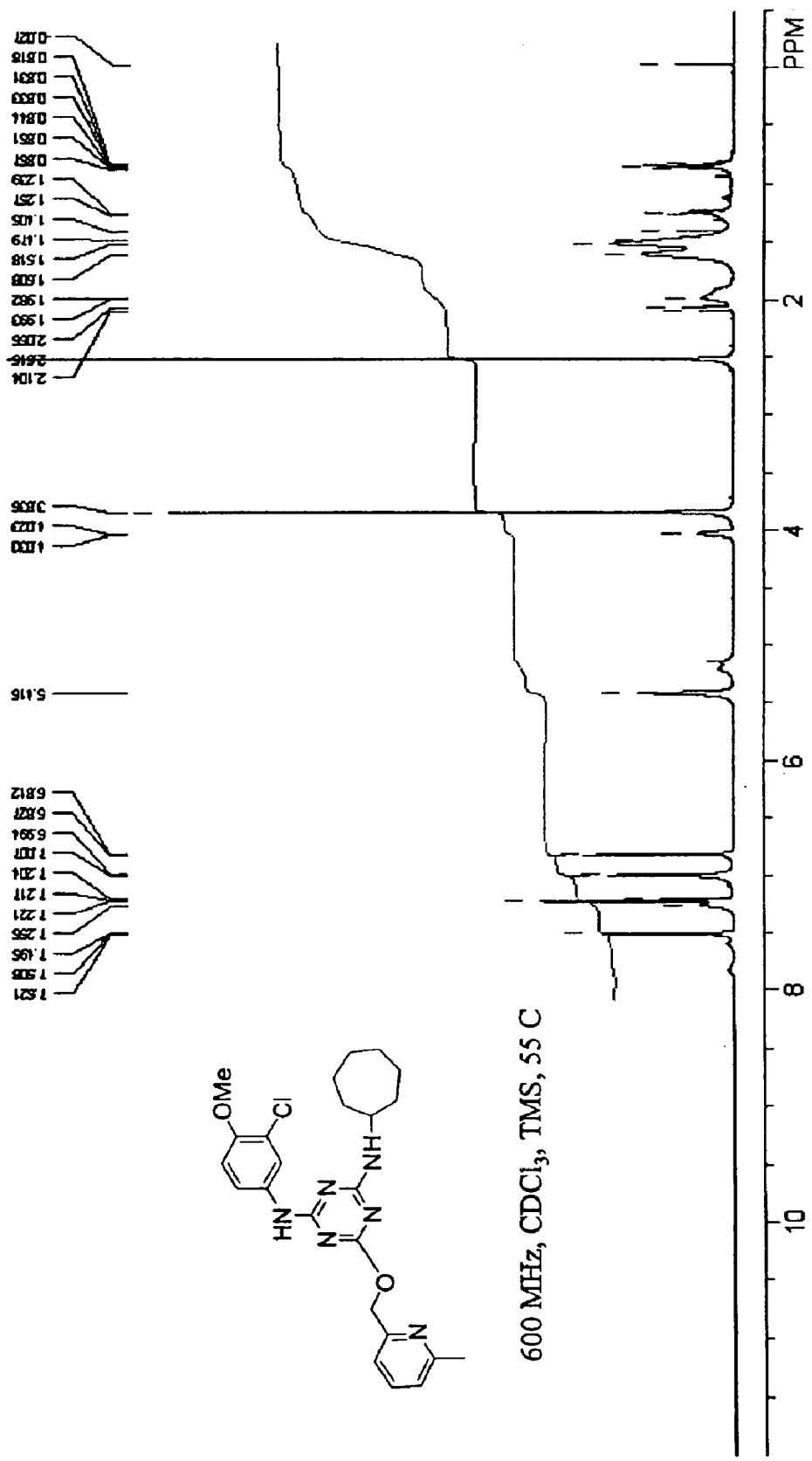
FIG. 82. ¹H NMR of $N^2$-(3-chloro-4-methoxyphenyl)-$N^4$-cycloheptyl-6-(6-methyl-2-pyryl methoxy]-1,3,5-triazine-4,2-diamine.
Figure 83:
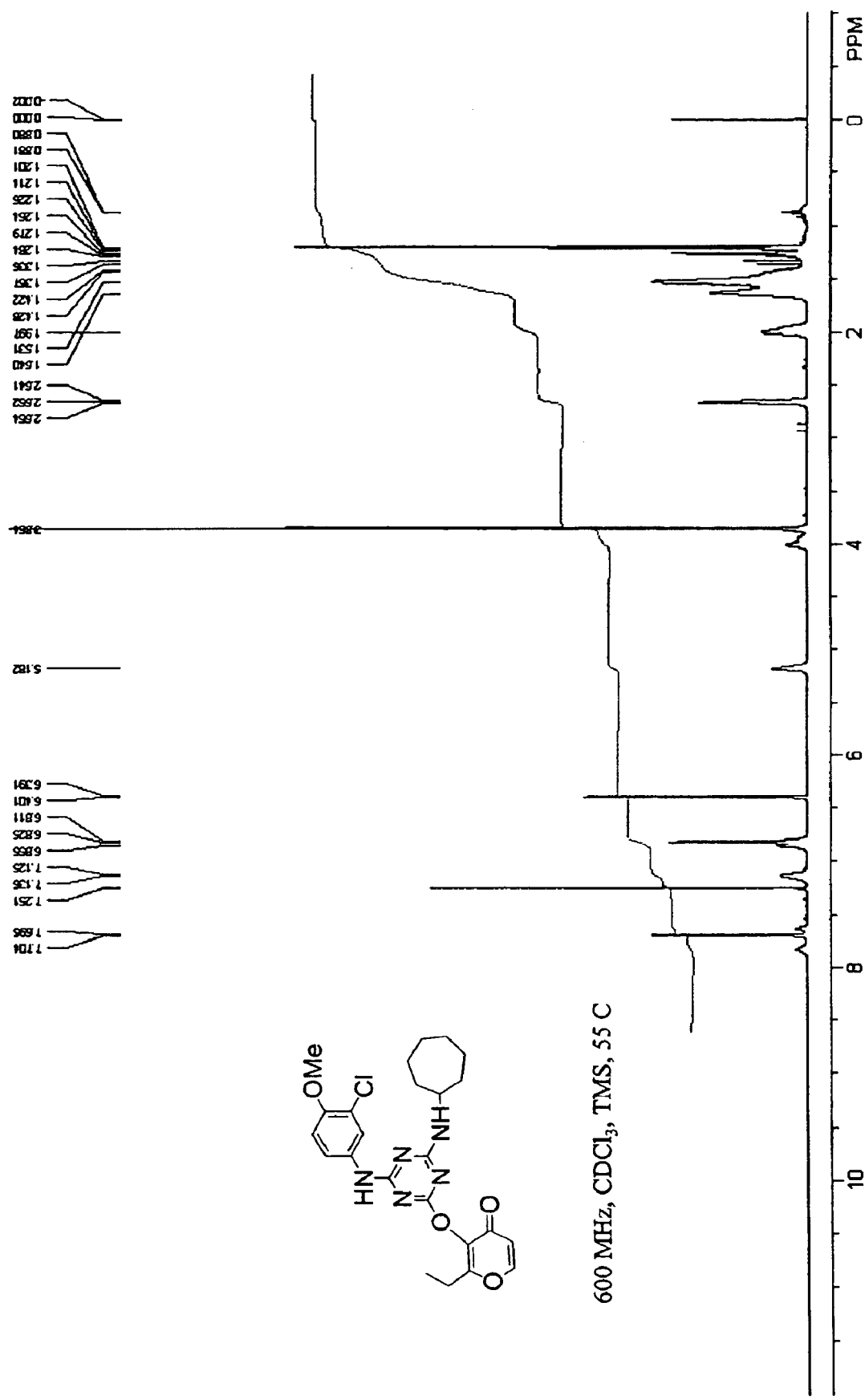
FIG. 83. ¹H NMR of 3-[4-(3-chloro-4-methoxyanilino)-6-cycloheptylamino-1,3,5-triazin-2-yloxy]-2-ethyl-4H-4-pyranone.
Figure 84:
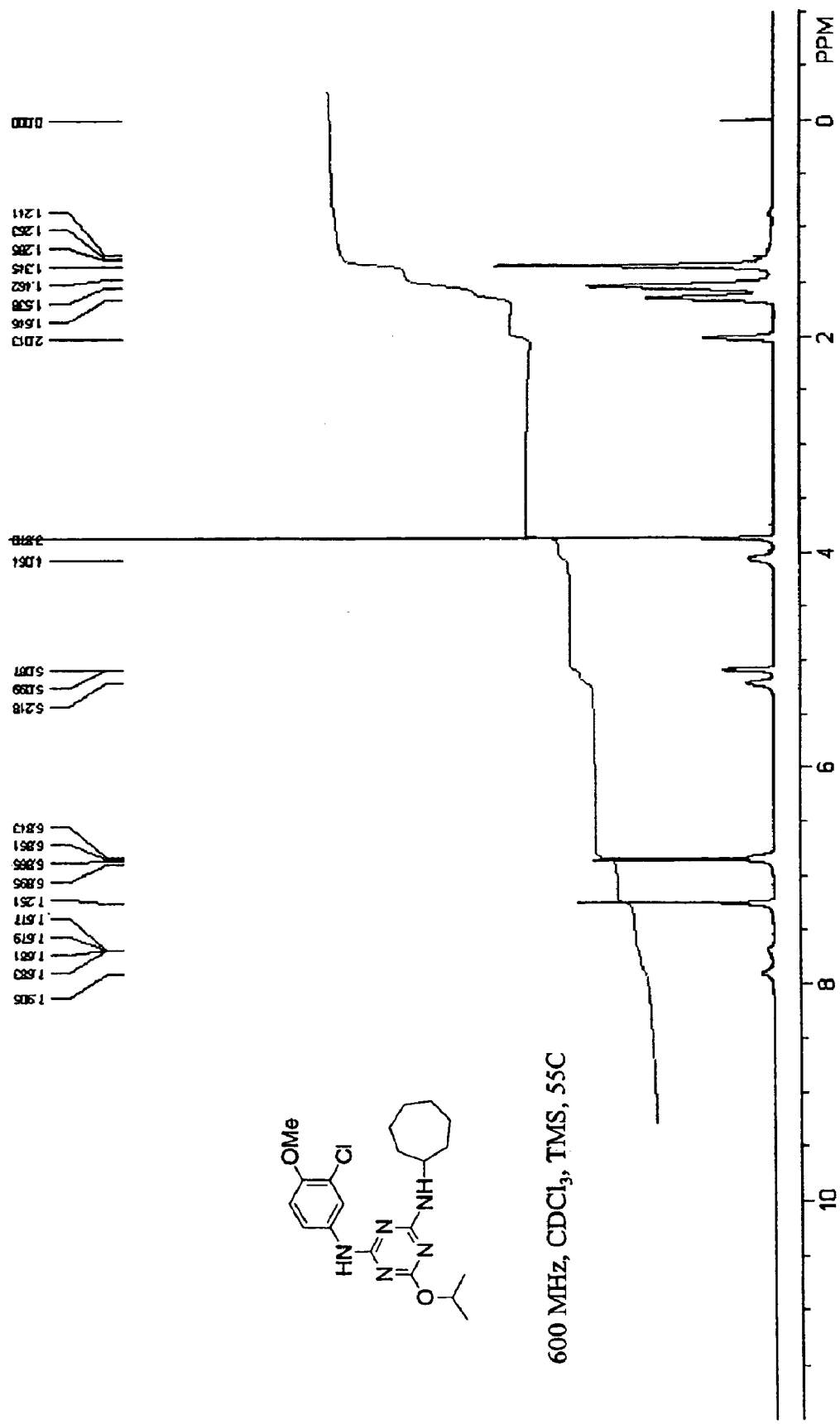
FIG. 84. ¹H NMR of $N^2$-(3-chloro-4-methoxyphenyl)-$N^4$-cycloheptyl-6-isopropoxy-1,3,5-triazine-2,4-diamine.
Figure 85:
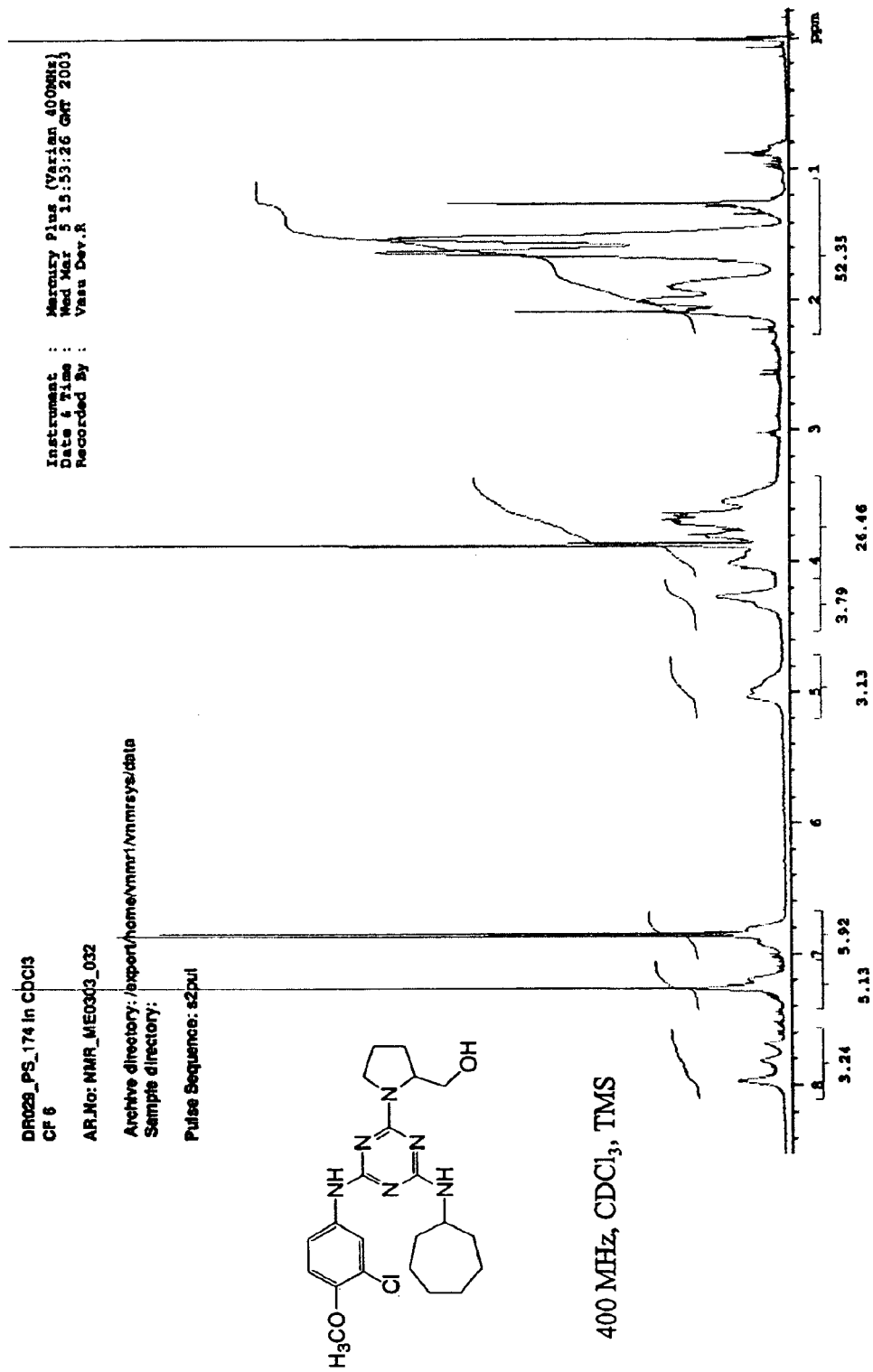
FIG. 85. ¹H NMR of 1-[4-(3-chloro-4-methoxyanilino)-cycloheptyl amino-1,3,5-triazin-2-yl]-2-azoloamymethanol.
Figure 86:
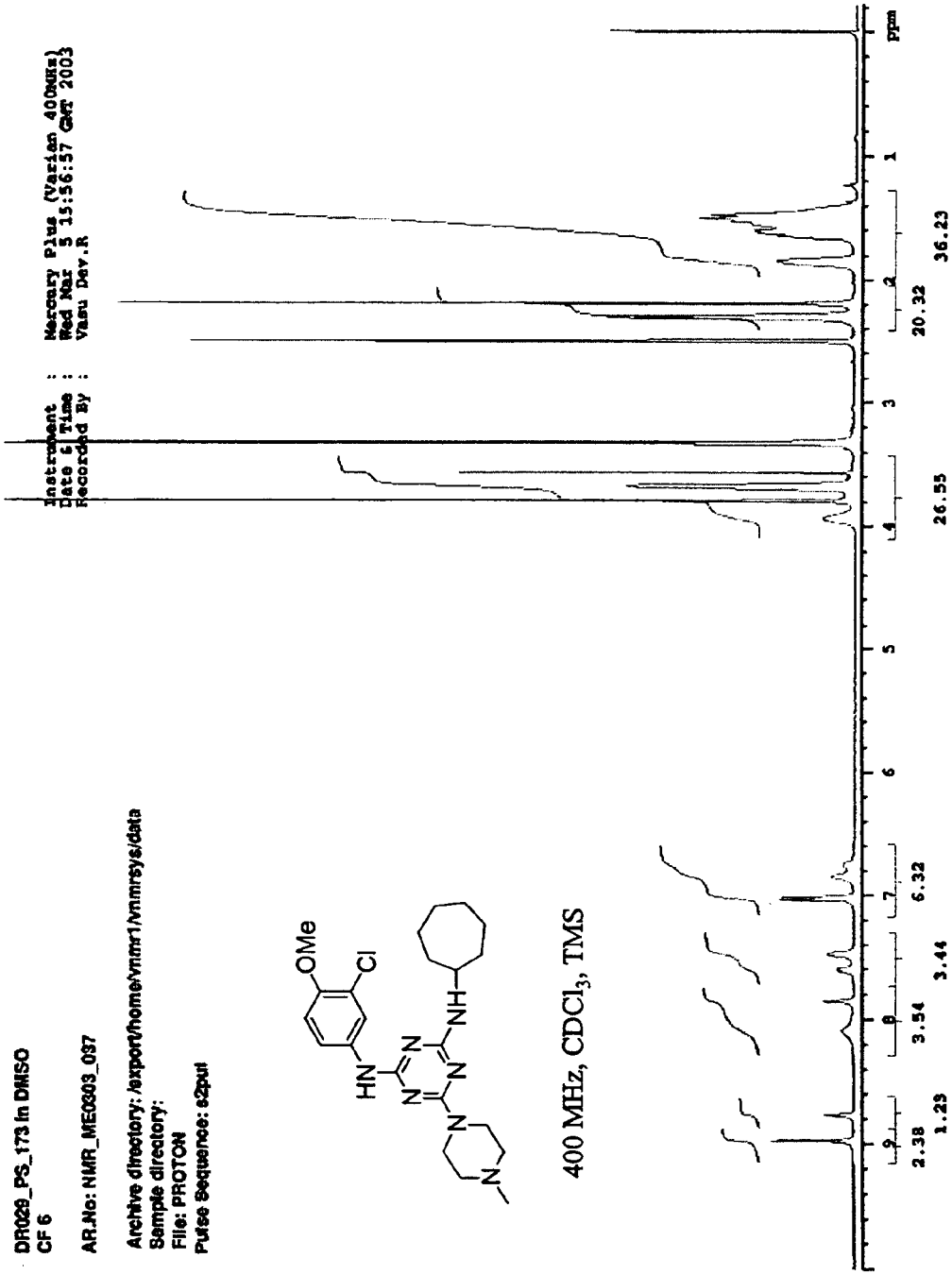
FIG. 86. ¹H NMR of $N^2$-(3-chloro-4-methoxyphenyl)-$N^4$-cycloheptyl-6-(4-methylpiperzino)-1,3,5-triazine-4,2-diamine.

The effects of compounds of the present invention on G-HSA induced IL-6 are shown in FIG. 54. G is G-HSA, and C is control, no treatment with compounds or G-HSA. Endothelial cells under basal conditions secreted about 25 pg/ml of IL-6. Incubation of endothelial cells with G-HSA induced a 3 fold increase in IL-6 secretion by endothelial cells. Addition of compounds of the present invention, as indicated by each compound's number, to G-HSA containing media significantly reduced endothelial secretion of IL-6. These inhibitory effects varied, the most effective compounds showed an 80% decrease in IL-6 secretion. These data show the compounds of the present invention have anti-inflammatory activity.

Example 87

Cytotoxicity/Lactate Dehydrogenase Assay

An appropriate number of cells are plated in four 96-well plates, one plate for "day 0" and three plates for days 1–3. Cells are treated with at least one compound of the present invention in varying concentrations with and without the apoptosis inducer cisplatin (2 µM) ("+cis" or "–cis"). Untreated cells are also assayed with and without cisplatin. After transfection, the plates are incubated at 37° C. overnight.

An appropriate number of cells are plated in four 96-well plates, one plate for "day 0" and three plates for days 1–3. Cells are treated with at least one compound of the present invention in varying concentrations. The negative control cells have normal media conditions, a duplicate set of wells is treated with the composition in which the compound is provided, but there is no added compound and the positive control cells are treated with the apoptosis inducer cisplatin (2 µM). All of the cells are transfected with a vector having a promoter that is responsive to apoptosis conditions. When apoptosis occurs, the promoter is turned on and the lactic dehydrogenase gene is activated and the enzyme protein is made and active. Activity is easily detected with a color change. After transfection, the plates are incubated at 37° C. overnight.

About 8 mls of warmed alpha MEM LDH lysis buffer (2% Triton X100) and about 8 mls of culture media (1/2 dilution) are combined. Two 96-well v-bottom plates are prepared, one labeled "lysis" and one labeled "supernatant." To lyse the cells, about 200 µl Alpha MEM lysis buffer (diluted 1/2 ) is added to one test plate from which the supernatant has been removed and added to the plate labeled supernatant. After mixing, about 200 µl of lysed cells are transferred to the lysis plate. Both the lysis and supernatant plates are centrifuged at about 1600 rpm for about 10 min. After centrifugation, about 100 µl of both the supernatant or lysate is transferred to corresponding 96-well flat-bottomed plates.

The assay for cytotoxicity uses the Cytotoxicity Detection Kit (LDH) from Roche Diagnostics Corp. (Indianapolis, Ind.). Using the directions provided, the dye solution is mixed and added each well of the lysate and supernatant plate and incubated for up to 20–25 min at 15–25° C. in the dark.

The difference in the amount of lactate dehydrogenase released from cells in untreated cells when compared to cells treated with cisplatin or compounds of the present invention having cytotoxic activity shows the cytotoxic activity of the compounds tested.

Example 88

Synthesis of 4-Benzyloxy-3-chloro-phenylamine (E1)

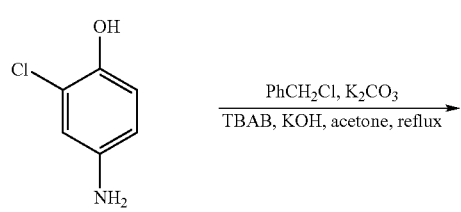

PhCH₂Cl, K₂CO₃
TBAB, KOH, acetone, reflux

-continued

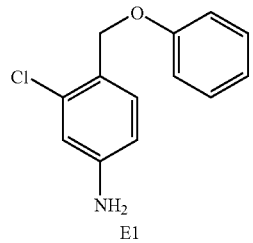

E1

To 4-amino-2-chlorophenol (7.23 g, 50 mmol) dissolved in acetone (250 mL), was added potassium carbonate (6.94 g, 50 mmol), followed by the addition of benzyl chloride (5.8 mL, 50 mmol), tetrabutylammonium bromide (TBAB) (1.66 g, 5 mmol), and potassium hydroxide (2.84 g, 50 mmol). The reaction mixture was allowed to stir at reflux overnight under nitrogen. The reaction mixture was extracted three times using dichloromethane; the combined organic layers were washed with brine and dried over potassium carbonate. The sample was concentrated and the resulting oil was dried overnight under vacuum. The material was purified by silica gel flash column chromatography eluting with 50:50 v:v hexanes:ethyl acetate and the collected fractions were concentrated in vacuo to give E1 (9.3 g, 80%); mp 54° C.; HPLC: Inertsil ODS 3V C18, 40:30:30 [KH₂PO₄ (0.01 M, pH 3.2):CH₃OH:CH₃CN], 264 nm, R$_t$ 14.8 min, 98.7% purity; MS (TOF ES+) m/z 234 (M+H, 100).

Example 89

Synthesis of N-(4-Benzyloxy-3-chloro-phenyl)-N'-cycloheptyl-N''-(1-methyl-piperidin-4-yl)-[1,3,5]triazine-2,4,6-triamine (E2)

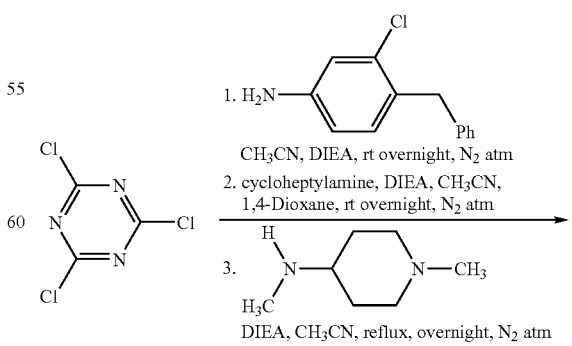

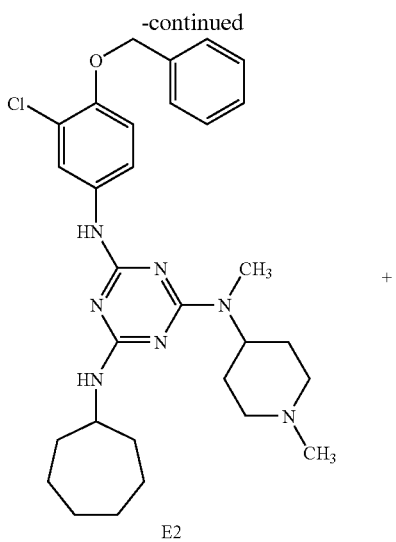

E2

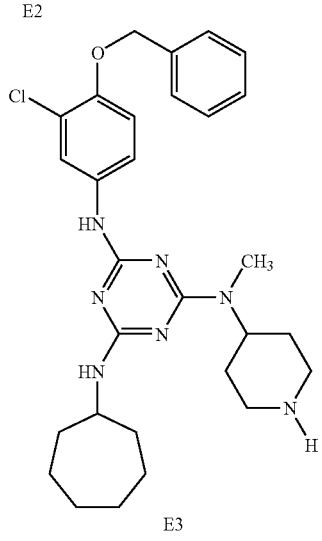

E3

To cyanuric chloride (3.148 g, 17.0 mmol) dissolved in acetonitrile (70 mL) stirring at −20° C., was added a solution of 4-benzyloxy-3-chloro-phenylamine (4.0188 g, 17.0 mmol) in acetonitrile (40 mL) followed by the addition of diisopropylethylamine (DIEA) (3 mL, 17.0 mmol), and was stirred at −20° C. for 1 hour under a nitrogen atmosphere. The mixture was allowed to warm to room temperature and then cycloheptylamine (2.2 mL, 17.0 mmol) was added in anhydrous acetonitrile (5 mL) followed by addition of a DIEA (3.2 mL, 18.7 mmol), and the mixture was stirred at room temperature overnight. To this reaction mixture was added DIEA (3.2 mL, 18.7 mmol) followed by addition of N-methyl-4-(methylamino)piperidine (2.5 mL, 17.0 mmol) and was stirred and heated at reflux overnight. The reaction mixture was extracted 3 times with methylene chloride; the combined organic layers were washed one time with brine and dried over anhydrous potassium carbonate. The organic layer was concentrated in vacuo and dried overnight under vacuum. Column chromatography (90:9:1 v:v:v dichloromethane:methanol:ammonium hydroxide) yielded E2 (619 mg, 7%); mp 84° C.; HPLC: Inertsil ODS 3V C18, 40:30:30 [$KH_2PO_4$ (0.01 M, pH 3.2):$CH_3OH$:$CH_3CN$], 264 nm, $R_t$ 37.1 min, 99.4% purity; MS (TOF ES+) m/z 550 (M+H, 100), 276 (M+2H, 34.9), 275.5 (83.9).

Example 90

Synthesis of N-(4-benzyloxy-3-chloro-phenyl)-N'-cycloheptyl-N''-methyl-N''-piperidin-4-yl-[1,3,5]triazine-2,4,6-triamine (E3)

Compound E3 was obtained as a side product (2.63 g) via column chromatography (silica gel; 90:9:1 v:v:v dichloromethane:methanol:ammonium hydroxide); mp 74° C.; HPLC: Inertsil ODS 3V C18, 40:30:30 [$KH_2PO_4$(0.01 M, pH 3.2):$CH_3OH$:$CH_3CN$], 264 nm, $R_t$ 38.6 min, 99.8% purity; MS (TOF ES+) mn/z 536 (M+H, 100), 269 (44.6), 268.5 (M+2H, 97.9).

Example 91

Synthesis of 4-[4-Cycloheptylamino-6-(methyl-piperidin-4-yl-amino)-[1,3,5]triazin-2-ylamino]-phenol (E4)

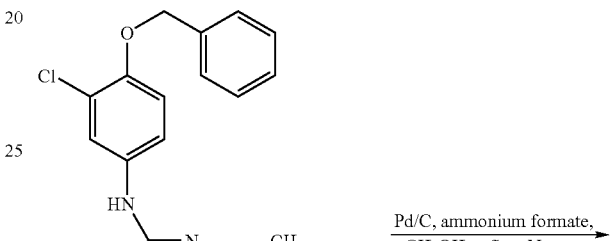

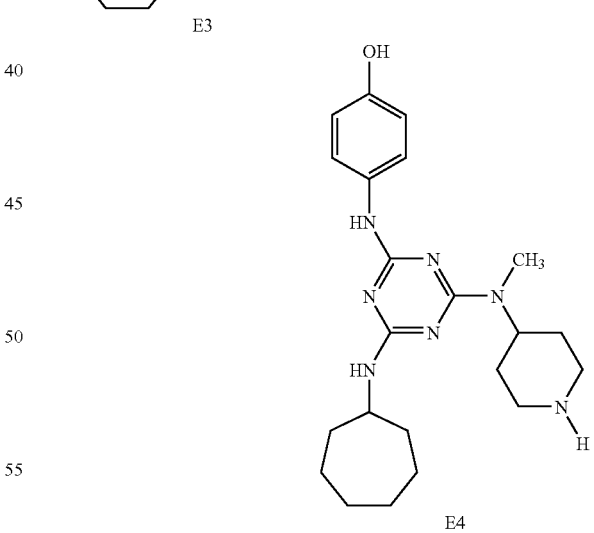

E4

In a dry round bottomed flask was added 10% Pd/C (301.5 mg) and was wetted with 3–5 drops of water. Nitrogen was blown over the Pd/C for about 5 minutes, then methanol (10 mL) was added cautiously and nitrogen was blown on the mixture for another 5 minutes. Triazine E3 (251.8 mg, 0.50 mmol) dissolved in methanol (5 mL) was added followed by ammonium formate (381.5 mg, 6.0 mmol), and the reaction was stirred and heated reflux for about 1.5 hours. Methylene chloride was added and allowed to cool to room temperature. The mixture was filtered by vacuum through Celite with a methylene chloride rinsing and the filtrate was concentrated in vacuo. The material was purified by silica gel flash chromatography eluting with 90:9:1 by volume methylene chloride:methanol:ammonium hydroxide, and the collected fractions were dried over anhydrous magnesium sulfate, filtered and then concentrated in vacuo to give a light yellow solid (E4) (98 mg, 44%); mp: 130° C.; HPLC: Inertsil ODS 3V C18, 40:30:30 [$KH_2PO_4$(0.01 M, pH 3.2): $CH_3OH$:$CH_3CN$], 264 nm, $R_t$ 3.2 min, 99.6% purity; MS (TOF ES+) m/z 412 (M+H, 100), 235.6 (87.2), 206.6 (16.1).

Example 92

Synthesis of 4-{4-Cycloheptylamino-6-[methyl-(1-methyl-piperidin-4-yl)-amino]-1,3,5]triazin-2-ylamino}-phenol (E5)

the Pd/C for about 5 minutes, then methanol (10 mL) was added cautiously, and nitrogen was blown over the mixture for another 5 minutes. Triazine E2 (250.5 mg, 0.45 mmol) dissolved in methanol (5 mL) was added followed by ammonium formate (340.5 mg, 5.4 mmol), and the reaction was stirred and heated at reflux for about 1.5 hours. Methylene chloride was added and allowed to cool to room temperature. The mixture was filtered by vacuum through Celite with a methylene chloride rinsing and the filtrate was concentrated in vacuo. The crude material was dried overnight under vacuum to give a light brown solid (E5) (144 mg, 70%); mp 157° C.; HPLC: Inertsil ODS 3V C18, 40:30:30 v:v:v [$KH_2PO_4$ (0.01 M, pH 3.2): $CH_3OH$:$CH_3CN$], 264 nm, $R_t$ 3.0 min, 93.8% purity; MS (TOF ES+) m/z 426.3 (M+H, 20.9), 234.1 (100).

Example 93

Synthesis of 2-Chloro-4-(4,6-dichloro-[1,3,5]triazin-2-ylamino)-phenol (E6)

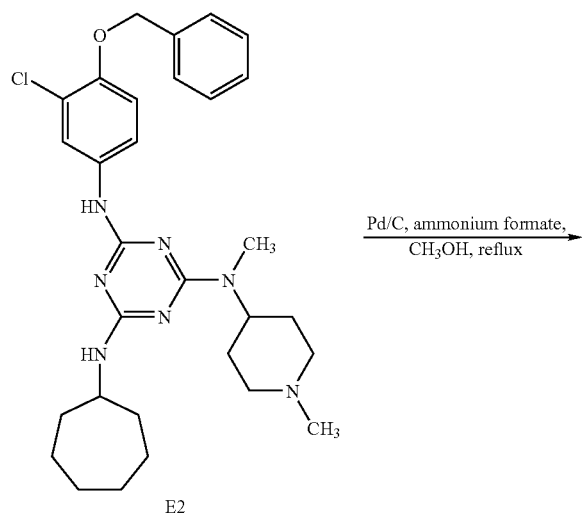

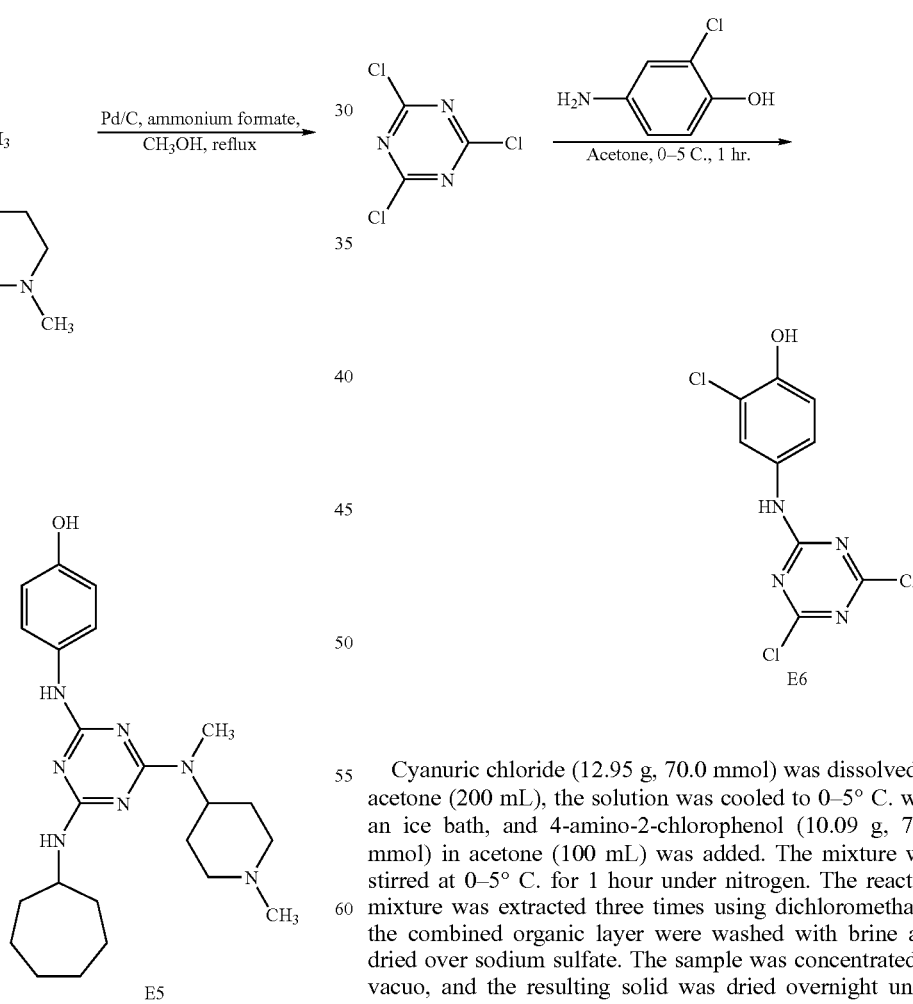

In a dry flask was added 10% Pd/C (301.0 mg) which was wetted with 3–5 drops of water. Nitrogen was blown over Cyanuric chloride (12.95 g, 70.0 mmol) was dissolved in acetone (200 mL), the solution was cooled to 0–5° C. with an ice bath, and 4-amino-2-chlorophenol (10.09 g, 70.0 mmol) in acetone (100 mL) was added. The mixture was stirred at 0–5° C. for 1 hour under nitrogen. The reaction mixture was extracted three times using dichloromethane; the combined organic layer were washed with brine and dried over sodium sulfate. The sample was concentrated in vacuo, and the resulting solid was dried overnight under vacuum to yield E6 (20.2 g, 99%); mp 180° C.; HPLC: Inertsil ODS 3V C18, 40:30:30 v:v:v [$KH_2PO_4$ (0.01 M, pH 3.2):$CH_3OH$:$CH_3CN$], 264 nm, $R_t$ 11.6 min, 99.4% purity; MS (TOF ES+) m/z 293 (97.5), 291 (M+H, 100).

Example 94

Synthesis of 2-Chloro-4-(4-chloro-6-cycloheptylamino-[1,3,5]triazin-2-ylamino)-phenol (E7)

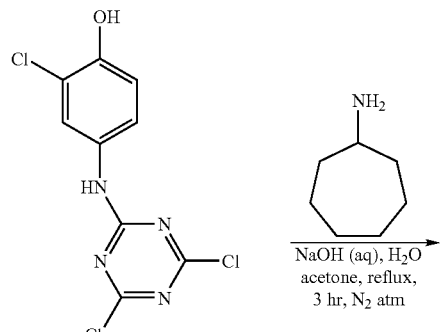

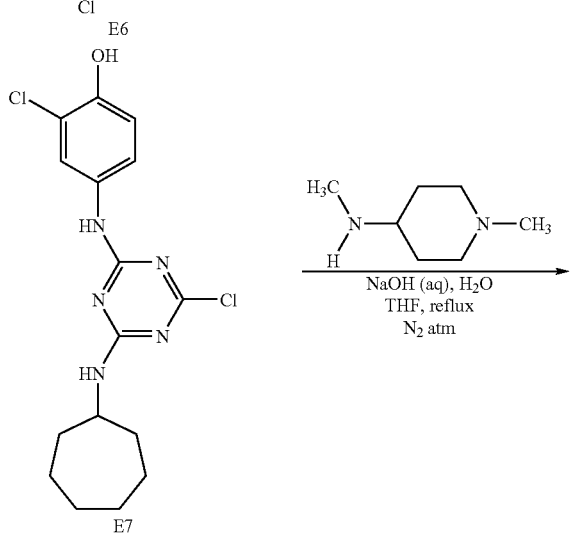

To E7 (1.06 g, 3.4 mmol) dissolved in acetone (25 mL) was added a solution of cycloheptylamine (0.44 mL, 3.4 mmol) in acetone (5 mL) followed by addition of 2.5 N NaOH (1.4 mL, 3.4 mmol) and water (3.5 mL). The reaction mixture was stirred and heated at reflux for 3 hours. The reaction mixture was extracted three times using dichloromethane; the combined organic layers were washed with brine and dried over sodium sulfate. The sample was concentrated and was dried overnight under vacuum to yield a light brown solid (E7) (1.25 g, 99%); mp 91° C.; HPLC: Inertsil ODS 3V C18, 40:30:30 v:v:v [KH$_2$PO$_4$ (0.01 M, pH 3.2): CH$_3$OH:CH$_3$CN], 264 nm, R$_t$ 42.9 min, 92.1% purity; MS (TOF ES+) m/z 370 (65.9), 368 (M+H, 100).

Example 95

Alternative Synthesis of 2-Chloro-4-{4-cycloheptylamino-6-[methyl-(1-methyl-piperidin-4-yl)-amino]-[1,3,5]triazin-2-ylamino}-phenol (138)

To E7 (1.00 g, 2.7 mmol) dissolved in THF (25 mL) was added a solution of N-methyl-4-(methylamino)-piperidine (0.45 mL, 3.1 mmol) in THF (5 mL) followed by addition of 2.5 N NaOH (1.1 mL, 2.7 mmol) and 2.5 mL of water. The reaction mixture was stirred and heated at reflux overnight. The reaction mixture was extracted three times using dichloromethane, the combined organic layers were washed with a brine and dried over sodium sulfate. The sample was concentrated and the resulting solid was dried overnight under vacuum. Column chromatography (silica gel, 100% methanol) yielded an off-white solid (138) (177 mg, 14%); mp 68° C.; HPLC: Inertsil ODS 3V C18, 40:30:30 v:v:v [KH$_2$PO$_4$ (0.01 M, pH 3.2):CH$_3$OH: CH$_3$CN], 264 nm, R$_t$ 4.7 min, 99.6% purity; MS (TOF ES+) m/z 460 (M+H, 55.3), 251 (100), 224 (51.1).

Example 96

Synthesis of N-(1-Benzyl-piperidin-4-yl)-N'-(3-fluoro-4-methoxy-phenyl)-N''-cycloheptyl-[1,3,5]triazine-2,4,6-diamine (E8)

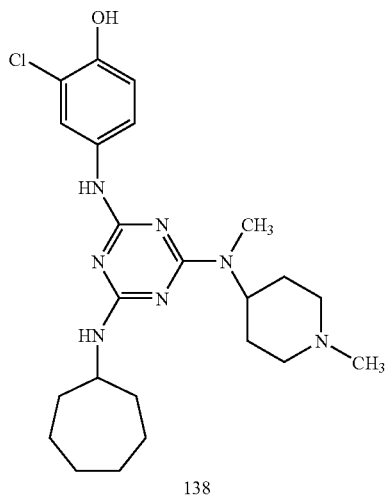

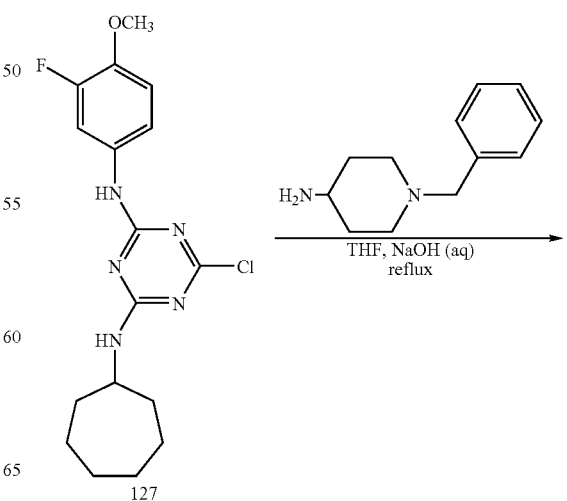

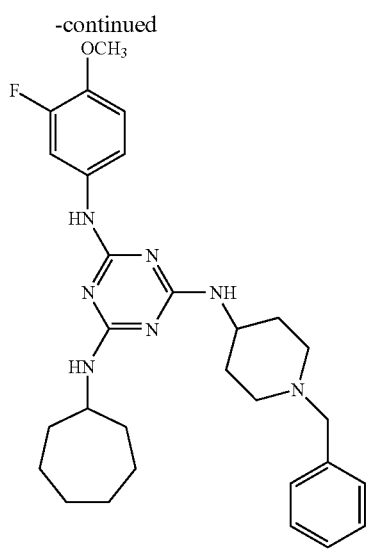

E8

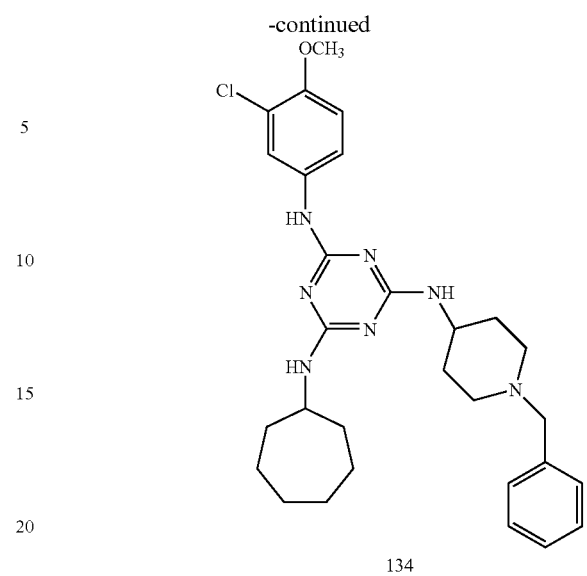

134

To 127 (6.00 g, 16.4 mmol) dissolved in THF (100 mL) was added 4-amino-1-benzylpiperidine (3.6 mL, 18.9 mmol) in THF (5 mL), followed by addition of $H_2O$ (17 mL) and 2.5 N NaOH (6.6 mL, 16.4 mmol). The reaction mixture was stirred and heated at reflux for about 12 hours under nitrogen. The reaction mixture was extracted three times with dichloromethane; the combined organic layers were washed with brine and dried over potassium carbonate. The sample was filtered, concentrated, and the resulting solid was dried overnight under vacuum. Column chromatography (93:6:1 v:v:v dichloromethane:methanol:ammonium hydroxide) gave a light yellow solid (E8) (2.98 g, 35%); mp 87° C.; HPLC: Inertsil ODS 3V C18, 40:30:30 [$KH_2PO_4$ (0.01 M, pH 3.2):$CH_3OH$:$CH_3CN$], 264 nm, $R_t$ 11.1 min, 93.9% purity; MS (TOF ES+) m/z 520 (M+H, 66.3), 430 (100).

To 133 (6.04 g, 15.7 mmol) dissolved in THF (100 mL) was added 4-amino-1-benzylpiperidine (3.4 mL, 18 mmol) in THF (5 mL), followed by addition of water (16 mL) and 2.5 N NaOH (6.3 mL, 15.7 mmol). The reaction mixture was stirred and heated at reflux for about 12 hours under a nitrogen atmosphere. The reaction mixture was extracted three times with dichloromethane; the combined organic layers were washed with brine and dried over potassium carbonate. The sample was filtered, concentrated, and the resulting solid was dried overnight under vacuum. Column chromatography (93:6:1 v:v:v dichloromethane:methanol:ammonium hydroxide) gave a light yellow solid (134) (3.71 g, 44%). mp 90° C.; HPLC: Inertsil ODS 3V C18, 40:30:30 [$KH_2PO_4$ (0.01 M, pH 3.2):$CH_3OH$:$CH_3CN$], 264 nm, $R_t$ 14.6 min, 99.5% purity; MS (TOF ES+) m/z 538 (27.8), 536 (M+H, 72.1), 448 (39.2), 446 (100).

Example 97

Alternative Synthesis of N-(1-Benzyl-piperidin-4-yl)-N'-(3-chloro-4-methoxy-phenyl)-N"-cycloheptyl-[1,3,5]triazine-2,4,6-diamine (134)

Example 98

Synthesis of N-Cycloheptyl-N'-(4-methoxy-phenyl)-N"-piperidin-4-yl-[1,3,5]triazine-2,4,6-triamine (E9)

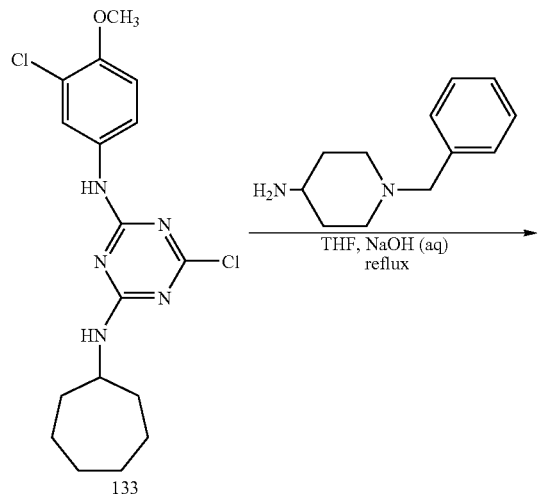

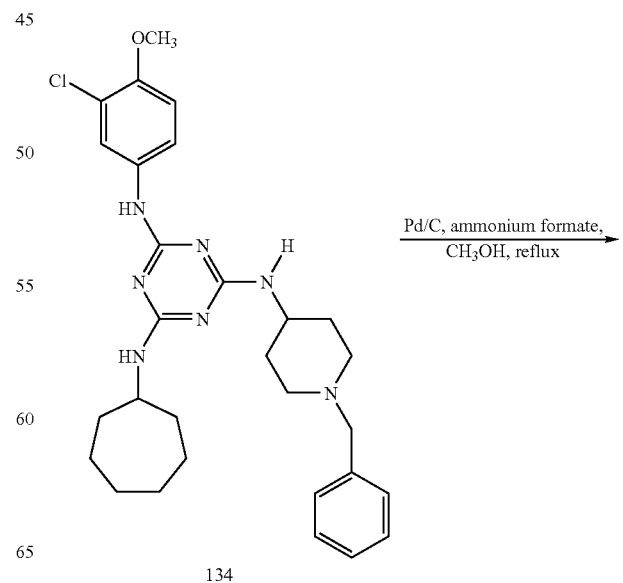

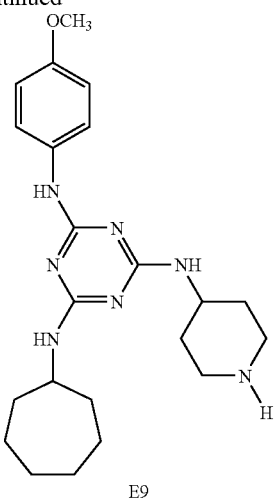

E9

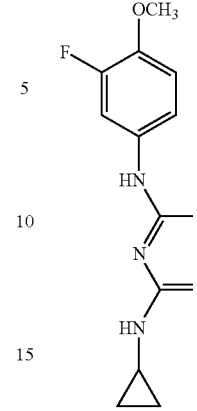

E10

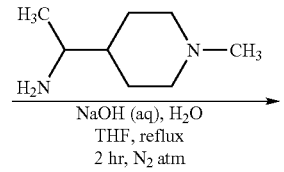

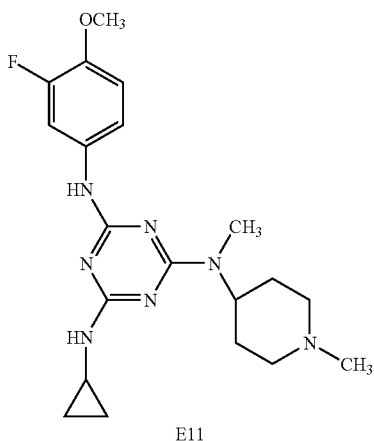

E11

In a dry round bottomed flask, 10% Pd/C (600.2 mg) was added and was wetted with 3–5 drops of water. Nitrogen was blown over the Pd/C for about 5 minutes, then methanol (25 mL) was added cautiously, and nitrogen was again blown over the mixture for about 5 minutes. Triazine 134 (501.2 mg, 0.93 mmol) dissolved in methanol (15 mL) was added followed by ammonium formate (708.4 mg, 11.2 mmol), and the reaction was stirred and heated at reflux for about 1.5 hours. Methylene chloride was added and allowed to cool to room temperature. The mixture was filtered by vacuum through Celite with a methylene chloride rinsing, the filtrate was concentrated, and the material was dried overnight under vacuum. Column chromatography (90:9:1 v:v:v dichloromethane:methanol:ammonium hydroxide) yielded a light yellow solid (E9) (226 mg, 55%); mp 118° C.; HPLC: Inertsil ODS 3V C18, 40:30:30 [KH$_2$PO$_4$ (0.01 M, pH 3.2):CH$_3$OH:CH$_3$CN], 264 nm, R$_t$ 4.6 min, 99.6% purity; MS (TOF ES+) m/z 412 (M+H, 39.8), 247.9 (63), 227.3 (100).

Example 99

Synthesis of 6-Chloro-N-cyclopropyl-N'-(3-fluoro-4-methoxy-phenyl)-[1,3,5]triazine-2,4-diamine (E10)

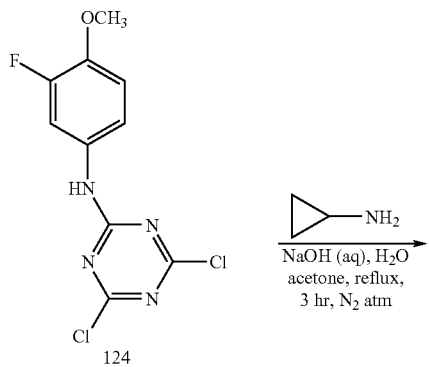

To 124 (2.01 g, 7.0 mmol) dissolved in acetone (40 mL) was added a solution of cyclopropylamine (0.5 mL, 7 mmol) in acetone (5 mL) followed by addition of NaOH (2.8 mL, 2.5 N, 7.0 mmol) and 8 mL of water. The reaction was stirred and heated at reflux for 3 hours. The reaction mixture was poured over crushed ice. The solid that formed was collected by vacuum filtration and was dried overnight under vacuum to afford unpurified E10 (1.8 g). {A separate reaction [124, (2.00 g, 7 mmol) and cyclopropylamine (0.5 mL, 7 mmol)] yielded unpurified E10 (1.9 g).} The two lots (1.8 g and 1.9 g) were combined for purification. Column chromatography (50:50 v:v hexane:ethyl acetate) yielded a faint yellow solid (E10) (2.89 g, 67%); mp 186° C.; HPLC: Inertsil ODS 3V C18, 40:30:30 [KH$_2$PO$_4$ (0.01 M, pH 3.2):CH$_3$OH:CH$_3$CN], 264 nm, R$_t$ 16.6 min, 94.9% purity; MS (TOF ES+) m/z 310 (M+H, 100), 312 (44.4).

Example 100

Synthesis of N-Cyclopropyl-N'-(3-flouro-4-methoxy-phenyl)-N''-methyl-N''-(1-methyl-piperidin-4-yl)-[1,3,5]triazine-2,4,6-triamine (E11)

To E10 (1.04 g, 3.2 mmol) dissolved in THF (40 mL) was added a solution of N-methyl-4-(methyl-amino)-piperidine (0.5 mL, 3.2 mmol) in THF (2 mL) followed by addition of NaOH (1.3 mL, 2.5 N, 3.2 mmol) and 3.5 mL of water. The reaction mixture stirred and heated at reflux for 2 hours. The reaction mixture was extracted 3 times using dichloromethane; the combined organic layers were washed with brine and dried over potassium carbonate. The sample was filtered, concentrated, and the resulting solid was dried overnight under vacuum. Column chromatography (90:9:1 v:v:v dichloromethane:methanol:ammonium hydroxide) yielded a light yellow solid (E1i) (164 mg, 13%); mp 94° C.; HPLC: Inertsil ODS 3V C18, 40:30:30 [KH$_2$PO$_4$ (0.01 M, pH 3.2):CH$_3$OH:CH$_3$CN], 264 nm, R$_t$ 3.2 min, 96.7% purity; MS (TOF ES+) m/z 402.1 (M+H, 100), 231 (41.5), 202.1 (6).

Example 101

Synthesis of N-Cyclopropyl-N'-(1-ethyl-pyrrolidin-2-ylmethyl)-N"-(3-fluoro-4-methoxy-phenyl)-[1,3,5]triazine-2,4,6-triamine (E12)

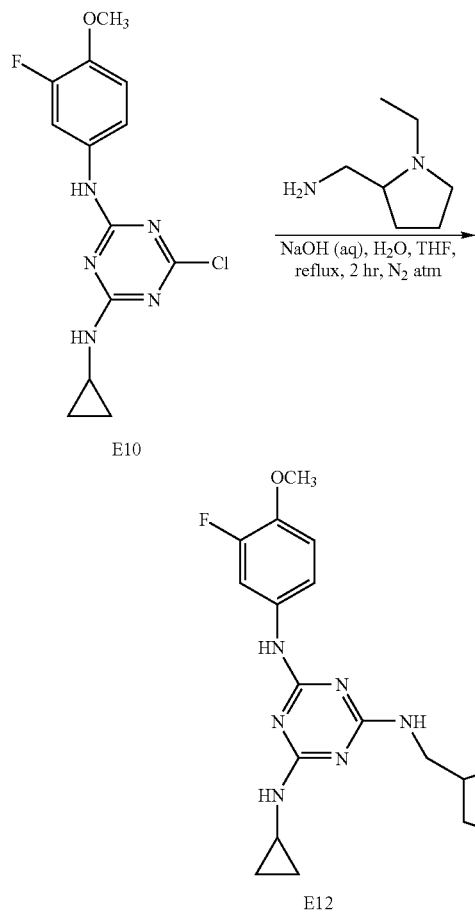

To E10 (1.05 g, 3.2 mmol) dissolved in THF (40 mL) was added a solution of 2-(aminomethyl)-1-ethylpyrrolidine (0.5 mL, 3.2 mmol) in THF (2 mL) followed by addition of NaOH (1.3 mL, 2.5 N, 3.2 mmol) and 3.5 mL of water. The reaction mixture was stirred and heated at reflux for 2 hours. The reaction mixture was extracted 3 times using dichloromethane; combined organic layers were washed with brine and dried over potassium carbonate. The sample was filtered, concentrated, and dried overnight under vacuum. Column chromatography (90:9:1 v:v:v dichloromethane:methanol:ammonium hydroxide) yielded a light yellow solid (E12) (755 mg, 59%); mp 68° C.; HPLC: Inertsil ODS 3V C18, 40:30:30 [KH$_2$PO$_4$(0.01 M, pH 3.2): CH$_3$OH:CH$_3$CN], 264 nm, R$_t$ 3.2 min, 95.5% purity; MS (TOF ES+) m/z 402.1 (M+H, 100), 231. (23.4).

Example 102

Synthesis of 6-Chloro-N-(3-chloro-4-methoxy-phenyl)-N'-cyclopropyl-[1,3,5]triazine-2,4-diamine (E13)

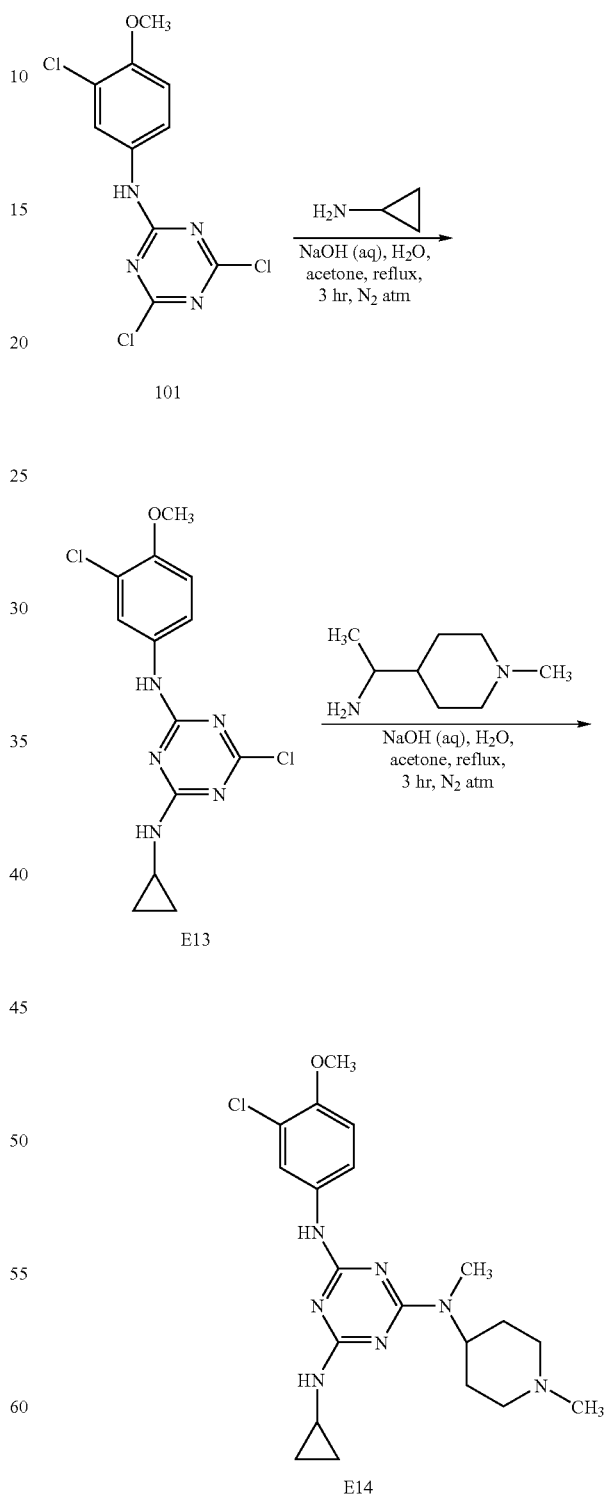

To 101 (2.01 g, 6.5 mmol) dissolved in acetone (35 mL) was added a solution of cyclopropylamine (0.45 mL, 6.5 mmol) in acetone (5 mL) followed by addition of NaOH (2.6 mL, 2.5 N, 7.0 mmol) and 6.5 mL of water. The reaction mixture was stirred and heated at reflux for 3 hours. The reaction mixture was extracted 3 times with dichloromethane; the combined organic layers were washed with brine and dried over potassium carbonate. The sample was filtered, concentrated, and dried overnight under vacuum. Column chromatography (50:50 v:v hexane:ethyl acetate) yielded a faint yellow solid (E13) (1.12 g, 53%); mp 172° C.; HPLC: Inertsil ODS 3V C18, 40:30:30 [$KH_2PO_4$ (0.01 M, pH 3.2):$CH_3OH$:$CH_3CN$], 264 nm, $R_t$ 24.6 min, 99% purity; MS (TOF ES+) m/z 328 (72.6), 326 (M+H, 100).

Example 103

Synthesis of N-Cyclopropyl-N'-(3-chloro-4-methoxy-phenyl)-N''-methyl-"N-(1-methyl-piperidin-4-yl)-[1,3,5]triazine-2,4,6-triamine (E14)

To E13 (0.88 g, 2.7 mmol) dissolved in THF (40 mL) was added a solution of N-methyl-4-(methyl-amino)-piperidine (0.4 mL, 2.7 mmol) in THF (2 mL) followed by addition of NaOH (1.1 mL, 2.5 N, 2.7 mmol) and 3 mL of water. The reaction mixture was stirred and heated at reflux for 2 hours. The reaction mixture was extracted 3 times with dichloromethane; the combined organic layers were washed with brine and dried over potassium carbonate. The sample was filtered, concentrated, and the resulting solid was dried overnight under vacuum. Column chromatography (90:9:1 v:v:v dichloromethane:methanol:ammonium hydroxide) yielded a light yellow solid (E14) (93 mg, 8.3%); mp 92° C.; HPLC: Inertsil ODS 3V C18, 40:30:30 [$KH_2PO_4$ (0.01 M, pH 3.2):$CH_3OH$:$CH_3CN$], 264 nm, $R_t$ 3.4 min, 96.9% purity; MS (TOF ES+) m/z 418.1 (M+H, 100), 210.1 (12.3).

Example 104

Synthesis of 6-Chloro-N,N'-bis-(3-fluoro-4-methoxy-phenyl)-[1,3,5]triazine-2,4-diamine (E15)

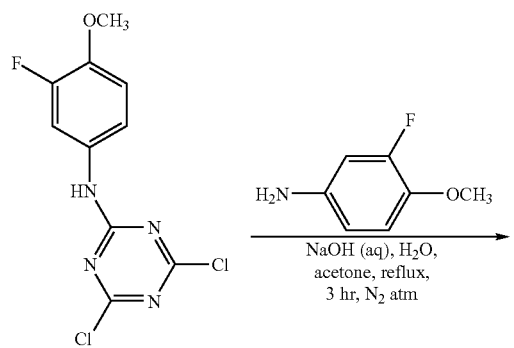

124

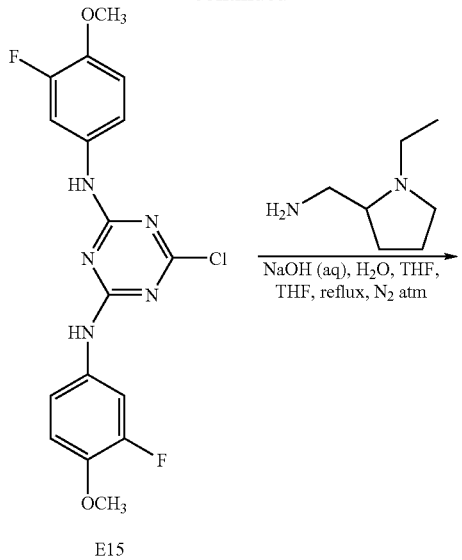

E15

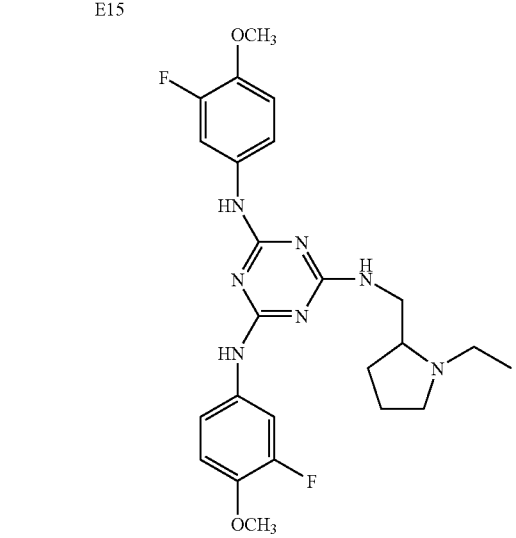

E16

To 124 (1.09 g, 3.5 mmol) dissolved in acetone (25 mL) was added 3-fluoro-p-anisidine (0.54 g, 3.5 mmol) in acetone (5 mL) followed by addition of 2.5 N NaOH (1.4 mL, 3.5 mmol) and water (3.5 mL). The reaction mixture was stirred and heated at reflux for 3 hours. The reaction mixture was extracted three times using dichloromethane; the combined organic layers were washed with brine and dried over potassium carbonate. The sample was filtered, concentrated in vacuo, and the resulting solid was dried overnight under vacuum to yield white solid (E15) (1.332 g, 97%); mp 194° C.; HPLC: Inertsil ODS 3V C18, 40:30:30 v:v:v [$KH_2PO_4$ (0.01 M, pH 3.2):$CH_3OH$:$CH_3CN$], 264 nm, $R_t$ 33.2 min, 97.6% purity; MS (TOF ES+) m/z 396 (35.0); 394 (M+H, 100).

Example 105

Synthesis of N-(1-Ethyl-pyrrolidin-2-ylmethyl)-N', N''-bis-(3-fluoro-4-methoxy-phenyl)-[1,3,5]triazine-2,4,6-triamine (E16)

To E15 (1.01 g, 2.5 mmol) dissolved in THF (25 mL) was added a solution of 2-(aminomethyl)-ethyl pyrrolidine (0.42 mL, 2.9 mmol) in THF (5 mL) followed by addition of 2.5 N NaOH (1.0 mL, 2.5 mmol) and 2.5 mL of water. The reaction mixture was stirred and heated at reflux overnight. The reaction mixture was extracted three times using dichloromethane; the combined organic layers were washed with brine and dried over potassium carbonate. The sample was filtered, concentrated in vacuo, and the resulting solid was dried overnight under vacuum. Column chromatography (90:9:1 v:v:v dichloromethane:methanol:ammonium hydroxide) yielded a light yellow solid (E16) (570 mg, 47%); mp 66° C.; HPLC: Inertsil ODS 3V C18, 40:30:30 v:v:v [$KH_2PO_4$ (0.01 M, pH 3.2):$CH_3OH$:$CH_3CN$], 264 nm, $R_t$ 4.7 min, 99.3% purity; MS (TOF ES+) m/z 486 (68.4, M+H), 264 (100), 244 [(M+2H)++, 48.1]).

Example 106

Synthesis of 1-[4-(3-chloro-4-methoxyanilino)-cycloheptyl amino-1,3,5-triazin-2-yl]-2-azoloamymethanol (E17)

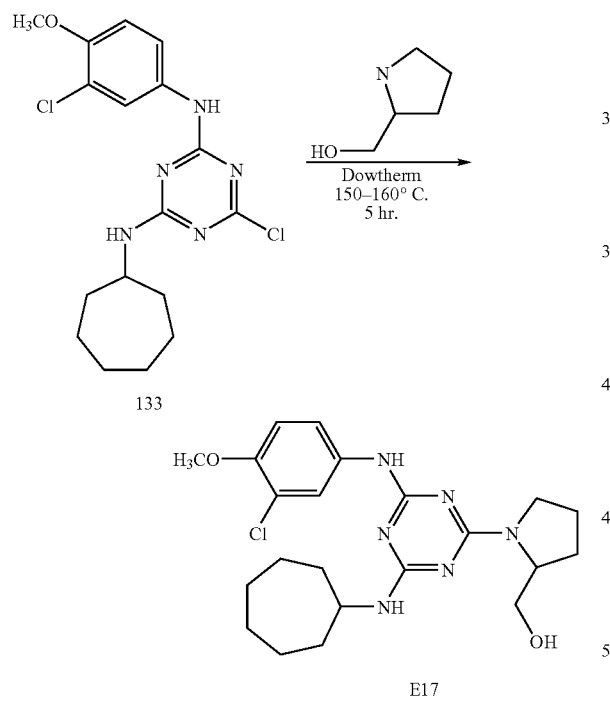

To 133 (0.2 g, 0.52 mmol) in Dowtherm (5 mL) was added slowly prolinol (0.16 g, 1.57 mmol) and the mixture was heated to 150–160° C. for 5 hours with stirring. After completion of the reaction the mixture was cooled to 25° C. and then transferred directly to a silica gel column for purification purpose. The column was eluted using 1:1 (by volume) EtOAc-Petroleum ether to afford E17 as a light brown solid (0.14 g, 60%), mp 82–84° C.; HPLC: Inertsil ODS 3V (250×4.6 mm) 5 microns 50:50 [0.01 M $KH_2PO_4$ (0.1% TFA):$CH_3CN$], 223 nm, $R_t$ 11.86 min, 97.49% purity); MS (CI): m/z 447 ($M^+$, 100), 416 (35).

Example 107

Synthesis of $N^2$-(3-chloro-4-methoxyphenyl)-$N^4$-cycloheptyl-6-(4-methylpiperzino)-1,3,5-triazine-4,2-diamine (E18)

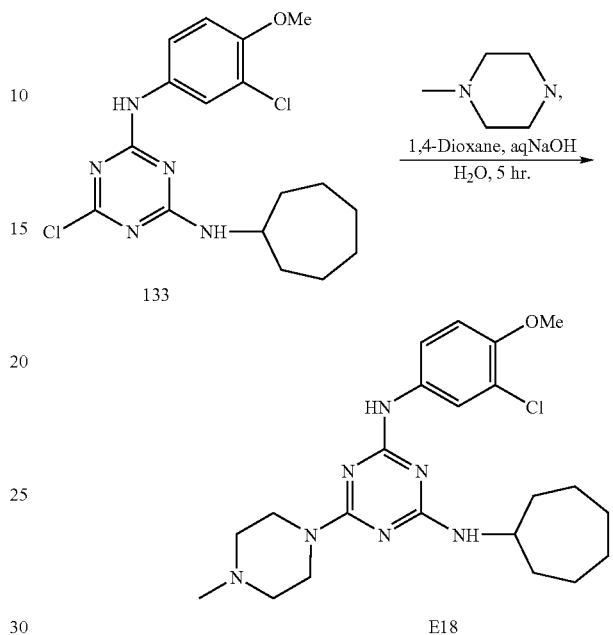

To a solution of 133 (0.5 g, 1.31 mmol) in 1,4-dioxane (5 mL) was added slowly a solution of 1-methylpiperizine (0.13 g, 1.31 mmol) in 1,4-dioxane (5 mL) followed by 2.5 N sodium hydroxide solution (0.5 mL, 1.31 mmol) and water (1.2 mL). The mixture was heated to reflux for 2.5–3 hours with stirring under nitrogen atmosphere and then cooled to 25° C. and diluted with water (10 mL). The mixture was then stirred for 10–15 min., the precipitated solid was filtered off and dried under vacuum to afford the title compound E18 as an off-white solid (0.5 g, 86%). mp 120–122° C.; HPLC: Inertsil ODS 3V (250×4.6 mm) 5 microns 65:35 [0.01 M $KH_2PO_4$ (0.1% TFA):$CH_3CN$], 223 nm, $R_t$ 10.23 min, 98.50% purity); MS (CI): m/z 446 (M+H, 100), 375 (25).

Example 108

Synthesis, of 3-[4-(3-chloro-4-methoxyanilino)-6-cycloheptylamino-1,3,5-triazin-2-yloxy]-2-ethyl-4H-4-pyranone (E19)

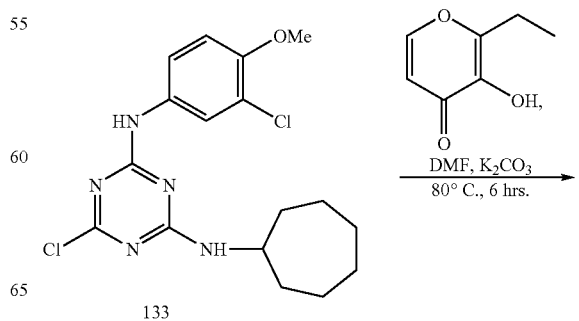

-continued

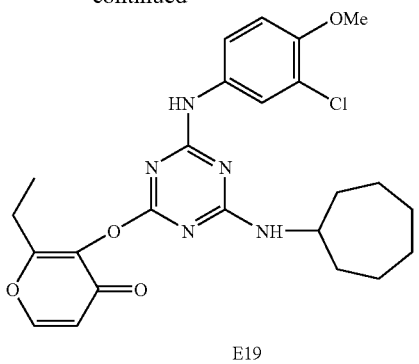

E19

A mixture of 133 (0.3 g, 0.78 mmol), 2-ethyl-3-hydroxy-4H-pyran-4-one (0.11 g, 0.78 mmol) and $K_2CO_3$ (0.54 g, 3.91 mmol) in dimethylformamide (15 mL) was stirred at 80° C. for 6 hours under nitrogen atmosphere. After completion of the reaction the mixture was cooled to 25° C. and diluted with water (50 mL). The precipitated solid was filtered off and dried under vacuum to afford the title compound E19 as an off-white solid (0.2 g, 52%). mp 124–126° C.; HPLC: Inertsil ODS 3V (250×4.6 mm) 5 microns 50:50 [0.01 M $KH_2PO_4$ (0.1% TFA):$CH_3CN$], 223 nm, $R_t$ 18.47 min, 98.18% purity); MS (CI): m/z 486 ($M^+$, 100), 382 (90).

Example 109

Synthesis of 1-[3-{4-(3-chloro-4-methoxyanilino)-6-cycloheptylamino-1,3,5-triazine-2-yloxy}piperidino]-1-ethanone (E20)

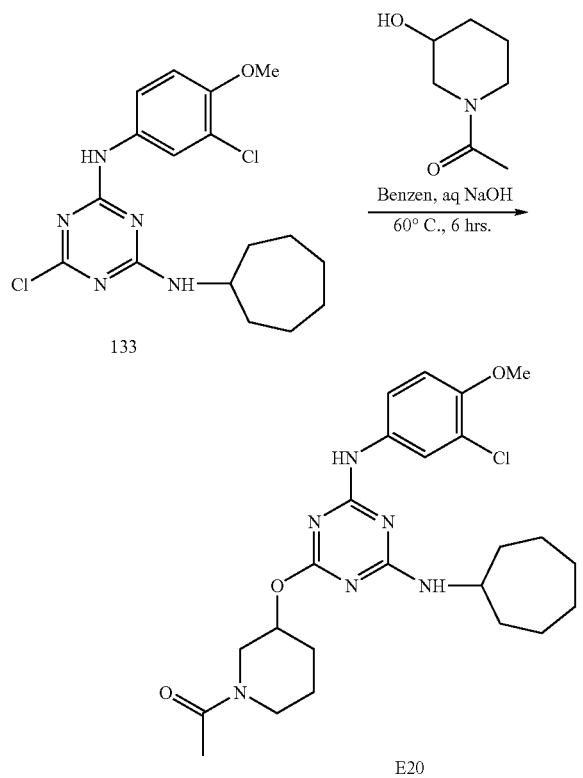

E20

A mixture of N-acetyl-3-hydroxypiperidine (0.335 g, 2.27 mmol) and sodium hydroxide (95 mg, 2.27 mmol) in benzene (10 mL) was heated to reflux for 2 hours with stirring under nitrogen atmosphere and then cooled to 25° C. followed by the addition of compound 133 (0.3 g, 0.78 mmol) at same temperature. The mixture was heated to reflux for 6 hours, concentrated under vacuum and diluted with water (10 mL). The precipitated solid was filtered off and purified by column chromatography to afford the title compound E20 as an off-white solid (0.35 g, 91%). mp 138–140° C.; HPLC: Inertsil ODS 3V (250×4.6 mm) 5 microns [solvent A=0.01 M $KH_2PO_4$ (pH 7.0); solvent B=$CH_3CN$], Gradient elution program: T/% B=0/60, 10/60,25/80, 40/80, 45/60, 50/60; 268 nm, $R_t$ 17.20 min, 91.70% purity; MS (CI): m/z 489 ($M^+$, 100).

Example 110

Synthesis of $N^2$-(3-chloro-4-methoxyphenyl)-$N^4$-cycloheptyl-6-isopropoxy-1,3,5-triazine-2,4-diamine (E21)

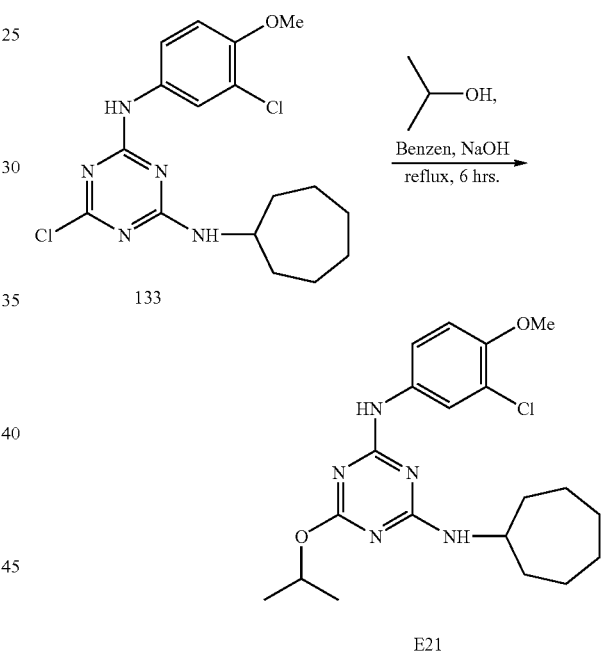

E21

A mixture of isopropanol (2 mL) and sodium hydroxide (95 mg, 2.27 mmol) in benzene (10 mL) was heated to reflux for 2 hours with stirring under nitrogen atmosphere and then cooled to 25° C. followed by the addition of compound 133 (0.3 g, 0.78 mmol) at same temperature. The mixture was heated to reflux for 6 hours, concentrated under vacuum and diluted with water (10 mL). The precipitated solid was filtered off and purified by column chromatography (1–2% MeOH—$CHCl_3$) to afford the title compound E21 as an off-white solid (0.30 g, 94%). mp 136–138° C.; HPLC: Inertsil ODS 3V (250×4.6 mm) 5 microns [solvent A=0.01 M $KH_2PO_4$ (pH 7.0); solvent B=$CH_3CN$], Gradient elution program: T/% B=0/60, 10/60, 25/80, 40/80, 45/60, 50/60; 268 nm, $R_t$ 30.06 min, 98.78% purity; MS (CI): m/z 406 (M+H, 100).

Example 111

Synthesis of N²-(3-chloro-4-methoxyphenyl)-N⁴-cycloheptyl-6-(2-azolanylmethoxy)-1,3,5-triazine-2,4-diamine (E22)

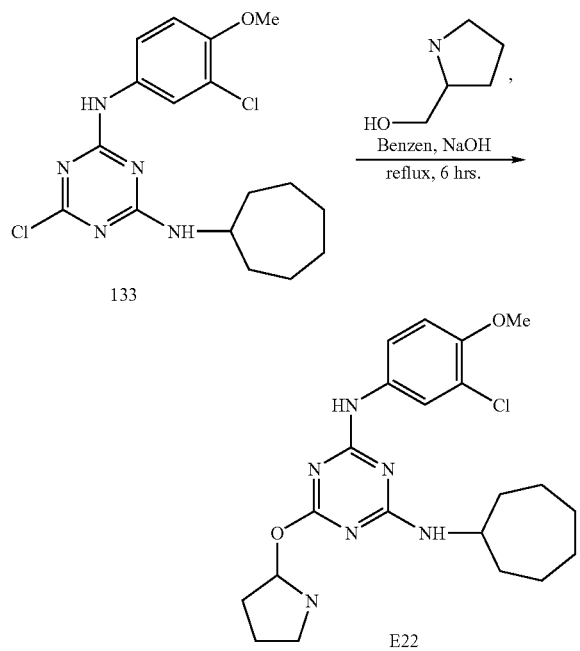

A mixture of prolinol (0.0243 g, 2.27 mmol) and sodium hydroxide (95 mg, 2.27 mmol) in benzene (10 mL) was heated to reflux for 2 hours with stirring under nitrogen atmosphere and then cooled to 25° C. followed by the addition of compound 133 (0.3 g, 0.78 mmol) at same temperature. The mixture was heated to reflux for 6 hours, concentrated under vacuum and diluted with water (10 mL). The precipitated solid was filtered off and purified by column chromatography (1–2% MeOH—CHCl₃) to afford the title compound E22 as an off-white solid (0.35 g, quantitative). mp 84–86° C.; HPLC: Inertsil ODS 3V (250×4.6 mm) 5 microns [solvent A=0.01 M KH₂PO₄ (pH 7.0); solvent B=CH₃CN], Gradient elution program: T/% B=0/60, 10/60, 25/80, 40/80, 45/60, 50/60; 268 nm, R$_t$ 24.67 min, 99.59% purity; MS (CI): m/z 447 (M+H, 100).

Example 112

Synthesis of 1-[4-(3-chloro-4-methoxyphenylamino)-6-cycloheptylamino-[1,3,5]triazine-2-yl]-piperidin-3-ol] (E23)

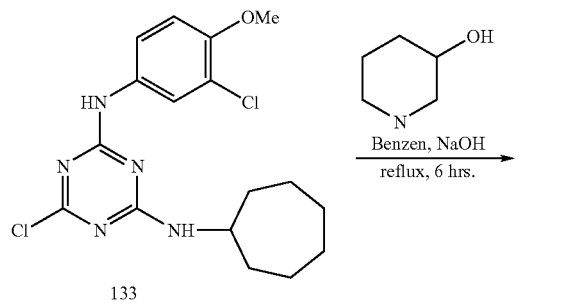

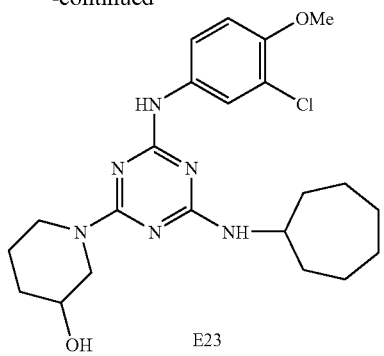

A mixture of 3-hydroxypiperidine (0.198 g, 1.96 mmol) and sodium hydroxide (79 mg, 1.96 mmol) in benzene (10 mL) was heated to reflux for 2 hours with stirring under nitrogen atmosphere and then cooled to 25° C. followed by the addition of compound 133 (0.25 g, 0.65 mmol) at same temperature. The mixture was heated to reflux for 6 hours, concentrated under vacuum and diluted with water (10 mL). The precipitated solid was filtered off and purified by column chromatography (1–2% MeOH—CHCl₃) to afford the title compound E23 as an off-white solid (0.06 g, 21%). mp 100–102° C.; HPLC: Hichrom RPB (250×4.6 mm) 5 microns [solvent A=0.01 M KH₂PO₄ (pH 5.5); solvent B=CH₃CN], Gradient elution program: T/% B=0/20, 10/20, 25/80, 40/80, 55/60, 65/20, 70/20; 270 nm, R$_t$ 41.95 min, 98.43% purity; MS (CI): m/z 447 (M+H, 100).

Example 113

Synthesis of 1-[4-(3-chloro-4-methoxyphenylamino)-6-cycloheptylamino-[1,3,5]triazine-2-yl]-piperidin-4-ol] (E24)

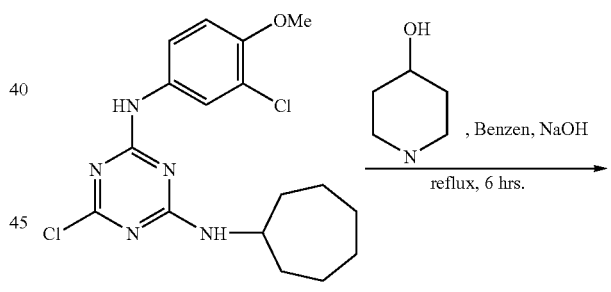

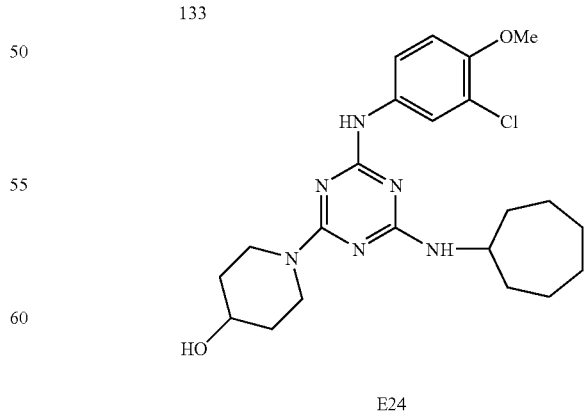

A mixture of 4-hydroxypiperidine (0.198 g, 1.96 mmol) and sodium hydroxide (79 mg, 1.96 mmol) in benzene (10 mL) was heated to reflux for 2 hours with stirring under nitrogen atmosphere and then cooled to 25° C. followed by the addition of compound 133 (0.25 g, 0.65 mmol) at same temperature. The mixture was heated to reflux for 6 hours, concentrated under vacuum and diluted with water (10 mL). The precipitated solid was filtered off and purified by column chromatography (1–2% MeOH—CHCl$_3$) to afford the title compound E24 as an off-white solid (0.20 g, 58%). mp 142–144° C.; HPLC: Hichrom RPB (250×4.6 mm) 5 microns [solvent A=0.01 M KH$_2$PO$_4$ (pH 5.5); solvent B=CH$_3$CN], Gradient elution program: T/% B=0/20, 10/20, 25/80, 40/80, 55/60, 65/20, 70/20; 270 nm, R$_t$ 40.56 min, 98.60% purity; MS (CI): m/z 447 (M+H, 100).

Example 114

Synthesis of N$^2$-(3-chloro-4-methoxyphenyl)-N$^4$-cycloheptyl-6-(1-methyl-2-azolanylmethoxy)-1,3,5-triazine-2,4-diamine (E25)

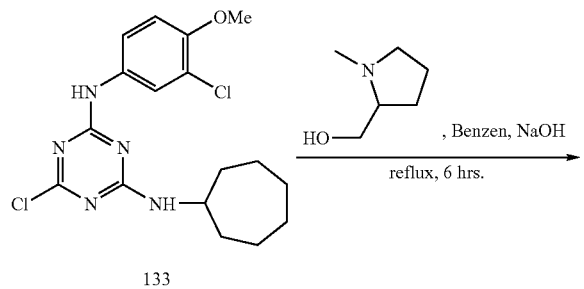

133

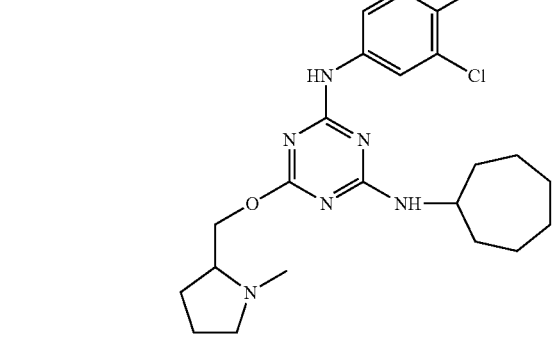

E25

A mixture of N-methyl prolinol (0.226 g, 1.96 mmol) and sodium hydroxide (79 mg, 1.96 mmol) in benzene (10 mL) was heated to reflux for 2 hours with stirring under nitrogen atmosphere and then cooled to 25° C. followed by the addition of compound 133 (0.25 g, 0.65 mmol) at same temperature. The mixture was heated to reflux for 6 hours, concentrated under vacuum and diluted with water (3 mL). The gum which separated was collected (by decanting out the liquid portion) and purified by column chromatography (1–3% MeOH—CHCl$_3$) to afford the title compound E25 as a semi-solid (0.06 g, 20%). HPLC: Symmetry shield RP18 (250×4.6 mm) 5 microns [solvent A=0.01 M KH$_2$PO$_4$ (pH 3.0); solvent B=CH$_3$CN], Gradient elution program: T/% B=0/35, 10/35, 40/80, 50/80, 55/35, 60/35; 270 nm, R$_t$ 15.51 min, 99.55% purity; MS (CI): m/z 461 (M+H, 100).

Example 115

Synthesis of N$^2$-(3-chloro-4-methoxyphentyl)-N-cycloheptyl-6-(1-methyl-4-piperidyloxy)-1,3,5-triazine-2,4-diamine (E26)

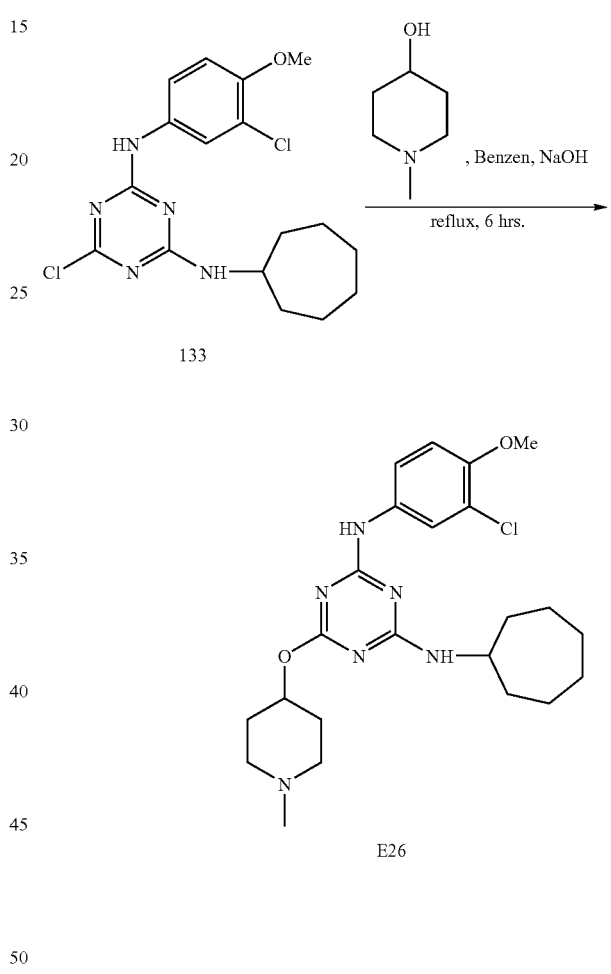

A mixture of N-methyl piperidinol (0.22 g, 1.96 mmol) and sodium hydroxide (79 mg, 1.96 mmol) in benzene (10 mL) was heated to reflux for 2 hours with stirring under nitrogen atmosphere and then cooled to 25° C. followed by the addition of compound 133 (0.25 g, 0.65 mmol) at same temperature. The mixture was heated to reflux for 6 hours, concentrated under vacuum and diluted with water (10 mL). The precipitated solid was filtered and purified by column chromatography (5–10% MeOH—CHCl$_3$) to afford the title compound E26 as a pale yellow solid (0.16 g, 53%). HPLC: Hichrom RPB (250×4.6 mm) 5 microns [solvent A=0.01 M KH$_2$PO$_4$ (pH 7.0); solvent B=CH$_3$CN], Gradient elution program: T/% B=0/60, 10/60, 25/80, 40/80, 45/60, 50/60; 270 nm, R$_t$ 35.21 min, 98.09% purity; MS (CI): m/z 461 (M+H, 50), 364 (100).

Example 116

Synthesis of N²-(3-chloro-4-methoxyphenyl)-N⁴-cycloheptyl-6-(1,4-thiazinan-4-yl)-1,3,5-triazine-4,2-diamine (E27)

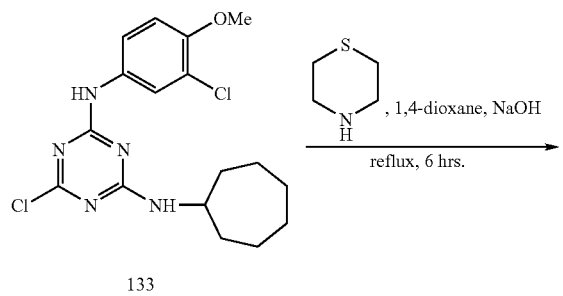

A mixture of thiomorpholine (97 mg, 0.942 mmol), sodium hydroxide (31.4 mg, 0.785 mmol) and water (0.5 mL) in 1,4-dioxane (15 mL) was heated to reflux for 3 hours with stirring under nitrogen atmosphere and then cooled to 25° C. followed by the addition of compound 133 (0.30 g, 0.785 mmol) at same temperature. The mixture was heated to reflux for 12 hours, concentrated under vacuum and diluted with water (20 mL). The mixture was then extracted with EtOAc (2×20 mL). The combined organic layers were washed with water (2×10 mL), dried over anhydrous $Na_2SO_4$ and concentrated under vacuum. The residue thus obtained was purified by column chromatography (10–20% EtOAc-Hexane) to afford the title compound E27 as a pale yellow solid (0.26 g, 74%). mp 78–80° C.; HPLC: Inertsil ODS 3V (250×4.6 mm) 5 microns [solvent A=0.01 M $KH_2PO_4$; solvent B=$CH_3CN$], A:B=20:80; 220 nm, $R_t$ 20.36 min, 97.15% purity; MS (CI): m/z 449 (M+H, 100).

Example 117

Synthesis of N²-(3-chloro-4-methoxyphenyl)-N⁴-cycloheptyl-6-(2-fluorophenoxy)-1,3,5-triazine-4,2-diamine (E28)

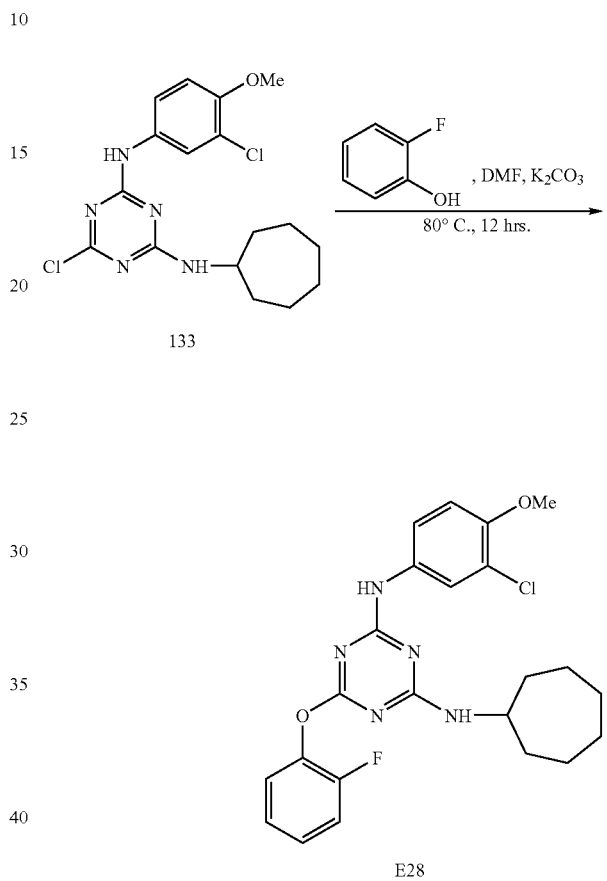

A mixture of compound 133 (0.3 g, 0.785 mmol), 2-fluorophenol (0.106 g, 0.942 mmol) and potassium carbonate (541 mg, 3.93 mmol) in dimethylformamide (3 mL) was heated to 80° C. for 12 hours with stirring under nitrogen atmosphere. The mixture was then cooled, diluted with water (20 mL) and extracted with EtOAc (2×20 mL). The combined organic layers were washed with water (2×10 mL), dried over anhydrous sodium sulphate and concentrated under vacuum. The residue thus obtained was purified by column chromatography (10–20% EtOAc-Hexane) to afford the title compound E28 as a pale yellow solid (0.2 g, 56%). mp 98–100° C.; HPLC: Inertsil ODS 3V (250×4.6 mm) 5 microns [solvent A=0.01 M $KH_2PO_4$ (pH 7.0); solvent B=$CH_3CN$], Gradient elution program: T/% B=0/60, 10/60, 25/80, 40/80, 45/60, 50/60; 268 nm, $R_t$ 29.79 min, 99.82% purity; MS (CI): m/z 458 (M+H, 100).

Example 118

Synthesis of $N^2$-(3-chloro-4-methoxyphenyl)-$N^4$-cycloheptyl-6-[2-(2-fluorophenoxy) ethoxy]-1,3,5-triazine-4,2-diamine (E29)

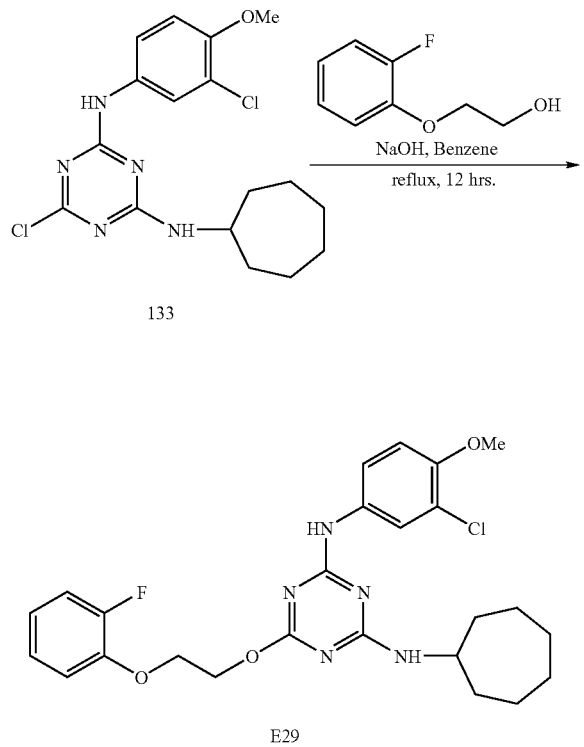

A mixture of 2-(2-fluorophenoxy)-1-ethanol (367 mg, 2.356 mmol) and sodium hydroxide (94 mg, 2.356 mmol) in benzene (15 mL) was heated to reflux for 3 hours with stirring under nitrogen atmosphere and then cooled to 25° C. followed by the addition of compound 1 (0.30 g, 0.785 mmol) at same temperature. The mixture was heated to reflux for 12 hours, concentrated under vacuum and diluted with water (20 mL). The mixture was then extracted with EtOAc (2×20 mL). The combined organic layers were washed with water (2×10 mL), dried over anhydrous sodium sulphate and concentrated under vacuum. The residue thus obtained was purified by column chromatography (10–20% EtOAc-Hexane) to afford the title compound E29 as a semi solid (90 mg, 23%). HPLC: Inertsil ODS 3V (250×4.6 mm) 5 microns [solvent A=0.01 M $KH_2PO_4$ (pH 7.0); solvent B=$CH_3CN$], Gradient elution program: T/% B=0/60, 10/60, 25/80, 40/80, 45/60, 50/60; 268 nm, $R_t$ 32.31 min, 99.30% purity; MS (CI): m/z 502 (M+H, 100).

Example 119

Synthesis of $N^2$-(3-chloro-4-methoxyphenyl)-$N^4$-cycloheptyl-6-(6-methyl-2-pyrylmethoxy]-1,3,5-triazine-4,2-diamine (E30)

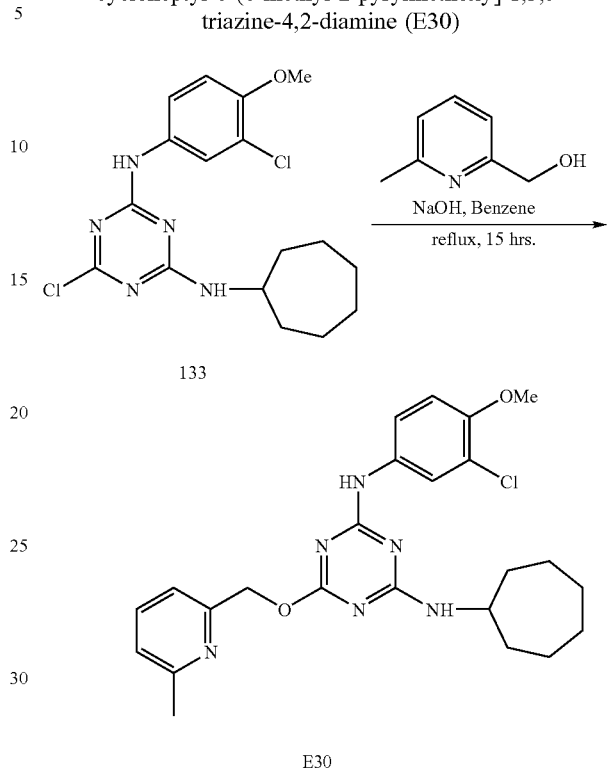

A mixture of 6-methyl-2-pyridylmethanol (145 mg, 1.17 mmol) and sodium hydroxide (63 mg, 1.57 mmol) in benzene (15 mL) was heated to reflux for 3 hours with stirring under nitrogen atmosphere and then cooled to 25° C. followed by the addition of compound 133 (0.30 g, 0.785 mmol) at same temperature. The mixture was heated to reflux for 12 hours, concentrated under vacuum and diluted with water (20 mL). The mixture was then extracted with EtOAc (2×20 mL). The combined organic layers were washed with water (2×10 mL), dried over anhydrous sodium sulphate and concentrated under vacuum. The residue thus obtained was purified by column chromatography (70–80% EtOAc-Hexane) to afford the title compound E30 as a hygroscopic solid (257 mg, 70%). HPLC: Inertsil ODS 3V (250×4.6 mm) 5 microns [solvent A=0.01 M $KH_2PO_4$ (pH 7.0); solvent B=$CH_3CN$], Gradient elution program: T/% B=0/60, 10/60, 25/80, 40/80, 45/60, 50/60; 268 nm, $R_t$ 23.93 min, 99.14% purity; MS (CI): m/z 469 ($M^+$, 100).

Example 120

Synthesis of N-(3-chloro-4-methoxyphenyl)-N'-cycloheptyl-N"-methyl-N"-(1-methyl piperidin-4-yl)[1,3,5]triazine-2,4,6-triamine (137)

N-(3-chloro-4-methoxyphenyl)-N'-cycloheptyl-N"-methyl-N"-(1-methyl piperidin-4-yl)[1,3,5]triazine-2,4,6-triamine (137) is a 1,3,5-triazine derivative which is synthesized from 2,4,6-trichloro-1,3,5-triazine (cyanuric chloride) by serial substitution of amines, for example, 3-chloro-4-methoxyaniline, cycloheptylamine, and 1-methyl-(4-methylamino)piperidine, respectively.

241

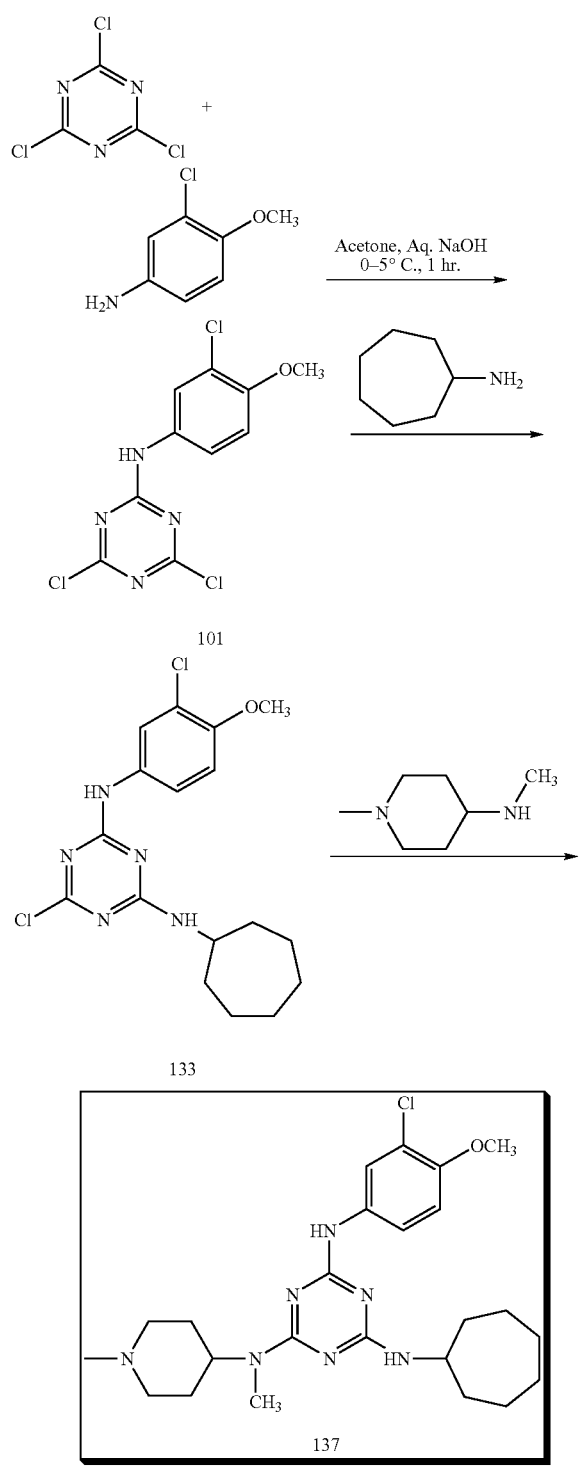

This reaction scheme illustrates synthesis of compound 137 by reaction of cyanuric chloride with 3-chloro-4-methoxyaniline using sodium hydroxide (NaOH) as base at 0–5° C. to yield (3-chloro-4-methoxy phenyl)-(4,6-dichloro-[1,3,5]triazine-2-yl) amine (compound 101), which on reaction with cycloheptylamine in presence of NaOH under reflux gave 6-chloro-N-(3-Chloro-4-methoxyphenyl)-N'-cycloheptyl-[1,3,5]triazine-2,4-diamine (compound 133). Compound 133 on reaction with 1-methyl-(4-methylamino) piperidine yields, the final compound 137.

242

Example 121

Alternative Synthesis of N-(3-chloro-4-methoxyphenyl)-N'-cycloheptyl-N''-methyl-N''-(1-methyl piperidin-4-yl)[1,3,5]triazine-2,4,6-triamine (137)

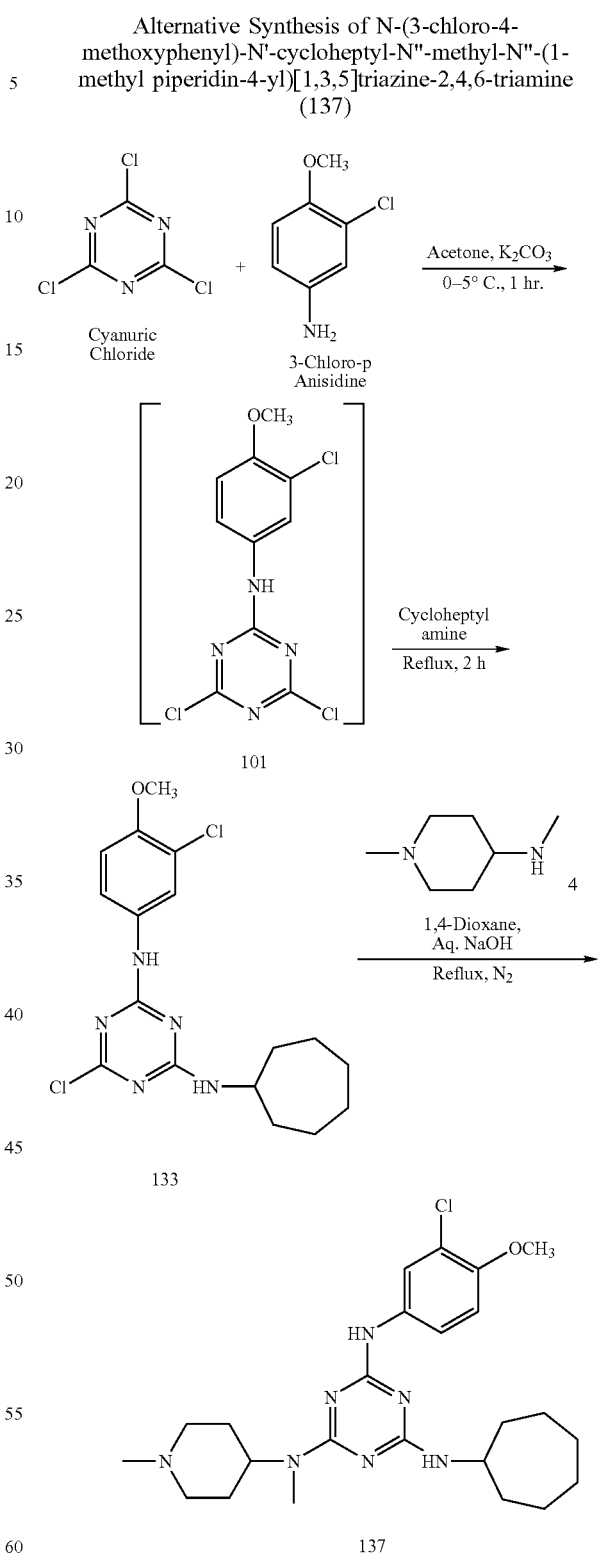

A 1 kg campaign was conducted to develop a process which avoids multiple column purifications and employs a suitable recrystallisation method to produce compound 137. This scheme was stabilized for the campaign, however the scale up of compound 133 by one pot synthesis resulted in the formation of an impurity, which was carried over to the final step and was difficult to remove. The impurity was isolated and characterized to be 6-chloro-N-(3-chloro-4-methoxyphenyl)-N'-(3-chloro-4-ethoxyphenyl)[1,3,5]triazine-2,4-diamine. To avoid the impurity, the single pot reaction was avoided and compound 101 was isolated and purified by recrystallisation in ethylacetate.

Attempts to minimize the impurity involved scanning several bases and solvents, but the production 6-chloro-N-(3-chloro-4-methoxyphenyl)-N'-(3-chloro-4-methoxyphenyl)[1,3,5]triazine-2,4-diamine remained. The preparation of compound 101 was then carried out without addition of base, resulting in the levels of the impurity being negligible. Compound 133 was prepared from compound 101 using aqueous NaOH as base.

Example 122

General Large Scale Synthesis of N-(3-chloro-4-methoxyphenyl)-N'-cycloheptyl-N''-methyl-N''-(1-methyl piperidin-4-yl)[1,3,5]triazine-2,4,6-triamine (137)

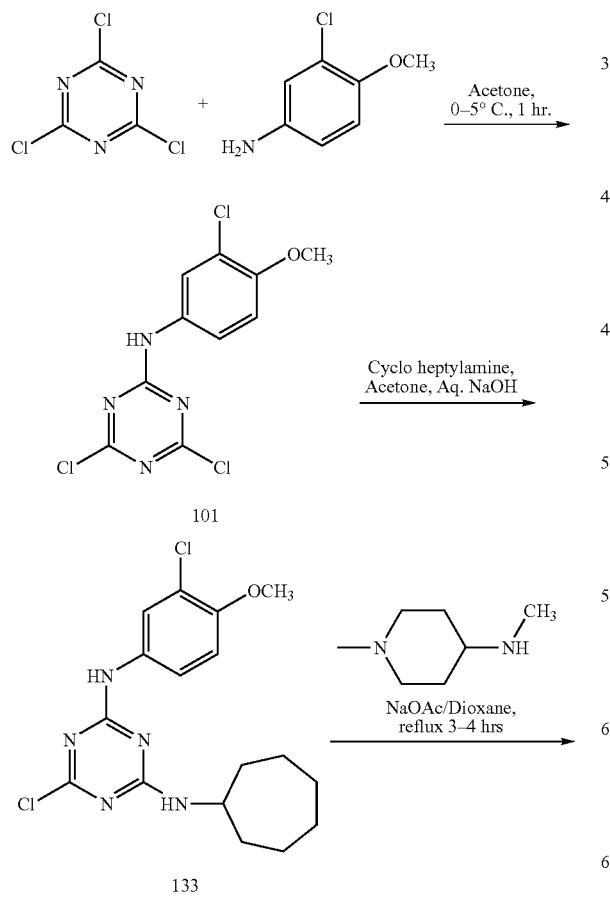

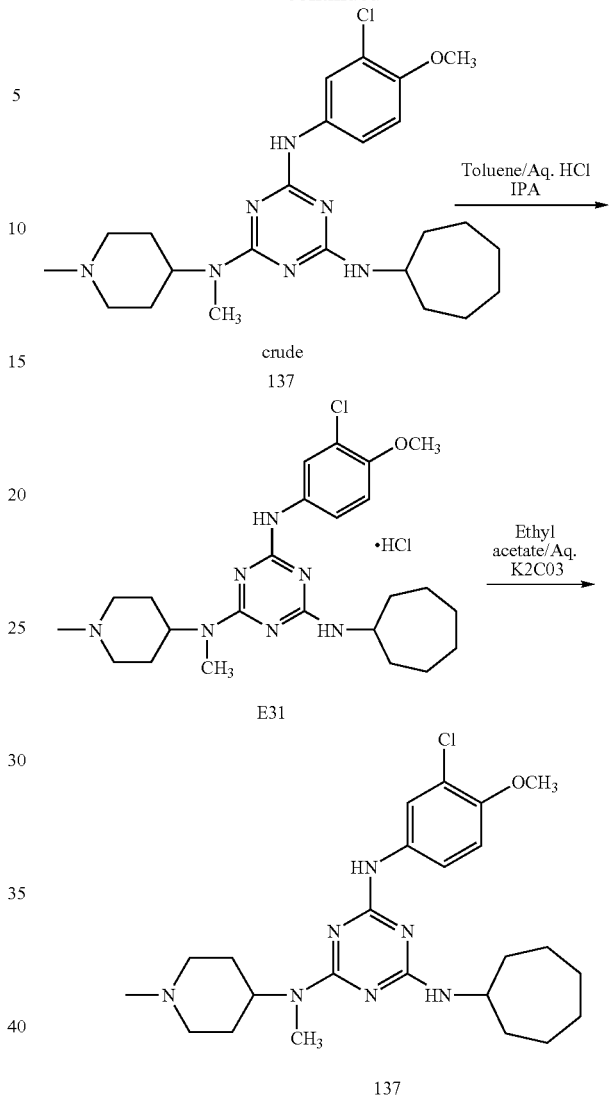

Among the bases and solvents screened, sodium acetate (NaOAc) and 1,4-dioxane showed consistently good results for a 1 kg preparation. This scheme involves the preparation of compound 101 by reaction of cyanuric chloride with 3-chloro-4-methoxyaniline in acetone at 0–5° C. in the absence of base, which is then made to react with cycloheptylamine in presence of NaOH under reflux to give compound 133. This compound 133 was reacted with 1-methyl-(4-methylamino)piperidine using NaOAc in 1,4-dioxane solvent to yield the crude compound 137 which is purified by making hydrochloride salt, N-(3-chloro-4-methoxyphenyl)-N'-cycloheptyl-N''-methyl-N''-(1-methyl piperidin-4-yl)[1,3,5]triazine-2,4,6-triamine, HCl salt, compound E31 and by recrystallisation in isopropanol. The hydrochloride salt was then released to give the free base, compound 137. Compound obtained in this manner exhibited the same high quality of appearance, purity, low residual solvents, assay and impurity profile, and the like.

Example 123

Large Scale Synthesis of (3-chloro-4-methoxyphenyl)-(4,6-dichloro-[1,3,5] triazine-2-yl) amine (101)

As provided in the reaction scheme above, a solution of 3-chloro-4-methoxyaniline (42.5 g) in acetone was slowly added to the cyanuric chloride solution (50 g dissolved in acetone at −10–0° C. The reaction mass was maintained at the same temperature for about 1hour after addition. The progress of the reaction was monitored by TLC. After the completion of the reaction, the reaction mass was poured over crushed ice under stirring. The solid compound thrown out was filtered under vacuum, washed thoroughly with water and then dried. The above compound was recrystallised from ethylacetate (Wt. 60 g Y: 73%).

The following Table illustrates the results obtained using various bases, solvents, and other reaction conditions.

| Rxn No. | Base | Solvent | Yield (%) | Temp. °C. | Cmpdd Purity (%) | Disub (%) | Trisubstit (%) | Remarks |
|---|---|---|---|---|---|---|---|---|
| 1 | NaOH | Acetone | 92 | 0–5 | 90 | 4–6 | 1–2 | |
| 2 | NaOH | Acetone | 75 | 5–10 | 86 | 7–8 | 2–3 | |
| 3 | NaOH | Acetone | 80 | 0–5 | 40 | 35 | 20 | Reverse addition |
| 4 | NaOH | Acetone | 85 | 30 | 65 | 15–20 | 5–8 | |
| 5 | NaOH | Acetone | 89 | Reflux | 20 | 60 | 10–15 | |
| 6 | $K_2CO_3$ | Acetone | 90 | 0–5 | 91 | 7–8 | 1–2 | |
| 7 | $K_2CO_3$ | Toluene | 90 | 0–5 | 91 | 7–8 | 1–2 | |
| 8 | NaOH | Toluene | 80 | 0–5 | 85 | 6–7 | 1–2 | |
| 9 | NaOH | Dioxane | 85 | 0–5 | 92 | 5–6 | — | |
| 10 | $K_2CO_3$ | Dioxane | 90 | 0–5 | 91 | 5–6 | — | |
| 11 | $K_2CO_3$ | Dioxane | 85 | 0–5 | 55 | 20–25 | 4–5 | Reverse addition |
| 12 | — | Acetone | 95 | 0–5 | 95 | 1–2 | — | |
| 13 | — | Acetone | 98 | <0 | 99 | — | — | |
| 14 | Basic resin | Acetone | 85 | 0–5 | 95 | — | — | |

Example 124

Large Scale Synthesis of 6-chloro-N-(3-chloro-4-methoxyphenyl)-N'-cycloheptyl-[1,3,5]triazine-2,4-diamine (133)

As provided in the reaction scheme above, a solution of cycloheptylamine (20.4 g) in acetone was slowly added to the 101 solution (50 g dissolved in acetone) at 20–30° C. To this stirring solution water (100 ml) was added followed by Aq. sodium hydroxide solution (6.5 g dissolved in water). Then the temperature of the reaction mass raised to reflux and maintained for about 2–3 h. TLC was monitored. After completion of the reaction, temperature of the RM (reaction mixture) was brought to 25–30° C. and the reaction mass was poured over chilled water under stirring. The solid compound thrown out was filtered and dried (Wt. 60 g Y: 95.8%).

The following Table illustrates the results obtained using various bases, solvents, and other reaction conditions.

| Rxn No. | Base | Solvent | Yield (%) | Cmpd Purity(%) | Remarks |
|---|---|---|---|---|---|
| 1 | NaOH | Acetone | 92 | 95 | |
| 2 | NaOH | Toluene | 80 | 90 | |
| 3 | NaOH | Dioxane | 80 | 82 | |
| 4 | $K_2CO_3$ | Acetone | 95 | 99 | |
| 5 | $K_2CO_3$ | Dioxane | 89 | 85 | |
| 6 | $Et_3N$ | Acetone | 85 | 75 | |
| 7 | $Et_3N$ | Dioxane | 75 | 60 | |
| 8 | $Et_3N$ | Toluene | 70 | 65 | |

Example 125

One-Pot Synthesis of 6-chloro-N-(3-chloro-4-methoxyphenyl)-N'-cycloheptyl-[1,3,5]triazine-2,4-diamine (133)

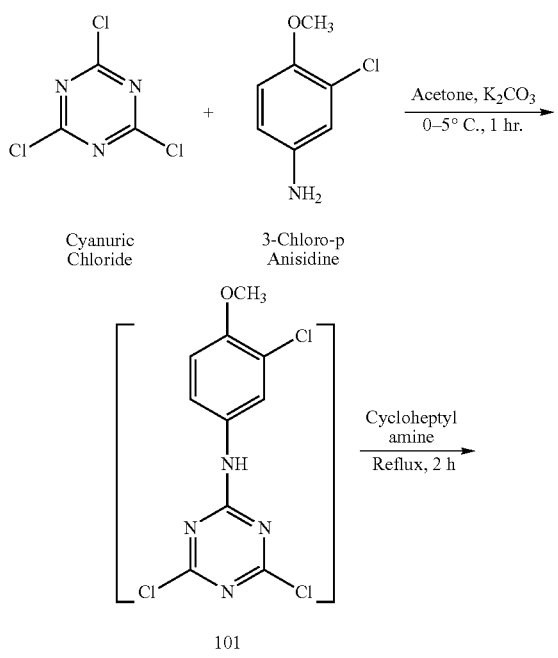

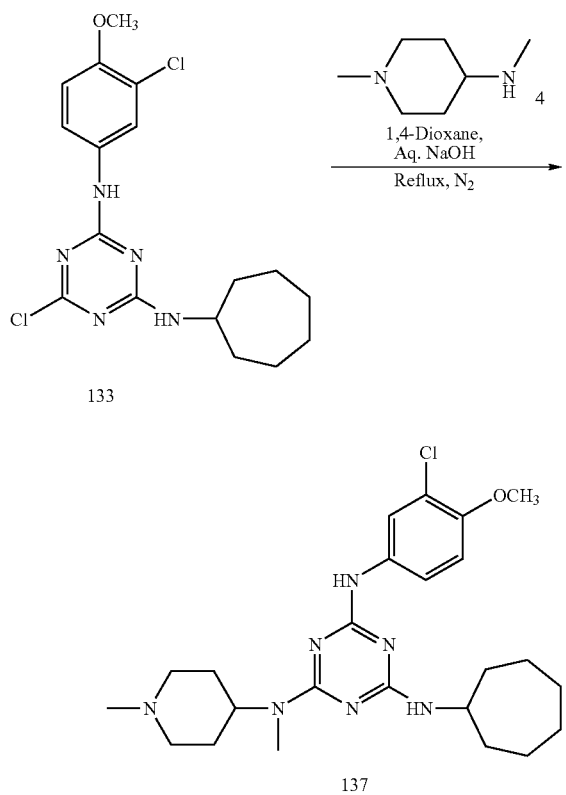

133

137

A convenient, one-pot synthesis of 6-chloro-N-(3-chloro-4-methoxyphenyl)-N'-cycloheptyl-[1,3,5] triazine-2,4-diamine was carried out as follows. To cyanuric chloride (50 g) dissolved in acetone was added a solution of 3-chloro-4-methoxyaniline (42.5 g) in acetone at 0–5° C. followed by the addition of potassium carbonate (112 g). The reaction mass was maintained at the same temperature for about 1hour. The progress of the reaction was monitored by TLC. When the reaction was complete, cycloheptylamine (29 g dissolved in acetone) was added at 0–10° C. The reaction mass was maintained under reflux for about 2–3hours. Completion of the reaction was checked by TLC. The reaction mass was cooled to 20–30° C. and poured over crushed ice under stirring. The solid compound thrown out was filtered and dried. The crude compound was then recrystallised from ethylacetate (Wt.50 g Y:48%).

Example 126

Large-Scale Synthesis of N-(3-chloro-4-methoxyphenyl)-N'-cycloheptyl-N'''-methyl-N''-(1-methyl piperidin-4-yl)[1,3,5]triazine-2,4,6-triamine (137)

1-Methyl-(4-methylamino)piperidine (17 g in 1,4-dioxane) was added to the solution of 6-chloro-N-(3-chloro-4-methoxyphenyl)-N'-cycloheptyl-[1,3,5] triazine-2,4-diamine (50 g dissolved in 1,4-dioxane) at RT followed by addition of sodium acetate (21.5 g). The RM (reaction mixture) was maintained under reflux for about 2–3 hours. The progress of the reaction was monitored by TLC. After the completion of the reaction, the reaction mass was cooled to 20–30° C. and filtered through hi-flow bed. The filtrate was evaporated to minimum volume and was diluted with toluene. This was acidified with dilute HCl under stirring conditions. The solid obtained was filtered and dried. The above crude compound was recrystallised from isopropanol (Wt. 20 g Y: 30%).

The HCl salt (20 g) was dissolved in methanol, diluted with ethylacetate and made basic with aqueous potassium carbonate solution. The organic layer was separated and the aqueous layer was again extracted into ethylacetate. The organic layers were combined, washed with water and evaporated to yield the compound (Wt. 20 g Y: 30%).

Example 127

General Synthesis of Akoxide Derivatives of 6-chloro-N-(3-chloro-4-methoxyphenyl)-N'-cycloheptyl-[1,3,5] triazine-2,4-diamine

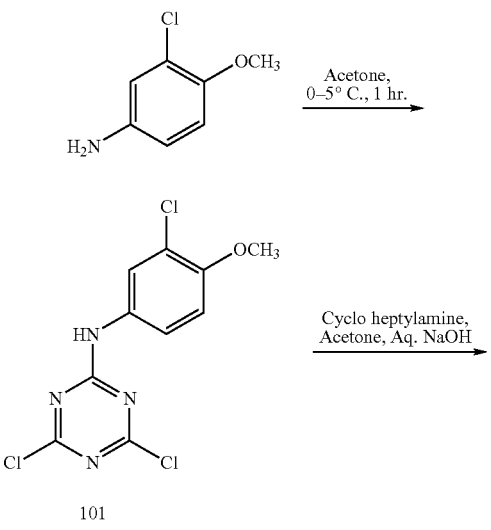

Cyanuric chloride

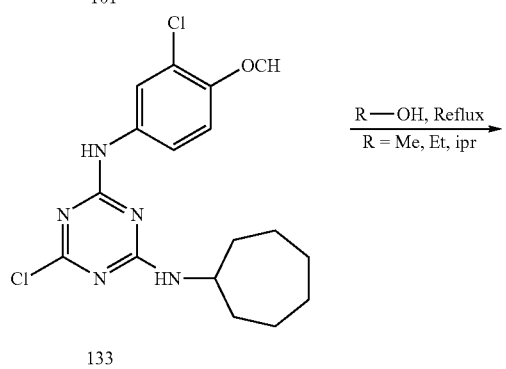

133

-continued

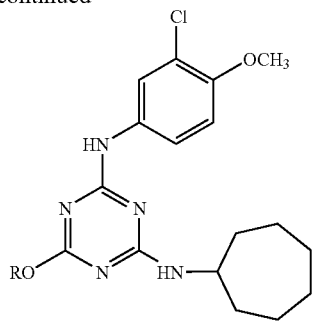

R = Me, Et, i-Pr

The sequential substitution at the triazine core permitted the convenient formation of alkoxide derivatives of triazines. The procedure involves the preparation of compound 101 by reaction of cyanuric chloride with 3-chloro-4-methoxyaniline in acetone at 0–5° C. in the absence of base, which is then made to react with cycloheptylamine in presence of sodium hydroxide under reflux to give compound 133. This compound 133 was refluxed in alcohols like methanol, ethanol, isopropanol, etc., with base to yield alkoxide compounds whose structures are confirmed by the spectral data.

Example 128

Synthesis of 6-methoxy-N-(3-Chloro-4-methoxy phenyl)-N'-cyclo heptyl-[1,3,5]triazine-2,4 diamine (E32)

To 6-chloro-N-(3-chloro-4-methoxyphenyl)-N'-cycloheptyl-[1,3,5] triazine-2,4-diamine (5 g) dissolved in methanol was added $K_2CO_3$ (3.2 g) and refluxed for about 6–8 h. TLC was monitored. After the completion of the reaction, the reaction mass was filtered through vacuum and the filtrate was evaporated to yield the title compound. (Wt. 4.7 g Y: 95%)

Example 129

Synthesis of 6-ethoxy-N-(3-Chloro-4-methoxy phenyl)-N'-cyclo heptyl-[1,3,5]triazine-2,4 diamine (E33)

A portion of 6-chloro-N-(3-chloro-4-methoxyphenyl)-N'-cycloheptyl-[1,3,5]triazine-2,4-diamine (5 g) was refluxed in ethanol in presence of $K_2CO_3$ (3.2 g) for about 8–10 h. TLC was monitored. After the completion of the reaction, the reaction mass was filtered through vacuum and the filtrate was evaporated to yield the title compound. (Wt. 4.6 g Y: 90%).

Example 130

Synthesis of 6-isopropoxy-N-(3-Chloro-4-methoxy phenyl)-N'-cyclo heptyl-[1,3,5] triazine-2,4 diamine (E34)

To a portion of 6-chloro-N-(3-chloro-4-methoxyphenyl)-N'-cycloheptyl-[1,3,5] triazine-2,4-diamine (5 g) in isopropanol was added $K_2CO_3$ (3.2 g) and refluxed for about 10–12 h. TLC was monitored. After the completion of the reaction, the reaction mass was filtered through vacuum and the filtrate was evaporated to yield the title compound. (Wt. 3.7 g Y: 70%).

Example 131

Alternative Synthesis of 6-alkoxy-N-(3-Chloro-4-methoxy phenyl)-N'-cyclo heptyl-[1,3,5] triazine-2, 4 diamine

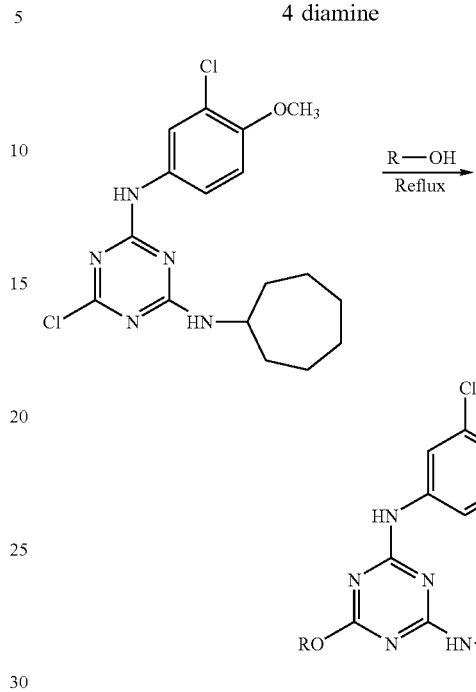

R = Me, Et, i-Pr

To 6-chloro-N-(3-chloro-4-methoxyphenyl)-N'-cycloheptyl-[1,3,5] triazine-2,4-diamine (5 g) dissolved in solvent (Methanol, Ethanol, Isopropanol) was added $K_2CO_3$ (3.2 g) and refluxed for about 8–10 h. TLC was monitored. After completion of the reaction, the reaction mass was filtered through vacuum and the filtrate was evaporated to yield the title compounds, E32, E33, and E34, respectively.

| Rxn No. | Solvent | Yield (%) | Purity (%) |
|---|---|---|---|
| 1 | Methanol | 90 | 95 |
| 2 | Ethanol | 85 | 96 |
| 3 | Isopropanol | 50 | 80 |

Example 132

Biological Activity Data

Additional bioactivity data for compounds of the present invention are presented in Table 8, where compounds that have at least the activity of effecting cellular proliferation or at least the activity of modulating inflammation activity, as measured by the assays taught herein, are provided. For compounds that show at least the activity of modulating inflammation activity, the activity is typically measured and reported relative to IL6 production compared to cells that did not receive compound (or per cent of control IL6 production). The inclusion of compounds in the categories of the Tables disclosed herein, including this Table, is not to be seen as limiting, in that compounds included in such Tables have at least the activity shown for inclusion in the Table and may have more or other activities. Nor are the Tables to be seen as limiting in that these are the only compounds disclosed herein that have that activity, representative compounds are shown in the Tables that have at least that particular activity for inclusion in the Table. One or more compounds disclosed herein have at least an activity that has utility in treatment of disease states. Note that any hydrogen atoms that are required for any atom to attain its usual valence in a structure presented in Table 8, whether a carbon atom or a heteroatom, should be inferred if it is not specifically indicated.

REFERENCES

1. Brownlee et al., 101 ANN. INTERN. MED. 527–37 (1984)
2. Yang et al., 91 PROC NATL. ACAD. SCI. USA 9436–40 (1994)
3. Tanji et al.,11 J. AM. SOC. NEPHROL. 1656–66 (2000)
4. Schmidt et al., 84 CIRC. RES. 489–97 (1999)
5. Yamamoto et al., 902 ANN. N.Y. ACAD. SCI. 163–70 (2000)
6. Yano et al., 8 DIABETES RES. CLIN. PRACT. 215–19 (1990)
7. Cohen et al., Vol. 7 J. AM. SOC. NEPHROL. 183–90 (1996)
8. Brownlee et al., 232 SCIENCE 1629–32 (1986)
9. Li et al., 93 PROC. NATL. ACAD. SCI. USA 3902–07 (1996)
10. Piercy et al. 47 METABOLISM 1477–80 (1998)
11. Wautier et al., 97 J. CLIN. INVEST. 238–43 (1996)
12. Schmidt et al., 96 J. CLIN. INVEST. 1395–1403 (1995)
13. Park et al., 4 NAT. MED. 1025–31 (1998)
14. Taguchi et al., 405 NATURE 354–60 (2000)
15. Hofinann et al., 97 CELL 889–901 (1999)
16. Du Yan et al., 94 PROC. NATL. ACAD. SCI. U.S.A. 5296–5301 (1997)
17. Lander et al., 272 J. BIOL. CHEM. 7810–4 (1997).
18. Thomalley, 44 CELL MOL. BIOL. 1013–23 (1998)
19. Orford et al., 86 AM. J. CARDIOL. 6H-11H. (2000)
20. Bult, 21 PHARMACOL. SCI. 274–79 (2000)
21. Schwartz, 100 J. CLIN. INVEST. S87–89 (1997)
22. Cooper et al., 43 DIABETOLOGIA 660–64 (2000)
23. Birrell et al., 4 DIABETOLOGIA 110–16 (2000)
24. Wada et al., 42 DIABETOLOGIA 743–47 (1999)
25. Soulis et al., 50 KIDNEY INT. 627–34 (1996)
26. Cooper et al., 43 DIABETOLOGIA 660–64 (2000)
27. Oturai et al., 49(8) METABOLISM 996–1000 (2000)
28. Laight et al., 15 DIABETES METAB. RES. REV. 274–82 (1999)
29. Stehouwer et al., 34 CARDIOVASC. 55–68 (1997)
30. Libby, 247 J. INTERN. MED. 349–58 (2000)
31. Van Lente, 293 CLINICA. CHIMICA. ACTA. 31–52 (2000)
32. Horii et al., 39 KIDNEY INT. SUPPL. S71–75 (1993)
33. Huber et al., 19 ARTERIOSCLER THROMB. VASC. BIOL. 2364–67 (1999)
34. Shikano et al., 85 NEPHRON 81–5 (2000)
35. Pickup et al., 8(67) LIFE SCI. 291–300 (2000)
36. Kado et al., 36 ACTA. DIABETOL. 67–72 (1999)
37. Eitneretal., 51 KIDNEY INT. 69–78 (1997)
38. Banba et al. 58 KIDNEY INT. 684–690 (2000)
39. Campbell et al., 48 ANNU. REV. PHYSIOL. 295–306 (1986)
40. Kamovsky, 105 ROUS—WHIPPLE AWARD LECTURE. AM. J. PATHOL. 200–206 (1981)
41. Gustafson et al., 54 TETRAHEDRON 4051–4065 (1998)
42. Shah et al., 2 J. COMB. CHEM. 453–460 (2000)
43. Johnson et al., 54 TETRAHEDRON 4097–4106 (1998)
44. Ichihara et al., CHEM. LETT. 631–632 (1995)
45. Kaiser et al., 73 J. AM. CHEM. SOC. 2984–2986 (1951)
46. Thurston et al., 73 J. AM. CHEM. SOC. 2981–2983 (1951)
47. Campbell et al., 26 ORG. CHEM. 2786–2789 (1961)
48. Koopman et al., 77 RECUEIL 235–240 (1958)
49. Whitten et al., 39 J. MED. CHEM. 4354–4357 (1996)
50. JP Patent No. 2001–145355 (issued Jan. 12, 2201)
51. Masquelin et al., 48 HETEROCYCLES, 2489–2505 (1998)
52. Scharn et al., 2 J. COMB. CHEM. 361–369 (2000)
53. Silen et al., 42 ANTIMICROB. AGENTS CHEMOTHER. 1447–53 (1998)
54. Scharn et al., 66 J. ORG. CHEM. 507–513 (2001)
55. Masala et al., 1 ORG. LETT. 1355–1357 (1999)
56. Miyaura et al., 95 CHEM. REV. 2457–2483 (1995)
57. Suzuki et al., 576 ORGANOMET. CHEM. 147–168 (1999)
58. Antilla et al., 3 ORG. LETT. 2077–2079 (2001)
59. Janietz et al., SYNTHESIS 33–34 (1993)

TABLE 1B

Representative Compounds of the Present Invention

| Cmpd | Structure | Name |
| --- | --- | --- |
| B1 | 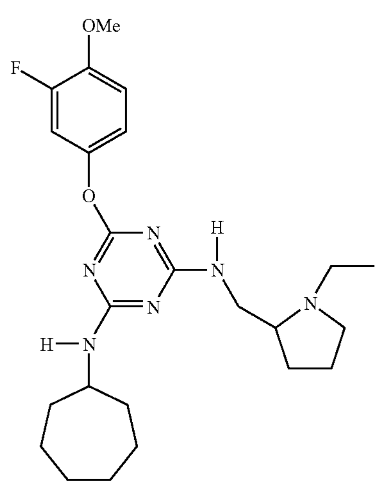 | N-Cycloheptyl-N'(1-ethyl-pyrrolidin-2-ylmethyl)-6-(3-fluoro-4-methoxy-phenoxy)-[1,3,5]triazine-2,4-diamine |

TABLE 1B-continued

Representative Compounds of the Present Invention

| Cmpd | Structure | Name |
| --- | --- | --- |
| B2 | 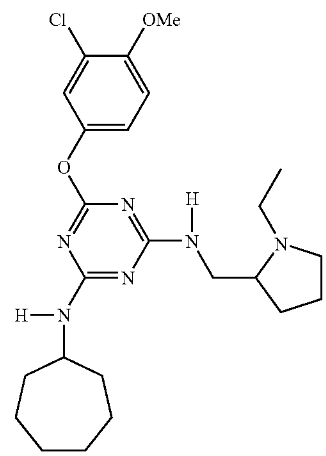 | 6-(3-Chloro-4-methoxy-phenoxy-)-N-cycloheptyl-N'-(1-ethyl-pyrrolidin-2-ylmethyl)-[1,3,5]triazine-2,4-diamine |
| B3 | 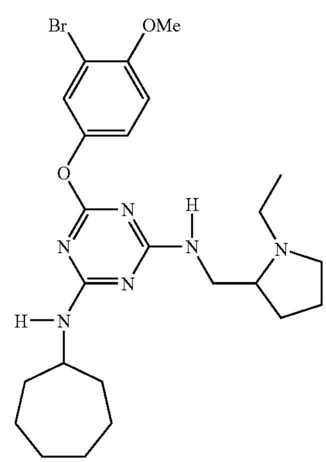 | 6-(3-Bromo-4-methoxy-phenoxy-)-N-cycloheptyl-N'-(1-ethyl-pyrrolidin-2-ylmethyl)-[1,3,5]triazine-2,4-diamine |
| B4 | 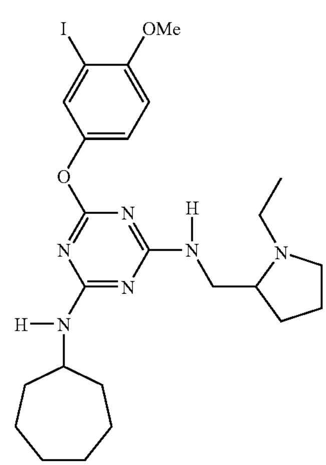 | N-Cycloheptyl-N'(1-ethyl-pyrrolidin-2-ylmethyl)-6-(3-iodo-4-methoxy-phenoxy)-[1,3,5]triazine-2,4-diamine |

TABLE 1B-continued

Representative Compounds of the Present Invention

| Cmpd | Structure | Name |
|---|---|---|
| B5 | 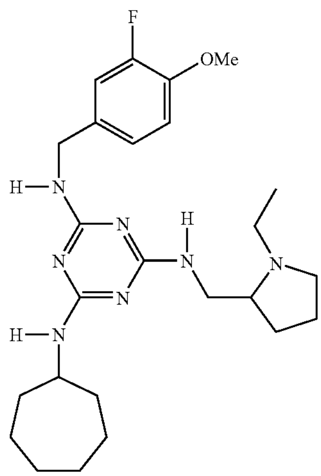 | N-Cycloheptyl-N'-(1-ethyl-pyrrolidin-2-ylmethyl)-N''-(3-fluoro-4-methoxy-benzyl)-[1,3,5]triazine-2,4-diamine |
| B6 | 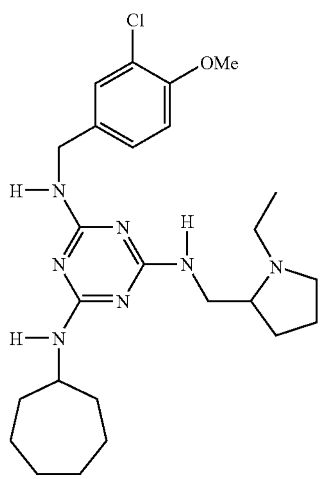 | N-(3-Chloro-4-methoxy-benzyl)-N'-cycloheptyl-N''-(1-ethyl-pyrrolidin-2-ylmethyl)-[1,3,5]triazine-2,4,6-triamine |
| B7 | 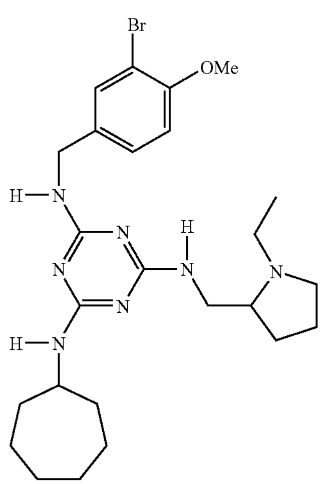 | N-(3-Bromo-4-methoxy-benzyl)-N'-cycloheptyl-N''-(1-ethyl-pyrrolidin-2-ylmethyl)-[1,3,5]triazine-2,4,6-triamine |

TABLE 1B-continued

Representative Compounds of the Present Invention

| Cmpd | Structure | Name |
|---|---|---|
| B8 | 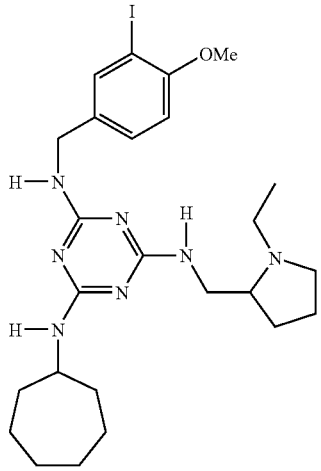 | N-Cycloheptyl-N'-(1-ethyl-pyrrolidin-2-ylmethyl)-N''-(3-iodo-4-methoxy-benzyl)-[1,3,5]triazine-2,4,6-triamine |
| B9 | 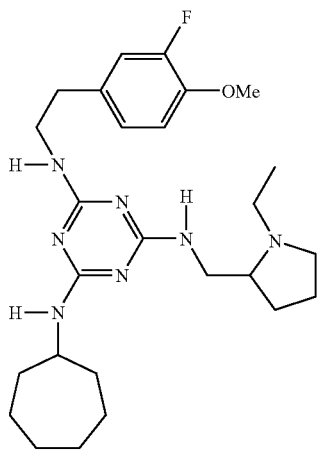 | N-Cycloheptyl-N'-(1-ethyl-pyrrolidin-2-ylmethyl)-N''-[2-(3-fluoro-4-methoxy-phenyl)-ethyl]-[1,3,5]-triazine-2,4,6-triamine |
| B10 | 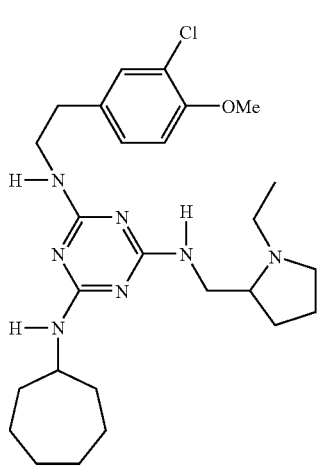 | N-[2-(3-Chloro-4-methoxy-phenyl)-ethyl]-N'-cycloheptyl-N''-(1-ethyl-pyrrolidin-2-ylmethyl)-[1,3,5]-triazine-2,4,6-triamine |

TABLE 1B-continued

Representative Compounds of the Present Invention

| Cmpd | Structure | Name |
|---|---|---|
| B11 | 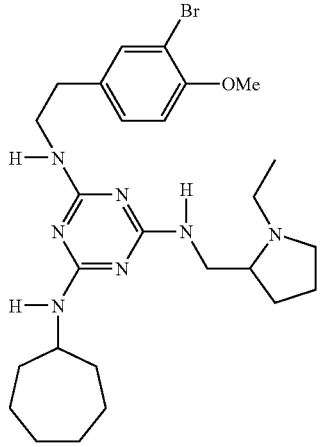 | N-[2-(3-Bromo-4-methoxy-phenyl)-ethyl]-N'-cycloheptyl-N''-(1-ethyl-pyrrolidin-2-ylmethyl)-[1,3,5]-triazine-2,4,6-triamine |
| B12 | 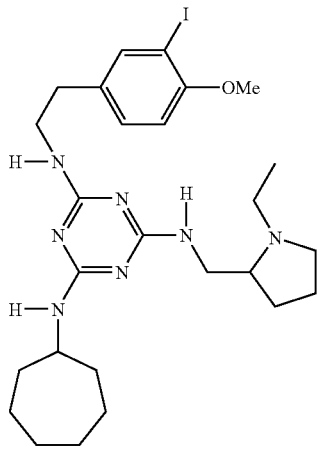 | N-Cycloheptyl-N'-(1-ethyl-pyrrolidin-2-ylmethyl)-N''-[2-(3-iodo-4-methoxy-phenyl)-ethyl]-[1,3,5]-triazine-2,4,6-triamine |
| B13 | 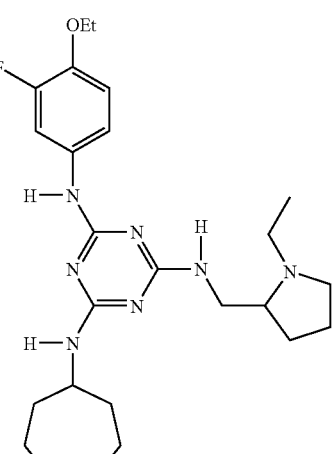 | N-Cycloheptyl-N'-(4-ethoxy-3-fluoro-phenyl)-N''-(1-ethyl-pyrrolidin-2-ylmethyl)-[1,3,5]triazine-2,4,6-triamine |

TABLE 1B-continued
Representative Compounds of the Present Invention
| Cmpd | Structure | Name |
|---|---|---|
| B14 | 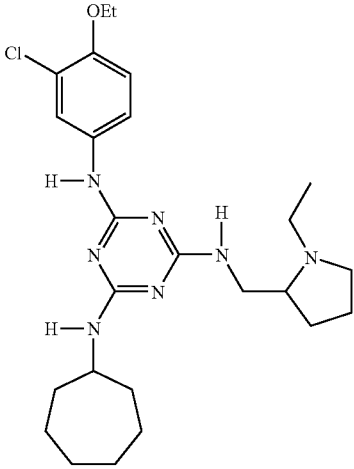 | N-(3-Chloro-4-ethoxy-phenyl)-N'-cycloheptyl-N''-(1-ethyl-pyrrolidin-2-ylmethyl)-[1,3,5]triazine-2,4,6-triamine |
| B15 | 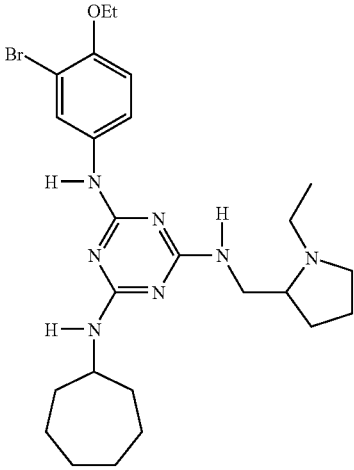 | N-(3-Bromo-4-ethoxy-phenyl)-N'-cycloheptyl-N''-(1-ethyl-pyrrolidin-2-ylmethyl)-[1,3,5]triazine-2,4,6-triamine |
| B16 | 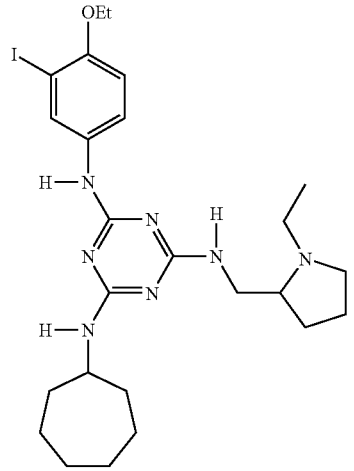 | N-Cycloheptyl-N'-(4-ethoxy-3-iodo-phenyl)-N''-(1-ethyl-pyrrolidin-2-ylmethyl)-[1,3,5]triazine-2,4,6-triamine |

TABLE 1B-continued

Representative Compounds of the Present Invention

| Cmpd | Structure | Name |
|---|---|---|
| B17 | 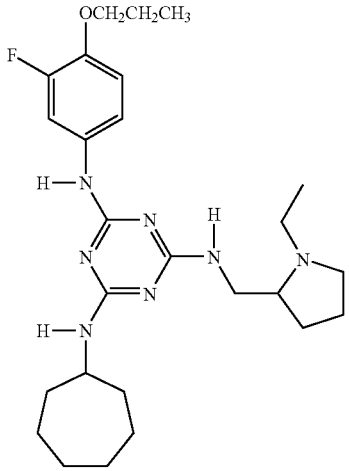 | N-Cycloheptyl-N'-(1-ethyl-pyrrolidin-2-ylmethyl-N''-(3-fluoro-4-propoxy-phenyl)-[1,3,5]triazine-2,4,6-triamine |
| B18 | 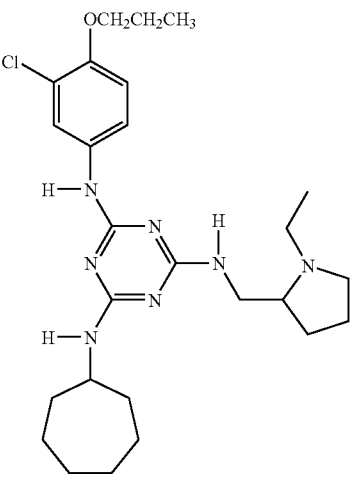 | N-(3-Chloro-4-propoxy-phenyl)-N'-cycloheptyl-N''-(1-ethyl-pyrrolidin-2-ylmethyl)-[1,3,5]triazine-2,4,6-triamine |
| B19 | 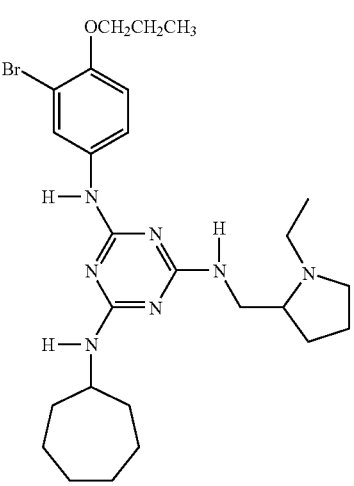 | N-(3-Bromo-4-propoxy-phenyl)-N'-cycloheptyl-N''-(1-ethyl-pyrrolidin-2-ylmethyl)-[1,3,5]triazine-2,4,6-triamine |

TABLE 1B-continued

Representative Compounds of the Present Invention

| Cmpd | Structure | Name |
|---|---|---|
| B20 | 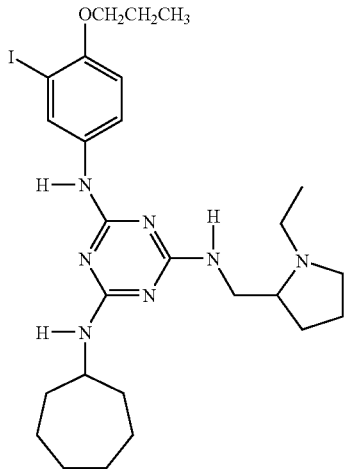 | N-Cycloheptyl-N'-(1-ethyl-pyrrolidin-2-ylmethyl-N''-(3-iodo-4-propoxy-phenyl)-[1,3,5]triazine-2,4,6-triamine |
| B21 | 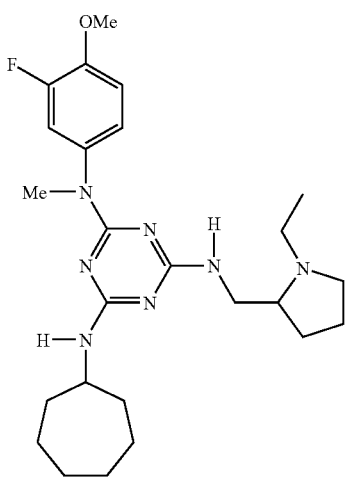 | N-Cycloheptyl-N'-(1-ethyl-pyrrolidin-2-ylmethyl-N''-(3-fluoro-4-methoxy-phenyl)-N'''-methyl-[1,3,5]triazine-2,4,6-triamine |
| B22 | 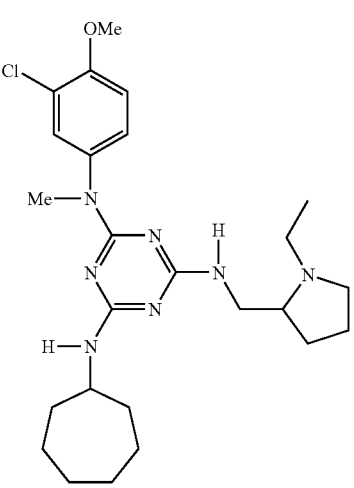 | N-(3-Chloro-4-methoxy-phenyl)-N'-cycloheptyl-N''-(1-ethyl-pyrrolidin-2-ylmethyl)-[1,3,5]triazine-2,4,6-triamine |

TABLE 1B-continued

Representative Compounds of the Present Invention

| Cmpd | Structure | Name |
|---|---|---|
| B23 | 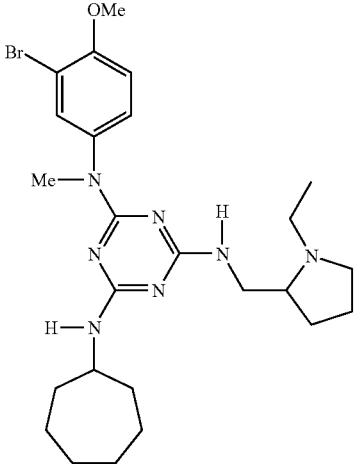 | N-(3-Bromo-4-methoxy-phenyl)-N'-cycloheptyl-N''-(1-ethyl-pyrrolidin-2-ylmethyl)-[1,3,5]triazine-2,4,6-triamine |
| B24 | 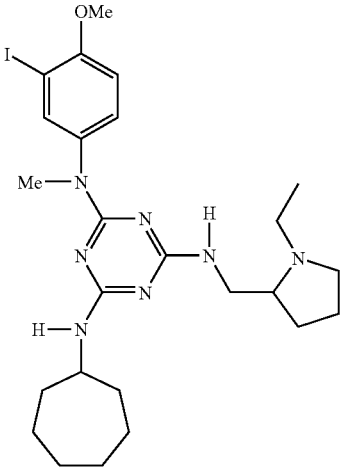 | N-Cycloheptyl-N'-(1-ethyl-pyrrolidin-2-ylmethyl)-N''-(3-iodo-4-methoxy-phenyl)-[1,3,5]triazine-2,4,6-triamine |
| B25 | 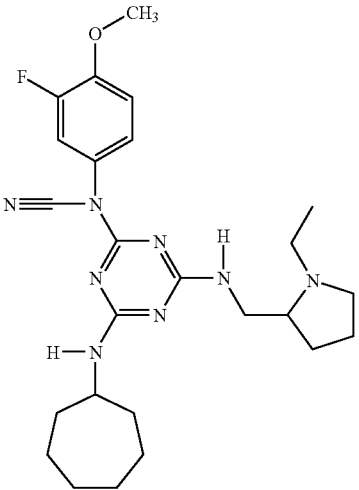 | {4-Cycloheptylamino-6-[(1-ethyl-pyrrolidin-2-ylmethyl)-amino]-[1,3,5]triazin-2-yl}-(3-fluoro-4-methoxy-phenyl)-cyanamide |

TABLE 1B-continued

Representative Compounds of the Present Invention

| Cmpd | Structure | Name |
| --- | --- | --- |
| B26 | 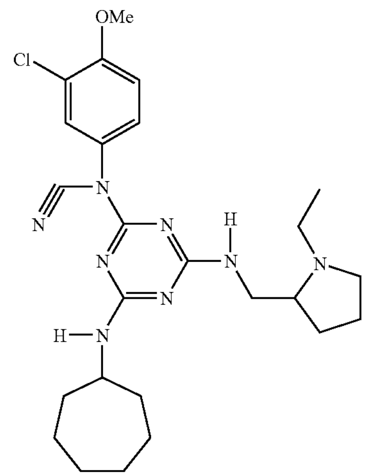 | (3-Chloro-4-methoxy-phenyl)-{4-cycloheptyamino-6-[(1-ethyl-pyrrolidin-2-ylmethyl)-amino]-[1,3,5]triazin-2-yl}-cyanamide |
| B27 | 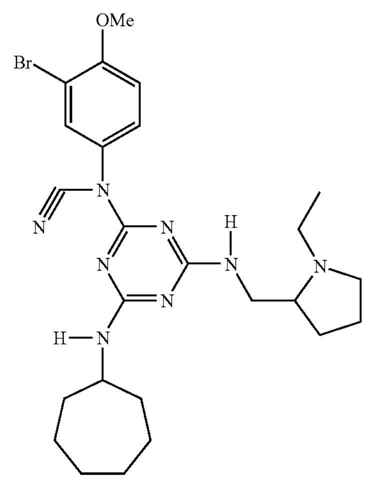 | (3-Bromo-4-methoxy-phenyl)-{4-cycloheptylamino-6-[(1-ethyl-pyrrolidin-2-ylmethyl)-amino]-[1,3,5]triazin-2-yl}-cyanamide |
| B28 | 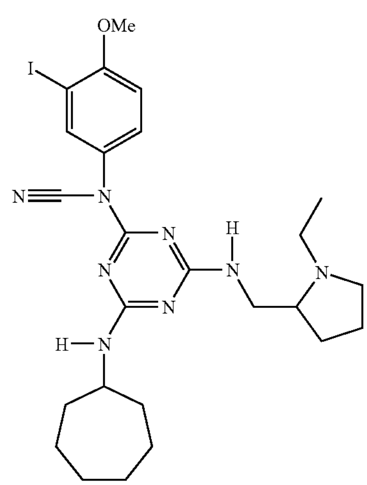 | {4-Cycloheptylamino-6-[(1-ethyl-pyrrolidin-2-ylmethyl)-amino]-[1,3,5]triazin-2-yl}-(3-iodo-4-methoxy-phenyl)-cyanamide |

TABLE 1B-continued
Representative Compounds of the Present Invention
| Cmpd | Structure | Name |
|---|---|---|
| B29 | 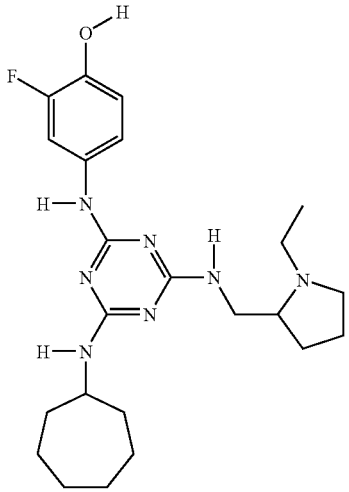 | 4-{4-Cycloheptylaminamino-6-[(1-ethyl-pyrrolidin-2-ylmethyl)-amino]-[1,3,5]triazin-2-ylamino}-2-fluoro-phenol |
| B30 | 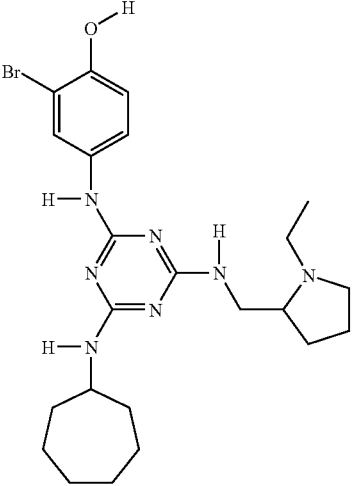 | 2-Bromo-4-{4-cycloheptylamino-6-[(1-ethyl-pyrrolidin-2-ylmethyl)-amino]-[1,3,5]triazin-2-ylamino}-phenol |
| B31 | 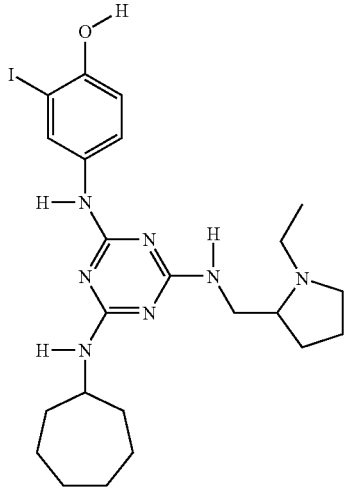 | 4-{4-Cycloheptylaminamino-6-[(1-ethyl-pyrrolidin-2-ylmethyl)-amino]-[1,3,5]triazin-2-ylamino}-2-iodo-phenol |

TABLE 1B-continued

Representative Compounds of the Present Invention

| Cmpd | Structure | Name |
| --- | --- | --- |
| B32 | 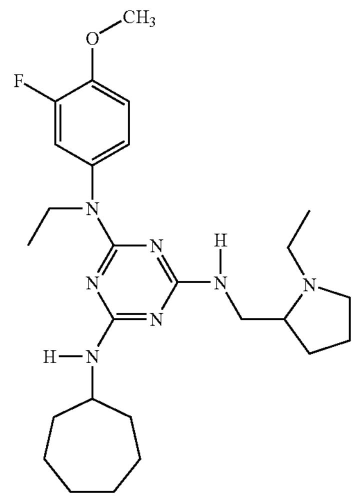 | N-Cycloheptyl-N'-ethyl-N''-(1-ethyl-pyrrolidin-2-ylmethyl)-N'-(3-fluoro-4-methoxy-phenyl)-[1,3,5]triazin-2,4,6-triamine |
| B33 | 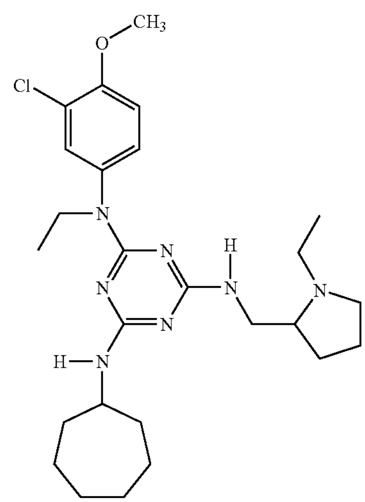 | N-(3-Chloro-4-methoxy-phenyl)-N'-cycloheptyl-N-ethyl-N''-(1-ethyl-pyrrolidin-2-ylmethyl)-[1,3,5]-triazine-2,4,6-triamine |
| B34 | 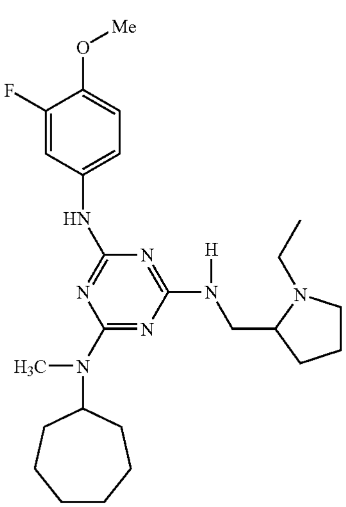 | N-Cycloheptyl-N'-(1-ethyl-pyrrolidin-2-ylmethyl)-N''-(3-fluoro-4-methoxy-phenyl)-N-methyl-[1,3,5]triazine-2,4,6-triamine |

TABLE 1B-continued

Representative Compounds of the Present Invention

| Cmpd | Structure | Name |
|---|---|---|
| B35 | 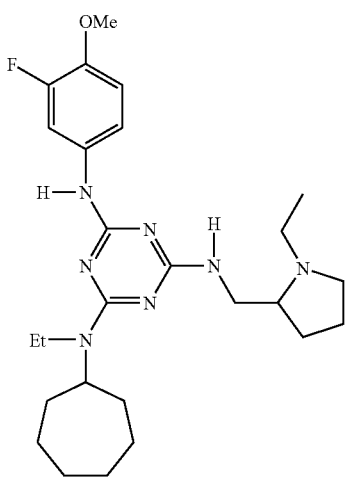 | N-Cycloheptyl-N-ethyl-N'-(1-ethyl-pyrrolidin-2-ylmethyl)-N''-(3-fluoro-4-methoxy-phenyl)-[1,3,5]triazine-2,4,6-triamine |
| B36 | 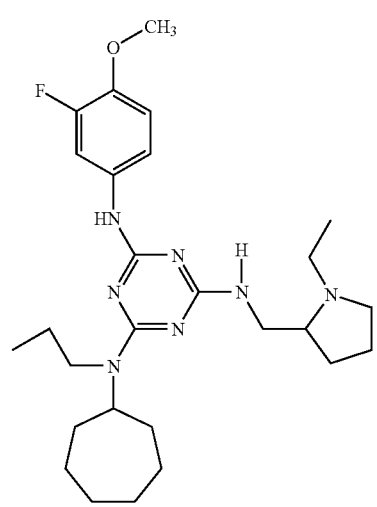 | N-Cycloheptyl-N'-(1-ethyl-pyrrolidin-2-ylmethyl)-N''-(3-fluoro-4-methoxy-phenyl)-N-propyl-[1,3,5]triazine-2,4,6-triamine |
| B37 | 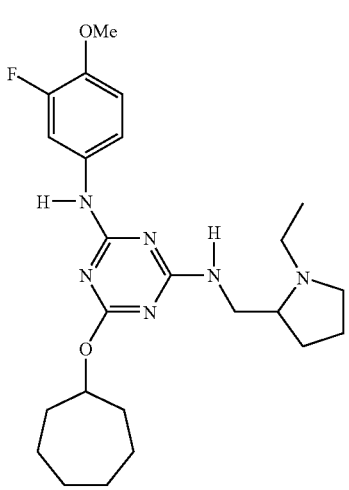 | 6-Cycloheptyloxy-N-(1-ethyl-pyrrolidin-2-ylmethyl)-N'-(3-fluoro-4-methoxy-phenyl)-[1,3,5]triazine-2,4,6-triamine |

TABLE 1B-continued

Representative Compounds of the Present Invention

| Cmpd | Structure | Name |
|---|---|---|
| B38 | 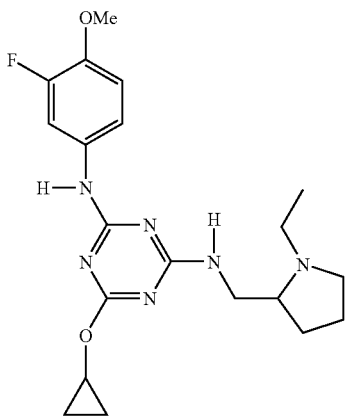 | 6-Cyclopropoxy-N-(1-ethyl-pyrrolidin-2-ylmethyl)-N'-(3-fluoro-4-methoxy-phenyl)-[1,3,5]triazine-2,4,6-triamine |
| B39 | 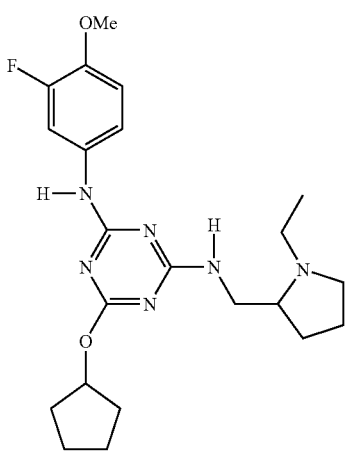 | 6-Cyclopentyloxy-N-(1-ethyl-pyrrolidon-2-ylmethyl)-N'-(3-fluoro-4-methoxy-phenyl)-[1,3,5]triazine-2,4,6-triamine |
| B40 | 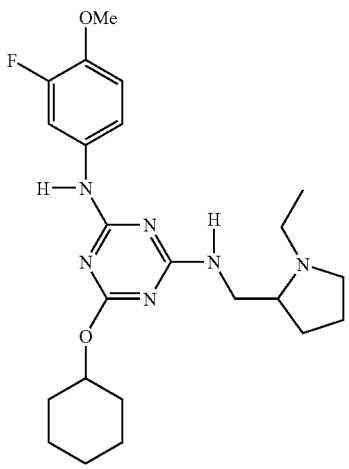 | 6-Cyclohexyloxy-N-(1-ethyl-pyrrolidin-2-ylmethyl)-N'-(3-fluoro-4-methoxy-phenyl)-[1,3,5]triazine-2,4,6-triamine |

TABLE 1B-continued

Representative Compounds of the Present Invention

| Cmpd | Structure | Name |
|---|---|---|
| B41 | 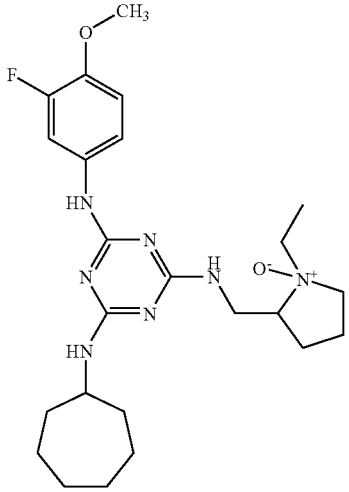 | N-Cycloheptyl-N'-(1-ethyl-1-oxy-pyrrolidin-2-ylmethyl-N''-(3-fluoro-4-methoxy-phenyl)-[1,3,5]triazine-2,4,6-triamine |
| B42 | 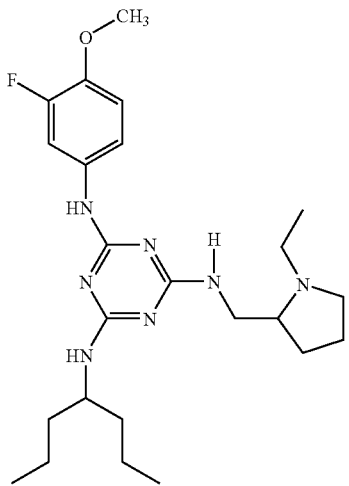 | N-(1-Ethyl-pyrrolidin-2-ylmethyl)-N'-(3-fluoro-2-methoxy-phenyl)-N''-(1-propyl-butyl)-[1,3,5]triazine-2,4,6-triamine |
| B43 | 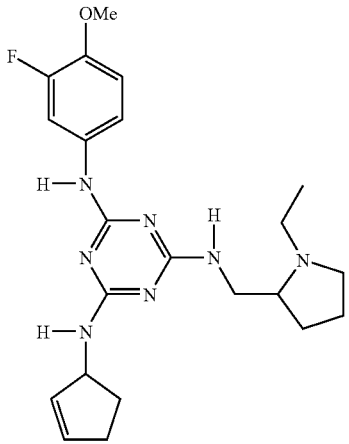 | N-Cyclopent-2-enyl-(1-ethyl-pyrrolidin-2-ylmethyl)-N''-(3-fluoro-4-methoxy-phenyl)-[1,3,5]triazine-2,4,6-triamine |

TABLE 1B-continued

Representative Compounds of the Present Invention

| Cmpd | Structure | Name |
|---|---|---|
| B44 | 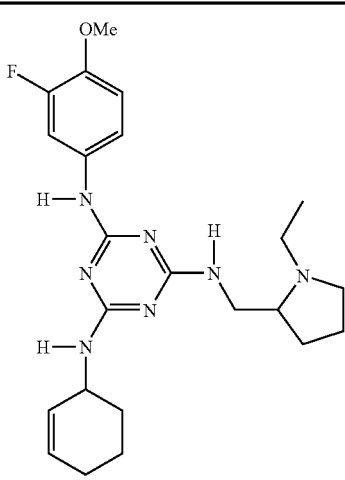 | N-Cyclohex-2-enyl-(1-ethyl-pyrrolidin-2-ylmethyl)-N''-(3-fluoro-4-methoxy-phenyl)-[1,3,5]triazine-2,4,6-triamine |
| B45 | 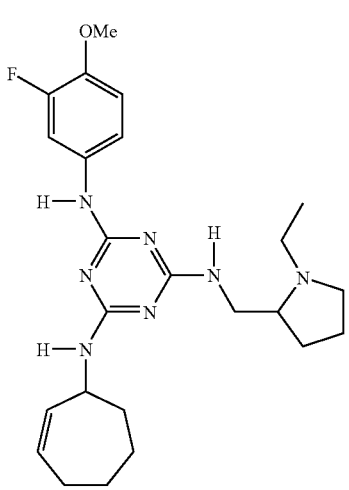 | N-Cyclohept-2-enyl-(1-ethyl-pyrrolidin-2-ylmethyl)-N''-(3-fluoro-4-methoxy-phenyl)-[1,3,5]triazine-2,4,6-triamine |
| B46 | 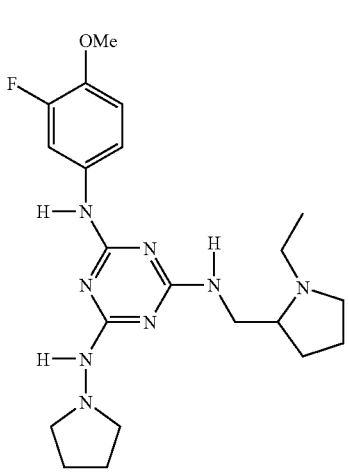 | N-(1-Ethyl-pyrrolidin-2-ylmethyl)-N'-(3-fluoro-4-methoxy-phenyl)-N''-pyrrolidin-1-yl-[1,3,5]triazine-2,4,6-triamine |

TABLE 1B-continued
Representative Compounds of the Present Invention
| Cmpd | Structure | Name |
|---|---|---|
| B47 | 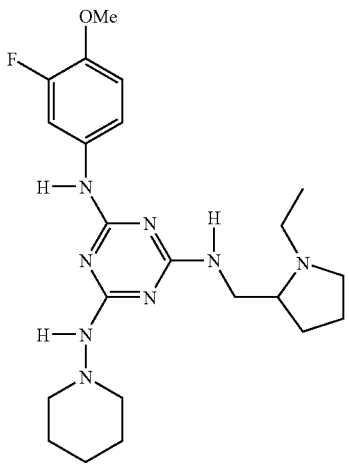 | N-(1-Ethyl-pyrrolidin-2-ylmethyl)-N'-(3-fluoro-4-methoxy-phenyl)-N''-piperidin-1-yl-[1,3,5]triazine-2,4,6-triamine |
| B48 | 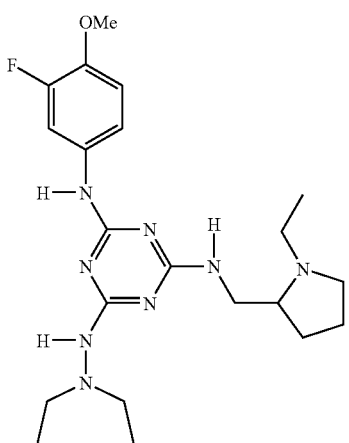 | N-Azepan-1-yl-N'-(1-ethyl-pyrrolidin-2-ylmethyl-N''-(3-fluoro-4-methoxy-phenyl)-[1,3,5]triazine-2,4,6-triamine |
| B49 | 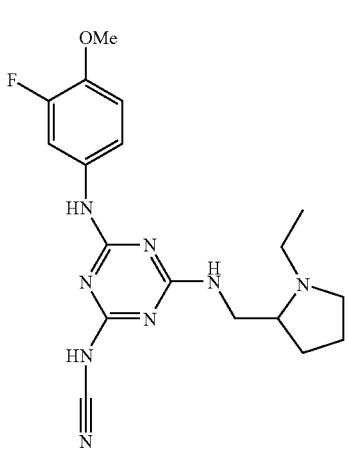 | 4-[(1-Ethyl-pyrrolidin-2-ylmethyl)-amino]-6-(3-fluoro-4-methoxy-phenylamino)-[1,3,5]triazine-2-yl-cyanamide |

TABLE 1B-continued

Representative Compounds of the Present Invention

| Cmpd | Structure | Name |
|---|---|---|
| B50 | 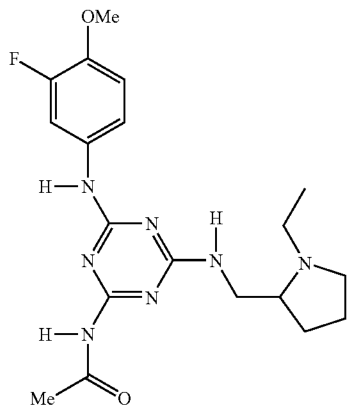 | N-[4-[(1-Ethyl-pyrrolidin-2-ylmethyl)-amino]-6-(3-fluoro-4-methoxy-phenylamino)-[1,3,5]-triazin-2-yl]-acetamide |
| B51 | 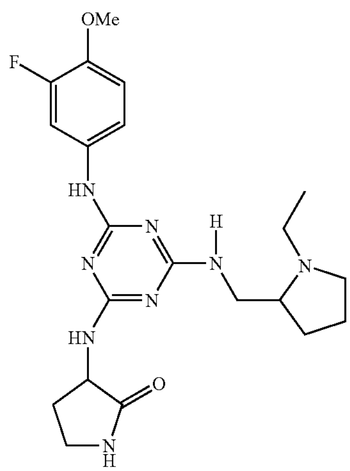 | 3-[4-[(1-Ethyl-pyrrolidin-2-ylmethyl)-amino]-6-(3-fluoro-4-methoxy-phenylamino)-[1,3,5]triazin-2-ylamino]-pyrrolidin-2-one |
| B52 | 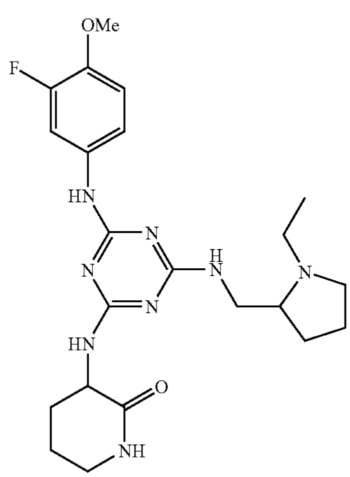 | 3-[4-[(1-Ethyl-pyrrolidin-2-ylmethyl)-amino]-6-(3-fluoro-4-methoxy-phenylamino)-[1,3,5]triazin-2-ylamino]-piperidin-2-one |

TABLE 1B-continued

Representative Compounds of the Present Invention

| Cmpd | Structure | Name |
|---|---|---|
| B53 | 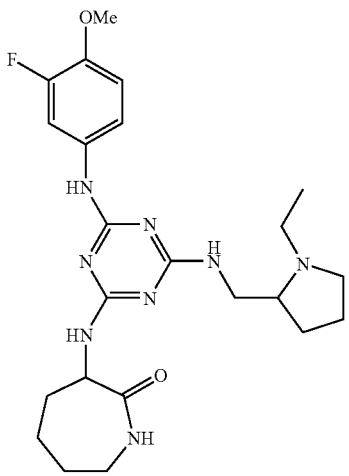 | 3-[4-[(1-Ethyl-pyrrolidin-2-ylmethyl)-amino]-6-(3-fluoro-4-methoxy-phenylamino)-[1,3,5]triazin-2-ylamino]-azepan-2-one |
| B54 | 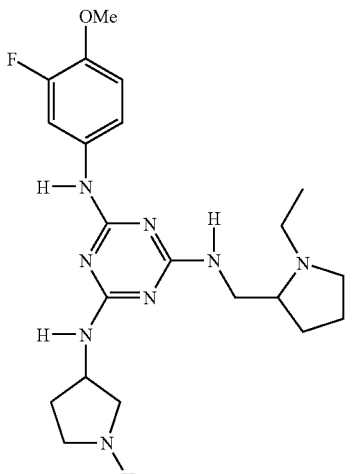 | N-(1-Ethyl-pyrrolidin-2-ylmethyl)-N'-(3-fluoro-4-methoxy-phenyl)-N''-pyrrolidin-3-yl-[1,3,5]triazine-2,4,6-triamine |
| B55 | 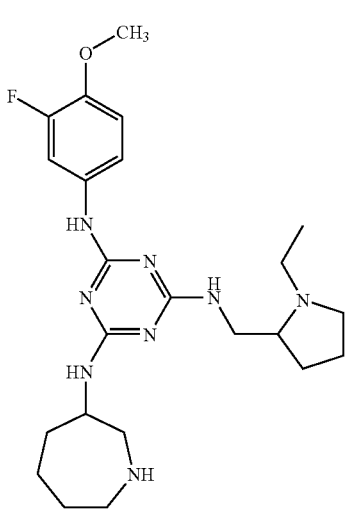 | N-Azepan-3-yl-N'-(1-ethyl-pyrrolidin-2-ylmethyl)-N''-(3-fluoro-4-methoxy-phenyl)-[1,3,5]triazine-2,4,6-triamine |

TABLE 1B-continued

Representative Compounds of the Present Invention

| Cmpd | Structure | Name |
|---|---|---|
| B56 | 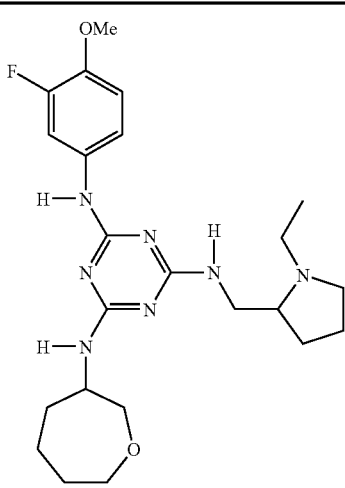 | N-(1-Ethyl-pyrrolidin-2-ylmethyl)-N'-(3-fluoro-4-methoxy-phenyl)-N''-oxepan-3-yl-[1,3,5]triazine-2,4,6-triamine |
| B57 | 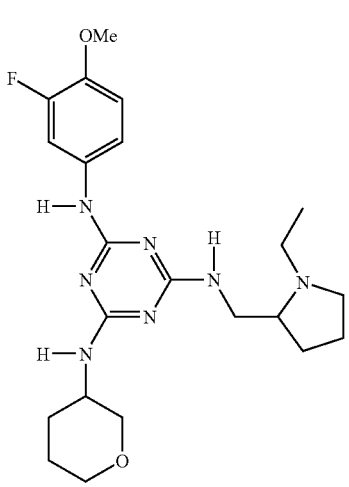 | N-(1-Ethyl-pyrrolidin-2-ylmethyl)-N'-(3-fluoro-4-methoxy-phenyl)-N''-(tetrahydropyran-3-yl)-[1,3,5]triazine-2,4,6-triamine |
| B58 | 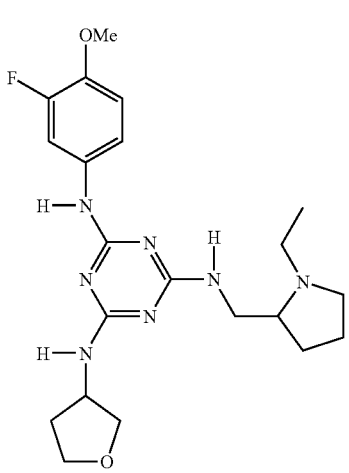 | N-(1-Ethyl-pyrrolidin-2-ylmethyl)-N'-(3-fluoro-4-methoxy-phenyl)-N''-(tetrahydro-furan-3-yl)-[1,3,5]-triazine-2,4,6-triamine |

TABLE 1B-continued

Representative Compounds of the Present Invention

| Cmpd | Structure | Name |
|---|---|---|
| B59 | 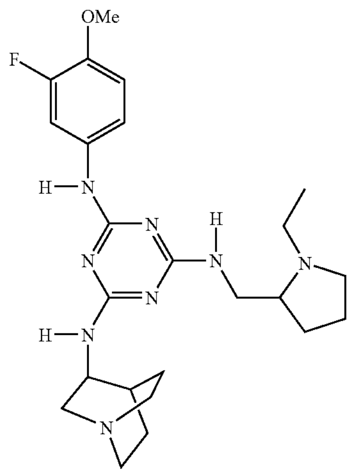 | N-(1-Aza-bicyclo[2.2.2]oct-3-yl)-N'-(1-ethyl-pyrrolidin-2-ylmethyl)-N''-(3-fluoro-4-methoxy-phenyl)-[1,3,5]triazine-2,4,6-triamine |
| B60 | 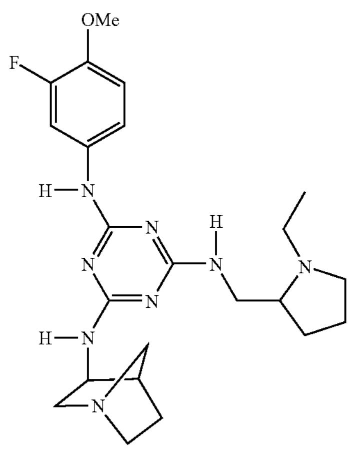 | N-(1-Aza-bicyclo[2.2.1]hept-3-yl)-N'-(1-ethyl-pyrrolidin-2-ylmethyl)-N''-(3-fluoro-4-methoxy-phenyl)-[1,3,5]triazine-2,4,6-triamine |
| B61 | 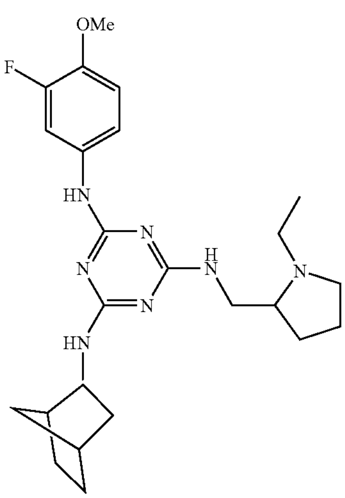 | N-Bicyclo[2.2.1]hept-2-yl-N'-(1-ethyl-pyrrolidin-2-ylmethyl)-N''-(3-fluoro-4-methoxy-phenyl)-[1,3,5]triazine-2,4,6-triamine |

TABLE 1B-continued
Representative Compounds of the Present Invention
| Cmpd | Structure | Name |
|---|---|---|
| B62 | 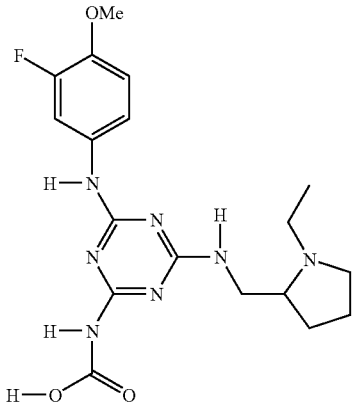 | [4-[(1-Ethyl-pyrrolidin-2-ylmethyl)-amino]-6-(3-fluoro-3-methoxy-phenylamino)-[1,3,5]triazin-2-yl]-carbamic acid |
| B63 | 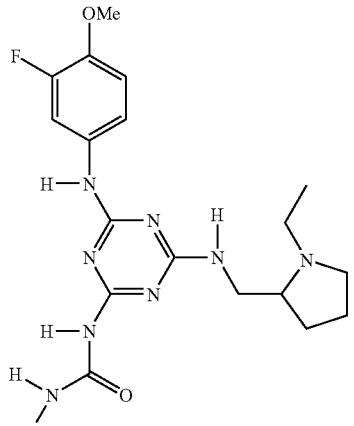 | [4-[(1-Ethyl-pyrrolidin-2-ylmethyl)-amino]-6-(3-fluoro-3-methoxy-phenylamino)-[1,3,5]triazin-2-yl]-urea |
| B64 | 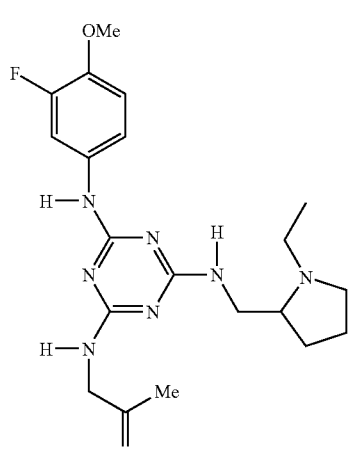 | [4-[(1-Ethyl-pyrrolidin-2-ylmethyl)-amino]-6-(3-fluoro-3-methoxy-phenylamino)-[1,3,5]triazin-2-yl]-propan-2-one |

TABLE 1B-continued
Representative Compounds of the Present Invention
| Cmpd | Structure | Name |
|---|---|---|
| B65 | 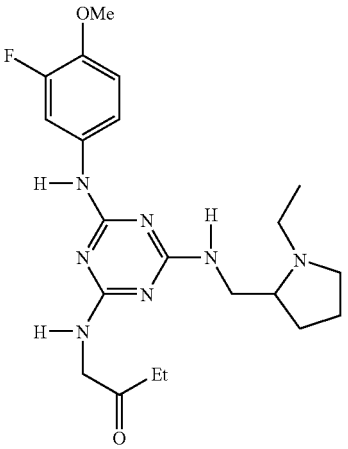 | [4-[(1-Ethyl-pyrrolidin-2-ylmethyl)-amino]-6-(3-fluoro-4-methoxy-phenylamino)-[1,3,5]triazin-2-yl]-pentan-2-one |
| B66 | 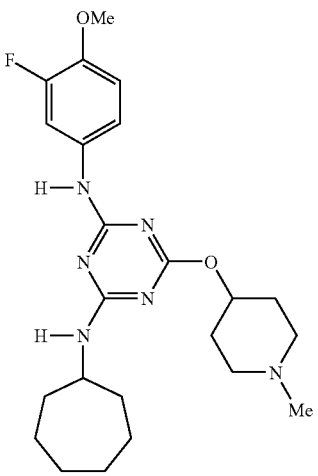 | N-Cycloheptyl-N'-(3-fluoro-4-methoxy-phenyl)-6-(1-methyl-piperidin-4-yloxy)-[1,3,5]triazine-2,4-diamine |
| B67 | 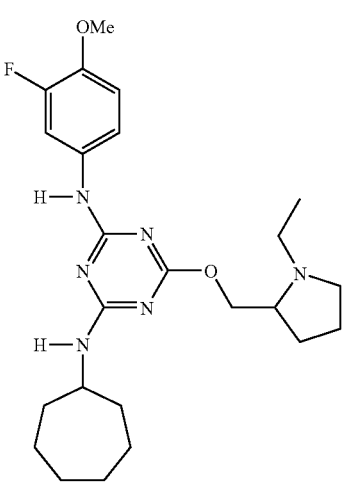 | N-Cycloheptyl-6-(1-ethyl-pyrrolidin-2-ylmethoxy)-N'-(3-fluoro-4-methoxy-phenyl)-[1,3,5]triazine-2,4-diamine |

TABLE 1B-continued

Representative Compounds of the Present Invention

| Cmpd | Structure | Name |
|---|---|---|
| B68 | 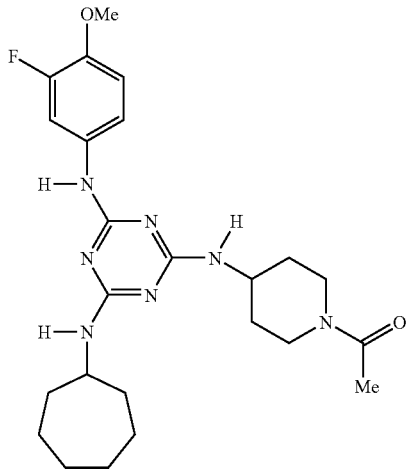 | 1-{4-{[4-Cycloheptylamino-6-(3-fluoro-4-methoxy-phenylamino)-[1,3,5]triazin-2-yl]-methyl-amino}-piperidin-1-yl}-ethanone |
| B69 | 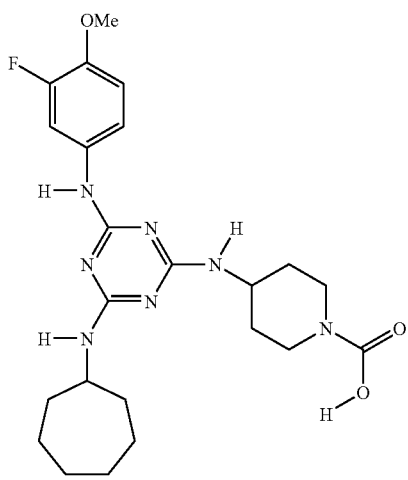 | 4-[4-Cycloheptylamino-6-(3-fluoro-4-methoxy-phenylamino)-[1,3,5]triazin-2-ylamino]-piperidine-1-carboxylic acid |
| B70 | 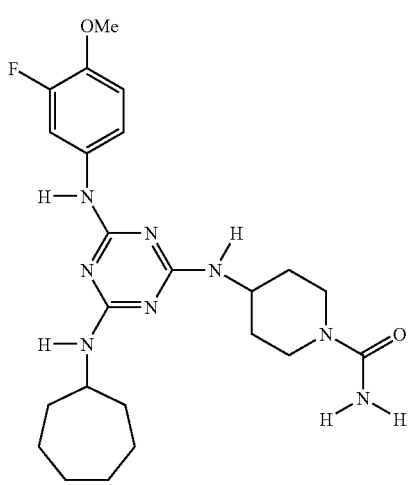 | 4-[4-Cycloheptylamino-6-(3-fluoro-4-methoxy-phenylamino)-[1,3,5]triazin-2-ylamino]-piperidine-1-carboxylic acid amide |

TABLE 1B-continued
Representative Compounds of the Present Invention
| Cmpd | Structure | Name |
|---|---|---|
| B71 | 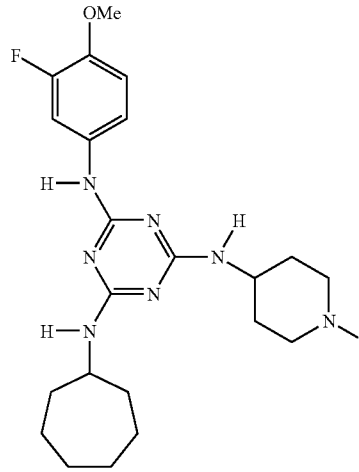 | 4-[4-Cycloheptylamino-6-(3-fluoro-4-methoxy-phenylamino)-[1,3,5]triazin-2-ylamino]-piperidin-1-ol |
| B72 | 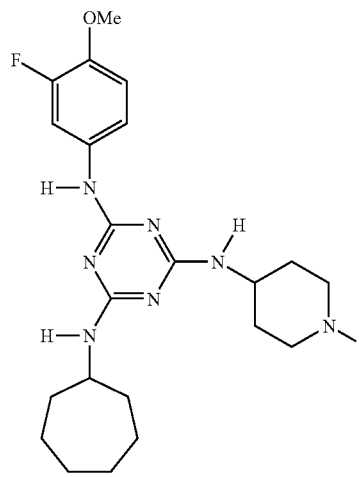 | N-Cycloheptyl-N'-(3-fluoro-4-methoxy-phenyl)-N''-piperidin-4-yl-[1,3,5]triazine-2,4,6-triazine |
| B73 | 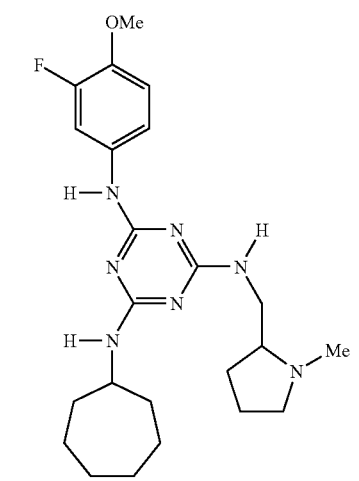 | N-Cycloheptyl-N'-(3-fluoro-4-methoxy-phenyl)-N''-(1-methyl-pyrrolidin-2-ylmethyl)-[1,3,5]triazine-2,4,6-triazine |

TABLE 1B-continued

Representative Compounds of the Present Invention

| Cmpd | Structure | Name |
|---|---|---|
| B74 | 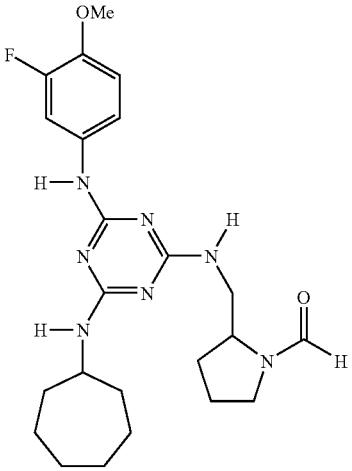 | 2-{[4-Cycloheptylamino-6-(3-fluoro-4-methoxy-phenylamino)-[1,3,5]triazin-2-ylamino]-methyl}-pyrrolidine-1-carbaldehyde |
| B75 | 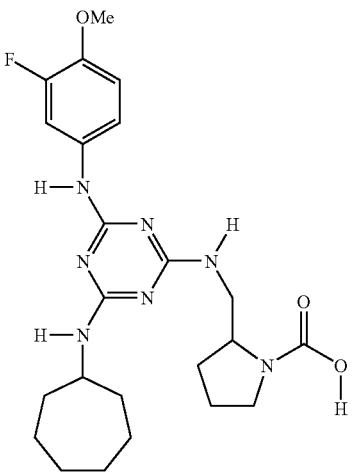 | 2-{[4-Cycloheptylamino-6-(3-fluoro-4-methoxy-phenylamino)-[1,3,5]triazin-2-ylamino]-methyl}-pyrrolidine-1-carboxylic acid |
| B76 | 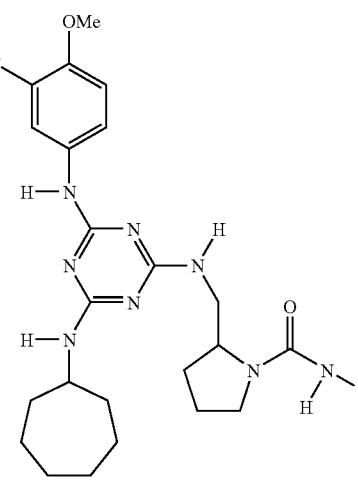 | 2-{[4-Cycloheptylamino-6-(3-fluoro-4-methoxy-phenylamino)-[1,3,5]triazin-2-ylamino]-methyl}-pyrrolidine-1-carboxylic acid amide |

TABLE 1B-continued
Representative Compounds of the Present Invention
| Cmpd | Structure | Name |
|---|---|---|
| B77 | 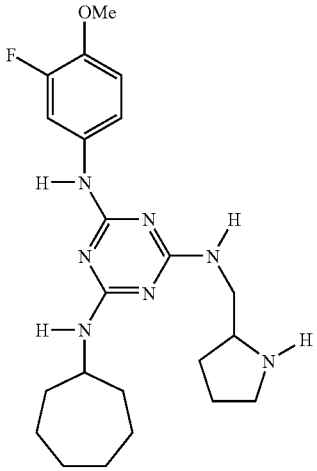 | N-Cycloheptyl-N'-(3-fluoro-4-methoxy-phenyl)-N''-pyrrolidin-2-ylmethyl-[1,3,5]triazine-2,4,6-triamine |
| B78 | 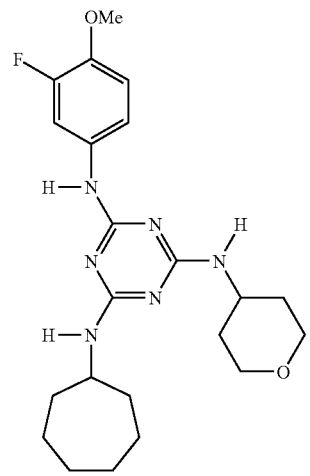 | N-Cycloheptyl-N'-(3-fluoro-4-methoxy-phenyl)-N''-(tetrahydro-pyran-4-yl)-[1,3,5]triazine-2,4,6-triamine |
| B79 | 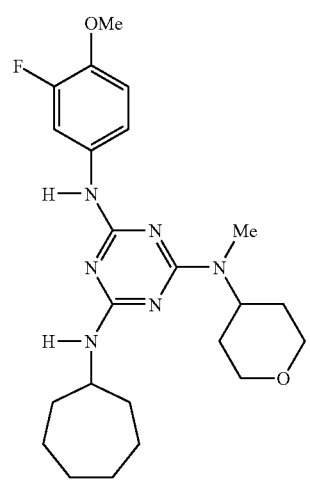 | N-Cycloheptyl-N'-(3-fluoro-4-methoxy-phenyl)-N''-methyl-(tetrahydro-pyran-4-yl)-[1,3,5]triazine-2,4,6-triamine |

TABLE 1B-continued

Representative Compounds of the Present Invention

| Cmpd | Structure | Name |
| --- | --- | --- |
| B80 | 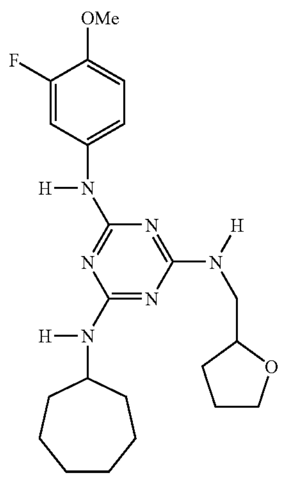 | N-Cycloheptyl-N'-(3-fluoro-4-methoxy-phenyl)-N''-tetrahydro-furan-2-ylmethyl)-[1,3,5]triazine-2,4,6-triamine |
| B81 | 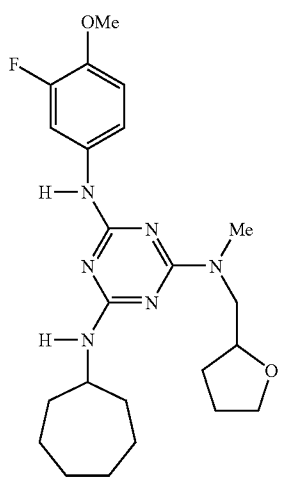 | N-Cycloheptyl-N'-(3-fluoro-4-methoxy-phenyl)-N''-methyl-N''-(tetrahydro-furan-2-ylmethyl)-[1,3,5]triazine-2,4,6-triamine |
| B82 | 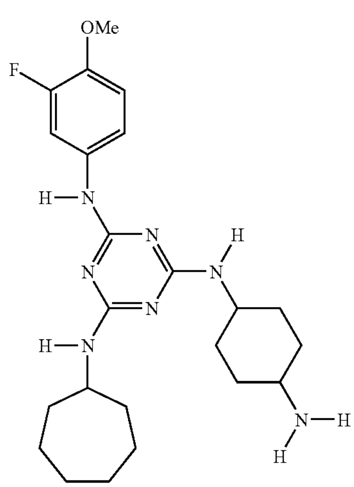 | N-(4-Amino-cyclohexyl)-N'-cycloheptyl-N''-(3-fluoro-4-methoxy-phenyl)-[1,3,5]triazine-2,4,6-triamine |

TABLE 1B-continued
Representative Compounds of the Present Invention
| Cmpd | Structure | Name |
|---|---|---|
| B83 | 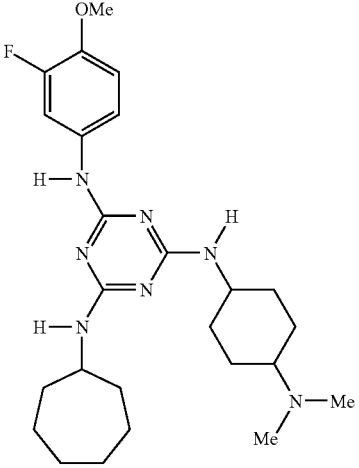 | N-Cycloheptyl-N'-(4-dimethylamino-cyclohexyl)-N''-(3-fluoro-4-methoxy-phenyl)-[1,3,5]triazine-2,4,6-triamine |
| B84 | 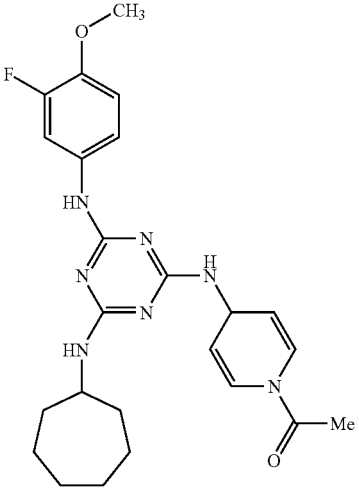 | 1-{4-[4-Cycloheptylamino-6-(3-fluoro-4-methoxy-phenylamino)-[1,3,5]triazin-2-ylamino]-4H-pyridin-1-yl}-ethanone |
| B85 | 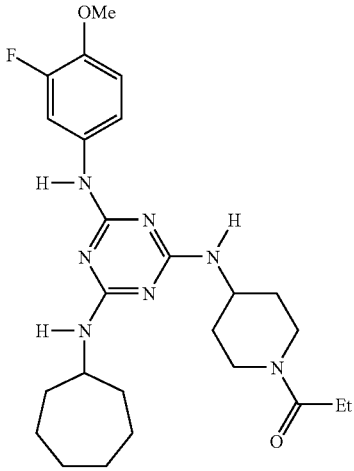 | 1-{4-[4-cycloheptylamino-6-(3-fluoro-4-methoxy-phenylamino-[1,3,5]triazin-2-ylamino]-piperidin-1-yl}-butan-1-one |

TABLE 1B-continued

Representative Compounds of the Present Invention

| Cmpd | Structure | Name |
|---|---|---|
| B86 | 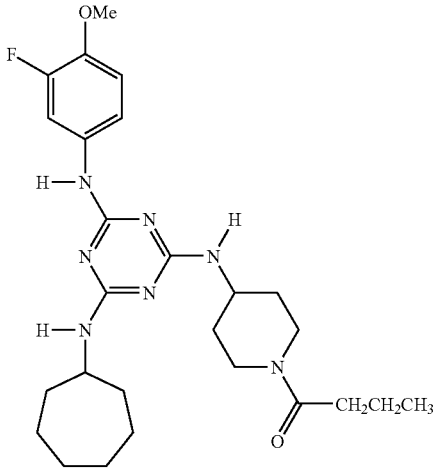 | 1-{4-[4-cycloheptylamino-6-(3-fluoro-4-methoxy-phenylamino-[1,3,5]triazin-2-ylamino]-piperidin-1-yl}-pentan-1-one |
| B87 | 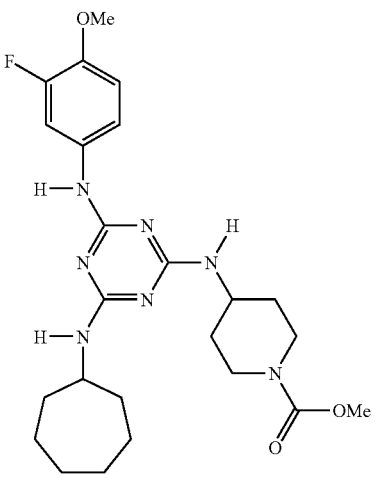 | 4-[4-Cycloheptylamino-6-(3-fluoro-4-methoxy-phenylamino-[1,3,5]triazin-2-ylamino]-piperidine-1-carboxylic acid methyl ester |
| B88 | 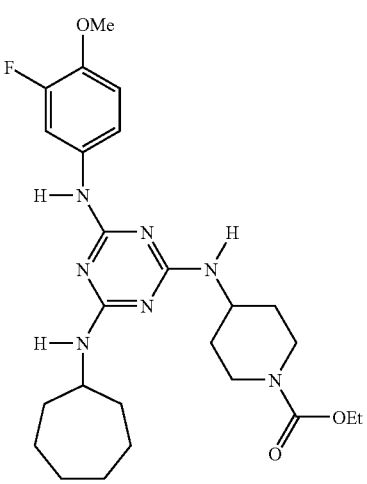 | 4-[4-Cycloheptylamino-6-(3-fluoro-4-methoxy-phenylamino)-[1,3,5]triazin-2-ylamino]-piperidine-1-carboxylic acid ethyl ester |

TABLE 1B-continued

Representative Compounds of the Present Invention

| Cmpd | Structure | Name |
|---|---|---|
| B89 | 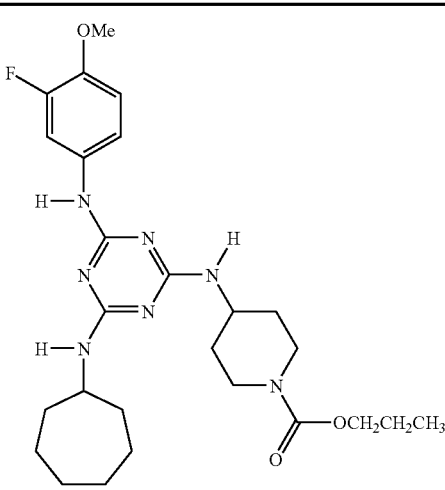 | 4-[4-Cycloheptylamino-6-(3-fluoro-4-methoxy-phenylamino)-[1,3,5]triazin-2-ylamino]-piperidine-1-carboxylic acid propyl ester |
| B90 | 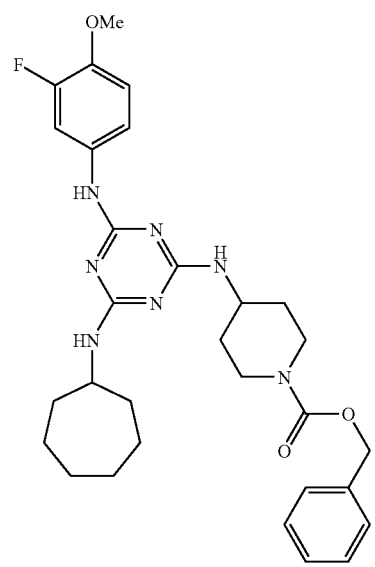 | 4-[4-Cycloheptylamino-6-(3-fluoro-4-methoxy-phenylamino)-[1,3,5]triazin-2-ylamino]-piperidine-1-carboxylic acid benzyl ester |
| B91 | 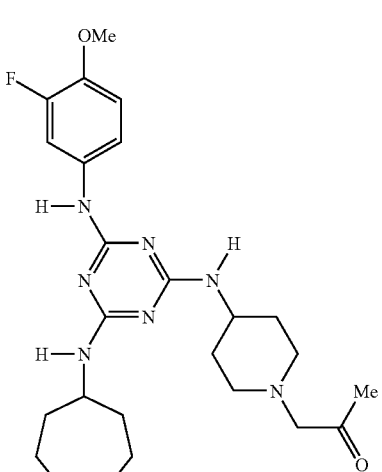 | 1-{4-[4-Cycloheptylamino-6-(3-fluoro-4-methoxy-phenylamino)-[1,3,5]triazin-2-ylamino]-piperidin-1-yl}-propan-2-one |

TABLE 1B-continued

Representative Compounds of the Present Invention

| Cmpd | Structure | Name |
|---|---|---|
| B92 | 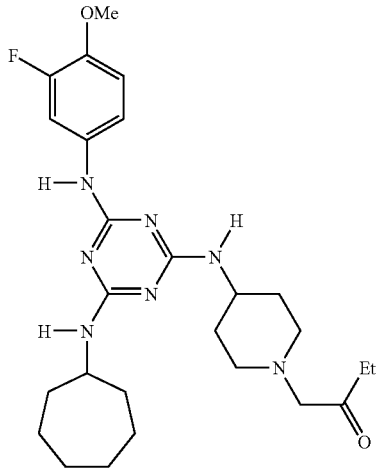 | 1-{4-[4-Cycloheptylamino-6-(3-fluoro-4-methoxy-phenylamino)-[1,3,5]triazin-2-ylamino]-piperidin-1-yl}-pentan-2-one |
| B93 | 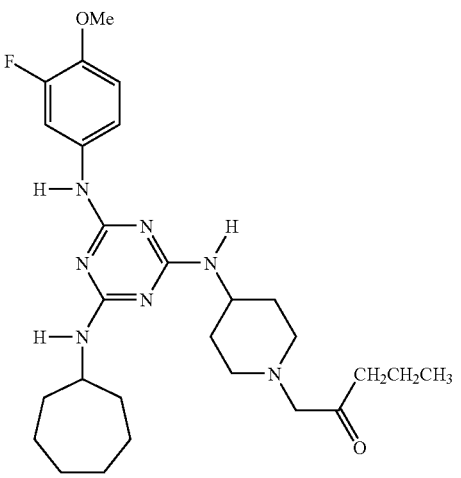 | 1-{4-[4-Cycloheptylamino-6-(3-fluoro-4-methoxy-phenylamino-[1,3,5]triazin-2-ylamino]-piperidin-1-yl}-hexan-2-one |
| B94 | 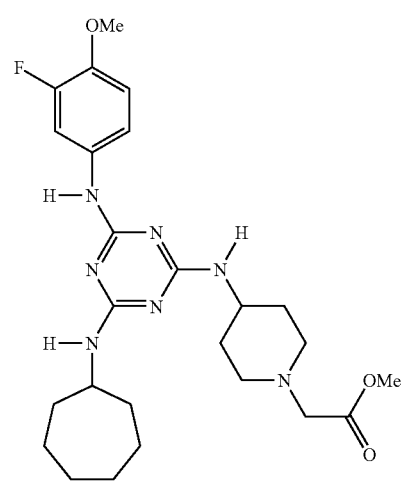 | {4-[4-Cycloheptylamino-6-(3-fluoro-4-methoxy-phenylamino)-[1,3,5]triazin-2-ylamino]-piperidin-1-yl}-acetic acid methyl ester |

TABLE 1B-continued

Representative Compounds of the Present Invention

| Cmpd | Structure | Name |
|---|---|---|
| B95 | 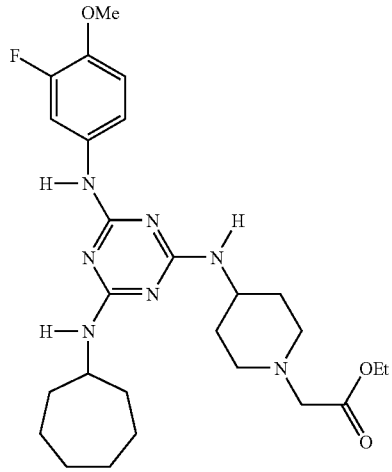 | {4-[4-Cycloheptylamino-6-(3-fluoro-4-methoxy-phenylamino)-[1,3,5]triazin-2-ylamino]-piperidin-1-yl}-acetic acid ethyl ester |
| B96 | 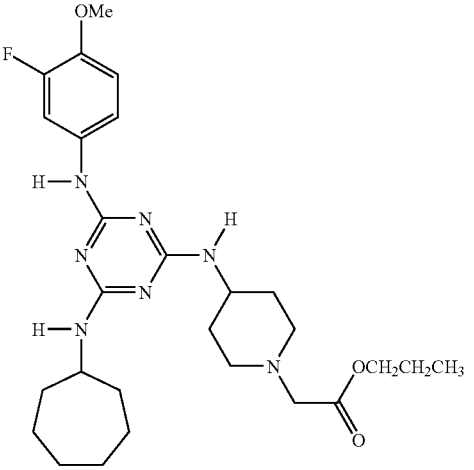 | {4-[4-Cycloheptylamino-6-(3-fluoro-4-methoxy-phenylamino)-[1,3,5]triazin-2-ylamino]-piperidin-1-yl}-acetic acid propyl ester |
| B97 | 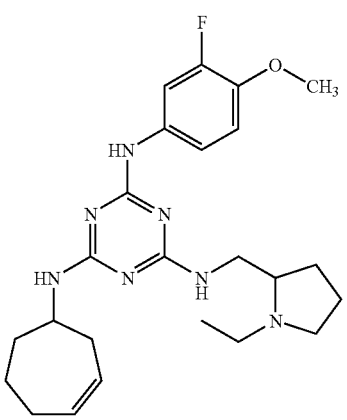 | N-Cyclohept-3-enyl-N'-(1-ethyl-pyrrolidin-2-ylmethyl)-N''-(3-fluoro-4-methoxy-phenyl)-[1,3,5]triazine-2,4,6-triamine |

TABLE 1B-continued

Representative Compounds of the Present Invention

| Cmpd | Structure | Name |
|---|---|---|
| B98 | 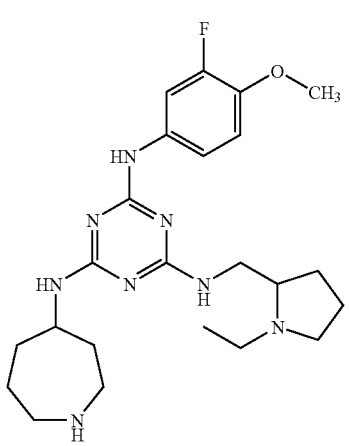 | N-Azepan-4-yl-N'-(1-ethyl-pyrrolidin-2-ylmethyl)-N''-(3-fluoro-4-methoxy-phenyl)-[1,3,5]triazine-2,4,6-triamine |
| B99 | 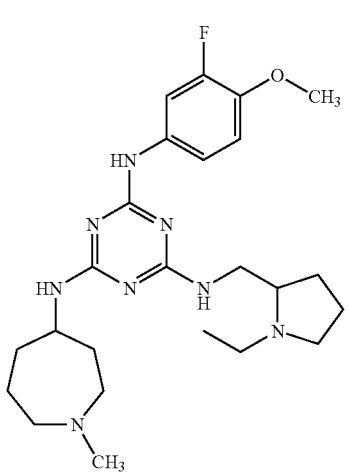 | N-(1-Ethyl-pyrrolidin-2-ylmethyl)-N'-(3-fluoro-4-methoxy-phenyl)-N''-(1-methyl-azepan-4-yl)-[1,3,5]triazine-2,4,6-triamine |
| B100 | 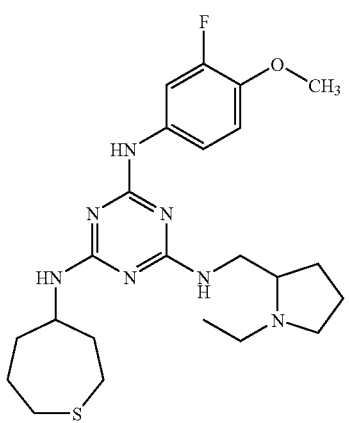 | N-(1-Ethyl-pyrrolidin-2-ylmethyl)-N'-(3-fluoro-4-methoxy-phenyl)-N''-thiepan-4-yl-[1,3,5]triazine-2,4,6-triamine |

TABLE 1B-continued

Representative Compounds of the Present Invention

| Cmpd | Structure | Name |
| --- | --- | --- |
| B101 | 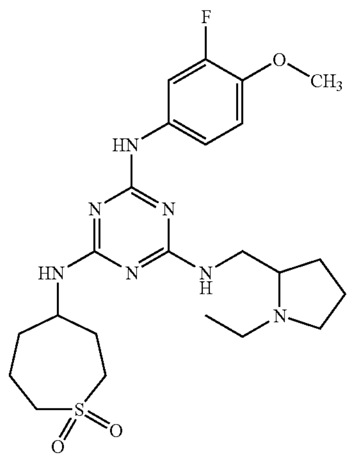 | N-(1,1-Dioxo-1lambda*6*-thiepan-4-yl)-N'-(1-ethyl-pyrrolidin-2-ylmethyl)-N''-(3-fluoro-4-methoxy-phenyl)-[1,3,5]triazine-2,4,6-triamine |
| B102 | 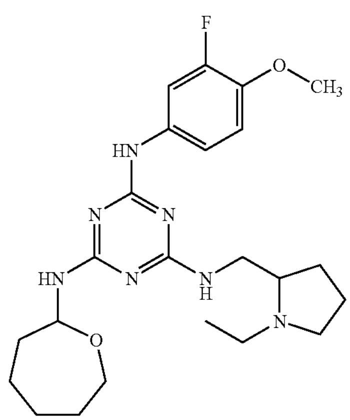 | N-(1-Ethyl-pyrrolidin-2-ylmethyl)-N'-(3-fluoro-4-methoxy-phenyl)-N''-oxepan-2-yl-[1,3,5]triazine-2,4,6-triamine |
| B103 | 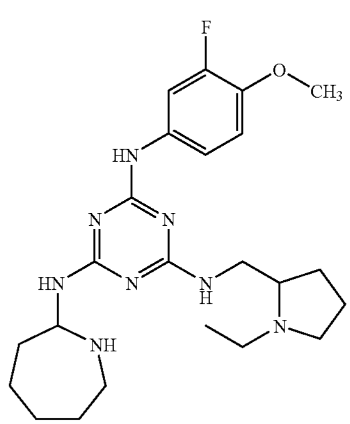 | N-Azepan-2-yl-N'-(1-ethyl-pyrrolidin-2-ylmethyl)-N''-(3-fluoro-4-methoxy-phenyl)-[1,3,5]triazine-2,4,6-triamine |

TABLE 1B-continued

Representative Compounds of the Present Invention

| Cmpd | Structure | Name |
|---|---|---|
| B104 | 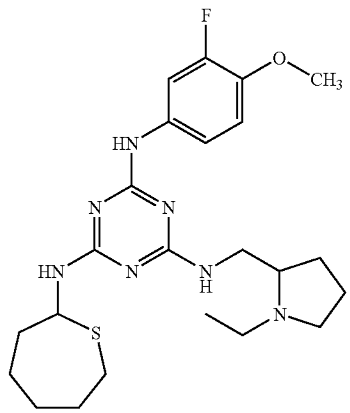 | N-(1-Ethyl-pyrrolidin-2-ylmethyl)-N'-(3-fluoro-4-methoxy-phenyl)-N''-thiepan-2-yl-[1,3,5]triazine-2,4,6-triamine |
| B105 | 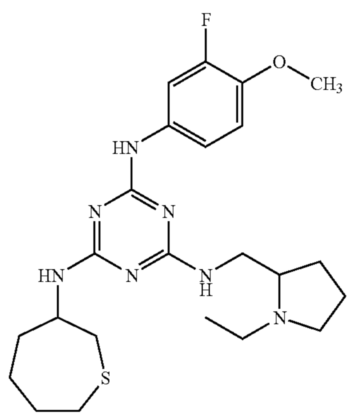 | N-(1-Ethyl-pyrrolidin-2-ylmethyl)-N'-(3-fluoro-4-methoxy-phenyl)-N''-thiepan-3-yl-[1,3,5]triazine-2,4,6-triamine |
| B106 | 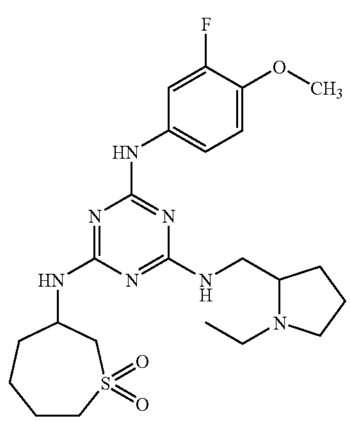 | N-(1,1-Dioxo-1lambda*6*-thiepan-3-yl)-N'-(1-ethyl-pyrrolidin-2-ylmethyl)-N''-(3-fluoro-4-methoxy-phenyl)-[1,3,5]triazine-2,4,6-triamine |

TABLE 1B-continued

Representative Compounds of the Present Invention

| Cmpd | Structure | Name |
| --- | --- | --- |
| B107 | 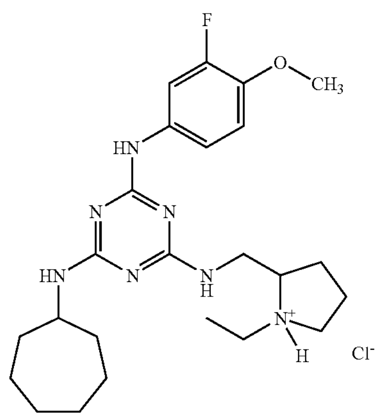 | 2-{[4-Cycloheptylamino-6-(3-fluoro-4-methoxy-phenylamino)-[1,3,5]triazin-2-ylamino]-methyl}-1-ethyl-pyrrolidinium; chloride |
| B108 | 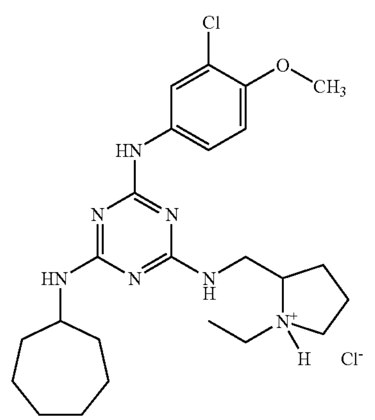 | 2-{[4-(3-Chloro-4-methoxy-phenylamino-6-cycloheptylamino-[1,3,5]triazin-2-ylamino]-methyl}-1-ethyl-pyrrolidinium; chloride |
| B109 | 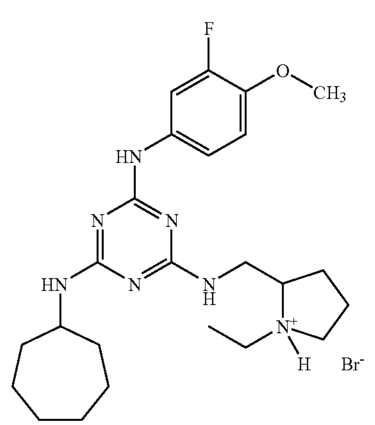 | 2-{[4-Cycloheptylamino-6-(3-fluoro-4-methoxy-phenylamino)-[1,3,5]triazin-2-ylamino]-methyl}-1-ethyl-pyrrolidinium; bromide |

TABLE 1B-continued

Representative Compounds of the Present Invention

| Cmpd | Structure | Name |
|------|-----------|------|
| B110 | 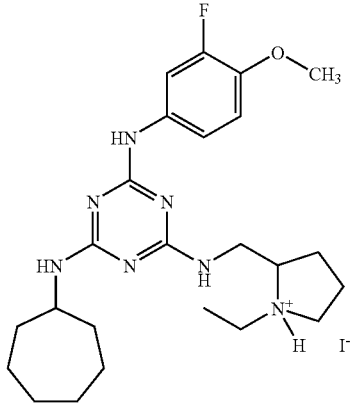 | 2-{[4-Cycloheptylamino-6-(3-fluoro-4-methoxy-phenylamino)-[1,3,5]triazin-2-ylamino]-methyl}-1-ethyl-1-methyl-pyrrolidinium; iodide |
| B111 | 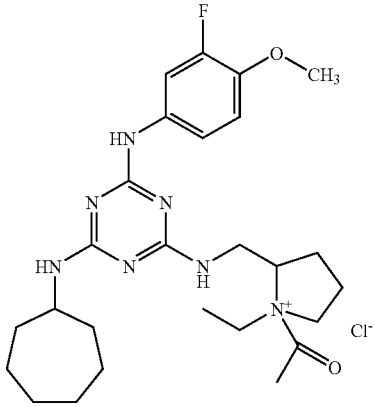 | 1-Acetyl-2-{[4-cycloheptylamino-6-(3-fluoro-4-methoxy-phenylamino)-[1,3,5]triazin-2-ylamino]-methyl}-1-ethyl-pyrrolidinium; chloride |
| B112 | 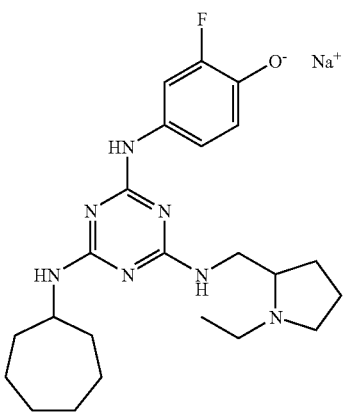 | Sodium; 4-{4-cycloheptylamino-6-[(1-ethyl-pyrrolidin-2-ylmethyl)-amino]-[1,3,5]triazin-2-ylamino}-2-fluoro-phenolate |

TABLE 1B-continued

Representative Compounds of the Present Invention

| Cmpd | Structure | Name |
|---|---|---|
| B113 | 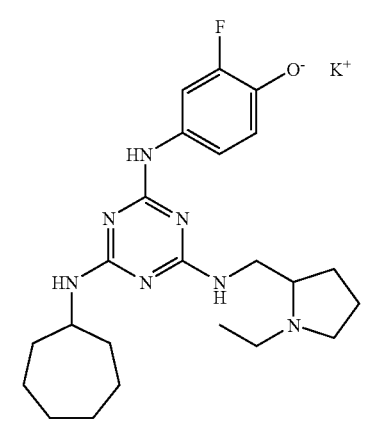 | Potassium; 4-{4-cycloheptylamino-6-[(1-ethyl-pyrrolidin-2-ylmethyl)-amino]-[1,3,5]triazin-2-ylamino}-2-fluoro-phenolate |
| B114 | 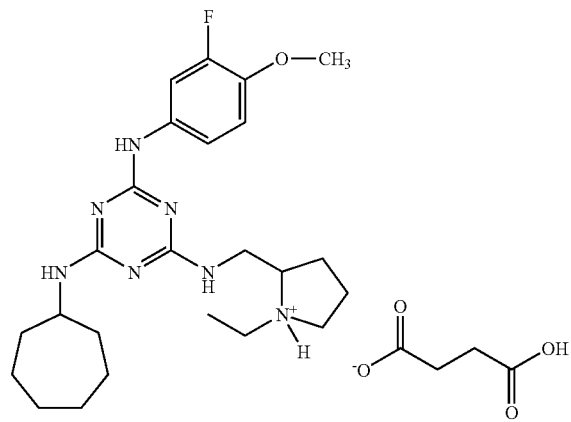 | 3-Carboxy-propionate2-{[4-cycloheptylamino-6-(3-fluoro-4-methoxy-phenylamino)-[1,3,5]triazin-2-ylamino]-methyl}-1-ethyl-pyrrolidinium; |
| B115 | 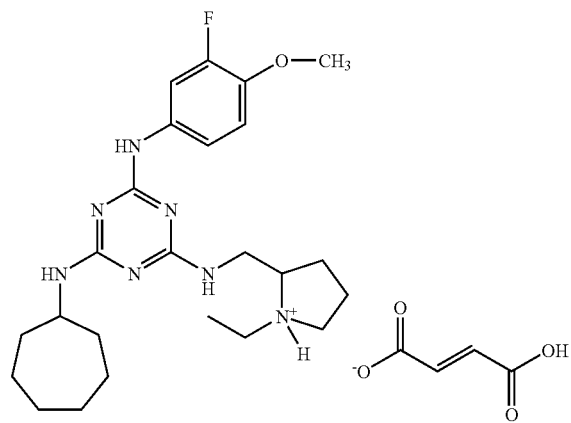 | 3-Carboxy-acrylate2-{[4-cycloheptylamino-6-(3-fluoro-4-methoxy-phenylamino)-[1,3,5]triazin-2-ylamino]-methyl}-1-ethyl-pyrrolidinium; |

TABLE 1B-continued
Representative Compounds of the Present Invention
| Cmpd | Structure | Name |
|---|---|---|
| B116 | 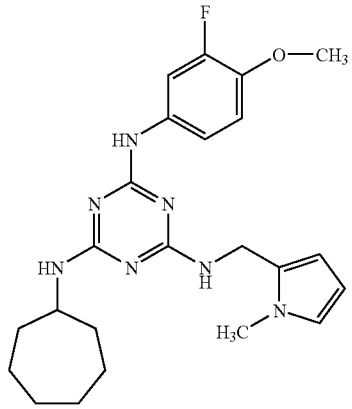 | N-Cycloheptyl-N'-(3-fluoro-4-methoxy-phenyl)-N''-(1-methyl-1H-pyrrol-2-ylmethyl)-[1,3,5]triazine-2,4,6-triamine |
| B117 | 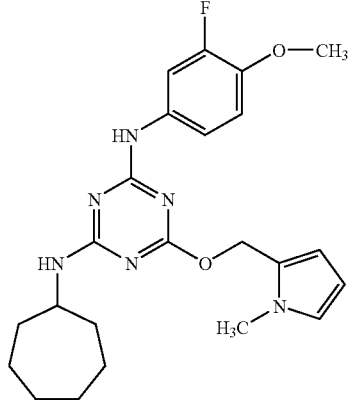 | N-Cycloheptyl-N'-(3-fluoro-4-methoxy-phenyl)-6-(1-methyl-1H-pyrrol-2-ylmethyl)-[1,3,5]triazine-2,4-diamine |
| B118 | 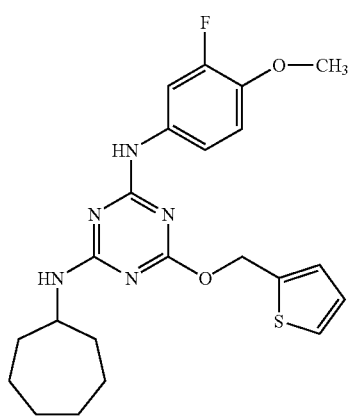 | N-Cycloheptyl-N'-(3-fluoro-4-methoxy-phenyl)-6-(thiophen-2-ylmethoxy)-[1,3,5]triazine-2,4-diamine |

TABLE 1B-continued
Representative Compounds of the Present Invention
| Cmpd | Structure | Name |
|---|---|---|
| B119 | 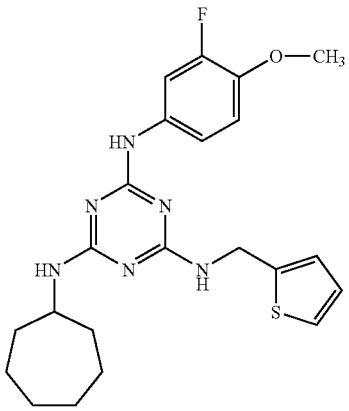 | N-Cycloheptyl-N'-(3-fluoro-4-methoxy-phenyl)-N''-thiophen-2-ylmethyl-[1,3,5]triazine-2,4,6-triamine |
| B120 | 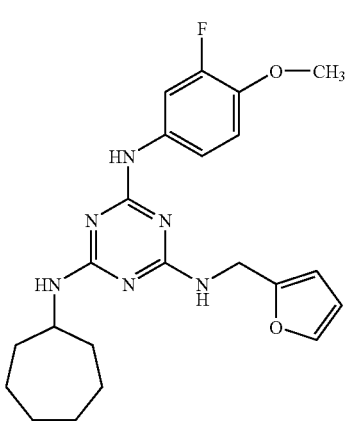 | N-Cycloheptyl-N'-(3-fluoro-4-methoxy-phenyl)-N''-furan-2-ylmethyl-[1,3,5]triazine-2,4,6-triamine |
| B121 | 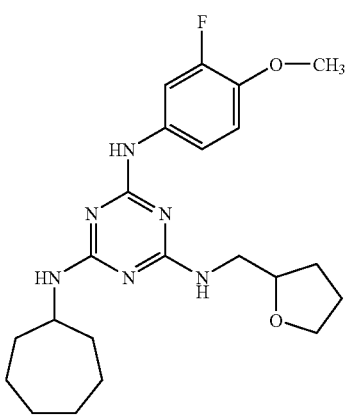 | N-Cycloheptyl-N'-(3-fluoro-4-methoxy-phenyl)-N''-(tetrahydro-furan-2-ylmethyl)-[1,3,5]triazine-2,4,6-triamine |

TABLE 1B-continued

Representative Compounds of the Present Invention

| Cmpd | Structure | Name |
|---|---|---|
| B122 | 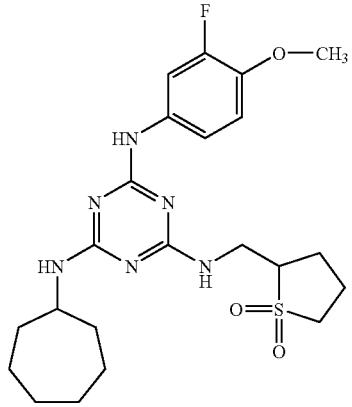 | N-Cycloheptyl-N'-(1,1-dioxo-tetrahydro-1lambda*6*-thiophen-2-ylmethyl)-N''-(3-fluoro-4-methoxy-phenyl)-[1,3,5]triazine-2,4,6-triamine |
| B123 | 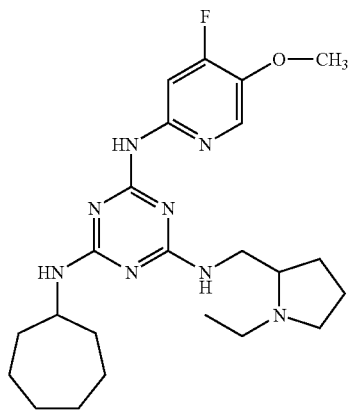 | N-Cycloheptyl-N'-(1-ethyl-pyrrolidin-2-ylmethyl)-N''-(5-fluoro-6-methoxy-pyridin-3-yl)-[1,3,5]triazine-2,4,6-triamine |
| B124 | 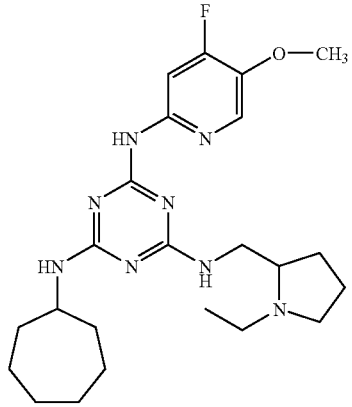 | N-Cycloheptyl-N'-(1-ethyl-pyrrolidin-2-ylmethyl)-N''-(4-fluoro-5-methoxy-pyridin-2-yl)-[1,3,5]triazine-2,4,6-triamine |

TABLE 1B-continued
Representative Compounds of the Present Invention
| Cmpd | Structure | Name |
|------|-----------|------|
| B125 | 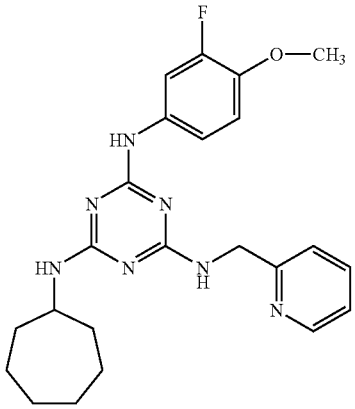 | N-Cycloheptyl-N'-(3-fluoro-4-methoxy-phenyl)-N''-pyridin-2-ylmethyl-[1,3,5]triazine-2,4,6-triamine |
| B126 | 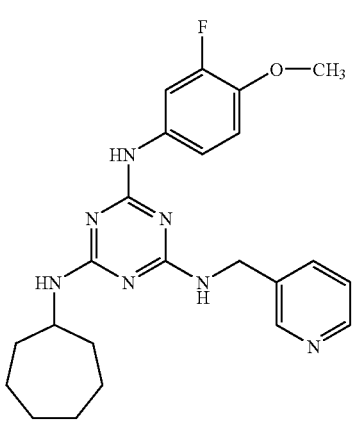 | N-Cycloheptyl-N'-(3-fluoro-4-methoxy-phenyl)-N''-pyridin-3-ylmethyl-[1,3,5]triazine-2,4,6-triamine |
| B127 | 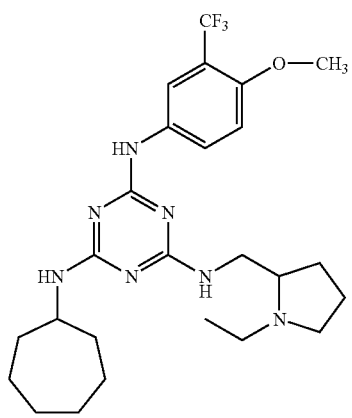 | N-Cycloheptyl-N'-(1-ethyl-pyrrolidin-2-ylmethyl)-N''-(4-methoxy-3-trifluoromethyl-phenyl)-[1,3,5]triazine-2,4,6-triamine |

TABLE 1B-continued

Representative Compounds of the Present Invention

| Cmpd | Structure | Name |
| --- | --- | --- |
| B128 | 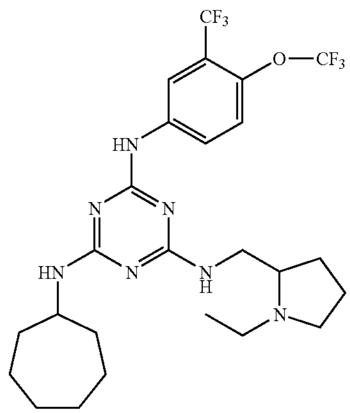 | N-Cycloheptyl-N'-(1-ethyl-pyrrolidin-2-ylmethyl)-N''-(4-trifluoromethoxy-3-trifluoromethyl-phenyl)-[1,3,5]triazine-2,4,6-triamine |
| B129 | 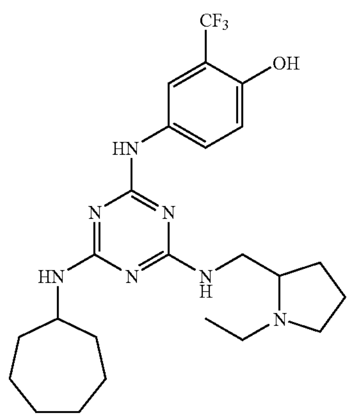 | 4-{4-Cycloheptylamino-6-[(1-ethyl-pyrrolidin-2-ylmethyl)-amino]-[1,3,5]triazin-2-ylamino}-2-trifluoromethyl-phenol |
| B130 | 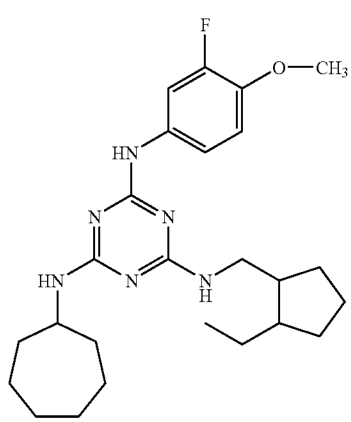 | N-Cycloheptyl-N'-(2-ethyl-cyclopentylmethyl)-N''-(3-fluoro-4-methoxy-phenyl)-[1,3,5]triazine-2,4,6-triamine |

TABLE 1B-continued

Representative Compounds of the Present Invention

| Cmpd | Structure | Name |
|---|---|---|
| B131 | 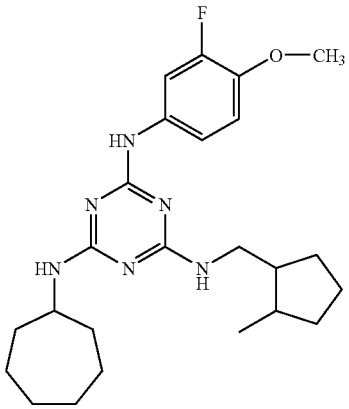 | N-Cycloheptyl-N'-(3-fluoro-4-methoxy-phenyl)-N''-(2-methyl-cyclopentylmethyl)-[1,3,5]triazine-2,4,6-triamine |
| B132 | 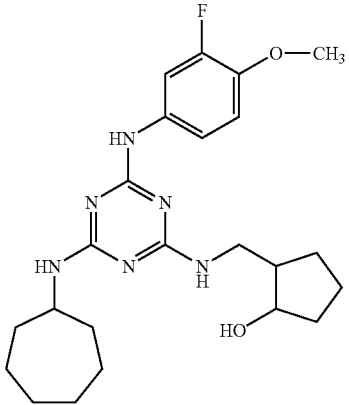 | 2-{[4-Cycloheptylamino-6-(3-fluoro-4-methoxy-phenylamino)-[1,3,5]triazin-2-ylamino]-methyl}-cyclopentanol |
| B133 | 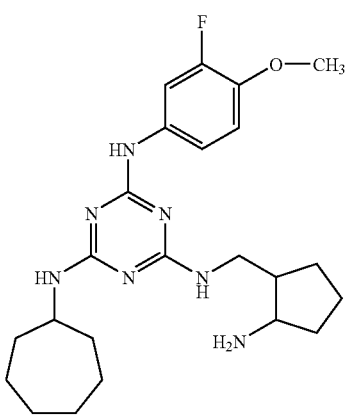 | N-(2-Amino-cyclopentylmethyl)-N'-cycloheptyl-N''-(3-fluoro-4-methoxy-phenyl-[1,3,5]triazine-2,4,6-triamine |

TABLE 1B-continued
Representative Compounds of the Present Invention
| Cmpd | Structure | Name |
|---|---|---|
| B134 | 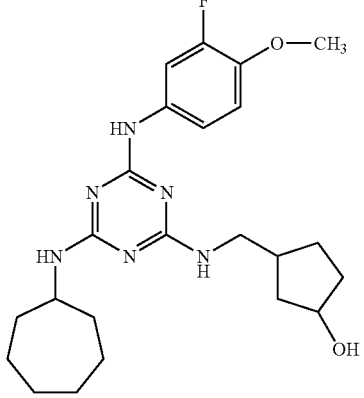 | 3-{[4-Cycloheptylamino-6-(3-fluoro-4-methoxy-phenylamino)-[1,3,5]triazin-2-ylamino]-methyl}-cyclopentanol |
| B135 | 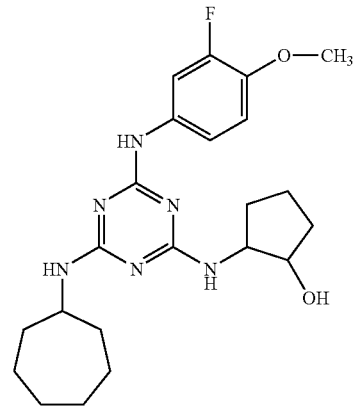 | 2-[4-Cycloheptylamino-6-(3-fluoro-4-methoxy-phenylamino)-[1,3,5]triazin-2-ylamino]-cyclopentanol |
| B136 | 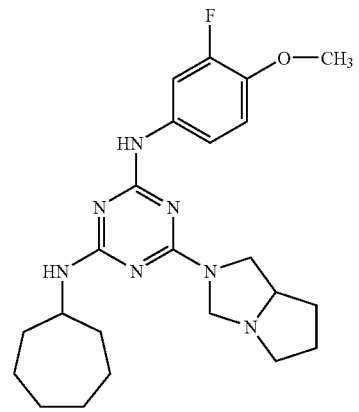 | N-Cycloheptyl-N'-(3-fluoro-4-methoxy-phenyl)-6-(tetrahydro-pyrrolo[1,2-c]imidazol-2-yl)-[1,3,5]triazine-2,4-diamine |

TABLE 1B-continued

Representative Compounds of the Present Invention

| Cmpd | Structure | Name |
| --- | --- | --- |
| B137 | 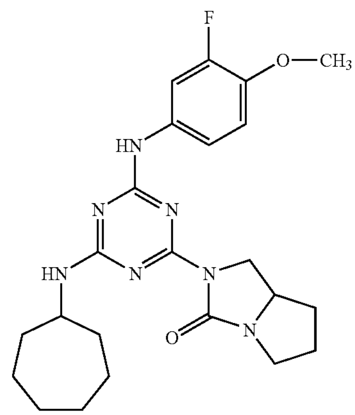 | 2-[4-Cycloheptylamino-6-(3-fluoro-4-methoxy-phenylamino)-[1,3,5]triazin-2-yl]-hexahydro-pyrrolo[1,2-c]imidazol-3-one |
| B138 | 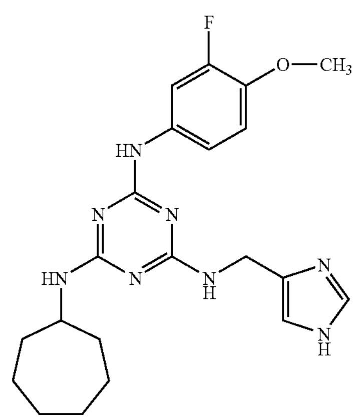 | N-Cycloheptyl-N'-(3-fluoro-4-methoxy-phenyl)-N''-(1H-imidazol-4-ylmethyl)-[1,3,5]triazine-2,4,6-triamine |
| B139 | 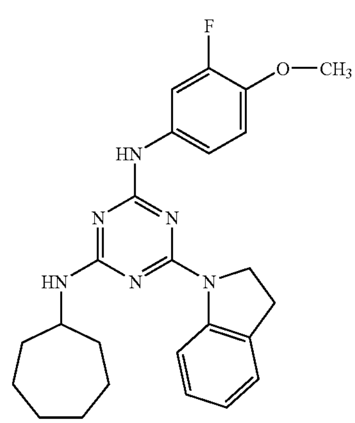 | N-Cycloheptyl-6-(2,3-dihydro-indol-1-yl)-N'-(3-fluoro-4-methoxy-phenyl)-[1,3,5]triazine-2,4,6-triamine |

TABLE 1B-continued

Representative Compounds of the Present Invention

| Cmpd | Structure | Name |
|---|---|---|
| B140 | 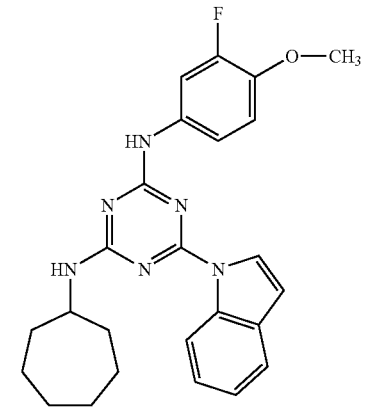 | N-Cycloheptyl-N'-(3-fluoro-4-methoxy-phenyl)-6-indol-1-yl-[1,3,5]triazine-2,4,6-triamine |
| B141 | 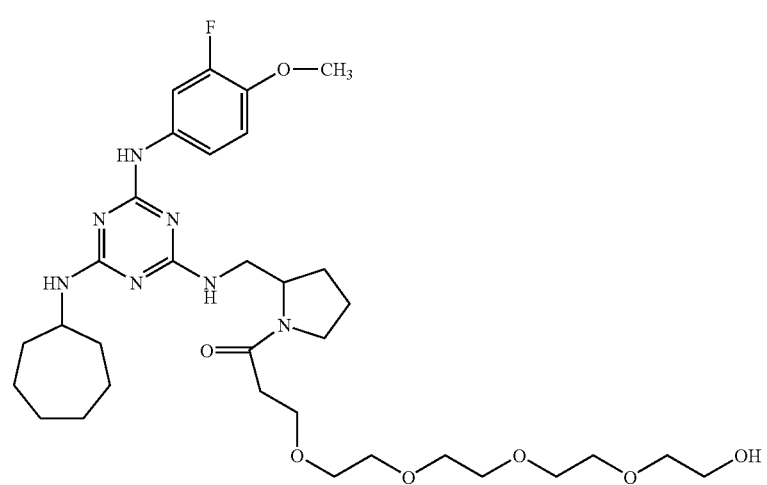 | 1-(2-{[4-Cycloheptylamino-6-(3-fluoro-4-methoxy-phenylamino)-[1,3,5]triazin-2-ylamino]-methyl}-pyrrolidin-1-yl)-3-(2-{2-[2-(2-hydroxy-ethoxy)-ethoxy]-ethoxy}-ethoxy)-propan-1-one |
| B142 | 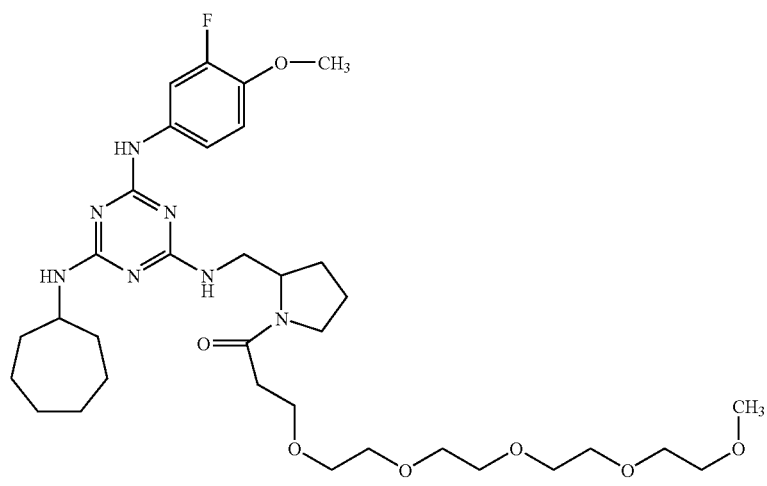 | 1-(2-{[4-Cycloheptylamino-6-(3-fluoro-4-methoxy-phenylamino)-[1,3,5]triazin-2-ylamino]-methyl}-pyrrolidin-1-yl)-3-(2-{2-[2-(2-methoxy-ethoxy)-ethoxy]-ethoxy}-ethoxy)-propan-1-one |

TABLE 1B-continued

Representative Compounds of the Present Invention

| Cmpd | Structure | Name |
| --- | --- | --- |
| B143 | 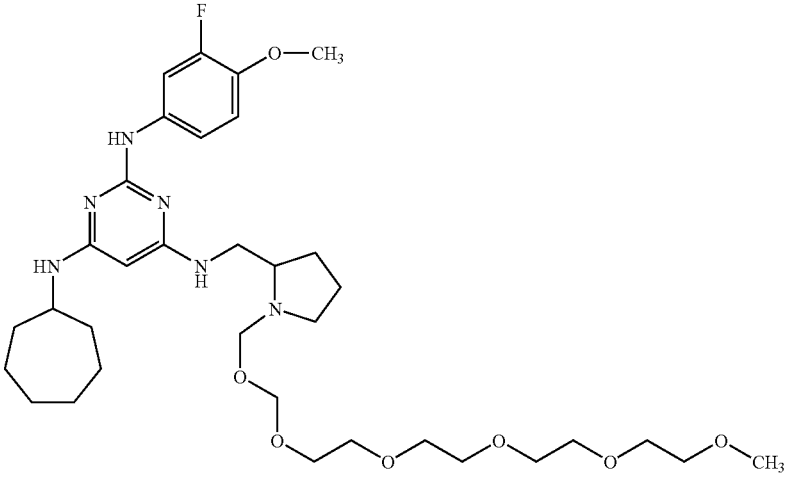 | N-Cycloheptyl-N'-(3-fluoro-4-methoxy-phenyl)-N''-[1-(2-{2-[2-(2-methoxy-ethoxy)-ethoxy]-ethoxy}-ethoxymethyl)-pyrrolidin-2-ylmethyl]-[1,3,5]triazine-2,4,6-triamine |
| B144 | 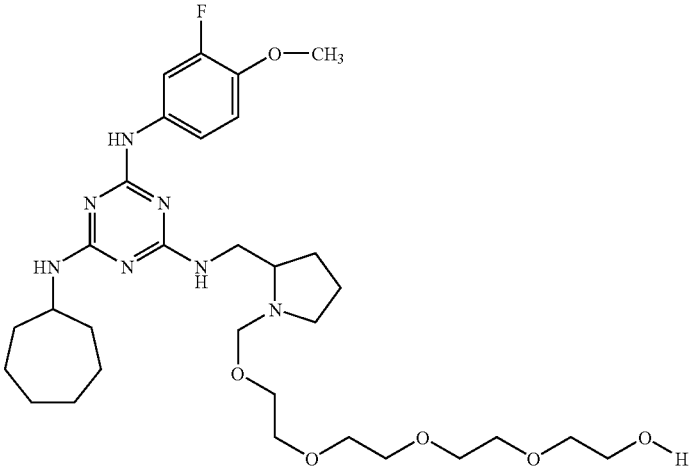 | 2-(2-{2-[2-(2-{[4-Cycloheptylamino-6-(3-fluoro-4-methoxy-phenylamino)-[1,3,5]triazin-2-ylamino]-methyl}-pyrrolidin-1-ylmethoxy)-ethoxy]-ethoxy}-ethoxy)-ethanol |
| B145 | 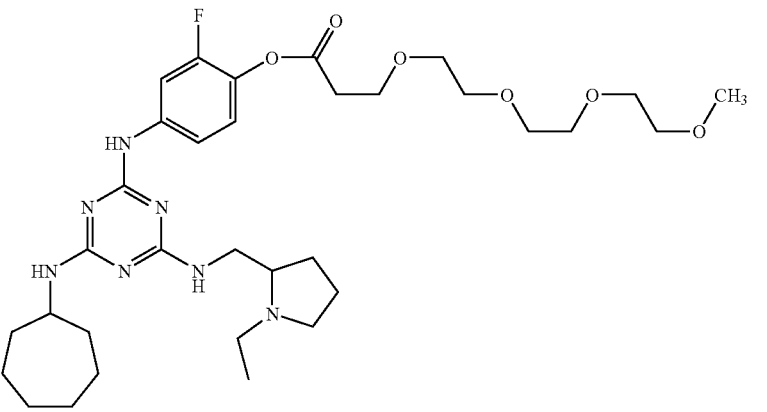 | 3-{2-[2-(2-Methoxy-ethoxy)-ethoxy]-ethoxy}-propionic acid 4-{4-cycloheptylamino-6-[(1-ethyl-pyrrolidin-2-ylmethyl)-amino]-[1,3,5]triazin-2-ylamino}-2-fluoro-phenyl ester |

TABLE 1B-continued

Representative Compounds of the Present Invention

| Cmpd | Structure | Name |
|---|---|---|
| B146 | 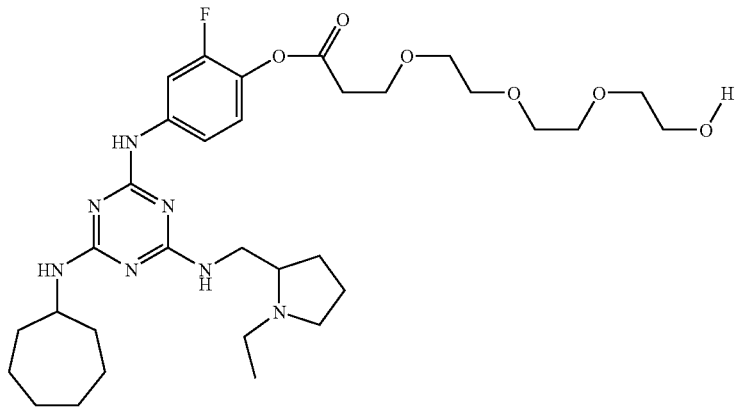 | 3-{2-[2-(2-Hydroxy-ethoxy)-ethoxy]-ethoxy}-propionic acid 4-{4-cycloheptylamino-6-[(1-ethyl-pyrrolidin-2-ylmethyl)-amino]-[1,3,5]triazin-2-ylamino}-2-fluoro-phenyl ester |
| B147 | 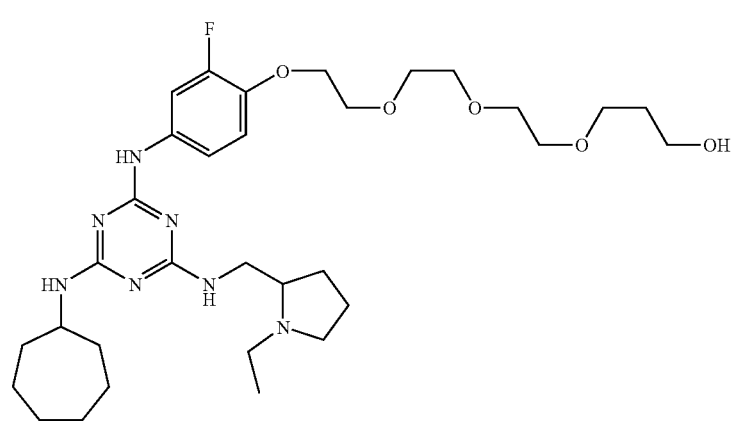 | 3-(2-{2-[2-(4-{4-Cycloheptylamino-6-[(1-ethyl-pyrrolidin-2-ylmethyl)-amino]-[1,3,5]triazin-2-ylamino}-2-fluoro-phenoxy)-ethoxy]-ethoxy}-ethoxy)-propan-1-ol |
| B148 | 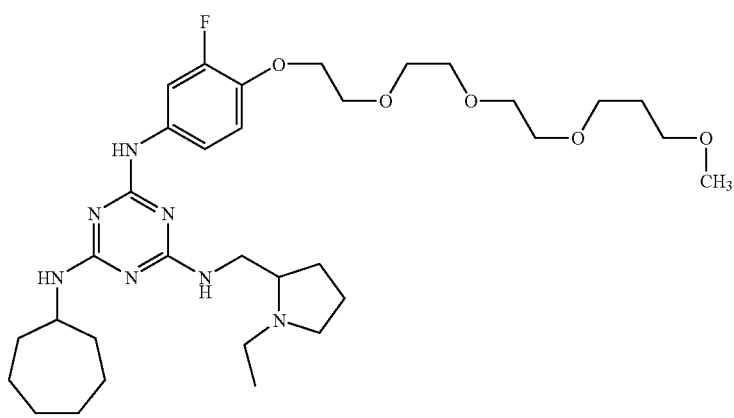 | N-Cycloheptyl-N'-(1-ethyl-pyrrolidin-2-ylmethyl)-N''-[3-fluoro-4-(2-{2-[2-(3-methoxy-propoxy)-ethoxy]-ethoxy}-ethoxy)-phenyl]-[1,3,5]triazine-2,4,6-triamine |

TABLE 1B-continued

Representative Compounds of the Present Invention

| Cmpd | Structure | Name |
| --- | --- | --- |
| B149 | 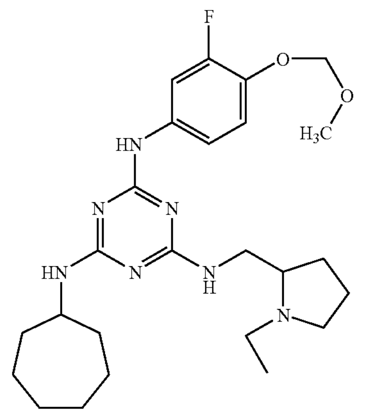 | N-Cycloheptyl-N'-(1-ethyl-pyrrolidin-2-ylmethyl)-N''-(3-fluoro-4-methoxymethoxy-phenyl)-[1,3,5]triazine-2,4,6-triamine |
| B150 | 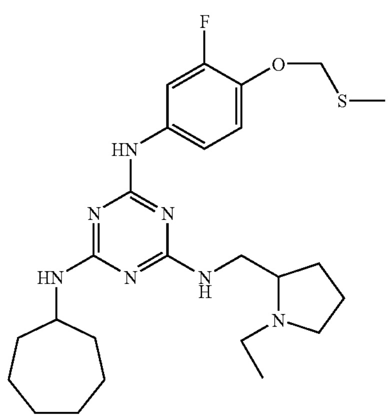 | N-Cycloheptyl-N'-(1-ethyl-pyrrolidin-2-ylmethyl)-N''-(3-fluoro-4-methylsulfanylmethoxy-phenyl)-[1,3,5]triazine-2,4,6-triamine |
| B151 | 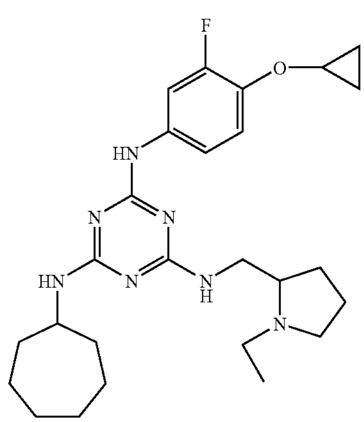 | N-Cycloheptyl-N'-(4-cyclopropoxy-3-fluoro-phenyl)-N''-(1-ethyl-pyrrolidin-2-ylmethyl)-[1,3,5]triazine-2,4,6-triamine |

TABLE 1B-continued

Representative Compounds of the Present Invention

| Cmpd | Structure | Name |
|---|---|---|
| B152 | 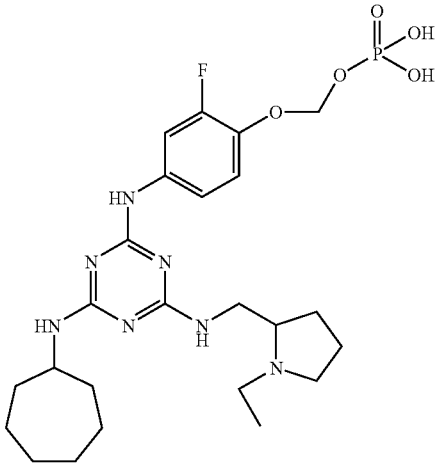 | 4-{4-Cycloheptylamino-6-[(1-ethyl-pyrrolidin-2-ylmethyl)-amino]-[1,3,5]triazin-2-ylamino}-2-fluoro-phenol; compound with phosphoric acid monoethyl ester |
| B153 | 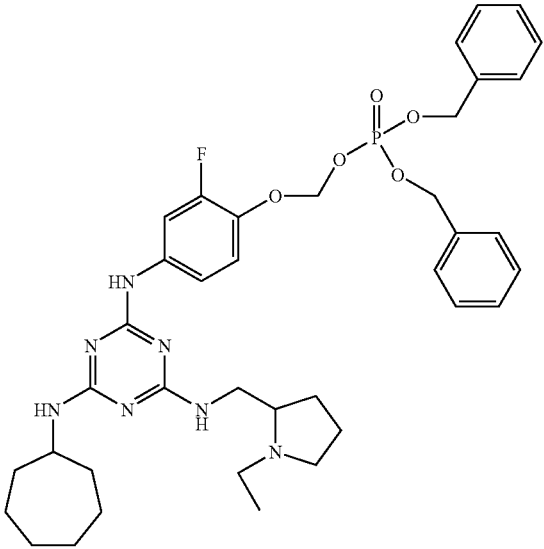 | 4-{4-Cycloheptylamino-6-[(1-ethyl-pyrrolidin-2-ylmethyl)-amino]-[1,3,5]triazin-2-ylamino}-2-fluoro-phenol; compound with phosphoric acid dibenzyl ester ethyl ester |
| B154 | 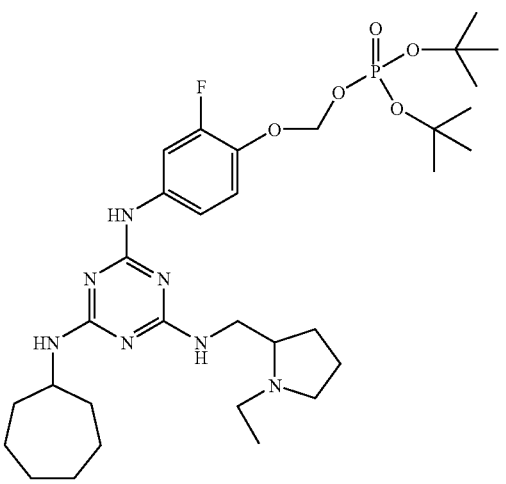 | 4-{4-Cycloheptylamino-6-[(1-ethyl-pyrrolidin-2-ylmethyl)-amino]-[1,3,5]triazin-2-ylamino}-2-fluoro-phenol; compound with phosphoric acid dibert-butyl ester ethyl ester |

TABLE 1B-continued

Representative Compounds of the Present Invention

| Cmpd | Structure | Name |
|---|---|---|
| B155 | 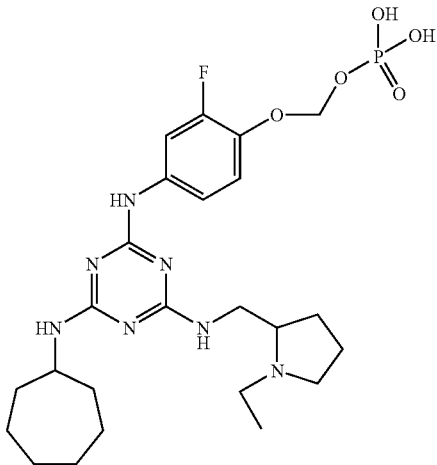 | Phosphoric acid mono-(4-{4-cycloheptylamino-6-[(1-ethyl-pyrrolidin-2-ylmethyl)-amino]-[1,3,5]triazin-2-yl amino}-2-fluoro-phenyl) ester |
| B156 | 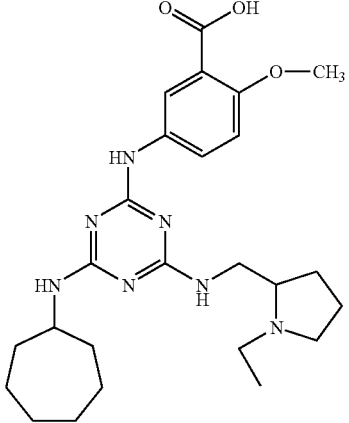 | 5-{4-Cycloheptylamino-6-[(1-ethyl-pyrrolidin-2-ylmethyl)-amino]-[1,3,5]triazin-2-ylamino}-2-hydroxy-benzolic ; compound with ethane |
| B157 | 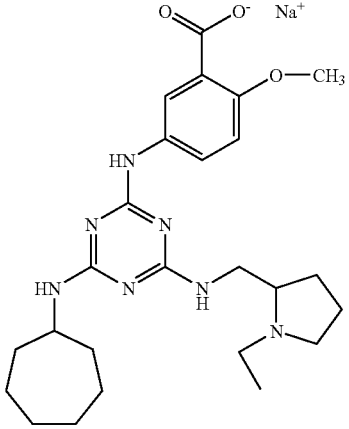 | Sodium; 5-{4-cycloheptylamino-6-[(1-ethyl-pyrrolidin-2-ylmethyl)-amino]-[1,3,5]triazin-2-ylamino}-2-methoxy-benzoate |

TABLE 1B-continued

Representative Compounds of the Present Invention

| Cmpd | Structure | Name |
|---|---|---|
| B158 | 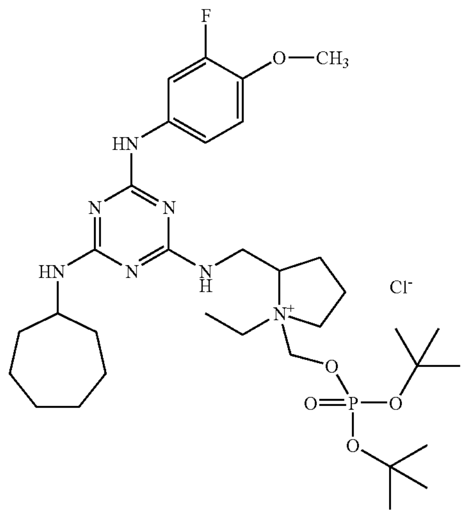 | 2-{[4-Cycloheptylamino-6-(3-fluoro-4-methoxy-phenylamino)-[1,3,5]triazin-2-ylamino]-methyl}-1-(di-tert-butoxy-phosphoryloxymethyl)-1-ethyl-pyrrolidinium; chloride |
| B159 | 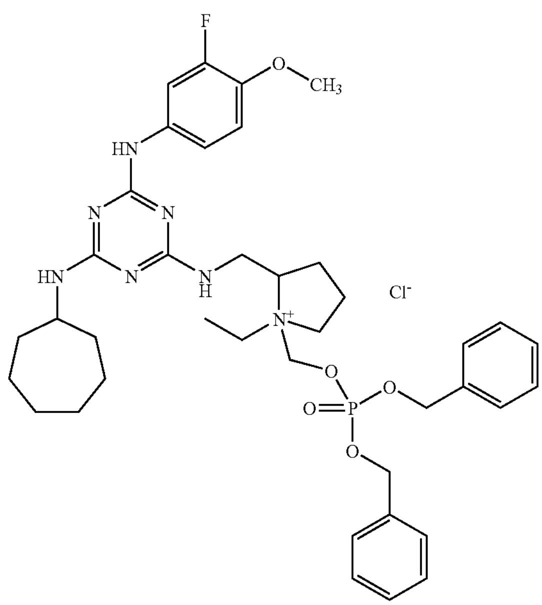 | 1-(Bis-benzyloxy-phosphoryloxy-methyl)-2-{[4-cylcoheptylamino-6-(3-fluoro-4-methoxy-phenylamino)-[1,3,5]triazin-2-ylamino]-methyl}-1-ethyl-pyrrolidinium; chloride |
| B160 | 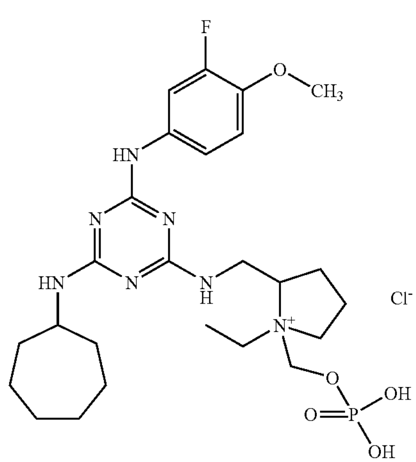 | 2-{[4-Cycloheptylamino-6-(3-fluoro-4-methoxy-phenylamino)-[1,3,5]triazin-2-ylamino]-methyl}-1-ethyl-1-phosphonooxymethyl-pyrrolidinium; chloride |

… 359 …

TABLE 1B-continued

Representative Compounds of the Present Invention

| Cmpd | Structure | Name |
|---|---|---|
| B161 | 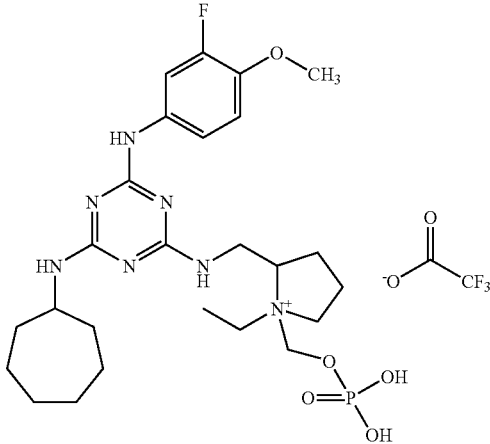 | Trifluoro-acetate2-{[4-cycloheptylamino-6-(3-fluoro-4-methoxy-phenylamino)-[1,3,5]triazin-2-ylamino]-methyl}-1-ethyl-1-phosphonooxymethyl-pyrrolidinium; |
| B162 | 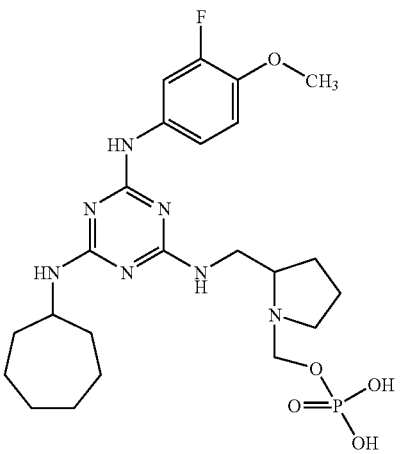 | Phosphoric acid mono-(2-{[4-cycloheptylamino-6-(3-fluoro-4-hydroxy-phenylamino)-[1,3,5]triazin-2-ylamino]-methyl}-pyrrolidin-1-ylmethyl) ester; compound with ethane |

TABLE 2

Representative compounds of the present invention prepared by parallel synthethis reactions, including amine monomers, products, and characterization data

| Cmpd. No. | R1 (Monomer 1) | R2 (Monomer 2) | R3 (Monomer 3) |
|---|---|---|---|
| 1 | 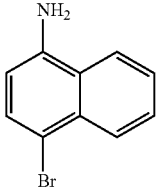 | 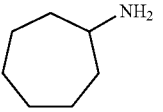 | 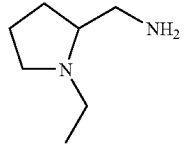 |
| 2 | 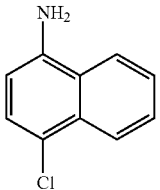 | 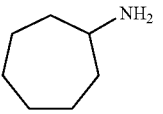 | 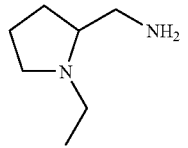 |

TABLE 2-continued
Representative compounds of the present invention prepared by parallel synthethis reactions, including amine monomers, products, and characterization data
| | | | |
|---|---|---|---|
| 3 | 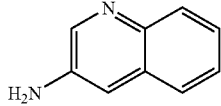 | 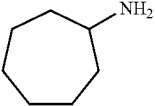 | 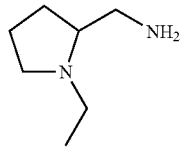 |
| 4 | 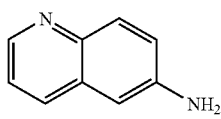 | 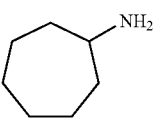 | 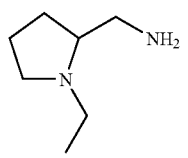 |
| 5 | 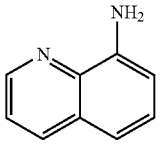 | 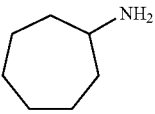 | 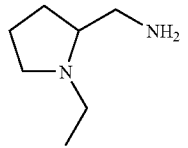 |
| 6 | 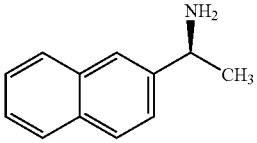<br>chiral | 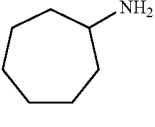 | 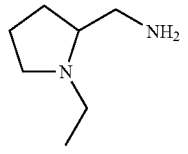 |
| 7 | 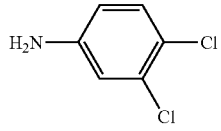 | 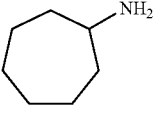 | 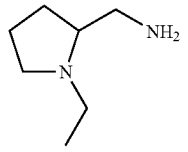 |
| 8 | 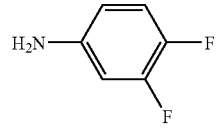 | 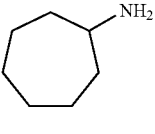 | 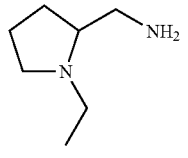 |
| 9 | 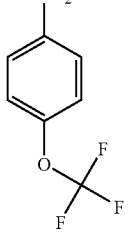 | 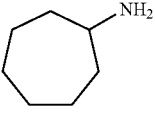 | 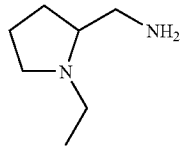 |
| 10 | 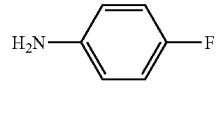 | 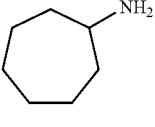 | 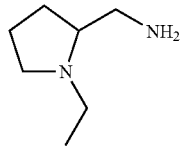 |

TABLE 2-continued
Representative compounds of the present invention prepared by parallel synthethis reactions, including amine monomers, products, and characterization data
| | | | |
|---|---|---|---|
| 11 | 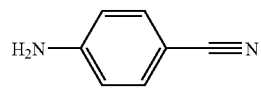 | 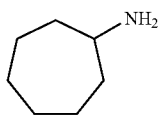 | 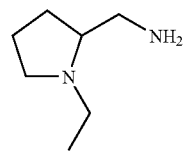 |
| 12 | 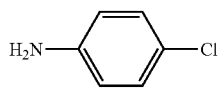 | 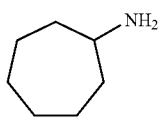 | 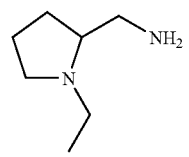 |
| 13 | 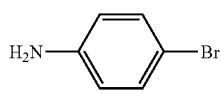 | 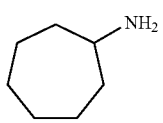 | 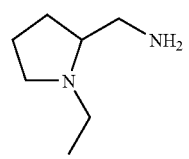 |
| 14 | 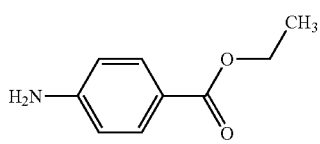 | 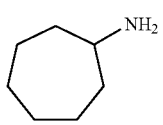 | 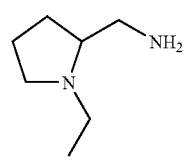 |
| 15 | 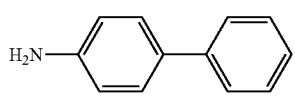 | 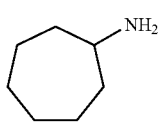 | 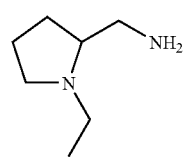 |
| 16 | 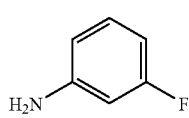 | 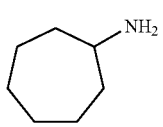 | 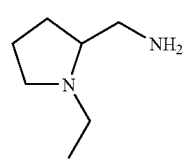 |
| 17 | 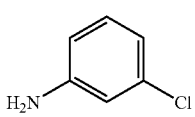 | 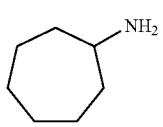 | 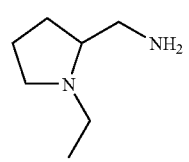 |
| 18 | 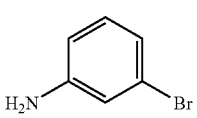 | 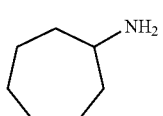 | 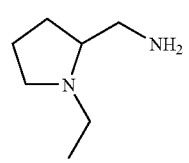 |
| 19 | 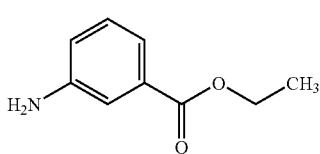 | 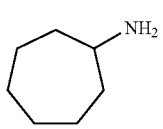 | 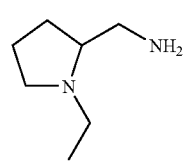 |

TABLE 2-continued

Representative compounds of the present invention prepared by parallel synthethis reactions, including amine monomers, products, and characterization data TABLE 2-continued
Representative compounds of the present invention prepared by parallel synthethis reactions, including amine monomers, products, and characterization data
| 29 | 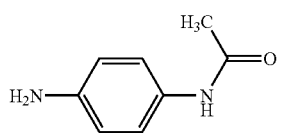 | 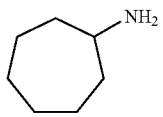 | 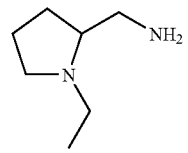 |
| --- | --- | --- | --- |
| 30 | 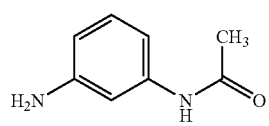 | 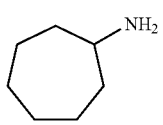 | 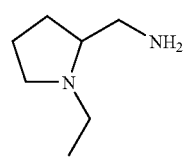 |
| 31 | 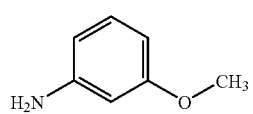 | 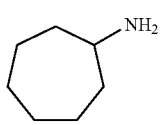 | 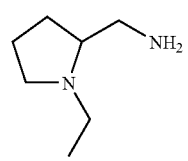 |
| 32 | 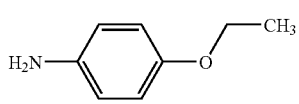 | 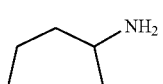 | 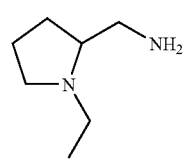 |
| 33 | 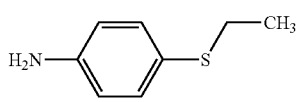 | 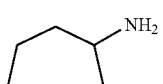 | 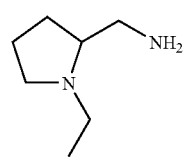 |
| 34 | 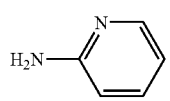 | 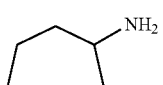 | 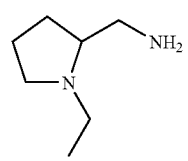 |
| 35 | 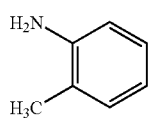 | 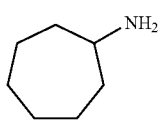 | 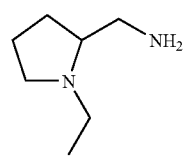 |
| 36 | 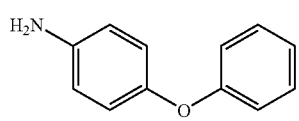 | 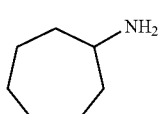 | 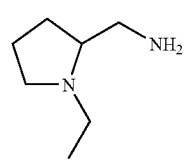 |
| 37 | 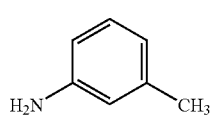 | 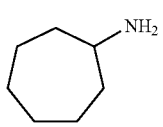 | 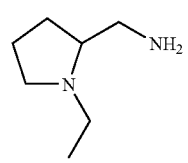 |

TABLE 2-continued
Representative compounds of the present invention prepared by parallel synthethis reactions, including amine monomers, products, and characterization data
| | | | |
|---|---|---|---|
| 38 |  | 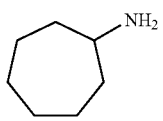 | 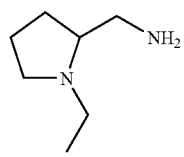 |
| 39 |  | 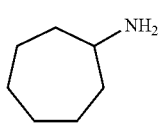 | 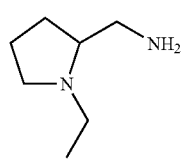 |
| 40 | 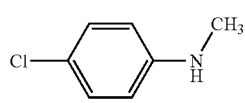 | 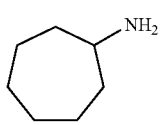 | 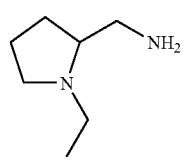 |
| 41 | 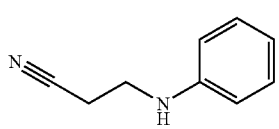 | 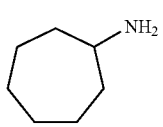 | 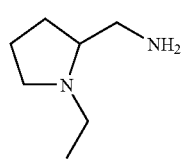 |
| 42 | 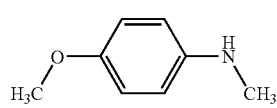 | 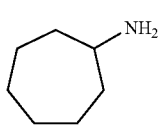 | 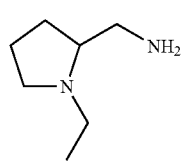 |
| 43 | 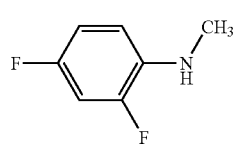 | 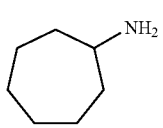 | 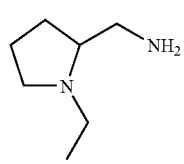 |
| 44 | 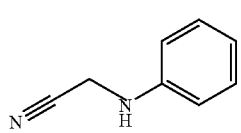 | 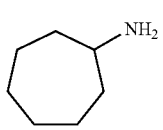 | 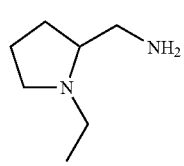 |
| 45 | 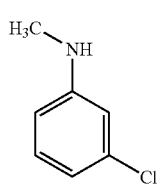 | 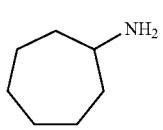 | 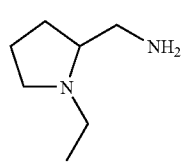 |
| 46 | 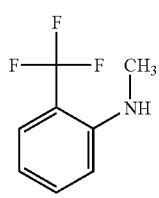 | 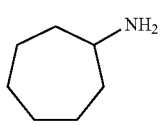 | 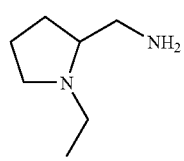 |

TABLE 2-continued
Representative compounds of the present invention prepared by parallel synthethis reactions, including amine monomers, products, and characterization data
| 47 | 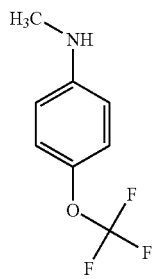 | 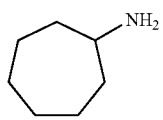 | 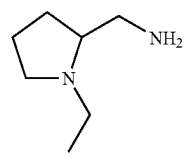 |
| --- | --- | --- | --- |
| 48 | 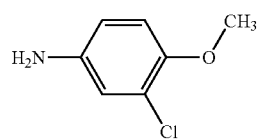 | 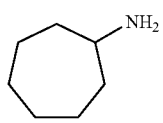 | 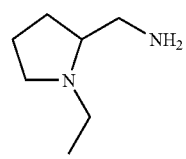 |
| 49 | 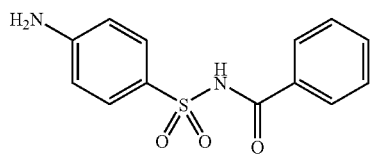 | 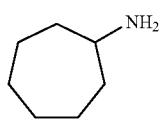 | 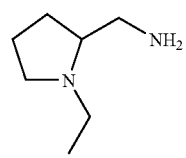 |
| 50 | 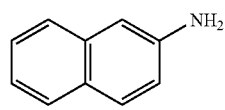 | 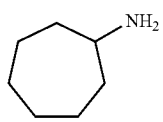 | 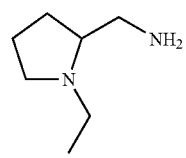 |
| 51 | 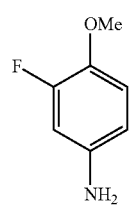 | 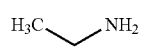 | 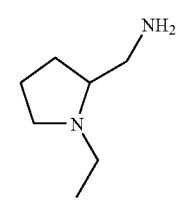 |
| 52 | 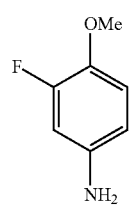 | 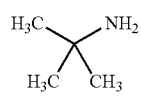 | 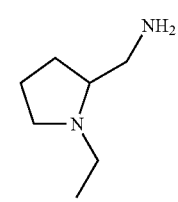 |
| 53 | 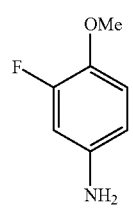 | 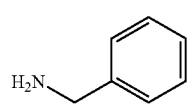 | 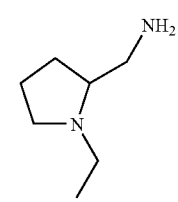 |

TABLE 2-continued

Representative compounds of the present invention prepared by parallel synthethis reactions, including amine monomers, products, and characterization data

| # | | | |
|---|---|---|---|
| 54 | 3-F-4-OMe-aniline | cyclooctylamine | (1-ethylpyrrolidin-2-yl)methanamine |
| 55 | 3-F-4-OMe-aniline | cyclohexylamine | (1-ethylpyrrolidin-2-yl)methanamine |
| 56 | 3-F-4-OMe-aniline | cyclopentylamine | (1-ethylpyrrolidin-2-yl)methanamine |
| 57 | 3-F-4-OMe-aniline | pyrrolidine | (1-ethylpyrrolidin-2-yl)methanamine |
| 58 | 3-F-4-OMe-aniline | azepane | (1-ethylpyrrolidin-2-yl)methanamine |
| 59 | 3-F-4-OMe-aniline | decahydroquinoline | (1-ethylpyrrolidin-2-yl)methanamine |
| 60 | 3-F-4-OMe-aniline | 4-methylcyclohexylamine | (1-ethylpyrrolidin-2-yl)methanamine |

TABLE 2-continued
Representative compounds of the present invention prepared by parallel synthethis reactions, including amine monomers, products, and characterization data
| 61 | 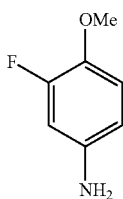 | 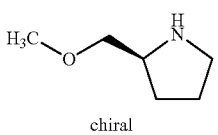 chiral | 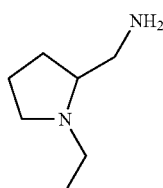 |
| 62 | 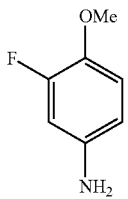 | 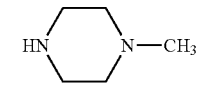 | 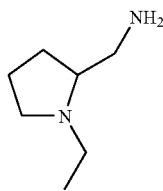 |
| 63 | 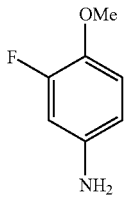 | 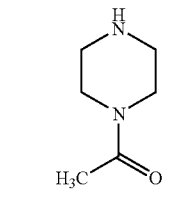 | 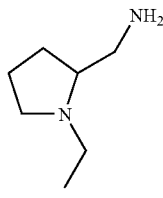 |
| 64 | 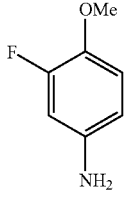 | 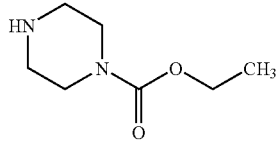 | 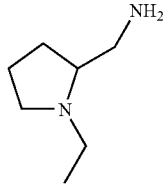 |
| 65 | 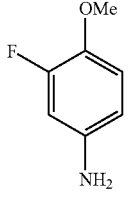 | 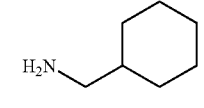 | 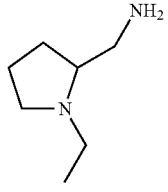 |
| 66 | 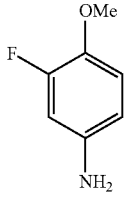 | 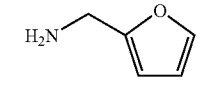 | 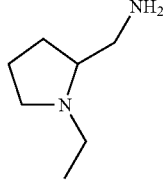 |
| 67 | 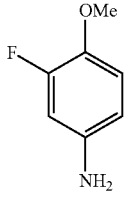 | 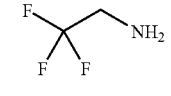 | 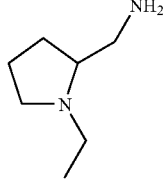 |

TABLE 2-continued
Representative compounds of the present invention prepared by parallel synthethis reactions, including amine monomers, products, and characterization data
| 68 | 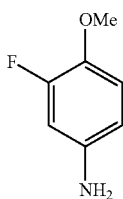 | 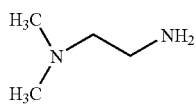 | 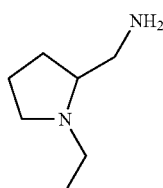 |
| --- | --- | --- | --- |
| 69 | 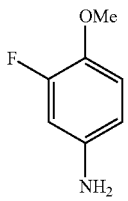 | 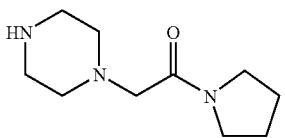 | 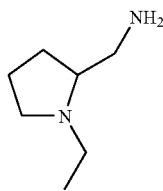 |
| 70 | 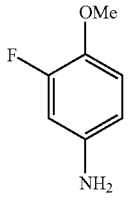 | 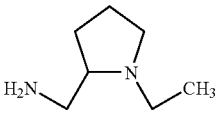 | 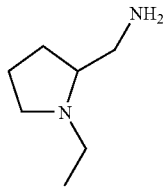 |
| 71 | 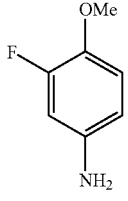 | 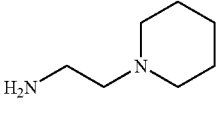 | 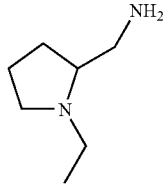 |
| 72 | 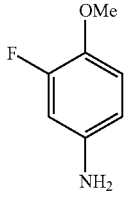 | 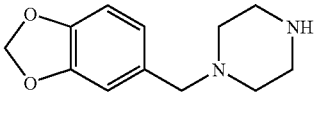 | 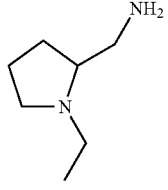 |
| 73 | 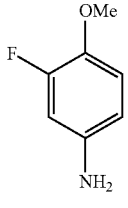 | 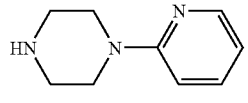 | 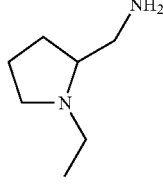 |
| 74 | 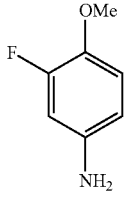 | 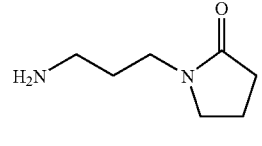 | 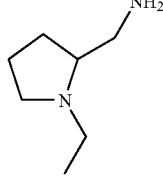 |

TABLE 2-continued

Representative compounds of the present invention prepared by parallel synthethis reactions, including amine monomers, products, and characterization data

| # | | | |
|---|---|---|---|
| 75 | 4-methoxy-3-fluoroaniline | H₂N(CH₂)₃-imidazole | (1-ethylpyrrolidin-2-yl)methanamine |
| 76 | 4-methoxy-3-fluoroaniline | cycloheptylamine | ethylamine |
| 77 | 4-methoxy-3-fluoroaniline | cycloheptylamine | tert-butylamine |
| 78 | 4-methoxy-3-fluoroaniline | cycloheptylamine | benzylamine |
| 79 | 4-methoxy-3-fluoroaniline | cycloheptylamine | cyclooctylamine |
| 80 | 4-methoxy-3-fluoroaniline | cycloheptylamine | cyclohexylamine |
| 81 | 4-methoxy-3-fluoroaniline | cycloheptylamine | cyclopentylamine |

TABLE 2-continued

Representative compounds of the present invention prepared by parallel synthethis reactions, including amine monomers, products, and characterization data

| | | | |
|---|---|---|---|
| 82 | 4-methoxy-3-fluoroaniline | cycloheptylamine | pyrrolidine |
| 83 | 4-methoxy-3-fluoroaniline | cycloheptylamine | hexamethyleneimine (azepane) |
| 84 | 4-methoxy-3-fluoroaniline | cycloheptylamine | decahydroquinoline |
| 85 | 4-methoxy-3-fluoroaniline | cycloheptylamine | 4-methylcyclohexylamine |
| 86 | 4-methoxy-3-fluoroaniline | cycloheptylamine | (S)-2-(methoxymethyl)pyrrolidine (chiral) |
| 87 | 4-methoxy-3-fluoroaniline | cycloheptylamine | 1-methylpiperazine |
| 88 | 4-methoxy-3-fluoroaniline | cycloheptylamine | 1-acetylpiperazine |

TABLE 2-continued

Representative compounds of the present invention prepared by parallel synthethis reactions, including amine monomers, products, and characterization data

| # | Aryl amine | Amine 2 | Amine 3 |
|---|---|---|---|
| 89 | 4-methoxy-3-fluoro-1,3-phenylenediamine | cycloheptylamine | ethyl piperazine-1-carboxylate |
| 90 | 4-methoxy-3-fluoro-1,3-phenylenediamine | cycloheptylamine | cyclohexylmethylamine |
| 91 | 4-methoxy-3-fluoro-1,3-phenylenediamine | cycloheptylamine | furfurylamine |
| 92 | 4-methoxy-3-fluoro-1,3-phenylenediamine | cycloheptylamine | 2,2,2-trifluoroethylamine |
| 93 | 4-methoxy-3-fluoro-1,3-phenylenediamine | cycloheptylamine | N,N-dimethylethylenediamine |
| 94 | 4-methoxy-3-fluoro-1,3-phenylenediamine | cycloheptylamine | 1-(2-oxo-2-pyrrolidin-1-ylethyl)piperazine |
| 95 | 4-methoxy-3-fluoro-1,3-phenylenediamine | cycloheptylamine | (1-ethylpyrrolidin-2-yl)methylamine |

TABLE 2-continued
Representative compounds of the present invention prepared by parallel synthethis reactions, including amine monomers, products, and characterization data
| 96 | 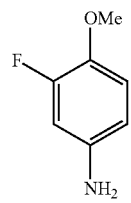 | 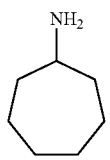 | 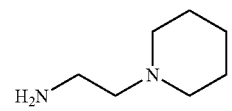 |
| 97 | 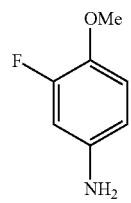 | 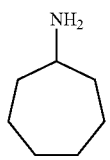 | 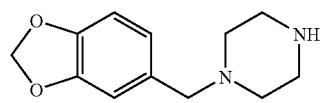 |
| 98 | 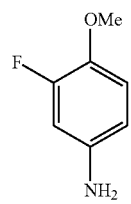 | 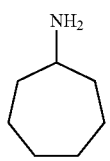 | 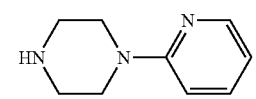 |
| 99 | 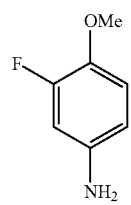 | 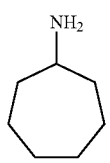 | 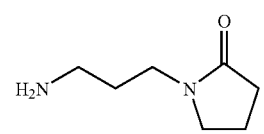 |
| 100 | 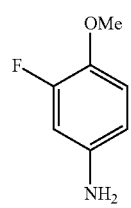 | 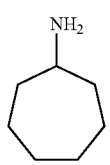 | 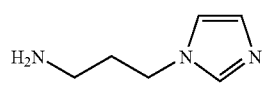 |
| Cmpd. No. | Product Structure | Product Name |
|---|---|---|
| 1 | 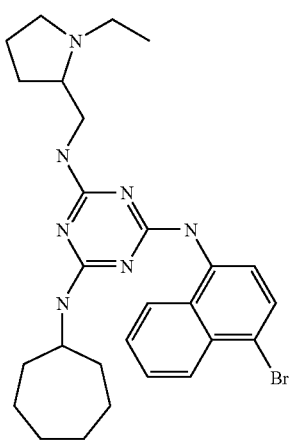 | N2-(4-bromo-1-naphthyl)-N4-cycloheptyl-N6-[(1-ethyl-2-pyrrolidinyl)methyl]-1,3,5-triazine-2,4,6-triamine |

TABLE 2-continued

Representative compounds of the present invention prepared by parallel synthethis reactions, including amine monomers, products, and characterization data 2 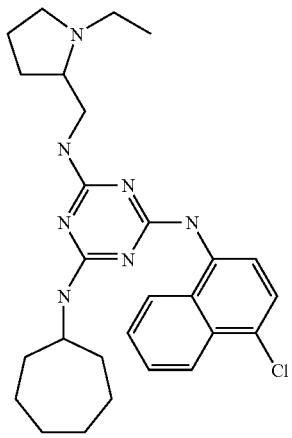 N2-(4-chloro-1-naphthyl)-N4-cycloheptyl-N6-[(1-ethyl-2-pyrrolidinyl)methyl]-1,3,5-triazine-2,4,6-triamine 3 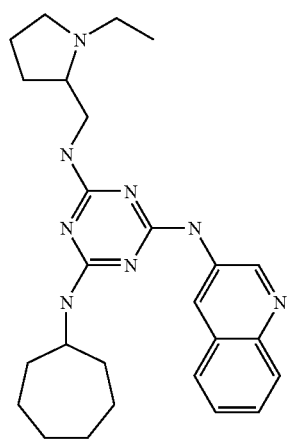 N2-cycloheptyl-N4-[(1-ethyl-2-pyrrolidinyl)methyl]-N6-(3-quinolinyl)-1,3,5-triazine-2,4,6-triamine 4 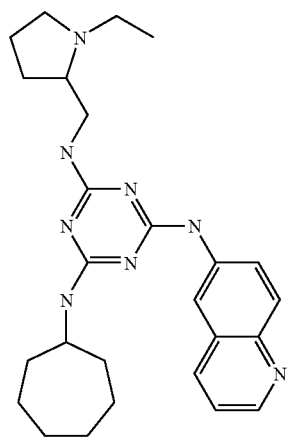 N2-cycloheptyl-N4-[(1-ethyl-2-pyrrolidinyl)methyl]-N6-(6-quinolinyl)-1,3,5-triazine-2,4,6-triamine TABLE 2-continued Representative compounds of the present invention prepared by parallel synthethis reactions, including amine monomers, products, and characterization data

| | | |
|---|---|---|
| 5 | 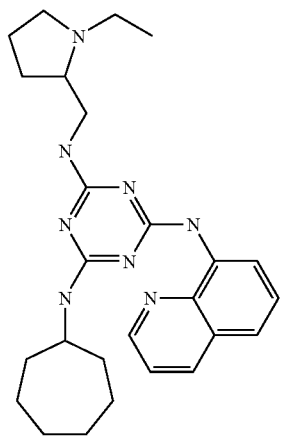 | N2-cycloheptyl-N4-[(1-ethyl-2-pyrrolidinyl)methyl]-N6-(8-quinolinyl)-1,3,5-triazine-2,4,6-triamine |
| 6 | 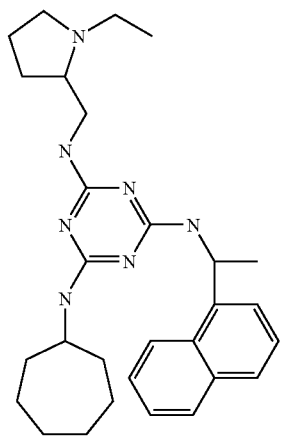 | N2-cycloheptyl-N4-[(1-ethyl-2-pyrrolidinyl)methyl]-N6-[1-(2-naphthyl)ethyl]-1,3,5-triazine-2,4,6-triamine |
| 7 | 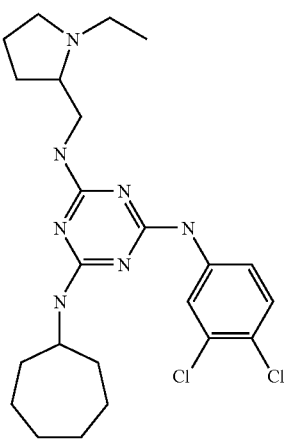 | N2-cycloheptyl-N4-(3,4-dichlorophenyl)-N6-[(1-ethyl-2-pyrrolidinyl)methyl]-1,3,5-triazine-2,4,6-triamine |

TABLE 2-continued

Representative compounds of the present invention prepared by parallel synthethis reactions, including amine monomers, products, and characterization data

| 8 | 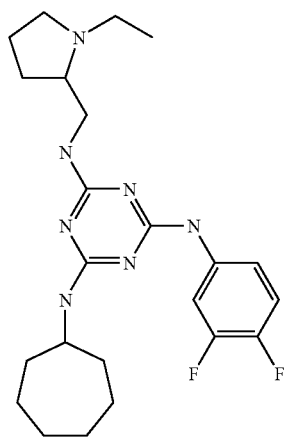 | N2-cycloheptyl-N4-(3,4-difluorophenyl)-N6-[(1-ethyl-2-pyrrolidinyl)methyl]-1,3,5-triazine-2,4,6-triamine |
| 9 | 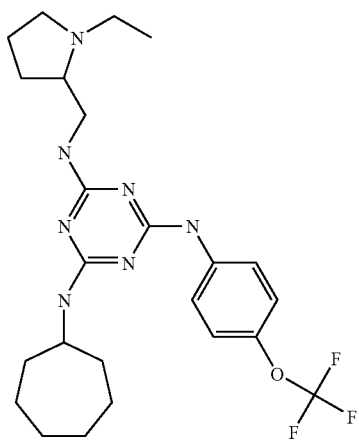 | N2-cycloheptyl-N4-[(1-ethyl-2-pyrrolidinyl)methyl]-N6-[4-(trifluoromethoxy)phenyl]-1,3,5-triazine-2,4,6-triamine |
| 10 | 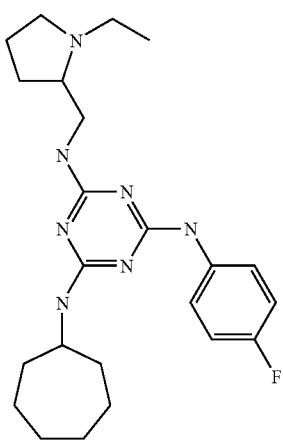 | N2-cycloheptyl-N4-[(1-ethyl-2-pyrrolidinyl)methyl]-N6-(4-fluorophenyl)-1,3,5-triazine-2,4,6-triamine |

TABLE 2-continued

Representative compounds of the present invention prepared by parallel synthethis reactions, including amine monomers, products, and characterization data 11 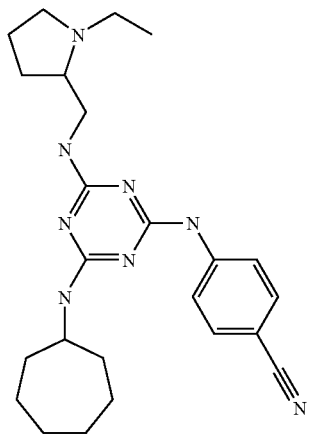 4-[(4-(cycloheptylamino)-6-{[(1-ethyl-2-pyrrolidinyl)methyl]amino}-1,3,5-triazin-2-yl)-amino]benzonitrile 12 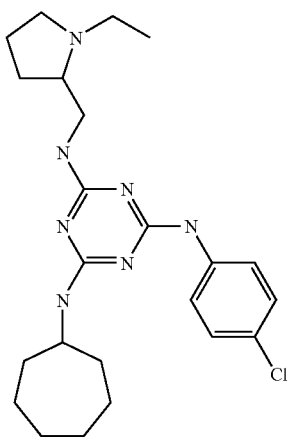 N2-(4-chlorophenyl)-N4-cycloheptyl-N6-[(1-ethyl-2-pyrrolidinyl)methyl]-1,3,5-triazine-2,4,6-triamine 13 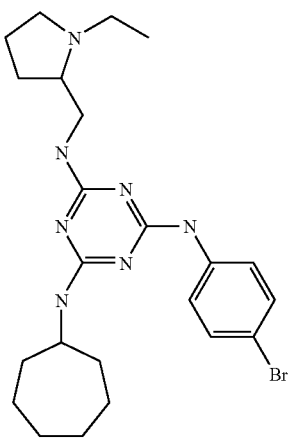 N2-(4-bromophenyl)-N4-cycloheptyl-N6-[(1-ethyl-2-pyrrolidinyl)methyl]-1,3,5-triazine-2,4,6-triamine TABLE 2-continued Representative compounds of the present invention prepared by parallel synthethis reactions, including amine monomers, products, and characterization data

| 14 | 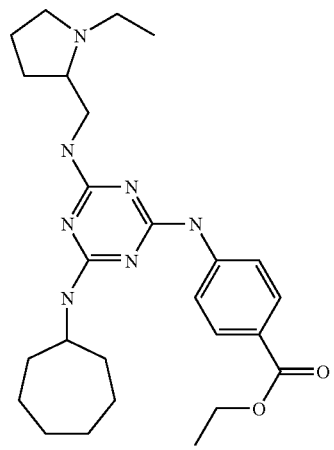 | 4-[(4-(cycloheptylamino)-6-{[(1-ethyl-2-pyrrolidinyl)methyl]amino}-1,3,5-triazin-2-yl)-amino]benzoate |
| --- | --- | --- |
| 15 | 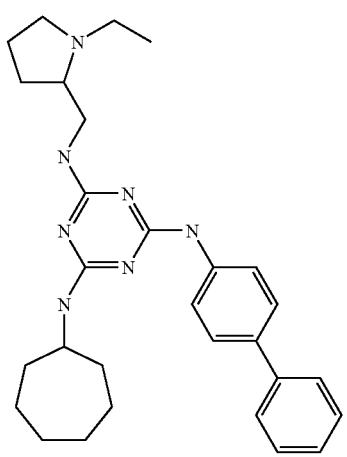 | N2-(1,1'-biphenyl-4-yl)-N4-cycloheptyl-N6-[(1-ethyl-2-pyrrolidinyl)methyl]-1,3,5-triazine-2,4,6-triamine |
| 16 | 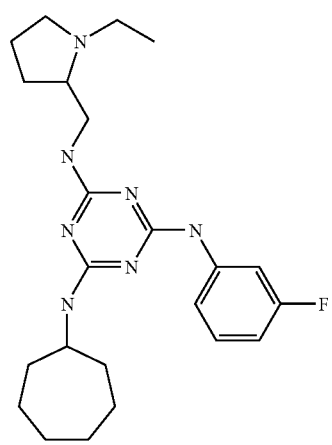 | N2-cycloheptyl-N4-[(1-ethyl-2-pyrrolidinyl)methyl]-N6-(3-fluorophenyl)-1,3,5-triazine-2,4,6-triamine |

TABLE 2-continued

Representative compounds of the present invention prepared by parallel synthethis reactions, including amine monomers, products, and characterization data

| | | |
|---|---|---|
| 17 | 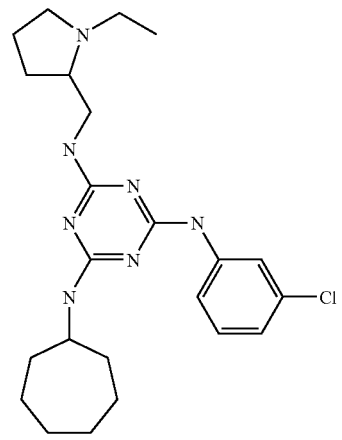 | N2-(3-chlorophenyl)-N4-cycloheptyl-N6-[(1-ethyl-2-pyrrolidinyl)methyl]-1,3,5-triazine-2,4,6-triamine |
| 18 | 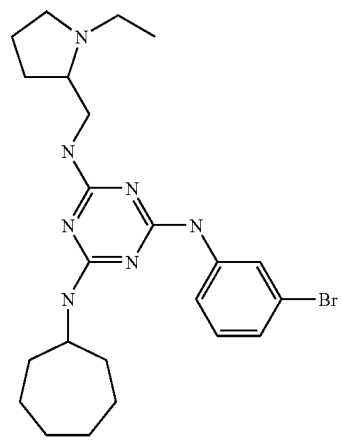 | N2-(3-bromophenyl)-N4-cycloheptyl-N6-[(1-ethyl-2-pyrrolidinyl)methyl]-1,3,5-triazine-2,4,6-triamine |
| 19 | 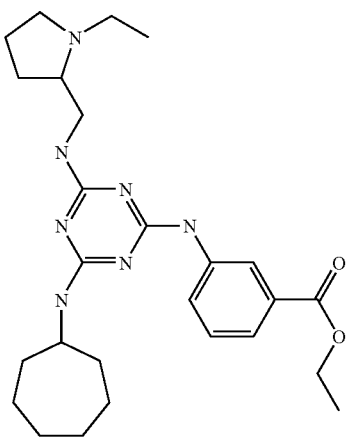 | 3-[(4-(cycloheptylamino)-6-{[(1-ethyl-2-pyrrolidinyl)methyl]amino}-1,3,5-triazin-2-yl)-amino]benzoate |

TABLE 2-continued

Representative compounds of the present invention prepared by parallel synthethis reactions,
including amine monomers, products, and characterization data

| 20 | 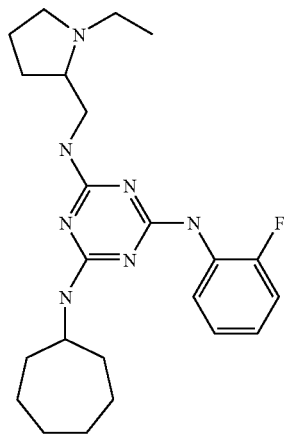 | N2-cycloheptyl-N4-[(1-ethyl-2-pyrrolidinyl)methyl]-N6-(2-fluorophenyl)-1,3,5-triazine-2,4,6-triamine |
| 21 | 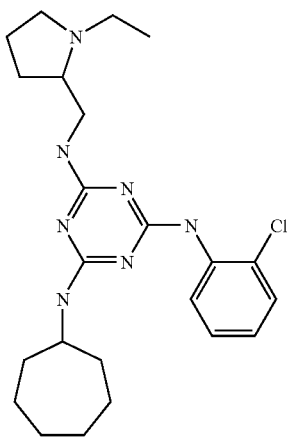 | N2-(2-chlorophenyl)-N4-cycloheptyl-N6-[(1-ethyl-2-pyrrolidinyl)methyl]-1,3,5-triazine-2,4,6-triamine |
| 22 | 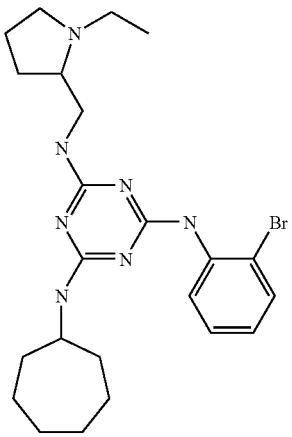 | N2-(2-bromophenyl)-N4-cycloheptyl-N6-[(1-ethyl-2-pyrrolidinyl)methyl]-1,3,5-triazine-2,4,6-triamine |

TABLE 2-continued

Representative compounds of the present invention prepared by parallel synthethis reactions, including amine monomers, products, and characterization data 23 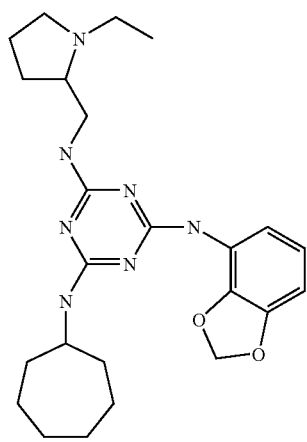 N2-(1,3-benzodioxol-5-yl)-N4-cycloheptyl-N6-[(1-ethyl-2-pyrrolidinyl)methyl]-1,3,5-triazine-2,4,6-triamine 24 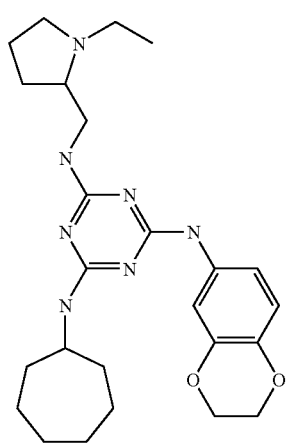 N2-cycloheptyl-N4-(2,3-dihydro-1,4-benzodioxin-6-yl)-N6-[(1-ethyl-2-pyrrolidinyl)methyl]-1,3,5-triazine-2,4,6-triamine 25 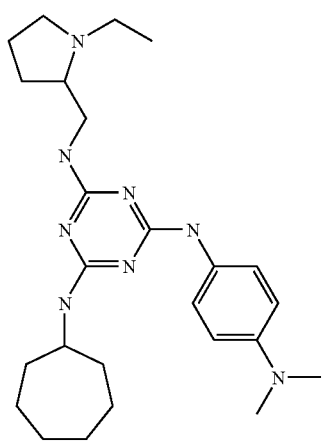 N2-cycloheptyl-N4-[4-(dimethylamino)phenyl]-N6-[(1-ethyl-2-pyrrolidinyl)methyl]-1,3,5-triazine-2,4,6-triamine TABLE 2-continued Representative compounds of the present invention prepared by parallel synthethis reactions, including amine monomers, products, and characterization data 26 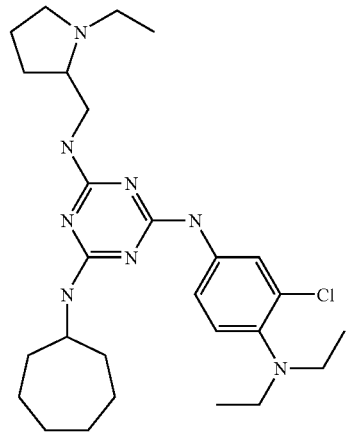 N2-[3-chloro-4-(dimethylamino)phenyl]-N4-cycloheptyl-N6-[(1-ethyl-2-pyrrolidinyl)methyl]-1,3,5-triazine-2,4,6-triamine 27 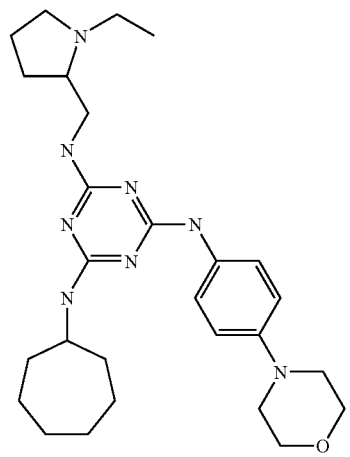 N2-cycloheptyl-N4-[(1-ethyl-2-pyrrolidinyl)methyl]-N6-[4-(4-morpholinyl)phenyl]-1,3,5-triazine-2,4,6-triamine 28 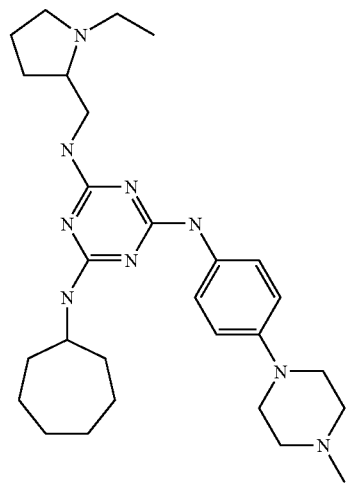 N2-cycloheptyl-N4-[(1-ethyl-2-pyrrolidinyl)methyl]-N6-[4-(4-methyl-1-piperazinyl)phenyl]-1,3,5-triazine-2,4,6-triamine TABLE 2-continued Representative compounds of the present invention prepared by parallel synthethis reactions, including amine monomers, products, and characterization data

| 29 | 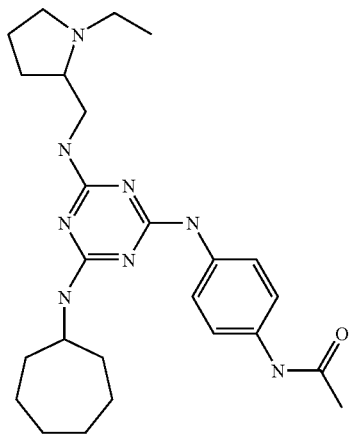 | N-{4-[(4-(cycloheptylamino)-6-{[(1-ethyl-2-pyrrolidinyl)methyl]amino)-1,3,5-triazin-2-yl)-amino]phenyl}acetamide |
| --- | --- | --- |
| 30 | 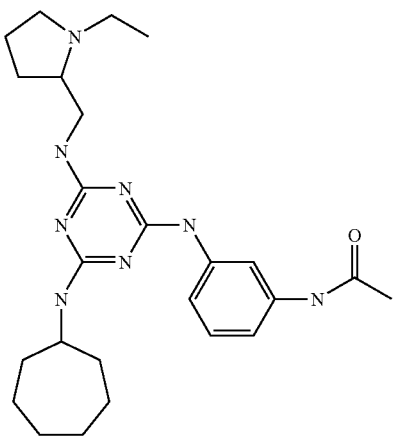 | N-{3-[(4-(cycloheptylamino)-6-{[(1-ethyl-2-pyrrolidinyl)methyl]amino)-1,3,5-triazin-2-yl)-amino]phenyl}acetamide |
| 31 | 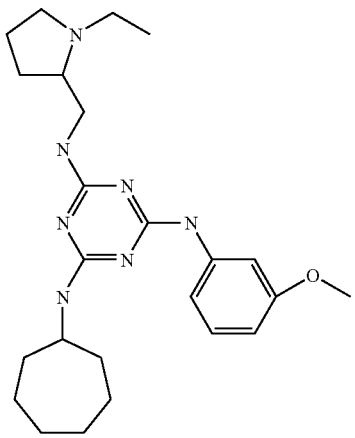 | N2-cycloheptyl-N4-[(1-ethyl-2-pyrrolidinyl)methyl]-N6-(3-methoxyphenyl)-1,3,5-triazine-2,4,6-triamine |

TABLE 2-continued

Representative compounds of the present invention prepared by parallel synthethis reactions, including amine monomers, products, and characterization data

| | | |
|---|---|---|
| 32 | 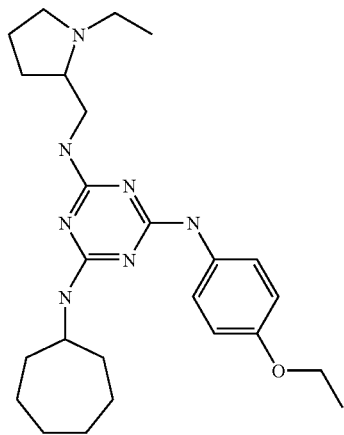 | N2-cycloheptyl-N4-(4-ethoxyphenyl)-N6-[(1-ethyl-2-pyrrolidinyl)methyl]-1,3,5-triazine-2,4,6-triamine |
| 33 | 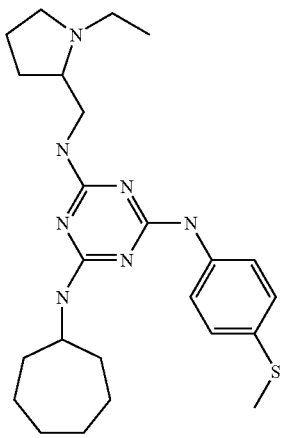 | N2-cycloheptyl-N4-[(1-ethyl-2-pyrrolidinyl)methyl]-N6-[4-(methylthio)phenyl]-1,3,5-triazine-2,4,6-triamine |
| 34 | 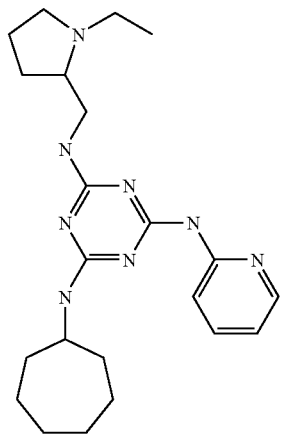 | N2-cycloheptyl-N4-[(1-ethyl-2-pyrrolidinyl)methyl]-N6-(2-pyridinyl)-1,3,5-triazine-2,4,6-triamine |

TABLE 2-continued

Representative compounds of the present invention prepared by parallel synthethis reactions, including amine monomers, products, and characterization data

| 35 | 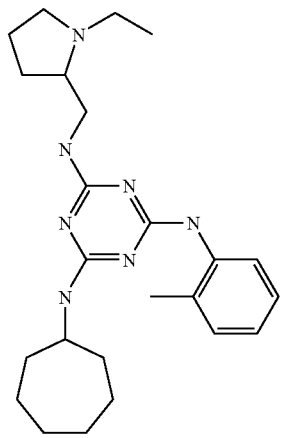 | N2-cycloheptyl-N4-[(1-ethyl-2-pyrrolidinyl)methyl]-N6-(2-methylphenyl)-1,3,5-triazine-2,4,6-triamine |
| --- | --- | --- |
| 36 | 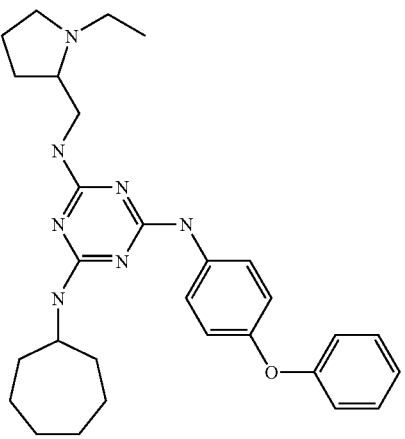 | N2-cycloheptyl-N4-[(1-ethyl-2-pyrrolidinyl)methyl]-N6-(4-phenoxyphenyl)-1,3,5-triazine-2,4,6-triamine |
| 37 | 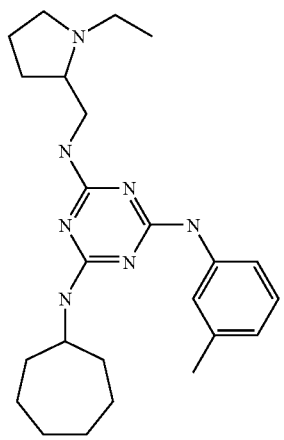 | N2-cycloheptyl-N4-[(1-ethyl-2-pyrrolidinyl)methyl]-N6-(3-methylphenyl)-1,3,5-triazine-2,4,6-triamine |

TABLE 2-continued

Representative compounds of the present invention prepared by parallel synthethis reactions, including amine monomers, products, and characterization data 38 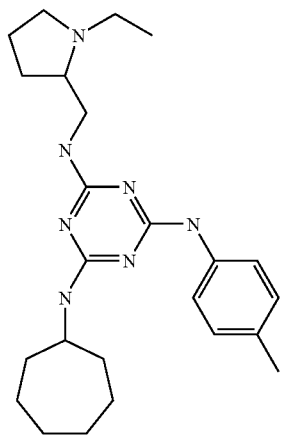 N2-cycloheptyl-N4-[(1-ethyl-2-pyrrolidinyl)methyl]-N6-(4-methylphenyl)-1,3,5-triazine-2,4,6-triamine 39 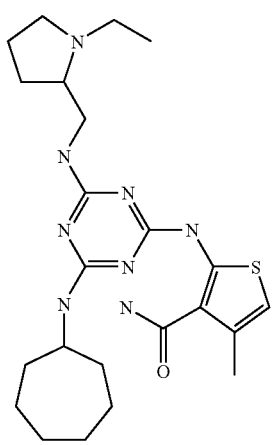 2-[(4-(cycloheptylamino)-6-{[(1-ethyl-2-pyrrolidinyl)methyl]amino}-1,3,5-triazin-2-yl)-amino]-4-methyl-3-thiophenecarboxamide 40 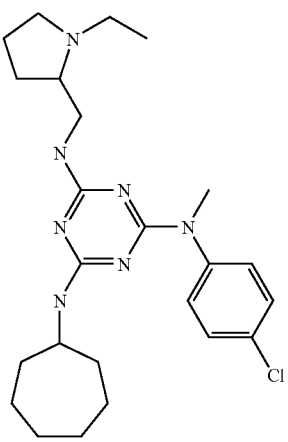 N2-(4-chlorophenyl)-N4-cycloheptyl-N6-[(1-ethyl-2-pyrrolidinyl)methyl]-N2-methyl-1,3,5-triazine-2,4,6-triamine TABLE 2-continued Representative compounds of the present invention prepared by parallel synthethis reactions, including amine monomers, products, and characterization data

| 41 | 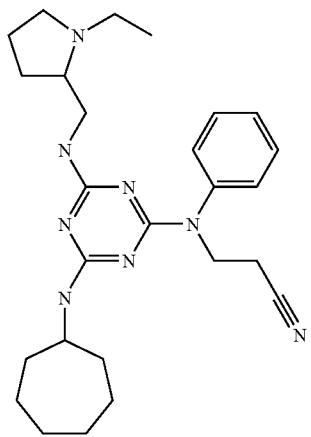 | 3-[(4-(cycloehyptylamino)-6-{[(1-ethyl-2-pyrrolidinyl)methyl]amino}-1,3,5-triazin-2-yl)-(phenyl)amino]-propanenitrile |
| --- | --- | --- |
| 42 | 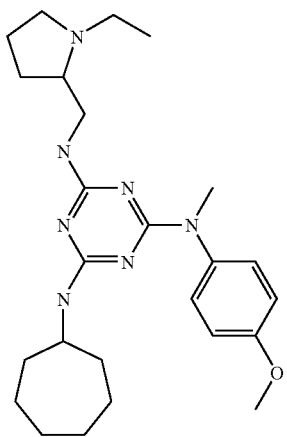 | N2-cycloheptyl-N4-[(1-ethyl-2-pyrrolidinyl)methyl]-N6-(4-methoxyphenyl)-N6-methyl-1,3,5-triazine-2,4,6-triamine |
| 43 | 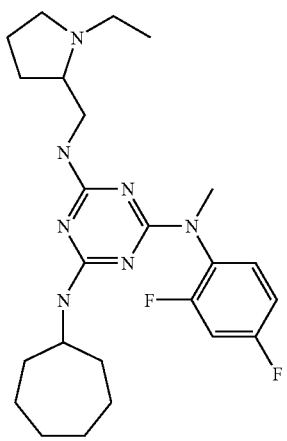 | N2-cycloheptyl-N4-(2,4-difluorophenyl)-N6-[(1-ethyl-2-pyrrolidinyl)methyl]-N4-methyl-1,3,5-triazine-2,4,6-triamine |

TABLE 2-continued

Representative compounds of the present invention prepared by parallel synthethis reactions, including amine monomers, products, and characterization data

| 44 | 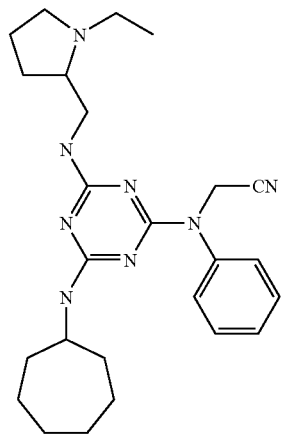 | [(4-(cyclophetylamino)-6-{[(1-ethyl-2-pyrrolidinyl)methyl]amino}-1,3,5-triazin-2-yl)(phenyl)amino]acetonitrile |
|---|---|---|
| 45 | 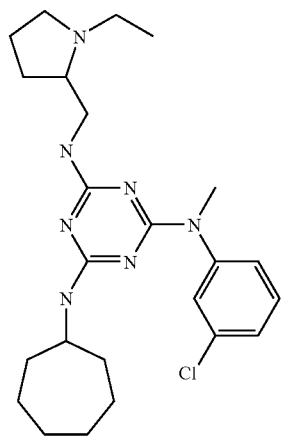 | N2-(3-chlorophenyl)-N4-cycloheptyl-N6-[(1-ethyl-2-pyrrolidinyl)methyl]-N2-methyl-1,3,5-triazine-2,4,6-triamine |
| 46 | 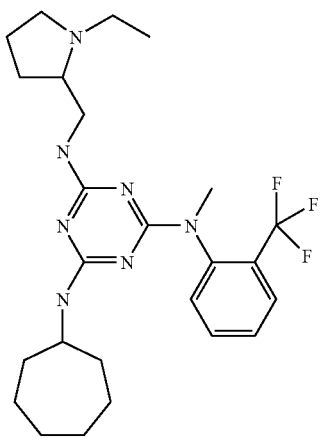 | N2-cycloheptyl-N4-[(1-ethyl-2-pyrrolidinyl)methyl]-N6-methyl-N6-[2-(trifluoromethyl)phenyl]-1,3,5-triazine-2,4,6-triamine |

TABLE 2-continued

Representative compounds of the present invention prepared by parallel synthethis reactions, including amine monomers, products, and characterization data

| 47 | 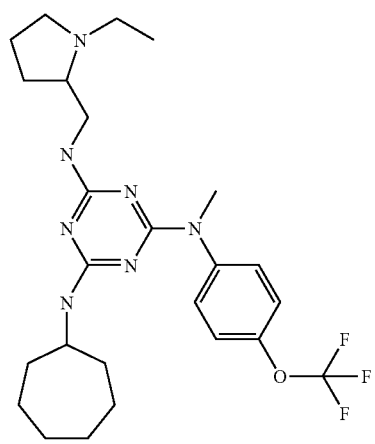 | N2-cycloheptyl-N4-[(1-ethyl-2-pyrrolidinyl)methyl]-N6-methyl-N6-[2-(trifluoromethoxy)phenyl]-1,3,5-triazine-2,4,6-triamine |
| --- | --- | --- |
| 48 | 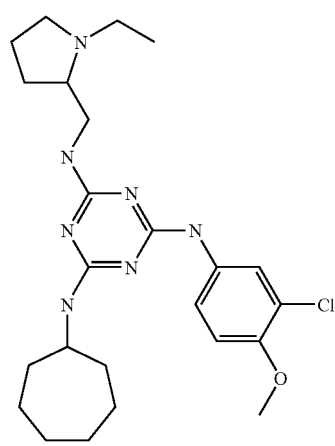 | N2-(3-chloro-4-methoxyphenyl)-N4-cycloheptyl-N6-[(1-ethyl-2-pyrrolidinyl)methyl]-1,3,5-triazine-2,4,6-triamine |
| 49 | 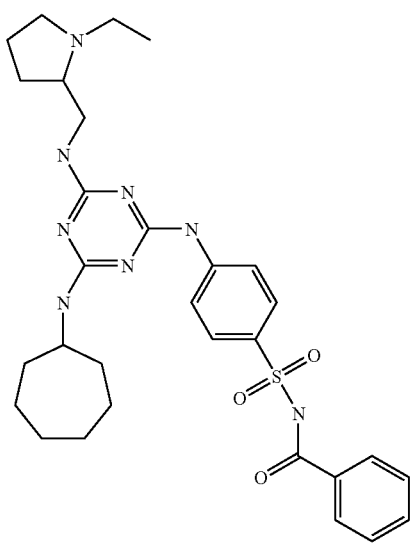 | N-benzoyl-4-[(4-(cycloheptylamino)-6-([(1-ethyl-2-pyrrolidinyl)methyl]amino}-1,3,5-triazin-2-yl)-amino]benzenesulfonamide |

TABLE 2-continued

Representative compounds of the present invention prepared by parallel synthethis reactions, including amine monomers, products, and characterization data

| 50 | 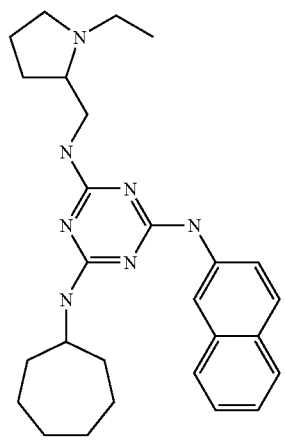 | N2-cycloheptyl-N4-[(1-ethyl-2-pyrrolidinyl)methyl]-N6-(2-naphthyl)-1,3,5-triazine-2,4,6-triamine |
| --- | --- | --- |
| 51 | 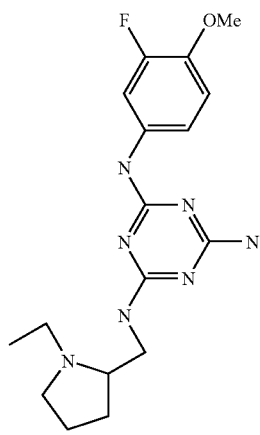 | $N^2$-ethyl-$N^4$-[(1-ethyl-2-pyrrolidinyl)methyl]-$N^6$-(3-fluoro-4-methoxyphenyl)-1,3,5-triazine-2,4,6-triamine |
| 52 | 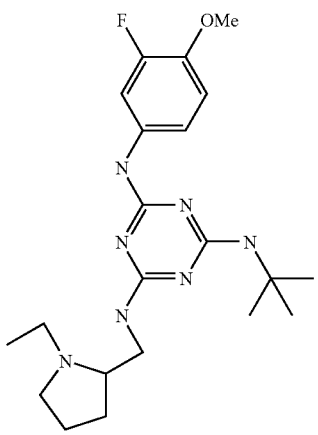 | $N^2$-(tert-butyl)-$N^4$-[(1-ethyl-2-pyrrolidinyl)methyl]-$N^6$-(3-fluoro-4-methoxyphenyl)-1,3,5-triazine-2,4,6-triamine |

TABLE 2-continued

Representative compounds of the present invention prepared by parallel synthethis reactions, including amine monomers, products, and characterization data 53 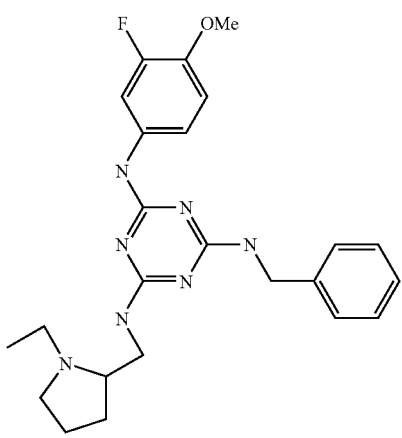 $N^2$-benzyl-$N^4$-[(1-ethyl-2-pyrrolidinyl)methyl]-$N^6$-(3-fluoro-4-methoxyphenyl)-1,3,5-triazine-2,4,6-triamine 54 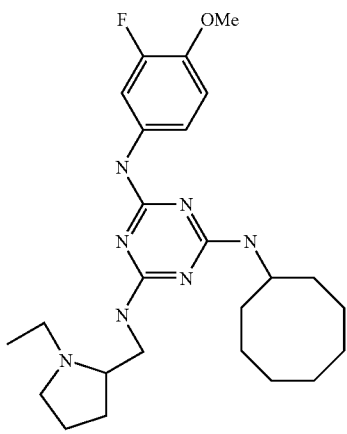 $N^2$-cyclooctyl-$N^4$-[(1-ethyl-2-pyrrolidinyl)methyl]-$N^6$-(3-fluoro-4-methoxyphenyl)-1,3,5-triazine-2,4,6-triamine 55 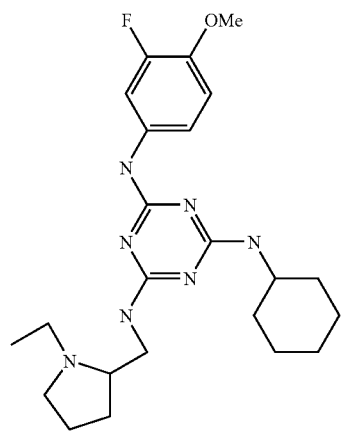 $N^2$-cyclohexyl-$N^4$-[(1-ethyl-2-pyrrolidinyl)methyl]-$N^6$-(3-fluoro-4-methoxyphenyl)-1,3,5-triazine-2,4,6-triamine

TABLE 2-continued

Representative compounds of the present invention prepared by parallel synthethis reactions, including amine monomers, products, and characterization data

| 56 | 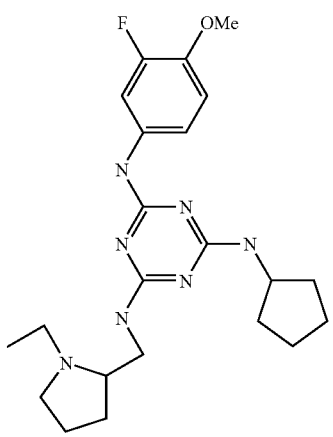 | $N^2$-cyclopentyl-$N^4$-[(1-ethyl-2-pyrrolidinyl)methyl]-$N^6$-(3-fluoro-4-methoxyphenyl)-1,3,5-triazine-2,4,6-triamine |
| --- | --- | --- |
| 57 | 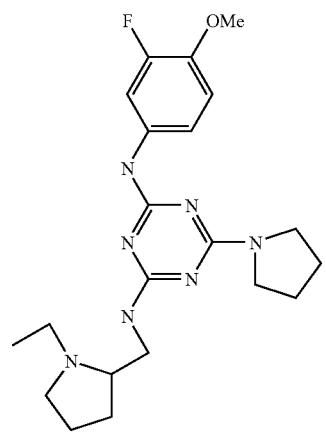 | $N^2$-[(1-ethyl-2-pyrrolidinyl)methyl]-$N^4$-(3-fluoro-4-methoxyphenyl)-6-(1-pyrrolidinyl)-1,3,5-triazine-2,4-diamine |
| 58 | 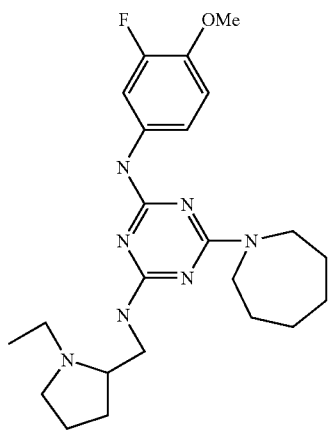 | $N^2$-[(1-ethyl-2-pyrrolidinyl)methyl]-$N^4$-(3-fluoro-4-methoxyphenyl)-6-hexahydro-1H-azepin-1-yl-1,3,5-triazine-2,4-diamine |

TABLE 2-continued

Representative compounds of the present invention prepared by parallel synthethis reactions, including amine monomers, products, and characterization data

| | | |
|---|---|---|
| 59 | 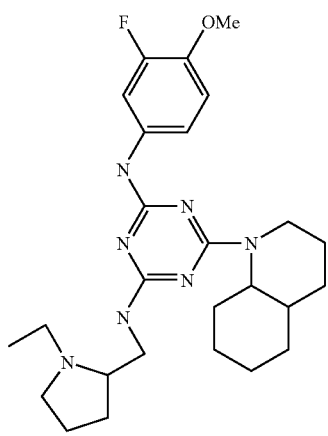 | N²-[(1-ethyl-2-pyrrolidinyl)methyl]-N⁴-(3-fluoro-4-methoxyphenyl)-6-octahydro-1(2H)-quinolinyl-1,3,5-triazine-2,4-diamine |
| 60 | 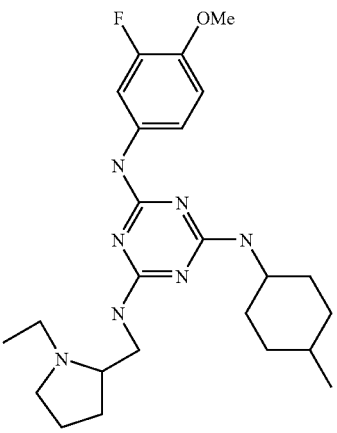 | N²-[(1-ethyl-2-pyrrolidinyl)methyl]-N⁴-(3-fluoro-4-methoxyphenyl)-N⁶-(4-methylcyclohexyl)-1,3,5-triazine-2,4,6-triamine |
| 61 | 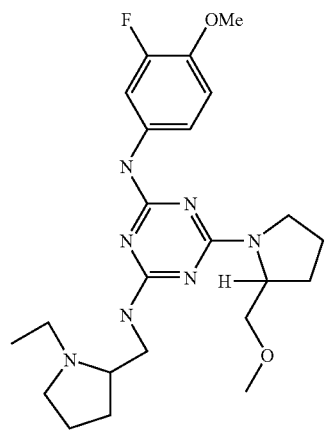 | N²-(1-ethyl-2-pyrrolidin-2-ylmethyl]-N⁴-(3-fluoro-4-methoxyphenyl)-6-((S)-2-methoxymethyl-pyrrolidin-1-yl)-1,3,5-triazine-2,4-diamine |

TABLE 2-continued

Representative compounds of the present invention prepared by parallel synthethis reactions, including amine monomers, products, and characterization data 62 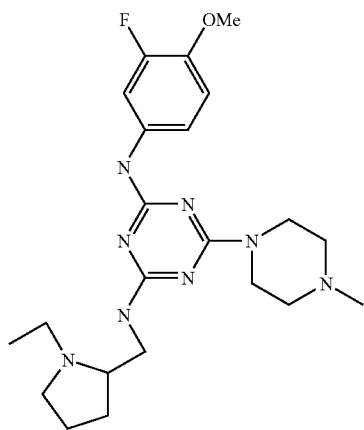 $N^2$-[(1-ethyl-2-pyrrolidinyl)methyl]-$N^4$-(3-fluoro-4-methoxyphenyl)-6-(4-methyl-1-piperazinyl)-1,3,5-triazine-2,4-diamine 63 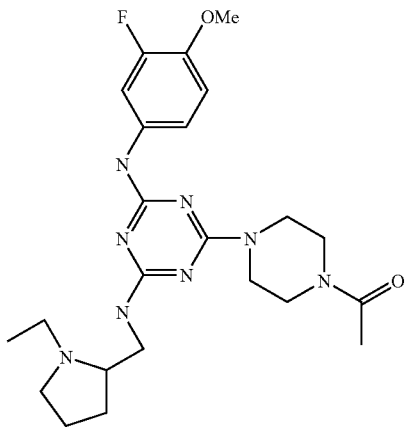 6-(4-acetyl-1-piperazinyl)-$N^2$-[(1-ethyl-2-pyrrolidinyl)methyl]-$N^4$-(3-fluoro-4-methoxyphenyl)-1,3,5-triazine-2,4-diamine 64 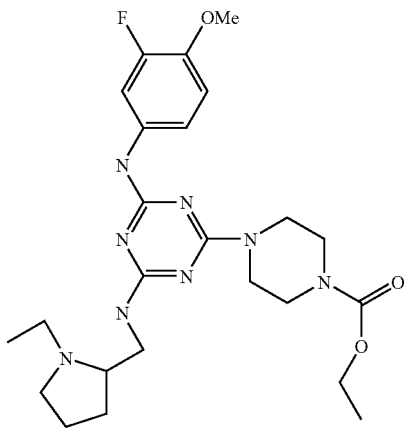 Ethyl 4-{4-([(1-ethyl-2-pyrrolidinyl)methyl]amino)-$N^6$-[(3-fluoro-4-methoxyphenyl)-amino]-1,3,5-triazin-2-yl}-1-piperazinecarboxylate TABLE 2-continued Representative compounds of the present invention prepared by parallel synthethis reactions, including amine monomers, products, and characterization data 65 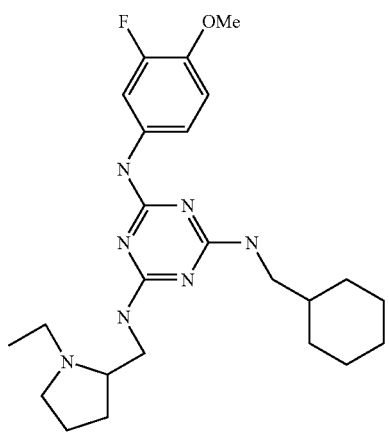 N²-(cylcohexylmethyl)-N⁴-[(1-ethyl-2-pyrrolidinyl)methyl]-N⁶-(3-fluoro-4-methoxyphenyl)-1,3,5-triazine-2,4,6-triamine 66 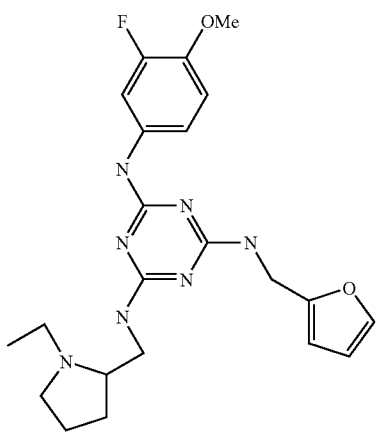 N²-[(1-ethyl-2-pyrrolidinyl)methyl]-N⁴-(3-fluoro-4-methoxyphenyl)-N⁶-(2-furylmethyl)-1,3,5-triazine-2,4,6-triamine 67 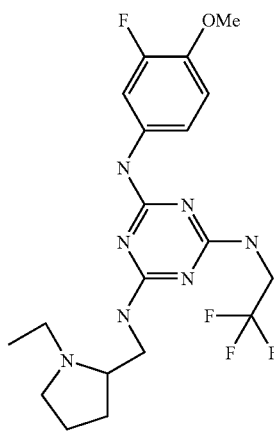 N²-[(1-ethyl-2-pyrrolidinyl)methyl]-N⁴-(3-fluoro-4-methoxyphenyl)-N⁶-(2,2,2-trifluoroethyl)-1,3,5-triazine-2,4,6-triamine TABLE 2-continued Representative compounds of the present invention prepared by parallel synthethis reactions, including amine monomers, products, and characterization data

| 68 | 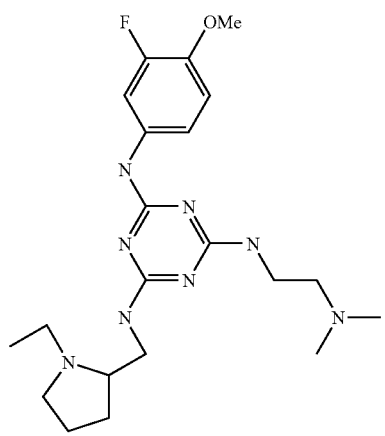 | $N^2$-[2-(dimethylamino)ethyl]-$N^4$-[(1-ethyl-2-pyrrolidinyl)methyl]-$N^6$-(3-fluoro-4-methoxyphenyl)-1,3,5-triazine-2,4,6-triamine |
| --- | --- | --- |
| 69 | 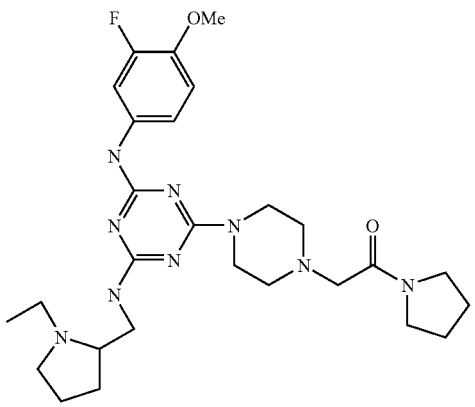 | $N^2$-[(1-ethyl-2-pyrrolidinyl)methyl]-$N^4$-(3-fluoro-4-methoxyphenyl)-$N^6$-(4-[2-oxo-2-(1-pyrrolidinyl)ethyl]-1-piperazinyl)-1,3,5-triazine-2,4-diamine |
| 70 | 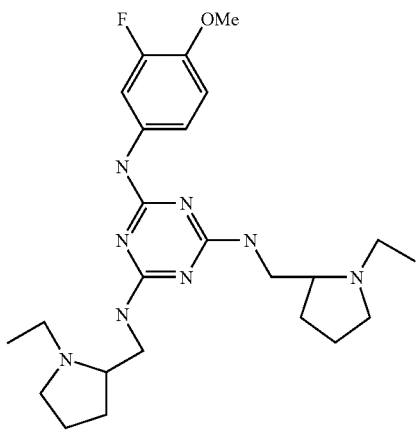 | $N^2,N^4$-bis[(1-ethyl-2-pyrrolidinyl)methyl]-$N^6$-(3-fluoro-4-methoxyphenyl)-1,3,5-triazine-2,4,6-triamine |

TABLE 2-continued

Representative compounds of the present invention prepared by parallel synthethis reactions, including amine monomers, products, and characterization data

| 71 | 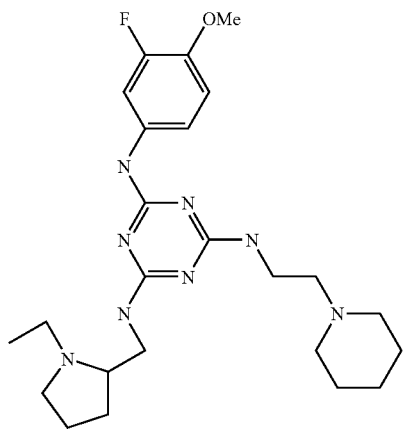 | $N^2$-[(1-ethyl-2-pyrrolidinyl)methyl]-$N^4$-(3-fluoro-4-methoxyphenyl)-$N^6$-[2-(1-piperidinyl)ethyl]-1,3,5-triazine-2,4,6-triamine |
| --- | --- | --- |
| 72 | 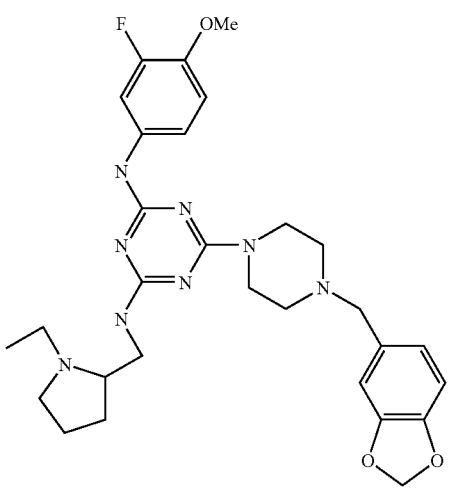 | $N^6$-[4-(1,3-benzodioxol-5-ylmethyl)-1-piperazinyl]-$N^2$-[(1-ethyl-2-pyrrolidinyl)methyl]-$N^4$-(3-fluoro-4-methoxyphenyl)-1,3,5-triazine-2,4-diamine |
| 73 | 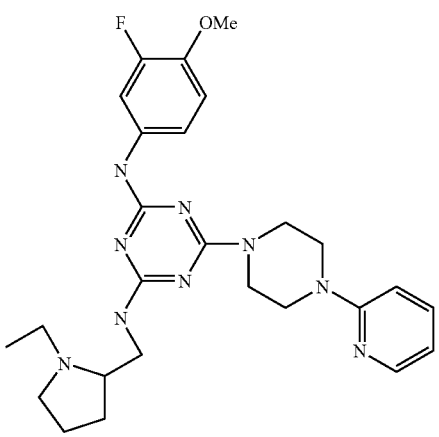 | $N^2$-[(1-ethyl-2-pyrrolidinyl)methyl]-$N^4$-(3-fluoro-4-methoxyphenyl)-$N^6$-[4-(2-pyridinyl)-1-piperazinyl]-1,3,5-triazine-2,4-diamine |

TABLE 2-continued

Representative compounds of the present invention prepared by parallel synthethis reactions, including amine monomers, products, and characterization data 74 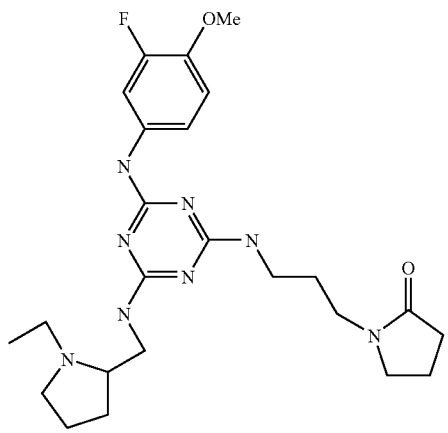 1-[3-((4-{[(1-ethyl-2-pyrrolidinyl)methyl[amino}-6-[(3-fluoro-4-methoxyphenyl)amino]-1,3,5-triazin-2-yl)amino)propyl]-2-pyrrolidinone 75 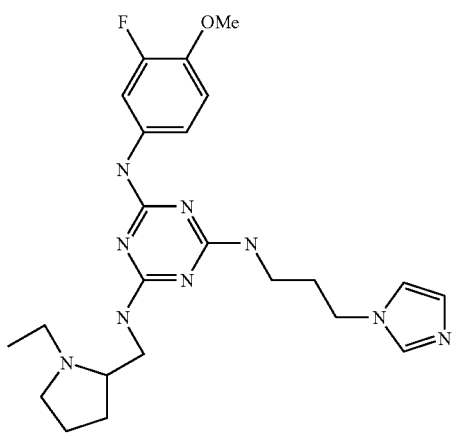 $N^2$-[(1-ethyl-2-pyrrolidinyl)methyl]-$N^4$-(3-fluoro-4-methoxyphenyl)-$N^6$-[3-(1H-imidazol-1-yl)propyl]-1,3,5-triazine-2,4,6-triamine 76 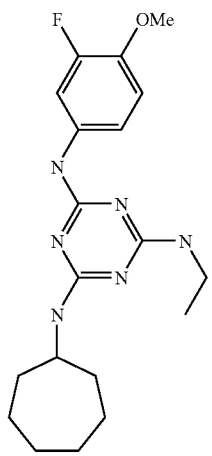 N2-cycloheptyl-N4-ethyl-N6-(3-fluoro-4-methoxyphenyl)-1,3,5-triazine-2,4,6-triamine TABLE 2-continued Representative compounds of the present invention prepared by parallel synthethis reactions, including amine monomers, products, and characterization data 77 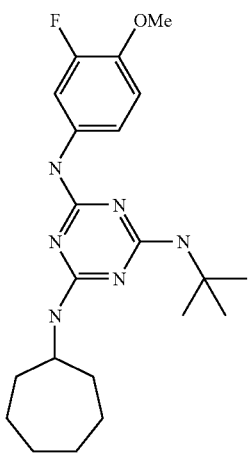 N2-(tert-butyl)-N4-cycloheptyl-N6-(3-fluoro-4-methoxyphenyl)-1,3,5-triazine-2,4,6-triamine 78 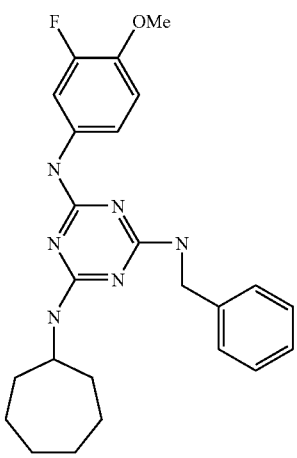 N2-benzyl-N4-cycloheptyl-N6-(3-fluoro-4-methoxyphenyl)-1,3,5-triazine-2,4,6-triamine 79 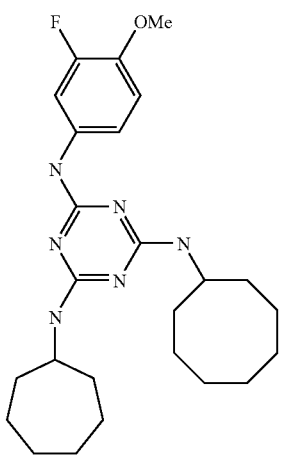 N2-cycloheptyl-N4-cyclooctyl-N6-(3-fluoro-4-methoxyphenyl)-1,3,5-triazine-2,4,6-triamine TABLE 2-continued Representative compounds of the present invention prepared by parallel synthethis reactions, including amine monomers, products, and characterization data

| 80 | 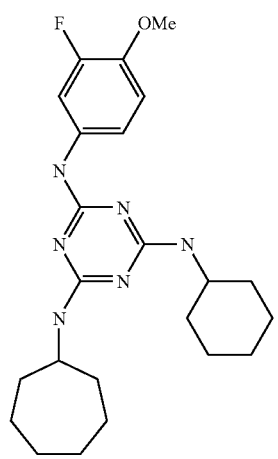 | N2-cycloheptyl-N4-cyclohexyl-N6-(3-fluoro-4-methoxyphenyl)-1,3,5-triazine-2,4,6-triamine |
| --- | --- | --- |
| 81 | 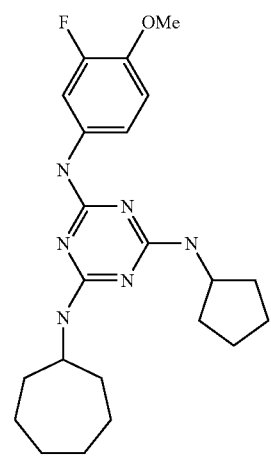 | N2-cycloheptyl-N4-cyclopentyl-N6-(3-fluoro-4-methoxyphenyl)-1,3,5-triazine-2,4,6-triamine |
| 82 | 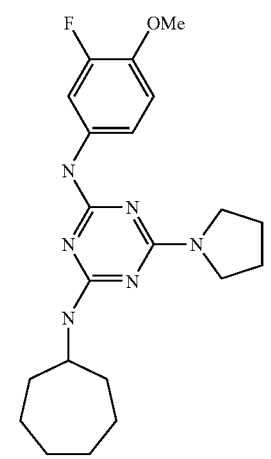 | N2-cycloheptyl-N4-(3-fluoro-4-methoxyphenyl)-6-(1-pyrrolidinyl)-1,3,5-triazine-2,4-diamine |

TABLE 2-continued

Representative compounds of the present invention prepared by parallel synthethis reactions, including amine monomers, products, and characterization data

| 83 | 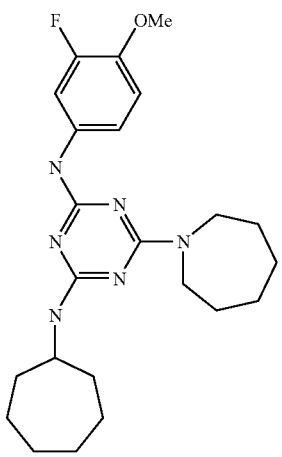 | N2-cycloheptyl-N4-(3-fluoro-4-methoxyphenyl)-6-hexahydro-1H-azepin-1-yl-1,3,5-triazine-2,4-diamine |
| --- | --- | --- |
| 84 | 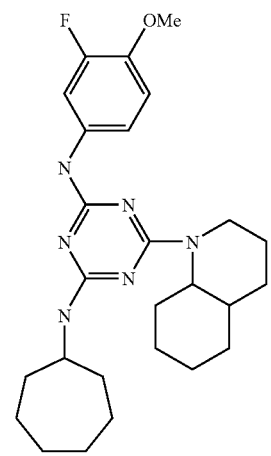 | N2-cycloheptyl-N4-(3-fluoro-4-methoxyphenyl)-6-octahydro-1(2H)-quinolinyl-1,3,5-triazine-2,4-diamine |
| 85 | 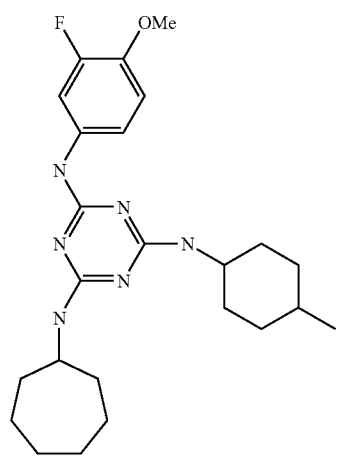 | N2-cycloheptyl-N4-(3-fluoro-4-methoxyphenyl)-N6-(4-methylcyclohexyl)-1,3,5-triazine-2,4,6-triamine |

TABLE 2-continued

Representative compounds of the present invention prepared by parallel synthethis reactions, including amine monomers, products, and characterization data

| 86 | 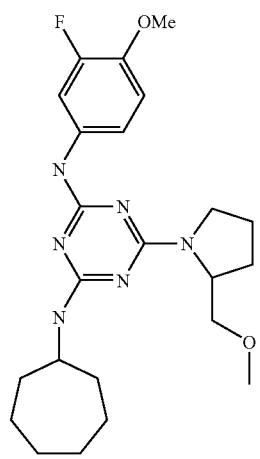 | N2-cycloheptyl-N4-(3-fluoro-4-methoxyphenyl)-6-[(2S)-2-(methoxymethyl)-1-pyrrolidinyl]-1,3,5-triazine-2,4-diamine |
| --- | --- | --- |
| 87 | 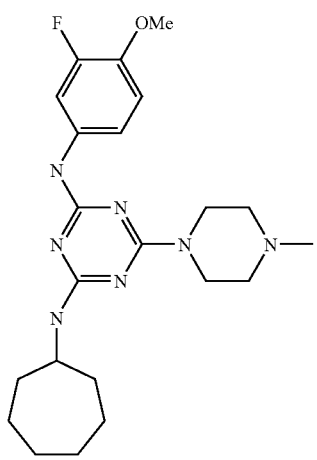 | N2-cycloheptyl-N4-(3-fluoro-4-methoxyphenyl)-6-[(4-methyl-1-piperazinyl)-1,3,5-triazine-2,4-diamine |
| 88 | 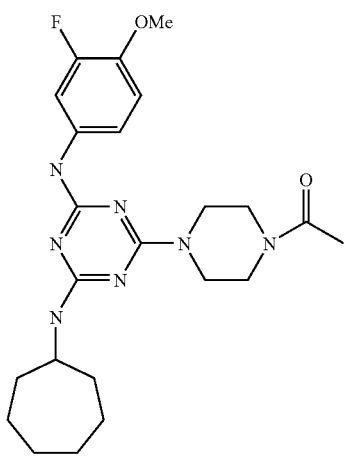 | 6-(4-acetyl-1-piperazinyl)-N2-cycloheptyl-N4-(3-fluoro-4-methoxyphenyl)-1,3,5-triazine-2,4-diamine |

TABLE 2-continued

Representative compounds of the present invention prepared by parallel synthethis reactions, including amine monomers, products, and characterization data

| 89 | 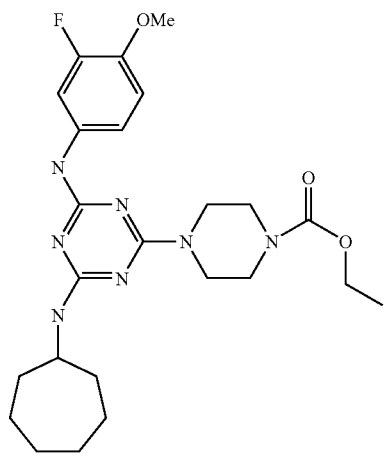 | ethyl-4-{4-cycloheptylamino-6-[(3-fluoro-methylphenyl)amino]-1,3,5-triazin-2-yl}-1-piperazinecarboxylate |
| 90 | 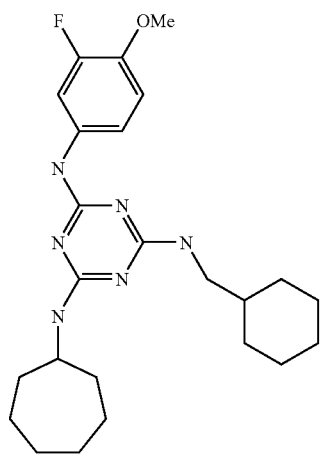 | N2-cycloheptyl-N4-(cyclohexylmethyl)-N6-(3-fluoro-4-methoxyphenyl)-1,3,5-triazine-2,4,6-triamine |
| 91 | 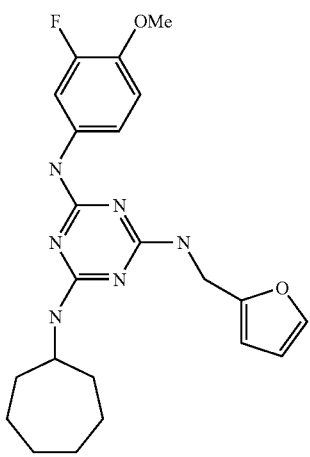 | N2-cycloheptyl-N4-(3-fluoro-4-methoxyphenyl)-N6-(2-furanylmethyl)-1,3,5-triazine-2,4,6-triamine |

TABLE 2-continued

Representative compounds of the present invention prepared by parallel synthethis reactions, including amine monomers, products, and characterization data 92 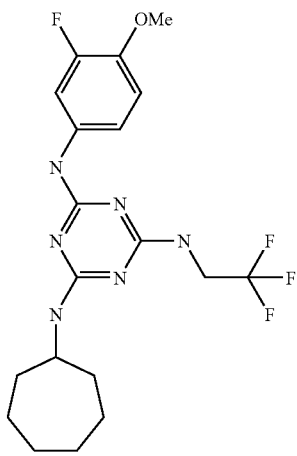 N2-cycloheptyl-N4-(3-fluoro-4-methoxyphenyl)-N6-(2,2,2-trifluoroethyl)-1,3,5-triazine-2,4,6-triamine 93 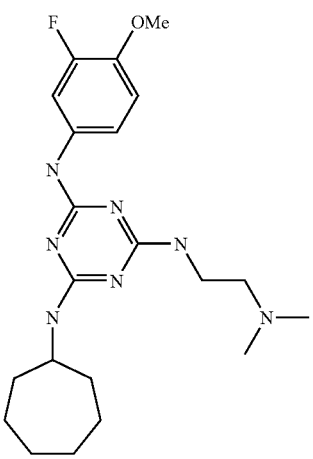 N2-cycloheptyl-N4-[2-(dimethylamino)ethyl]-N6-(3-fluoro-4-methoxyphenyl)-1,3,5-triazine-2,4,6-triamine 94 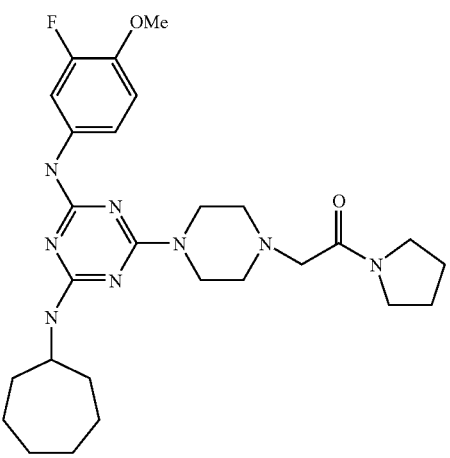 N2-cycloheptyl-N4-(3-fluoro-4-methoxyphenyl)-6-(4-[2-oxo-(1-pyrrolidinyl)ethyl]-1-piperazinyl)-1,3,5-triazine-2,4,6-triamine TABLE 2-continued Representative compounds of the present invention prepared by parallel synthethis reactions, including amine monomers, products, and characterization data

| | | |
|---|---|---|
| 95 | 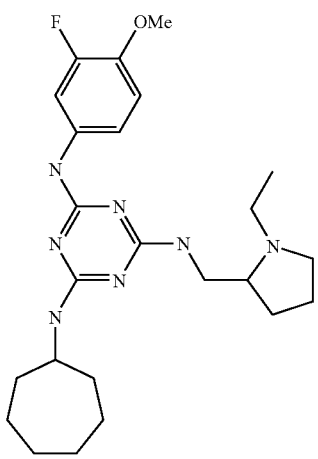 | N2-cycloheptyl-N4-[(1-ethyl-2-pyrrolidinyl)methyl]-N6-(3-fluoro-4-methoxyphenyl)-1,3,5-triazine-2,4,6-triamine |
| 96 | 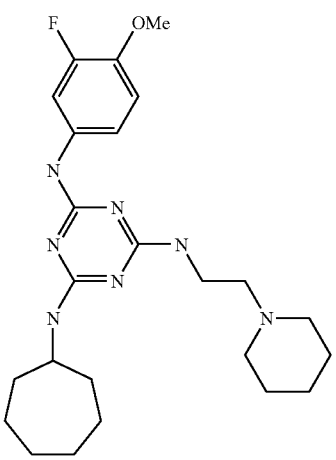 | N2-cycloheptyl-N4-(3-fluoro-4-methoxyphenyl)-N6-[2-(1-piperidinyl)ethyl]-1,3,5-triazine-2,4,6-triamine |
| 97 | 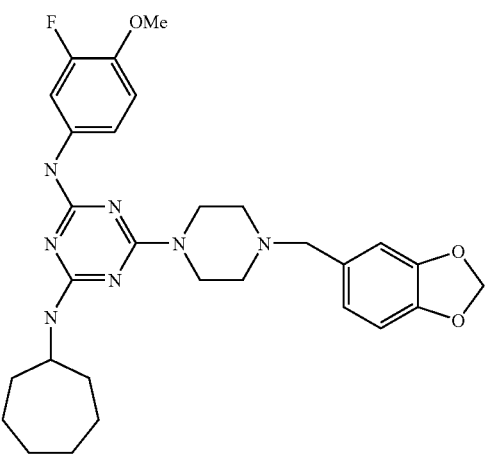 | 6-[4-(1,3-benzodioxol-5-ylmethyl) 1-piperazinyl]-N2-cycloheptyl-N4-(3-fluoro-4-methoxyphenyl)--1,3,5-triazine-2,4-diamine |

TABLE 2-continued

Representative compounds of the present invention prepared by parallel synthethis reactions, including amine monomers, products, and characterization data

| 98 | [structure] | N2-cycloheptyl-N4-(3-fluoro-methoxyphenyl)-6-[4-(2-pyridinyl)-1-piperazinyl]-1,3,5-triazine-2,4,6-triamine |
| 99 | [structure] | 1-[3-((4-(cycloheptylamino)-6-[(3-fluoro-4-methoxyophenyl)amino]-1,3,5-triazin-2-yl)amino)propyl]-2-pyrrolidinone |
| 100 | [structure] | N2-cycloheptyl-N4-(3-fluoro-methoxyphenyl)-N6-[3-(1H-imidazol-1-yl)propyl]-1,3,5-triazine-2,4,6-triamine |

| Cmpd. No. | Synthetic Procedure | LC-MS (Calc'd MW) Observed MW (M + H) | LC Purity | Yield Based on Purity | Purification Method |
|---|---|---|---|---|---|
| 1 | Parallel synthethis method A | (538) 540.4 | 63 | 23 | ISCO |
| 2 | Parallel synthethis method A | (493) 494.3 | 54 | 18 | ISCO |
| 3 | Parallel synthethis method A | (460) 461.5 | 95 | 25 | ISCO |
| 4 | Parallel synthethis method A | (460) 461.4 | 97 | 26 | ISCO |

TABLE 2-continued

Representative compounds of the present invention prepared by parallel synthethis reactions, including amine monomers, products, and characterization data

| | | | | | |
|---|---|---|---|---|---|
| 5 | Parallel synthethis method A | (460) 461.4 | 98 | 61 | ISCO |
| 6 | Parallel synthethis method A | (487) 488.5 | 94 | 39 | ISCO |
| 7 | Parallel synthethis method A | (478) 478.3 | 94 | 53 | ISCO |
| 8 | Parallel synthethis method A | 445 (446.3) | 98 | 55 | ISCO |
| 9 | Parallel synthethis method A | (493) 494.3 | 96 | 40 | ISCO |
| 10 | Parallel synthethis method A | (493) 426.4 | 90 | 37 | ISCO |
| 11 | Parallel synthethis method A | (434) 435.5 | 76 | 64 | none |
| 12 | Parallel synthethis method A | (444) 444.3 | 76 | 69 | none |
| 13 | Parallel synthethis method A | (488) 488.4 | 77 | 70 | none |
| 14 | Parallel synthethis method A | (481) 482.5 | 96 | 46 | ISCO |
| 15 | Parallel synthethis method A | (485) 486.5 | 75 | 69 | none |
| 16 | Parallel synthethis method A | (427) 428.3 | 78 | 75 | none |
| 17 | Parallel synthethis method A | (444) 444.3 | 77 | 74 | none |
| 18 | Parallel synthethis method A | (488) 488.4 | 82 | 75 | none |
| 19 | Parallel synthethis method A | (481) 482.4 | 98 | 45 | ISCO |
| 20 | Parallel synthethis method A | (427) 426.4 | 60 | 23 | ISCO |
| 21 | Parallel synthethis method A | (444) 444.3 | 53 | 26 | ISCO |
| 22 | Parallel synthethis method A | (488) 490.3 | 51 | 17 | ISCO |
| 23 | Parallel synthethis method A | (453) 454.4 | 16 | 4 | ISCO |
| 24 | Parallel synthethis method A | (467) 454.4 | 91 | 30 | ISCO |
| 25 | Parallel synthethis method A | (452) 453.5 | 67 | 17 | ISCO |
| 26 | Parallel synthethis method A | (515) 515.5 | 91 | 46 | ISCO |
| 27 | Parallel synthethis method A | (494) 495.4 | 92 | 41 | ISCO |
| 28 | Parallel synthethis method A | (507) 508.5 | 4 | 0.004 | none |
| 29 | Parallel synthethis method A | (466) 467.3 | 91 | 26 | ISCO |
| 30 | Parallel synthethis method A | (466) 467.4 | 100 | 38 | ISCO |
| 31 | Parallel synthethis method A | (439) 440.4 | 96 | 42 | ISCO |
| 32 | Parallel synthethis method A | (453) 454.2 | 97 | 47 | ISCO |
| 33 | Parallel synthethis method A | (455) 456.4 | 93 | 49 | ISCO |
| 34 | Parallel synthethis method A | (410) 411.3 | 27 | 7 | ISCO |
| 35 | Parallel synthethis method A | (423) | 72 | 76 | none |
| 36 | Parallel synthethis method A | (501) 502.3 | 100 | 46 | ISCO |
| 37 | Parallel synthethis method A | (423) 424.4 | 86 | 46 | ISCO |
| 38 | Parallel synthethis method A | (423) 424.3 | 98 | 44 | ISCO |
| 39 | Parallel synthethis method A | (472) 473.3 | 63 | 16 | ISCO |
| 40 | Parallel synthethis method A | (458) 458.5 | 98 | 42 | ISCO |
| 41 | Parallel synthethis method A | (462) 463.4 | 97 | 45 | ISCO |
| 42 | Parallel synthethis method A | (543) 454.4 | 89 | 36 | ISCO |
| 43 | Parallel synthethis method A | (459) 460.3 | 73 | 74 | none |
| 44 | Parallel synthethis method A | (448) 449.3 | 85 | 76 | none |
| 45 | Parallel synthethis method A | (458) 458.5 | 98 | 37 | ISCO |
| 46 | Parallel synthethis method A | (491) 492.3 | 82 | 21 | ISCO |
| 47 | Parallel synthethis method A | (507) 508.3 | 100 | 41 | ISCO |
| 48 | Parallel synthethis method A | (474) 474.3 | 93 | 51 | ISCO |
| 49 | Parallel synthethis method A | (592) 593.4 | 14 | 2 | none |
| 50 | Parallel synthethis method A | (459) 460.4 | 83 | 36 | ISCO |
| 51 | Parallel synthethis method B | (389) 390.2 | 48 | 36 | none |
| 52 | Parallel synthethis method B | (417) 418.4 | 38 | 28 | none |
| 53 | Parallel synthethis method B | (451) 452.3 | 87 | 75 | none |
| 54 | Parallel synthethis method B | (471) 472.4 | 83 | 66 | none |
| 55 | Parallel synthethis method B | (443) 444.3 | 75 | 80 | none |
| 56 | Parallel synthethis method B | (429) 430.3 | 79 | 75 | none |
| 57 | Parallel synthethis method B | (415) 416.3 | 84 | 45 | ISCO |
| 58 | Parallel synthethis method B | (443) 444.4 | 90 | 51 | ISCO |
| 59 | Parallel synthethis method B | (483) 484.5 | 86 | 47 | ISCO |
| 60 | Parallel synthethis method B | 457 (458.4) | 88 | 50 | ISCO |
| 61 | Parallel synthethis method B | (459) 460.4 | 81 | 36 | ISCO |
| 62 | Parallel synthethis method B | (444) 445.3 | 30 | 10 | none |
| 63 | Parallel synthethis method B | 472 (473.3) | 83 | 43 | ISCO |
| 64 | Parallel synthethis method B | (502) 503.2 | 75 | 74 | none |
| 65 | Parallel synthethis method B | (457) 458.4 | 76 | 77 | none |
| 66 | Parallel synthethis method B | (441) 442.2 | 77 | 70 | none |
| 67 | Parallel synthethis method B | (443) 444.1 | 77 | 69 | none |
| 68 | Parallel synthethis method B | (432) 433.5 | 6 | 2 | none |
| 69 | Parallel synthethis method B | (541) 542.4 | 78 | 39 | ISCO |
| 70 | Parallel synthethis method B | (472) 473.3 | 63 | 20 | ISCO |
| 71 | Parallel synthethis method B | (472) 473.3 | 67 | 28 | ISCO |
| 72 | Parallel synthethis method B | (564) 565.4 | 87 | 83 | none |
| 73 | Parallel synthethis method B | (507) 508.3 | 86 | 41 | ISCO |
| 74 | Parallel synthethis method B | (486) 487.5 | 85 | 31 | ISCO |
| 75 | Parallel synthethis method B | (469) 470.3 | 90 | 38 | ISCO |
| 76 | Parallel synthethis method C | (374) 375.3 | 85 | 18 | preparative HPLC |
| 77 | Parallel synthethis method C | (402) 403.4 | 81 | 3 | preparative HPLC |
| 78 | Parallel synthethis method C | (436) 436.9 | 96 | 15 | preparative HPLC |
| 79 | Parallel synthethis method C | (456) 457.3 | 96 | 5 | preparative HPLC |
| 80 | Parallel synthethis method C | (428) 429.3 | 100 | 10 | preparative HPLC |

TABLE 2-continued

Representative compounds of the present invention prepared by parallel synthethis reactions, including amine monomers, products, and characterization data

| 81 | Parallel synthethis method C | (414) 415.2 | 89 | 26 | preparative HPLC |
|---|---|---|---|---|---|
| 82 | Parallel synthethis method C | (400) 400.9 | 98 | 22 | preparative HPLC |
| 83 | Parallel synthethis method C | (428) 429 | 96 | 5 | preparative HPLC |
| 84 | Parallel synthethis method C | (468) 469.3 | 67 | 21 | preparative HPLC |
| 85 | Parallel synthethis method C | (442) 443.3 | 64 | 4 | preparative HPLC |
| 86 | Parallel synthethis method C | (444) 444.9 | 100 | 17 | preparative HPLC |
| 87 | Parallel synthethis method C | (429) 430.3 | 94 | 13 | preparative HPLC |
| 88 | Parallel synthethis method C | (457) Wrong MW observed | 100 | compound not observed after prep HPLC | preparative HPLC |
| 89 | Parallel synthethis method C | (487) 488.3 | 97 | 4 | preparative HPLC |
| 90 | Parallel synthethis method C | (442) | 100 | 16 | preparative HPLC |
| 91 | Parallel synthethis method C | (426) 426.9 | 59 | 31 | preparative HPLC |
| 92 | Parallel synthethis method C | (428) 352.1 | 93 | 1 | preparative HPLC |
| 93 | Parallel synthethis method C | (417) 418.3 | 76 | 11 | preparative HPLC |
| 94 | Parallel synthethis method C | (526) 527.3 | 27 | 15 | preparative HPLC |
| 95 | Parallel synthethis method C | (457) 458.4 | 80 | 24 | preparative HPLC |
| 96 | Parallel synthethis method C | (457) 458.4 | 86 | 21 | preparative HPLC |
| 97 | Parallel synthethis method C | (549) 493.2 | 94 | 21 | preparative HPLC |
| 98 | Parallel synthethis method C | (492) Incorrect MW observed | 70 | compound not observed after prep HPLC | preparative HPLC |
| 99 | Parallel synthethis method C | (471) 472.3 | 96 | 29 | preparative HPLC |
| 100 | Parallel synthethis method C | (454) 455.3 | 94 | 24 | preparative HPLC |

TABLE 3

Triazine compounds active in anti-proliferation assay (perlecan), generally useful in treating cardiovascular disorders associated with

| Patent # | STRUCTURE | CAS NAME | Activity (note 1) | Avg IC-50 |
|---|---|---|---|---|
| 160 | 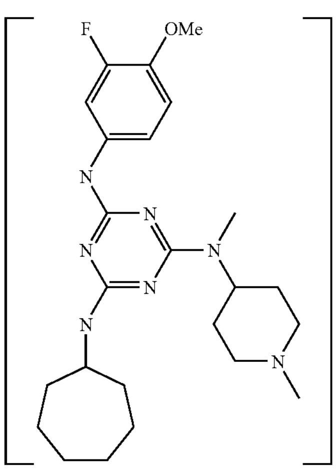 | HCl<br>N2-cycloheptyl-N4-(3-fluoro-4-methoxy-phenyl)-N6-methyl-N6-(1-methyl-piperidin-4-yl)-1,3,5-triazine-2,4,6-triamine hydrogen chloride | + + | 4–5 |

TABLE 3-continued

Triazine compounds active in anti-proliferation assay (perlecan),
generally useful in treating cardiovascular disorders associated with

| Patent # | STRUCTURE | CAS NAME | Activity (note 1) | Avg IC-50 |
|---|---|---|---|---|
| 95 | 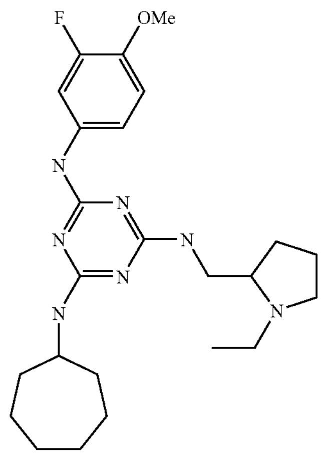 | N2-cycloheptyl-N4-(1-ethyl-pyrrolidin-2-ylmethyl)-N6-(3-fluoro-4-methoxy-phenyl)-1,3,5-triazine-2,4,6-triamine | + | 7.3 |
| 26 | 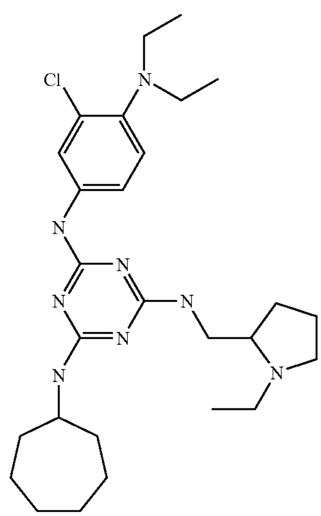 | N2-(3-chloro-4-diethylamino-phenyl)-N4-cycloheptyl-N6-(1-ethyl-pyrrolidin-2-ylmethyl)-1,3,5-triazine-2,4,6-triamine | + | 7.73 |
| 139 | 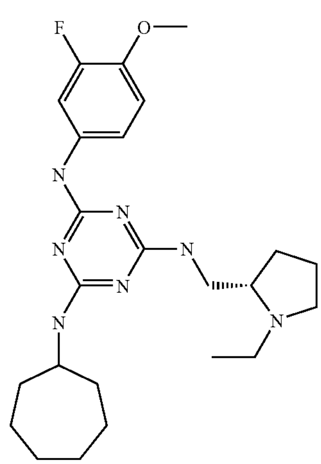 | N2-cycloheptyl-N4-((S)-1-ethyl-pyrrolidin-2-ylmethyl)-N6-(3-fluoro-4-methoxy-phenyl)-1,3,5-triazine-2,4,6-triamine | ++ | 4–5 |

TABLE 3-continued

Triazine compounds active in anti-proliferation assay (perlecan),
generally useful in treating cardiovascular disorders associated with

| Patent # | STRUCTURE | CAS NAME | Activity (note 1) | Avg IC-50 |
|---|---|---|---|---|
| 140 | 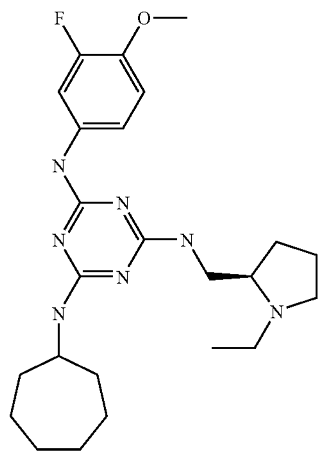 | N2-cycloheptyl-N4-((R)-1-ethyl-pyrrolidin-2-ylmethyl)-N6-(3-fluoro-4-methoxy-phenyl)-1,3,5-triazine-2,4,6-triamine | + + | 4–5 |
| 163 | 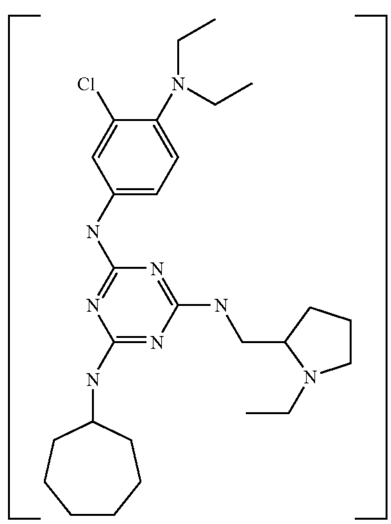 | N2-(3-chloro-4-diethylamino-phenyl)-N4-cycloheptyl-N6-(1-ethyl-pyrrolidin-2-ylmethyl)-1,3,5-triazine-2,4,6-triamine hydrogen chloride · HCl | + | 8–10 |
| 123 | 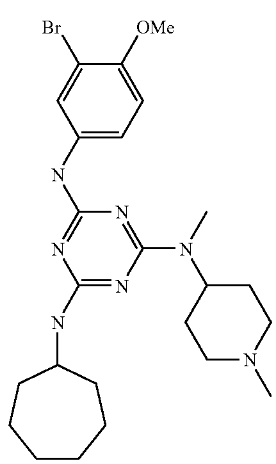 | N2-(3-bromo-4-methoxy-phenyl)-N4-cycloheptyl-N6-methyl-N6-(1-methyl-piperidin-4-yl)-1,3,5-triazine-2,4,6-triamine | + | |

TABLE 3-continued

Triazine compounds active in anti-proliferation assay (perlecan),
generally useful in treating cardiovascular disorders associated with

| Patent # | STRUCTURE | CAS NAME | Activity (note 1) | Avg IC-50 |
|---|---|---|---|---|
| 170 | 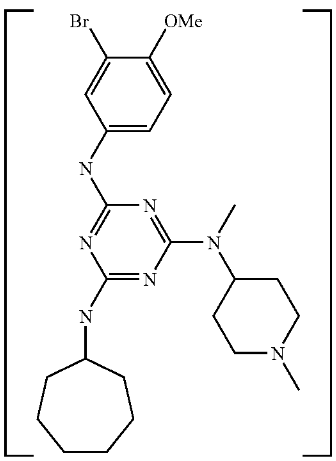 | HCl<br>N2-(3-bromo-methoxy-phenyl)-N4-cycloheptyl-N6-methyl-N6-(1-methyl-piperidin-4-yl)-1,3,5-triazine-2,4,6-triamine hydrogen chloride | + | 8–9 |
| 137 | 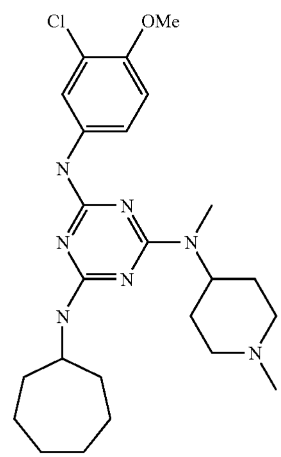 | N2-(3-chloro-4-methoxy-phenyl)-N4-cycloheptyl-N6-methyl-N6-(1-methyl-piperidin-4-yl)-1,3,5-triazine-2,4,6-triamine | + + | 4–5 |
| 103 | 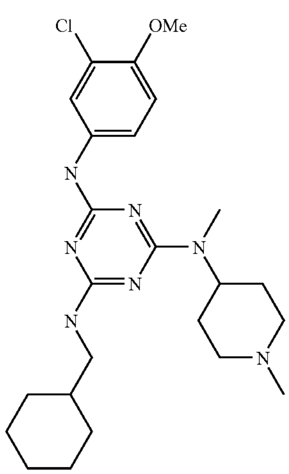 | N2-(3-chloro-4-methoxy-phenyl)-N4-cyclohexylmethyl-N6-methyl-N6-(1-methyl-piperidin-4-yl)-1,3,5-triazine-2,4,6-triamine | + | ~7 uM |

TABLE 3-continued

Triazine compounds active in anti-proliferation assay (perlecan),
generally useful in treating cardiovascular disorders associated with

| Patent # | STRUCTURE | CAS NAME | Activity (note 1) | Avg IC-50 |
|---|---|---|---|---|
| 105 | 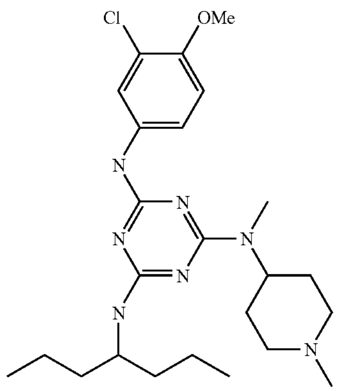 | N2-(3-chloro-4-methoxy-phenyl)-N4-methyl-N4-(1-methyl-piperidin-4-yl)-N6-(1-propyl-butyl)-1,3,5-triazine-2,4,6-triamine | + | ~7 um |
| 148 | 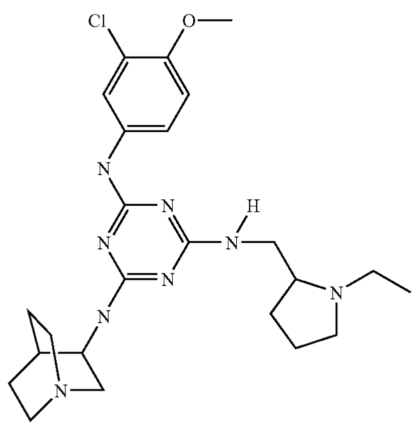 | N2-(1-aza-bicyclo[2.2.2]oct-3-yl)-N4-(3-chloro-4-methoxy-phenyl)-N6-(1-ethyl-pyrrolidin-2-ylmethyl)-1,3,5-triazine-2,4,6-triamine | + + | less than 5 uM |
| 146 | 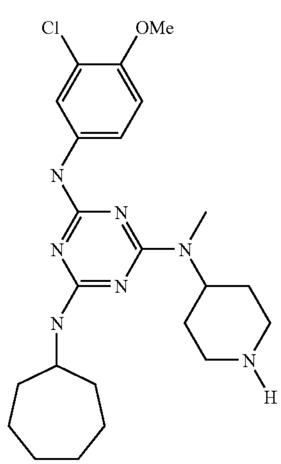 | $N^2$-(3-chloro-4-methoxy-phenyl)-$N^4$-cycloheptyl-$N^6$-methyl-$N^6$-piperidin-4-yl-1,3,5-triazine-2,4,6-triamine | + + + | ~2.2 |

TABLE 3-continued

Triazine compounds active in anti-proliferation assay (perlecan),
generally useful in treating cardiovascular disorders associated with

| Patent # | STRUCTURE | CAS NAME | Activity (note 1) | Avg IC-50 |
|---|---|---|---|---|
| 138 | 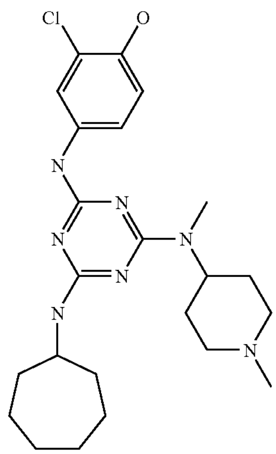 | 2-chloro-4-{4-cycloheptylamino-6-[methyl-(1-methyl-piperidin-4-yl-amino]-1,3,5-triazin-2-ylamino}-phenol | + + | 4.03 uM |
| 135 | 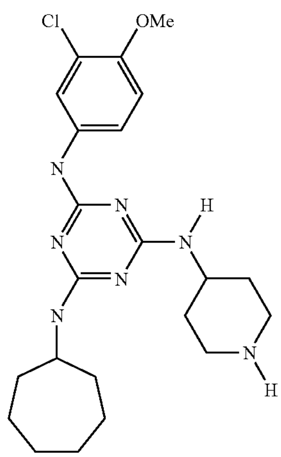 | N2-(3-chloro-4-methoxy-phenyl)-N4-cycloheptyl-N6-piperidin-4-yl-1,3,5-triazine-2,4,6-triamine | + + | 5.83 uM |
| 169 | · Succinic Acid | N2-cycloheptyl-N4-(3-fluoro-4-methoxy-phenyl)-N6-methyl-N6-(1-methyl-piperidin-4-yl)-1,3,5-triazine-2,4,6-triamine succinate | + | 7.2 uM |

TABLE 3-continued

Triazine compounds active in anti-proliferation assay (perlecan),
generally useful in treating cardiovascular disorders associated with

| Patent # | STRUCTURE | CAS NAME | Activity (note 1) | Avg IC-50 |
|---|---|---|---|---|
| 167 | 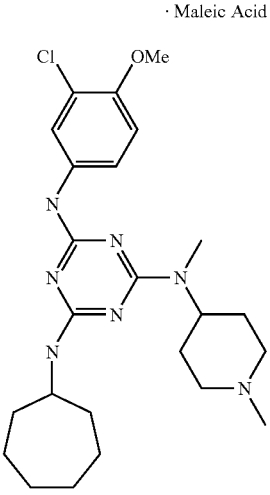 · Maleic Acid | N2-cycloheptyl-N4-(3-fluoro-4-methoxy-phenyl)-N6-methyl-N6-(1-methyl-piperidin-4-yl)-1,3,5-triazine-2,4,6-triamine maleate | + | 6.8 uM |
| 159 | 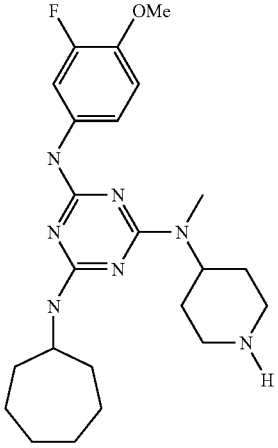 | $N^2$-Cycloheptyl-$N^4$-(3-fluoro-4-methoxy-phenyl)-$N^6$-methyl-$N^6$-piperidin-4-yl-1,3,5-triazine-2,4,6-triamine | + + | 5.7–6.9 uM |
| 125 | 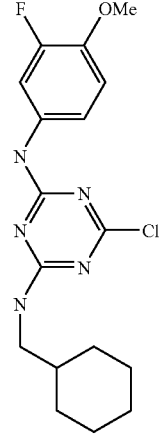 | 6-chloro-N-cyclohexylmethyl-N'-(3-fluoro-4-methoxy-phenyl)-[1,3,5]triazine-2,4-diamine | + | 10 uM |

TABLE 3-continued

Triazine compounds active in anti-proliferation assay (perlecan),
generally useful in treating cardiovascular disorders associated with

| Patent # | STRUCTURE | CAS NAME | Activity (note 1) | Avg IC-50 |
|---|---|---|---|---|
| 127 | 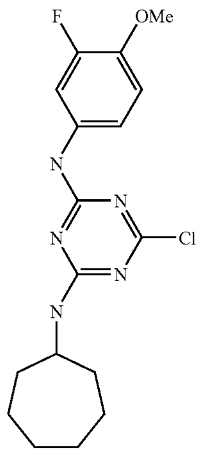 | 6-Chloro-N-cyclohexylheptyl-N'-(3-fluoro-4-methoxy-phenyl)-[1,3,5]triazine-2,4-diamine | + | 10 uM |

NOTE 1:
The activity scale is as follows (inclusive): (1) "+ + +" = IC50 < 3 uM; (2) "+ +" = IC50 is 3–7 uM; (3) "+" = IC50 is > 7 uM.

TABLE 4A

| Patent Number | STRUCTURE | Name Generated by Autonom TM | Toxicity |
|---|---|---|---|
| 93 | 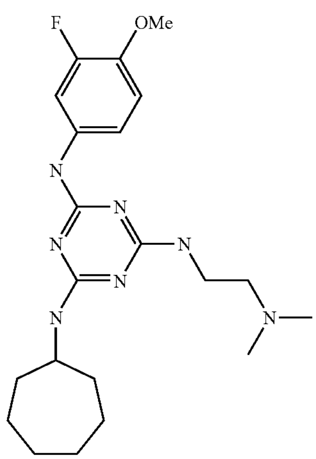 | N2-cycloheptyl-N4-[2-(dimethylamino)ethyl]-N6-(3-fluoro-4-methoxyphenyl)-1,3,5-triazine-2,4,6-triamine | toxic |

TABLE 4A-continued

| Patent Number | STRUCTURE | Name Generated by Autonom TM | Toxicity |
|---|---|---|---|
| 3 | 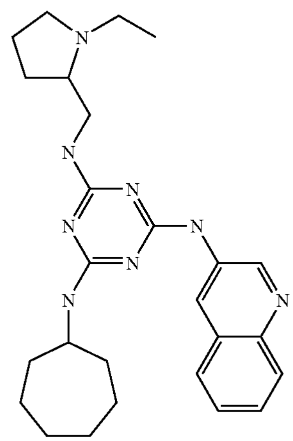 | N2-cycloheptyl-N4-[(1-ethyl-2-pyrrolidinyl)methyl]-N6-(3-quinolinyl)-1,3,5-triazine-2,4,6-triamine | toxic |
| 5 | 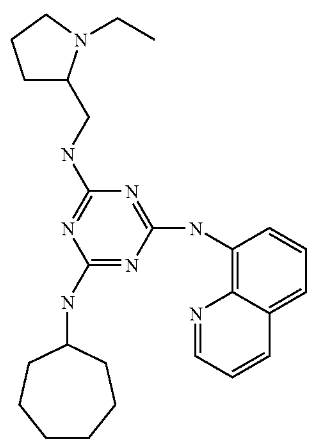 | N2-cycloheptyl-N4-[(1-ethyl-2-pyrrolidinyl)methyl]-N6-(8-quinolinyl)-1,3,5-triazine-2,4,6-triamine | toxic |
| 6 | 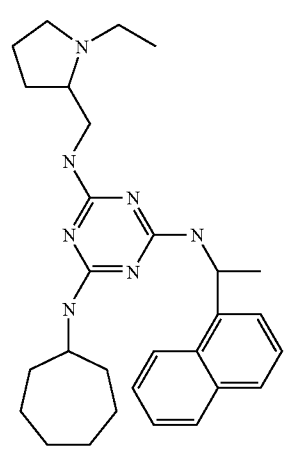 | N2-cycloheptyl-N4-[(1-ethyl-2-pyrrolidinyl)methyl]-N6-[1-(2-naphthyl)ethyl]-1,3,5-triazine-2,4,6-triamine | toxic |

TABLE 4A-continued

| Patent Number | STRUCTURE | Name Generated by Autonom TM | Toxicity |
|---|---|---|---|
| 7 | 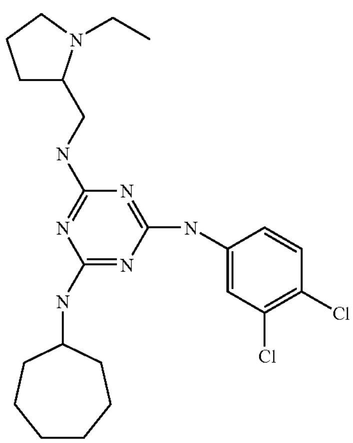 | N2-cycloheptyl-N4-(3,4-dichlorophenyl)-N6-[(1-ethyl-2-pyrrolidinyl)methyl]-1,3,5-triazine-2,4,6-triamine | toxic |
| 8 | 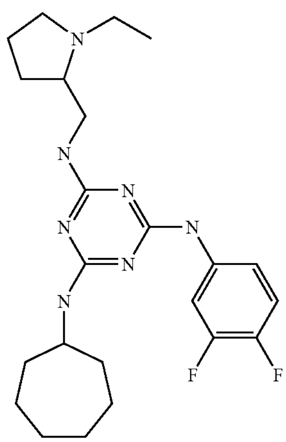 | N2-cycloheptyl-N4-(3,4-difluorophenyl)-N6-[(1-ethyl-2-pyrrolidinyl)methyl]-1,3,5-triazine-2,4,6-triamine | toxic |
| 9 | 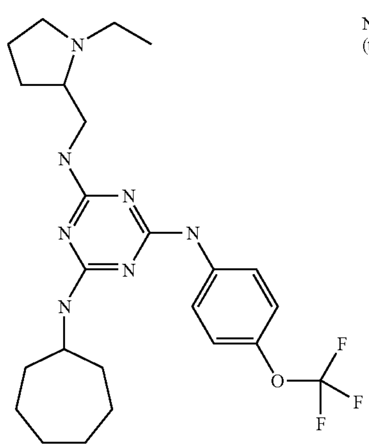 | N2-cycloheptyl-N4-[(1-ethyl-2-pyrrolidinyl)methyl]-N6-[4-(trifluoromethoxy)phenyl]-1,3,5-triazine-2,4,6-triamine | toxic |

TABLE 4A-continued

| Patent Number | STRUCTURE | Name Generated by Autonom TM | Toxicity |
|---|---|---|---|
| 12 | 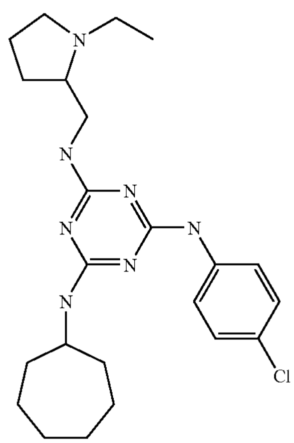 | N2-(4-chlorophenyl)-N4-cycloheptyl-N6-[(1-ethyl-2-pyrrolidinyl)methyl]-1,3,5-triazine-2,4,6-triamine | toxic |
| 13 | 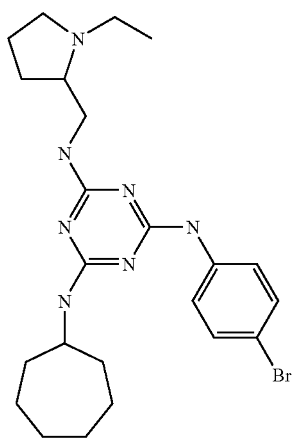 | N2-(4-bromophenyl)-N4-cycloheptyl-N6-[(1-ethyl-pyrrolidinyl)methyl]-1,3,5-triazine-2,4,6-triamine | toxic |
| 14 | 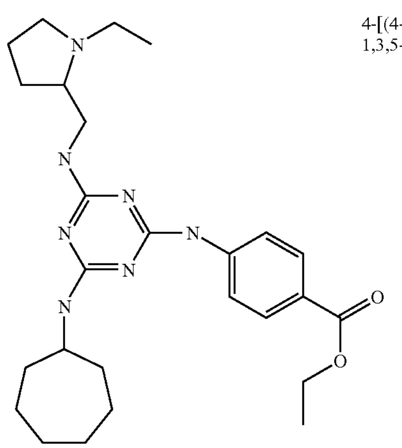 | 4-[(4-(cycloheptylamino)-6-{[(1-ethyl-2-pyrrolidinyl)-methyl]amino}-1,3,5-triazine-2,4,6-triamine | toxic |

TABLE 4A-continued

| Patent Number | STRUCTURE | Name Generated by Autonom TM | Toxicity |
|---|---|---|---|
| 16 | 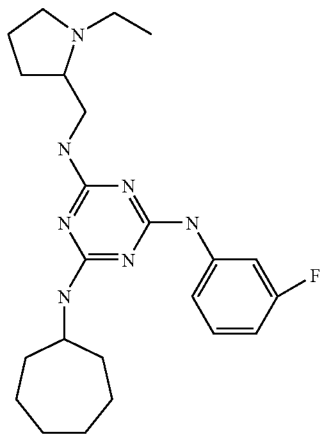 | N2-cycloheptyl-N4-[(1-ethyl-2-pyrrolidinyl)methyl]-N6-(3-fluorophenyl)-1,3,5-triazine-2,4,6-triamine | toxic |
| 21 | 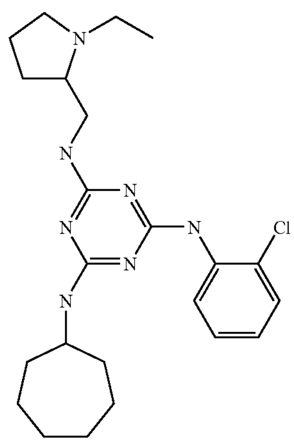 | N2-(2-chlorophenyl)-N4-cycloheptyl-N6-[(1-ethyl-2-pyrrolidinyl)methyl]-1,3,5-triazine-2,4,6-triamine | toxic |
| 22 | 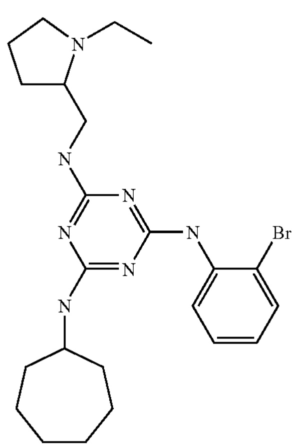 | N2-(2-bromophenyl)-N4-cycloheptyl-N6-[(1-ethyl-2-pyrrolidinyl)methyl]-1,3,5-triazine-2,4,6-triamine | toxic |

TABLE 4A-continued

| Patent Number | STRUCTURE | Name Generated by Autonom TM | Toxicity |
| --- | --- | --- | --- |
| 36 | 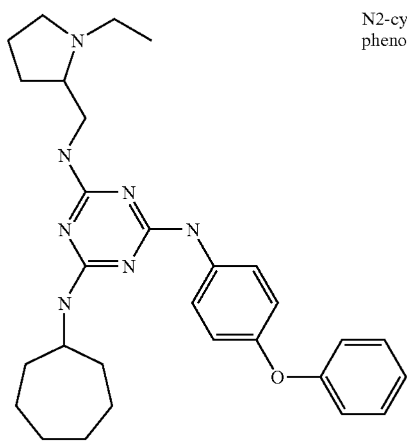 | N2-cycloheptyl-N4-[(1-ethyl-2-pyrrolidinyl)methyl]-N6-(4-phenoxyphenyl)-1,3,5-triazine-2,4,6-triamine | toxic |
| 47 | 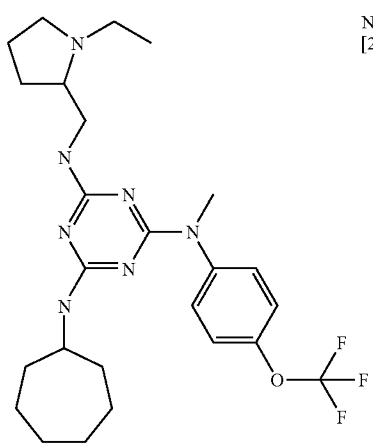 | N2-cycloheptyl-N4-[(1-ethyl-2-pyrrolidinyl)methyl]-N6-methyl-N6-[2-(trifluoromethoxy)phenyl]-1,3,5-triazine-2,4,6-triamine | toxic |
| 54 | 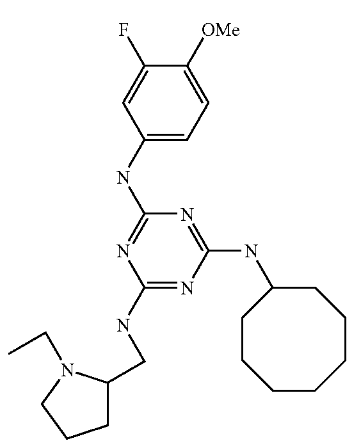 | N2-cylcooctyl-N4-[(1-1-ethyl-2-pyrrolidinyl)methyl]-N6-(4-fluoro-3-methoxyphenyl)-1,3,5-triazine-2,4,6-triamine | toxic |

TABLE 4A-continued

| Patent Number | STRUCTURE | Name Generated by Autonom TM | Toxicity |
|---|---|---|---|
| 59 | 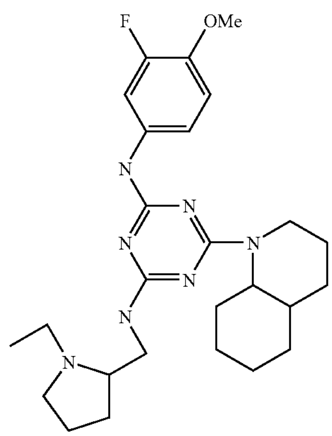 | N2-[(1-ethyl-2-pyrrolidinyl)methyl]-N4-(4-fluoro-3-methoxyphenyl)-6-octahydro-1(2H)-quinolinyl-1,3,5-triazine-2,4-diamine | toxic |
| 121 | 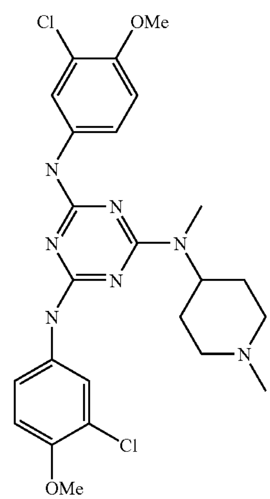 | N,N'-Bis-(3-chloro-4-methoxy-phenyl)-N''-methyl-N''-(1-methyl-piperin-4-yl)-1,3,5-triazine-2,4,6-triamine | Toxic by toxicity assay at 0.75 uM. Starts blunting by 1 uM and rounding by 5 uM |
| 111 | 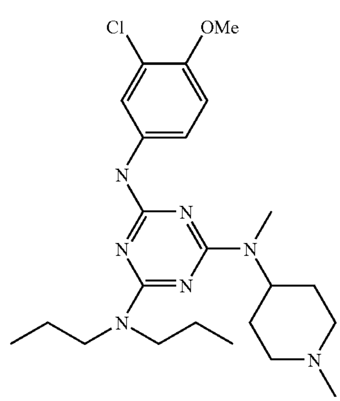 | N-Butyl-N'-(3-chloro-4-methoxy-phenyl)-N''-methyl-N''-(1-methyl-piperin-4-yl)-N-propyl-[1,3,5]triazine-2,4,6-triamine | Toxic by eye at 50 and 10 uM no blunt/round just death |

TABLE 4A-continued

| Patent Number | STRUCTURE | Name Generated by Autonom TM | Toxicity |
|---|---|---|---|
| 112 | 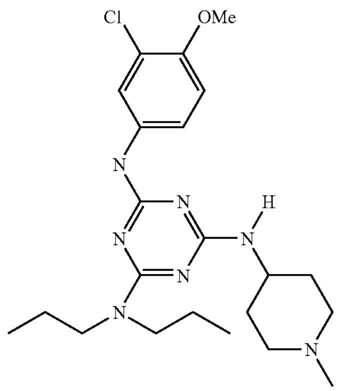 | N2-Butyl-N4-(3-chloro-4-methoxy-phenyl)-N6-methyl-N6-piperidin-4-yl-N2-propyl-1,3,5-triazine-2,4,6-triamine | Toxic by eye at 50 and 10 uM no blunt/round just death |
| 136 | 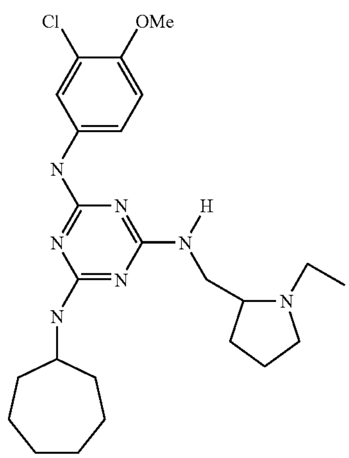 | N-(3-Chloro-4-methoxy-phenyl)-N'-cycloheptyl-N''-(1-ethyl-pyrrolidin-2-ylmethyl)-[1,3,5]triazine-2,4,6-triamine | Nothing but cell debris at 3 uM very toxic |
| 119 | 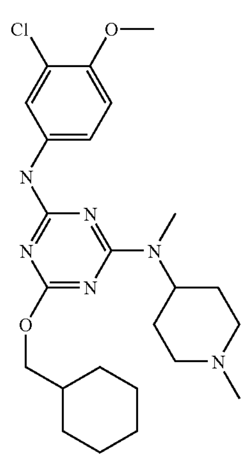 | N2-(3-chloro-4-methoxyphenyl)-6-cyclohexylmethoxy-N4-methyl-N4-(1-methyl-piperidin-4-yl)-1,3,5-triazine-2,4,6-triamine | toxic |

TABLE 4B

Triazine compunds toxic to endothelial cells when AGE stimulated

| Compound Number | STRUCTURE | Name Generated by AutonomTM | Toxic (AGE-treated) | Toxic (TNF-treated) | % IL6 production compare to TNF stimulation of IL6 (100%), Compds tested @ 10 uM HAEC, IL6 | % IL6 production compare to AGE stimulation of IL6 (100%), Compds tested @ 10 uM HAEC, IL6 |
|---|---|---|---|---|---|---|
| 121 | 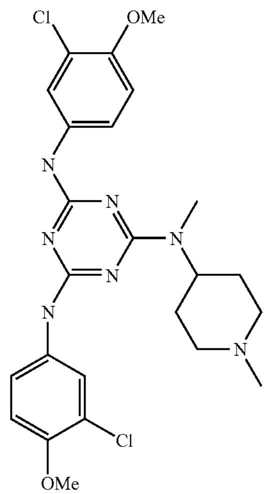 | N,N'-Bis-(3-chloro-4-methoxy-phenyl)-N''-methyl-N''-(4-methyl-cyclohexyl)-[1,3,5]triazine-2,4,6-triamine | toxic | n.d. | total cell death @ 10 uM [50 @ 5 uM, but some toxicity (~20%)] | n.d. |
| 168 | · Citric Acid | N2-cycloheptyl-N4-(3-fluoro-4-methoxy-phenyl)-N6-methyl-N6-(1-methyl-piperidin-4-yl)-1,3,5-triazine-2,4,6-triamine citrate salt | toxic | n.d. | total cell death @ 10 uM [40 @ 5 uM] | n.d. |
| 159 | 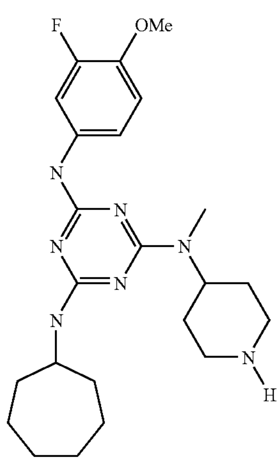 | N2-Cycloheptyl-N4-(3-fluoro-4-methoxy-phenyl)-N6-methyl-N6-piperidin-4-yl-1,3,5-triazine-2,4,6-triamine | toxic | n.d. | total cell death @ 5 uM and 10 uM | n.d. |

TABLE 4B-continued

Triazine complunds toxic to endothelial cells when AGE stimulated

| Compound Number | STRUCTURE | Name Generated by AutonomTM | Toxic (AGE-treated) | Toxic (TNF-treated) | % IL6 production compare to TNF stimulation of IL6 (100%), Compds tested @ 10 uM HAEC, IL6 | % IL6 production compare to AGE stimulation of IL6 (100%), Compds tested @ 10 uM HAEC, IL6 |
|---|---|---|---|---|---|---|
| 167 | · Maleic Acid | N2-cycloheptyl-N4-(3-fluoro-4-methoxy-phenyl)-N6-methyl-N6-(1-methyl-piperidin-4-yl)-1,3,5-triazine-2,4,6-triamine maleate salt | toxic | n.d. | total cell death @ 10 uM [25 @ 5 uM] | n.d. |
| 169 | · Succinic Acid | N2-cycloheptyl-N4-(3-fluoro-4-methoxy-phenyl)-N6-methyl-N6-(1-methyl-piperidin-4-yl)-1,3,5-triazine-2,4,6-triamine succinate salt | toxic | n.d. | total cell death @ 10 uM [45 @ 5 uM] | n.d. |
| 148 | 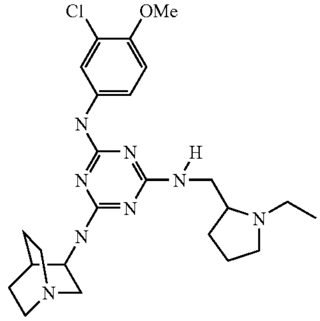 | N-(1-Aza-bicyclo[2.2.2]oct-3-yl)-N'-(3-chloro-4-methoxy-phenyl)-N''-)1-ethyl-pyrrolidin-2-ylmethyl)-[1,3,5]triazine-2,4,6-triamine | toxic | n.d. | total cell death @ 10 uM [60 @ 5 uM] | n.d. |

TABLE 4B-continued

Triazine complunds toxic to endothelial cells when AGE stimulated

| Compound Number | STRUCTURE | Name Generated by AutonomTM | Toxic (AGE-treated] | Toxic (TNF-treated] | % IL6 production compare to TNF stimulation of IL6 (100%), Compds tested @ 10 uM HAEC, IL6 | % IL6 production compare to AGE stimulation of IL6 (100%), Compds tested @ 10 uM HAEC, IL6 |
|---|---|---|---|---|---|---|
| 134 | 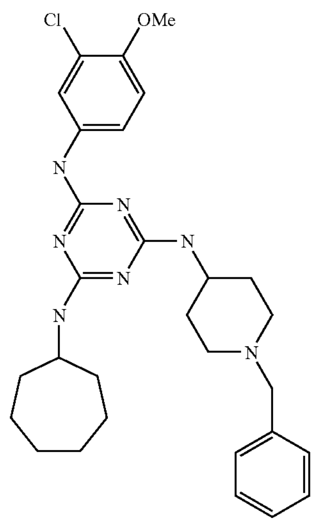 | N-(1-benzyl-piperidin-4-yl)-N'-(3-chloro-4-methoxy-phenyl)-N''-cycloheptyl-[1,3,5]triazine-2,4,6-triamine | toxic | n.d. | total cell death @ 10 uM [55 @ 5 uM] | n.d. |
| 135 | 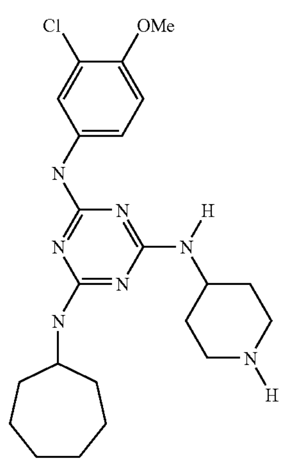 | N2-(3-chloro-4-methoxy-phenyl)-N4-cycloheptyl-N6-piperidin-4-yl-1,3,5-triazine-2,4,6-triamine | toxic | n.d. | total cell death @ 10 uM [60 @ 5 uM] | n.d. |

TABLE 4B-continued

Triazine complunds toxic to endothelial cells when AGE stimulated

| Compound Number | STRUCTURE | Name Generated by AutonomTM | Toxic (AGE-treated] | Toxic (TNF-treated] | % IL6 production compare to TNF stimulation of IL6 (100%), Compds tested @ 10 uM HAEC, IL6 | % IL6 production compare to AGE stimulation of IL6 (100%), Compds tested @ 10 uM HAEC, IL6 |
|---|---|---|---|---|---|---|
| 138 | 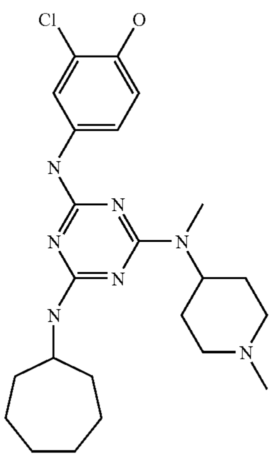 | 2-chloro-4-{4-cycloheptylamino-6-[methyl-(1-methyl-piperidin-4-yl-amino]-1,3,5-triazin-2-ylamino}-phenol | toxic | n.d. | toxic | n.d. |

TABLE 5

Triazine compounds useful in treating inflammatory disorders generally, and all diseases related to inhibition of IL6.

| Patent Number | STRUCTURE | Name Generated by Autonom (TM) | Inhibition of TNF-induced IL6 production (See NOTE) | Inhibition of TNF-induced IL6 production | % IL6 production compare to TNF stimulation of IL6 (100%). Compds tested @ 10 uM HAEC, IL6 | % IL6 production compare to AGE stimulation of IL6 (100%). Compds tested @ 10 uM HAEC, IL6 |
|---|---|---|---|---|---|---|
| 76 | 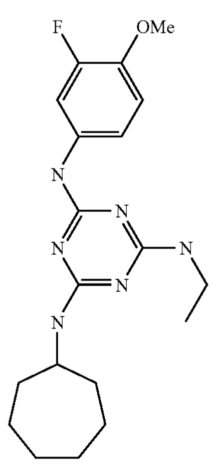 | N2-cycloheptyl-N4-ethyl-N6-(3-fluoro-4-methoxyphenyl)-1,3,5-triazine-2,4,6-triamine | ++++ | n.d. | 18 | n.d. |

TABLE 5-continued

Triazine compounds useful in treating inflammatory disorders generally, and all diseases related to inhibition of IL6.

| Patent Number | STRUCTURE | Name Generated by Autonom (TM) | Inhibition of TNF-induced IL6 production (See NOTE) | Inhibition of TNF-induced IL6 production | % IL6 production compare to TNF stimulation of IL6 (100%). Compds tested @ 10 uM HAEC, IL6 | % IL6 production compare to AGE stimulation of IL6 (100%). Compds tested @ 10 uM HAEC, IL6 |
|---|---|---|---|---|---|---|
| 77 | 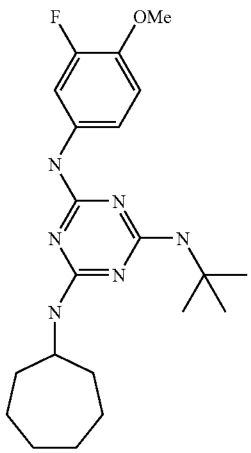 | N2-(tert-butyl)-N4-cycloheptyl-N6-(3-fluoro-4-methoxyphenyl)-1,3,5-triazine-2,4,6-triamine | ++++ | n.d. | 21 | n.d. |
| 78 | 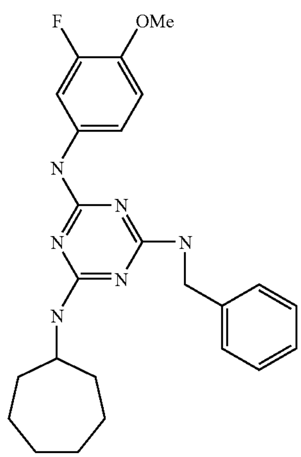 | N2-benzyl-N4-cycloheptyl-N6-(3-fluoro-4-methoxyphenyl)-1,3,5-triazine-2,4,6-triamine | +++ | n.d. | 47 | n.d. |
| 82 | 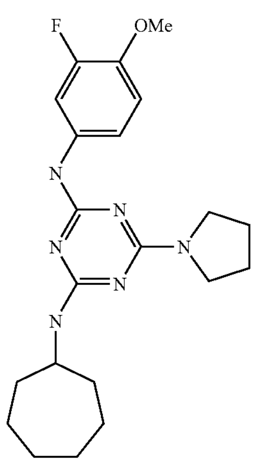 | N2-cycloheptyl-N4-(3-fluoro-4-methoxyphenyl)-6-(1-pyrrolidinyl)-1,3,5-triazine-2,4-diamine | +++ | n.d. | 34 | n.d. |

TABLE 5-continued

Triazine compounds useful in treating inflammatory disorders generally, and all diseases related to inhibition of IL6.

| Patent Number | STRUCTURE | Name Generated by Autonom (TM) | Inhibition of TNF-induced IL6 production (See NOTE) | Inhibition of TNF-induced IL6 production | % IL6 production compare to TNF stimulation of IL6 (100%). Compds tested @ 10 uM HAEC, IL6 | % IL6 production compare to AGE stimulation of IL6 (100%). Compds tested @ 10 uM HAEC, IL6 |
|---|---|---|---|---|---|---|
| 83 | 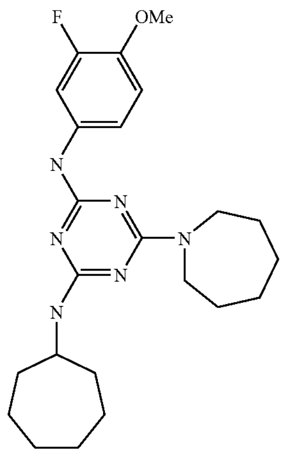 | N2-cycloheptyl-N4-(3-fluoro-4-methoxyphenyl)-6-hexahydro-1H-azepin-1-yl-1,3,5-triazine-2,4-diamine | ++++ | n.d. | 18 | n.d. |
| 84 | 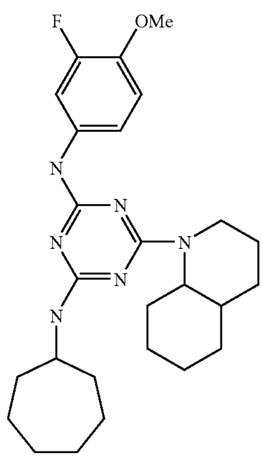 | N2-cycloheptyl-N4-(3-fluoro-4-methoxyphenyl)-6-octahydro-1(2H)-quinolinyl-1,3,5-triazine-2,4-diamine | +++ | n.d. | 33 | n.d. |
| 85 | 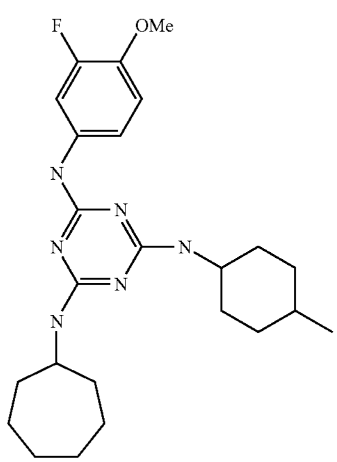 | N2-cycloheptyl-N4-(3-fluoro-4-methoxyphenyl)-N6-(4-methylcyclohexyl)-1,3,5-triazine-2,4,6-triamine | +++ | n.d. | n.d. | n.d. |

TABLE 5-continued

Triazine compounds useful in treating inflammatory disorders generally, and all diseases related to inhibition of IL6.

| Patent Number | STRUCTURE | Name Generated by Autonom (TM) | Inhibition of TNF-induced IL6 production (See NOTE) | Inhibition of TNF-induced IL6 production | % IL6 production compare to TNF stimulation of IL6 (100%). Compds tested @ 10 uM HAEC, IL6 | % IL6 production compare to AGE stimulation of IL6 (100%). Compds tested @ 10 uM HAEC, IL6 |
|---|---|---|---|---|---|---|
| 86 | 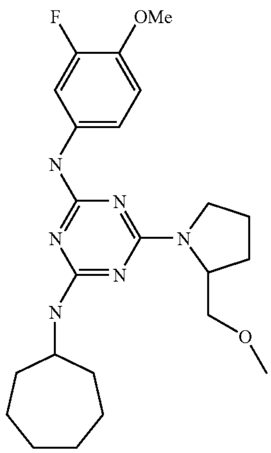 | N2-cycloheptyl-N4-(3-fluoro-4-methoxyphenyl)-6-[(2S)-2-(methoxymethyl)-1-pyrrolidinyl]-1,3,5-triazine-2,4-diamine | ++++ | n.d. | 19 | n.d. |
| 87 | 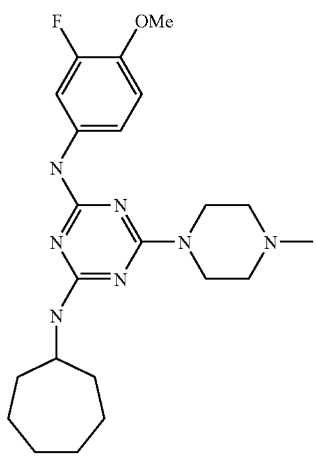 | N2-cycloheptyl-N4-(3-fluoro-4-methoxyphenyl)-6-(4-methyl-1-piperazinyl)-1,3,5-triazine-2,4-diamine | n.d. | ++++ | n.d | 5 |
| 88 | 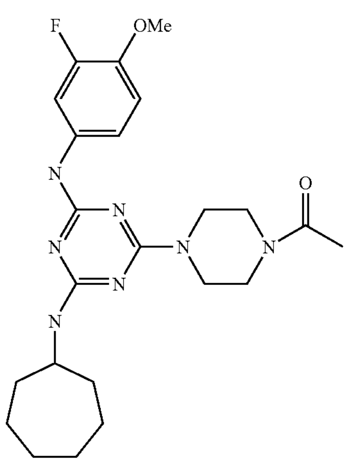 | 6-(4-acetyl-1-piperazinyl)-N2-cycloheptyl-N4-(3-fluoro-4-methoxyphenyl)-1,3,5-triazine-2,4-diamine | ++++ | n.d. | 19 | n.d. |

TABLE 5-continued

Triazine compounds useful in treating inflammatory disorders generally, and all diseases related to inhibition of IL6.

| Patent Number | STRUCTURE | Name Generated by Autonom (TM) | Inhibition of TNF-induced IL6 production (See NOTE) | Inhibition of TNF-induced IL6 production | % IL6 production compare to TNF stimulation of IL6 (100%). Compds tested @ 10 uM HAEC, IL6 | % IL6 production compare to AGE stimulation of IL6 (100%). Compds tested @ 10 uM HAEC, IL6 |
|---|---|---|---|---|---|---|
| 91 | 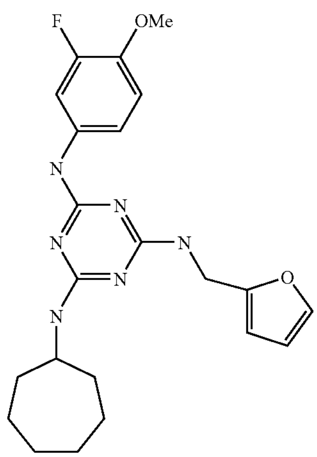 | N2-cycloheptyl-N4-(3-fluoro-4-methoxyphenyl)-N6-(2-furanylmethyl)-1,3,5-triazine-2,4,6-triamine | +++ | n.d. | 28 | n.d. |
| 93 | 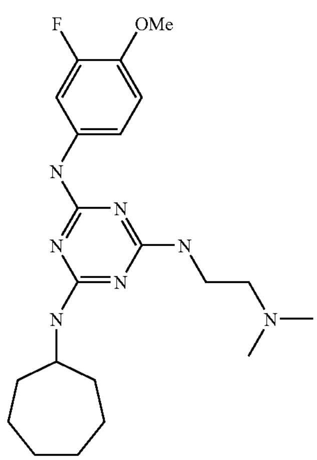 | N2-cycloheptyl-N4-[2-(dimethylamino)ethyl]-N6-(3-fluoro-4-methoxyphenyl)-1,3,5-triazine-2,4,6-triamine | ++++ | ++++ | 13 | 6 (IC50 = 3.36) |
| 94 | 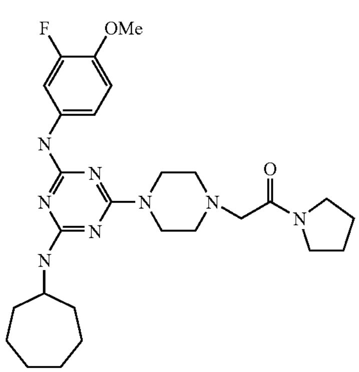 | N2-cycloheptyl-N4-(3-fluoro-4-methoxyphenyl)-6-{4-[2-oxo-(1-pyrrolidinyl)ethyl]-1-piperazinyl}-1,3,5-triazine-2,4,6-triamine | +++ | ++++ | 32 | 10 (IC50 = 5.8) |

TABLE 5-continued

Triazine compounds useful in treating inflammatory disorders generally, and all diseases related to inhibition of IL6.

| Patent Number | STRUCTURE | Name Generated by Autonom (TM) | Inhibition of TNF-induced IL6 production (See NOTE) | Inhibition of TNF-induced IL6 production | % IL6 production compare to TNF stimulation of IL6 (100%). Compds tested @ 10 uM HAEC, IL6 | % IL6 production compare to AGE stimulation of IL6 (100%). Compds tested @ 10 uM HAEC, IL6 |
|---|---|---|---|---|---|---|
| 95 | 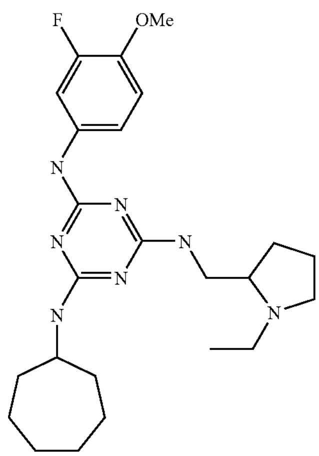 | N-Cycloheptyl-N'-(1-ethyl-pyrrolidin-2-ylmethyl)-N''-(3-fluoro-4-methoxy-phenyl)-[1,3,5]triazine-2,4,6-triamine | ++++ | ++++ | 5 (IC50 = 2.8) | 1 (IC50 = 6.6) |
| 96 | 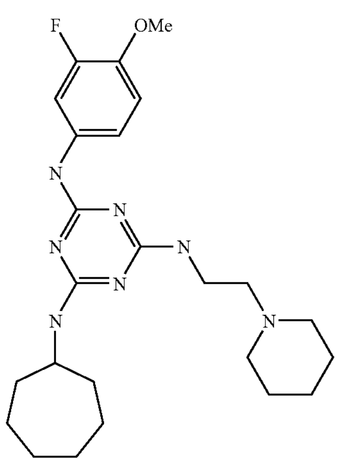 | N2-cycloheptyl-N4-(3-fluoro-4-methoxyphenyl)-N6-[2-(1-piperidinyl)ethyl]-1,3,5-triazine-2,4,6-triamine | ++++ | n.d. | 6 | n.d. |
| 99 | 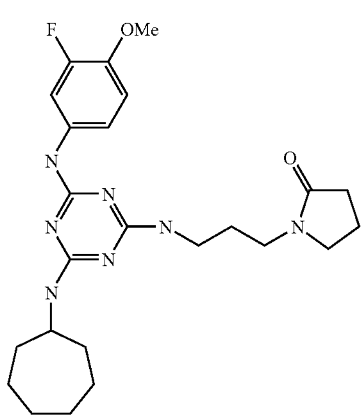 | 1-[3-({4-(cycloheptylamino)-6-[(3-fluoro-4-methoxyphenyl)-amino]-1,3,5-triazin-2-yl}amino)propyl]-2-pyrrolidinone | +++ | ++++ | 39 | 8 (IC50 = 6.04) |

TABLE 5-continued

Triazine compounds useful in treating inflammatory disorders generally, and all diseases related to inhibition of IL6.

| Patent Number | STRUCTURE | Name Generated by Autonom (TM) | Inhibition of TNF-induced IL6 production (See NOTE) | Inhibition of TNF-induced IL6 production | % IL6 production compare to TNF stimulation of IL6 (100%). Compds tested @ 10 uM HAEC, IL6 | % IL6 production compare to AGE stimulation of IL6 (100%). Compds tested @ 10 uM HAEC, IL6 |
|---|---|---|---|---|---|---|
| 100 | 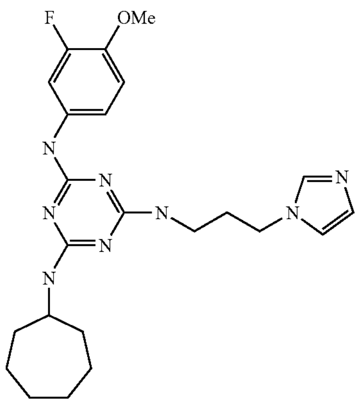 | N2-cycloheptyl-N4-(3-fluoro-4-methoxyphenyl)-N6-[3-(1H-imidazol-1-yl)propyl]-1,3,5-triazine-2,4,6-triamine | n.d. | ++++ | n.d | 1 |
| 3 | 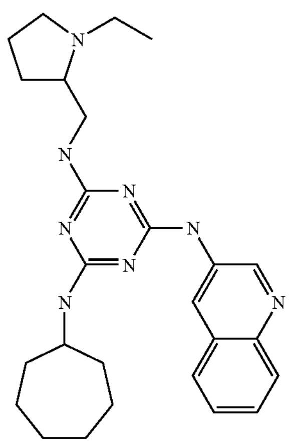 | N2-cycloheptyl-N4-[(1-ethyl-2-pyrrolidinyl)-methyl]-N6-(3-quinolinyl)-1,3,5-triazine-2,4,6-triamine | n.d. | ++++ | n.d | 1 |
| 4 | 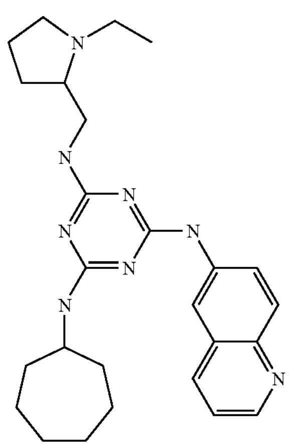 | N2-cycloheptyl-N4-[(1-ethyl-2-pyrrolidinyl)-methyl]-N6-(6-quinolinyl)-1,3,5-triazine-2,4,6-triamine | n.d. | ++++ | n.d | 1 |

TABLE 5-continued

Triazine compounds useful in treating inflammatory disorders generally, and all diseases related to inhibition of IL6.

| Patent Number | STRUCTURE | Name Generated by Autonom (TM) | Inhibition of TNF-induced IL6 production (See NOTE) | Inhibition of TNF-induced IL6 production | % IL6 production compare to TNF stimulation of IL6 (100%). Compds tested @ 10 uM HAEC, IL6 | % IL6 production compare to AGE stimulation of IL6 (100%). Compds tested @ 10 uM HAEC, IL6 |
|---|---|---|---|---|---|---|
| 10 | 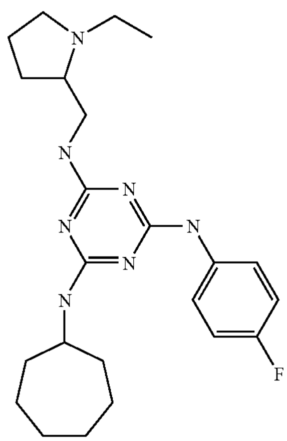 | N2-cycloheptyl-N4-[(1-ethyl-2-pyrrolidinyl)-methyl]-N6-(4-fluorophenyl)-1,3,5-triazine-2,4,6-triamine | n.d. | ++++ | n.d | 1 |
| 11 | 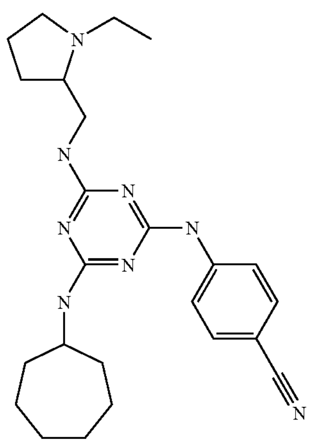 | 4-[(4-(cycloheptylamino)-6-{[(1-ethyl-2-pyrrolidinyl)-methyl]amino}-1,3,5-triazin-2-yl)-amino]benzonitrile | n.d. | ++++ | n.d | 1 (IC50 = 8.87) |
| 24 | 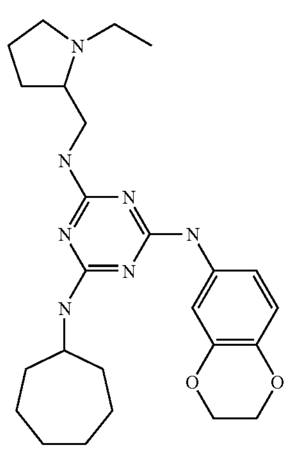 | N2-cylcoheptyl-N4-(2,3-dihydro-1,4-benzodioxin-6-yl)-N6-[(1-ethyl-2-pyrrolidinyl)methyl]-1,3,5-triazine-2,4,6-triamine | n.d. | ++++ | n.d | 1 |

TABLE 5-continued

Triazine compounds useful in treating inflammatory disorders generally, and all diseases related to inhibition of IL6.

| Patent Number | STRUCTURE | Name Generated by Autonom (TM) | Inhibition of TNF-induced IL6 production (See NOTE) | Inhibition of TNF-induced IL6 production | % IL6 production compare to TNF stimulation of IL6 (100%). Compds tested @ 10 uM HAEC, IL6 | % IL6 production compare to AGE stimulation of IL6 (100%). Compds tested @ 10 uM HAEC, IL6 |
|---|---|---|---|---|---|---|
| 25 | 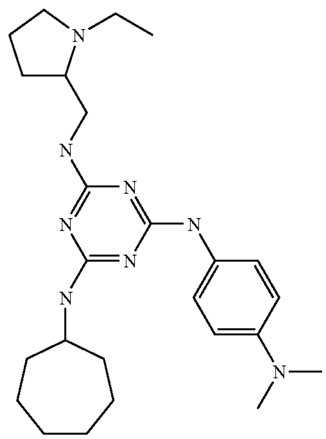 | N2-cycloheptyl-N4-[4-(dimethylamino)phenyl]-N6-[(1-ethyl-2-pyrrolidinyl)methyl]-1,3,5-triazine-2,4,6-triamine | n.d. | ++++ | n.d. | 1 |
| 26 | 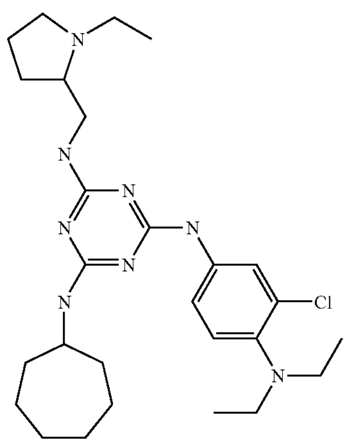 | $N^2$-(3-chloro-4-diethylamino-phenyl)-$N^4$-cycloheptyl-$N^6$-(1-ethyl-pyrrolidin-2-ylmethyl)-1,3,5-triazine-2,4,6-triamine | ++++ | n.d. | 1 (over 50% of cells were floating) | n.d. |
| 27 | 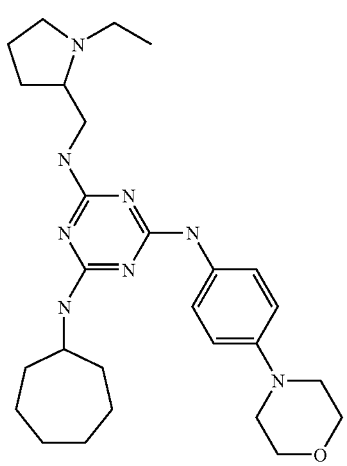 | N2-cycloheptyl-N4-[(1-ethyl-2-pyrrolidinyl)-methyl]-N6-[4-(4-morpholinyl)phenyl]-1,3,5-triazine-2,4,6-triamine | ++++ | ++++ | 3 | 1 |

TABLE 5-continued

Triazine compounds useful in treating inflammatory disorders generally, and all diseases related to inhibition of IL6.

| Patent Number | STRUCTURE | Name Generated by Autonom (TM) | Inhibition of TNF-induced IL6 production (See NOTE) | Inhibition of TNF-induced IL6 production | % IL6 production compare to TNF stimulation of IL6 (100%). Compds tested @ 10 uM HAEC, IL6 | % IL6 production compare to AGE stimulation of IL6 (100%). Compds tested @ 10 uM HAEC, IL6 |
|---|---|---|---|---|---|---|
| 28 | 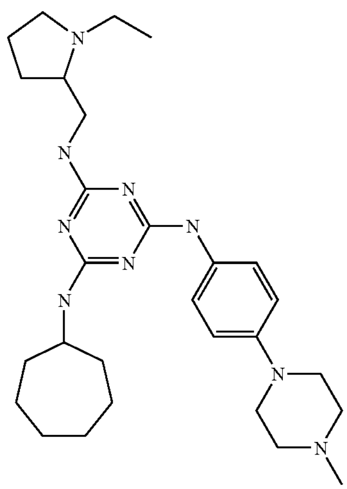 | N2-cycloheptyl-N4-[(1-ethyl-2-pyrrolidinyl)-methyl]-N6-[4-(4-methyl-1-piperazinyl)phenyl]-1,3,5-triazine-2,4,6-triamine | ++++ | n.d. | 23 | n.d. |
| 29 | 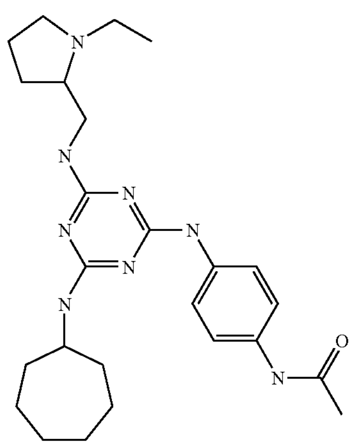 | N-{4-[(4-(cycloheptylamino)-6-{[(1-ethyl-2-pyrrolidinyl)methyl]amino)-1,3,5-triazin-2-yl)-amino]phenyl}acetamide | ++++ | ++++ | 13 | 7 |
| 30 | 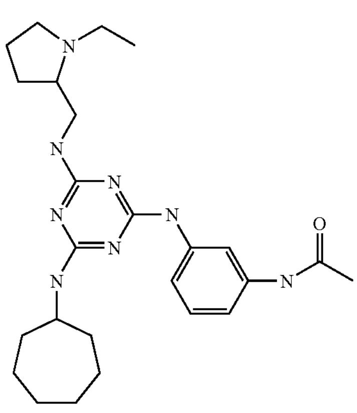 | N-{3-[(4-(cycloheptylamino)-6-{[(1-ethyl-2-pyrrolidinyl)methyl]amino}-1,3,5-triazin-2-yl)-amino]phenyl}acetamide | ++++ | ++++ | 9 | 17 |

TABLE 5-continued

Triazine compounds useful in treating inflammatory disorders generally, and all diseases related to inhibition of IL6.

| Patent Number | STRUCTURE | Name Generated by Autonom (TM) | Inhibition of TNF-induced IL6 production (See NOTE) | Inhibition of TNF-induced IL6 production | % IL6 production compare to TNF stimulation of IL6 (100%). Compds tested @ 10 uM HAEC, IL6 | % IL6 production compare to AGE stimulation of IL6 (100%). Compds tested @ 10 uM HAEC, IL6 |
|---|---|---|---|---|---|---|
| 32 | 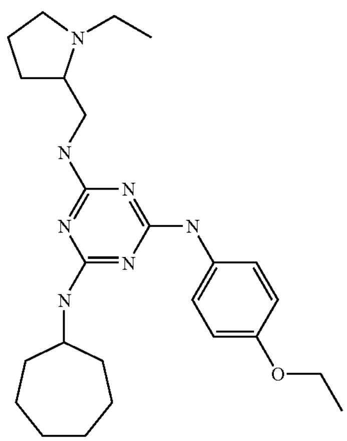 | N2-cycloheptyl-N4-(4-ethoxyphenyl)-N6-[(1-ethyl-2-pyrrolidinyl)methyl]-1,3,5-triazine-2,4,6-triamine | n.d. | ++++ | n.d. | 1 |
| 34 | 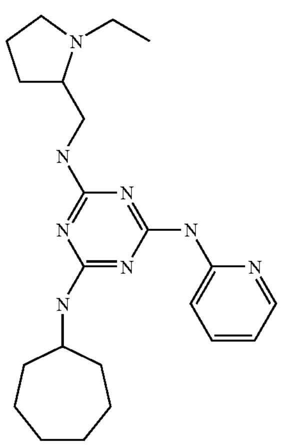 | N2-cycloheptyl-N4-[(1-ethyl-2-pyrrolidinyl)methyl]-N6-(2-pyridinyl)-1,3,5-triazine-2,4,6-triamine | ++++ | ++++ | 3 | 1 |
| 35 | 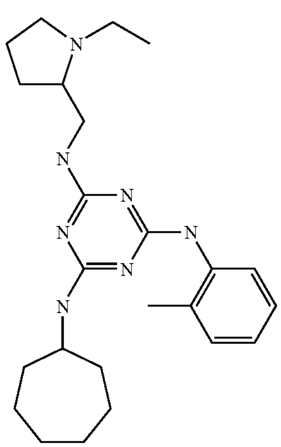 | N2-cycloheptyl-N4-[(1-ethyl-2-pyrrolidinyl)methyl]-N6-(2-methylphenyl)-1,3,5-triazine-2,4,6-triamine | +++ | ++++ | 34 | 4 |

TABLE 5-continued

Triazine compounds useful in treating inflammatory disorders generally, and all diseases related to inhibition of IL6.

| Patent Number | STRUCTURE | Name Generated by Autonom (TM) | Inhibition of TNF-induced IL6 production (See NOTE) | Inhibition of TNF-induced IL6 production | % IL6 production compare to TNF stimulation of IL6 (100%). Compds tested @ 10 uM HAEC, IL6 | % IL6 production compare to AGE stimulation of IL6 (100%). Compds tested @ 10 uM HAEC, IL6 |
|---|---|---|---|---|---|---|
| 39 | 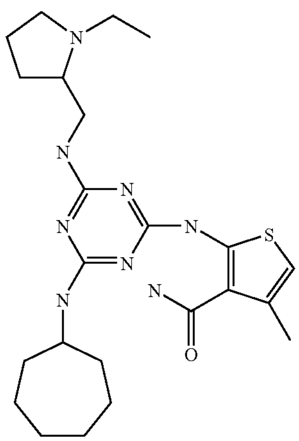 | 2-[(4-cycloheptylamino)-6-{[(1-ethyl-2-pyrrolidinyl)methyl]amino)-1,3,5-triazin-2-yl)-amino]-4-methyl-3-thiophenecarboxamide | n.d. | +++ | n.d. | 28 |
| 40 | 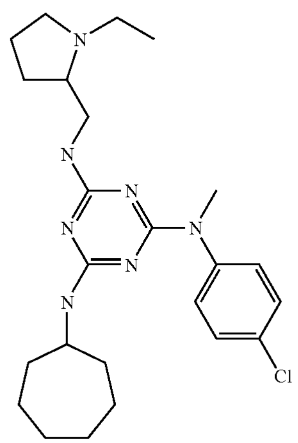 | N2-(4-chlorophenyl)-N4-cycloheptyl-N6-[(1-ethyl-2-pyrrolidinyl)methyl]-N2-methyl-1,3,5-triazine-2,4,6-triamine | n.d. | ++++ | n.d. | 19 |
| 41 | 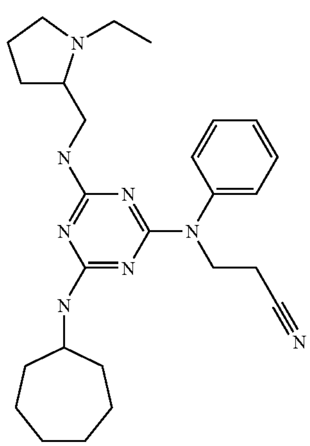 | 3-[(4-(cycloheptylamino)-6-{[(1-ethyl-2-pyrrolidinyl)methyl]amino)-1,3,5-triazin-2-yl)-(phenyl)-amino]propanenitrile | n.d. | ++++ | n.d. | 18 |

TABLE 5-continued

Triazine compounds useful in treating inflammatory disorders generally, and all diseases related to inhibition of IL6.

| Patent Number | STRUCTURE | Name Generated by Autonom (TM) | Inhibition of TNF-induced IL6 production (See NOTE) | Inhibition of TNF-induced IL6 production | % IL6 production compare to TNF stimulation of IL6 (100%). Compds tested @ 10 uM HAEC, IL6 | % IL6 production compare to AGE stimulation of IL6 (100%). Compds tested @ 10 uM HAEC, IL6 |
|---|---|---|---|---|---|---|
| 42 | 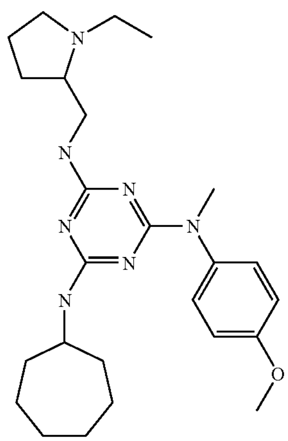 | N2-cycloheptyl-N4-[(1-ethyl-2-pyrrolidinyl)methyl]-N6-(4-methoxyphenyl)-N6-methyl-1,3,5-triazine-2,4,6-triamine | ++++ | ++++ | 1 | 1 |
| 43 | 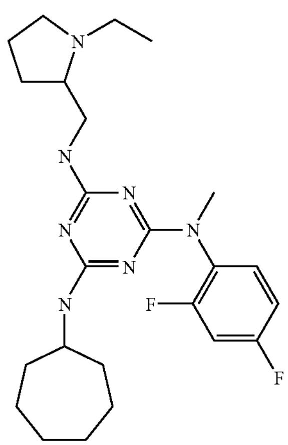 | N2-cycloheptyl-N4-(2,4-difluorophenyl)-N6-[(1-ethyl-2-pyrrolidinyl)methyl]-N4-methyl-1,3,5-triazine-2,4,6-triamine | n.d. | ++++ | n.d. | 4 |
| 44 | 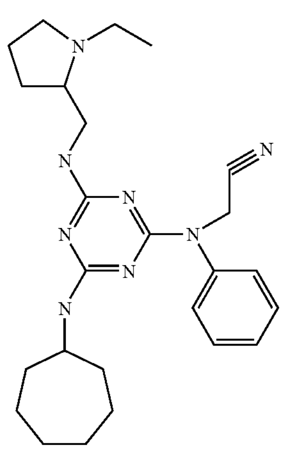 | [(4-(cycloheptylamino)-6-{[(1-ethyl-2-pyrrolidinyl)methyl]amino}-1,3,5-triazin-2-yl)(phenyl)amino]-acetonitrile | n.d. | ++++ | n.d. | 1 (IC50 = 7.1) |

TABLE 5-continued

Triazine compounds useful in treating inflammatory disorders generally, and all diseases related to inhibition of IL6.

| Patent Number | STRUCTURE | Name Generated by Autonom (TM) | Inhibition of TNF-induced IL6 production (See NOTE) | Inhibition of TNF-induced IL6 production | % IL6 production compare to TNF stimulation of IL6 (100%). Compds tested @ 10 uM HAEC, IL6 | % IL6 production compare to AGE stimulation of IL6 (100%). Compds tested @ 10 uM HAEC, IL6 |
|---|---|---|---|---|---|---|
| 45 | 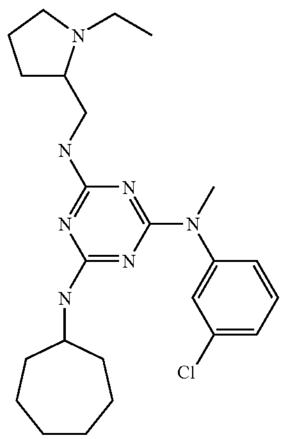 | N2-(3-chlorophenyl)-N4-cycloheptyl-N6-[(1-ethyl-2-pyrrolidinyl)methyl]-N2-methyl-1,3,5-triazine-2,4,6-triamine | n.d. | ++++ | n.d. | 1 |
| 46 | 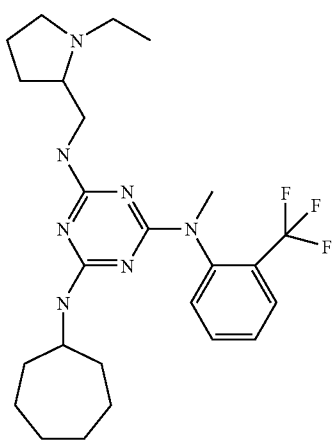 | N2-cyclophenyl-N4-[(1-ethyl-2-pyrrolidinyl)methyl]-N6-methyl-[2-(trifluoromethyl)phenyl]-1,3,5-triazine-2,4,6-triamine | n.d. | ++++ | n.d. | 3 |
| 48 | 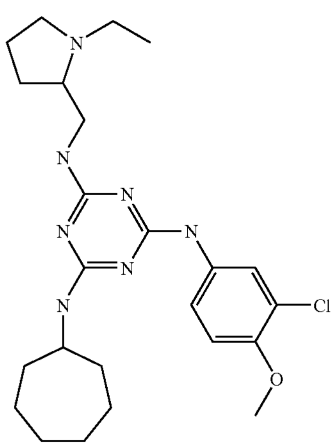 | N2-(3-chloro-4-methoxyphenyl)-N4-cycloheptyl-N6-[(1-ethyl-2-pyrrolidinyl)methyl]-1,3,5-triazine-2,4,6-triamine | +++ | n.d. | 3074 (IC50 = 4.3) | n.d. |

TABLE 5-continued

Triazine compounds useful in treating inflammatory disorders generally, and all diseases related to inhibition of IL6.

| Patent Number | STRUCTURE | Name Generated by Autonom (TM) | Inhibition of TNF-induced IL6 production (See NOTE) | Inhibition of TNF-induced IL6 production | % IL6 production compare to TNF stimulation of IL6 (100%). Compds tested @ 10 uM HAEC, IL6 | % IL6 production compare to AGE stimulation of IL6 (100%). Compds tested @ 10 uM HAEC, IL6 |
|---|---|---|---|---|---|---|
| 51 | 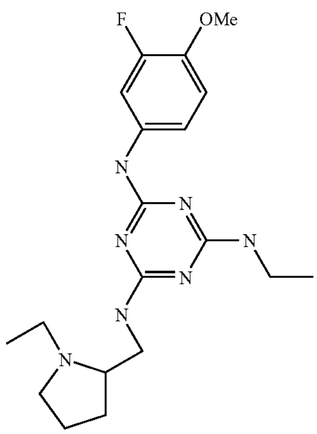 | N2-ethyl-N4-[(1-ethyl-2-pyrrolidinyl)methyl]-N6-(3-fluoro-4-methoxyphenyl)-1,3,5-triazine-2,4,6-triamine | ++++ | n.d. | 1 | n.d. |
| 52 | 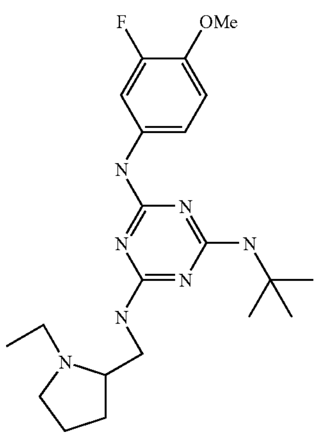 | N2-(tert-butyl)-N4-[(1-ethyl-2-pyrrolidinyl)methyl]-N6-(3-fluoro-4-methoxyphenyl)-1,3,5-triazine-2,4,6-triamine | ++++ | +++ | 1 | 35 |
| 53 | 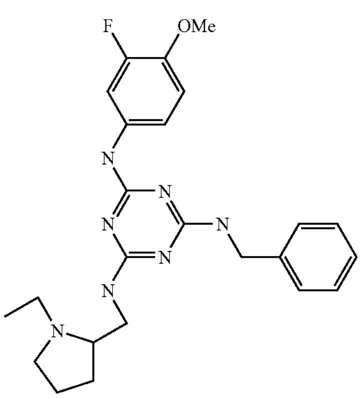 | N2-benzyl-N4-[(1-ethyl-2-pyrrolidinyl)methyl]-N6-(3-fluoro-4-methoxyphenyl)-1,3,5-triazine-2,4,6-triamine | ++++ | +++ | 1 | 32 |

TABLE 5-continued

Triazine compounds useful in treating inflammatory disorders generally, and all diseases related to inhibition of IL6.

| Patent Number | STRUCTURE | Name Generated by Autonom (TM) | Inhibition of TNF-induced IL6 production (See NOTE) | Inhibition of TNF-induced IL6 production | % IL6 production compare to TNF stimulation of IL6 (100%). Compds tested @ 10 uM HAEC, IL6 | % IL6 production compare to AGE stimulation of IL6 (100%). Compds tested @ 10 uM HAEC, IL6 |
|---|---|---|---|---|---|---|
| 55 | 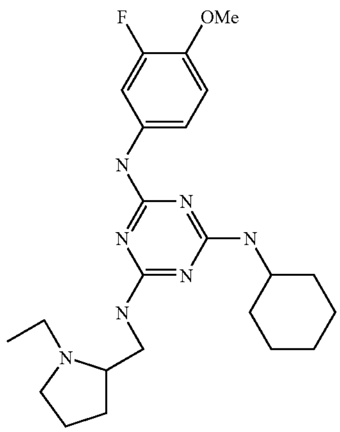 | N2-cyclohexyl-N4-[(1-ethyl-2-pyrrolidinyl)methyl]-N6-(3-fluoro-4-methoxyphenyl)-1,3,5-triazine-2,4,6-triamine | ++++ | n.d. | 1 | n.d. |
| 56 | 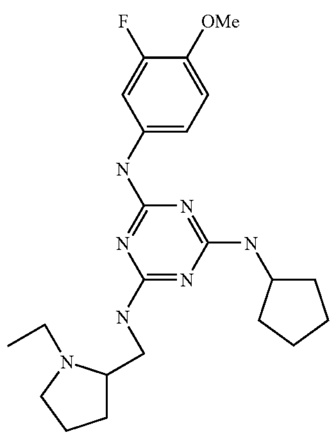 | N2-cyclopentyl-N4-[(1-ethyl-2-pyrrolidinyl)methyl]-N6-(3-fluoro-4-methoxyphenyl)-1,3,5-triazine-2,4,6-triamine | ++++ | n.d. | 1 | n.d. |
| 57 | 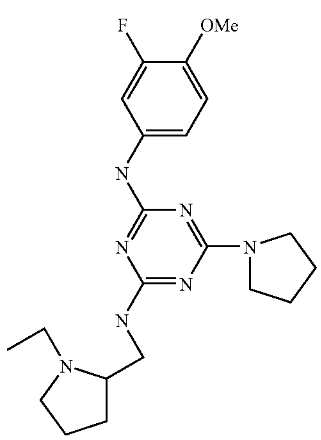 | N2-[(1-ethyl-2-ethyl-2-pyrrolidinyl)methyl]-N4-(3-fluoro-4-methoxyphenyl)-6-(1-pyrrolidinyl)-1,3,5-triamine-2,4-diamine | ++++ | +++ | 1 | 25 |

TABLE 5-continued

Triazine compounds useful in treating inflammatory disorders generally, and all diseases related to inhibition of IL6.

| Patent Number | STRUCTURE | Name Generated by Autonom (TM) | Inhibition of TNF-induced IL6 production (See NOTE) | Inhibition of TNF-induced IL6 production | % IL6 production compare to TNF stimulation of IL6 (100%). Compds tested @ 10 uM HAEC, IL6 | % IL6 production compare to AGE stimulation of IL6 (100%). Compds tested @ 10 uM HAEC, IL6 |
|---|---|---|---|---|---|---|
| 58 | 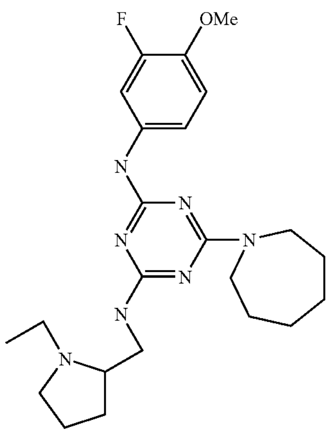 | N2-[(1-ethyl-2-ethyl-2-pyrrolidinyl)methyl]-N4-(3-fluoro-4-methoxyphenyl)-6-hexahydro-1H-azepin-1-yl-1,3,5-triazine-2,4-diamine | ++++ | +++ | 1 | 30 |
| 60 | 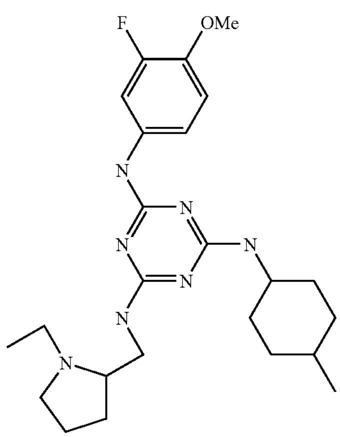 | N2-[(1-ethyl-2-pyrrolidinyl)methyl]-N4-(3-fluoro-4-methoxyphenyl)-N6-(4-methylcyclohexyl-1,3,5-triazine-2,4,6-triamine | ++++ | n.d. | 1 | n.d. |
| 61 | 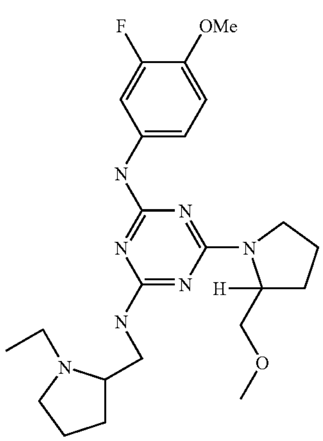 | N2-[(1-ethyl-2-pyrrolidinyl)methyl]-N4-(4-fluoro-3-methoxyphenyl)-6-[2-(methoxymethyl)-1-pyrrolidinyl]-1,3,5-triazine-2,4-diamine | ++++ | +++ | 2 | 38 (IC50 = 6.47) |

TABLE 5-continued

Triazine compounds useful in treating inflammatory disorders generally, and all diseases related to inhibition of IL6.

| Patent Number | STRUCTURE | Name Generated by Autonom (TM) | Inhibition of TNF-induced IL6 production (See NOTE) | Inhibition of TNF-induced IL6 production | % IL6 production compare to TNF stimulation of IL6 (100%). Compds tested @ 10 uM HAEC, IL6 | % IL6 production compare to AGE stimulation of IL6 (100%). Compds tested @ 10 uM HAEC, IL6 |
|---|---|---|---|---|---|---|
| 62 | 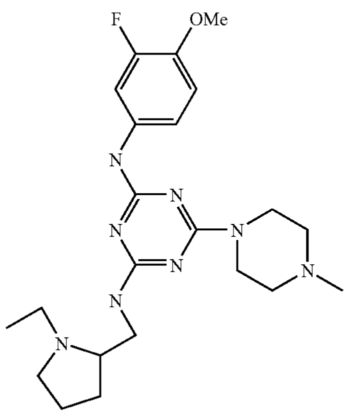 | N2-[(1-ethyl-2-pyrrolidinyl)methyl]-N4-(3-fluoro-3-methoxyphenyl)-6-(4-methyl-1-piperazinyl]-1,3,5-triamine-2,4-diamine | n.d. | +++ | n.d. | 42 |
| 63 | 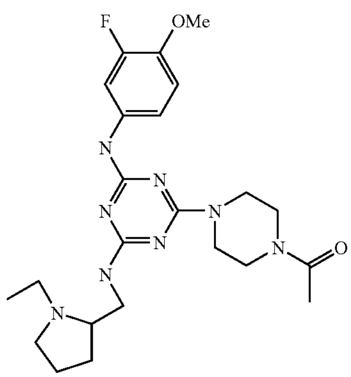 | 6-(4-acetyl-1-piperazinyl)-N2-[(1-ethyl-2-pyrrolidinyl)methyl]-N4-(3-fluoro-4-methoxyphenyl)-1,3,5-triazine-2,4,6-triamine | +++ | n.d | 26 | n.d. |
| 64 | 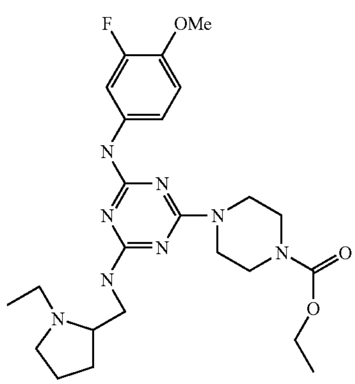 | 4-{4-{[(1-ethyl-2-pyrrolidinyl)methyl]-amino}-6-[(3-fluoro-4-methoxyphenyl)amino]-1,3,5-triazin-2-yl}-1-piperazinecarboxylate | +++ | n.d. | 23 | n.d. |

TABLE 5-continued

Triazine compounds useful in treating inflammatory disorders generally, and all diseases related to inhibition of IL6.

| Patent Number | STRUCTURE | Name Generated by Autonom (TM) | Inhibition of TNF-induced IL6 production (See NOTE) | Inhibition of TNF-induced IL6 production | % IL6 production compare to TNF stimulation of IL6 (100%). Compds tested @ 10 uM HAEC, IL6 | % IL6 production compare to AGE stimulation of IL6 (100%). Compds tested @ 10 uM HAEC, IL6 |
|---|---|---|---|---|---|---|
| 65 | 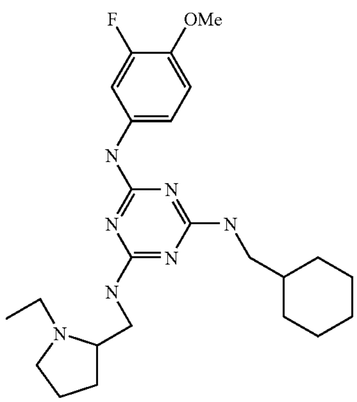 | N2-(cyclohexylmethyl)-N4-[(1-ethyl-2-pyrrolidinyl)methyl]-N6-(3-fluoro-4-methoxyphenyl)-1,3,5-triazine-2,4,6-triamine | ++++ | +++ | 1 (IC50 = 6.7) | 45 (IC50 = 3.24) |
| 66 | 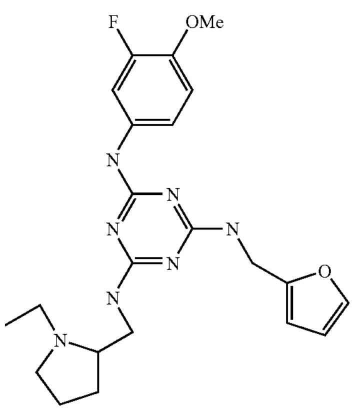 | N2-[(1-ethyl-2-pyrrolidinyl)methyl]-N4-(3-fluoro-4-methoxyphenyl)-N6-(2-furylmethyl)-1,3,5-triazine-2,4,6-triamine | ++++ | ++++ | 1 | 23 |
| 67 | 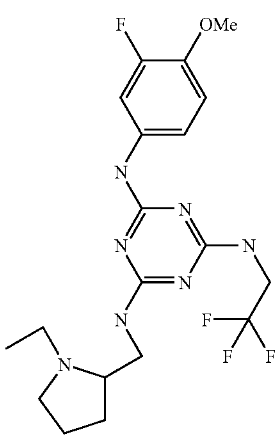 | N2-[(1-ethyl-2-pyrrolidinyl)methyl]-N4-(3-fluoro-4-methoxyphenyl)-N6-(2,2,2-trifluoroethyl)-1,3,5-triazine-2,4,6-triamine | n.d. | +++ | n.d. | 39 |

TABLE 5-continued

Triazine compounds useful in treating inflammatory disorders generally, and all diseases related to inhibition of IL6.

| Patent Number | STRUCTURE | Name Generated by Autonom (TM) | Inhibition of TNF-induced IL6 production (See NOTE) | Inhibition of TNF-induced IL6 production | % IL6 production compare to TNF stimulation of IL6 (100%). Compds tested @ 10 uM HAEC, IL6 | % IL6 production compare to AGE stimulation of IL6 (100%). Compds tested @ 10 uM HAEC, IL6 |
|---|---|---|---|---|---|---|
| 68 | 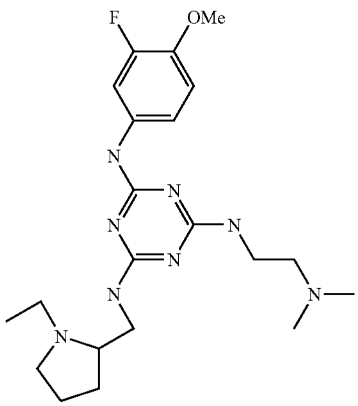 | N2-[2-(dimethylamino)-ethyl]-N4-[(1-ethyl-2-pyrrolidinyl)methyl]-N6-(3-fluoro-4-methoxyphenyl)-1,3,5-triazine-2,4,6-triamine | ++++ | +++ | 1 | 40 (IC50 = 7.7) |
| 69 | 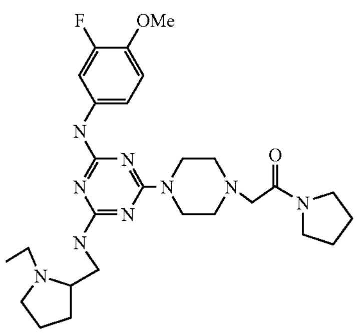 | N2-[(1-ethyl-2-pyrrolidinyl)methyl]-N4-(3-fluoro-4-methoxyphenyl)-6-{4-[2-oxo-2-(1-pyrrolidinyl)ethyl]-1-piperazinyl}-1,3,5-triazine-2,4-diamine | ++++ | ++++ | 1 | 5 |
| 70 | 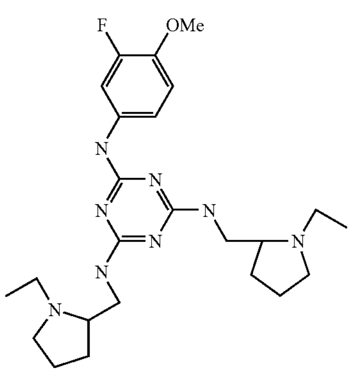 | N2-N4-bis[(1-ethyl-2-pyrrolidinyl)methyl]-N6-(3-fluoro-4-methoxyphenyl)-1,3,5-triazine-2,4,6-triamine | ++++ | +++ | 1 | 35 |

TABLE 5-continued

Triazine compounds useful in treating inflammatory disorders generally, and all diseases related to inhibition of IL6.

| Patent Number | STRUCTURE | Name Generated by Autonom (TM) | Inhibition of TNF-induced IL6 production (See NOTE) | Inhibition of TNF-induced IL6 production | % IL6 production compare to TNF stimulation of IL6 (100%). Compds tested @ 10 uM HAEC, IL6 | % IL6 production compare to AGE stimulation of IL6 (100%). Compds tested @ 10 uM HAEC, IL6 |
|---|---|---|---|---|---|---|
| 71 | 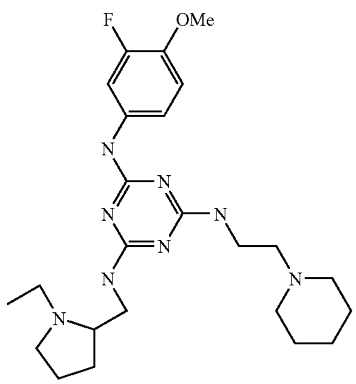 | N2-[(1-ethyl-2-pyrrolidinyl)methyl]-N4-(3-fluoro-4-methoxyphenyl)-N6-[2-(1-piperidinyl)ethyl]-1,3,5-triazine-2,4,6-triamine | ++++ | +++ | 1 | 29 |
| 72 | 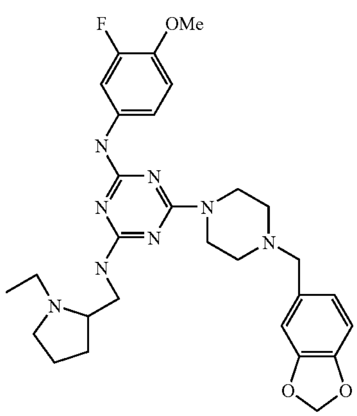 | 6-[4-(1,3-benzodioxol-5-ylmethyl)-1-piperazinyl]-N2-[(1-ethyl-2-pyrrolidinyl)methyl[-N4-(3-fluoro-4-methoxyphenyl)-1,3,5-triazine-2,4-diamine | ++++ | +++ | 5 | 31 |
| 73 | 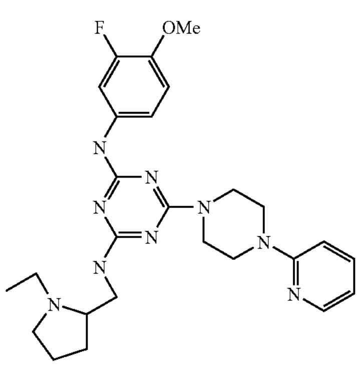 | N2-[(1-ethyl-2-pyrrolidinyl)methyl]-N4-(3-fluoro-4-methoxyphenyl)-6-[4-(2-pyridinyl)-1-piperazinyl]-1,3,5-triazine-2,4-diamine | ++++ | ++++ | 1 (IC50 = 8.7) | 20 (IC50 = 7.5) |

TABLE 5-continued

Triazine compounds useful in treating inflammatory disorders generally, and all diseases related to inhibition of IL6.

| Patent Number | STRUCTURE | Name Generated by Autonom (TM) | Inhibition of TNF-induced IL6 production (See NOTE) | Inhibition of TNF-induced IL6 production | % IL6 production compare to TNF stimulation of IL6 (100%). Compds tested @ 10 uM HAEC, IL6 | % IL6 production compare to AGE stimulation of IL6 (100%). Compds tested @ 10 uM HAEC, IL6 |
|---|---|---|---|---|---|---|
| 74 | 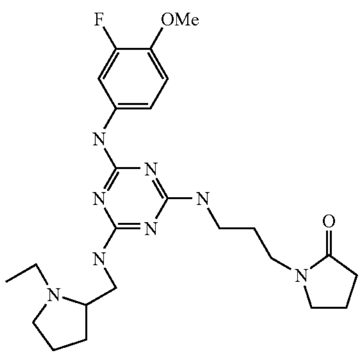 | 1-[3-({4-{[(1-ethyl-2-pyrrolidinyl)methyl]-amino}-6-[(3-fluoro-4-methoxyphenyl)amino]-1,3,5-triazin-2-yl}amino)propyl]-2-pyrrolidinone | n.d. | +++ | n.d. | 49 |
| 75 | 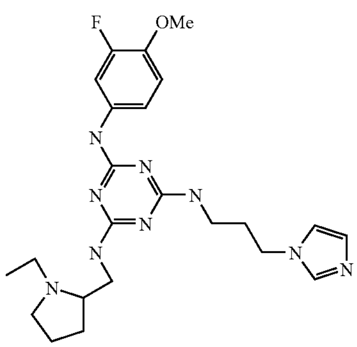 | N2-[(1-ethyl-2-pyrrolidinyl)methyl]-N4-(3-fluoro-4-methoxyphenyl)-N6-[3-(1H-imidazol-1-yl)propyl]-1,3,5-triazine-2,4,6-triamine | ++++ | +++ | 43 | 46 |
| 140 | 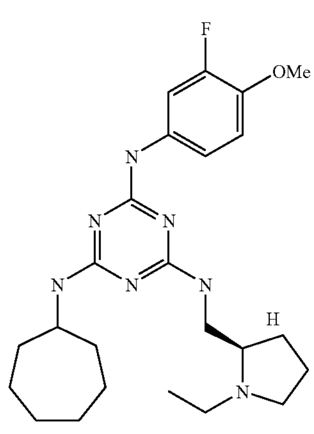 | $N^2$-cycloheptyl-$N^4$-((R)-1-ethyl-pyrrolidin-2-ylmethyl)-$N^6$-(3-fluoro-4-methoxyphenyl)-1,3,5-triazine-2,4,6-triamine | ++++ | n.d. | 12.57 | n.d. |

TABLE 5-continued

Triazine compounds useful in treating inflammatory disorders generally, and all diseases related to inhibition of IL6.

| Patent Number | STRUCTURE | Name Generated by Autonom (TM) | Inhibition of TNF-induced IL6 production (See NOTE) | Inhibition of TNF-induced IL6 production | % IL6 production compare to TNF stimulation of IL6 (100%). Compds tested @ 10 uM HAEC, IL6 | % IL6 production compare to AGE stimulation of IL6 (100%). Compds tested @ 10 uM HAEC, IL6 |
|---|---|---|---|---|---|---|
| 139 | 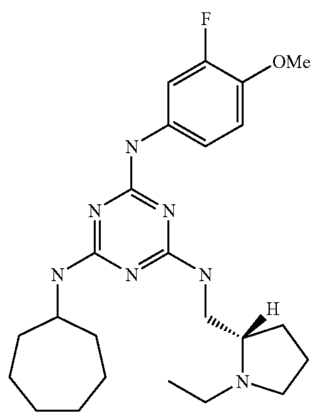 | $N^2$-cycloheptyl-$N^4$-((S)-1-ethyl-pyrrolidin-2-ylmethyl)-$N^6$-(3-fluoro-4-methoxyphenyl)-1,3,5-triazine-2,4,6-triamine | ++++ | n.d. | 16.08 | n.d. |
| 127 | 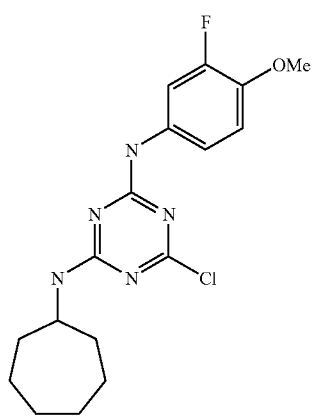 | 6-Chloro-N-cycloheptyl-N'-(3-fluoro-4-methoxyphenyl)-[1,3,5]triazine-2,4-diamine | +++ | n.d. | 48 | n.d. |
| 141 | 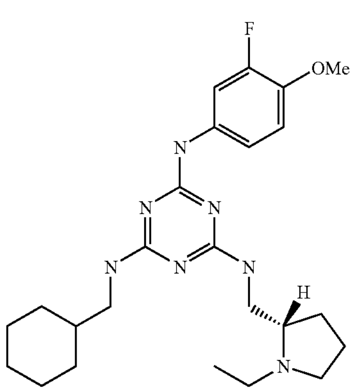 | $N^2$-cyclohexylmethyl-$N^4$-((S)-1-ethyl-pyrrolidin-2-ylmethyl)-$N^6$-(3-fluoro-4-methoxyphenyl)-1,3,5-triazine-2,4,6-triamine | ++++ | n.d. | 23.44 | n.d. |

TABLE 5-continued

Triazine compounds useful in treating inflammatory disorders generally, and all diseases related to inhibition of IL6.

| Patent Number | STRUCTURE | Name Generated by Autonom (TM) | Inhibition of TNF-induced IL6 production (See NOTE) | Inhibition of TNF-induced IL6 production | % IL6 production compare to TNF stimulation of IL6 (100%). Compds tested @ 10 uM HAEC, IL6 | % IL6 production compare to AGE stimulation of IL6 (100%). Compds tested @ 10 uM HAEC, IL6 |
|---|---|---|---|---|---|---|
| 142 | 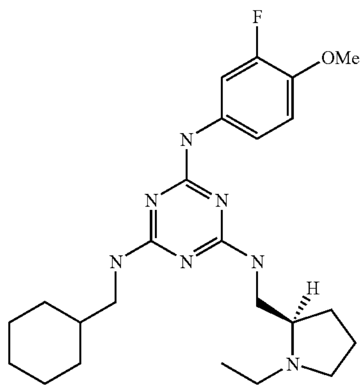 | $N^2$-cyclohexylmethyl-$N^4$-((R)-1-ethyl-pyrrolidin-2-ylmethyl)-$N^6$-(3-fluoro-4-methoxyphenyl)-1,3,5-triazine-2,4,6-triamine | ++++ | n.d. | 21.62 | n.d. |
| 143 | 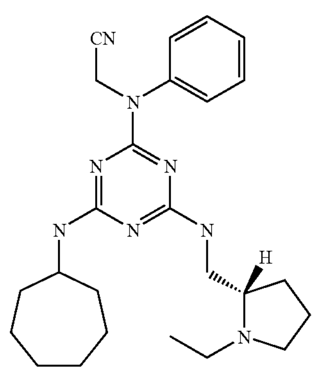 | ({4-cycloheptylamino-6-[((S)-1-ethyl-pyrrolidin-2-ylmethyl)-amino]-1,3,5-triazin-2-yl}-phenyl-amino)-acetonitrile | ++++ | n.d. | 18.88 | n.d. |
| 144 | 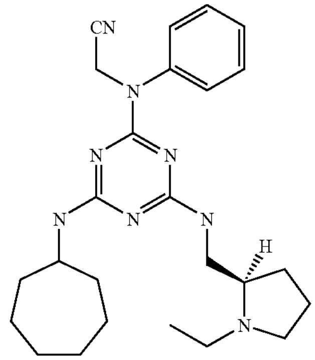 | ({4-cycloheptylamino-6-[((R)-1-ethyl-pyrrolidin-2-ylmethyl)-amino]-1,3,5-triazin-2-yl}-phenyl-amino)-acetonitrile | ++++ | n.d. | | |

TABLE 5-continued

Triazine compounds useful in treating inflammatory disorders generally, and all diseases related to inhibition of IL6.

| Patent Number | STRUCTURE | Name Generated by Autonom (TM) | Inhibition of TNF-induced IL6 production (See NOTE) | Inhibition of TNF-induced IL6 production | % IL6 production compare to TNF stimulation of IL6 (100%). Compds tested @ 10 uM HAEC, IL6 | % IL6 production compare to AGE stimulation of IL6 (100%). Compds tested @ 10 uM HAEC, IL6 |
|---|---|---|---|---|---|---|
| 157 | 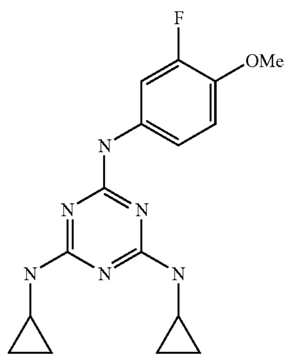 | N,N'-dicyclopropyl-N''-(3-fluoro-4-methoxy-phenyl)-1,3,5-triazine-2,4,6-triamine | ++ | n.d. | 60.48 | n.d. |
| 160 | HCl | $N^2$-cycloheptyl-$N^4$-(3-fluoro-4-methoxyphenyl)-$N^6$-methyl-$N^6$-(1-methyl-piperidin-4-yl)-1,3,5-triazine-2,4,6-triamine, hydrogen chloride salt | ++++ | n.d. | 1 | n.d. |
| 101 | 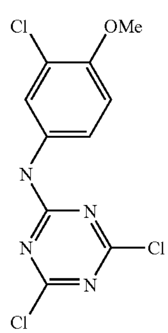 | (3-Chloro-4-methoxy-phenyl)-(4,6-dichloro-[1,3,5]triazin-2-yl)-amine | n.d. | n.d. | n.d. | n.d. |

TABLE 5-continued

Triazine compounds useful in treating inflammatory disorders generally, and all diseases related to inhibition of IL6.

| Patent Number | STRUCTURE | Name Generated by Autonom (TM) | Inhibition of TNF-induced IL6 production (See NOTE) | Inhibition of TNF-induced IL6 production | % IL6 production compare to TNF stimulation of IL6 (100%). Compds tested @ 10 uM HAEC, IL6 | % IL6 production compare to AGE stimulation of IL6 (100%). Compds tested @ 10 uM HAEC, IL6 |
|---|---|---|---|---|---|---|
| 107 | 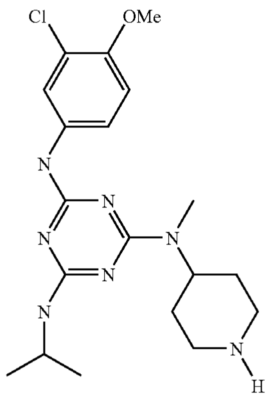 | $N^2$-(3-chloro-4-methoxy-phenyl)-$N^4$-isopropyl-$N^6$-methyl-$N^6$-piperidin-4-yl-1,3,5-triazine-2,4,6-triamine | ++ | n.d. | 60 @ 5 uM | n.d. |
| 108 | 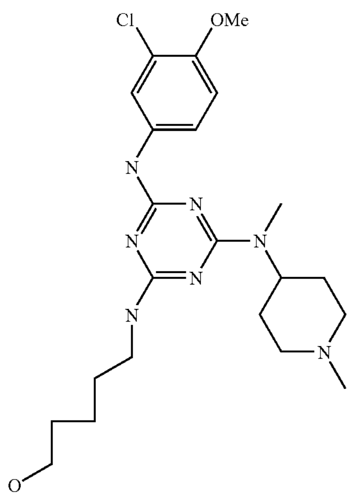 | 5-(4-(3-Chloro-4-methoxy-phenylamino)-6-[methyl-(1-methyl-piperidin-4-yl)-amino]-[1,3,5]triazin-2-ylamino}-pentan-1-ol | +++ | n.d. | 25 | n.d. |
| 109 | 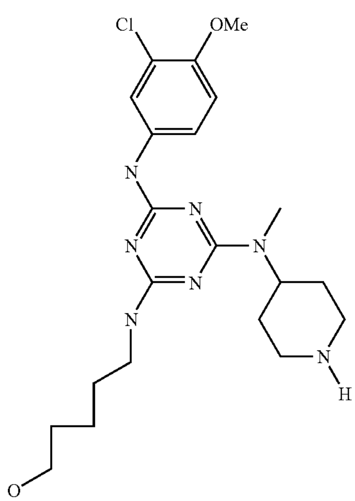 | 5-[4-(3-chloro-4-methoxy-phenylamino)-6-(methyl-piperidin-4-yl-amino)-1,3,5-triazin-2-ylamino]-pentan-1-ol | +++ | n.d. | 40 | n.d. |

TABLE 5-continued

Triazine compounds useful in treating inflammatory disorders generally, and all diseases related to inhibition of IL6.

| Patent Number | STRUCTURE | Name Generated by Autonom (TM) | Inhibition of TNF-induced IL6 production (See NOTE) | Inhibition of TNF-induced IL6 production | % IL6 production compare to TNF stimulation of IL6 (100%). Compds tested @ 10 uM HAEC, IL6 | % IL6 production compare to AGE stimulation of IL6 (100%). Compds tested @ 10 uM HAEC, IL6 |
|---|---|---|---|---|---|---|
| 111 | 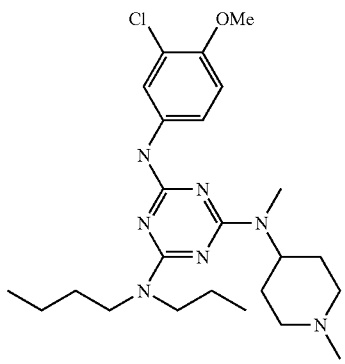 | N-Butyl-N'-(3-chloro-4-methoxy-phenyl)-N''-(1-methyl-piperidin-4-yl)-N-propyl-[1,3,5]triazine-2,4,6-triamine | + | n.d. | >90 [46 @ 5 uM] did not see toxicity | n.d. |
| 112 | 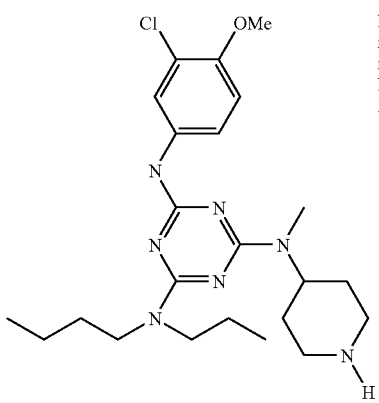 | $N^2$-Butyl-$N^4$-(3-chloro-4-methoxy-phenyl)-$N^6$-methyl-$N^6$-piperidin-4-yl-$N^2$-propyl-1,3,5-triazine-2,4,6-triamine | + | n.d. | 90 @ 5 uM did not see toxicity | n.d. |

NOTE: The scale is as follows:

(1) "++++" = 0–25% of IL6 production compared to cells that did not receive compound (or per cent of control IL6 production);

(2) "+++" = >2514 50% of control IL6 production; and (3) "++" = >50–75% of control IL6 production; and, (4) "+" = >75–100% of control IL6 production.

"n.d." means that the activity of the compound was not determined in the given assay.

TABLE 6

| Patent # | STRUCTURE | Name Generated by Autonom ™ | Relative Activity | Activity |
|---|---|---|---|---|
| 76 | 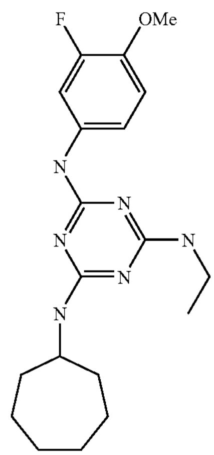 | N2-cycloheptyl-N4-ethyl-N6-(3-fluoro-4-methoxyphenyl)-1,3,5-triazine-2,4,6-triamine | ++ | 50% inhibition @ 5 uM |
| 82 | 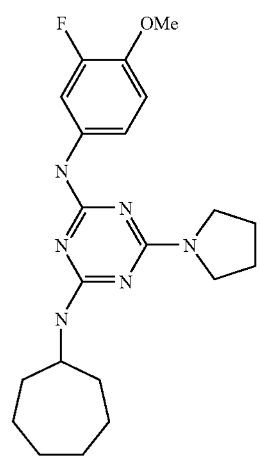 | N2-cycloheptyl-N4-(3-fluoro-4-methoxyphenyl)-6-(1-pyrrolidinyl)-1,3,5-triazine-2,4-diamine | +++ | 73% inhibition @ 5 uM |
| 87 | 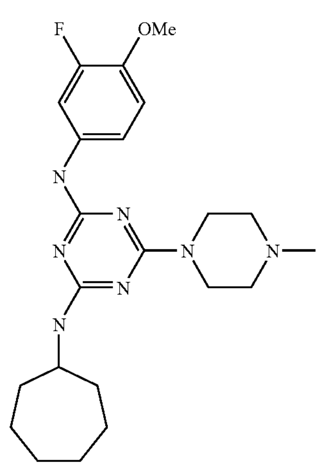 | N2-cycloheptyl-N4-(3-fluoro-4-methoxyphenyl)-6-(4-methyl-1-piperazinyl)-1,3,5-triazine-2,4-diamine | + | 40–60% inhibition @ 10 uM |

TABLE 6-continued

Inhibition of TNF-induced heparanase secretion

| Patent # | STRUCTURE | Name Generated by Autonom ™ | Relative Activity | Activity |
|---|---|---|---|---|
| 94 | 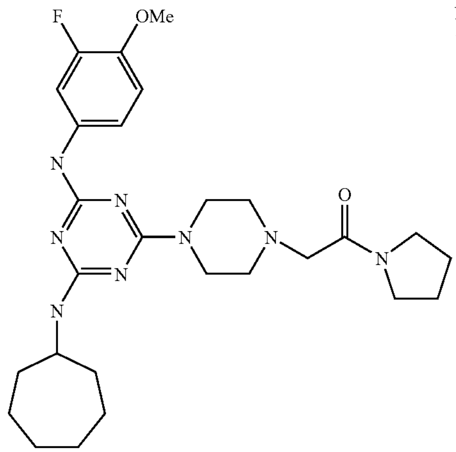 | N2-cycloheptyl-N4-(3-fluoro-4-methoxyphenyl)-6-{4-[2-oxo-(1-pyrrolidinyl)ethyl]-1-piperazinyl}-1,3,5-triazine-2,4-diamine | + | 40–60% inhibition @ 10 uM |
| 35 | 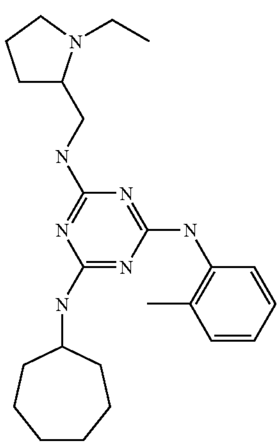 | N2-cycloheptyl-N4-[(1-ethyl-2-pyrrolidinyl)methyl]-N6-(2-methylphenyl)-1,3,5-triazine-2,4,6-triamine | ++ | 53% inhibition @ 5 uM |
| 52 | 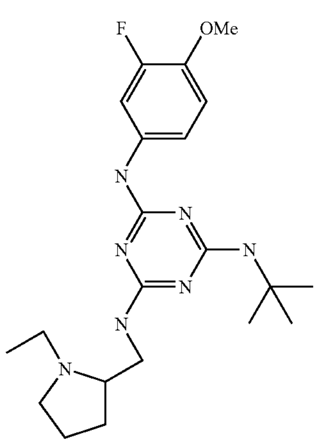 | N2-(tert-butyl)-N4-[(1-ethyl-2-pyrrolidinyl)methyl]-N6-(3-fluoro-4-methoxyphenyl)-1,3,5-triazine-2,4,6-triamine | + | 40–60% inhibition @ 10 uM |

TABLE 6-continued

Inhibition of TNF-induced heparanase secretion

| Patent # | STRUCTURE | Name Generated by Autonom ™ | Relative Activity | Activity |
|---|---|---|---|---|
| 58 | 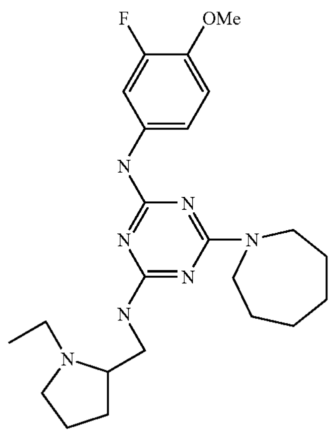 | N2-[(1-ethyl-2-pyrrolidinyl)methyl]-N4-(3-fluoro-4-methoxyphenyl)-6-hexahydro-1H-azepin-1-yl-1,3,5-triazine-2,4-diamine | + | 40–60% inhibition @ 10 uM |
| 61 | 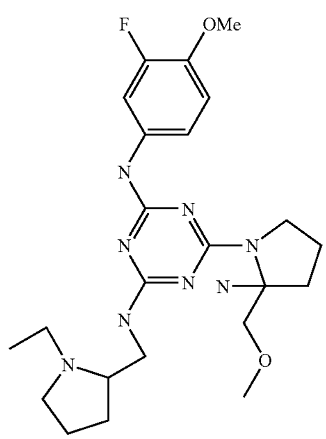 | N2-[(1-ethyl-2-pyrrolidinyl)methyl]-N4-(3-fluoro-4-methoxyphenyl)-6-[2-(methoxymethyl)-1-pyrrolidinyl]-1,3,5-triazine-2,4-diamine | + | 40–60% inhibition @ 10 uM |

NOTE: The scale is as follows:

(1) "+++" = 70–100% inhibition;

(2) "++" = 30–40% inhibition; and (3) "+" = 0–30% inhibition all at 5 uM compound concentration.

TABLE 7

*Triazine compounds useful in treating inflammatory disorders generally, and all diseases related to inhibition of IL6.*

| Compound Number | STRUCTURE | Name (IUPAC-Generated by Autonom) | Inhibition of TNF-induced IL6 production | Inhibition of TNF-induced IL6 production | % IL6 production compare to TNF stimulation of IL6 (100%) Compds tested @ 10 uM HAEC, IL6 | % IL6 production compare to AGE stimulation of IL6 (100%) Compds tested @ 10 uM HAEC, IL6 |
|---|---|---|---|---|---|---|
| 172 | 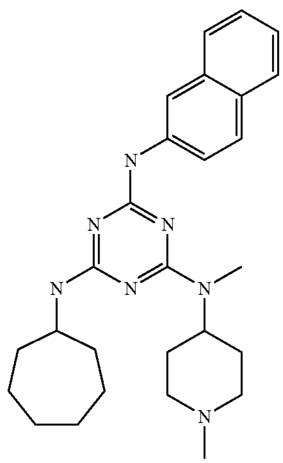 | N-Cycloheptyl-N'-methyl-N'-(1-methyl-piperidin-4-yl)-N''-napthalen-2-yl-[1,3,5]triazine-2,4,6-triamine | +++ | ++ | 18 | n.d. |
| 171 | 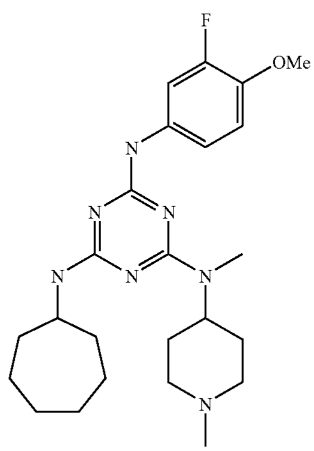 | N-Cycloheptyl-N'-(3-fluoro-4-methoxy-phenyl)-N'''-methyl-N''-(1-methyl-piperidin-4-yl)-[1,3,5]triazine-2,4,6-triamine | +++ | ++ | 21 | n.d. |
| 173 | 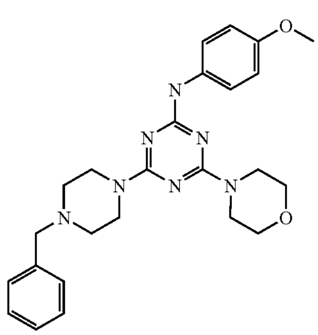 | [4-(4-Benzyl-piperidin-1-yl)-6-morpholin-4-yl-[1,3,5]triazin-2-yl]-(4-methoxy-phenyl)-amine | ++ | | 47 | n.d. |

TABLE 7-continued

Triazine compounds useful in treating inflammatory disorders generally, and all diseases related to inhibition of IL6.

| Compound Number | STRUCTURE | Name (IUPAC-Generated by Autonom) | Inhibition of TNF-induced IL6 production | Inhibition of TNF-induced IL6 production | % IL6 production compare to TNF stimulation of IL6 (100%) Compds tested @ 10 uM HAEC, IL6 | % IL6 production compare to AGE stimulation of IL6 (100%) Compds tested @ 10 uM HAEC, IL6 |
|---|---|---|---|---|---|---|
| 174 | 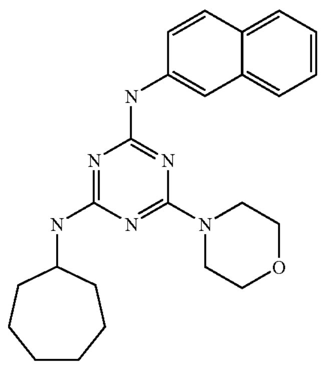 | N-Cycloheptyl-6-morpholin-4-yl-N'-napthalen-2-yl-[1,3,5]triazine-2,4-diamine | +++ | | 34 | n.d. |
| 175 | 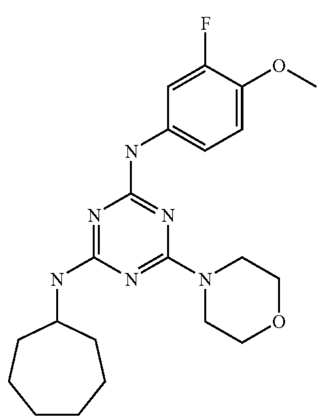 | N-Cycloheptyl-N'-(3-fluoro-4-methoxy-phenyl)-6-morpholin-4-yl-[1,3,5]triazine-2,4-diamine | +++ | | 18 | n.d. |
| 176 | 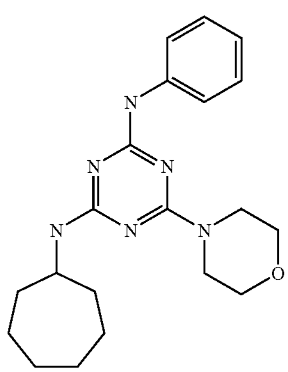 | N-Cycloheptyl-6-morpholin-4-yl-N'-phenyl-[1,3,5]triazine-2,4-diamine | +++ | | 33 | n.d. |

TABLE 7-continued

Triazine compounds useful in treating inflammatory disorders generally, and all diseases related to inhibition of IL6.

| Compound Number | STRUCTURE | Name (IUPAC-Generated by Autonom) | Inhibition of TNF-induced IL6 production | Inhibition of TNF-induced IL6 production | % IL6 production compare to TNF stimulation of IL6 (100%) Compds tested @ 10 uM HAEC, IL6 | % IL6 production compare to AGE stimulation of IL6 (100%) Compds tested @ 10 uM HAEC, IL6 |
|---|---|---|---|---|---|---|
| 177 | 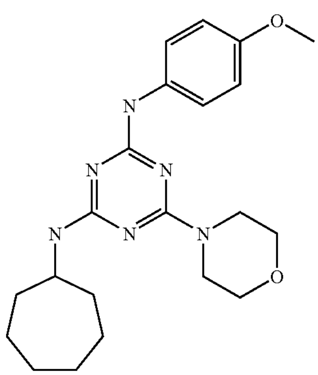 | N-Cycloheptyl-N'-(4-methoxy-phenyl)-6-morpholin-4-yl-[1,3,5]triazine-2,4-diamine | +++ | ++ | | n.d. |
| 178 | 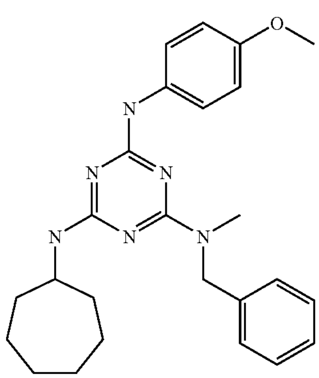 | N-Benzyl-N'-cycloheptyl-N''-(4-methoxy-phenyl)-N-methyl-[1,3,5]triazine-2,4,6-triamine | ++ | | 19 | n.d. |
| 179 | 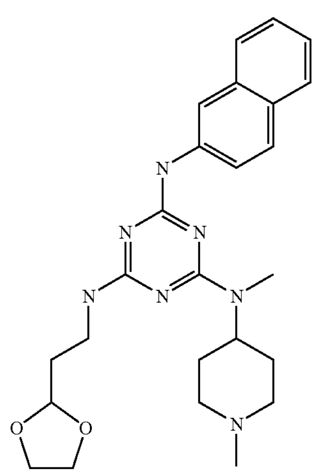 | N-(2-[1,3]Dioxolan-2-yl-ethyl)-N'-methyl-N'-(1-methyl-piperidin-4-yl)-N''-naphthalen-2-yl-[1,3,5]triazine-2,4,6-triamine | ++ | + | | |

TABLE 7-continued

Triazine compounds useful in treating inflammatory disorders generally, and all diseases related to inhibition of IL6.

| Compound Number | STRUCTURE | Name (IUPAC-Generated by Autonom) | Inhibition of TNF-induced IL6 production | Inhibition of TNF-induced IL6 production | % IL6 production compare to TNF stimulation of IL6 (100%) Compds tested @ 10 uM HAEC, IL6 | % IL6 production compare to AGE stimulation of IL6 (100%) Compds tested @ 10 uM HAEC, IL6 |
|---|---|---|---|---|---|---|
| 180 | 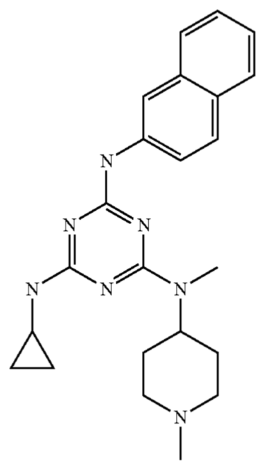 | N-Cyclopropyl-N'-methyl-N'-(1-methyl-piperidin-4-yl)-N''-naphthalen-2-yl-[1,3,5]triazine-2,4,6-triamine | +++ | + | n.d. | 5 |

NOTE:
"+++" represents between about 85 to 100% inhibition of IL6 production in the presence of AGE or TNF, as compared to cells that did not receive any compound;
"++" represents between about 65 and about 85% inhibition of IL6 production in the presence of AGE or TNF; and
"+" represents between about 50 and about 65% inhibition of IL6 production in the presence of AGE or TNF.

TABLE 8

| Cmpd No. | Structure | Proliferation Data | Inflammation Data |
|---|---|---|---|
| | | Did not pass 5 & 10 uM screens; rounding | Not Active |
| | | Did not pass 5 & 10 uM screens; blunting and rounding | total cell death at 10uM (75% inhibition); 25% cell death at 5 uM (not active) |

TABLE 8-continued

| Cmpd No. | Structure | Proliferation Data | Inflammation Data |
|---|---|---|---|
|  |  | Not active at 5 & 10 uM | 48% inhibition at 10 uM with 20% cell death |
|  |  | Not active at 5 & 10 uM | complete inhibition at 10 uM |
|  |  | Not active | <25% inhibition at 10 uM |
|  |  | Not active at 5 & 10 uM | 75% inhibition at 10 uM |

TABLE 8-continued

| Cmpd No. | Structure | Proliferation Data | Inflammation Data |
|---|---|---|---|
| | [structure: 4-OMe, 3-Cl phenyl-NH-triazine-NH-cycloheptyl with O-linked piperidin-3-yl] | 4.9 uM average IC50 | 60% inhibition at 10 uM with 20% cell death |
| | [structure: 4-OMe, 3-Cl phenyl-NH-triazine-NH-cycloheptyl with O-linked piperidin-4-yl] | 1.85 uM average IC50 | 85% inhibition at 10 uM with 20% cell death |
| | [structure: 4-OMe, 3-Cl phenyl-NH-triazine-NH-cycloheptyl with O-CH2-(1-methylpyrrolidin-2-yl)] | 5.25 uM average IC50 | total cell deat at 10 uM (complete inhibition) |
| | [structure: 4-OMe, 3-Cl phenyl-NH-triazine-NH-cycloheptyl with O-linked 1-methylpiperidin-4-yl] | rounding at 5 & 10 uM | total cell deat at 10 uM (95% inhibition) |

TABLE 8-continued
| Cmpd No. | Structure | Proliferation Data | Inflammation Data |
|---|---|---|---|
| | 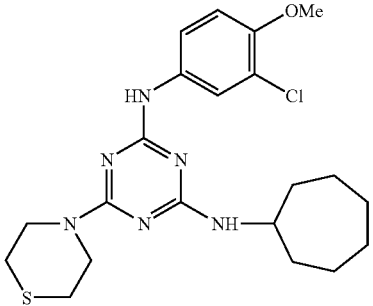 | Not active | Not Active |
| | 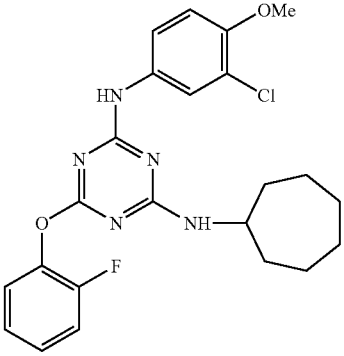 | Not active | Not Active |
| | 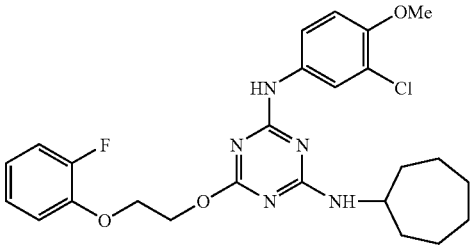 | Not active | Not Active |
| | 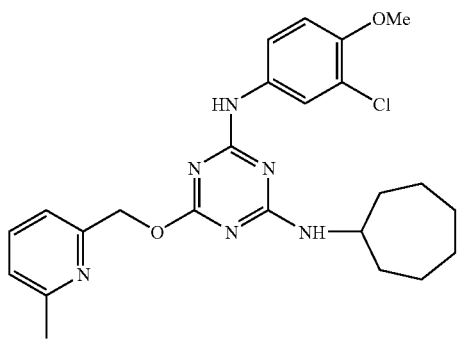 | Not active | 60% inhibition at 10 uM |

TABLE 8-continued

| Cmpd No. | Structure | Proliferation Data | Inflammation Data |
|---|---|---|---|
| | 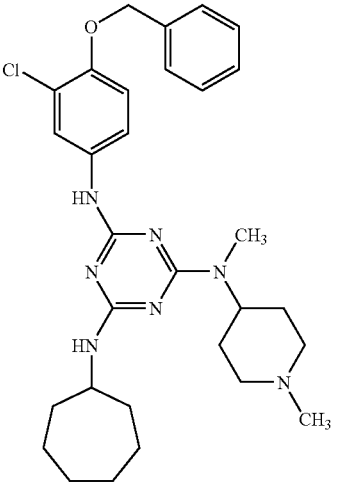 | 6.37 uM; cell morphology change at 5 & 10 uM; no cell death | Not active at 1 or 5 uM; 30% cell death at 5 uM and total death at 10 uM |
| | 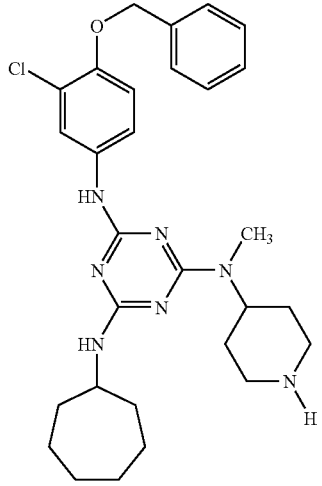 | 6.1 uM; cell morphology change at 7.5 uM and cell death at 10 uM | total cell death at 10 uM; 58% inhibition at 5 uM, but may be due to cell death (50% death), not active at 1 uM |
| | 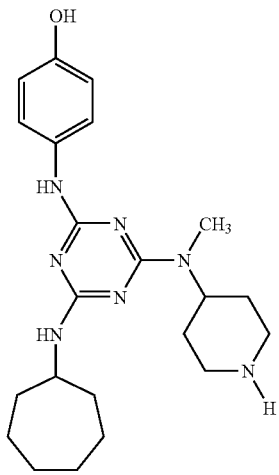 | 5.5 uM | total cell death at 10 uM; 50% inhibition at 5 uM, with 20% cell death |

TABLE 8-continued
| Cmpd No. | Structure | Proliferation Data | Inflammation Data |
|---|---|---|---|
| | 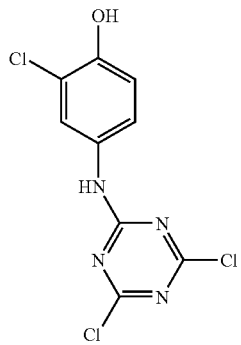 | Not active | 35% inhibition at 10 uM |
| | 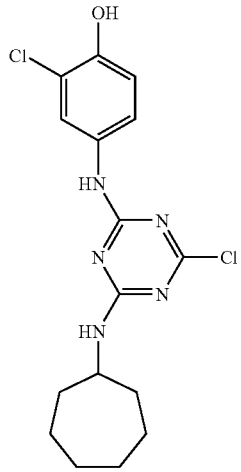 | Not active | 25% inhibition at 5 uM and 10 uM |
| | 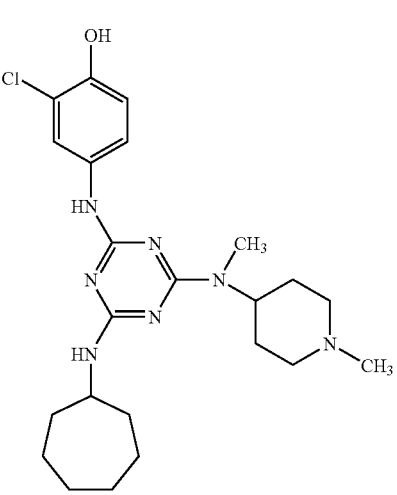 | 3.3 uM; 4.5 uM; cell blunting at 3 to 10 uM | total cell death at 10 uM (84% inhibition); 64% inhibition at 5 uM |

TABLE 8-continued

| Cmpd No. | Structure | Proliferation Data | Inflammation Data |
|---|---|---|---|
| | (4-methoxy-3-fluorophenyl)-cycloheptyl-(1-benzylpiperidin-4-yl) triazine structure | 1.5 uM; 4.2 uM; cell blunting at 3 uM and rounding at 5 uM | total cell death at 10 uM (97% inhibition); 43% inhibition at 5 uM with 25% cell death |
| | (4-methoxy-3-chlorophenyl)-cycloheptyl-(1-benzylpiperidin-4-yl) triazine structure | 1.9 uM; cell blunting at 1 uM and rounding at 5 uM | 41% inhibition at 10 uM with >50% cell death; 37% inhibition at 5 uM with 20% cell death |

TABLE 8-continued
| Cmpd No. | Structure | Proliferation Data | Inflammation Data |
|---|---|---|---|
| | 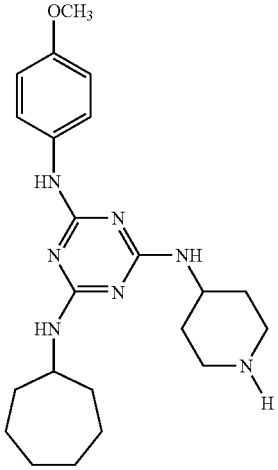 | 6.6 uM | 88% inhibition at 10 uM with >50% cell death; 69% inhibition at 5 uM with 20%l cell death |
| | 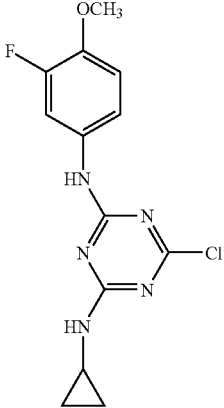 | Not active | 36% inhibition at 10 uM |
| | 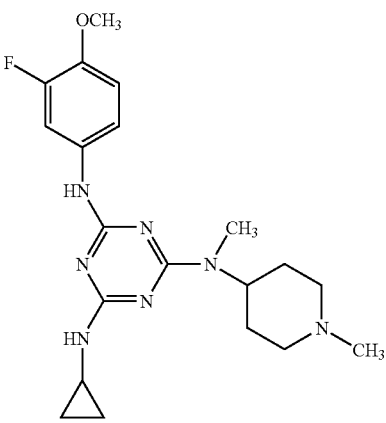 | Not active | 25% inhibition at 10 uM |

TABLE 8-continued

| Cmpd No. | Structure | Proliferation Data | Inflammation Data |
|---|---|---|---|
| | [triazine with 3-fluoro-4-methoxyanilino, cyclopropylamino, and (1-ethylpyrrolidin-2-yl)methylamino substituents] | Not active | 23% inhibition at 10 uM |
| | [triazine with 3-chloro-4-methoxyanilino, cyclopropylamino, and chloro substituents] | Not tested | Not tested |
| | [triazine with 3-chloro-4-methoxyanilino, cyclopropylamino, and N-methyl-N-(1-methylpiperidin-4-yl)amino substituents] | 4.1 uM | Not active with 15% cell death at 10 uM |

TABLE 8-continued
| Cmpd No. | Structure | Proliferation Data | Inflammation Data |
|---|---|---|---|
| | 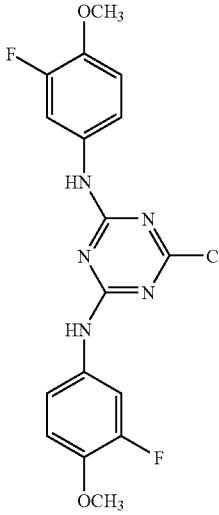 | Not active | 20% inhibition at 10 uM, no effect at 5 uM |
| | 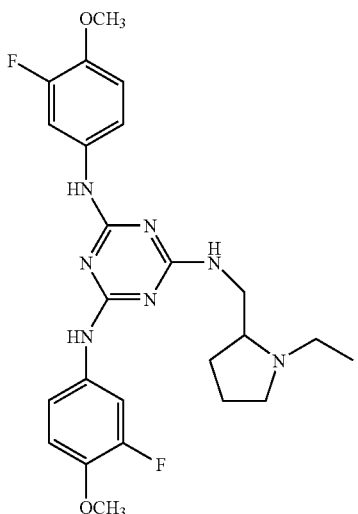 | 7.8 uM; 5.3 uM | 35% inhibition at 10 uM, 25% inhibition at 5 uM |
We claim:
1. A compound of the formula Ib:
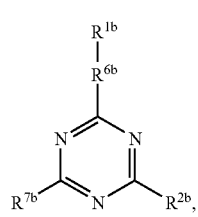
(Ib)
wherein:
$R^{1b}$ is selected from
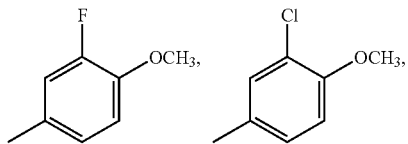

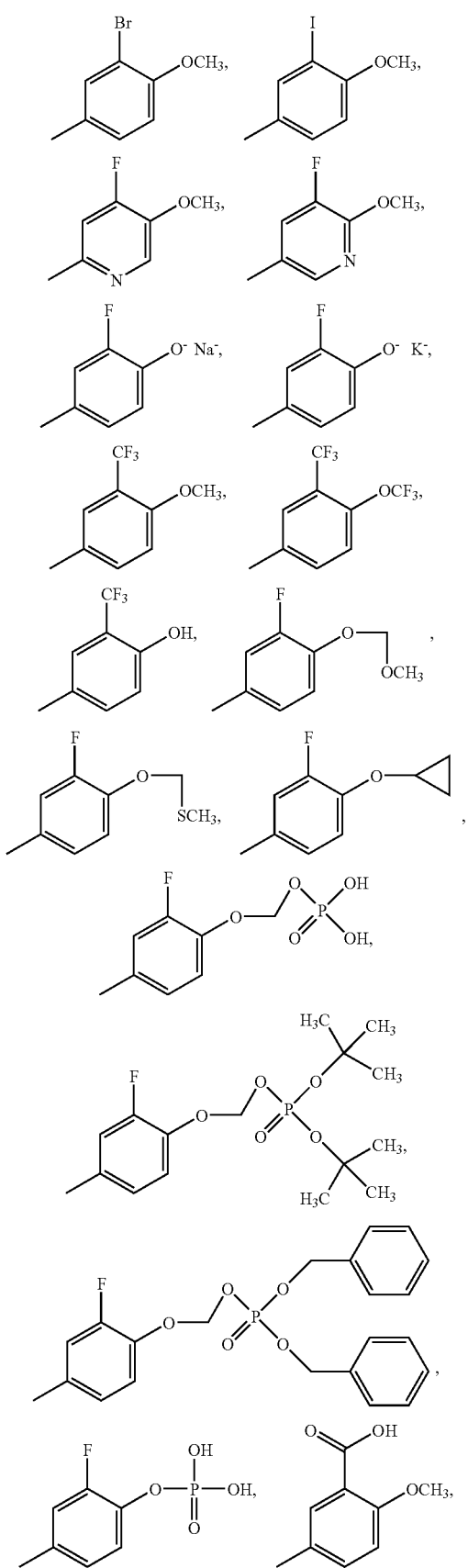
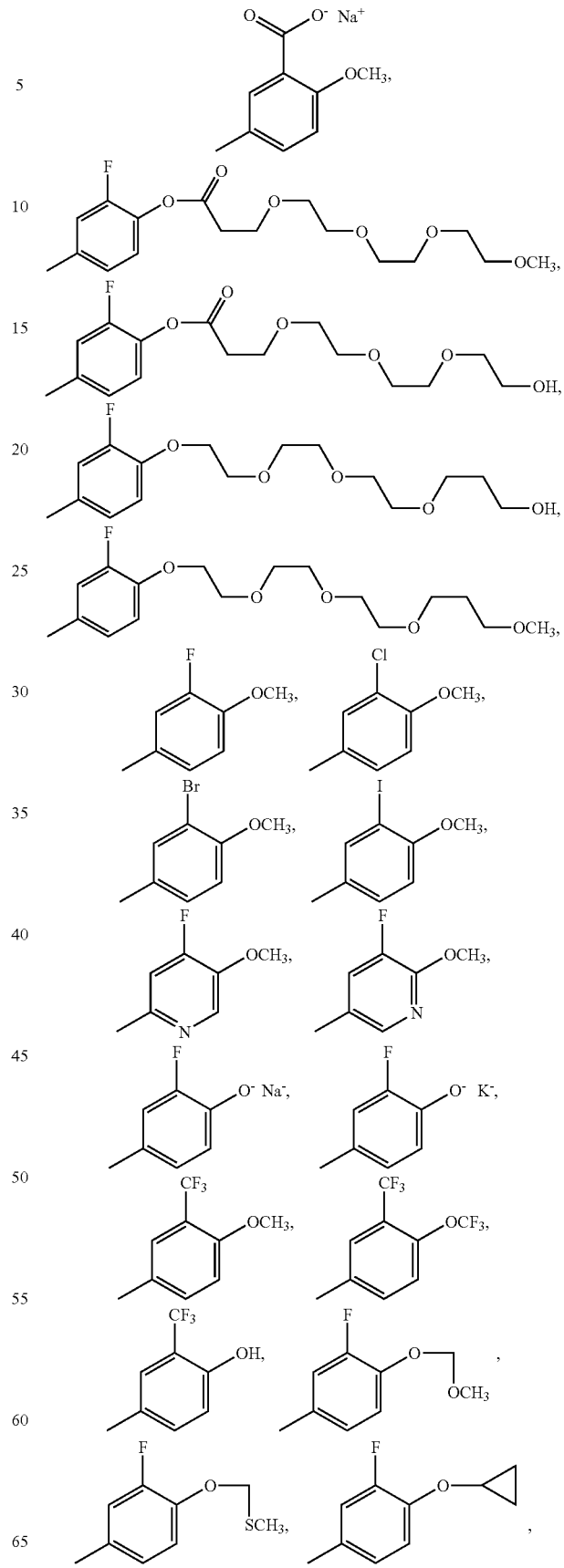

579
-continued
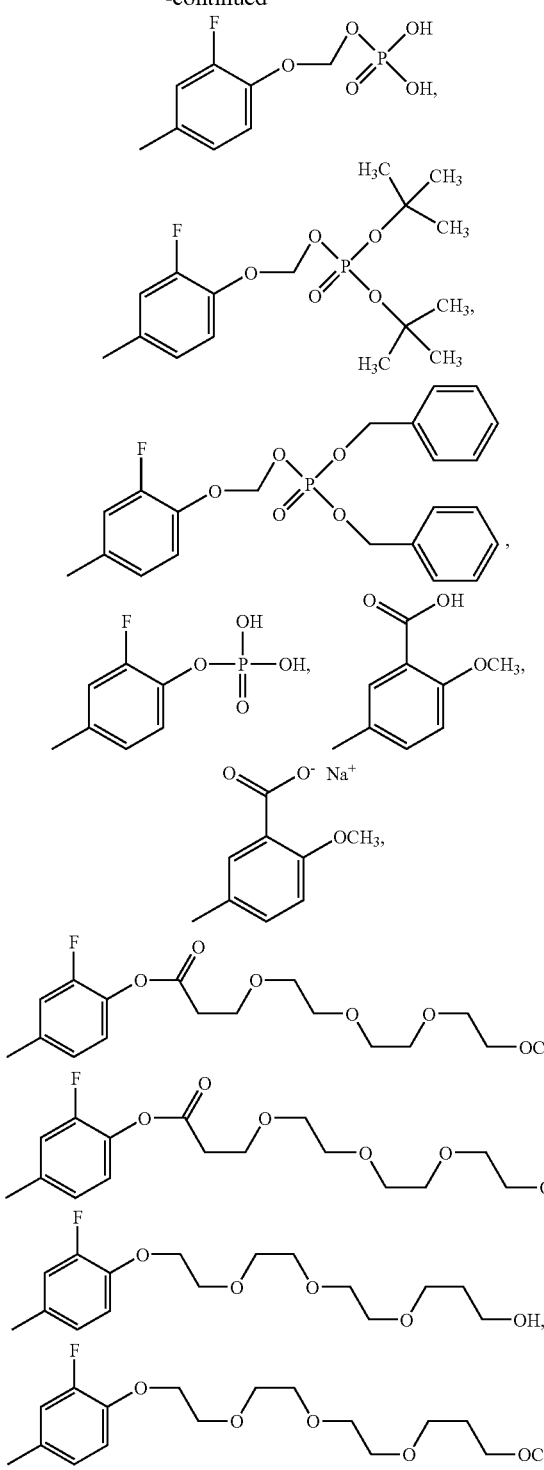
$R^{2b}$ is selected from
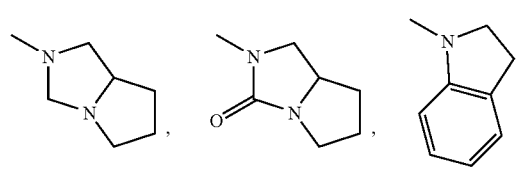
580
-continued
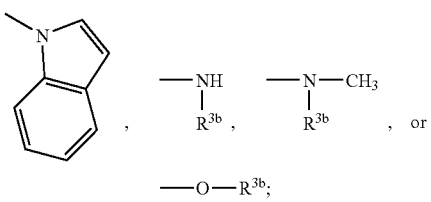, —NH—R$^{3b}$, —N(CH$_3$)—R$^{3b}$, or
—O—R$^{3b}$;
$R^{3b}$ is selected from
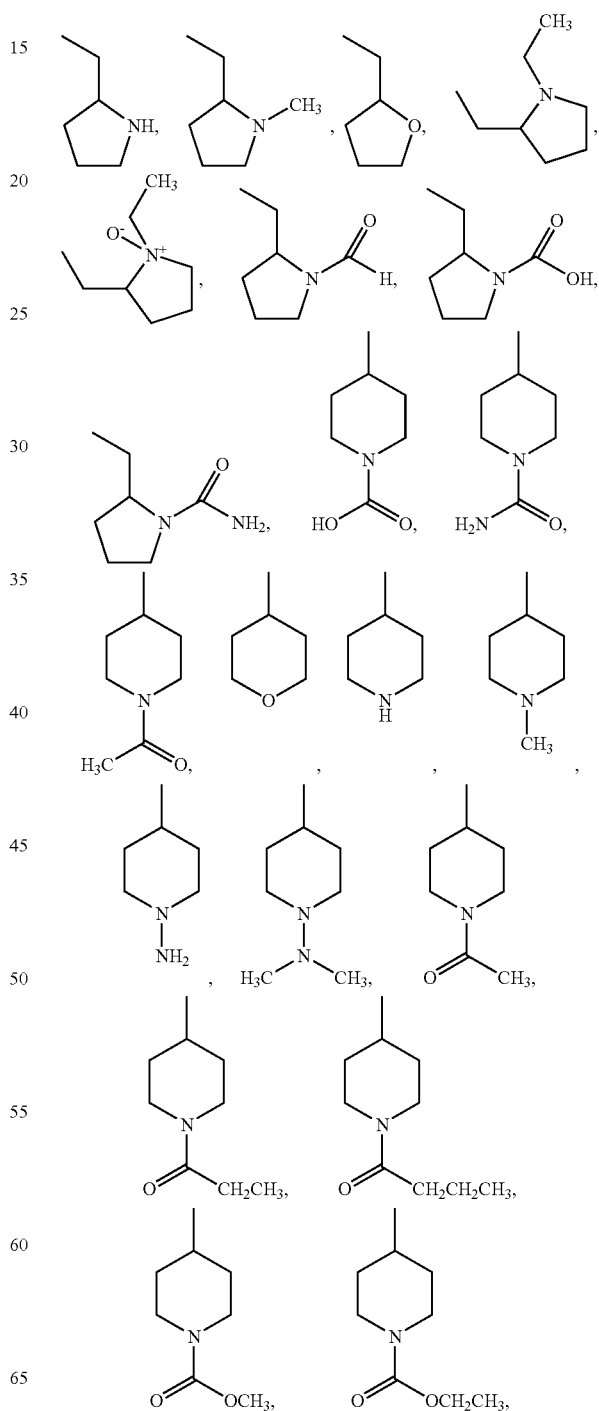

-continued
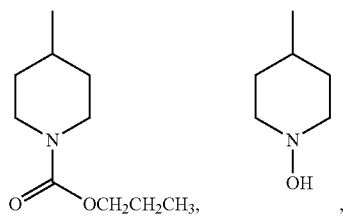
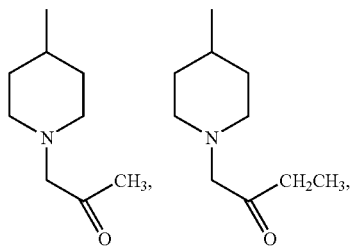
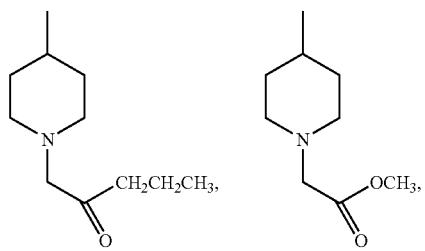
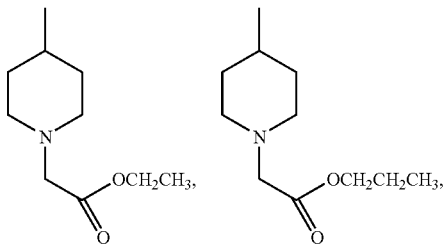
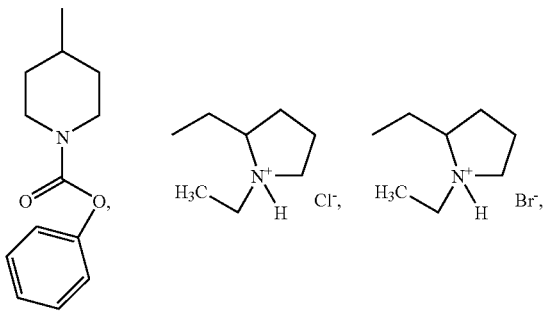
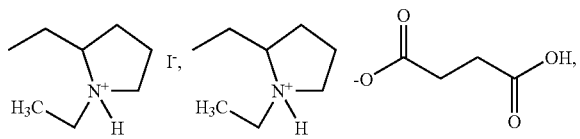
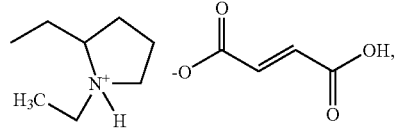
-continued
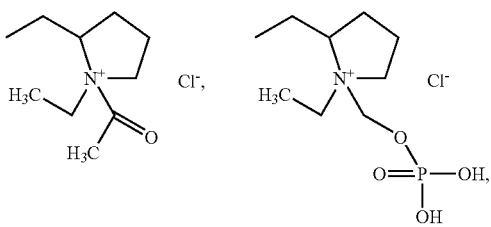
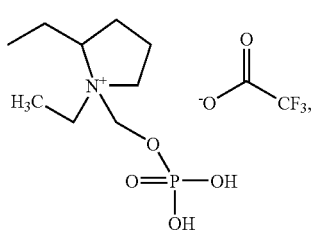
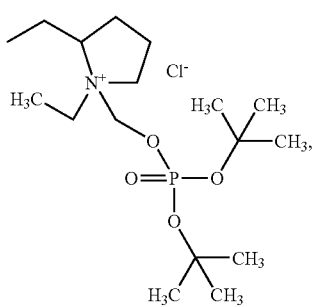
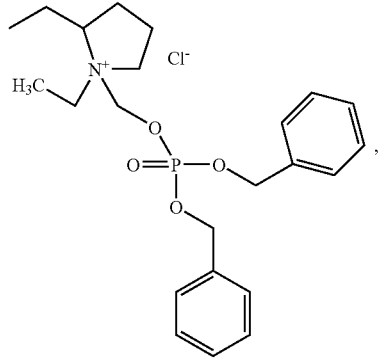
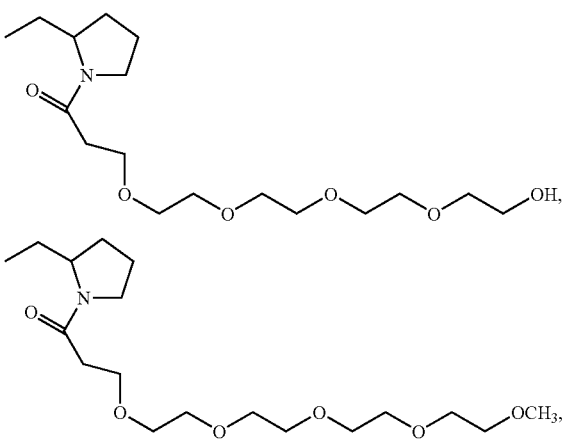

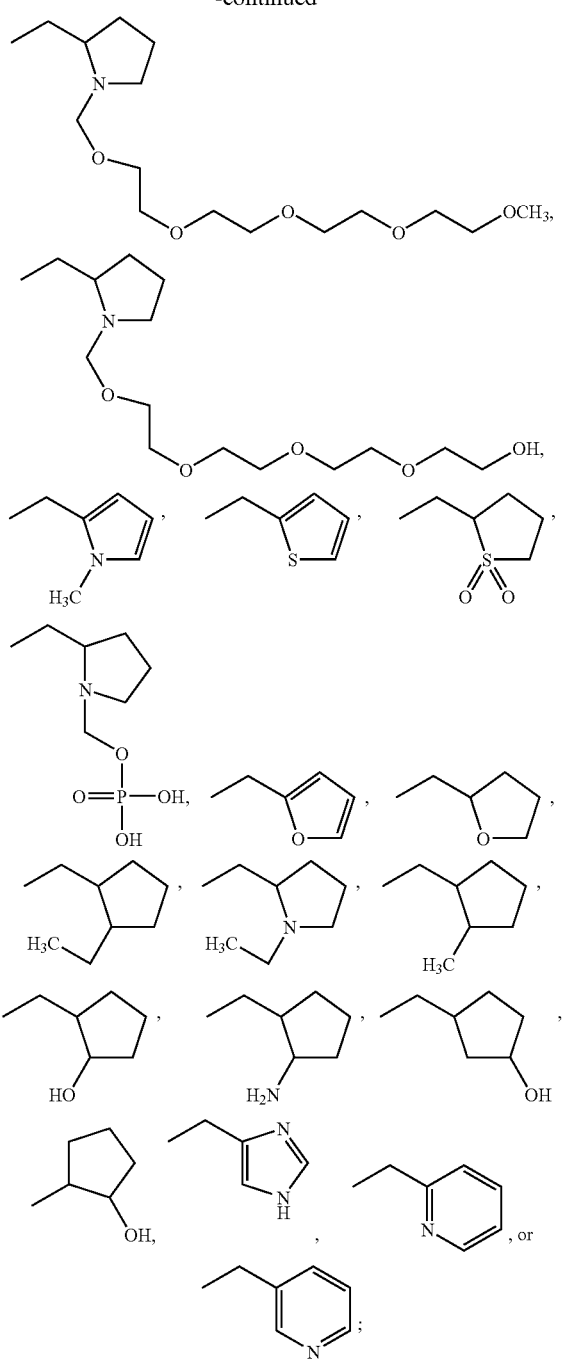
$R^{4b}$ is selected from —H, —CH$_3$, —CH$_2$CH$_3$, or —CH$_2$CH$_2$CH$_3$;
$R^{5b}$ is selected from
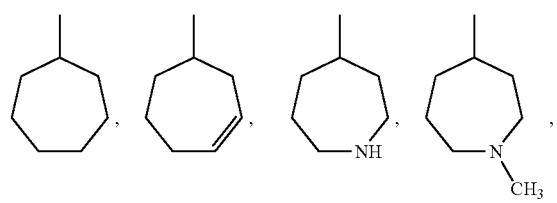
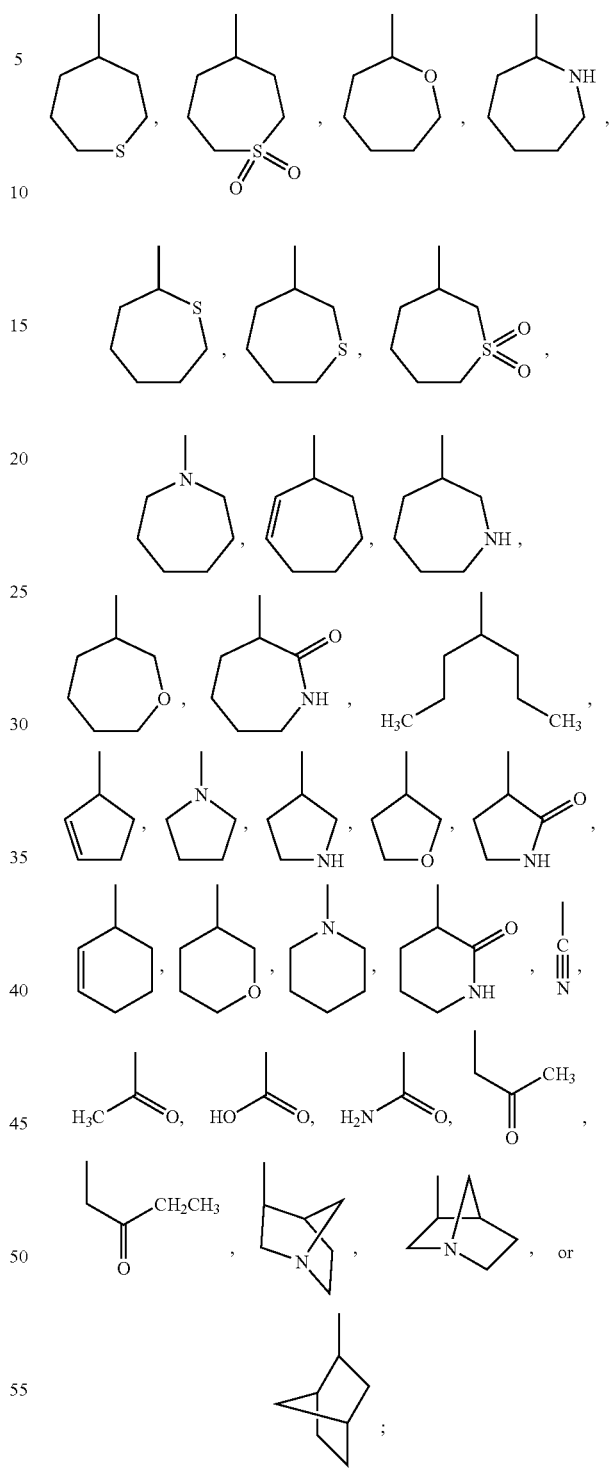
$R^{6b}$ is selected from
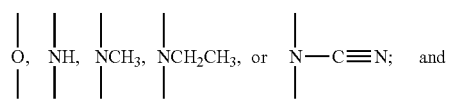
; and R$^{7b}$ is selected from

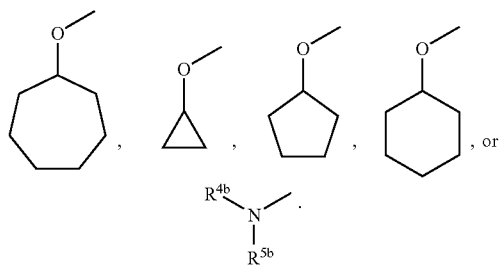

2. A compound as claimed in claim 1, wherein the compound is:
N-Cycloheptyl-N'(1-ethyl-pyrrolidin-2-ylmethyl)-6-(3-fluoro-4-methoxy-phenoxy)-[1,3,5]triazine-2,4-diamine;
6-(3-Chloro-4-methoxy-phenoxy)-N-cycloheptyl-N'-(1-ethyl-pyrrolidin-2-ylmethyl)-[1,3,5]triazine-2,4-diamine;
6-(3-Bromo-4-methoxy-phenoxy)-N-cycloheptyl-N'-(1-ethyl-pyrrolidin-2-ylmethyl)-[1,3,5]triazine-2,4-diamine;
N-Cycloheptyl-N'(1-ethyl-pyrrolidin-2-ylmethyl)-6-(3-iodo-4-methoxy-phenoxy)-[1,3,5]triazine-2,4-diamine;
N-Cycloheptyl-N'-(1-ethyl-pyrrolidin-2-ylmethyl)-N''-(3-fluoro-4-methoxy-benzyl)-[1,3,5]triazine-2,4,6-triamine;
N-(3-Chloro-4-methoxy-benzyl)-N'-cycloheptyl-N''-(1-ethyl-pyrrolidin-2-ylmethyl)-[1,3,5]triazine-2,4,6-triamine;
N-(3-Bromo-4-methoxy-benzyl)-N'-cycloheptyl-N''-(1-ethyl-pyrrolidin-2-ylmethyl)-[1,3,5]triazine-2,4,6-triamine;
N-Cycloheptyl-N'-(1-ethyl-pyrrolidin-2-ylmethyl)-N''-(3-iodo-4-methoxy-benzyl)-[1,3,5]triazine-2,4,6-triamine;
N-Cycloheptyl-N'-(1-ethyl-pyrrolidin-2-ylmethyl)-N''-[2-(3-fluoro-4-methoxyphenyl)-ethyl]-[1,3,5]triazine-2,4,6-triamine;
N-[2-(3-Chloro-4-methoxy-phenyl)-ethyl]-N'-cycloheptyl-N''-(1-ethyl-pyrrolidin-2-ylmethyl)-[1,3,5]triazine-2,4,6-triamine;
N-[2-(3-Bromo-4-methoxy-phenyl)-ethyl]-N'-cycloheptyl-N''-(1-ethyl-pyrrolidin-2-ylmethyl)-[1,3,5]triazine-2,4,6-triamine;
N-Cycloheptyl-N'-(1-ethyl-pyrrolidin-2-ylmethyl)-N''-[2-(3-iodo-4-methoxy-phenyl)-ethyl]-[1,3,5]triazine-2,4,6-triamine;
N-Cycloheptyl-N'-(4-ethoxy-3-fluoro-phenyl)-N''-(1-ethyl-pyrrolidin-2-ylmethyl)-[1,3,5]triazine-2,4,6-triamine;
N-(3-Chloro-4-ethoxy-phenyl)-N'-cycloheptyl-N''-(1-ethyl-pyrrolidin-2-ylmethyl)-[1,3,5]triazine-2,4,6-triamine;
N-(3-Bromo-4-ethoxy-phenyl)-N'-cycloheptyl-N''-(1-ethyl-pyrrolidin-2-ylmethyl)-[1,3,5]triazine-2,4,6-triamine;
N-Cycloheptyl-N'-(4-ethoxy-3-iodo-phenyl)-N''-(1-ethyl-pyrrolidin-2-ylmethyl)-[1,3,5]triazine-2,4,6-triamine;
N-Cycloheptyl-N'-(1-ethyl-pyrrolidin-2-ylmethyl)-N''-(3-fluoro-4-propoxy-phenyl)-[1,3,5]triazine-2,4,6-triamine;
N-(3-Chloro-4-propoxy-phenyl)-N'-cycloheptyl-N''-(1-ethyl-pyrrolidin-2-ylmethyl)-[1,3,5]triazine-2,4,6-triamine;
N-(3-Bromo-4-propoxy-phenyl)-N'-cycloheptyl-N''-(1-ethyl-pyrrolidin-2-ylmethyl)-[1,3,5]triazine-2,4,6-triamine;
N-Cycloheptyl-N'-(1-ethyl-pyrrolidin-2-ylmethyl)-N''-(3-iodo-4-propoxy-phenyl)-[1,3,5]triazine-2,4,6-triamine;
N-Cycloheptyl-N'-(1-ethyl-pyrrolidin-2-ylmethyl)-N''-(3-fluoro-4-methoxy-phenyl)-N'''-methyl-[1,3,5]triazine-2,4,6-triamine;
N-(3-Chloro-4-methoxy-phenyl)-N'-cycloheptyl-N''-(1-ethyl-pyrrolidin-2-ylmethyl)-[1,3,5]triazine-2,4,6-triamine;
N-(3-Bromo-4-methoxy-phenyl)-N'-cycloheptyl-N''-(1-ethyl-pyrrolidin-2-ylmethyl)-[1,3,5]triazine-2,4,6-triamine;
N-Cycloheptyl-N'-(1-ethyl-pyrrolidin-2-ylmethyl)-N''-(3-iodo-4-methoxy-phenyl)-[1,3,5]triazine-2,4,6-triamine;
{4-Cycloheptylamino-6-[(1-ethyl-pyrrolidin-2-ylmethyl)-amino]-[1,3,5]triazin-2-yl}-(3-fluoro-4-methoxy-phenyl)-cyanamide;
(3-Chloro-4-methoxy-phenyl)-{4-cycloheptylamino-6-[(1-ethyl-pyrrolidin-2-ylmethyl)-amino]-[1,3,5]triazin-2-yl}-cyanamide;
(3-Bromo-4-methoxy-phenyl)-{4-cycloheptylamino-6-[(1-ethyl-pyrrolidin-2-ylmethyl)-amino]-[1,3,5]triazin-2-yl}-cyanamide;
{4-Cycloheptylamino-6-[(1-ethyl-pyrrolidin-2-ylmethyl)-amino]-[1,3,5]triazin-2-yl}-(3-iodo-4-methoxy-phenyl)-cyanamide;
4-{4-Cycloheptylaminamino-6-[(1-ethylpyrrolidin-2-ylmethyl)-amino]-[1,3,5]triazin-2-ylamino}-2-fluoro-phenol;
2-Bromo-4-{4-cycloheptylamino-6-[(1-ethylpyrrolidin-2-ylmethyl)-amino]-[1,3,5]triazin-2-ylamino}-phenol;
4-{4-Cycloheptylaminamino-6-[(1-ethylpyrrolidin-2-ylmethyl)-amino]-[1,3,5]triazin-2-ylamino}-2-iodo-phenol;
N-Cycloheptyl-N'-ethyl-N''-(1-ethyl-pyrrolidin-2-ylmethyl)-N'''-(3-fluoro-4-methoxy-phenyl)-[1,3,5]triazine-2,4,6-triamine;
N-(3-Chloro-4-methoxy-phenyl)-N'-cycloheptyl-N-ethyl-N''-(1-ethyl-pyrrolidin-2-ylmethyl)-[1,3,5]triazine-2,4,6-triamine;
N-Cycloheptyl-N'-(1-ethyl-pyrrolidin-2-ylmethyl)-N''-(3-fluoro-4-methoxy-phenyl)-N-methyl-[1,3,5]triazine-2,4,6-triamine;
N-Cycloheptyl-N-ethyl-N'-(1-ethylpyrrolidin-2-ylmethyl)-N''-(3-fluoro-4-methoxy-phenyl)-[1,3,5]triazine-2,4,6-triamine;
N-Cycloheptyl-N'-(1-ethyl-pyrrolidin-2-ylmethyl)-N''-(3-fluoro-4-methoxy-phenyl)-N-propyl-[1,3,5]triazine-2,4,6-triamine;
6-Cycloheptyloxy-N-(1-ethyl-pyrrolidin-2-ylmethyl)-N'-(3-fluoro-4-methoxy-phenyl)-[1,3,5]triazine-2,4,6-triamine;
6-Cyclopropoxy-N-(1-ethyl-pyrrolidin-2-ylmethyl)-N'-(3-fluoro-4-methoxy-phenyl)-[1,3,5]triazine-2,4,6-triamine;
6-Cyclopentyloxy-N-(1-ethyl-pyrrolidin-2-ylmethyl)-N'-(3-fluoro-4-methoxy-phenyl)-[1,3,5]triazine-2,4,6-triamine;

6-Cyclohexyloxy-N-(1-ethyl-pyrrolidin-2-ylmethyl)-N'-(3-fluoro-4-methoxy-phenyl)-[1,3,5]triazine-2,4,6-triamine;

N-Cycloheptyl-N'-(1-ethyl-1-oxy-pyrrolidin-2-ylmethyl)-N''-(3-fluoro-4-methoxy-phenyl)-[1,3,5]triazine-2,4,6-triamine;

N-(1-Ethyl-pyrrolidin-2-ylmethyl)-N'-(3-fluoro-4-methoxy-phenyl)-N''-(1-propyl-butyl)-[1,3,5]triazine-2,4,6-triamine;

N-Cyclopent-2-enyl-(1-ethyl-pyrrolidin-2-ylmethyl)-N''-(3-fluoro-4-methoxy-phenyl)-[1,3,5]triazine-2,4,6-triamine;

N-Cyclohex-2-enyl-(1-ethyl-pyrrolidin-2-ylmethyl)-N''-(3-fluoro-4-methoxy-phenyl)-[1,3,5]triazine-2,4,6-triamine;

N-Cyclohept-2-enyl-(1-ethyl-pyrrolidin-2-ylmethyl)-N''-(3-fluoro-4-methoxy-phenyl)-[1,3,5]triazine-2,4,6-triamine;

N-(1-Ethyl-pyrrolidin-2-ylmethyl)-N'-(3-fluoro-4-methoxy-phenyl)-N''-pyrrolidin-1-yl-[1,3,5]triazine-2,4,6-triamine;

N-(1-Ethyl-pyrrolidin-2-ylmethyl)-N'-(3-fluoro-4-methoxy-phenyl)-N''-piperidin-1-yl-[1,3,5]triazine-2,4,6-triamine;

N-Azepan-1-yl-N'-(1-ethyl-pyrrolidin-2-ylmethyl)-N''-(3-fluoro-4-methoxy-phenyl)-[1,3,5]triazine-2,4,6-triamine;

4-[(1-Ethyl-pyrrolidin-2-ylmethyl)-amino]-6-(3-fluoro-4-methoxy-phenylamino)-[1,3,5]triazin-2-yl-cyanamide;

N-[4-[(1-Ethyl-pyrrolidin-2-ylmethyl)-amino]-6-(3-fluoro-4-methoxy-phenylamino)-[1,3,5]triazin-2-yl]-acetamide;

3-[4-[(1-Ethyl-pyrrolidin-2-ylmethyl)-amino]-6-(3-fluoro-4-methoxy-phenylamino)-[1,3,5]triazin-2-ylamino]-pyrrolidin-2-one;

3-[4-[(1-Ethyl-pyrrolidin-2-ylmethyl)-amino]-6-(3-fluoro-4-methoxy-phenylamino)-[1,3,5]triazin-2-ylamino]-piperidin-2-one;

3-[4-[(1-Ethyl-pyrrolidin-2-ylmethyl)-amino]-6-(3-fluoro-4-methoxy-phenylamino)-[1,3,5]triazin-2-ylamino]-azepan-2-one;

N-(1-Ethyl-pyrrolidin-2-ylmethyl)-N'-(3-fluoro-4-methoxy-phenyl)-N''-pyrrolidin-3-yl-[1,3,5]triazine-2,4,6-triamine;

N-Azepan-3-yl-N'-(1-ethyl-pyrrolidin-2-ylmethyl)-N''-(3-fluoro-4-methoxy-phenyl)-[1,3,5]triazine-2,4,6-triamine;

N-(1-Ethyl-pyrrolidin-2-ylmethyl)-N'-(3-fluoro-4-methoxy-phenyl)-N''-oxepan-3-yl-[1,3,5]triazine-2,4,6-triamine;

N-(1-Ethyl-pyrrolidin-2-ylmethyl)-N'-(3-fluoro-4-methoxy-phenyl)-N''-(tetrahydropyran-3-yl)-[1,3,5]triazine-2,4,6-triamine;

N-(1-Ethyl-pyrrolidin-2-ylmethyl)-N'-(3-fluoro-4-methoxy-phenyl)-N''-(tetrahydrofuran-3-yl)-[1,3,5]triazine-2,4,6-triamine;

N-(1-Aza-bicyclo[2.2.2]oct-3-yl)-N'-(1-ethylpyrrolidin-2-ylmethyl)-N-''-(3-fluoro-4-methoxy-phenyl)-[1,3,5]triazine-2,4,6-triamine;

N-(1-Aza-bicyclo[2.2.1]hept-3-yl)-N'-(1-ethyl-pyrrolidin-2-ylmethyl)-N-''-(3-fluoro-4-methoxy-phenyl)-[1,3,5]triazine-2,4,6-triamine;

N-Bicyclo[2.2.1]hept-2-yl-N'-(1-ethyl-pyrrolidin-2-ylmethyl)-N''-(3-fluoro-4-methoxy-phenyl)-[1,3,5]triazine-2,4,6-triamine;

[4-[(1-Ethyl-pyrrolidin-2-ylmethyl)-amino]-6-(3-fluoro-4-methoxy-phenylamino)-[1,3,5]triazin-2-yl]-carbamic acid;

[4-[(1-Ethyl-pyrrolidin-2-ylmethyl)-amino]-6-(3-fluoro-4-methoxy-phenylamino)-[1,3,5]triazin-2-yl]-urea;

[4-[(1-Ethyl-pyrrolidin-2-ylmethyl)-amino]-6-(3-fluoro-4-methoxy-phenylamino)-[1,3,5]triazin-2-yl]-propan-2-one;

[4-[(1-Ethyl-pyrrolidin-2-ylmethyl)-amino]-6-(3-fluoro-4-methoxy-phenylamino)-[1,3,5]triazin-2-yl]-pentan-2-one;

N-Cycloheptyl-N'-(3-fluoro-4-methoxyphenyl)-6-(1-methyl-piperidin-4-yloxy)-[1,3,5]triazine-2,4-diamine;

N-Cycloheptyl-6-(1-ethyl-pyrrolidin-2-ylmethoxy)-N'-(3-fluoro-4-methoxy-phenyl)-[1,3,5]triazine-2,4-diamine;

1-{4-{[4-Cycloheptylamino-6-(3-fluoro-4-methoxy-phenylamino)-[1,3,5]triazin-2-yl]-methyl-amino}-piperidin-1-yl}-ethanone;

4-[4-Cycloheptylamino-6-(3-fluoro-4-methoxy-phenylamino)-[1,3,5]triazin-2-ylamino]-piperidine-1-carboxylic acid;

4-[4-Cycloheptylamino-6-(3-fluoro-4-methoxy-phenylamino)-[1,3,5]triazin-2-ylamino]-piperidine-1-carboxylic acid amide;

4-[4-Cycloheptylamino-6-(3-fluoro-4-methoxy-phenylamino)-[1,3,5]triazin-2-ylamino]-piperidin-1-ol;

N-Cycloheptyl-N'-(3-fluoro-4-methoxyphenyl)-N''-piperidin-4-yl-[1,3,5]triazine-2,4,6-triamine;

N-Cycloheptyl-N'-(3-fluoro-4-methoxyphenyl)-N''-(1-methyl-pyrrolidin-2-ylmethyl)-[1,3,5]triazine-2,4,6-triamine;

2-{[4-Cycloheptylamino-6-(3-fluoro-4-methoxy-phenylamino)-[1,3,5]triazin-2-ylamino]-methyl}-pyrrolidine-1-carbaldehyde;

2-{[4-Cycloheptylamino-6-(3-fluoro-4-methoxy-phenylamino)-[1,3,5]triazin-2-ylamino]-methyl}-pyrrolidine-1-carboxylic acid;

2-{[4-Cycloheptylamino-6-(3-fluoro-4-methoxy-phenylamino)-[1,3,5]triazin-2-ylamino]-methyl}-pyrrolidine-1-carboxylic acid amide;

N-Cycloheptyl-N'-(3-fluoro-4-methoxyphenyl)-N''-pyrrolidin-2-ylmethyl-[1,3,5]triazine-2,4,6-triamine;

N-Cycloheptyl-N'-(3-fluoro-4-methoxyphenyl)-N''-(tetrahydro-pyran-4-yl)-[1,3,5]triazine-2,4,6-triamine;

N-Cycloheptyl-N'-(3-fluoro-4-methoxyphenyl)-N''-methyl-(tetrahydro-pyran-4-yl)-[1,3,5]triazine-2,4,6-triamine;

N-Cycloheptyl-N'-(3-fluoro-4-methoxyphenyl)-N''-(tetrahydro-furan-2-ylmethyl)-[1,3,5]triazine-2,4,6-triamine;

N-Cycloheptyl-N'-(3-fluoro-4-methoxyphenyl)-N''-methyl-N''-(tetrahydro-furan-2-ylmethyl)-[1,3,5]triazine-2,4,6-triamine;

N-(4-Amino-cyclohexyl)-N'-cycloheptyl-N''-(3-fluoro-4-methoxy-phenyl)-[1,3,5]triazine-2,4,6-triamine;

N-Cycloheptyl-N'-(4-dimethylaminocyclohexyl)-N''-(3-fluoro-4-methoxy-phenyl)-[1,3,5]triazine-2,4,6-triamine;

1-{4-[4-Cycloheptylamino-6-(3-fluoro-4-methoxy-phenylamino)-[1,3,5]triazin-2-ylamino]-4H-pyridin-1-yl}-ethanone;

1-{4-[4-cycloheptylamino-6-(3-fluoro-4-methoxy-phenylamino)-[1,3,5]triazin-2-ylamino]-piperidin-1-yl}-butan-1-one;

1-{4-[4-cycloheptylamino-6-(3-fluoro-methoxy-phenylamino)-[1,3,5]triazin-ylamino]-piperidin-1-yl}-pentan-1-one;

4-[4-Cycloheptylamino-6-(3-fluoro-4-methoxy-phenylamino)-[1,3,5]triazin-ylamino]-piperidine-1-carboxylic acid methyl ester;

4-[4-Cycloheptylamino-6-(3-fluoro-4-methoxy-phenylamino)-[1,3,5]triazin-2-ylamino]-piperidine-1-carboxylic acid ethylester;

4-[4-Cycloheptylamino-6-(3-fluoro-4-methoxy-phenylamino)-[1,3,5]triazin-ylamino]-piperidine-1-carboxylic acid propyl ester;

4-[4-Cycloheptylamino-6-(3-fluoro-4-methoxy-phenylamino)-[1,3,5]triazin-2-ylamino]-piperidine-1-carboxylic acid benzyl ester;

1-{4-[4-Cycloheptylamino-6-(3-fluoro-4-methoxy-phenylamino)-[1,3,5]triazin-2-ylamino]-piperidin-1-yl}-propan-2-one;

1-{4-[4-Cycloheptylamino-6-(3-fluoro-4-methoxy-phenylamino)-[1,3,5]triazin-2-ylamino]-piperidin-1-yl}-pentan-2-one;

1-{4-[4-Cycloheptylamino-6-(3-fluoro-4-methoxy-phenylamino)-[1,3,5]triazin-2-ylamino]-piperidin-1-yl}-hexan-2-one;

{4-[4-Cycloheptylamino-6-(3-fluoro-4-methoxy-phenylamino)-[1,3,5]triazin-2-ylamino]-piperidin-1-yl}-acetic acid methyl ester;

{4-[4-Cycloheptylamino-6-(3-fluoro-4-methoxy-phenylamino)-[1,3,5]triazin-2-ylamino]-piperidin-1-yl}-acetic acid ethyl ester;

{4-[4-Cycloheptylamino-6-(3-fluoro-4-methoxy-phenylamino)-[1,3,5]triazin-2-ylamino]-piperidin-1-yl}-acetic acid propyl ester;

N-Cyclohept-3-enyl-N'-(1-ethyl-pyrrolidin-2-ylmethyl)-N''-(3-fluoro-4-methoxy-phenyl)-[1,3,5]triazine-2,4,6-triamine;

N-Azepan-4-yl-N'-(1-ethyl-pyrrolidin-2-ylmethyl)-N''-(3-fluoro-4-methoxy-phenyl)-[1,3,5]triazine-2,4,6-triamine;

N-(1-Ethyl-pyrrolidin-2-ylmethyl)-N'-(3-fluoro-4-methoxy-phenyl)-N''-(1-methyl-azepan-4-yl)-[1,3,5]triazine-2,4,6-triamine;

N-(1-Ethyl-pyrrolidin-2-ylmethyl)-N'-(3-fluoro-4-methoxy-phenyl)-N''-thiepan-4-yl-[1,3,5]triazine-2,4,6-triamine;

N-(1,1-Dioxo-1lambda*6*-thiepan-4-yl)-N'-(1-ethyl-pyrrolidin-2-ylmethyl)-N''-(3-fluoro-4-methoxy-phenyl)-[1,3,5]triazine-2,4,6-triamine;

N-(1-Ethyl-pyrrolidin-2-ylmethyl)-N'-(3-fluoro-4-methoxy-phenyl)-N''-oxepan-2-yl-[1,3,5]triazine-2,4,6-triamine;

N-Azepan-2-yl-N'-(1-ethyl-pyrrolidin-2-ylmethyl)-N''-(3-fluoro-4-methoxy-phenyl)-[1,3,5]triazine-2,4,6-triamine;

N-(1-Ethyl-pyrrolidin-2-ylmethyl)-N'-(3-fluoro-4-methoxy-phenyl)-N''-thiepan-2-yl-[1,3,5]triazine-2,4,6-triamine;

N-(1-Ethyl-pyrrolidin-2-ylmethyl)-N'-(3-fluoro-4-methoxy-phenyl)-N''-thiepan-3-yl-[1,3,5]triazine-2,4,6-triamine;

N-(1,1-Dioxo-1lambda*6*-thiepan-3-yl)-N'-(1-ethyl-pyrrolidin-2-ylmethyl)-N''-(3-fluoro-4-methoxy-phenyl)-[1,3,5]triazine-2,4,6-triamine;

2-{[4-Cycloheptylamino-6-(3-fluoro-4-methoxy-phenylamino)-[1,3,5]triazin-2-ylamino]-methyl}-1-ethyl-pyrrolidinium; chloride;

2-{[4-(3-Chloro-4-methoxy-phenylamino)-6-cycloheptylamino-[1,3,5]triazin-2-ylamino]-methyl}-1-ethyl-pyrrolidinium; chloride;

2-{[4-Cycloheptylamino-6-(3-fluoro-4-methoxy-phenylamino)-[1,3,5]triazin-2-ylamino]-methyl}-1-ethyl-pyrrolidinium; bromide;

2-{[4-Cycloheptylamino-6-(3-fluoro-4-methoxy-phenylamino)-[1,3,5]triazin-2-ylamino]-methyl}-1-ethyl-1-methyl-pyrrolidinium; iodide;

1-Acetyl-2-{[4-cycloheptylamino-6-(3-fluoro-4-methoxy-phenylamino)-[1,3,5]triazin-2-ylamino]-methyl}-1-ethyl-pyrrolidinium; chloride;

Sodium; 4-{4-cycloheptylamino-6-[(1-ethyl-pyrrolidin-2-ylmethyl)-amino]-[1,3,5]triazin-2-ylamino}-2-fluoro-phenolate;

Potassium; 4-{4-cycloheptylamino-6-[(1-ethyl-pyrrolidin-2-ylmethyl)-amino]-[1,3,5]triazin-2-ylamino}-2-fluoro-phenolate;

3-Carboxy-propionate-2-{[4-cycloheptylamino-6-(3-fluoro-4-methoxy-phenylamino)-[1,3,5]triazin-2-ylamino]methyl}-1-ethyl-pyrrolidinium;

3-Carboxy-acrylate-2-{[4-cycloheptylamino-6-(3-fluoro-4-methoxy-phenylamino)-[1,3,5]triazin-2-ylamino]-methyl}-1-ethyl-pyrrolidinium;

N-Cycloheptyl-N'-(3-fluoro-4-methoxy-phenyl)-N''-(1-methyl-1H-pyrrol-2-ylmethyl)-[1,3,5]triazine-2,4,6-triamine;

N-Cycloheptyl-N'-(3-fluoro-4-methoxy-phenyl)-6-(1-methyl-1H-pyrrol-2-ylmethoxy)-[1,3,5]triazine-2,4-diamine;

N-Cycloheptyl-N'-(3-fluoro-4-methoxy-phenyl)-6-(thiophen-2-ylmethoxy)-[1,3,5]triazine-2,4-diamine;

N-Cycloheptyl-N'-(3-fluoro-4-methoxy-phenyl)-N''-thiophen-2-ylmethyl-[1,3,5]triazine-2,4,6-triamine;

N-Cycloheptyl-N'-(3-fluoro-4-methoxy-phenyl)-N''-furan-2-ylmethyl-[1,3,5]triazine-2,4,6-triamine;

N-Cycloheptyl-N'-(3-fluoro-4-methoxy-phenyl)-N''-(tetrahydro-furan-2-ylmethyl)-[1,3,5]triazine-2,4,6-triamine;

N-Cycloheptyl-N'-(1,1-dioxo-tetrahydro-1lambda*6*-thiophen-2-ylmethyl)-N''-(3-fluoro-4-methoxy-phenyl)-[1,3,5]triazine-2,4,6-triamine;

N-Cycloheptyl-N'-(1-ethyl-pyrrolidin-2-ylmethyl)-N''-(5-fluoro-6-methoxy-pyridin-3-yl)-[1,3,5]triazine-2,4,6-triamine;

N-Cycloheptyl-N'-(1-ethyl-pyrrolidin-2-ylmethyl)-N''-(4-fluoro-5-methoxy-pyridin-2-yl)-[1,3,5]triazine-2,4,6-triamine;

N-Cycloheptyl-N'-(3-fluoro-4-methoxy-phenyl)-N''-pyridin-2-ylmethyl-[1,3,5]triazine-2,4,6-triamine;

N-Cycloheptyl-N'-(3-fluoro-4-methoxy-phenyl)-N''-pyridin-3-ylmethyl-[1,3,5]triazine-2,4,6-triamine;

N-Cycloheptyl-N'-(1-ethyl-pyrrolidin-2-ylmethyl)-N''-(4-methoxy-3-trifluoromethyl-phenyl)-[1,3,5]triazine-2,4,6-triamine;

N-Cycloheptyl-N'-(1-ethyl-pyrrolidin-2-ylmethyl)-N''-(4-trifluoromethoxy-3-trifluoromethyl-phenyl)-[1,3,5]triazine-2,4,6-triamine;

N-(1-Ethyl-pyrrolidin-2-ylmethyl)-N'-(3-fluoro-4-methoxy-phenyl)-N''-thiepan-3-yl-[1,3,5]triazine-2,4,6-triamine;

N-(1,1-Dioxo-1lambda*6*-thiepan-3-yl)-N'-(1-ethyl-pyrrolidin-2-ylmethyl)-N''-(3-fluoro-4-methoxy-phenyl)-[1,3,5]triazine-2,4,6-triamine;

4-{4-Cycloheptylamino-6-[(1-ethyl-pyrrolidin-2-ylmethyl)-amino]-[1,3,5]triazin-2-ylamino}-2-trifluoromethyl-phenol;

N-Cycloheptyl-N'-(2-ethyl-cyclopentylmethyl)-N''-(3-fluoro-4-methoxy-phenyl)-[1,3,5]triazine-2,4,6-triamine;

N-Cycloheptyl-N'-(3-fluoro-4-methoxy-phenyl)-N''-(2-methyl-cyclopentyl methyl)-[1,3,5]triazine-2,4,6-triamine;

2-{[4-Cycloheptylamino-6-(3-fluoro-4-methoxy-phenylamino)-[1,3,5]triazin-2-ylamino]-methyl}-cyclopentanol;

N-(2-Amino-cyclopentylmethyl)-N'-cycloheptyl-N''-(3-fluoro-4-methoxy-phenyl)-[1,3,5]triazine-2,4,6-triamine;

3-{[4-Cycloheptylamino-6-(3-fluoro-4-methoxy-phenylamino)-[1,3,5]triazin-2-ylamino]-methyl}-cyclopentanol;

2-[4-Cycloheptylamino-6-(3-fluoro-4-methoxy-phenylamino)-[1,3,5]triazin-2 ylamino]-cyclopentanol;

N-Cycloheptyl-N'-(3-fluoro-4-methoxy-phenyl)-6-(tetrahydro-pyrrolo[1,2-c]imidazol-2-yl)-[1,3,5]triazine-2,4-diamine;

2-[4-Cycloheptylamino-6-(3-fluoro-4-methoxy-phenylamino)-[1,3,5]triazin-2-yl]-hexahydro-pyrrolo[1,2-c]imidazol-3-one;

N-Cycloheptyl-N'-(3-fluoro-4-methoxy-phenyl)-N''-(1H-imidazol-4-ylmethyl)-[1,3,5]triazine-2,4,6-triamine;

N-Cycloheptyl-6-(2,3-dihydro-indol-1-yl)-N'-(3-fluoro-4-methoxy-phenyl)-[1,3,5]triazine-2,4-diamine;

N-Cycloheptyl-N'-(3-fluoro-4-methoxy-phenyl)-6-indol-1-yl-[1,3,5]triazine-2,4-diamine;

1-(2-{[4-Cycloheptylamino-6-(3-fluoro-4-methoxy-phenylamino)-[1,3,5]triazin-2-ylamino]-methyl}-pyrrolidin-1-yl)-3-(2-{2-[2-(2-hydroxy-ethoxy)-ethoxy]-ethoxy}-ethoxy)-propan-1-one;

1-(2-{[4-Cycloheptylamino-6-(3-fluoro-4-methoxy-phenylamino)-[1,3,5]triazin-2-ylamino]-methyl}-pyrrolidin-1-yl)-3-(2-{2-[2-(2-methoxy-ethoxy)-ethoxy]-ethoxy}-ethoxy)-propan-1-one;

N-Cycloheptyl-N'-(3-fluoro-4-methoxy-phenyl)-N''-[1-(2-{2-[2-(2-methoxy-ethoxy)-ethoxy]-ethoxy}-ethoxymethyl)-pyrrolidin-2-ylmethyl]-[1,3,5]triazine-2,4,6-triamine;

2-(2-{2-[2-(2-{[4-Cycloheptylamino-6-(3-fluoro-4-methoxy-phenylamino)-1,3,5]triazin-2-ylamino]-methyl}-pyrrolidin-1-ylmethoxy)-ethoxy]-ethoxy}-ethoxy)-ethanol;

3-{2-[2-(2-Methoxy-ethoxy)-ethoxy]-ethoxy}-propionic acid 4-{4-cycloheptylamino-6-[(1-ethyl-pyrrolidin-2-ylmethyl)-amino]-[1,3,5]triazin-2-ylamino}-2-fluoro-phenyl ester;

3-{2-[2-(2-Hydroxy-ethoxy)-ethoxy]-ethoxy}-propionic acid 4-{4-cycloheptylamino-6-[(1-ethyl-pyrrolidin-2-ylmethyl)-amino]-[1,3,5]triazin-2-ylamino}-2-fluoro-phenyl ester;

3-(2-{2-[2-(4-{4-Cycloheptylamino-6-[(1-ethyl-pyrrolidin-2-ylmethyl)-amino]-[1,3,5]triazin-2-ylamino}-2-fluoro-phenoxy)-ethoxy]-ethoxy}-ethoxy)-propan-1-ol;

N-Cycloheptyl-N'-(1-ethyl-pyrrolidin-2-ylmethyl)-N''-[3-fluoro-4-(2-{2-[2-(3-methoxy-propoxy)-ethoxy]-ethoxy}-ethoxy)-phenyl]-[1,3,5]triazine-2,4,6-triamine;

N-Cycloheptyl-N'-(1-ethyl-pyrrolidin-2-ylmethyl)-N''-(3-fluoro-4-methoxymethoxy-phenyl)-[1,3,5]triazine-2,4,6-triamine;

N-Cycloheptyl-N'-(1-ethyl-pyrrolidin-2-ylmethyl)-N''-(3-fluoro-4-methylsulfanylmethoxy-phenyl)-[1,3,5]triazine-2,4,6-triamine;

N-Cycloheptyl-N'-(4-cyclopropoxy-3-fluoro-phenyl)-N''-(1-ethyl-pyrrolidin-2-ylmethyl)-[1,3,5]triazine-2,4,6-triamine;

4-{4-Cycloheptylamino-6-[(1-ethyl-pyrrolidin-2-ylmethyl)-amino]-[1,3,5]triazin-2-ylamino}-2-fluoro-phenol; compound with phosphoric acid monoethyl ester;

4-{4-Cycloheptylamino-6-[(1-ethyl-pyrrolidin-2-ylmethyl)-amino]-[1,3,5]triazin-2-ylamino}-2-fluoro-phenol; compound with phosphoric acid dibenzyl ester ethyl ester;

4-{4-Cycloheptylamino-6-[(1-ethyl-pyrrolidin-2-ylmethyl)-amino]-[1,3,5]triazin-2-ylamino}-2-fluoro-phenol; compound with phosphoric acid ditert-butyl ester ethyl ester;

Phosphoric acid mono-(4-{4-cycloheptylamino-6-[(1-ethyl-pyrrolidin-2-ylmethyl)-amino]-[1,3,5]triazin-2-ylamino}-2-fluoro-phenyl) ester;

5-{4-Cycloheptylamino-6-[(1-ethyl-pyrrolidin-2-ylmethyl)-amino]-[1,3,5]triazin-2-ylamino}-2-hydroxy-benzoic acid; compound with ethane;

Sodium; 5-{4-cycloheptylamino-6-[(1-ethyl-pyrrolidin-2-ylmethyl)-amino]-[1,3,5]triazin-2-ylamino)}-2-methoxy-benzoate;

2-{[4-Cycloheptylamino-6-(3-fluoro-4-methoxy-phenylamino)-[1,3,5]triazin-2-ylamino]-methyl}-1-(di-tert-butoxy-phosphoryloxymethyl)-1-ethyl-pyrrolidinium; chloride;

1-(Bis-benzyloxy-phosphoryloxymethyl)-2-{[4-cycloheptylamino-6-(3-fluoro-4-methoxy-phenylamino)-[1,3,5]triazin-2-ylamino]-methyl}-1-ethyl-pyrrolidinium; chloride;

2-{[4-Cycloheptylamino-6-(3-fluoro-4-methoxy-phenylamino)-[1,3,5]triazin-2-ylamino]-methyl}-1-ethyl-1-phosphonooxymethyl-pyrrolidinium; chloride;

Trifluoro-acetate2-{[4-cycloheptylamino-6-(3-fluoro-4-methoxy-phenylamino)-[1,3,5]triazin-2-ylamino]-methyl}-1-ethyl-1-phosphonooxymethyl-pyrrolidinium; or Phosphoric acid mono-(2-{[4-cycloheptylamino-6-(3-fluoro-4-hydroxy-phenylamino)-[1,3,5]triazin-2-ylamino]-methyl}-pyrrolidin-1-ylmethyl) ester; compound with ethane.

3. A composition comprising a pharmaceutically acceptable carrier and a compound of the formula Ib:

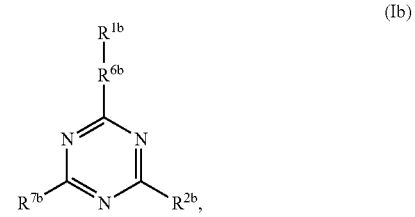

(Ib)

wherein:

$R^{1b}$ is selected from
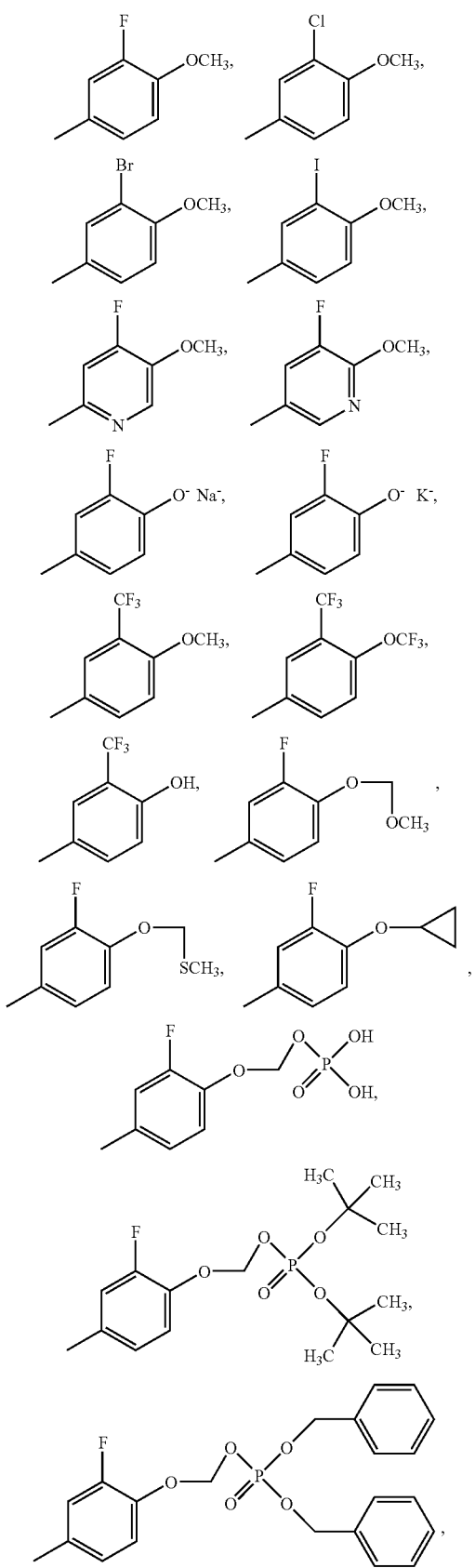
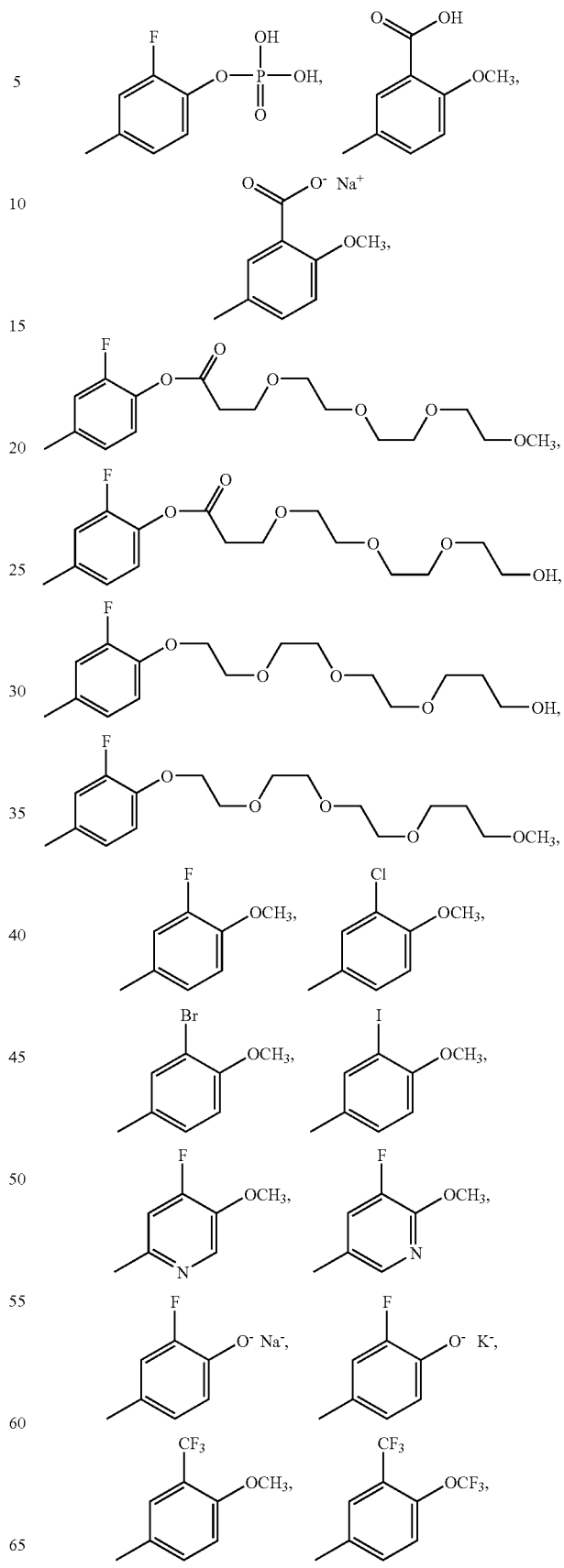

-continued
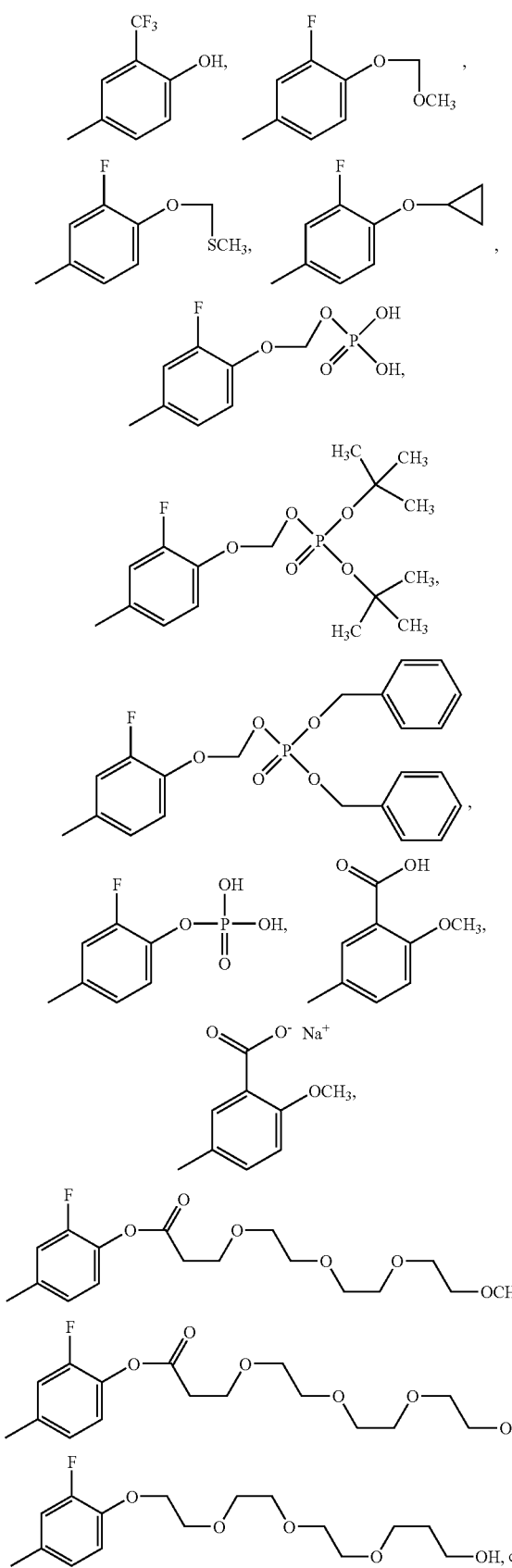
-continued
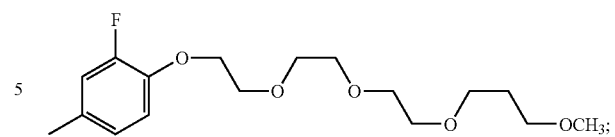
$R^{2b}$ is selected from
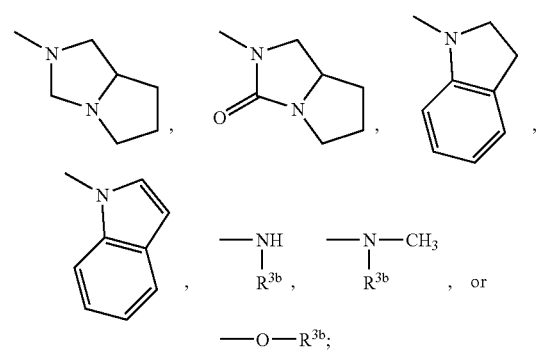
$R^{3b}$ is selected from
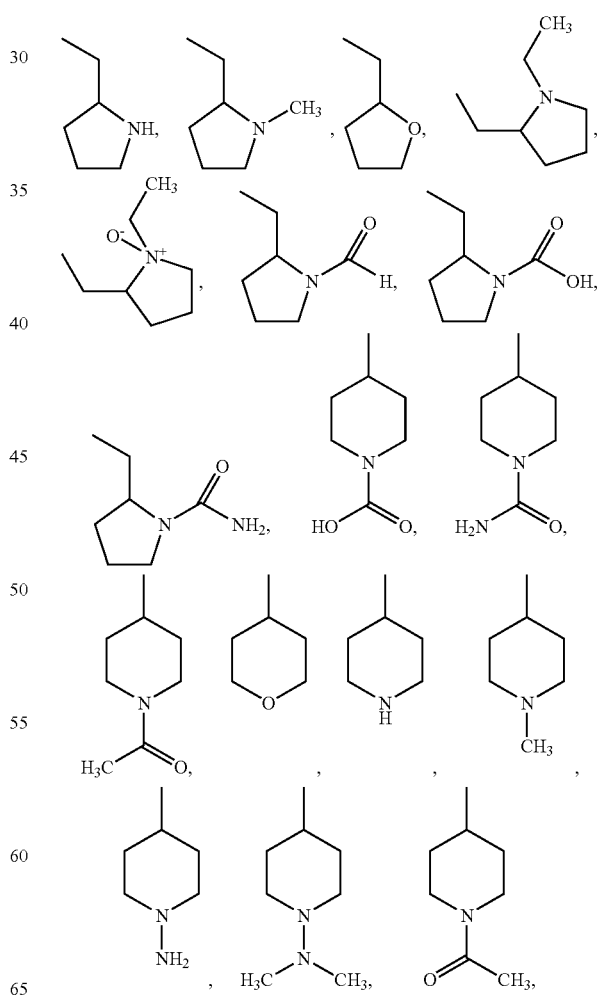

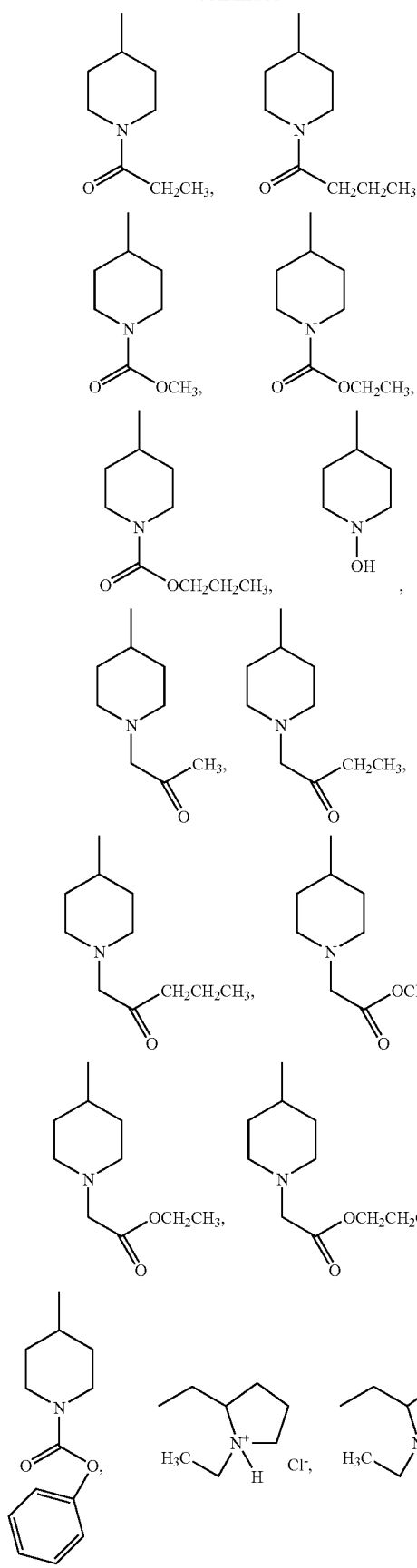
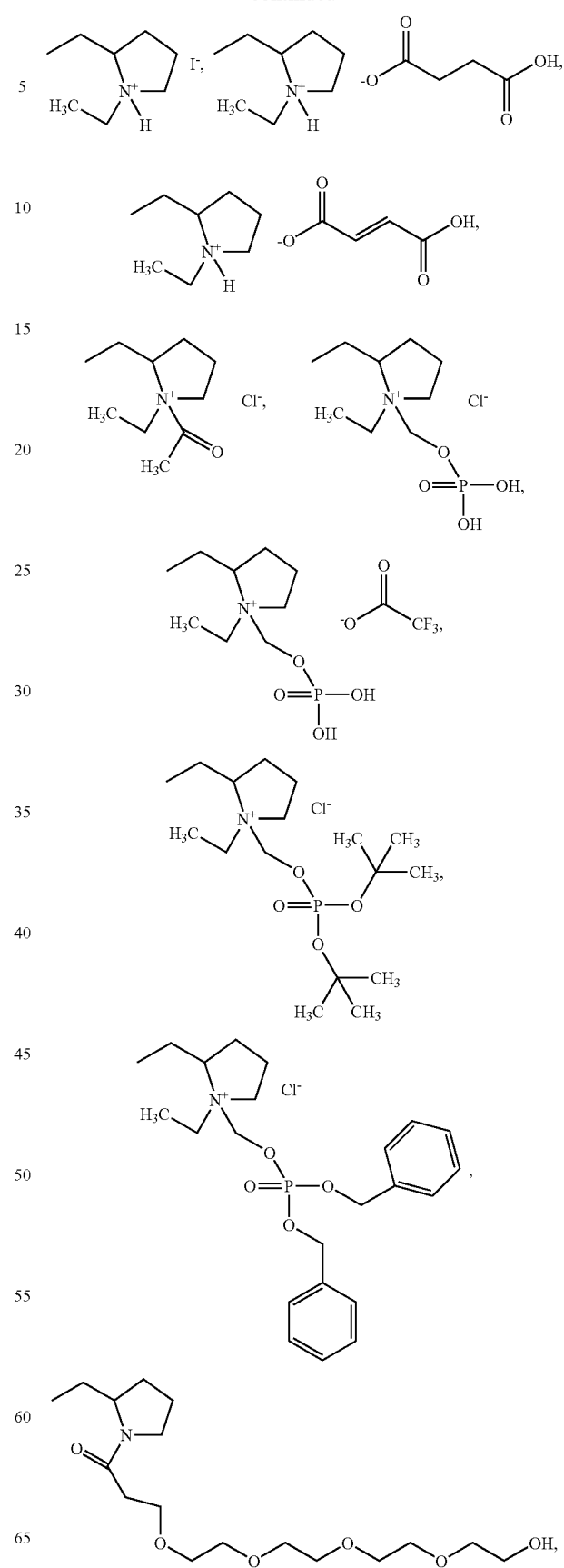

599
-continued
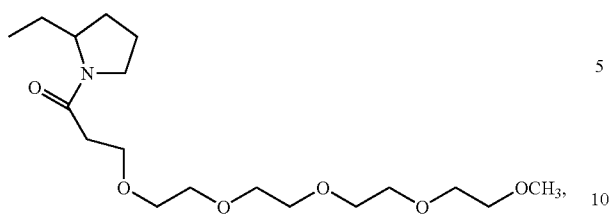
$R^{4b}$ is selected from —H, —CH$_3$, —CH$_2$CH$_3$, or —CH$_2$CH$_2$CH$_3$;
600
$R^{5b}$ is selected from
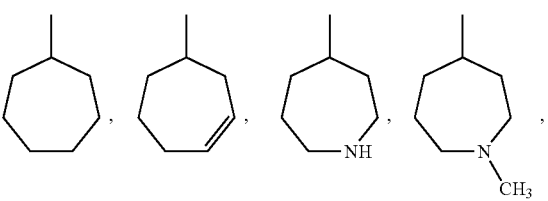
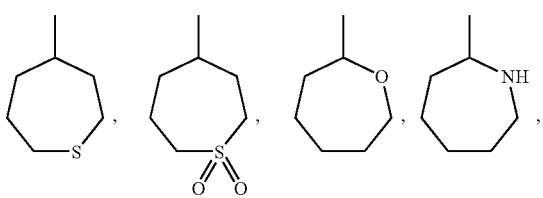
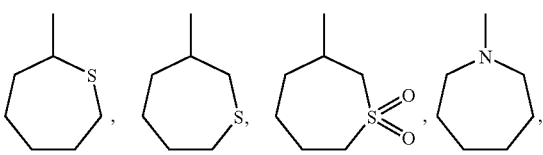
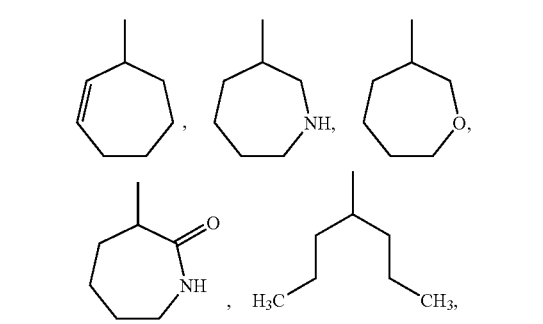
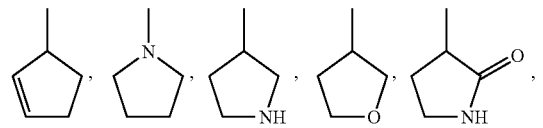
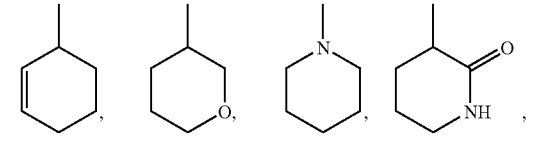
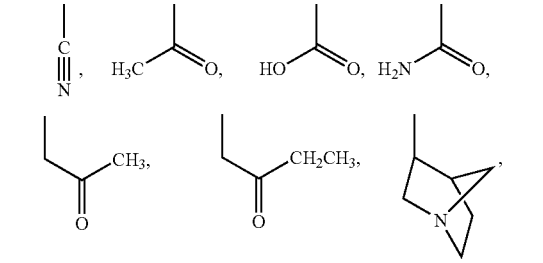

$R^{6b}$ is selected from

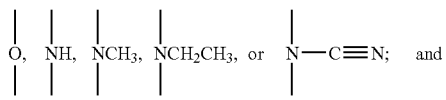

$R^{7b}$ is selected from

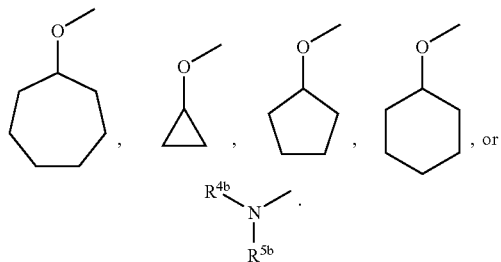

4. The composition as claimed in claim 3, wherein the compound is selected from:
N-Cycloheptyl-N'(1-ethyl-pyrrolidin-2-ylmethyl)-6-(3-fluoro-4-methoxy-phenoxy)-[1,3,5]triazine-2,4-diamine;
6-(3-Chloro-4-methoxy-phenoxy)-N-cycloheptyl-N'-(1-ethyl-pyrrolidin-2-ylmethyl)-[1,3,5]triazine-2,4-diamine;
6-(3-Bromo-4-methoxy-phenoxy)-N-cycloheptyl-N'-(1-ethyl-pyrrolidin-2-ylmethyl)-[1,3,5]triazine-2,4-diamine;
N-Cycloheptyl-N'(1-ethyl-pyrrolidin-2-ylmethyl)-6-(3-iodo-4-methoxy-phenoxy)-[1,3,5]triazine-2,4-diamine;
N-Cycloheptyl-N'-(1-ethyl-pyrrolidin-2-ylmethyl)-N"-(3-fluoro-4-methoxy-benzyl)-[1,3,5]triazine-2,4,6-triamine;
N-(3-Chloro-4-methoxy-benzyl)-N'-cycloheptyl-N"-(1-ethyl-pyrrolidin-2-ylmethyl)-[1,3,5]triazine-2,4,6-triamine;
N-(3-Bromo-4-methoxy-benzyl)-N'-cycloheptyl-N"-(1-ethyl-pyrrolidin-2-ylmethyl)-[1,3,5]triazine-2,4,6-triamine;
N-Cycloheptyl-N'-(1-ethyl-pyrrolidin-2-ylmethyl)-N"-(3-iodo-4-methoxy-benzyl)-[1,3,5]triazine-2,4,6-triamine;
N-Cycloheptyl-N'-(1-ethyl-pyrrolidin-2-ylmethyl)-N"-[2-(3-fluoro-4-methoxyphenyl)-ethyl]-[1,3,5]triazine-2,4,6-triamine;
N-[2-(3-Chloro-4-methoxy-phenyl)-ethyl]-N'-cycloheptyl-N"-(1-ethyl-pyrrolidin-2-ylmethyl)-[1,3,5]triazine-2,4,6-triamine;
N-[2-(3-Bromo-4-methoxy-phenyl)-ethyl]-N'-cycloheptyl-N"-(1-ethyl-pyrrolidin-2-ylmethyl)-[1,3,5]triazine-2,4,6-triamine;
N-Cycloheptyl-N'-(1-ethyl-pyrrolidin-2-ylmethyl)-N"-[2-(3-iodo-4-methoxy-phenyl)-ethyl]-[1,3,5]triazine-2,4,6-triamine;
N-Cycloheptyl-N'-(4-ethoxy-3-fluoro-phenyl)-N"-(1-ethyl-pyrrolidin-2-ylmethyl)-[1,3,5]triazine-2,4,6-triamine;
N-(3-Chloro-4-ethoxy-phenyl)-N'-cycloheptyl-N"-(1-ethyl-pyrrolidin-2-ylmethyl)-[1,3,5]triazine-2,4,6-triamine;
N-(3-Bromo-4-ethoxy-phenyl)-N'-cycloheptyl-N"-(1-ethyl-pyrrolidin-2-ylmethyl)-[1,3,5]triazine-2,4,6-triamine;
N-Cycloheptyl-N'-(4-ethoxy-3-iodo-phenyl)-N"-(1-ethyl-pyrrolidin-2-ylmethyl)-[1,3,5]triazine-2,4,6-triamine;
N-Cycloheptyl-N'-(1-ethyl-pyrrolidin-2-ylmethyl)-N"-(3-fluoro-4-propoxy-phenyl)-[1,3,5]triazine-2,4,6-triamine;
N-(3-Chloro-4-propoxy-phenyl)-N'-cycloheptyl-N"-(1-ethyl-pyrrolidin-2-ylmethyl)-[1,3,5]triazine-2,4,6-triamine;
N-(3-Bromo-4-propoxy-phenyl)-N'-cycloheptyl-N"-(1-ethyl-pyrrolidin-2-ylmethyl)-[1,3,5]triazine-2,4,6-triamine;
N-Cycloheptyl-N'-(1-ethyl-pyrrolidin-2-ylmethyl)-N"-(3-iodo-4-propoxy-phenyl)-[1,3,5]triazine-2,4,6-triamine;
N-Cycloheptyl-N'-(1-ethyl-pyrrolidin-2-ylmethyl)-N"-(3-fluoro-4-methoxy-phenyl)-N"'-methyl-[1,3,5]triazine-2,4,6-triamine;
N-(3-Chloro-4-methoxy-phenyl)-N'-cycloheptyl-N"-(1-ethyl-pyrrolidin-2-ylmethyl)-[1,3,5]triazine-2,4,6-triamine;
N-(3-Bromo-4-methoxy-phenyl)-N'-cycloheptyl-N"-(1-ethyl-pyrrolidin-2-ylmethyl)-[1,3,5]triazine-2,4,6-triamine;
N-Cycloheptyl-N'-(1-ethyl-pyrrolidin-2-ylmethyl)-N"-(3-iodo-4-methoxy-phenyl)-[1,3,5]triazine-2,4,6-triamine;
{4-Cycloheptylamino-6-[(1-ethyl-pyrrolidin-2-ylmethyl)-amino]-[1,3,5]triazin-2-yl}-(3-fluoro-4-methoxy-phenyl)-cyanamide;
(3-Chloro-4-methoxy-phenyl)-{4-cycloheptylamino-6-[(1-ethyl-pyrrolidin-2-ylmethyl)-amino]-[1,3,5]triazin-2-yl}-cyanamide;
(3-Bromo-4-methoxy-phenyl)-{4-cycloheptylamino-6-[(1-ethyl-pyrrolidin-2-ylmethyl)-amino]-[1,3,5]triazin-2-yl}-cyanamide;
{4-Cycloheptylamino-6-[(1-ethyl-pyrrolidin-2-ylmethyl)-amino]-[1,3,5]triazin-2-yl}-(3-iodo-4-methoxy-phenyl)-cyanamide;
4-{4-Cycloheptylamino-6-[(1-ethylpyrrolidin-2-ylmethyl)-amino]-[1,3,5]triazin-2-ylamino}-2-fluoro-phenol;
2-Bromo-4-{4-cycloheptylamino-6-[(1-ethylpyrrolidin-2-ylmethyl)-amino]-[1,3,5]triazin-2-ylamino}-phenol;
4-{4-Cycloheptylamino-6-[(1-ethylpyrrolidin-2-ylmethyl)-amino]-[1,3,5]triazin-2-ylamino}-2-iodo-phenol;
N-Cycloheptyl-N'-ethyl-N"-(1-ethyl-pyrrolidin-2-ylmethyl)-N'-(3-fluoro-4-methoxy-phenyl)-[1,3,5]triazine-2,4,6-triamine;
N-(3-Chloro-4-methoxy-phenyl)-N'-cycloheptyl-N-ethyl-N"-(1-ethyl-pyrrolidin-2-ylmethyl)-[1,3,5]triazine-2,4,6-triamine;
N-Cycloheptyl-N'-(1-ethyl-pyrrolidin-2-ylmethyl)-N"-(3-fluoro-4-methoxy-phenyl)-N-methyl-[1,3,5]triazine-2,4,6-triamine;
N-Cycloheptyl-N-ethyl-N'-(1-ethylpyrrolidin-2-ylmethyl)-N"-(3-fluoro-4-methoxy-phenyl)-[1,3,5]triazine-2,4,6-triamine;
N-Cycloheptyl-N'-(1-ethyl-pyrrolidin-2-ylmethyl)-N"-(3-fluoro-4-methoxy-phenyl)-N-propyl-[1,3,5]triazine-2,4,6-triamine;
6-Cycloheptyloxy-N-(1-ethyl-pyrrolidin-2-ylmethyl)-N'-(3-fluoro-4-methoxy-phenyl)-[1,3,5]triazine-2,4,6-triamine;

6-Cyclopropoxy-N-(1-ethyl-pyrrolidin-2-ylmethyl)-N'-(3-fluoro-4-methoxy-phenyl)-[1,3,5]triazine-2,4,6-triamine;

6-Cyclopentyloxy-N-(1-ethyl-pyrrolidin-2-ylmethyl)-N'-(3-fluoro-4-methoxy-phenyl)-[1,3,5]triazine-2,4,6-triamine;

6-Cyclohexyloxy-N-(1-ethyl-pyrrolidin-2-ylmethyl)-N'-(3-fluoro-4-methoxy-phenyl)-[1,3,5]triazine-2,4,6-triamine;

N-Cycloheptyl-N'-(1-ethyl-1-oxy-pyrrolidin-2-ylmethyl)-N"-(3-fluoro-4-methoxy-phenyl)-[1,3,5]triazine-2,4,6-triamine;

N-(1-Ethyl-pyrrolidin-2-ylmethyl)-N'-(3-fluoro-4-methoxy-phenyl)-N"-(1-propyl-butyl)-[1,3,5]triazine-2,4,6-triamine;

N-Cyclopent-2-enyl-(1-ethyl-pyrrolidin-2-ylmethyl)-N"-(3-fluoro-4-methoxy-phenyl)-[1,3,5]triazine-2,4,6-triamine;

N-Cyclohex-2-enyl-(1-ethyl-pyrrolidin-2-ylmethyl)-N"-(3-fluoro-4-methoxy-phenyl)-[1,3,5]triazine-2,4,6-triamine;

N-Cyclohept-2-enyl-(1-ethyl-pyrrolidin-2-ylmethyl)-N"-(3-fluoro-4-methoxy-phenyl)-[1,3,5]triazine-2,4,6-triamine;

N-(1-Ethyl-pyrrolidin-2-ylmethyl)-N'-(3-fluoro-4-methoxy-phenyl)-N"-pyrrolidin-1-yl-[1,3,5]triazine-2,4,6-triamine;

N-(1-Ethyl-pyrrolidin-2-ylmethyl)-N'-(3-fluoro-4-methoxy-phenyl)-N"-piperidin-1-yl-[1,3,5]triazine-2,4,6-triamine;

N-Azepan-1-yl-N'-(1-ethyl-pyrrolidin-2-ylmethyl)-N"-(3-fluoro-4-methoxy-phenyl)-[1,3,5]triazine-2,4,6-triamine;

4-[(1-Ethyl-pyrrolidin-2-ylmethyl)-amino]-6-(3-fluoro-4-methoxy-phenylamino)-[1,3,5]triazin-2-yl-cyanamide;

N-[4-[(1-Ethyl-pyrrolidin-2-ylmethyl)-amino]-6-(3-fluoro-4-methoxy-phenylamino)-[1,3,5]triazin-2-yl]-acetamide;

3-[4-[(1-Ethyl-pyrrolidin-2-ylmethyl)-amino]-6-(3-fluoro-4-methoxy-phenylamino)-[1,3,5]triazin-2-ylamino]-pyrrolidin-2-one;

3-[4-[(1-Ethyl-pyrrolidin-2-ylmethyl)-amino]-6-(3-fluoro-4-methoxy-phenylamino)-[1,3,5]triazin-2-ylamino]-piperidin-2-one;

3-[4-[(1-Ethyl-pyrrolidin-2-ylmethyl)-amino]-6-(3-fluoro-4-methoxy-phenylamino)-[1,3,5]triazin-2-ylamino]-azepan-2-one;

N-(1-Ethyl-pyrrolidin-2-ylmethyl)-N'-(3-fluoro-4-methoxy-phenyl)-N"-pyrrolidin-3-yl-[1,3,5]triazine-2,4,6-triamine;

N-Azepan-3-yl-N'-(1-ethyl-pyrrolidin-2-ylmethyl)-N"-(3-fluoro-4-methoxy-phenyl)-[1,3,5]triazine-2,4,6-triamine;

N-(1-Ethyl-pyrrolidin-2-ylmethyl)-N'-(3-fluoro-4-methoxy-phenyl)-N"-oxepan-3-yl-[1,3,5]triazine-2,4,6-triamine;

N-(1-Ethyl-pyrrolidin-2-ylmethyl)-N'-(3-fluoro-4-methoxy-phenyl)-N"-(tetrahydropyran-3-yl)-[1,3,5]triazine-2,4,6-triamine;

N-(1-Ethyl-pyrrolidin-2-ylmethyl)-N'-(3-fluoro-4-methoxy-phenyl)-N"-(tetrahydrofuran-3-yl)-[1,3,5]triazine-2,4,6-triamine;

N-(1-Aza-bicyclo[2.2.2]oct-3-yl)-N'-(1-ethylpyrrolidin-2-ylmethyl)-N"-(3-fluoro-4-methoxy-phenyl)-[1,3,5]triazine-2,4,6-triamine;

N-(1-Aza-bicyclo[2.2.1]hept-3-yl)-N'-(1-ethyl-pyrrolidin-2-ylmethyl)-N"-(3-fluoro-4-methoxy-phenyl)-[1,3,5]triazine-2,4,6-triamine;

N-Bicyclo[2.2.1]hept-2-yl-N'-(1-ethyl-pyrrolidin-2-ylmethyl)-N"-(3-fluoro-4-methoxy-phenyl)-[1,3,5]triazine-2,4,6-triamine;

[4-[(1-Ethyl-pyrrolidin-2-ylmethyl)-amino]-6-(3-fluoro-4-methoxy-phenylamino)-[1,3,5]triazin-2-yl]-carbamic acid;

[4-[(1-Ethyl-pyrrolidin-2-ylmethyl)-amino]-6-(3-fluoro-4-methoxy-phenylamino)-[1,3,5]triazin-2-yl]-urea;

[4-[(1-Ethyl-pyrrolidin-2-ylmethyl)-amino]-6-(3-fluoro-4-methoxy-phenylamino)-[1,3,5]triazin-2-yl]-propan-2-one;

[4-[(1-Ethyl-pyrrolidin-2-ylmethyl)-amino]-6-(3-fluoro-4-methoxy-phenylamino)-[1,3,5]triazin-2-yl]-pentan-2-one;

N-Cycloheptyl-N'-(3-fluoro-4-methoxyphenyl)-6-(1-methyl-piperidin-4-yloxy)-[1,3,5]triazine-2,4-diamine;

N-Cycloheptyl-6-(1-ethyl-pyrrolidin-2-ylmethoxy)-N'-(3-fluoro-4-methoxy-phenyl)-[1,3,5]triazine-2,4-diamine;

1-{4-{[4-Cycloheptylamino-6-(3-fluoro-4-methoxy-phenylamino)-[1,3,5]triazin-2-yl]-methyl-amino}-piperidin-1-yl}-ethanone;

4-[4-Cycloheptylamino-6-(3-fluoro-4-methoxy-phenylamino)-[1,3,5]triazin-2-ylamino]-piperidine-1-carboxylic acid;

4-[4-Cycloheptylamino-6-(3-fluoro-4-methoxy-phenylamino)-[1,3,5]triazin-2-ylamino]-piperidine-1-carboxylic acid amide;

4-[4-Cycloheptylamino-6-(3-fluoro-4-methoxy-phenylamino)-[1,3,5]triazin-2-ylamino]-piperidin-1-ol;

N-Cycloheptyl-N'-(3-fluoro-4-methoxyphenyl)-N"-piperidin-4-yl-[1,3,5]triazine-2,4,6-triamine;

N-Cycloheptyl-N'-(3-fluoro-4-methoxyphenyl)-N"-(1-methyl-pyrrolidin-2-ylmethyl)-[1,3,5]triazine-2,4,6-triamine;

2-{[4-Cycloheptylamino-6-(3-fluoro-4-methoxy-phenylamino)-[1,3,5]triazin-2-ylamino]-methyl}-pyrrolidine-1-carbaldehyde;

2-{[4-Cycloheptylamino-6-(3-fluoro-4-methoxy-phenylamino)-[1,3,5]triazin-2-ylamino]-methyl}-pyrrolidine-1-carboxylic acid;

2-{[4-Cycloheptylamino-6-(3-fluoro-4-methoxy-phenylamino)-[1,3,5]triazin-2-ylamino]-methyl}-pyrrolidine-1-carboxylic acid amide;

N-Cycloheptyl-N'-(3-fluoro-4-methoxyphenyl)-N"-pyrrolidin-2-ylmethyl-[1,3,5]triazine-2,4,6-triamine;

N-Cycloheptyl-N'-(3-fluoro-4-methoxyphenyl)-N"-(tetrahydro-pyran-4-yl)-[1,3,5]triazine-2,4,6-triamine;

N-Cycloheptyl-N'-(3-fluoro-4-methoxyphenyl)-N"-methyl-(tetrahydro-pyran-4-yl)-[1,3,5]triazine-2,4,6-triamine;

N-Cycloheptyl-N'-(3-fluoro-4-methoxyphenyl)-N"-(tetrahydro-furan-2-ylmethyl)-[1,3,5]triazine-2,4,6-triamine;

N-Cycloheptyl-N'-(3-fluoro-4-methoxyphenyl)-N"-methyl-N"-(tetrahydro-furan-2-ylmethyl)-[1,3,5]triazine-2,4,6-triamine;

N-(4-Amino-cyclohexyl)-N'-cycloheptyl-N"-(3-fluoro-4-methoxy-phenyl)-[1,3,5]triazine-2,4,6-triamine;

N-Cycloheptyl-N'-(4-dimethylaminocyclohexyl)-N''-(3-fluoro-4-methoxy-phenyl)-[1,3,5]triazine-2,4,6-triamine;

1-{4-[4-Cycloheptylamino-6-(3-fluoro-4-methoxy-phenylamino)-[1,3,5]triazin-2-ylamino]-4H-pyridin-1-yl}-ethanone;

1-{4-[4-cycloheptylamino-6-(3-fluoro-4-methoxy-phenylamino)-[1,3,5]triazin-2-ylamino]-piperidin-1-yl}-butan-1-one;

1-{4-[4-cycloheptylamino-6-(3-fluoro-methoxy-phenylamino)-[1,3,5]triazin-ylamino]-piperidin-1-yl}-pentan-1-one;

4-[4-Cycloheptylamino-6-(3-fluoro-4-methoxy-phenylamino)-[1,3,5]triazin-ylamino]-piperidine-1-carboxylic acid methyl ester;

4-[4-Cycloheptylamino-6-(3-fluoro-4-methoxy-phenylamino)-[1,3,5]triazin-2-ylamino]-piperidine-1-carboxylic acid ethylester;

4-[4-Cycloheptylamino-6-(3-fluoro-4-methoxy-phenylamino)-[1,3,5]triazin-ylamino]-piperidine-1-carboxylic acid propyl ester;

4-[4-Cycloheptylamino-6-(3-fluoro-4-methoxy-phenylamino)-[1,3,5]triazin-2-ylamino]-piperidine-1-carboxylic acid benzyl ester;

1-{4-[4-Cycloheptylamino-6-(3-fluoro-4-methoxy-phenylamino)-[1,3,5]triazin-2-ylamino]-piperidin-1-yl}-propan-2-one;

1-{4-[4-Cycloheptylamino-6-(3-fluoro-4-methoxy-phenylamino)-[1,3,5]triazin-2-ylamino]-piperidin-1-yl}-pentan-2-one;

1-{4-[4-Cycloheptylamino-6-(3-fluoro-4-methoxy-phenylamino)-[1,3,5]triazin-2-ylamino]-piperidin-1-yl}-hexan-2-one;

{4-[4-Cycloheptylamino-6-(3-fluoro-4-methoxy-phenylamino)-[1,3,5]triazin-2-ylamino]-piperidin-1-yl}-acetic acid methyl ester;

{4-[4-Cycloheptylamino-6-(3-fluoro-4-methoxy-phenylamino)-[1,3,5]triazin-2-ylamino]-piperidin-1-yl}-acetic acid ethyl ester;

{4-[4-Cycloheptylamino-6-(3-fluoro-4-methoxy-phenylamino)-[1,3,5]triazin-2-ylamino]-piperidin-1-yl}-acetic acid propyl ester;

N-Cyclohept-3-enyl-N'-(1-ethyl-pyrrolidin-2-ylmethyl)-N''-(3-fluoro-4-methoxy-phenyl)-[1,3,5]triazine-2,4,6-triamine;

N-Azepan-4-yl-N'-(1-ethyl-pyrrolidin-2-ylmethyl)-N''-(3-fluoro-4-methoxy-phenyl)-[1,3,5]triazine-2,4,6-triamine;

N-(1-Ethyl-pyrrolidin-2-ylmethyl)-N'-(3-fluoro-4-methoxy-phenyl)-N''-(1-methyl-azepan-4-yl)-[1,3,5]triazine-2,4,6-triamine;

N-(1-Ethyl-pyrrolidin-2-ylmethyl)-N'-(3-fluoro-4-methoxy-phenyl)-N''-thiepan-4-yl-[1,3,5]triazine-2,4,6-triamine;

N-(1,1-Dioxo-1lambda*6*-thiepan-4-yl)-N'-(1-ethyl-pyrrolidin-2-ylmethyl)-N''-(3-fluoro-4-methoxy-phenyl)-[1,3,5]triazine-2,4,6-triamine;

N-(1-Ethyl-pyrrolidin-2-ylmethyl)-N'-(3-fluoro-4-methoxy-phenyl)-N''-oxepan-2-yl-[1,3,5]triazine-2,4,6-triamine;

N-Azepan-2-yl-N'-(1-ethyl-pyrrolidin-2-ylmethyl)-N''-(3-fluoro-4-methoxy-phenyl)-[1,3,5]triazine-2,4,6-triamine;

N-(1-Ethyl-pyrrolidin-2-ylmethyl)-N'-(3-fluoro-4-methoxy-phenyl)-N''-thiepan-2-yl-[1,3,5]triazine-2,4,6-triamine;

N-(1-Ethyl-pyrrolidin-2-ylmethyl)-N'-(3-fluoro-4-methoxy-phenyl)-N''-thiepan-3-yl-[1,3,5]triazine-2,4,6-triamine;

N-(1,1-Dioxo-1lambda*6*-thiepan-3-yl)-N'-(1-ethyl-pyrrolidin-2-ylmethyl)-N''-(3-fluoro-4-methoxy-phenyl)-[1,3,5]triazine-2,4,6-triamine;

2-{[4-Cycloheptylamino-6-(3-fluoro-4-methoxy-phenylamino)-[1,3,5]triazin-2-ylamino]-methyl}-1-ethyl-pyrrolidinium; chloride;

2-{[4-(3-Chloro-4-methoxy-phenylamino)-6-cycloheptylamino-[1,3,5]triazin-2-ylamino]-methyl}-1-ethyl-pyrrolidinium; chloride;

2-{[4-Cycloheptylamino-6-(3-fluoro-4-methoxy-phenylamino)-[1,3,5]triazin-2-ylamino]-methyl}-1-ethyl-pyrrolidinium; bromide;

2-{[4-Cycloheptylamino-6-(3-fluoro-4-methoxy-phenylamino)-[1,3,5]triazin-2-ylamino]-methyl}-1-ethyl-1-methyl-pyrrolidinium; iodide;

1-Acetyl-2-{[4-cycloheptylamino-6-(3-fluoro-4-methoxy-phenylamino)-[1,3,5]triazin-2-ylamino]-methyl}-1-ethyl-pyrrolidinium; chloride;

Sodium; 4-{4-cycloheptylamino-6-[(1-ethyl-pyrrolidin-2-ylmethyl)-amino]-[1,3,5]triazin-2-ylamino}-2-fluoro-phenolate;

Potassium; 4-{4-cycloheptylamino-6-[(1-ethyl-pyrrolidin-2-ylmethyl)-amino]-[1,3,5]triazin-2-ylamino}-2-fluoro-phenolate;

3-Carboxy-propionate-2-{[4-cycloheptylamino-6-(3-fluoro-4-methoxy-phenylamino)-[1,3,5]triazin-2-ylamino]methyl}-1-ethyl-pyrrolidinium;

3-Carboxy-acrylate-2-{[4-cycloheptylamino-6-(3-fluoro-4-methoxy-phenylamino)-[1,3,5]triazin-2-ylamino]-methyl}-1-ethyl-pyrrolidinium;

N-Cycloheptyl-N'-(3-fluoro-4-methoxy-phenyl)-N''-(1-methyl-1H-pyrrol-2-ylmethyl)-[1,3,5]triazine-2,4,6-triamine;

N-Cycloheptyl-N'-(3-fluoro-4-methoxy-phenyl)-6-(1-methyl-1H-pyrrol-2-ylmethoxy)-[1,3,5]triazine-2,4-diamine;

N-Cycloheptyl-N'-(3-fluoro-4-methoxy-phenyl)-6-(thiophen-2-ylmethoxy)-[1,3,5]triazine-2,4-diamine;

N-Cycloheptyl-N'-(3-fluoro-4-methoxy-phenyl)-N''-thiophen-2-ylmethyl-[1,3,5]triazine-2,4,6-triamine;

N-Cycloheptyl-N'-(3-fluoro-4-methoxy-phenyl)-N''-furan-2-ylmethyl-[1,3,5]triazine-2,4,6-triamine;

N-Cycloheptyl-N'-(3-fluoro-4-methoxy-phenyl)-N''-(tetrahydro-furan-2-ylmethyl)-[1,3,5]triazine-2,4,6-triamine;

N-Cycloheptyl-N'-(1,1-dioxo-tetrahydro-1lambda*6*-thiophen-2-ylmethyl)-N''-(3-fluoro-4-methoxy-phenyl)-[1,3,5]triazine-2,4,6-triamine;

N-Cycloheptyl-N'-(1-ethyl-pyrrolidin-2-ylmethyl)-N''-(5-fluoro-6-methoxy-pyridin-3-yl)-[1,3,5]triazine-2,4,6-triamine;

N-Cycloheptyl-N'-(1-ethyl-pyrrolidin-2-ylmethyl)-N''-(4-fluoro-5-methoxy-pyridin-2-yl)-[1,3,5]triazine-2,4,6-triamine;

N-Cycloheptyl-N'-(3-fluoro-4-methoxy-phenyl)-N''-pyridin-2-ylmethyl-[1,3,5]triazine-2,4,6-triamine;

N-Cycloheptyl-N'-(3-fluoro-4-methoxy-phenyl)-N''-pyridin-3-ylmethyl-[1,3,5]triazine-2,4,6-triamine;

N-Cycloheptyl-N'-(1-ethyl-pyrrolidin-2-ylmethyl)-N''-(4-methoxy-3-trifluoromethyl-phenyl)-[1,3,5]triazine-2,4,6-triamine;

N-Cycloheptyl-N'-(1-ethyl-pyrrolidin-2-ylmethyl)-N''-(4-trifluoromethoxy-3-trifluoromethyl-phenyl)-[1,3,5]triazine-2,4,6-triamine;

4-{4-Cycloheptylamino-6-[(1-ethyl-pyrrolidin-2-ylmethyl)-amino]-[1,3,5]triazin-2-ylamino}-2-trifluoromethyl-phenol;

N-Cycloheptyl-N'-(2-ethyl-cyclopentylmethyl)-N"-(3-fluoro-4-methoxy-phenyl)-[1,3,5]triazine-2,4,6-triamine;

N-Cycloheptyl-N'-(3-fluoro-4-methoxy-phenyl)-N"-(2-methyl-cyclopentyl methyl)-[1,3,5]triazine-2,4,6-triamine;

2-{[4-Cycloheptylamino-6-(3-fluoro-4-methoxy-phenylamino)-[1,3,5]triazin-2-ylamino]-methyl}-cyclopentanol;

N-(2-Amino-cyclopentylmethyl)-N'-cycloheptyl-N"-(3-fluoro-4-methoxy-phenyl)-[1,3,5]triazine-2,4,6-triamine;

3-{[4-Cycloheptylamino-6-(3-fluoro-4-methoxy-phenylamino)-[1,3,5]triazin-2-ylamino]-methyl}-cyclopentanol;

2-[4-Cycloheptylamino-6-(3-fluoro-4-methoxy-phenylamino)-[1,3,5]triazin-2 ylamino]-cyclopentanol;

N-Cycloheptyl-N'-(3-fluoro-4-methoxy-phenyl)-6-(tetrahydro-pyrrolo[1,2-c]imidazol-2-yl)-[1,3,5]triazine-2,4-diamine;

2-[4-Cycloheptylamino-6-(3-fluoro-4-methoxy-phenylamino)-[1,3,5]triazin-2-yl]-hexahydro-pyrrolo[1,2-c]imidazol-3-one;

N-Cycloheptyl-N'-(3-fluoro-4-methoxy-phenyl)-N"-(1H-imidazol-4-ylmethyl)-[1,3,5]triazine-2,4,6-triamine;

N-Cycloheptyl-6-(2,3-dihydro-indol-1-yl)-N'-(3-fluoro-4-methoxy-phenyl)-[1,3,5]triazine-2,4-diamine;

N-Cycloheptyl-N'-(3-fluoro-4-methoxy-phenyl)-6-indol-1-yl-[1,3,5]triazine-2,4-diamine;

1-(2-{[4-Cycloheptylamino-6-(3-fluoro-4-methoxy-phenylamino)-[1,3,5]triazin-2-ylamino]-methyl}-pyrrolidin-1-yl)-3-(2-{2-[2-(2-hydroxy-ethoxy)-ethoxy]-ethoxy}-ethoxy)-propan-1-one;

1-(2-{[4-Cycloheptylamino-6-(3-fluoro-4-methoxy-phenylamino)-[1,3,5]triazin-2-ylamino]-methyl}-pyrrolidin-1-yl)-3-(2-{2-[2-(2-methoxy-ethoxy)-ethoxy]-ethoxy}-ethoxy)-propan-1-one;

N-Cycloheptyl-N'-(3-fluoro-4-methoxy-phenyl)-N"-[1-(2-{2-[2-(2-methoxy-ethoxy)-ethoxy]-ethoxy}-ethoxymethyl)-pyrrolidin-2-ylmethyl]-[1,3,5]triazine-2,4,6-triamine 2-(2-{2-[2-(2-{[4-Cycloheptylamino-6-(3-fluoro-4-methoxy-phenylamino)-1,3,5]triazin-2-ylamino]-methyl}-pyrrolidin-1-ylmethoxy)-ethoxy]-ethoxy}-ethoxy)-ethanol;

3-{2-[2-(2-Methoxy-ethoxy)-ethoxy]-ethoxy}-propionic acid 4-{4-cycloheptylamino-6-[(1-ethyl-pyrrolidin-2-ylmethyl)-amino]-[1,3,5]triazin-2-ylamino}-2-fluoro-phenyl ester;

3-{2-[2-(2-Hydroxy-ethoxy)-ethoxy]-ethoxy}-propionic acid 4-{4-cycloheptylamino-6-[(1-ethyl-pyrrolidin-2-ylmethyl)-amino]-[1,3,5]triazin-2-ylamino}-2-fluoro-phenyl ester;

3-(2-{2-[2-(4-{4-Cycloheptylamino-6-[(1-ethyl-pyrrolidin-2-ylmethyl)-amino]-[1,3,5]triazin-2-ylamino)}-2-fluoro-phenoxy)-ethoxy]-ethoxy}-ethoxy)-propan-1-ol;

N-Cycloheptyl-N'-(1-ethyl-pyrrolidin-2-ylmethyl)-N"-[3-fluoro-4-(2-{2-[2-(3-methoxy-propoxy)-ethoxy]-ethoxy}-ethoxy)-phenyl]-[1,3,5]triazine-2,4,6-triamine;

N-Cycloheptyl-N'-(1-ethyl-pyrrolidin-2-ylmethyl)-N"-(3-fluoro-4-methoxymethoxy-phenyl)-[1,3,5]triazine-2,4,6-triamine;

N-Cycloheptyl-N'-(1-ethyl-pyrrolidin-2-ylmethyl)-N"-(3-fluoro-4-methylsulfanylmethoxy-phenyl)-[1,3,5]triazine-2,4,6-triamine;

N-Cycloheptyl-N'-(4-cyclopropoxy-3-fluoro-phenyl)-N"-(1-ethyl-pyrrolidin-2-ylmethyl)-[1,3,5]triazine-2,4,6-triamine;

4-{4-Cycloheptylamino-6-[(1-ethyl-pyrrolidin-2-ylmethyl)-amino]-[1,3,5]triazin-2-ylamino}-2-fluoro-phenol; compound with phosphoric acid monoethyl ester;

4-{4-Cycloheptylamino-6-[(1-ethyl-pyrrolidin-2-ylmethyl)-amino]-[1,3,5]triazin-2-ylamino}-2-fluoro-phenol; compound with phosphoric acid dibenzyl ester ethyl ester;

4-{4-Cycloheptylamino-6-[(1-ethyl-pyrrolidin-2-ylmethyl)-amino]-[1,3,5]triazin-2-ylamino}-2-fluoro-phenol; compound with phosphoric acid ditert-butyl ester ethyl ester;

Phosphoric acid mono-(4-{4-cycloheptylamino-6-[(1-ethyl-pyrrolidin-2-ylmethyl)-amino]-[1,3,5]triazin-2-ylamino}-2-fluoro-phenyl) ester;

5-{4-Cycloheptylamino-6-[(1-ethyl-pyrrolidin-2-ylmethyl)-amino]-[1,3,5]triazin-2-ylamino}-2-hydroxy-benzoic acid; compound with ethane;

Sodium; 5-{4-cycloheptylamino-6-[(1-ethyl-pyrrolidin-2-ylmethyl)-amino]-[1,3,5]triazin-2-ylamino}-2-methoxy-benzoate;

2-{[4-Cycloheptylamino-6-(3-fluoro-4-methoxy-phenylamino)-[1,3,5]triazin-2-ylamino]-methyl}-1-(di-tert-butoxy-phosphoryloxymethyl)-1-ethyl-pyrrolidinium; chloride;

1-(Bis-benzyloxy-phosphoryloxymethyl)-2-{[4-cycloheptylamino-6-(3-fluoro-4-methoxy-phenylamino)-[1,3,5]triazin-2-ylamino]-methyl}-1-ethyl-pyrrolidinium; chloride;

2-{[4-Cycloheptylamino-6-(3-fluoro-4-methoxy-phenylamino)-[1,3,5]triazin-2-ylamino]-methyl}-1-ethyl-1-phosphonooxymethyl-pyrrolidinium; chloride;

Trifluoro-acetate2-{[4-cycloheptylamino-6-(3-fluoro-4-methoxy-phenylamino)-[1,3,5]triazin-2-ylamino]-methyl}-1-ethyl-1-phosphonooxymethyl-pyrrolidinium; or Phosphoric acid mono-(2-{[4-cycloheptylamino-6-(3-fluoro-4-hydroxy-phenylamino)-[1,3,5]triazin-2-ylamino]-methyl}-pyrrolidin-1-ylmethyl) ester; compound with ethane.

5. The composition as claimed in claim 3, further comprising:

optionally, a pharmaceutically acceptable auxiliary;

optionally, a pharmaceutically acceptable preservative; and optionally, a pharmaceutically acceptable excipient.

6. The composition as claimed in claim 3, wherein the composition is in the form of a tablet, a capsule, a cachet, a powder, a granule, a solution, a suspension, an emulsion, a bolus, a lozenge, a suppository, a pessary, a tamport, a cream, a gel, a paste, a foam, a spray, an aerosol, a microcapsule, a liposome, a transdermal patch, a pastille, a paste, or a mouthwash.

* * * * *